(12) United States Patent
Grainger et al.

(10) Patent No.: US 7,989,466 B2
(45) Date of Patent: Aug. 2, 2011

(54) METHODS TO INHIBIT OR AUGMENT AN INFLAMMATORY RESPONSE

(75) Inventors: David J. Grainger, Cambridge (GB); Lauren Marie Tatalick, Redmond, WA (US)

(73) Assignee: Cambridge Enterprise Limited, Cambridge (GB)

( * ) Notice: Subject to any disclaimer, the term of this patent is extended or adjusted under 35 U.S.C. 154(b) by 981 days.

(21) Appl. No.: 11/682,931

(22) Filed: Mar. 7, 2007

(65) Prior Publication Data

US 2008/0045557 A1    Feb. 21, 2008

Related U.S. Application Data

(60) Division of application No. 09/452,406, filed on Dec. 1, 1999, now Pat. No. 7,238,711, which is a continuation-in-part of application No. 09/271,192, filed on Mar. 17, 1999, now abandoned.

(51) Int. Cl.
*A61K 31/44* (2006.01)
(52) U.S. Cl. .................................................. 514/280
(58) Field of Classification Search .................. 514/280
See application file for complete search history.

(56) References Cited

U.S. PATENT DOCUMENTS

| | | | |
|---|---|---|---|
| 2,726,243 A | 12/1955 | Huebner | |
| 2,740,788 A | 4/1956 | Grussner et al. | |
| 2,743,270 A | 4/1956 | Blicke | |
| 3,168,565 A | 2/1965 | Palopoli et al. | |
| 4,108,855 A | 8/1978 | Mago nee Karacsony et al. | |
| 4,724,232 A | 2/1988 | Rideout et al. | |
| 4,737,580 A | 4/1988 | Twardzik et al. | |
| 4,774,318 A | 9/1988 | Marquardt et al. | |
| 5,028,594 A | 7/1991 | Carson | |
| 5,079,228 A | 1/1992 | Cohen et al. | |
| 5,155,038 A | 10/1992 | Eyal et al. | |
| 5,190,918 A | 3/1993 | Deutch et al. | |
| 5,190,920 A | 3/1993 | Eyal et al. | |
| 5,192,744 A | 3/1993 | Bouck et al. | |
| 5,202,118 A | 4/1993 | Gillis et al. | |
| 5,212,073 A | 5/1993 | Rollins et al. | |
| 5,248,666 A | 9/1993 | Twardzik et al. | |
| 5,302,384 A | 4/1994 | Gimbrone, Jr. et al. | |
| 5,357,041 A | 10/1994 | Roberts et al. | |
| 5,401,651 A | 3/1995 | Walz | |
| 5,426,100 A | 6/1995 | Deutch et al. | |
| 5,458,874 A | 10/1995 | Pereira et al. | |
| 5,459,128 A | 10/1995 | Rollins et al. | |
| 5,474,983 A | 12/1995 | Kuna et al. | |
| 5,491,130 A | 2/1996 | Roberts et al. | |
| 5,529,904 A | 6/1996 | Ginsburg et al. | |
| 5,532,144 A | 7/1996 | Yoshimura et al. | |
| 5,545,623 A | 8/1996 | Matsumori | |

(Continued)

FOREIGN PATENT DOCUMENTS

DE        24 36 820        2/1975

(Continued)

OTHER PUBLICATIONS

Harrison et al., Am J Respir Crit Care Med, 1999;159:1918-1924.*

(Continued)

*Primary Examiner* — San-ming Hui
(74) *Attorney, Agent, or Firm* — Schwegman, Lundberg & Woessner, P.A.

(57) ABSTRACT

Isolated and purified chemokine peptides, variants, and derivatives thereof, as well as chemokine peptide analogs, are provided.

6 Claims, 75 Drawing Sheets

TOP COMPARTMENT

LOWER COMPARTMENT

U.S. PATENT DOCUMENTS

| | | | |
|---|---|---|---|
| 5,556,757 A | 9/1996 | Alstyne et al. |
| 5,571,713 A | 11/1996 | Lyle et al. |
| 5,578,714 A | 11/1996 | Pogo et al. |
| 5,589,458 A | 12/1996 | Jameson et al. |
| 5,597,578 A | 1/1997 | Brown et al. |
| 5,605,671 A | 2/1997 | Lyle et al. |
| 5,627,156 A | 5/1997 | Talmadge |
| 5,627,265 A | 5/1997 | Frazier et al. |
| 5,629,327 A | 5/1997 | D'Amato |
| 5,645,837 A | 7/1997 | Jameson et al. |
| 5,646,117 A | 7/1997 | Matsushima et al. |
| 5,650,150 A | 7/1997 | Gillies |
| 5,661,132 A | 8/1997 | Eriksson et al. |
| 5,663,294 A | 9/1997 | Colman et al. |
| 5,684,032 A | 11/1997 | Elliott et al. |
| 5,700,821 A | 12/1997 | Lazo et al. |
| 5,705,360 A | 1/1998 | Rollins et al. |
| 5,707,814 A | 1/1998 | Levy et al. |
| 5,707,815 A | 1/1998 | Charo et al. |
| 5,770,609 A | 6/1998 | Grainger et al. |
| 5,807,482 A | 9/1998 | House |
| 5,811,449 A | 9/1998 | Medford et al. |
| 5,817,911 A | 10/1998 | Williams et al. |
| 5,824,299 A | 10/1998 | Luster et al. |
| 5,824,551 A | 10/1998 | Damme et al. |
| 5,824,647 A | 10/1998 | Postlethwaite et al. |
| 5,827,821 A | 10/1998 | Pierschbacher et al. |
| 5,831,032 A | 11/1998 | Schraufstatter et al. |
| 5,871,740 A | 2/1999 | Smith |
| 5,877,276 A | 3/1999 | Talmadge |
| 5,908,829 A | 6/1999 | Kelly |
| 5,955,485 A | 9/1999 | De Brabander et al. |
| 5,955,492 A | 9/1999 | Thompson et al. |
| 6,162,455 A | 12/2000 | Cleale et al. |
| 6,989,435 B2 | 1/2006 | Grainger et al. |
| 7,067,117 B1 | 6/2006 | Grainger et al. |
| 7,238,711 B1 | 7/2007 | Grainger et al. |
| 7,700,087 B2 | 4/2010 | Grainger et al. |
| 2002/0182650 A1 | 12/2002 | Sworin et al. |
| 2006/0073114 A1 | 4/2006 | Grainger et al. |

FOREIGN PATENT DOCUMENTS

| | | |
|---|---|---|
| DE | 2710246 | 9/1977 |
| EP | 0 281 363 | 9/1988 |
| EP | 0 353 772 | 2/1990 |
| EP | 0 373 994 | 6/1990 |
| EP | 0807439 | 11/1997 |
| EP | 0860446 | 8/1998 |
| EP | 0905241 | 3/1999 |
| FR | 2183578 | 12/1973 |
| FR | 2239471 | 2/1975 |
| GB | 1359260 | 7/1974 |
| GB | 1414589 | 11/1975 |
| GB | 2 319 252 A | 5/1998 |
| JP | 36-14610 | 8/1961 |
| JP | 06-025288 | 2/1994 |
| JP | 7-67689 | 3/1995 |
| JP | 09255570 | 9/1997 |
| JP | 11124393 | 5/1999 |
| JP | 11127859 | 5/1999 |
| JP | 11128208 | 5/1999 |
| JP | 11130767 | 5/1999 |
| JP | 11130778 | 5/1999 |
| JP | 11130792 | 5/1999 |
| JP | 11137283 | 5/1999 |
| JP | 11137299 | 5/1999 |
| WO | WO-86/04334 | 7/1986 |
| WO | WO-90/07863 | 7/1990 |
| WO | WO-91/03491 | 3/1991 |
| WO | WO-91/08483 | 6/1991 |
| WO | WO-91/17179 | 11/1991 |
| WO | WO-92/04372 | 3/1992 |
| WO | WO-92/14455 | 9/1992 |
| WO | WO-92/20372 | 11/1992 |
| WO | 93/10796 | 6/1993 |
| WO | WO-93/10796 | 6/1993 |
| WO | WO-93/11159 | 6/1993 |
| WO | WO-9310796 A1 | 6/1993 |
| WO | WO-94/11014 | 5/1994 |
| WO | WO-94/20116 | 9/1994 |
| WO | WO-94/20117 | 9/1994 |
| WO | WO-94/20126 | 9/1994 |
| WO | WO-94/20127 | 9/1994 |
| WO | WO-94/20512 | 9/1994 |
| WO | WO-95/05191 | 2/1995 |
| WO | WO-95/17420 | 6/1995 |
| WO | WO-95/17421 | 6/1995 |
| WO | WO-95/20973 | 8/1995 |
| WO | WO-95/26982 | 10/1995 |
| WO | WO-96/20722 | 7/1996 |
| WO | WO-96/22371 | 7/1996 |
| WO | WO-9625157 A1 | 8/1996 |
| WO | WO-96/29074 | 9/1996 |
| WO | WO-97/01350 | 1/1997 |
| WO | WO-97/12615 | 4/1997 |
| WO | WO-97/19173 | 5/1997 |
| WO | WO-97/21812 | 6/1997 |
| WO | WO-97/22698 | 6/1997 |
| WO | WO-97/24325 | 7/1997 |
| WO | WO-97/25427 | 7/1997 |
| WO | WO-97/29192 | 8/1997 |
| WO | WO-97/31098 | 8/1997 |
| WO | WO-97/31949 | 9/1997 |
| WO | WO-97/32019 | 9/1997 |
| WO | WO-97/32993 | 9/1997 |
| WO | WO-97/35010 | 9/1997 |
| WO | WO-97/35982 | 10/1997 |
| WO | WO-97/44462 | 11/1997 |
| WO | WO-97/45543 | 12/1997 |
| WO | WO-98/06703 | 2/1998 |
| WO | WO-98/09171 | 3/1998 |
| WO | WO-98/12324 | 3/1998 |
| WO | WO-98/13495 | 4/1998 |
| WO | WO-98/23750 | 6/1998 |
| WO | WO-98/24808 | 6/1998 |
| WO | 98/42354 | 10/1998 |
| WO | WO-98/42484 | 10/1998 |
| WO | WO-9842354 A1 | 10/1998 |
| WO | WO-98/00535 | 12/1998 |
| WO | WO-98/54326 | 12/1998 |
| WO | WO-99/04770 | 2/1999 |
| WO | WO-99/04791 | 2/1999 |
| WO | WO-99/05279 | 2/1999 |
| WO | WO-99/12968 | 3/1999 |
| WO | WO-99/37617 | 7/1999 |
| WO | WO-99/37619 | 7/1999 |
| WO | WO-99/37651 | 7/1999 |
| WO | WO-99/42461 | 8/1999 |
| WO | WO-99/42463 | 8/1999 |
| WO | WO-00/00821 | 1/2000 |
| WO | WO-00/42071 | 7/2000 |
| WO | WO-02076399 A2 | 10/2002 |
| WO | WO-02094270 A2 | 11/2002 |
| WO | WO-2007042504 A2 | 4/2007 |

OTHER PUBLICATIONS

"Blocking CCR5 Stops M-tropic HIV Infection", *Biotechnology News*, 17, (1997),3.

"Developed Adjuvant Polyarthritis Assay in Rats (Therapeutic)", Product and Services Information, Chrysalis Company, Olyphant, PA,(1997),1 p.

"Developing Adjuvant Polyarthritis Assay in Rats (Prophylactic)", Product and Services Information, Chrysalis Company, Olyphant, PA,(1997),1 p.

"Leukotrine Antagonists Making Their Mark in Asthma", *SCRIP*, No. 2376, John Davis, (ed.),(Oct. 7, 1998),23.

Adkins, J. C., et al., "Zafirlukast—A Review of its Pharmacology and Therapeutic Potential in the Management of Asthma", *Drugs*, 55, (1998),121-144.

Albanesi, C., et al., "Cetirizine and Hydrocortisone Differentially Regulate ICAM-I Expression and Chemokine Release in Cultured Human Keratinocytes", *Clinical and Experimental Allergy*, 28(1), (Jan. 1998),101-109.

Albini, A., et al., "Hiv-1 Tat Protein Mimicry of Chemokines", *Proceedings of the National Academy of Sciences USA*, 95(22), (Oct. 27, 1998),13153-13158.

Alkhatib, G., et al., "HIV-1 Coreceptor Activity of CCR5 and Its Inhibition by Chemokines: Independence from G Protein Signaling and Importance of Coreceptor Downmodulation", *Virology*, 234(2), (Aug. 4, 1997),340-348.

Amann, B., et al., "Urinary Levels of Monocyte Chemo-Attractant Protein-1 Correlate with Tumour Stage and Grade in Patients with Bladder Cancer", *British Journal of Urology*, 82(1), (Jul. 1998),118-121.

Arenzana-Seisdedos, F., et al., "HIV Blocked by Chemokine Antagonists", *Nature*, 383(6599), (Oct. 3, 1996),400.

Auditore-Hargreaves, K., et al., "The Pan-Chemokine Inhibitor NR58-3.14.3 Mediates Regression of Allergic Inflammation in the Mouse Lung", An unpublished manuscript,.

Auer, M., et al., "Crystallization and Preliminary X-ray Crystallographic Study of Interleukin-8", *FEBS Letters*, 265(1-2), (Jun. 1990),30-32.

Aukrust, Pal, et al., "Elevated CirCulating Levels of C-C Chemokines in Patients with Congestive Heart Failure", *Circulation*, 97(12), (Mar. 31, 1998),1136-1143.

Bacon, K. B., et al., "Activation of Dual T Cell Signaling Pathways by the Chemokine RANTES", *Science*, 269, (1995),1727-1730.

Bacon, K. B., et al., "Chemokines in Disease Models and Pathogenesis", *Cytokine and Growth Factor Reviews*, 9, (1998),167-173.

Baldwin, E. T., et al., "Crystal Structure of Interleukin 8: Symbiosis of NMR and Crystallography", *Proceedings of the National Academy of Sciences USA*, .

Baldwin, Eric T., et al., "Crystallization of Human Interleukin-8", *Journal of Biological Chemistry*, 265(12), (Apr. 25, 1990),6851-6853.

Bauermeister, K., et al., "Distinct Regulation of IL-8 and MCP-1 by LPS and Interferon-gamma-treated Human Peritoneal Macrophages", *Nephrol Dial Transplant*, 13(6), (Jun. 1998),1412-1419.

Beck-Schimmer, B., et al., "Hyaluronan Induces Monocyte Chemoattractant Protein-1 Expression in Renal Tubular Epithelial Cells", *Journal of the American Society of Nephrology*, 9, (1988),2283-2290.

Bernstein, S. H., et al., "A Randomized Phase II Study of BB-10010: a Variant of Human Macrophage Inflammatory Protein-1alpha for Patients Receiving High-Dose Etoposide and Cyclophosphamide for Malignant Lymphoma and Breast Cancer", *British Journal of Haematology*, 99, (1997),888-895.

Berson, J. F., et al., "Structure-Function Studies of the HIV-1 Coreceptors", *Seminars in Immunology*, 10, (1998),237-248.

Bodaghi, B., et al., "Chemokine sequestration by viral chemoreceptors as a novel viral escape strategy: withdrawal of chemokines from the environment of cytomegalovirus-infected cells", *Journal of Experimental Medicine*, 188(5), (Sep. 7, 1998),855-866.

Boring, L., et al., "Decreased Lesion Formation in CCR2−/− Mice Reveals a Role for Chemokines in the Initiation of Artherosclerosis", *Nature*, 394(6696), (Aug. 27, 1998),894-897.

Bowie, James U., et al., "Deciphering the Message in Protein Sequences: Tolerance to Amino Acid Substitutions", *Science*, 247, (Mar. 16, 1990),1306-1310.

Brunden, K. R., et al., "pH-Dependent Binding of Synthetic Beta-Amyloid Peptides to Glycosaminoglycans", *J. Neurochem.*, 61, (1993),2147-2154.

Bucht, A., et al., "Expression of Interferon-Gamma (IFN-gamma), IL-10, IL-12 and Transforming Growth Factor Beta (TGF-beta) mRNA in Synovial Fluid Cells from Patients in the Early and Late Phases of Rheumatoid Arthritis (RA)", *Clin. Exp. Immunol.*, 103(3), (Mar. 1996),357-367.

Buckley, C. D., "Treatment of Rheumatoid Arthritis", *BMJ*, 315, (Jul. 26, 1997),236-238.

Cairns, J. S., et al., "Chemokines and HIV-1 Second Receptors: The Therapeutic Connection", *Nature Medicine*, 4, (May 1998),563-568.

Carr, D. J., et al., "Cytokine and Chemokine Production in HSV-1 Latently Infected Trigeminal Ganglion Cell Cultures: Effects of Hyperthermic Stress", *Journal of Neuroimmunology*, 85, (1998),111-121.

Carron, C. P., et al., "A Peptidomimetic Antagoinst of the Integrin alpha(sub v)beta(sub 3) Inhibits Leydig Cell Tumor Growth and the Development of Hypercalcemia of Malignancy", *Cancer Research*, 58, (May 1, 1998),1930-1935.

Cashman, J. D., et al., "MCP-1, not MIP-1alpha, Is the Endogenous Chemokine That Cooperates with TGF-beta to Inhibit the Cycling of Primitive Normal but not Leukemic (CML) Progenitors in Long-Term Human Marrow Cultures", *Blood*, 92, (Oct. 1, 1998),2338-2344.

Chakravarty, L., et al., "Lysine 58 and Histidine 66 at the C-terminal alpha- Helix of Monocyte Chemoattractant Protein-1 are Essential for Glycosaminoglycan Binding", *Journal of Biological Chemistry*, 273, (Nov. 6, 1988),29641-29647.

Chen, S., et al., "In Vivo Inhibition of CC and CX3C Chemokine-induced Leukocyte Infiltration and Attenuation of Glomerulonephritis in Wistar-Kyoto (WKY) Rats by vMIP-II", *J. Exp. Med.*, 188, (1998),193-198.

Chung, C. W., et al., "The Three-Dimensional Solutions Structure of RANTES", *Biochemistry*, 34, (1995),9307-9314.

Clark-Lewis, I., et al., "Platelet Factor 4 Binds to Interleukin 8 Receptors and Activates Neutrophils When its N Terminus is Modified with Glu-Leu-Arg", *Proceedings of the National Academy of Sciences, USA*, 90, (1993),3574-3577.

Clark-Lewis, I., et al., "Structural Requirements for Interleukin-8 Function Identified by Design of Analogs and CXC Chemokine Hybrids", *J. Biol. Chem.*, 269, (Jun. 10, 1994),16075-16801.

Clarke, D., et al., "Interaction of Interleukin 7 (IL-7) with Glycosaminoglycans and Its Biological Relevance", *Cytokine*, 7, (1995),325-330.

Clore, G. M., et al., "Comparison of the Solution Nuclear Magnetic Resonance and Crystal Structures of Interleukin-8", *J. Mol. Biol.*, 217, (1991),611-620.

Cocchi, F., et al., "Identification of RANRES, MIP-1(alpha), and MIP-1(beta) as the Major HIV-Suppressive Factors Produced by CD8(plus) T Cells", *Science*, 270, (Dec. 15, 1995),1811-1815.

Cocchi, F., et al., "The V3 Domain of the HIV-1 gp120 Envelope Glycoprotein is Critical for Chemokine-Mediated Blockade of Infection", *Nature Medicine*, 11, (Nov. 1996),1244-1247.

Conti, P., et al., "Will MCP-1 and RANTES Take Center Stage in Inflammatory Diseases Including Asthma?", *Allergy and Asthma Proc.*, 19, (1998),121-123.

Csernok, E, et al., "Transforming Growth Factor-beta (TGF-beta) Expression and Interaction with Proteinase 3 (PR3) in Anti-Neutrophil Cytoplasmic Antibody (ANCA)-associated Vasculitis", *Clin. Exp. Immunol.*, 105, (1996),104-111.

Cunningham, Brian C., et al., "High-Resolution Receptor Epitope Mapping of hGH-Receptor Interactions by Alanine-Scanning Mutagenesis", *Science*, 244, (1989),1081-1085.

Damon, I., et al., "Broad Spectrum Chemokine Antagonistic Activity of a Human Poxvirus Chemokine Homolog", *Proc. Natl. Acad. Sci. USA*, 95, (May 1998),6403-6407.

Davis, L. S., et al., "Disordered Differentiation of Memory T Cells in Rheumatoid Arthritis", *Revue de Rhumatisme*, 65, (1998),291-296.

De Vries, J. E., "The Role of IL-13 and Its Receptor in Allergy and Inflammation Responses", *J. Allergy Clin. Immunol.*, 102, (1998),165-169.

Debie, J. J., et al., "Modulation of Airway Hyperresponsiveness and Eosinophilia by Selective Histamine and 5-HT Receptor Antagonists in a Mouse Model of Allergic Asthma", *British Journal of Pharmacology*, 124, (1998),857-864.

Donzella, G. A., et al., "AMD3100, A Small Molecule Inhibition of HIV-1 Entry via the CXCR4 Co-receptor", *Nature Medicine*, 4, (Jan. 1998),72-77.

Doranz, B. J., et al., "A Small-Molecule Inhibitor Directed Against the Chemokine Receptor CXCR4 Prevents its Use as an HIV-1 Coreceptor", *J. Exp. Med.*, 186, (Oct. 20, 1997),1395-1400.

Drazen, J. M., et al., "Treatment of Chronic Stable Asthma with Drugs Active on the 5-Lipoxygenase Pathway", *Int. Arch. Allergy Immunol.*, 107, (1995),319-320.

Fairbrother, W. J., et al., "The Solution Structure of Melanoma Growth Stimulating Activity", *Journal of Molecular Biology*, 242, (1994),252-270.

Ferrero, E., et al., "Tumor-Driven Matrix Invasion by Infiltrating Lymphcytes: Involvement of the alpha1 Integrin I-domain", *Eur. J. Immunol.*, 28, (1998),2530-2536.

Fiocchi, C., "Inflammatory Bowel Disease: Etiology and Pathogenesis", *Gastroenterology*, 115, (1998),182-205.

Flesch, I. E., et al., "Differential Chemokine Response of Murine Macrophages Stimulated with Cytokines and Infected with *Listeria monocytogenes*", *International Immunology*, 10. (1998),757-765.

Frautschy, S A., et al., "Rodent Models of Alzheimer's Disease: Rat A Infusion Approaches to Amyloid Deposits", *Neurobiology of Aging*, 17, (1996),311-321.

Frevert, C. W., et al., "Rapid Fluorescence-based Measurement of Neutrophil Migration in Vitro", *Journal of Immunological Methods*, 213, (1998),41-52.

Gao, M., et al., "Differences in Susceptibility to CC-chemokines Among HIV-1 Isolates", *International Journal of STD & AIDS*, 9, (1998),471-475.

Gilmore, et al., "Protective Effects of BB-10010 Treatment on Chemotherapy-induced Neutropenia in Mice", *Experimental Hematology*, 29, (1999),195-202.

Gong, J. H., et al., "An Antagonist of Monocyte Chemoattractant Protein 1 (MCP-1) Inhibits Arthritis in the MRL-Ipr Mouse Model", *J. Exp. Med.*, 186 (1), (Jul. 7, 1997),131-137.

Gong, Jiang-Hong, et al., "Antagonists of Monocyte Chemoattractant Protein 1 Identified by Modification of Functionally Critical NH2-terminal Residues", *J. Exp. Med.*, 181, (1995),631-640.

Gosling, J., et al., "Molecular Uncoupling of C-C Chemokine Receptor 5-Induced Chemotaxis and Signal Transduction from HIV-1 Coreceptor Activity", *Proc. Natl. Acad. Sci. USA*, 94, (May 1997),5061-5066.

Grossman, J., et al., "Results of the First U.S. Double-Blind, Placebo-Controlled, Multicenter Clinical Study in Asthma with Pranlukast, a Novel Leukotriene Receptor Antagonist", *Journal of Asthma*, 34, (1997),321-328.

Gu, L., et al., "Absence of Monocyte Chemoattractant Protein-1 Reduces Atherosclerosis in Low Density Lipoprotein Receptor-Deficient Mice", *Molecular Cell*, 2, (Aug. 1998),275-281.

Hauser, S. L., "Therapeutic Strategies for Multiple Sclerosis", *J. Neurochem.*, 69, Suppl., Abstract A,(1997),S219.

Hendeles, L., et al., "Zafirlukast for Chronic Asthma: Convenient and Generally Safe, But Is It Effective?", *The Annals of Pharmacology*, 31, (Sep. 1997),1084-1086.

Herndon, et al., "Interactions of Neural Glycosamingoglycans and Proteoglycans with Protein Ligands: Assessment of Selectivity, Heterogeneity and the Participation of Core Proteins in Binding", *Glycobiology*, 9, (1999),143-155.

Hesselgesser, J., et al., "Identification and characterization of small molecule functional antagonists of the CCR1 chemokine receptor", *Journal of Biological Chemistry*, 273(25), (Jun. 19, 1998),15687-15692.

Heveker, N., et al., "Dissociation of the Signalling and Antiviral Properties of SDF-1-Derived Small Peptides", *Current Biology*, 8, (1998),369-376.

Hilliquin, P., et al., "Treatment of Rheumatoid Arthritis with Platelet Activating Factor Antagonist BN 50730", *J. Rheumatol.*, 22, (1995),1651-1654.

Hoffman, G. S., et al., "Wegner Granulomatosis: An Analysis of 158 Patients", *Annals of Internal Medicine*, 116, (Mar. 15, 1992),488-498.

Hogaboam, C. M., et al., "Monocyte Chemoattractant Protein-1 Synthesis by Murine Lung Fibroblasts Modulates CD4+ T Cell Activation", *The Journal of Immunology*, 160, (1998),4606-4614.

Hogan, S. P., et al., "Cytokines as Targets for the Inhibition of Eosinophilic Inflammation", *Pharmacol. Ther.*, 74, (1997),259-283.

Hoogewerf, et al., "Glycosaminoglycans Mediate Cell Surface Oligomerization of Chemokines", *Biochemistry*, 36, (1997),13570-13578.

Horuk, R., "Chemokines Beyond Inflammation", *Nature*, 393, (Jun. 11, 1998),524-525.

Howard, O. M., et al., "Inhibition of in Vitro and in Vivo HIV Replication by a Distamycin Analogue That Interferes with Chemokine Receptor Function: A Candidate for Chemotherapeutic and Microbicidal Application", *J. Med. Chem.*, 41, (1998),2184-2193.

Howard, O. M., et al., "Small Molecule Inhibitor of HIV-1 Cell Fusion Blocks Chemokine Receptor-Mediated Function", *Journal of Leukocyte Biology*, 64, (1998),6-13.

Hronowski, L J., et al., "Non-Specific Interaction of Proteoglycans with Surfaces and Matrices", *Biochemical and Biophysical Research Communications*, 167, (1990),81-88.

Hunt, III, S. W., et al., "Chemokine Receptors as HIV Co-Receptors: Targts for Therapeutic Intervention in AIDS", *Annual Reports in Medicinal Chemistry*, 33, (1998),263-272.

Hunter, M. G., et al., "BB-10010: An Active Variant of Human Macrophage Inflammatory Protein-1alpha With Improved Pharmaceutical Properties", *Blood*, 86, (Dec. 1995),4400-4408.

Ihm, C. G., et al., "A High Glucose Concentration Stimulates the Expression of Monocyte Chemotactic Peptide 1 in Human Mesangial Cells", *Nephron*, 79, (1998),33-37.

Imai, T., et al., "Identification and Molecular Characterization of Fractalkine Receptor CX3CR1, Which Mediates Both Leukocyte Migration and Adhesion", *Cell*, 91, (Nov. 14, 1997),521-530.

Ishikawa, J., et al., "Effect of YM934, a Novel Potassium-Channel Opener, in Various Experimental Asthma Models in Guinea-pigs", *J. Pharm. Pharmacol.*, 48, (1996),1034-1040.

Israel, E., et al., "Effect of Treatment With Zileuton, a 5-Lipoxygenase Inhibitor, in Patients With Asthma", *JAMA*, 275, (Mar. 27, 1996),931-936.

Jameson, Bradford A., et al., "A Rationally Designed CD4 Analogue Inhibits Experimental Allergic Encephalomyelitis", *Letters to Nature*, 368, (Apr. 21, 1994),744-746.

Jeffery, P. K., "Structural and Inflammatory Changes in COPD: A Comparison with Asthma", *Thorax*, 53, (1998),129-136.

Kaga, "Anti polypeptide monoclonal antibody diagnose treat auto immune diease ulcer colitis", This is really JP 7-67689.,.

Kanaly, S. T., et al., "A Pan-Chemokine Inhibitor Reduces Allergic Mediators and Inflammation in the Lung", *Keystone Symposia in Asthma*, (Sep. 15, 1998),.

Karpus, W., et al., "Differential CC Chemokine-Induced Enhancement of T Helper Cell Cytokine Production", *The Journal of Immunology*, 158, (1997),4129-4136.

Karpus, W. J., et al., "MIP-1alpha and MCP-1 Differentially Regulate Acute and Relapsing Autoimmune Encephalomyelitis as well as Th1/Th2 Lymphocyte Differentiation", *Journal of Leukocyte Biology*, 62, (Nov. 1997),681-687.

Karpus, W. J., et al., "Monocyte Chemotactic Protein 1 Regulates Oral Tolerance Induction by Inhibition of T Helper Cell 1-related Cytokines", *Journal of Experimental Medicine*, 187, (1998),733-741.

Katz, M. D., et al., "Octreotide, a New Somatostatin Analogue", *Clinical Pharmacy*, 8, (Apr. 1989),255-273.

Kelloway, J. S., "Zafirlukast: The First Leukotriene-Receptor Antagonist Approved for the Treatment of Asthma", *The Annals of Pharmacology*, 31, (Sep. 1997),1012-1021.

Kim, J. J., et al., "CD8 Positive T Cells Influence Antigen-Specific Immune Responses through the Expression of Chemokines", *Journal of Clinical Investigation*, 102, (1998),1112-1124.

Klareskog, L., et al., "Immunopathogenesis and Immunotherapy in Rheumatoid Arthritis: an Area in Transition", *Journal of Internal Medicine*, 238, (1995),191-206.

Kledel, T. N., et al., "A Broad-Spectrum Chemokine Antagonist Encoded by Kaposi's Sarcoma-Associated Herpesvirus", *Science*, 277, (Sep. 12, 1997),1656-1659.

Klein, R. D., et al., "Pulmonary LPS-Binding Protein (LBP) Upregulation Following LPS-Mediated Injury", *Journal of Surgical Research*, 78, (1998),42-47.

Klouche, M., et al., "Atherogenic Properties of Enzymatically Degraded LDL Selective Induction of MCP-1 and Cytotoxic Effects on Human Macrophages", *Arterioscler. Thromb. Vasc. Biol.*, 18, (1998),1376-1385.

Korom, S., et al., "Blockade of Very Late Antigen-4 Integrin Binding to Fibronectin in Allograft Recipients", *Transplantation*, 65. (Mar. 27, 1998),854-859.

Koyama, S., et al., "Human Lung Fibroblasts Release Chemokinetic Activity for Monocytes Constitutively", *Am. J. Physioll*, 275, (1998),L223-L230.

Kullberg, B. J., et al., "Cytokines as Therapy for Opportunistic Fungal Infections", *Res. Immunol.*, 149, (1998),478-488.

Kurup, V. P., et al., "Cytokines in Allergic Bronchopulmonary Aspergillosis", *Res. Immunol.*, 149, (1998),466-477.

Kuschert, et al., "Identification of a Glycosaminoglycan Binding Surface on Human Interleukin-8", *Biochemistry*, 37, (1998),11193-11201.

Lambert, A. L., et al., "Transfer of Allergic Airway Responses with Serum and Lymphocytes from Rats Sensitized to Dust Mite", *Am. J. Crit. Care Med.*, 157, (1998),1991-1999.

Lambrecht, B. , et al., "Dendritic Cells are Required for the Development of Chronic Eosinophilic Airway Inflammation in Response to Inhaled Antigen in Sensitized Mice", *The Journal of Immunology*, 160, (1998),4090-4097.

Larkin, et al., "Mycophenolate Mofetil: A New Immunosuppressive for Occular Inflammatory Disease", *Abstract 339; IOVS*, 39, (1998),S215.

Laycock, K. A., et al., "Reproduction of Antiviral Effect in adn in Vivo Model of Human Cytomegalovirus Retinal Infection", *Graefe's Arch. Clin. Exp. Opthalmol.*, 236 (1998),527-530.

Lecomte-Raclet, L. , et al., "New Insights into the Negative Regulation of Hematopoiesis by Chemokine Platelet Factor 4 and Related Peptides", *Blood*, 91, (Apr. 15, 1998),2772-2780.

Lee, M K., et al., "Analysis of Affinity and Structural Selectivity in the Binding of Proteins to Glycosaminoglycans: Development of a Sensitive Electrophorectic Approach", *Proc. Natl. Acad. Sci. USA*, 88, (1991),2768-2772.

Lee, B. , et al., "Influence of the CCR2-V64I Polymorphism on Human Immunodeficiency Virus Type 1 Coreceptor Activity and on Chemokine Receptor Function of CCR2b, CCR3, CCR5, and CXCR4", *Journal of Virology*, 72, (1998),7450-7458.

Leff, D. N., "Besides Hijacking Dividing T Cells, HIV Hides Latent Viral DNA in Resting Cells", *BioWorld Today*, 9, (Jul. 21, 1998),p. 1, 3.

Leong, Steven R., et al., "Complete mutagenesis of the extracellular domain of interleukin-8 (IL-8) type A receptor identifies charged residues mediating IL-8 binding and signal transduction", *Journal of Biological Chemistry*, 269(30), (Jul. 29, 1994),19343-19348.

Lettesjo, H , et al., "IgG2b Inducing Factor from Rheumatoid Arthritis Synovial Fluid Synergized with Transforming Growth Factor—in Promoting IgG2b Antibody Production in Mouse B Lymphocytes", *Scand. J. Imunol.*, 45, (1997),50-54.

Lind, M , et al., "Transforming Growth Factor-beta1 Enhances Bone Healing to Unloaded Tricalcium Phosphate Coated Implants: An Experimental Study in Dogs", *Journal of Orthopaedic Research*, 14, (1996),343-350.

Link, J , et al., "Transforming Growth Factor-beta1 Suppress Autoantigen-Induced Expression of Pro-Inflammatory Cytokines but Not of Interleukin-10 in Multiple Sclerosis and Myasthenia Gravis", *Journal of Neuroimmunology*, 58, (1995),21-35.

Loetscher, P , et al., "Interleukin-2 Regulates CC Chemokine Receptor Expression and Chemotactic Responsiveness in T Lymphocytes", *J. Exp. Med.*, 184(2), (Aug. 1, 1996),569-577.

Loetscher, Pius , et al., "N-terminal peptides of stromal cell-derived factor-1 with CXC chemokine receptor 4 agonist and antagonist activities", *Journal of Biological Chemistry*, 273(35), (Aug. 28, 1988),22279-22283.

Lowe, P. M., et al., "The Endothelium in Psoriasis", *British Journal of Dermatology*, 132, (1995),497-505.

Lu, B. B., et al., "Abnormalities in Monocyte Recruitment and Cytokine Expression in Monocyte Chemoattractant Protein 1-deficient Mice", *Journal of Experimental Medicine*, 187, (1998),601-6081.

Lubkowski, J. , et al., "The Structure of MCP-1 in Two Crystal Forms Provides a Rare Example of Variable Quaternary Interactions", *Nature Structural Biology*, 4, (Jan. 1997),64-69.

Lukacs, N. , et al., "Airway Hyperreactivity is Associated with Specific Leukocyte Subset Infiltration in a Mouse Model of Allergic Airway Inflammation", *Pathobiology*, 64, (1996),308-313.

Lukacs, N. W., et al., "C-C Chemokines Differentially Alter Interleukin-4 Production from Lymphocytes", *American Journal of Pathology*, 150, (1997),1861-1868.

Lummus, Z. L., et al., "Diisocyanate Antigen-Enhanced Production of Monocyte Chemoattractant Protein-1, IL-8, and Tumor Necrosis Factor-alpha by Peripheral Mononuclear Cells of Workers With Occupational Asthma", *J. Allergy Clin. Immunol.*, 102, (1998),265-274.

Luster, A. D., "Chemokines—Chemotactic Cytokines that Mediate Inflammation", *The New England Journal of Medicine*, 338, (Feb 12, 1998),436-445.

Lusti-Narasimhan, M. , et al., "A Molecular Switch of Chemokine Receptor Selectivity", *J. Biol. Chem.*, 271, (Feb. 9, 1996),3148-3153.

MacCarana, et al., "Mode of Interaction Between Platelet Factor 4 and Heparin", *Glycobiology*, 3, (1993),271-277.

Malkowski, M. G., et al., "The crystal structure of recombinant human neutrophil-activating peptide-2 (M6L) at 1.9-A resolution", *Journal of Biological Chemistry*, 270(13), (Mar. 31, 1995),7077-7087.

Marone, G. , "Asthma: Recent Advances", *Immunology Today*, 19, (1998),5-9.

Matsukawa, A. , et al., "Production and Regulation of Monocyte Chemoattractant Protein-1 in Lipopolysaccharide- or Monosodium Urate Crystal-Induced Arthritis in Rabbits: Roles of Tumor Necrosis Factor alpha, Interleukin-1, and Interleukin-8", *Laboratory Investigation*, 78, (Aug. 1998),973-985.

Mattapallil, J. J., et al., "Intestinal Intraepithelial Lymphocytes are Primed for Gamma Interferon and MIP-1beta Expression and Display Antiviral Cytotoxic Activity Despite Severe CD4-positive T-Cell Depletion in Primary Immunodeficiency Simian Virus Infection", *Journal of Virology*, 72, (Aug. 1998),6421-6429.

Maurer, A. M., et al., "Chemokines and the Regulation of Hematopoesis", *C.R. Seances Soc. Biol. Fil.*, 192, Translated abstract,(1998),917-923.

McClelland, B W., et al., "Synthesis and Characterization of Potent CXCR2 Antagonists Containing an Alkyl Substituent Adjacent to the Phenol", *Abstracts of Papers American Chemical Society*, 217, (1999),206.

McFadden, G. , et al., "Commentary: New Stratagies for Chemokine Induction and Modulation; You Take the High Road and I'll Take the Low Road", *Biochemical Pharmacology*, 54, (1997),1271-1280.

McTigue, D. M., et al., "Selective Chemokine mRNA Accumulation in the Rat Spinal Cord After Contusion Injury", *Journal of Neuroscience Research*, 53, (1998),368-376.

Mehlhop, P. , et al., "Allergen-induced Bronchial Hyperreactivity and Eosinophilic Inflammation Occur in the Absence of IgE in a Mouse Model of Asthma", *Proceedings of the National Academy of Sciences USA*, 94, (1997),1344-1349.

Mehlhop, P. D., et al., "Allergen-induced Bronchial Hyperreactivity and Eosinophilic Inflammation Ocur in teh Absence of IgE in a Mouse Model of Asthma", *Proceedings of the National Academy of Sciences USA*, 94 (1997),1344-1349.

Mekouar, K. , et al., "Styrylquinoline Derivatives: A New Class of Potent HIV-1 Integrase Inhibitors That Block HIV-1 Replication in CEM Cells", *J. Med. Chem.*, 41, (1998),2846-2857.

Meltzer, E. O., "Pharmacological Treatment Options for Allergic Rhinitis and Asthma", *Clinical and Experimental Allergy*, 28, (1998),27-36.

Meyer, D. , "Molecular Modeling: Overview", *NeoRx Modeling Protocol, Results and Figures*, (1998),1-14.

Mikayama, T. , et al., "Molecular Cloning and Functional Expression of a cDNA Encoding Glycosylation-inhibiting Factor", *Proc. Natl. Acad. Sci. USA*, 90, (Nov. 1993),10056-10060.

Miller, E. J., et al., "A Synthetic Peptide which Specifically Inhibits Heat-Treated Interleukin-8 Binding and Chemotaxis for Neutrophils", *Agents Actions*, 40, (1993),200-208.

Mogi, M , et al., "Transforming Growth Factor-beta1 Levels are Elevated in the Striatum and in Ventricular Cerebrospinal Fluid in Parkinson's Disease", *Neuroscience Letters*, 193, (1995),129-132.

Molling, K. , "Naked DNA for Vaccine or Therapy", *J. Mol. Med.*, 75, .

Monteclaro, F. S., et al., "Role of the Amino Terminus in Ligand Binding and Signal Transduction of the Human Monocyte Chemoattractant Protein-1 Receptor", *Circulation*, 92, (Oct. 15, 1995),1-160.

Moriuchi, M., et al., "Exposure to Bacterial Products Renders Macrophages Highly Susceptible to T-Tropic HIV-1", *The Journal of Clinical Investigation*, 102, (1998),1540-1550.

Moser, B., et al., "Interleukin-8 Antagonists Generated by N-Terminal Modification", *The Journal of Biological Chemistry*, 268(10), (Apr. 5, 1993),7125-7128.

Murakami, T., et al., "A Small Molecule CXCR4 Inhibitor that Blocks T Cell Line-tropic HIV-1 Infection", *J. Exp. Med.*, 186, (Oct. 20, 1997),1389-1393.

Myers, L. K., et al., "Collagen-Induced Arthritis, an Animal Model of Autoimmunity", *Life Sciences*, 61, (1997),1861-1878.

Nagamatsu, Atsuo, et al., "Hydrolysis of lysine peptides in plasmin", *Chem. Pharm. Bull.*, 22(11), (1974),2680-2684.

Negus, R. P., et al., "Hypoxia Down-Regulates MCP-1 Expression: Implications for Macrophage Distribution in Tumors", *Journal of Leukocyte Biology*, 63, (Jun. 1998),758-765.

Neumann, B., et al., "Distinct Functions of Interferon-gamma for Chemokine Expression in Models of Acute Lung Inflammation", *Immunology*, 95, (1998),512-521.

Nie, H, et al., "Discovery and Characterization of a Novel Series of N-[2-(Phenylsulfonylannino) Phenyl]-N'-Phenylureas as CXCR2 Antagonists", *Abstracts of Papers American Chemical Society*, 217, (1999),205.

Noguchi, Masatoshi, et al., "Isolation and identification of acidic oligopeptides occurring in a flavor potentiating fraction from a fish protein hydrolysate", *J. Agric. Food Chem.*, vol. 23, No. 1,(1975),pp. 49-53.

O'Brien, W. A., et al., "Anti-Human Immunodeficiency Virus Type 1 Activity of an Oligocationic Compound Mediated via gp120 V3 Interactions", *Journal of Virology*, 70, (May 1996),2825-2831.

O'Brien, A. D., et al., "Chemotaxis of Alveolar Macrophages in Response to Signals Derived from Alveolar Epithelial Cells", *J. Lab. Clin. Med.*, 131, (1998),417-424.

O'Hehir, R. E., et al., "Regulation of Cytokine and Chemokine Transcription in a Human TH2 Type T-cell Clone During the Phase of Anergy",*Clinical and Experimental Allergy*, 26, (1996),20-27.

Oracion, R, et al., "HIV-Related Eosinophilic Folliculitis is a TH2-Dominant Disease Characterized by Selective Expression of Eotaxin in Dendritic Cells and CCR3 in T-Cells", *Journal of Investigative Dermatology*, 110 (1998),663.

Panettieri, R. A., et al., "Effects of LTD4 on Human Airway Smooth Muscle Cell Proliferation, Matrix Expression, and Contraction In Vitro: Differential Sensitivity to Cysteinyl Leukotriene Receptors Antagonists", *American Journal of Respiratory Cell and Molecular Biology*, 19, (1998),453-461.

Parnaby-Price, A., et al., "Leukocyte Trafficking in Experimental Autoimmune Uveitis in Vivo", *Journal of Leukocyte Biology*, 64, (1998),434-440.

Paul, William E., "Fundamental Immunology", *3rd Edition*, (1993),822-826.

Pease, J. E., et al., "Microbial Corruption of the Chemokine System: An Expanding Paradigm", *Seminars in Immunology*, 10, (1998),169-178.

Pease, J. E., et al., "The N-terminal extracellular segments of the chemokine receptors CCR1 and CCR3 are determinants for MIP-1alpha and eotaxin binding, respectively, but a second domain is essential for efficient receptor activation", *Journal of Biological Chemistry*, 273(32), (Aug. 7, 1998),19972-19976.

Pilozzi, E., et al., "Monocyte Chemotactic Protein-1 in the Inflammatory Pseudotumour of the Lung",*J. Clin. Pathol.: Mol. Pathol.*, 51, (1998),50-52.

Ping, D., et al., "Nuclear Factor-kB p65 Mediates the Assembly and Activation of hte TNF-Responsive Element of the Murine Monocyte Chemoattractant-1 Gene", *The Journal of Immunology*, 162, (1999),727-734.

Plater-Zyberk, et al., "A Chemokine Receptor Antagonist Reduces the Incidence of Collagen Induced Arthritis", *Abstract No. 399 ; Arthritis & Rheumatism*, 41, (1998),S99.

Plater-Zyberk, C., et al., "Effect of a CC Chemokine Receptor Antagonist on Collagen Induced Arthritis in DBA/1 Mice", *Immunology Letters*, 57, (1997),117-120.

Porschke, Dietmar, et al., "The conformation of signle stranded oliogonucleotides and of oligonucleotide-olgopeptide complexes from their rotation relaxation in the nanosecond time range", *J. Biomol. Struct. Dyn*, vol. 2, No. 6,(1985),pp. 1173-1184.

Postlethwaite, A. E., "Identification of a Chemotactic Epitope in Human Transforming Growth Factor-Beta1 Spanning Amino Acid Residues 368-374", *Journal of Cellular Physiology*, 164, (1995),587-592.

Premack, B. A., et al., "Chemokine Receptors: Gateways to Inflammation and Infection", *Nature Medicine*, 2, (Nov. 1996),1174-1178.

Presti, R. M., et al., "Interferon gamma Regulates Acute and Latent Murine Cytomegalovirus Infection and Chronic Disease of the Great Vessels", *J. Exp. Med.*, 188, (Aug. 3, 1998),577-588.

Proost, P., et al., Cytokines, Mire-Sluis, "32. Monocyte Chemotactic Proteins 1, 2 and 3", in: a.R., et al., (eds.), Academic Press, San Diego,.

Proost, P., et al., "Amino-terminal truncation of chemokines by CD26/dipeptidyl-peptidase IV. Conversion of RANTES into a potent inhibitor of monocyte chemotaxis and HIV-1-infection", *Journal of Biological Chemistry*, 273(13), (Mar. 27, 1998),7222-7227.

Reckless, J, et al., "Monocyte Chemoattractant Protein-1 but Not Tumor Necrosis Factor-alpha Is Correlated with Monocyte Infiltration in Mouse Lipid Lesions", *Circulation*, 99, (1999),2310-2316.

Reid, S., et al., "Enhanced Myeloid Progenitor Cell Cycling and Apoptosis in Mice Lacking the Chemokine Receptor, CCR2", *Blood*, 93, (1999),1524-1533.

Reiss, T. F., et al., "Effects of Montelukast (MK-0476), a New Potent Cysteinyl Leukotriene (LTD4) Receptor Antagonist, in Patients with Chronic Asthma", *J. Allergy Clin. Immunol.*, 98, (Sep. 1996),528-534.

Roberts, D. J., "Towards the Optimal Antihistamine: Studies with Ebastine", *Inflammation Research*, 47, (1998),S36-S37.

Rosenberg, Y. J., et al., "HIV-induced Decline in Blood CD4/CD8 Ratios: Viral Killing or Altered Lymphocyte Trafficking?", *Immunology Today*, 19, (1998),10-17.

Ruiz-Ortega, M., et al., "Angiotensin II Participates in Mononuclear Cell Recruitment in Experimental Immune Complex Nephritis Through Nuclear Factor kappaB Activation and Monocyte Chemoattractant Protein-1 Synthesis", *The Journal of Immunology*, 161, (1998),430-439.

Sadek, M. I., et al., "Chemokines Induced by Infection of Mononuclear Phagocytes with Mycobacteria and Present in Lung Aveoli During Active Pulmonary Tuberculosis", *American Journal of Respiratory Cell and Molecular Biology*, 19, (1998),513-521.

Sanders, V. J., et al., "Chemokines and Receptors in HIV Encephalitis", *AIDS*, 12, (1998),1021-1026.

Sato, A., et al., "A Simple and Rapid Method for Preliminary Evaluation of In Vivo Efficacy of Anti-HIV Compounds in Mice",*Antiviral Research*, 27, (1995),151-163.

Schimmer, R. C., et al., "*Streptococcal* Cell Wall-Induced Arthritis: Requirements for IL-4, IL-10, IFN-gamma, and Monocyte Chemoattractant Protein-1", *The Journal of Immunology*, 160, (1998),1466-1471.

Schlesinger, David H., "Macromolecular Sequencing and Synthesis, Selected Methods and Applications", George, David G. et al., Chapter 12, *Current Methods in SEquence Comparison and Analysis*, (1988),127-149.

Schols, D., et al., "Inhibition of T-tropic HIV Strains by Selective Antagonization of the Chemokine Receptor CXCR4", *J. Exp. Med.*, 186, (Oct. 20, 1997),1383-1388.

Schratzberger, P., et al., "Release of Chemoattractants for Human Monoctyes from Endothelial Cells by Interaction with Neutrophils", *Cardiovascular Research*, 38, (1998),516-521.

Schultz-Cherry, S., et al., "Regulation of transforming growth factor-beta activation by discrete sequences of thrombospondin 1", *The Journal of Biological Chemistry*, 270(13), (Mar. 31, 1995),7304-7310.

Schultz-Cherry, S., et al., "The Type 1 Repeats of Thrombospondin 1 Activate Latent Transforming Growth Factor-Beta", *The Journal of Biological Chemistry*, 269(43), (Oct. 28, 1994),26783-26788.

Schultz-Cherry, S., et al., "Thrombospondin Causes Activation of Latent Transforming Growth Factor-Beta Secreted by Endothelial Cells by a Novel Mechanism", *The Journal of Cell Biology*, 122, (Aug. 1993),923-932.

Sekiguchi, K., et al., "Binding of Fibronectin and Its Proteolytic Fragments to Glycosaminoglycans", *J. Biol. Chem.*, 258, (1983),14359-14365.

Selvan, R S., et al., "Heparan Sulfate in Immune Responses", *Annals New York Academy of Sciences*, (1996),127-139.

Shibata, Yoshihiro, et al., "N-Alkylphtalimides: structural requirement of thalidomidal action on 12-0-Tetradecanoylphorbol-13-acetate induced tumor necrosis factor alpha production by human leukemia HL-60 cells", *Che. Pharm. Bull.*, 43(1), (1995),177-179.

Simmons, G., et al., "Potent Inhibition of HIV-1 Infectivity in Macrophages and Lymphocytes by a Novel CCR5 Antagonist", *Science*, 276, (Apr. 11, 1997),276-279.

Simpson, J. E., et al., "Expression of Monocyte Chemoattractant Protein-1 and Other beta-Chemokines by Resident Glia and Inflammatory Cells in Multiple Sclerosis Lesions", *Journal of Neuroimmunology*, 84, (1998),238-249.

Skelton, N. J., et al., "Proton NMR Assignments and Solution Conformation of RANTES, a Chemokine of the C-C Type", *Biochemistry*, 34, (1995),5329-5342.

Skelton, N. J., et al., "Structure of a CXC Chemokine-receptor Fragment in Complex with Interleukin-8", *Structure*, 7, (1999),157-168.

Smith, L. J., et al., "Inhibition of Leukotriene D4-Induced Bronchoconstriction in Subjects With Asthma: A Concentration-Effect Study of ICI 204,219", *Clin. Pharmacol. Ther.*, 54, (1993),430-436.

Sneller, M. C., et al., "An Analysis of Forty-Two Wegener's Granulomatosis Patients Treated with Methotrexate and Prednisone", *Arthritis and Rheumatism*, 38, (May 1995),608- 613.

Sozen, I., et al., "Expression and Hormonal Regulation of Monocyte Chemotactic Protein-1 in Myometrium and Leiomyomata", *Fertility and Sterility*, 59, (Jun. 1998),1095-1102.

Sozzani, S., et al., "Stimulating Properties of 5-Oxo-Eicosansoids for Human Monocytes", *The Journal of Immunology*, 157, (1996),4664-4671.

Spector, S. L., et al., "Effects of 6 Weeks of Therapy with Oral Doses of ICI 204,219, a Leukotriene D4 Receptor Antagonist, in Subjects with Bronchial Asthma", *Am. J. Respir. Crit. Care Med.*, 150 (1994),618-623.

Spector, S. L., "Leukotriene Activity Modulation in Asthma", *Drugs*, 54, (Sep. 1997),369-384.

Spence, J., "Advances in atherosclerosis", *Bailliere's Clinical Neurology*, 4(2), (1995),pp. 191-205.

Stanciu, L. A., et al., "The Role of ICAM-1 on T-Cells in the Pathogenesis of Asthma", *Eur. Respir. J.*, 11, (1998),949-957.

Steitz, S. A., et al., "Mapping of MCP-1 Functional Domains by Peptide Analysis and Site-Directed Mutagenesis", *FEBS Letters*, 430 (3), (Jul. 3, 1998),158-164.

Stringer, S E., et al., "Specific binding of the chemokine platelet factor 4 to heparan sulfate", *The Journal of Biological Chemistry*, 272(33), (Aug. 15, 1997),20508-20514.

Struyf, S., et al., "Cutting Edge: Enhanced Anti-HIV-1 Activity and Altered Chemotactic Potency of NH2-Terminally Processed Macrophage-Derived Chemokine (MDC) Imply an Additional MDC Receptor", *The Journal of Immunology*, 161, (1998),2672-2675.

Suda, T., et al., "Modulation of Osteoclast Differentiation by Local Factors", *Bone*, 17(2), (1995),pp. 87S-91S.

Suissa, S., et al., "Effectiveness of the Leukotriene Receptor Antagonist Zafirlukast for Mild-to-Moderate Asthma", *Ann. Intern. Med.*, 126, (1997),177-183.

Suzuki, G., et al., "Loss of SDF-1 Receptor Expression During Positive Selection in the Thymus", *International Immunology*, 10, (1998),1049-1056.

Szabo, M. C., et al., "Chemokine class differences in binding to the Duffy antigen-erythrocyte chemokine receptor", *The Journal of Biological Chemistry*, 270(43), (Oct. 27, 1995),25348-25351.

Tachibana, K., et al., "The Chemokine Receptor CXCR4 is Essential for Vascularization of the Gastrointestinal Tract", *Nature*, 393, (Jun. 11, 1998),591-594.

Tamura, G., et al., "Effect of a Potent Platelet-Activating Factor Antagonist, WEB-2086, on Asthma", *In: Platelet-Activating Factor and Related Lipid Mediators*, 2, Nigam, et al., (eds.), Plenum Press, New York,(1996),371-380.

Tanhehco, E J., et al., "Reduction of Myocardial infarct Size After Ischemia and Reperfusion by the Glycosaminoglycan Pentosan Polysulflate", *FASEB Journal*, 13, (1999),A21.

Tauber, M., et al., "Cytokines and Chemokines in Meningeal Inflammation: Biology and Clinical Implications", *Clinical Infectious Diseases*, 28, (1999),1-11.

Taylor, I. K., et al., "The Mechanism of Action of Corticosteroids in Asthma", *Respiratory Medicine*, 87, (1993),261-277.

Terkeltaub, R., et al., "The Murine Homolog of the Interleukin-8 Receptor CXCR-2 is Essential for the Occurrence of Neutrophilic Inflammation in the Air Pouch Model of Acute Urate Crystal-induced Gouty Synovitis", *Arthritis and Rheumatism*, 41, (1998),900-909.

Thompson, Scott K., et al., "Design and evaluation of small peptides mapping the exposed surface of IL-8", *Int. J. Peptide Protein Res*, vol. 47,,(1996),pp. 214-218.

Tian, S. S., et al., "A Small, Nonpeptidyl Mimic of Granulocyte—Colony-Stimulating Factor", *Science*, 281, (Jul. 10, 1998),257-259.

Toews, A. D., et al., "Monocyte Chemoattractant Protein 1 Is Responsible for Macrophage Recruitment Following Injury to Sciatic Nerve", *Journal of Neuroscience Research*, 53, (1998),260-267.

Tomita, H., et al., "Inhibition of NO Synthesis Induces Inflammatory Changes and Monocyte Chemoattractant Protein-1 Expression in Rat Hearts and Vessels", *Arterioscler. Thromb. Vasc. Biol.*, 18, (1998),1456-1464.

Tsao, P. S., et al., "Interaction of Diabetes and Hypertension on Determinants of Endothelial Adhesiveness", *Atheriosler. Thromb. Vasc. Biol.*, 18, (1998),947-953.

Valente, A. J., et al., "Characterization of Monocyte Chemotactic Protein-1 Binding to Human Monocytes", *Biochemical and Biophysical Research Communications*, 176, (Apr. 15, 1991),309-314.

Van Coillie, E., et al., "Functional Comparison of Two Human Monocyte Chemotactic Protein-2 Isoforms, Role of the Amino-Terminal Pyroglutamic Acid and Processing by CD26/Dipeptidyl Peptidase IV", *Biochemistry*, 37, (1998),12672-12680.

Voet, et al., *In: Biochemistry*, John Wiley & Sons, Inc.,(1990),p. 126-128, 228-234.

Walker, C., et al., "IL-5 Production by NK Cells Contributes to Eosinophil Infiltration in a Mouse Model of Allergic Inflammation", *The Jourl of Immunology*, 161, (1998),1962-1969.

Waltenberger, J., "Modulation of Growth Factor Action—Implications for the Treatment of Cardiovascular Diseases", *Circulation*, 96, (1997),4083-4094.

Wang, J. M., et al., "Chemokines, Receptors and Their Role in Cardiovascular Pathology", *Int. J. Clin. Lab. Res.*, 28, (1998),83-90.

Wang, N., et al., "Induction of Interleukin-8 in Foam Cells Induced by Acetylated LDL", *Circulation*, 92, (Oct. 15, 1995),1-160.

Weber, M., et al., "Deletion of the NH2-Terminal Residue Converts Monocyte Chemotactic Protein 1 from an Activator of Basophil Mediator Release to an Eosinophil Chemoattractant", *J. Exp. Med.*, 183, (Feb. 1996),681-685.

Weber, K. S., et al., "Differential Immobilization and Hierarchial Involvement of Chemokines in Monocyte Arrest and Transmigration on Inflamed Endothelium in Shear Flow", *Eur. J. Immunol.*, 29, (1999),700-712.

Wells, T. N., et al., "The Molecular Basis of Selectivity Between CC and CXC Chemokines: The Possibility of Chemokine Antagonists as Anti-Inflammatory Agents", *Annals of New York Academy of Sciences*, 796, (Oct. 31, 1996),245-257.

Wells, E A., "The Molecular Basis of the Chemokine/Chemokine Receptor Interaction—Scope for Design of Chemokine Antagonists", *Methods: A Companion to Methods in Enzymology*, 10, vol. 10,(1996),126-134.

White, J. R., et al., "Identification of a Potent, Selective Non-peptide CXCR2 Antagonist That Inhibits Interleukin-8-induced Neutrophil Migration", *Journal of Biological Chemistry*, 273(17), (Apr. 24, 1998),10095-10098.

Witt, D P., et al., "Differential Binding of Chemokines to Glycosaminoglycan Subpopulations", *Current Biology*, 4, (1994),394-400.

Wooley, P. H., et al., "Influence of a Recombinant Human Soluble Tumor Necrosis Factor Receptor FC Fusion Protein on Type II Collagen-Induced Arthritis in Mice", *The Journal of Immunology*, 151, (Dec. 1, 1993),6602-6607.

Wright, E., et al., "Monocyte Chemotactic Protein Expression in Allergy and Non-allergy-Associated Chronic Sinusitis", *The Journal of Otolaryngology*, 27,(1998),281-287.

Yahi, N., et al., "SPC3, a Synthetic Peptide Derived from the V3 Domain of Human Immunodeficiency Virus Type 1 (HIV-1) Gp120, Inhibits HIV-1 Entry into CD4(plus) and CD4(minus) Cells by Two Distinct Mechanisms", *Proc Natl Acad Sci U S A.*, 92(11), (May 1995),4867-4871.

Yamaoka, Y., et al., "Chemokines in the Gastric Mucosa in *Helicobacter pylori* Infection", *Gut*, 42, (1998),609-617.

Yamazaki, S., "TNF-alpha, RANTES, and MCP-1 are Major Chemoattractants of Murine Langerhans Cells to the Regional Lymph Nodes", *Experimental Dermatology*, 7, (1998),35-41.

Yang, Y., et al., "Antigen-Induced Eosinophilic Lung Inflammation Develops in Mice Deficient in Chemokine Eotaxin", *Blood*, 92, (1998),3912-3923.

Yang, A. G., et al., "Phenotypic Knockout of HIV Type 1 Chemokine Coreceptor CCR-5 by Intrakines as Potential Therapeutic Approach for HIV-1 Infection", *Proc. Natl. Acad. Sci. USA*, 94, (Oct. 1997),11567-11572.

Zagorski, J., et al., "Inhibition of Acute Peritoneal Inflammation in Rats by a Cytokine-induced Neutrophil Chemoattractant Receptor Antagonist", *The Journal of Immunology*, 159, (1997),1059-1062.

Zeyneloglu, H. B., et al., "The Effect of Monocyte Chemotactic Protein 1 in Intraperitoneal Adhesion Formation in a Mouse Model", *Am. J. Obstet. Gynecol.*, 179, (1998),438-443.

Zhang, Y., et al., "A Dominant Negative Inhibitor Indicates that Monocyte Chemoattractant Protein 1 Functions as a Dimer", *Mol. and Cell Biol.*, 15, (Sep. 1995),4851-4855.

Zhang, Y. J., et al., "Structure/Activity Analysis of Human Monocyte Chemoattractant Protein-1 (MCP-1) by Mutagenesis", *J. Biol. Chem.*, 269 (22), (1994),15918-15924.

Zou, Y-R., et al., "Function of the Chemokine Receptor CXCR4 in Haematopoiesis and in Cerebellar Development", *Nature*, 393, (1998),595-598.

Zou, L. P., et al., "Treatment with P2 Protein Peptide 57-81 by Nasal Route is Effective in Lewis Rat Experimental Autoimmune Neuritis", *Journal of Neuroimmunology*, 85, (1998),137-145.

"U.S. Appl. No. 08/927,939 Final Office Action mailed Oct. 12, 1999", 18 pgs.

"U.S. Appl. No. 08/927,939 Final Office Action mailed Sep. 29, 2003", 10 pgs.

"U.S. Appl. No. 08/927,939 Non-Final Office Action mailed Mar. 5, 2001", 12 pgs.

"U.S. Appl. No. 08/927,939 Non-Final Office Action mailed Apr. 7, 1999", 21 pgs.

"U.S. Appl. No. 08/927,939 Notice of Allowance mailed Aug. 30, 2005", 7 pgs.

"U.S. Appl. No. 08/927,939 Notice of Allowance mailed Sep. 3, 2004", 6 pgs.

"U.S. Appl. No. 08/927,939 Response to Final Office Action filed Jan. 29, 2004", 8 pgs.

"U.S. Appl. No. 08/927,939 Response to Final Office Action filed May 12, 2000", 12 pgs.

"U.S. Appl. No. 08/927,939 Response to Non-Final Office Action filed Oct. 7, 1999", 13 pgs.

"U.S. Appl. No. 08/927,939 Response to Non-Final Office Action filed Sep. 5, 2001", 5 pgs.

"U.S. Appl. No. 08/927,939 Supplemental Amendment filed Apr. 29, 2004", 3 pgs.

"U.S. Appl. No. 09/150,813 Advisory Action mailed Jan. 28, 2002", 4 pgs.

"U.S. Appl. No. 09/150,813 Advisory Action mailed Mar. 28, 2002", 3 pgs.

"U.S. Appl. No. 09/150,813 Final Office Action mailed Jun. 1, 2004", 8 pgs.

"U.S. Appl. No. 09/150,813 Final Office Action mailed Aug. 10, 2001", 13 pgs.

"U.S. Appl. No. 09/150,813 Non Final Office Action mailed Feb. 23, 2000", 24 pgs.

"U.S. Appl. No. 09/150,813 Non Final Office Action mailed Sep. 10, 2002", 11 pgs.

"U.S. Appl. No. 09/150,813 Non Final Office Action mailed Sep. 12, 2002", 13 pgs.

"U.S. Appl. No. 09/150,813 Non Final Office Action mailed Nov. 15, 2004", 5 pgs.

"U.S. Appl. No. 09/150,813 Non Final Office Action mailed Nov. 29, 2000", 13 pgs.

"U.S. Appl. No. 09/150,813 Non Final Office Action mailed Dec. 7, 2003", 10 pgs.

"U.S. Appl. No. 09/150,813 Notice of Allowance mailed Oct. 31, 2005", 7 pgs.

"U.S. Appl. No. 09/150,813 Response filed Feb. 11, 2002 to Advisory Action mailed Jan. 28, 2002", 7 pgs.

"U.S. Appl. No. 09/150,813 Response filed Feb. 15, 2005 to Non Final Office Action mailed Nov. 15, 2004", 7 pgs.

"U.S. Appl. No. 09/150,813 Response filed Mar. 18, 2004 to Non Final Office Action mailed Dec. 7, 2003", 11 pgs.

"U.S. Appl. No. 09/150,813 Response filed Apr. 11, 2002 to Advisory Action mailed Mar. 28, 2002", 5 pgs.

"U.S. Appl. No. 09/150,813 Response filed May 29, 2001 to Non Final Office Action mailed Nov. 29, 2000", 13 pgs.

"U.S. Appl. No. 09/150,813 Response filed Aug. 02, 2004 to Final Office Action mailed Jun. 1, 2004", 12 pgs.

"U.S. Appl. No. 09/150,813 Response filed Aug. 23, 2000 to Non Final Office Action mailed Feb. 23, 2000", 17 pgs.

"U.S. Appl. No. 09/150,813 Response filed Nov. 9, 2001 to Final Office Action mailed Aug. 10, 2001", 6 pgs.

"U.S. Appl. No. 09/452,406 Final Office Action mailed Oct. 6, 2004", 41 pgs.

"U.S. Appl. No. 09/452,406 Final Office Action mailed Dec. 15, 2005", 12 pgs.

"U.S. Appl. No. 09/452,406 Non-Final Office Action mailed Jan. 15, 2003", 11 pgs.

"U.S. Appl. No. 09/452,406 Non-Final Office Action mailed Jun. 6, 2005", 17 pgs.

"U.S. Appl. No. 09/452,406 Notice of Allowance mailed Mar. 20, 2006", 6 pgs.

"U.S. Appl. No. 09/452,406 Response to Final Office Action filed Dec. 29, 2005", 8 pgs.

"U.S. Appl. No. 09/452,406 Response to Final Office Action filed Mar. 7, 2005", 22 pgs.

"U.S. Appl. No. 09/452,406 Response to Non-Final Office Action filed May 14, 2003", 20 pgs.

"U.S. Appl. No. 09/452,406 Response to Non-Final Office Action filed Sep. 6, 2005", 18 pgs.

"U.S. Appl. No. 10/241,375 Response to Non-Final Office Action filed Nov. 12, 2007", 22 pgs.

"International Application No. PCT/US00/00821 Demand filed Aug. 10, 2000", 6 pgs.

"International Application No. PCT/US00/00821 International Preliminary Examination Report mailed Jan. 31, 2001", 8 pgs.

"International Application No. PCT/US00/00821 International Search Report mailed Sep. 26, 2000", 10 pgs.

"International Application No. PCT/US00/00821 Written Opinion mailed Nov. 2, 2000", 8 pgs.

"International Application No. PCT/US98/19052 Amendment filed Nov. 12, 1999", 16 pgs.

"International Application No. PCT/US98/19052 Demand filed Apr. 9, 1999", 7 pgs.

"International Application No. PCT/US98/19052 International Preliminary Examination Report mailed Jan. 19, 2000", 23 pgs.

"International Application No. PCT/US98/19052 Written Opinion mailed Jul. 13, 1999", 8 pgs.

Atuegbu, Andy, et al., "Combinatorial Modification of Natural Products: Preparation of Unencoded and Encoded Libraries of Rauwolfia Alkaloids", *Bioorganic & Medicinal Chemistry* 4(7), (1996),1097-1106.

Bavadekar, Supriya A., et al., "Tethered Yohimbine Analogs as Selective Human a2c-Adrenergic Receptor Ligands", *Journal of Pharmacology and Experimental Therapeutics* 319(2), (2006),739-748.

Baxter, Ellen W., et al., "Formal Total Synthesis of Deserpidine Demonstrating a Versatile Amino-Claisen Rearrangement/Wenkert Cyclization Strategy for the Preparation of Functionalized Yohimbine Ring Systems", *J. Am. Chem. Soc.* 112, (1990),7682-7692.

Beers, Mark, et al., "Myeloproliferative Disorders . . . ", *The Merck Manual 7th Edition*, (1999),1474-1476 & 895-902.

Bhat, U. G., et al., "A Structure-Function Relationship Among Reserpine and Yohimbine Analogues in Their Ability to Increase Expression of mdr1 and P-Glycoprotein in a Human Colon Carcinoma Cell Line", *American Society for Pharmacology and Experimental Therapeutics* 48, (1995),682-689.

Businco, L., et al., "From Atopic Dermatitis to Asthma: The Risl Factors and Preventive Measures", *Pediatric Pulmonology, Supplement*, 16, (1997),19-20.

Chanh, Pham H., et al., "Cardiovascular Effects of Some Acylated Derivatives of Yohimbo-hydrazide", *Drugs Exptl. Clin. Res.* 4(2), (1978),25-30.

Chanh, Pham H., et al., "Effect of the Hydrazide Function on the Cardiovascular Activities of Yohimbine", *Agressologie* 14(1), (1973),31-37.

Chanh, Pham H., et al., "Study of the Action of the N-Methyl-N'-yohimbohydrazide on General Metabolism and Respiration and on Systemic Hemodynamics", *Drug Res.* 23(8), (1973),1014-1016.

Clark-Lewis, Ian, et al., "Structure-Activity Relationships of Interleukin-8 Determined Using Chemically Synthesized Analogs", *Journal of Biological Chemistry*, 266(34), (Dec. 5, 1991),23128-23134.

Dossin, Olivier, et al., "Characterization of a new radioiodinated probe for the a2c adrenoreceptor in the mouse brain", *Neurochemistry International* 36, (2000),7-18.

Edwards, O. E., et al., "Atisine: The Functional Groups", *Canadian Journal of Chemistry* 33, (1955),448-451.

Elson, C., et al., "Experimental Models of Inflammatory Bowel Disease", *Gastroenterology*, 109, (1995),pp. 1344-1367.

Fox, David J., "Design, Synthesis, and Preliminary Pharmacological Evaluation of N-Acyl-3-aminoglutarimides as Broad-Spectrum Chemokine Inhibitors in Vitro and Anti-inflammatory Agents in Vivo", *J. Med. Chem.*, 45, (2002),360-370.

Frecker, M., et al., "Immunological Associations in Familial and Non-Familial Alzheimer Patients and Their Families", *The Canadian Journal of Neurological Sciences*, 21, (1994),pp. 112-119.

Gong, J H., et al., "RANTES and MCP-3 antagonists bind multiple chemokine receptors", *Journal of Biological Chemistry*, 271(18), (May 3, 1996),10521-10527.

Huebner, Charles F., et al., "Rauwolfia Alkaloids. XIV. Derivatives of Yohimbe Alkaloids", *Journal of the American Chemical Society* 77, (1955),469-72.

Ivacko, J., et al., "Hypoxic-Ischemic Injury Induces Monocyte Chemoattractant Protein-1 Expression in Neonatal Rat Brain", *Journal of Cerebral Blood Flow and Metabolism*, 17, (1997),pp. 759-770.

Jin, D., et al., "Complement 4 Locus II Gene Deletion and DQA1*0301 Gene: Contrasting Risk Factors for IgA Nephropathy and Henoch-Schonlein Nephritis", *Nephron*, 73, (1996),pp. 390-395.

Karpus, W., et al., "An Important Role for the Chemokine Macrophage Inflammatory Protein-1alpha in the Pathogenesis of the T Cell-Mediated Autoimmune Disease., Experimental Autoimmune Encephalomyelitis", *The Journal of Immunology*, (1995),pp. 5003-5010.

Kunkel, S., et al., "The role of chemokines in inflammatory joint disease", *Journal of Leukocyte Biology*, 59, (1996),pp. 6-12.

Lalchandani, Shilpa G., et al., "Yohimbine Dimers Exhibiting Selectivity for the Human a2c-Adrenoreceptor Subtype", *The Journal of Pharmacology and Experimental Therapeutics* 303(3), (2002),979-984.

Lanier, Stephen M., et al., "Photoaffinity labeling of the porcine brain a2-adrenergic receptor using a radioiodinated arylazide derivative of rauwolscine: Identification of the hormone-binding subunit", *Proc. Natl. Acad. Sci. USA* 83, (Dec. 1986),9358-9362.

Lanier, Stephen M., et al., "Synthesis and Characterization of a High Affinity Radioiodinated Probe for the a2-Adrenergic Receptor", *Molecular Pharmacology* 29, (1985),219-227.

Lucchinetti, C., et al., "Risk factors for developing multiple sclerosis after childhood optic neuritis", *The American Academy of Neurology*, 49, (1997),pp. 1413-1418.

Marone, M., et al., "Influence of body composition on the bone mass of post menopausal women", *Sao Paulo Medical Journal*, 115(6), (1997),pp. 1580-1588.

Marra, F., et al., "Increased Expression of Monocyte Chemotactic Protein-1 during Active Hepatic Fibrogenesis", *American Journal of Pathology*, 152, (1998),423-430.

McGeer, P., et al., "The inflammatory response system of brain: implications for thereapy of Alzheimer and other neurodegenerative deseases", *Brain Research Reviews*, 21, (1995),195-218.

Mustafa, Suni M., et al., "Synthesis and biological studies of yohimbine derivatives on human a2c-adrenergic receptors (abstract)", *Bioorganic & Medicinal Chemistry Letters* 15(11), (Jun. 2, 2005),2758-2760.

Naldi, L., et al., "Dietary factors and the risk of psoriasis. Results of an Italian case-control study", *British Journal of Dermatology*, 134, (1996),pp. 101-106.

Ono, K., et al., "Prevention of Myocardial Reperfusion Injury in Rats by an Antibody against Monocyte Chemotactic and Activating Factor/Monocyte Chemoattractant Protein-1", *Laboratory Investigation*, 79, (1999),pp. 195-203.

Paul, W. M., *Fundamental Immunology, Fourth Edition*, Lippincott-Raven Publ., Philadelphia,(1999),184-185.

Repaske, Mary G., et al., "Purification of the a2-Adrenergic Receptor from Porcine Brain Using a Yohimbine-Agarose Affinity Matrix", *Journal of Biological Chemistry* 262(25), (Sep. 5, 1987),12381-12386.

Rewers, M, et al., "Newborn screening for HLA markers associated with IDDM: Diabetes Autoimmunity Study in the Young (DAISY)", *Diabetologia*, 39, (1996),pp. 807-812.

Saint-Ruf, Germain, et al., "Sur quelques derives du yohimbohydrazide d'interet biologique (with English-language abstract)", *Chime therapeutique* 6, (Nov.-Dec. 1973),672-675.

Spence, J., "Advances in atherosclerosis", *Bailliere's Clinical Neurology*, 4(2), (1995),pp. 191-205.

Suda, T., et al., "Modulation of Osteoclast Differentiation by Local Factors", *Bone* 17(2), (1995),pp. 87S-91S.

Szantay, Csaba, et al., "Ueber eine einfache Synthese der Yohimbinalkaloide (with English-language abstract)", *Chem. Ber.* 109, (1976),1737-1748.

Toke, Laszlo, et al., "Die Totalsynthese des (+)-Yohimbins und (−)-B-Yohimbins1) (with English-language abstract)", *Chem. Ber.* 102, (1969),3248-3259.

Toke, Laszlo, et al., "Synthesis of Yohimbines. I. Total Synthesis of Alloyohimbine, a-Yohimbine, and Their Epimers. Revised Structure of Natural Alloyohimbine", *J. Org. Chem.* 38(14), (1973),2496-2500.

Toke, Laszlo, et al., "Synthesis of Yohimbines. II. An Alternative Route to Alloyohimbine Alkaloids", *J. Org. Chem.* 38(14), (1973),2501-2509.

Verma, M., et al., "Chemokines in acute anterior uveitis", *Current Eye. Research*, (1997),pp. 1202-1208.

Watanabe, T., et al., "Atherosclerosis and inflammation Mononuclear cell recruitment and adhesion molecules with reference to the implication of ICAM-1/LFA pathway in atherogenesis", *International Journal of Cardiology*, 66, (1998),pp. S45-S53.

Wells, J. A., "Additivity of Mutational Effects in Proteins", *Biochemistry*, 29(37), American Chemical Soc.,(Sep. 18, 1990),8509-8517.

Zheng, Weiping, et al., "Yohimbine Dimers Exhibiting Binding Selectivities for Human a2a-versus a2b Adrenergic Receptors", *Bioorganic & Medicinal Chemistry Letters* 10, (2000),627-630.

"U.S. Appl. No. 08/927,939, Advisory Action mailed Apr. 5, 2004", 3 pgs.

"U.S. Appl. No. 08/927,939, Advisory Action mailed May 22, 2000", 2 pgs.

"U.S. Appl. No. 08/927,939, Examiner Interview Summary filed Oct. 4, 2004", 1 pgs.

"U.S. Appl. No. 08/927,939, Final Office Action mailed Sep. 29, 2003", 9 pgs.

"U.S. Appl. No. 08/927,939, Final Office Action mailed Nov. 12, 1999", 12 pgs.

"U.S. Appl. No. 08/927,939, Non Final Office Action mailed Mar. 5, 2001", 9 pgs.

"U.S. Appl. No. 08/927,939, Non Final Office Action mailed Apr. 7, 1999", 15 pgs.

"U.S. Appl. No. 08/927,939, Notice of Allowance mailed Aug. 30, 2005", 4 pgs.

"U.S. Appl. No. 08/927,939, Notice of Allowance mailed Sep. 3, 2004", 5 pgs.

"U.S. Appl. No. 08/927,939, Preliminary Amendment filed Dec. 12, 2000", 14 pgs.

"U.S. Appl. No. 08/927,939, Response filed Jan. 29, 2004 to Non Final Office Action mailed Sep. 29, 2003", 8 pgs.

"U.S. Appl. No. 08/927,939, Response filed Feb. 11, 1999 to Restriction Requirement mailed Sep. 11, 1998", 8 pgs.

"U.S. Appl. No. 08/927,939, Response filed May 12, 2000 to Final Office Action mailed Nov. 12, 1999", 12 pgs.

"U.S. Appl. No. 08/927,939, Response filed Sep. 5, 2001 to Non Final Office Action mailed Mar. 5, 2001", 7 pgs.

"U.S. Appl. No. 08/927,939, Response filed Oct. 7, 1999 to Non Final Office Action mailed Apr. 7, 1999", 12 pgs.

"U.S. Appl. No. 08/927,939, Restriction Requirement mailed Sep. 11, 1998", 10 pgs.

"U.S. Appl. No. 08/927,939, Supplemental Response filed Apr. 29, 2004", 3 pgs.

"U.S. Appl. No. 09/150,813, Advisory Action mailed Jan. 28, 2002", 3 pgs.

"U.S. Appl. No. 09/150,813, Advisory Action mailed Mar. 28, 2002", 3 pgs.

"U.S. Appl. No. 09/150,813, Examiner Interview Summary mailed Jul. 30, 2003", 2 pgs.

"U.S. Appl. No. 09/150,813, Examiner Interview Summary mailed Jul. 30, 2003", 2 pgs.

"U.S. Appl. No. 09/150,813, Examiner Interview Summary mailed Sep. 5, 2002", 1 pg.

"U.S. Appl. No. 09/150,813, Final Office Action mailed Mar. 25, 2003", 10 pgs.

"U.S. Appl. No. 09/150,813, Final Office Action mailed Jun. 1, 2004", 7 pgs.

"U.S. Appl. No. 09/150,813, Final Office Action mailed Aug. 10, 2001", 9 pgs.

"U.S. Appl. No. 09/150,813, Final Office Action mailed Dec. 17, 2003", 7 pgs.

"U.S. Appl. No. 09/150,813, Non Final Office Action mailed Feb. 23, 2000", 9 pgs.

"U.S. Appl. No. 09/150,813, Non Final Office Action mailed Sep. 12, 2002", 10 pgs.

"U.S. Appl. No. 09/150,813, Non Final Office Action mailed Nov. 15, 2004", 5 pgs.

"U.S. Appl. No. 09/150,813, Non Final Office Action mailed Nov. 29, 2000", 11 pgs.

"U.S. Appl. No. 09/150,813, Notice of Allowance mailed Oct. 31, 2005", 6 pgs.

"U.S. Appl. No. 09/150,813, Response filed Feb. 15, 2005 to Non Final Office Action mailed Nov. 15, 2004", 14 pgs.

"U.S. Appl. No. 09/150,813, Response filed Mar. 18, 2004 to Non Final Office Action mailed Dec. 17, 2003", 11 pgs.

"U.S. Appl. No. 09/150,813, Response filed Apr. 11, 2002 to Final Office Action mailed Aug. 10, 2001", 10 pgs.

"U.S. Appl. No. 09/150,813, Response filed May 29, 2001 to Non Final Office Action mailed Nov. 29, 2000", 14 pgs.

"U.S. Appl. No. 09/150,813, Response filed Aug. 2, 2004 to Final Office Action mailed Jun. 1, 2004", 12 pgs.

"U.S. Appl. No. 09/150,813, Response filed Aug. 23, 2000 to Non Final Office Action mailed Feb. 23, 2000", 17 pgs.

" U.S. Appl. No. 09/150,813, Response filed Aug. 31, 1999 to Restriction Requirement mailed Mar. 3, 1999", 7 pgs.

"U.S. Appl. No. 09/150,813, Response filed Sep. 25, 2003 to Final Office Action mailed Mar. 25, 2003", 11 pgs.

"U.S. Appl. No. 09/150,813, Response filed Sep. 25, 2003 to Final Office Action mailed Mar. 25, 2003", 11 pgs.

"U.S. Appl. No. 09/150,813, Response filed Nov. 9, 2001 to Final Office Action mailed Aug. 10, 2001", 10 pgs.

"U.S. Appl. No. 09/150,813, Response filed Dec. 10, 2002 to Non Final Office Action mailed Sep. 12, 2002", 9 pgs.

"U.S. Appl. No. 09/150,813, Response filed Dec. 10, 2002 to Non Final Office Action mailed Sep. 12, 2002", 9 pgs.

"U.S. Appl. No. 09/150,813, Response filed Dec. 17, 1999 to Restriction Requirement mailed Oct. 18, 1999", 2 pgs.

"U.S. Appl. No. 09/150,813, Restriction Requirement mailed Mar. 3, 1999", 8 pgs.

"U.S. Appl. No. 09/150,813, Restriction Requirement mailed Mar. 3, 1999", 9 pgs.

"U.S. Appl. No. 09/150,813, Restriction Requirement mailed Oct. 18, 1999", 4 pgs.

"U.S. Appl. No. 09/150,813, Restriction Requirement mailed Oct. 18, 1999", 4 pgs.

"U.S. Appl. No. 09/150,813, Supplemental Notice of Allowability mailed Jan. 26, 2006", 3 pgs.

"U.S. Appl. No. 09/150,813, Supplemental Notice of Allowability mailed Jan. 26, 2006", 3 pgs.

"U.S. Appl. No. 09/150,813. Response filed Aug. 31, 1999 to Restriction Requirement mailed Mar. 3, 1999", 7 pgs.

"U.S. Appl. No. 09/150,813. Response filed Dec. 17, 1999 to Restriction Requirement mailed Oct. 18, 1999", 2 pgs.

"U.S. Appl. No. 09/452,406, 312 Amendment filed Mar. 19, 2007", 14 pgs.

"U.S. Appl. No. 09/452,406, 312 Amendment filed Mar. 19, 2007", 14 pgs.

"U.S. Appl. No. 09/452,406, Final Office Action mailed Oct. 6, 2004", 14 pgs.

"U.S. Appl. No. 09/452,406, Final Office Action mailed Dec. 15, 2005", 11 pgs.

"U.S. Appl. No. 09/452,406, Non Final Office Action mailed Jan. 15, 2003", 9 pgs.

"U.S. Appl. No. 09/452,406, Non Final Office Action mailed Jun. 6, 2005", 14 pgs.

"U.S. Appl. No. 09/452,406, Notice of Allowance mailed Mar. 20, 2006", 6 pgs.

"U.S. Appl. No. 09/452,406, Response filed Mar. 7, 2005 to Final Office Action mailed Oct. 6, 2004", 22 pgs.

"U.S. Appl. No. 09/452,406, Response filed May 14, 2003 to Non Final Office Action mailed Jan. 15, 2003", 20 pgs.

"U.S. Appl. No. 09/452,406, Response filed Jun. 3, 2002 to Restriction Requirement mailed Dec. 3, 2001", 1 pg.

"U.S. Appl. No. 09/452,406, Response filed Jun. 3, 2002 to Restriction Requirement mailed Dec. 3, 2001", 1 pg.

"U.S. Appl. No. 09/452,406, Response filed Sep. 6, 2005 to Non Final Office Action mailed Jun. 6, 2005", 18 pgs.

"U.S. Appl. No. 09/452,406, Response filed Sep. 28, 2001 to Restriction Requirement mailed Mar. 28, 2001", 39 pgs.

"U.S. Appl. No. 09/452,406, Response filed Oct. 15, 2002 to Restriction Requirement mailed Aug. 14, 2002", 3 pgs.

"U.S. Appl. No. 09/452,406, Response filed Oct. 15, 2002 to Restriction Requirement mailed Aug. 14, 2002", 3 pgs.

"U.S. Appl. No. 09/452,406, Response filed Dec. 29, 2005 to Final Office Action mailed Dec. 15, 2005", 8 pgs.

"U.S. Appl. No. 09/452,406, Restriction Requirement mailed Mar. 28, 2001", 8 pgs.

"U.S. Appl. No. 09/452,406, Restriction Requirement mailed Aug. 14, 2002", 4 pgs.

"U.S. Appl. No. 09/452,406, Restriction Requirement mailed Aug. 14, 2002", 4 pgs.

"U.S. Appl. No. 09/452,406, Restriction Requirement mailed Dec. 3, 2001", 4 pgs.

"U.S. Appl. No. 09/452,406, Restriction Requirement mailed Dec. 3, 2001", 4 pgs.

"U.S. Appl. No. 10/241,375, Advisory Action mailed Feb. 2, 2007", 3 pgs.

"U.S. Appl. No. 10/241,375, Examiner Interview Summary mailed Jun. 9, 2009", 2 pgs.

"U.S. Appl. No. 10/241,375, Final Office Action mailed Apr. 24, 2008", 16 pgs.

"U.S. Appl. No. 10/241,375, Final Office Action mailed Aug. 30, 2006", 9 pgs.

"U.S. Appl. No. 10/241,375, Non Final Office Action mailed Mar. 21, 2006", 11 pgs.

"U.S. Appl. No. 10/241,375, Non Final Office Action mailed May 11, 2007", 10 pgs.

"U.S. Appl. No. 10/241,375, Non-Final Office Action mailed Jan. 23, 2009", 20 pgs.

"U.S. Appl. No. 10/241,375, Notice of Allowance mailed Dec. 2, 2009", 9 pgs.

"U.S. Appl. No. 10/241,375, Preliminary Amendment mailed Sep. 11, 2002", 3 pgs.

"U.S. Appl. No. 10/241,375, Response filed Jun. 21, 2006 to Non Final Office Action mailed Mar. 21, 2006", 21 pgs.

"U.S. Appl. No. 10/241,375, Response filed Jun. 23, 2009 to Non Final Office Action mailed Jan. 23, 2009", 15 pgs.

"U.S. Appl. No. 10/241,375, Response filed Jun. 23, 2009 to Non Final Office Action mailed Jan. 23, 2009", 15 pgs.

"U.S. Appl. No. 10/241,375, Response filed Oct. 24, 2008 to Final Office Action mailed Apr. 24, 2008", 16 pgs.

"U.S. Appl. No. 10/241,375, Response filed Nov. 15, 2005 to Restriction Requirement mailed Jun. 13, 2005", 11 pgs.

"U.S. Appl. No. 10/241,375, Response filed Nov. 17, 2006 to Final Office Action mailed Aug. 30, 2006", 12 pgs.

"U.S. Appl. No. 10/241,375, Restriction Requirement mailed Mar. 18, 2005", 9 pgs.

"U.S. Appl. No. 10/241,375, Restriction Requirement mailed Jun. 13, 2005", 6 pgs.

"U.S. Appl. No. 10/241,375, Supplemental Preliminary Amendment filed Jan. 20, 2003", 10 pgs.

"U.S. Appl. No. 11/449,089, Response to Restriction Requirement", 9.

* cited by examiner

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

*FIG. 8*

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 9

Peptide 3

LFL peptide 3(1-12)[MCP-1]: Residues 50-61 of mature hMCP-1
E-I-C-A-D-P-K-Q-K-W-V-Q
L amino acids LFL peptide 3(3-12)[MCPI] Residues 52-61 of mature hMCP-1
C-A-D-P-K-Q-K-W-V-Q
L amino acids LFL peptide 3(1-6)[MCP1]: Residues 50-55 of mature hMCP-1
E-I-C-A-D-P
L amino acids LFL peptide 3(7-12)[MCP1]: Residues 56-61 of mature hMCP-1
K-Q-K-W-V-Q
L amino acids LFL Leu$_4$peptide3(1-12)[MCP-1]
E-I-C-L-D-P-K-Q-K-W-V-Q
L amino acids LFL Ser$_7$peptide3(1-12)[MCP-1]
E-I-C-A-D-P-S-Q-K-W-V-Q
L amino acids LFL Ile$_{11}$peptide3(1-12)[MCP-1]
E-I-C-A-D-P-K-Q-K-W-I-Q
L amino acids LFL Leu$_4$Ile$_{11}$peptide3(1-12)[MCP-1]
E-I-C-L-D-P-K-Q-K-W-I-Q
L amino acids CFL Cys$_0$Leu$_4$Ile$_{11}$Cys$_{13}$peptide3(1-12)[MCP-1]
C-E-I-C-L-D-P-K-Q-K-W-I-Q-C
L amino acids LRD Leu$_4$Ile$_{11}$ peptide 3(1-12)[MCP-1]
q-i-w-k-q-k-p-d-l-c-i-e
D amino acids

*FIG. 10A*

CRD Cys$_0$Leu$_4$Ile$_{11}$Cys$_{13}$peptide 3(1-12)[MCP-1]
c-q-i-w-k-q-k-p-d-l-c-i-e-c
D amino acids LFL Ser$_7$Glu$_8$Glu$_9$peptide3(1-12)[MCP1]:Residues 50-61 of mature hMIP1α
E-I-C-A-D-P-S-E-E-W-V-Q
L amino acids LFL peptide3(10-12)[MCP-1]
W-V-Q
L amino acids CFL Cys$_0$Cys$_4$ peptide3(10-12)[MCP-1]
C-W-V-Q-C
L amino acids LRD peptide3(10-12)[MCP-1]
q-v-w
D amino acids LFL peptide3(7-9)[MCP-1]
K-Q-K
L amino acids LRD peptide3(7-9)[MCP-1]
k-q-k
D amino acids LFL peptide 3(7-9)[MIP1α](MIP1α specific inhibitor)
S-E-E
L amino acids LRD peptide3(7-9)[MIP1α] (MIP1α specific inhibitor)
e-e-s
D amino acids LFL peptide3(7-9)[IL-8](IL-8 specific inhibitor)
K-E-N
L amino acids LRD peptide3(7-9)[IL-8](IL-8 specific inhibitor)
n-e-k
D amino acids

*FIG. 10B*

LFL peptide3(7-9)[SDF-1α](SDF-1α specific inhibitor)
K-L-K
L amino acids

LRD peptide3(7-9)[SDF1α] (SDF-1α specific inhibitor)
k-l-k
D amino acids

LFL Leu$_4$Ile$_{11}$Cys$_{13}$ peptide3(3-12)[MCP-1]
L-D-P-K-Q-K-W-I-Q-C
L amino acids CRD Leu$_4$Ile$_{11}$Cys$_{13}$ peptide3(3-12)[MCP-1]
c-q-i-w-k-q-k-p-d-l-c
D amino acids $^3$H-Ala CRD-Leu$_4$Ile$_{11}$ Cys$_{13}$ peptide 3(3-12)[MCP-1](D-Ala attached to Asp residue of CRD-Leu$_4$Ile$_{11}$Cys$_{13}$ peptide 3(3-12)[MCP-1])

$^3$H-L-Leu LRD Cys$_{13}$ peptide3(3-12)[MCP-1]
c-q-i-w-k-q-k-p-d-L-c
D and L amino acids LFL SES
S-E-S
L amino acids LFL KKK
K-K-K
L amino acids LFL Cys$_4$ peptide3(10-12)[MCP-1]
W-V-Q-C
L amino acids LRD Cys$_4$ peptide3(10-12)[MCP-1]
c-q-v-w
D amino acids LFL Ile$_{11}$Cys$_{13}$peptide3(10-12)[MCP-1]
W-I-Q-C
L amino acids

*FIG. 10C*

LRD Cys$_{13}$Ile$_{11}$peptide3(10-12)[MCP-1]
cqiw
D amino acids

LRD peptide3(7-12)[MCP-1]
q-v-w-k-q-k
D amino acids

CFL Cys$_0$Cys$_{13}$peptide3(7-12)[MCP-1]
C-K-Q-K-W-V-Q-C
L amino acids

CRD Cys$_0$Cys$_{13}$peptide3(7-12)[MCP-1]
c-q-v-w-k-q-k-c
D amino acids

LFL peptide3(10-12)[RANTES]
WVR
L amino acids

LRD peptide3(10-12)[RANTES]
rvw
D amino acids

LFL peptide3(10-12)[SDF-1]
W-I-Q
L amino acids

*FIG. 10D*

| Sequence | Mol Wt. | | Duffy Binding ED-50 | MCP-1 ED-50 | MIP-1α ED-50 | RANTES ED-50 | SDF-1α ED-50 | IL-8 ED-50 | Other Data |
|---|---|---|---|---|---|---|---|---|---|
| AQPDAINAPVTCC | 1302 | | 90μM | ns | ns | - | ns | ns | |
| SYRRITSSKCPKEAV | 1725 | | 100nM | ns | ns | - | ns | - | |
| vaekpcksstirrys | 1725 | | 18μM | ns | ns | - | ns | - | |
| HLKIIANTPNCALQIV | 1677.3 | | 19μM | 10μM | 40μM | - | 7μM | - | |
| DYFETSSQCSKPGV | 1549 | | >100μM | ns | ns | - | ns | - | |
| vgpkscqsstefyd | 1549 | | >100μM | ns | ns | - | ns | - | |
| SYRRITSSKC | 1097.4 | | 22μM | ns | ns | - | ns | - | |
| CPKEAV | 645.8 | | >100μM | ns | ns | - | ns | - | |
| SYRRI | 693.9 | | >100μM | ns | ns | - | ns | - | |
| TSSKC | 525.7 | | >100μM | ns | ns | - | ns | - | |
| DYFETSSQC | 1079.2 | | >100μM | ns | ns | - | ns | - | |
| CSKPGV | 589.8 | | >100μM | ns | ns | - | ns | - | |

FIG. 11A

| | | | | | | | |
|---|---|---|---|---|---|---|---|
| EICADPKQKWVQ | 1445 | 6μM | 8μM | 7.5μM | - | 13.5μM | 10μM |
| CADPKQKWVQ | 1202 | - | 8μM | 6.5μM | - | 9μM | 8.5μM |
| cqvwkqkpdac | 1305 | 3μM | 100nM | - | - | - | - |
| cqvwkqkpdac | 1305 | 40μM | 30nM | - | - | - | - |
| BICADP | 647 | - | 25μM | 20μM | - | 18.5μM | 16μM |
| KQKWVQ | 816 | 15μM | 7μM | 5μM | - | 5.5μM | 5μM |
| EICLDPKQKWVQ | 1487 | - | 8μM | 7μM | - | 2.5μM | 3μM |
| EICADPSQKWVQ | 1404 | 25μM | 7μM | 5.5μM | - | 4μM | 3μM |
| EICADPKQKWIQ | 1459 | - | 5.5μM | 35μM | - | 7μM | 2μM |
| EICLDPKQKWIQ | 1501 | 90μM | 2μM | 2μM | - | 4μM | 3.5μM |
| WVQ | 431.5 | 1μM | 8μM | 7.5μM | 1.5μM | 2.25μM | 1μM |
| KQK | 464.5 | 50μM | 7μM | >100μM | >100μM | >100μM | >100μM |
| SBB | 399.4 | >100μM | >100μM | - | >100μM | >100μM | >100μM |
| KEN | 425.4 | >100μM | >100μM | >100μM | >100μM | >100μM | - |

FIG. 11B

| | | | | | | | | |
|---|---|---|---|---|---|---|---|---|
| KLK | 516.6 | >100µM | >100µM | >100µM | >100µM | >100µM | - | >100µM | |
| cqiwkqkpdlc | 1359 | >100µM | - | 1nM | - | - | 350nM | 10nM | Note 1 |
| cqiwkqkpalc | 1448 | | - | >100µM | - | - | - | - | Note 2 |
| cqiwkqkpdlc | 1472.2 | | - | 10nM | - | - | - | - | |
| ses | 357.3 | >100µM | >100µM | >100µM | - | - | - | - | |
| kkk | 609.8 | >100µM | - | - | - | - | - | - | |

NOTE 1: In vivo effect-abolishes macrophages in an in vivo intradermal study by 500ng MCP–1. 300 ug iv and 10mg sq 30 minutes prior to MCP–1; D–ala ("a") is attached to D–asp ("d").

NOTE 2: In same study as note 1 above, no effect on macrophages seen.

*FIG. 11C*

STUDY DESIGN TABLE

| GROUP | ANIMAL # | N | RX | RX DOSE/ROUTE T=30 MIN | DERMAL AGONIST | DERMAL AGONIST DOSE (ng IN 50 ul) T=0 | HOUR OF SACRIFICE |
|---|---|---|---|---|---|---|---|
| 1 | 1,2,3 | 3 | PBS | 200 ul:IV<br>200 ul:SQ BACK | PBS<br>LPS<br>MCP-1<br>MCP-1 | 0<br>50<br>100<br>500 | 20-24 |
| 2 | 4,5,6 | 3 | NR58-3.14.3 | 3 ug:IV<br>100 ug:SQ BACK | PBS<br>LPS<br>MCP-1<br>MCP-1 | 0<br>50<br>100<br>500 | 20-24 |
| 3 | 7,8,9 | 3 | NR58-3.14.3 | 30 ug:IV<br>1 mg:SQ BACK | PBS<br>LPS<br>MCP-1<br>MCP-1 | 0<br>50<br>100<br>500 | 20-24 |
| 4 | 10,11,12 | 3 | NR58-3.14.3 | 300 ug:IV<br>10 mg:SQ BACK | PBS<br>LPS<br>MCP-1<br>MCP-1 | 0<br>50<br>100<br>500 | 20-24 |

*FIG. 12*

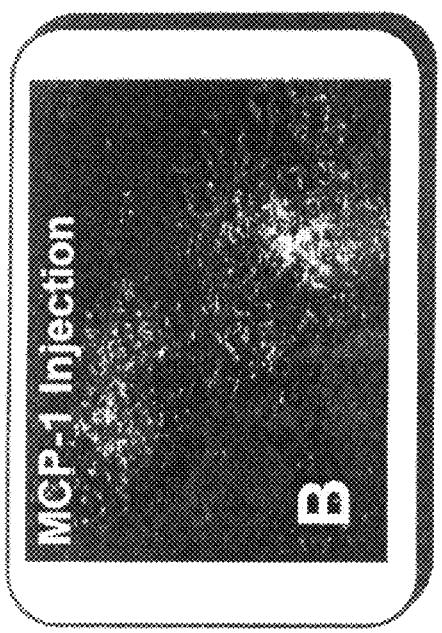
FIG. 14B
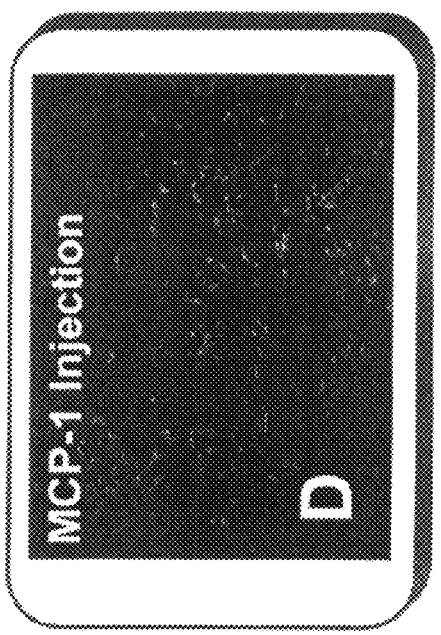
FIG. 14C
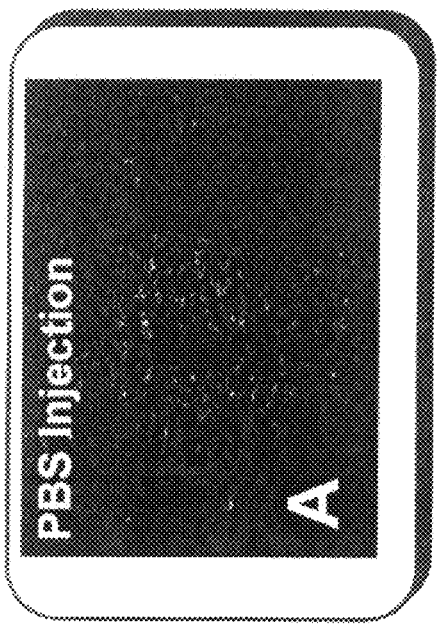
FIG. 14A
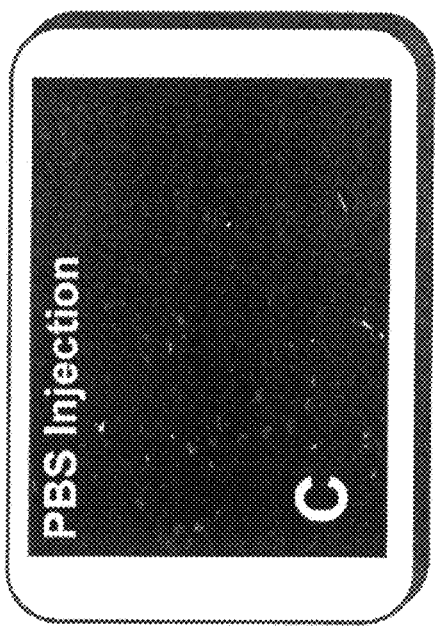
FIG. 14D

| Common Name | Sequence | SEQ ID NO: | L/D | Direction |
|---|---|---|---|---|
| Peptide 1 | AQPDAINAPVTCC | 2 | L | Forward |
| Peptide 2 | SYRRITSSKCPKEAV | 3 | L | Forward |
| Peptide 2 /control/ | SYRRITSSKCPKEAV | 3 | L | Forward |
| Biotin-Peptide 2 | biotin-SYRRITSSKCPKEAV | 3 | L | Forward |
| LRD-peptide 2 | vaekpcksstirrys | | D | Reversed |
| Cys10 (DTT)-Peptide 2 | SYRRITSSKC*PKEAV | 3 | L | Forward |
| Peptide 2 /dimer/ | SYRRITSSKC*PKEAV | 3 | L | Forward |
| Peptide 2 (SDP-1) | HLKILNTPNCALQIV | 4 | L | Forward |
| | | | | |
| Peptide 2 (MIP-1a) | DYFETSSQCSKPGV | 5 | L | Forward |
| LRD-Peptide 2 (MIP-1a) | vgpkscqsstefyd | | D | Reversed |
| Peptide 2 (IL-8) | ELRVIESGPHCANTEI | 6 | L | Forward |
| Peptide 2 (1-9) | SYRRITSSK | 132 | L | Forward |
| Peptide 2 (10-15) | CPKEAV | 125 | L | Forward |
| Peptide 2 (1-5) | SYRRI | 126 | L | Forward |
| Peptide 2 (6-10) | TSSKC | 127 | L | Forward |
| Peptide 2(1-9) (MIP-1a) | DYFETSSQC | 128 | L | Forward |
| Cys0Ser10Cys16-Peptide 2 | CSYRRITSSKSPKEAVC | 130 | L | Forward |
| LRD-Cys0Ser10Cys16-Peptide 2 | cvaekpsksstirrysc | | D | Forward |
| CRD-Cys0Ser10Cys16-Peptide 2 | cvaekpsksstirrysc | | D | Reversed |
| LariatFL-Cys0-Peptide 2 | CSYRRITSSKCPKEAV | 133 | L | Forward |
| LariatFL-Cys16-Peptide 2 | SYRRITSSKCPKEAVC | 134 | L | Forward |
| LariatRD-Cys0-Peptide 2 | vaekpcksstirrysc | | D | Reversed |
| LariatRD-Cys16-Peptide 2 | cvaekpcksstirrys | | D | Reversed |
| Ser16-Peptide 2 (SDF-1) | HLKILNTPNSALQIV | 135 | L | Forward |
| CRD-Cys0Ser10Cys16-Peptide 2 (SDF-1) | cviqlasnptaliklhc | | D | Reversed |
| Peptide 3 | EICADPKQKWVQ | 1 | L | Forward |
| Peptide 3 (3-12) | CADPKQKWVQ | 7 | L | Forward |
| LRD-Peptide 3 (3-12) | cqvwkqkpdac | | D | Reversed |
| CRD-Peptide 3 (3-12) | cqvwkqkpdac | | D | Reversed |
| Peptide 3 (1-6) | EICADP | 8 | L | Forward |
| Peptide 3 (7-12) | KQKWVQ | 9 | L | Forward |
| LRD-Peptide 3 (3-12) | qvwkqk | | D | Reversed |
| Leu4-Peptide 3 | EICLDPKQKWVQ | 10 | L | Forward |
| Peptide 3 (MIPla) | EICADPSEEWVQ | 12 | L | Forward |
| Peptide 3 (10-12) | WVQ | | L | Forward |
| Peptide 3 (7-9) | KQK | | L | Forward |
| Peptide 3(7-9), carbonate | KQK | | L | Forward |

FIG. 18A

| | | | | |
|---|---|---|---|---|
| Peptide 3(7-9) (MIP1a) | SEE | | L | Forward |
| Peptide 3(7-9) (IL-6) | KEN | | L | Forward |
| Peptide 3(7-9) (SDP1) | KLK | | L | Forward |
| Peptide 3(7-9) (SDP1)-acetate | KLK | | L | Forward |
| CRD-Leu4IlellCys13-Peptide 3 (3-12) | cqiwkqkpdlc | | D | Reversed |
| CRD-Leu4IlellCys13-Peptide 3 (3-12) /D-Ala/ | cqiwkqkpd*lc | | D | Reversed |
| CRD-Leu4IlellCys13 Peptide3 (3-12) /L-Leu4/acetate | cqiwkqkpdLc | | D | Reversed |
| CRD-Tyr-2pAla-1pAla0Leu4 IlellCys13-Peptide 3 (3-12) | YβAβAcqiwkqkpdlc | | D/L | Reversed |
| CRD-Leu4 IlellCys13βAlal4βAla5Tyr16-Peptide 3 (3-12) | cqiwkqkpnlcβAβAY | | D/L | Reversed |
| CRD-Leu4IlellCys13-Peptide 3 (3-12) /L-Ilell/ | cqIcwkqkpdlc | | D/L | Reversed |
| Peptide 3(7-9) (MIPIβ) | SES | | L | Forward |
| Peptide 3(7-9) Eotaxin) | KKK | | L | Forward |
| Cys13-Peptide 3(10-12) | WVQC | 122 | L | Forward |
| Cys13-Peptide 3(10-12) (SDP1) | WIQC | 123 | L | Forward |
| CRD-Leu4Cys13-Peptide 3 (3-12) | cqvwkqkpdlc | | D | Reversed |
| CFL-Cys4Cys13-Peptide3 (7-12) | CKQKWVQC | | L | Forward |
| CRD-Cys4Cys13-Peptide3 (7-12) | cqvwkqkc | | D | Reversed |
| Peptide 3(10-12) (RANTES) | WVR | | L | Forward |
| Peptide 3(10-12) (SDP1) | WIQ | | L | Forward |
| Peptide 3 (7-9) (RANTES) | EKK | | L | Forward |
| Biotin-Leu4 Ilell Peptide 3 (3-12) | biotin-CLDPKQKWIQ | 136 | L | Forward |
| Ala8-Peptide 3(7-9-amide | KAK | | L | Forward |
| Cys8-Peptide 3(7-9)-amide | KCK | | L | Forward |
| Asp8-Peptide 3(7-9)-amide | KDK | | L | Forward |
| Glu8-Peptide 3(7-9)-amide | KEK | | L | Forward |
| Phe8-Peptide 3(7-9) | KFK | | L | Forward |
| Gly8-Peptide 3(7-9)-amide | KGK | | L | Forward |
| His8-Peptide 3(7-9)-amide | KHK | | L | Forward |
| Ile8-Peptide 3(7-9)-amide | KIK | | L | Forward |
| Met8-Peptide 3(7-9)-amide | KMK | | L | Forward |
| Asn8-Peptide 3(7-9)-amide | KNK | | L | Forward |
| Pro8-Peptide 3(7-9)-amide | KPK | | L | Forward |
| Arg8-Peptide 3(7-9)-amide | KRK | | L | Forward |
| Ser8-Peptide 3(7-9) | KSK | | L | Forward |
| Thr8-Peptide 3(7-9)-amide | KTK | | L | Forward |

*FIG. 18B*

| | | | | |
|---|---|---|---|---|
| Val8-Peptide 3(7-9)-amide | KVK | | L | Forward |
| Try8-Peptide 3(7-9) | KWK | | L | Forward |
| Tyr8-Peptide 3(7-9) | KYK | | L | Forward |
| | | | | |
| Glyll-Peptide 3 (10-12) | WGQ | | L | Forward |
| Alall-Peptide 3 (10-12) | WAQ | | L | Forward |
| EthylGlyll-Peptide 3 (10-12) | W(EtGl)Q | | L | Forward |
| AlloIlell-Peptide 3 (10-12) | W(AlloI)Q | | L | Forward |
| LRL-Peptide 3(7-9) (MIPla) | EES | | L | Forward |
| Peptide 3(10-11) | WV | | L | Forward |
| APG | APG | | L | Forward |
| Furin substrate | pERTKR-AMC | 137 | L | Forward |
| GD | GD | | L | Forward |
| GGR | GGR | | L | Forward |
| Peptide F1 | SGPSIVHRKCF | 138 | L | Forward |
| Peptide F1-biotin | biotin-SGPSIVHRKCF | 138 | L | Forward |
| Peptide F2 | MCEEEDSTAL | 139 | L | Forward |
| Peptide F3 | SGPSIVHRKCFGMCEEEDSTAL | 140 | L | Forward |
| Peptide HIV-1 env V3 loop (MN) | CTRPNYNKRKRIHIGPGRAFYTTKNIIGTIRQAHC | 141 | L | Forward |
| Peptide HIV-A (1-24) | NNTRKSIRIQRGPGRAFVTIGKIG | 142 | L | Forward |
| Peptide HIV-A (11-20) | RGPGRAFVTI | 143 | L | Forward |
| Peptide HIV-A (11-20) biotin | biotin-RGPGRAPVTI | 150 | L | Forward |
| Peptide HIV-A (8-22) | RIQRGPGRAFVTIGK | 144 | L | Forward |
| Peptide T1 | LYIDFRQDLGWKW | 111 | L | Forward |
| Peptide T2 | HEPKGYHANFC | 112 | L | Forward |
| Peptide T3 | VYYVGRK | 113 | L | Forward |
| RGD | RGD | | L | Forward |
| RGD | RGD | | L | Forward |
| TGF-β1 (78) | CVPQALEPLPIVYYVGRKPHVEQLSNMIVRSC | 145 | L | Forward |
| TGF-β1 (pre 266) | ERAQHLQSSRHRRC | 146 | L | Forward |
| TGF-β1 (pre 274) | SRHRRALDTNYC | 147 | L | Forward |
| TGF-β1 (pre 40) | LVKRKRIEAIRC | 148 | L | Forward |
| TGF-β1 (pre-25) | RPAAGLSTCKTIDME | 149 | L | Forward |
| TTT | TTT | | L | Forward |
| VE | VE | | L | Forward |

*FIG. 18C*

| Name | Description | If not stated |
|---|---|---|
| Nterm | N-terminal modification (e.g. Biotin) | -NH2 |
| FORMAT | Is it linear/cyclised/reversed/D or L | LFL |
| Mut$_x$Mut$_y$ | Substitutions from human chemokine sequence | None |
| X | Peptide region (1,2 or 3) | - |
| a-b | Number of residues included (from - to) | Full length |
| Chemokine | Parental chemokine from which sequence came | MCP-1 |
| Cterm | C-terminal modification (e.g. amide) | -COOH |
| extra | Extra information (e.g. dimer, D-ala addition etc) | None |
| Salt | Salt of peptide (e.g. TFA, acetate, citrate, carbonate) | TFA |

FIG. 18D

ED-50's of Peptides 1 to 3 and its derivatives with CC and CXC Chemokines

| Peptide | Sequence | MCP-1 | IL-8 | fMLP |
|---|---|---|---|---|
| Peptide 1[1-13] | AQPDAINAPVTCC | >100 | >100 | >100 |
| Peptide 2[1-15] | SYRRTSSKCPKEAV | >100 | >100 | >100 |
| Peptide 3[1-12] | EICADPKQKWVQ | 8 ± 2 | 10 ± 1 | >100 |
| Peptide 3[1-6] | EICADP | 25 ± 5 | 16 ± 2 | >100 |
| Peptide 3[7-12] | KQKWVQ | 7 ± 1 | 5 ± 2 | >100 |
| Peptide 3[3-12] | CADPKQKWVQ | 8 ± 1 | 9 ± 4 | >100 |
| Leu$_4$ Peptide 3[1-12] | EICLDPKQKWVQ | 8 ± 2 | 3 ± 1 | >100 |
| Ser$_7$ Peptide 3[1-12] | EICADPSQKWVQ | 7 ± 1 | 3 ± 2 | >100 |
| Ile$_{11}$ Peptide 3[1-12] | EICADPKQKWIQ | 6 ± 3 | 2 ± 1 | >100 |
| Leu$_4$, Ile$_{11}$ Peptide 3[1-12] | EICLDPKQKWIQ | 2 ± 0 | 4 ± 2 | >100 |

FIG. 19

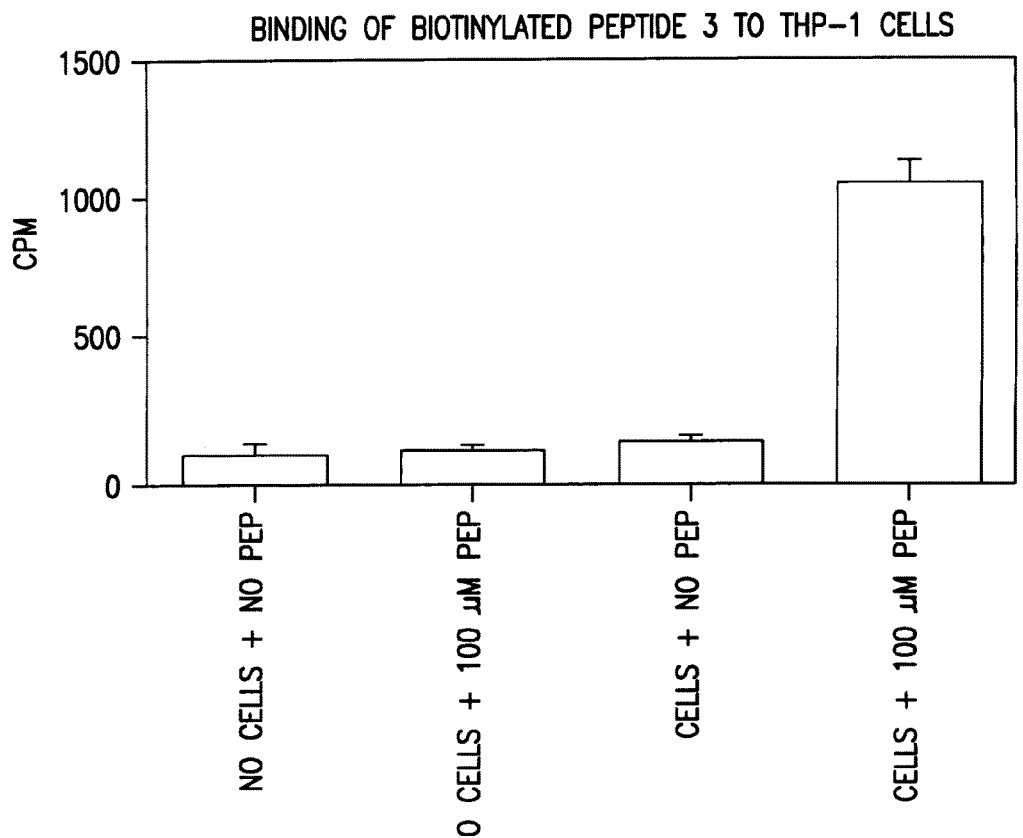
FIG. 26A
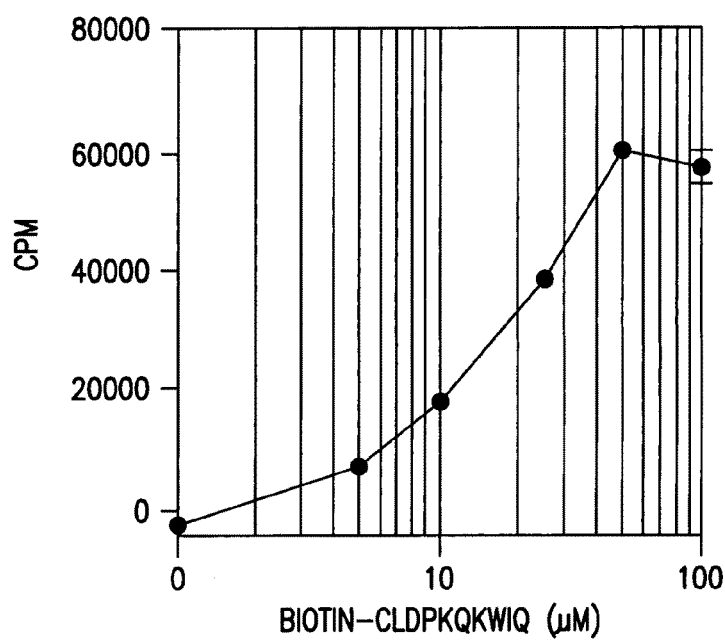
FIG. 26B  $K_A = 15 \mu M$

SUMMARY

SQ in BALB/c mice

| | Group 1-10.3 µg %ID/G 30 minute | SD | Group 2-103 µg %ID/G 30 minute | SD | Group 3-103 µg %ID/G 30 minute | SD | Group 4-103 µg %ID/G 3 Hour | SD | Group 5-103 µg %ID/G 3 Hour | SD | Group 6-103 µg %ID/G 3 Hour | SD | Group 7-103 µg %ID/G 24 Hour | SD | Group 8-103 µg %ID/G 24 Hour | SD | Group 9-1030 µg %ID/G 24 Hour | SD |
|---|---|---|---|---|---|---|---|---|---|---|---|---|---|---|---|---|---|---|
| Blood Pallet | 0.79 | 0.16 | 0.47 | 0.09 | 0.32 | 0.07 | 0.05 | 0.02 | 0.02 | 0.00 | 0.01 | 0.00 | 0.03 | 0.01 | 0.04 | 0.05 | 0.01 | 0.01 |
| Serum | 6.20 | 1.84 | 5.54 | 0.81 | 4.21 | 0.79 | 0.24 | 0.05 | 0.19 | 0.04 | 0.14 | 0.02 | 0.03 | 0.00 | 0.01 | 0.00 | 0.00 | 0.00 |
| Injection Site | 30.64 | 34.24 | 48.42 | 14.15 | 69.95 | 25.19 | 15.48 | 8.85 | 3.59 | 5.37 | 32.40 | 44.27 | .54 | 1.45 | 3.38 | 0.27 | 2.54 | 1.44 |
| Skin | 4.64 | 1.99 | 3.50 | 1.28 | 1.55 | 0.62 | 0.35 | 0.08 | 0.48 | 0.21 | 0.29 | 0.03 | 0.19 | 0.03 | 0.14 | 0.03 | 0.12 | 0.01 |
| Heart | 1.64 | 0.59 | 1.51 | 0.39 | 1.03 | 0.19 | 0.18 | 0.04 | 0.10 | 0.01 | 0.08 | 0.02 | 0.09 | 0.03 | 0.08 | 0.02 | 0.03 | 0.01 |
| Thymus | 1.43 | 0.48 | 1.41 | 0.05 | 0.89 | 0.76 | 0.18 | 0.06 | 0.15 | 0.03 | 0.10 | 0.01 | 0.11 | 0.05 | 0.07 | 0.02 | 0.04 | 0.01 |
| Lung | 2.79 | 0.52 | 2.81 | 0.72 | 1.38 | 0.12 | 0.35 | 0.11 | 0.25 | 0.04 | 0.19 | 0.01 | 0.14 | 0.01 | 0.10 | 0.03 | 0.07 | 0.01 |
| Liver | 1.15 | 0.36 | 1.20 | 0.30 | 0.59 | 0.12 | 0.18 | 0.07 | 0.13 | 0.03 | 0.10 | 0.06 | 0.21 | 0.05 | 0.18 | 0.02 | 0.11 | 0.02 |
| Spleen | 1.16 | 0.29 | 0.30 | 0.25 | 0.59 | 0.02 | 0.22 | 0.04 | 0.20 | 0.03 | 0.16 | 0.07 | 0.21 | 0.04 | 0.17 | 0.02 | 0.11 | 0.01 |
| Stomach | 1.37 | 0.28 | 2.99 | 3.38 | 2.18 | 1.78 | 1.10 | 0.39 | 0.46 | 0.37 | 0.52 | 0.09 | 0.12 | 0.02 | 0.07 | 0.02 | 0.06 | 0.01 |
| Kidneys | 24.20 | 12.53 | 21.98 | 1.94 | 16.31 | 0.06 | 68.14 | 5.13 | 60.34 | 3.29 | 27.47 | 1.29 | 52.58 | 9.20 | 51.74 | 11.29 | 25.54 | 3.75 |
| Adrenals | 6.68 | 0.13 | 2.25 | 0.15 | 2.40 | 0.42 | 8.05 | 4.15 | 4.28 | 0.59 | 2.16 | 1.54 | 5.37 | 5.85 | 3.23 | 2.17 | 2.20 | 1.10 |
| Duodenum | 1.73 | 0.43 | 3.34 | 2.30 | 1.40 | 1.31 | 6.12 | 2.53 | 1.42 | 0.16 | 1.33 | .061 | 0.47 | 0.01 | 0.28 | 0.03 | 0.20 | 0.07 |
| Jejunum | 1.02 | 0.20 | 1.28 | 0.50 | 1.52 | 0.73 | 9.47 | 3.47 | 6.57 | 2.14 | 2.50 | 1.76 | 0.76 | 0.08 | 0.31 | 0.03 | 0.22 | 0.02 |
| Ileum | 1.02 | 0.23 | 0.76 | 0.27 | 0.63 | 0.12 | 4.34 | 3.13 | 2.22 | 1.67 | 6.37 | 5.94 | 0.37 | 0.14 | 0.21 | 0.03 | 0.15 | 0.05 |
| Cacum & Colon | 0.77 | 0.11 | 0.68 | 0.08 | 0.45 | 0.04 | 2.36 | 0.71 | 4.08 | 1.21 | 3.59 | 5.55 | 1.38 | 0.35 | 0.34 | 0.02 | 0.50 | 0.26 |
| Mesenteric Nodes | 1.02 | 0.74 | 1.30 | 0.48 | 0.54 | 0.46 | 2.18 | 1.83 | 1.42 | 0.64 | 1.83 | 1.70 | 0.37 | 0.14 | 0.15 | 0.04 | 0.10 | 0.07 |
| Abdominal Fat | 1.08 | 6.00 | 0.24 | 0.05 | 0.31 | 0.54 | 0.15 | 0.12 | 0.33 | 0.29 | 0.10 | 0.07 | 0.08 | 0.02 | 0.03 | 0.01 | 0.03 | 0.01 |
| Bone Marrow | 3.76 | 0.54 | 0.56 | 0.51 | 0.10 | 0.31 | 0.17 | 0.05 | 0.25 | 0.05 | 0.19 | 0.22 | 0.17 | 0.04 | 0.04 | 0.01 | 0.04 | 0.01 |
| Skeletal Muscle | 0.70 | 0.04 | 0.34 | 0.17 | 0.02 | 0.10 | 0.14 | 0.04 | 0.09 | 0.03 | 0.04 | 0.00 | 0.06 | 0.02 | 0.03 | 0.00 | 0.02 | 0.01 |
| Brain | 0.24 | 0.59 | 2.08 | 3.07 | 2.45 | 0.02 | 0.03 | 0.01 | 0.07 | 0.09 | 0.01 | 0.00 | 0.03 | 0.01 | 0.06 | 0.09 | 0.00 | 0.00 |
| Ovaries | 1.62 | 0.64 | 1.21 | 1.00 | 0.23 | 2.45 | 0.21 | 0.04 | 0.30 | 0.28 | 2.10 | 3.43 | 0.15 | 0.02 | 0.57 | 0.90 | 0.06 | 0.01 |
| Uterus | 1.82 | | 1.52 | 0.85 | | 0.23 | 0.41 | 0.27 | 0.33 | 0.04 | 0.11 | 0.09 | 0.53 | 0.65 | 0.10 | 0.09 | 0.11 | 0.02 |

URINE

| | Group 1-10.3 µg nMOL/G 30 minute | SD | Group 2-103 µg nMOL/G 30 minute | SD | Group 3- 103 µg nMOL/G 30 minute | SD | Group 4-103 µg nMOL/G 3 Hour | SD | Group 5-103 µg nMOL/G 3 Hour | SD | Group 6- 103 µg nMOL/G 3 Hour | SD | Group 7-103 µg nMOL/G 24 Hour | SD | Group 8-103 µg nMOL/G 24 Hour | SD | Group 9- 1030 µg nMOL/G 24 Hour | SD |
|---|---|---|---|---|---|---|---|---|---|---|---|---|---|---|---|---|---|---|
| Blood Pallet | 0.053 | 0.011 | 0.318 | 0.058 | 2.137 | 0.487 | 0.003 | 0.001 | 0.012 | 0.003 | 0.080 | 0.019 | 0.002 | 0.001 | 0.025 | 0.035 | 0.055 | 0.043 |
| Serum | 0.415 | 0.123 | 3.707 | 0.545 | 28.204 | 5.283 | 0.016 | 0.002 | 0.128 | 0.028 | 0.367 | 0.154 | 0.002 | 0.000 | 0.010 | 0.001 | 0.026 | 0.005 |
| Injection Site | 6.057 | 2.292 | 32.410 | 9.473 | 468.257 | 165.612 | 1.035 | 0.391 | 5.418 | 3.595 | 215.383 | 295.316 | 0.243 | 0.097 | 2.245 | 0.180 | 16.369 | 9.824 |
| Skin | 0.304 | 0.133 | 2.345 | 0.857 | 10.382 | 4.137 | 0.024 | 0.005 | 0.318 | 0.141 | 1.331 | 0.222 | 0.012 | 0.002 | 0.091 | 0.021 | 0.305 | 0.089 |
| Heart | 0.110 | 0.040 | 1.010 | 0.258 | 6.880 | 1.291 | 0.012 | 0.003 | 0.063 | 0.009 | 0.515 | 0.104 | 0.005 | 0.002 | 0.036 | 0.016 | 0.235 | 0.044 |
| Thymus | 0.035 | 0.032 | 0.342 | 0.034 | 5.974 | 5.055 | 0.012 | 0.002 | 0.107 | 0.019 | 0.539 | 0.075 | 0.007 | 0.003 | 0.049 | 0.015 | 0.249 | 0.056 |
| Lung | 0.187 | 0.035 | 1.882 | 0.481 | 13.271 | 0.784 | 0.024 | 0.007 | 0.177 | 0.027 | 1.276 | 0.059 | 0.008 | 0.000 | 0.065 | 0.022 | 0.483 | 0.076 |
| Liver | 0.077 | 0.024 | 0.800 | 0.204 | 3.975 | 0.820 | 0.012 | 0.005 | 0.128 | 0.021 | 0.887 | 0.419 | 0.014 | 0.004 | 0.121 | 0.014 | 0.727 | 0.125 |
| Spleen | 0.077 | 0.020 | 0.602 | 0.165 | 3.962 | 0.133 | 0.015 | 0.003 | 0.137 | 0.027 | 1.056 | 0.441 | 0.014 | 0.003 | 0.112 | 0.014 | 0.707 | 0.088 |
| Stomach | 0.082 | 0.019 | 0.002 | 2.247 | 14.820 | 11.889 | 0.074 | 0.025 | 0.510 | 0.249 | 3.483 | 0.572 | 0.005 | 0.001 | 0.048 | 0.012 | 0.429 | 0.035 |
| Kidneys | 1.620 | 0.839 | 22.075 | 1.237 | 102.503 | 0.426 | 4.628 | 6.410 | 40.513 | 2.205 | 183.392 | 8.628 | 3.519 | 0.616 | 34.637 | 7.560 | 171.609 | 25.195 |
| Adrenals | 0.447 | 0.009 | 1.503 | 0.303 | 18.102 | 2.827 | 0.539 | 0.278 | 2.865 | 0.394 | 14.485 | 10.964 | 0.383 | 0.392 | 2.162 | 1.453 | 14.762 | 7.371 |
| Duodenum | 0.116 | 0.029 | 2.256 | 1.542 | 11.388 | 8.787 | 0.409 | 0.169 | 0.349 | 0.109 | 5.590 | 4.103 | 0.032 | 0.001 | 0.187 | 0.018 | 1.346 | 0.494 |
| Jejunum | 0.053 | 0.013 | 0.360 | 0.332 | 10.164 | 4.872 | 0.634 | 0.232 | 4.385 | 1.435 | 17.404 | 11.755 | 0.050 | 0.005 | 0.210 | 0.022 | 1.486 | 0.151 |
| Ileum | 0.068 | 0.015 | 0.500 | 0.183 | 4.203 | 0.826 | 0.291 | 0.210 | 1.439 | 1.118 | 42.809 | 39.756 | 0.025 | 0.009 | 0.139 | 0.017 | 1.054 | 0.342 |
| Cacum & Colon | 0.053 | 0.007 | 0.458 | 0.056 | 3.027 | 0.261 | 0.158 | 0.048 | 2.718 | 0.808 | 84.392 | 37.151 | 0.083 | 0.024 | 0.228 | 0.014 | 3.361 | 1.760 |
| Mesenteric Nodes | 0.089 | 0.049 | 0.869 | 0.308 | 6.755 | 3.101 | 0.146 | 0.122 | 0.351 | 0.429 | 10.390 | 11.393 | 0.025 | 0.009 | 0.102 | 0.025 | 0.681 | 0.502 |
| Abdominal Fat | 0.072 | 0.047 | 0.163 | 0.034 | 6.027 | 3.647 | 0.00 | 0.008 | 0.221 | 0.195 | 0.850 | 0.438 | 0.004 | 0.001 | 0.020 | 0.005 | 0.179 | 0.092 |
| Bone Marrow | 0.252 | 0.402 | 0.373 | 0.343 | 2.223 | 2.095 | 0.011 | 0.004 | 0.130 | 0.043 | 1.253 | 1.485 | 0.011 | 0.002 | 0.024 | 0.004 | 0.276 | 0.060 |
| Skeletal Muscle | 0.047 | 0.036 | 0.559 | 0.116 | 3.587 | 0.700 | 0.009 | 0.003 | 0.060 | 0.019 | 0.294 | 0.015 | 0.002 | 0.001 | 0.022 | 0.003 | 0.107 | 0.049 |
| Brain | 0.016 | 0.002 | 1.391 | 2.057 | 1.000 | 0.123 | 0.002 | 0.001 | 0.049 | 0.059 | 0.082 | 0.021 | 0.002 | 0.001 | 0.042 | 0.060 | 0.030 | 0.006 |
| Ovaries | 0.109 | 0.039 | 0.305 | 0.668 | 15.333 | 16.491 | 0.014 | 0.003 | 0.201 | 0.185 | 14.059 | 22.958 | 0.010 | 0.001 | 0.381 | 0.605 | 0.519 | 0.070 |
| Uterus | 0.129 | 0.043 | 1.017 | 0.570 | 7.873 | 1.511 | 0.027 | 0.018 | 0.222 | 0.025 | 0.746 | 0.572 | 0.036 | 0.043 | 0.070 | 0.059 | 0.727 | 0.143 |

CELL NUMBER = PRODUCT OF TOTAL CELL POPULATION FROM LUNG X% OF CELL POPULATION FROM FACS

CULTURED SERUM CELLS STIMULATED
WITH ANTIGEN (OVALBUMIN)

| GROUP | | MOUSE | 1ST ASSAY IL-4, pg/ml | AVG. | 2ND ASSAY IL-4, pg/ml | AVG. |
|---|---|---|---|---|---|---|
| 1 | POSITIVE CONTROL | m1 | 619 | 474 | 730 | 427 |
| | | m2 | 330 | | 123 | |
| | | m3 | CONTAMINATED | | CONTAMINATED | |
| | | | 204.3538598 | | | |
| 2 | 10 ug NR58-3.14.3 | m1 | CONTAMINATED | 115 | CONTAMINATED | 91 |
| | | m2 | 144 | | 104 | |
| | | m3 | 86 | | 78 | |
| | | | 41.01219331 | | | |
| 3 | 10 mg NR58-3.14.3 | m1 | 154 | 67 | 82 | 89 |
| | | m2 | 33 | | 135 | |
| | | m3 | 13 | | 51 | |
| | | | 85.55992052 | | | |
| 4 | 10 mg NR58-3.14.4 | m1 | 175 | 191 | 76 | 158 |
| | | m2 | 198 | | 316 | |
| | | m3 | 200 | | 81 | |
| | | | 16.26346697 | | | |
| 5 | NEGATIVE CONTROL | m1 | 19 | 9 | 9 | 9.5 |
| | | m2 | 0 | | 0 | |
| | | m3 | 8 | | 10 | |

| | | |
|---|---|---|
| POSITIVE CONTROL | 474 | 427 |
| LOW DOSE ACTIVE PEPTIDE | 115 | 91 |
| HIGH DOSE ACTIVE PEPTIDE | 67 | 89 |
| HIGH DOSE INACTIVE PEPTIDE | 191 | 158 |
| NEGATIVE CONTROL | 9 | 9 |

FIG. 40D

| SERUM IgE GROUP | | MOUSE | SERUM IgE ng/ml | BAL THROMBOXANE pg/ml | BAL LTB4 pg/ml | BAL PGE2 pg/ml |
|---|---|---|---|---|---|---|
| 1 | POSITIVE CONTROL-OVA | M1 | 160 | 12.7 | 2.6 | 93.1 |
| | | M2 | 145 | 10.3 | 2.81 | 25.4 |
| | | M3 | 180 | 34 | 29 | 116.8 |
| | | AVE | 161.6666667 | 19 | 11.47 | 78.43333333 |
| | | STDEV | 17.55942292 | 13.04568894 | 15.18178843 | 47.43230264 |
| 2 | 10 ug NR58-3.14.3 | M1 | 80 | 19.6 | 4.9 | 2.7 |
| | | M2 | 74 | 6.85 | 1.6 | 21.2 |
| | | M3 | 115 | 17.1 | 4.6 | 31.7 |
| | | AVE | 89.66666667 | 14.51666667 | 3.666666667 | 18.53333333 |
| | | STDEV | 22.14347157 | 6.75617002 | 1.800925688 | 14.68275633 |
| 3 | 1 mg NR58-3.14.3 | M1 | 65 | 5 | 4 | 109 |
| | | M2 | 98 | 8.1 | 1.1 | 11.7 |
| | | M3 | 38 | 4.7 | 4.8 | 196 |
| | | AVE | 67 | 5.933333333 | 3.3 | 55.33523484 |
| | | STDEV | 30.0499584 | 1.882374387 | 1.946792233 | 87.67841161 |
| 4 | 1 mg NR58-3.14.4 | M1 | 132 | 4.1 | 8.7 | 83 |
| | | M2 | 152 | 2.5 | 3.5 | 1.3 |
| | | M3 | 168 | 1.7 | 1.3 | 2 |
| | | AVE | 150.6666667 | 2.766666667 | 4.5 | 28.76666667 |
| | | STDEV | 18.03699901 | 1.222020185 | 3.8 | 46.96874848 |
| 5 | NEGATIVE CONTROL-PB | M1 | 14 | 6.9 | 1.3 | 0.1 |
| | | M2 | 12 | 7.2 | 1.5 | 1.1 |
| | | M3 | 3 | 8 | 0.4 | 0.1 |
| | | AVE | 7.366666667 | 7.366666667 | 1.066666667 | 0.433333333 |
| | | STDEV | 6.859465277 | 0.56862407 | 0.585946528 | 0.577350269 |

*FIG. 40E*

| | Glutamine | Glutamide | Benzyl-glutamide | Pyroglutamate |
|---|---|---|---|---|
| N-undec-10-enoyl | 58,1<br>>100% | 58,2<br>>100% | 58,3<br>90 ± 2% | 58,4<br>>100% |
| BOC | 58,5<br>>100% | 58,6<br>80 ± 10% | 58,7<br>34 ± 17% | 58,8<br>Not made |
| Benzoyl | 58,9<br>21 ± 13% | 58,10<br>28 ± 13% | 58,11<br>31 ± 17% | 58,12<br>39 ± 4% |
| -Glycylglutamine | 58,13<br>31 ± 35% | 58,14<br>36 ± 4% | 58,15<br>83 ± 2% | |
| | N-tert Butylcarbonyl | N-Benzoyl | N-Z | |

FIG. 44

|  | Glutamine | Glutamide | Benzyl-glutamide | Pyroglutamate |
|---|---|---|---|---|
| N-undec-10-enoyl | 58,1<br>13 μM | 58,2<br>15 μM | 58,3<br>40 μM | 58,4<br><100nM |
| BOC | 58,5<br>5-20 μM | 58,6<br>45 μM | 58,7<br>N/D | 58,8<br>Not made |
| Benzoyl | 58,9<br>N/D | 58,10<br>N/C | 58,11<br>N/D | 58,12<br>N/D |
| -Glycylglutamine | 58,13<br>N/D | 58,14<br>N/D | 58,15<br>38 μM | |
| N-tert Butylcarbonyl | | N-Benzoyl | N-Z | |

*FIG. 45*

ALKAPHORE SKELETONS
(XVI)
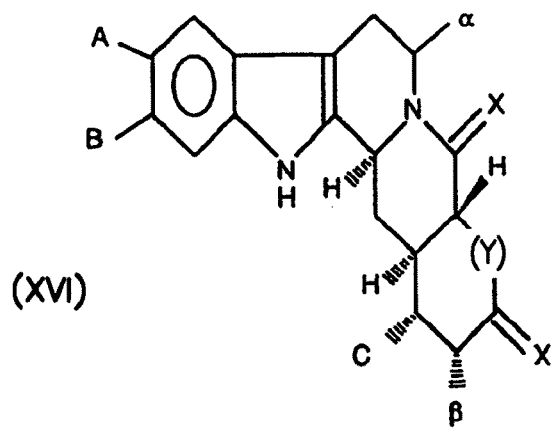
(XVII)
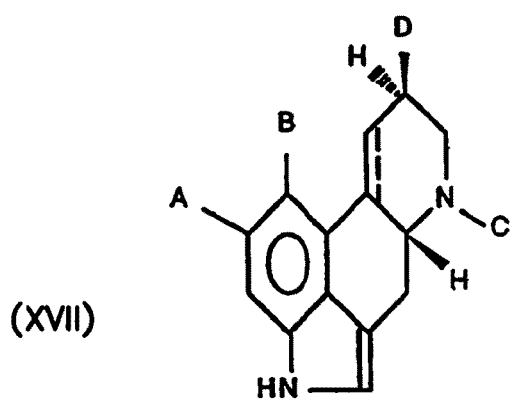
(XVIII)
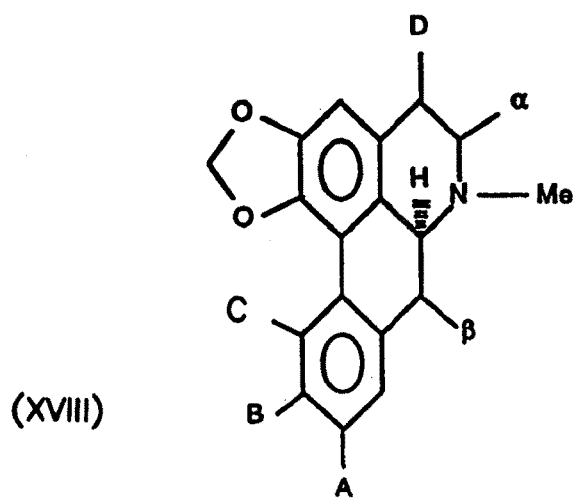
*FIG. 55*

METHODS TO INHIBIT OR AUGMENT AN INFLAMMATORY RESPONSE

CROSS-REFERENCE TO RELATED APPLICATIONS

This application is a of U.S. application Ser. No. 09/452,406, filed on Dec. 1, 1999 now U.S. Pat. No. 7,238,711, which is a continuation-in-part application of U.S. application Ser. No. 09/271,192, filed Mar. 17, 1999, now abandoned, the disclosures of which are incorporated by reference herein.

BACKGROUND OF THE INVENTION

Macrophage/monocyte recruitment plays a role in the morbidity and mortality of a broad spectrum of diseases, including autoimmune diseases, granulomatous diseases, allergic diseases, infectious diseases, osteoporosis and coronary artery disease. For example, in atherosclerosis early during lipid lesion formation, circulating monocytes adhere to the activated endothelium overlying the incipient plaque. Under appropriate conditions, the monocytes then migrate into the developing intima. In the intima, macrophage accumulate lipoprotein and excrete an excess of proteases relative to protease inhibitors. If the lipoproteins are oxidized, they are toxic to macrophage, which results in macrophage death and an increase in an unstable, necrotic, extracellular lipid pool. An excess of proteases results in loss of extracellular matrix and destabilization of the fibrous plaque. Plaque instability is the acute cause of myocardial infarction.

Many molecules have been identified that are necessary for the recruitment of monocytes and other inflammatory cell types to sites of injury or insult. These molecules represent targets for the inhibition of monocyte recruitment. One class of such molecules is adhesion molecules, e.g., receptors, for monocytes. Another class of molecules includes inflammatory mediators, such as TNF-α and related molecules, the interleukins, e.g., IL-1β, and chemokines, e.g., monocyte chemoattractant protein-1 (MCP-1). As a result, agents which modulate the activity of chemokines are likely to be useful to prevent and treat a wide range of diseases. For example, Rollins et al. (U.S. Pat. No. 5,459,128) generally disclose analogs of MCP-1 that inhibit the monocyte chemoattractant activity of endogenous MCP-1. Analogs that are effective to inhibit endogenous MCP-1 are disclosed as analogs which are modified at 28-tyrosine, 24-arginine, 3-aspartate and/or in amino acids between residues 2-8 of MCP-1. In particular, Rollins et al. state that "[s]uccessful inhibition of the activity is found where MCP-1 is modified in one or more of the following ways: a) the 28-tyrosine is substituted by aspartate, b) the 24-arginine is substituted by phenylalanine, c) the 3-aspartate is substituted by alanine, and/or d) the 2-8 amino acid sequence is deleted" (col. 1, lines 49-54). The deletion of amino acids 2-8 of MCP-1 ("MCP-1 (__2-8)") results in a polypeptide that is inactive, i.e., MCP-1 (__2-8) is not a chemoattractant (col. 5, lines 22-23). The only effective MCP-1 inhibitor disclosed in Rollins et al. is MCP-1 (__2-8).

Recent studies suggest that MCP-1 (__2-8) exhibits a dominant negative effect, i.e., it forms heterodimers with wild-type MCP-1 that cannot elicit a biological effect (Zhang et al., *J. Biol. Chem.*, 269, 15918 (1994); Zhang et al., *Mol. Cell. Biol.*, 15, 4851 (1995)). Thus, MCP-1 (__2-8) does not exhibit properties of a classic receptor antagonist. Moreover, MCP-1 (__2-8) is unlikely to be widely useful for inhibition of MCP-1 activity in vivo, as MCP-1 (__2-8) is a large polypeptide with undesirable pharmacodynamic properties. Furthermore, it is unknown whether MCP-1 (__2-8) is active as a dominant-negative inhibitor of other chemokines associated with inflammation.

Thus, there is a need to identify agents that inhibit or enhance chemokine-induced macrophage and/or monocyte recruitment and which have desirable pharmacodynamic properties. Moreover, there is a need to identify agents that inhibit or enhance chemokine-induced activities of other cell types, such as lymphocytes, neutrophils or eosinophils. Further, there is a need to identify agents that are pan-selective chemokine inhibitors.

SUMMARY OF THE INVENTION

The invention provides a therapeutic agent comprising an isolated and purified chemokine peptide, chemokine peptide variant, chemokine analog, or a derivative thereof. Preferably, the therapeutic agent of the invention inhibits the activity of more than one chemokine, although the agent may not inhibit the activity of all chemokines to the same extent. Alternatively, a preferred therapeutic agent of the invention specifically inhibits the activity of one chemokine to a greater extent than other chemokines. Yet another preferred therapeutic agent of the invention mimics the activity of a chemokine, e.g., it acts as an agonist. Thus, therapeutic agents that are chemokine antagonists and agonists are within the scope of the invention. A further preferred therapeutic agent of the invention is an agent that does not inhibit or mimic the activity of a chemokine but binds to or near the receptor for that chemokine, i.e., it is a neutral agent.

A preferred embodiment of the invention is an isolated and purified CC chemokine peptide 3, e.g., a peptide derived from MCP-1 which corresponds to about residue 46 to about residue 67 of mature MCP-1 ("peptide 3 [MCP-1]"), a variant, an analog, or a derivative thereof. It is contemplated that chemokine peptide 3, a variant, an analog or a derivative thereof is a chemokine receptor antagonist, although these therapeutic agents may exert their effect by a different mechanism, e.g., by inhibiting the arachidonic acid pathway (e.g., inhibition of leukotriene, thromboxane, or prostaglandin synthesis or stability) or by elevating TGF-beta levels, or by more than one mechanism.

A preferred peptide 3 of the invention is a compound of formula (I):

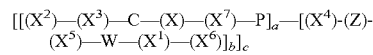

wherein $X^2$ is E, Q, D, N, L, P, I or M, wherein $X^3$ is I, V, M, A, P, norleucine or L, wherein X is A, L, V, M, P, norleucine or I, wherein $X^4$ is K, S, R, Q, N or T, wherein Z is Q, K, E, N, R, I, V, M, A, P, norleucine or L, wherein $X^7$ is D or P, wherein $X^5$ is K, E, R, S, Q, D, T, G, H or N, wherein $X^1$ is V, L, M, P, A, norleucine, or I, wherein $X^6$ is Q, N, K or R, wherein a is 0-6, wherein b is 0-6, and wherein c is 1-6, with the proviso that a and b cannot both be 0. The letters in formulas (I)-(III) that are not X, Y or Z represent peptidyl residues as shown in FIG. 9. A more preferred peptide 3 of the invention is a compound of formula (I):

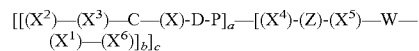

wherein $X^2$ is E, Q or M, wherein $X^3$ is I, V or L, wherein X is A, L or I, wherein $X^4$ is K, S or T, wherein Z is Q, K, E or L, wherein $X^5$ is K, E, R, S or T, wherein $X^1$ is V or I, wherein $X^6$ is Q or R, wherein a is 0-6, wherein b is 0-6, and wherein c is 1-6, with the proviso that a and b cannot both be 0.

Yet another preferred peptide 3 of the invention is a compound of formula (II):

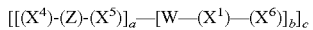

wherein $X^4$ is K, S or T, wherein Z is Q, K, E or L, wherein $X^5$ is K, E, R, S or T, wherein $X^1$ is V or I, wherein $X^6$ is Q or R, wherein a is 0-6, wherein b is 0-6, and wherein c is 1-6, with the proviso that a and b cannot both be 0.

Another preferred peptide 3 of the invention is a compound of formula (II):

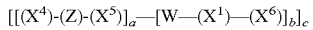

wherein $X^4$ is K, S, R, Q, N or T, wherein Z is Q, K, E, N, R, I, V, M, A, P, norleucine or L, wherein $X^5$ is K, E, R, S, Q, D, T, G, H or N, wherein $X^1$ is V, L, M, P, A, norleucine, or I, wherein $X^6$ is Q, N, K or R, wherein a is 0-6, wherein b is 0-6, and wherein c is 1-6, with the proviso that a and b cannot both be 0.

A more preferred peptide 3 of the invention is a compound of formula (XIII):

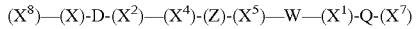

wherein X is A, L, V or I, wherein $X^2$ is P, G or L, wherein $X^4$ is K, T, R or N, wherein Z is Q, K, A or L, wherein $X^5$ is K, E, R, Q or P, wherein $X^1$ is V, L, A, M, F or I, and wherein $X^8$ and $X^7$ are independently C or absent.

A preferred embodiment of the invention is an isolated and purified CC chemokine peptide 3, e.g., a peptide derived from MCP-1 which corresponds to SEQ ID NO:1 ("peptide 3(1-12)[MCP-1]") or SEQ ID NO:7 ("peptide 3(3-12)[MCP-1]"), a fragment, a variant, an analog, or a derivative thereof. As described hereinbelow, peptide 3(1-12)[MCP-1](SEQ ID NO:1) and peptide 3(3-12)[MCP-1] (SEQ ID NO:7) are pan-chemokine inhibitors, bioavailable, and have desirable pharmacokinetics. Another preferred CC chemokine peptide 3 of the invention is peptide 3[MIP1α], and more preferably peptide 3(1-12)[MIP1α] which has an amino acid sequence corresponding to SEQ ID NO:42, a variant, an analog, a fragment or a derivative thereof.

Further preferred embodiments of the invention are a CC chemokine peptide 3 such as peptide 3(1-12)[MCP-4] (e.g., SEQ ID NO:65), peptide 3(1-12)[MCP-3](e.g., SEQ ID NO:66), peptide 3(1-12)[MCP-2] (e.g., SEQ ID NO:67), peptide 3(1-12)[eotaxin] (e.g., SEQ ID NO:68), peptide 3(1-12) [MIP1α], (e.g., SEQ ID NO:42), peptide 3(1-12)[MIP1β] (e.g., SEQ ID NO:43), peptide 3(1-12)[RANTES](e.g., SEQ ID NO:44), or a fragment thereof.

Another preferred embodiment of the invention includes a CXC chemokine peptide 3, a variant, an analog or a derivative thereof. A preferred CXC peptide 3 of the invention is a compound of formula (III):

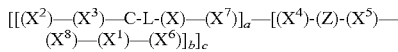

wherein $X^2$ is E or K, wherein $X^3$ is I, A, R or L, wherein X is D or N, wherein $X^7$ is Q, P or L, wherein $X^4$ is E, K, D, A or Q, wherein Z is A, R, S or E, wherein $X^5$ is P, N or K, wherein $X^8$ is F, W, R, I, M, L or A, wherein $X^1$ is L, V, Y or I, wherein $X^6$ is K or Q, wherein a is 0-6, wherein b is 0-6, and wherein c is 1-6, with the proviso that a and b cannot both be 0.

Further preferred embodiments of the invention are a CXC chemokine peptide 3 such as peptide 3(1-12)[IL8] (e.g., SEQ ID NO:40), peptide 3(1-12)[SDF-1](e.g., SEQ ID NO:38), peptide 3(1-12)[ENA-78], peptide 3(1-12)[GROα], peptide 3(1-12)[GROβ], peptide 3(1-12)[GROγ], or fragments thereof.

Yet other preferred embodiments of the invention are a $CX_2C$, $CX_3C$ or C chemokine peptide 3, a variant, an analog or a derivative thereof.

Preferably, a chemokine peptide 3, its variants, analogs or derivatives inhibits the arachidonic acid pathway, e.g., inhibits the synthesis or stability, or binding, of thromboxane, prostaglandin, leukotriene, or any combination thereof.

Another preferred embodiment of the invention includes a chemokine peptide 3 that is at least a tripeptide, a variant thereof or a derivative thereof. A preferred embodiment of the invention is the MCP-1 tripeptide KQK (i.e., peptide 3(9-12) [MCP-1], which specifically inhibits MCP-1, but not MIP1α, IL8 and SDF1α, chemokine-induced activity. Other preferred embodiments of the invention include isolated and purified chemokine tripeptides that specifically inhibit IL8, MIP1α, SDF1, MCP-1, MCP-2, MCP-3, and MIP1β, e.g., KEN, SEE, KLK, KKE, KER, TQK, and SES, respectively. A further preferred embodiment of the invention is a chemokine peptide 3 tripeptide that inhibits the activity of more than one chemokine, e.g., WVQ or WIQ. Preferably, a tripeptide of the invention is not RFK.

Yet another embodiment of the invention is a peptide which includes the amino acid sequence KXK, wherein X is an amino acid, preferably one of the twenty naturally occurring amino acids, and which peptide is a chemokine antagonist, activates TGF-beta (TGF-beta1, TGF-beta2, TGF-beta3, or a combination thereof), or a combination thereof. Preferably, the peptide increases the activation of TGF-beta1. It is preferred that a peptide which includes the amino acid sequence KXK is less than about 15, preferably about 10, and more preferably about 8 amino acid residues in length. Preferably, the peptide is not KKFK (SEQ ID NO:154) or RKPK (SEQ ID NO:155). A further embodiment of the invention is a peptide which includes a basic amino acid residue followed by phenylalanine followed by another basic residue, wherein the peptide is not RFK, is not KRFK (SEQ ID NO:156), or does not contain RFK or KRFK (SEQ ID NO:156).

Another preferred peptide of the invention is a compound of formula (VII):

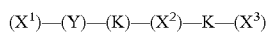

wherein $X^2$ is V, A, D, E, P, R, C, H, M, F, K, L, N, Q, Y, or I; wherein Y is absent or is an amino acid that is not R or K; and wherein $X^1$ and $X^3$ are independently 0-20 amino acid residues or absent. Preferably, $X^2$ is F, K, L, N, Q, Y, or I. More preferably, $X^2$ is F, K, L, N, Q, Y, or I, and Y, $X^1$ and $X^3$ are absent.

To identify a peptide of the invention useful in the methods of the invention, a sequence comparison of the receptor ligand under study from a variety of different species is performed, then the cross-reactivity of the receptor ligand from each species to the human receptor is assessed. The preferred sequence(s) are then obtained from the species which has the least sequence homology to the corresponding human receptor ligand, but which still binds and signals through the human receptor. The sequence of this most divergent but still functional receptor ligand is then aligned with the human sequence in order to identify regions that are conserved. Such conserved regions represent peptides of the invention useful in the methods of the invention. For example, the process has been applied to identify peptides in human MCP-1 having, for example, antagonists, agonists or neutral properties. Such peptides include, but are not limited to, peptide 3, peptide 2 (described below) and related molecules (see below).

Another example is the identification of peptides in the sequence of the cytokine TGF-beta having antagonist, agonist, or neutral receptor binding properties. The amino acid sequence of human TGF-beta1 was compared to that of *Xenopus*. Peptides identified by this method include LYID-FRQDLGWKW ("T1"; SEQ ID NO:111); HEPKGY-HANFC ("T2"; SEQ ID NO:112); VYYVGRK ("T3"; SEQ ID NO:113) and KVEQLSNMVVKSC ("T4"; SEQ ID NO:114). Biotinylated T1 bound to the TGF-beta receptor of THP-1 cells with an $ED_{50}$ of 18 μM and is a receptor neutral agent (i.e., neither agonist nor antagonist). Biotinylated T2 bound to the TGF-beta receptor of THP-1 cells with an $ED_{50}$ of 30 μM and is a weak receptor antagonist.

Also provided is an isolated and purified chemokine peptide variant, or a derivative thereof. A chemokine peptide variant has at least about 50%, preferably at least about 80%, and more preferably at least about 90% but less than 100%, contiguous amino acid sequence homology or identity to the amino acid sequence of the corresponding native chemokine, e.g., $Ser_7$ peptide 3(1-12)[MCP1] (SEQ ID NO:11) has less than 100% contiguous homology to the corresponding amino acid sequence of MCP-1, i.e., a peptide having SEQ ID NO:1. A preferred peptide 3 variant is $Leu_4Ile_{11}$peptide 3(3-12)[MCP-1], i.e., it is a ten amino acid peptide derived from peptide 3(1-12)[MCP-1] that lacks amino acid residues 1 and 2 of peptide 3(1-12)[MCP-1], and which has a leucine rather than alanine at position 4 of peptide 3(1-12)[MCP-1], and an isoleucine rather than valine at position eleven of peptide 3(1-12)[MCP-1].

The invention also provides derivatives of chemokine peptides and peptide variants. A preferred derivative is a cyclic reverse sequence D isomer (CRD) derivative of a chemokine peptide, a variant or an analog thereof of the invention. For example, CRD-$Cys_{13}Leu_4Ile_{11}$peptide 3(3-12)[MCP-1] are compounds of the invention that are particularly useful in the practice of the methods of the invention, as described hereinbelow.

Also provided are certain analogs of chemokines. In particular, analogs of chemokine peptide 3, or variants thereof are contemplated. A preferred analog of chemokine peptide 3 is an analog of WIQ, including a compound of formula (IV):

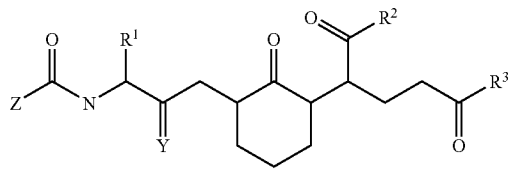

wherein $R^1$ is aryl, heteroaryl, aryl($C_1$-$C_3$)alkyl, heteroaryl ($C_1$-$C_3$)alkyl, coumaryl, coumaryl($C_1$-$C_3$)alkyl, chromanyl or chromanyl($C_1$-$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$-$C_6$)alkyl, ($C_1$-$C_6$)alkoxy, ($C_1$-$C_6$)alkanoyl, ($C_2$-$C_6$)alkanoyloxy, —C(=O)($C_1$-$C_6$)alkoxy, C(=O)$NR_gR^h$, $NR^iR^j$;

wherein $R^2$ is ($C_1$-$C_{10}$)alkyl, ($C_3$-$C_6$)cycloalkyl, ($C_3$-$C_6$) cycloalkyl($C_1$-$C_6$)alkyl, ($C_1$-$C_{10}$)alkoxy, ($C_3$-$C_6$)cycloalkyl ($C_1$-$C_6$)alkoxy or $N(R^a)(R^b)$;

wherein $R^3$ is ($C_1$-$C_{10}$)alkyl, ($C_3$-$C_6$)cycloalkyl, ($C_3$-$C_6$) cycloalkyl($C_1$-$C_6$)alkyl, ($C_1$-$C_{10}$C)alkoxy, ($C_3$-$C_6$)cycloalkyl($C_1$-$C_6$)alkoxy or $N(R^c)(R^d)$;

wherein Y is oxo or thioxo;

wherein Z is ($C_1$-$C_{15}$)alkyl, ($C_3$-$C_6$)cycloalkyl, ($C_3$-$C_6$) cycloalkyl($C_1$-$C_6$)alkyl, ($C_1$-$C_{15}$)alkoxy, ($C_3$-$C_6$)cycloalkyl ($C_1$-$C_6$)alkoxy or $N(R^e)(R^f)$; and wherein $R^a$-$R^j$ are each independently hydrogen, ($C_1$-$C_{10}$) alkyl, ($C_1$-$C_{10}$)alkanoyl, phenyl, benzyl, or phenethyl; or $R^a$ and $R^b$, $R^c$ and $R^d$, $R^e$ and $R^f$, $R^g$ and $R^h$, or $R^i$ and $R^j$ together with the nitrogen to which they are attached form a ring selected from pyrrolidino, piperidino, or morpholino; or a pharmaceutically acceptable salt thereof.

A preferred embodiment of a compound of formula (IV) includes a compound of a formula (IV) wherein $R^1$ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein $R^2$ is $N(R^a)(R^b)$; and $R^3$ is $N(R^c)(R^d)$. Yet another preferred embodiment of a compound of formula (IV) includes a compound of a formula (IV) wherein Z is ($C_1$-$C_{15}$)alkyl.

Another preferred compound of formula (IV) is wherein $R^1$ is aryl, heteroaryl, coumaryl or chromanyl; wherein $R^2$ is $N(R^a)(R^b)$; wherein $R^3$ is $N(R^c)(R^d)$; wherein Y is oxo or thioxo; wherein Z is ($C_1$-$C_{15}$)alkyl; wherein $R^a$-$R^d$ are each independently hydrogen, ($C_1$-$C_{10}$)alkyl, ($C_1$-$C_{10}$)alkanoyl, phenyl, benzyl or phenethyl; or wherein $R^a$ and $R^b$, or $R^c$ and $R^d$, together with the nitrogen to which they are attached form a pyrrolidino, piperidino or morpholino ring; or a pharmaceutically acceptable salt thereof.

A further preferred compound is a compound of formula (IV) wherein $R^1$ is indolyl; $R^2$ is $N(R^a)(R^b)$; $R^3$ is $N(R^c)(R^d)$; Y is S; Z is hydrogen; and $R^a$, $R^b$, $R^c$, and $R^d$ are each methyl.

A further preferred analog of WIQ is a compound of formula (XIV):

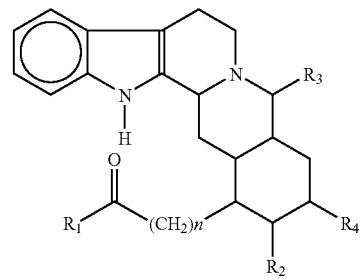

wherein $R_1$ is $O(R_a)$ wherein Ra is H, ($C_1$-$C_6$)alkyl, ($C_1$-$C_6$) alkanoyl, ($C_1$-$C_6$)alkanoyloxy, ($C_6$-$C_{10}$)aryl or ($C_6$-$C_{10}$)heteroaryl; or N(Rb)(Rc) wherein each Rb and Rc is independently H or ($C_1$-$C_6$)alkyl; $R_2$ is $O(Ra)$ wherein Ra is H, ($C_1$-$C_6$)alkyl, ($C_1$-$C_6$)alkanoyl, ($C_1$-$C_6$)alkanoyloxy, ($C_6$-$C_{10}$)aryl or ($C_6$-$C_{10}$)heteroaryl; or N(Rb)(Rc) wherein each Rb and Rc is independently H or ($C_1$-$C_6$)alkyl; $R_3$ is H, C(=O) or C(=S); $R_4$ is H, C(=O), C(=S), O(Ra), or N(Rb) (Rc); each Ra is H, ($C_1$-$C_6$)alkyl, ($C_1$-$C_6$)alkanoyloxy, ($C_1$-$C_6$)alkanoyl, ($C_6$-$C_{10}$)aryl or ($C_6$-$C_{10}$)heteroaryl; each Rb and Rc is independently H or ($C_1$-$C_6$)alkyl; and n is an integer between 0 and 6, inclusive; wherein any ($C_6$-$C_{10}$)aryl, ($C_1$-$C_6$)alkyl, ($C_1$-$C_6$)alkanoyloxy, ($C_6$-$C_{10}$)heteroaryl or ($C_1$-$C_6$) alkanoyl or the benzo ring in formula (XIV) is optionally substituted with at least one substituent (e.g. 1, 2, 3, or 4) selected from the group consisting of halo, cyano, nitro, trifluoromethyl, trifluoromethoxy, ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, methoxydioxy, hydroxy, C(=O), sulfino ($SO_2H$), sulfo ($SO_3H$), and N(Rb)(Rc) wherein or a pharmaceutically acceptable salt thereof.

Another preferred analog of WIQ is a compound of formula (XIV) wherein $R_1$ is $O(R_a)$, an amino acid, or $N(R_b)$ $(R_c)$; $R_2$ is $O(R_a)$ or $N(R_b)(R_c)$; $R_3$ is H, oxo or thioxo; $R_4$ is H, oxo, thioxo, O($R_a$) or N($R_b$)($R_c$); n is 0, 1, 2, 3, 4, 5 or 6; each $R_a$ is independently hydrogen, ($C_1$-$C_6$)alkyl, ($C_1$-$C_6$) alkanoyl, aryl, heteroaryl, or a saccharide; $R_b$ and $R_c$ are each independently H or ($C_1$-$C_6$)alkyl; wherein any ($C_1$-$C_6$)alkyl, ($C_1$-$C_6$)alkanoyl, ($C_1$-$C_6$)alkanoyloxy, aryl or heteroaryl is optionally substituted with one or more (e.g. 1, 2, 3, or 4) substituents selected from the group consisting of halo, cyano, nitro, trifluoromethyl, trifluoromethoxy, ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, hydroxy, oxo, sulfino ($SO_2H$), sulfo ($SO_3H$), and N($R_b$)($R_c$); or a pharmaceutically acceptable salt thereof.

For a compound of formula (XIV), $R_1$ can specifically be N(Rb)(Rc) wherein Rb is H and Rc is H; $R_2$ can specifically be O(Ra) wherein Ra is H, —$CH_2$C(OH)C(OH)C(OH)C(OH)CHO or —$CH_2$C(OH)C(OH)C(OH)C($NH_2$)CHO; $R_3$ can specifically be H; $R_4$ can specifically be H; and n can specifically be 1.

Specific compounds of formula (XIV) are compounds wherein $R_1$ is amino, methylamino, dimethylamino or N-linked-glutamine; $R_2$ is hydroxy, $R_3$ is hydrogen, $R_4$ is hydrogen, and n is 0 or 1; or a pharmaceutically acceptable salt thereof.

Other specific compounds of formula (XIV) are compounds wherein the benzo ring of formula (XIV) is optionally substituted.

Preferred compounds of formula (XIV) possess the ring stereochemistry of yohimbine, however, the invention also provides compounds of formula (XIV) having the alloyohimbine and the rauwolscine ring systems.

The compounds of the invention preferably exclude compounds of formula (XIV) wherein $R_1$ is a β-amino, hydroxy, or methoxy, when n is 0, $R_2$ is an α-methoxy, $R_3$ is hydrogen, and $R_4$ is hydroxy (Baxter et al., J. Am. Chem. Soc., 1990, 112, 7682-7692); compounds of formula (XIV) wherein $R_1$ is methoxy, when n is 0, $R_2$ is hydroxy or acetoxy, $R_3$ is hydrogen, and $R_4$ is hydrogen (Szantay et al., Chem. Ber., 1976, 109, 1737-1748; Toke et al., J. Org. Chem., 1973, 38, 2496-2500 and 2501-2509); compounds of formula (XIV) wherein $R_1$ is methoxy or amino, when n is 0, $R_2$ is hydroxy, $R_3$ is hydrogen, and $R_4$ is hydrogen (Toke et al., J. Org. Chem., 1973, 38, 2501-2509; Toke et al, Chem. Ber., 1969, 102, 3249-3259); and compounds of formula (XIV) wherein $R_1$ is a β-O($R_a$) or N($R_b$)($R_c$) wherein $R_a$ is hydrogen or ($C_1$-$C_6$) alkyl and $R_b$ and $R_c$ are each hydrogen, when, n is 0, $R_2$ is an α-O($R_a$) wherein $R_a$ is hydrogen, ($C_1$-$C_6$)alkyl, or ($C_1$-$C_6$) alkanoyl, $R_3$ is hydrogen, and $R_4$ is hydrogen (U.S. Pat. No. 5,807,482).

Another analog of WGQ useful in the methods of the invention is a compound of formula (X):

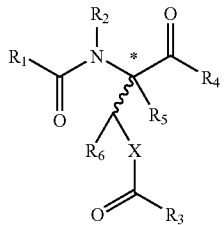

wherein: $R_1$ is ($C_1$-$C_{15}$)alkyl, ($C_2$-$C_{15}$)alkenyl, ($C_2$-$C_{15}$)alkynyl, ($C_1$-$C_{15}$)alkoxy, aryl, heteroaryl, aryl($C_1$-$C_6$)alkyl, heteroaryl($C_1$-$C_6$)alkyl; and $R_2$ is hydrogen or ($C_1$-$C_{15}$)alkyl; or $R_1$ and $R_2$ together with the atoms to which they are attached are a five or six membered heterocyclic ring comprising four or five carbon atoms, optionally substituted on carbon with oxo, and optionally substituted with a fused benzo group; $R_3$ is hydroxy, ($C_1$-$C_6$)alkoxy, or N($R_a$)($R_b$); and $R_4$ is hydroxy, ($C_1$-$C_6$)alkoxy, or N($R_a$)($R_b$); or $R_3$ and $R_4$ together with the atoms to which they are attached are a five or six membered heterocyclic ring comprising four or five carbon atoms and N($R_c$); $R_5$ is hydrogen or ($C_1$-$C_6$)alkyl; $R_6$ is hydrogen or oxo; X is a direct bond, N(H), or methylene (—$CH_2$—); each $R_a$ and $R_b$ is independently hydrogen, ($C_1$-$C_6$)alkyl, ($C_1$-$C_6$)alkanoyl, ($C_1$-$C_6$)alkoxycarbonyl, aryl, aryl($C_1$-$C_6$)alkyl, aryl ($C_1$-$C_6$)alkoxy, aryl($C_1$-$C_6$)alkanoyl, aryl($C_1$-$C_6$)alkoxycarbonyl, heteroaryl, heteroaryl($C_1$-$C_6$)alkyl, heteroaryl($C_1$-$C_6$) alkoxy, heteroaryl($C_1$-$C_6$)alkanoyl, or heteroaryl($C_1$-$C_6$) alkoxycarbonyl; and $R_c$ is hydrogen or ($C_1$-$C_6$)alkyl; wherein any ($C_1$-$C_{15}$)alkyl, ($C_2$-$C_{15}$)alkenyl, ($C_2$-$C_{15}$)alkynyl, or ($C_1$-$C_{15}$)alkoxy of $R_1$ is optionally substituted with one or more substituents selected from the group consisting of halo, cyano, nitro, carboxy, trifluoromethyl, trifluoromethoxy, ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, hydroxy, oxo, and N($R_a$)($R_b$); and wherein any aryl, heteroaryl, or benzo of $R_1$, $R_a$, and $R_b$, is optionally substituted with 1, 2, 3, or 4 substituents independently selected from the group consisting of halo, cyano, hydroxy, nitro, trifluoromethyl, trifluoromethoxy, ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, sulfino ($SO_2H$), sulfo ($SO_3H$), and methylenedioxy; or a pharmaceutically acceptable salt thereof.

A preferred group of compounds of formula (X) are compounds wherein $R_1$ is 9-decenyl, tert-butoxy, phenyl, 4-hydroxyphenyl, tert-butylcarbonyl-aminomethyl, benzoylaminomethyl, 4-hydroxybenzyloxycarbonylaminomethyl; and $R_2$ is hydrogen; or $R_1$ and $R_2$ together with the atoms to which they are attached are 2-(1,3-dioxo-1H-isoindolyl); $R_3$ is amino or hydroxy; and $R_4$ is hydroxy, amino, or 4-hydroxybenzylamino; or $R_3$ and $R_4$ together with the atoms to which they are attached are a six membered heterocyclic ring comprising five carbon atoms and N(H); $R_5$ is hydrogen; and $R_6$ is hydrogen. Preferably the center marked * has the (S) absolute configuration in a compound of formula (X).

A preferred group of compounds of formula (X) are compounds wherein $R_5$ is ($C_1$-$C_6$)alkyl.

Another analog of WGQ useful in the methods of the invention is a compound of formula (XI):

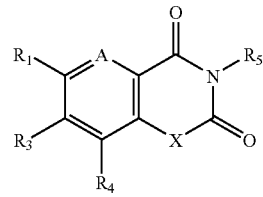

wherein: A is C($R_2$) or N; $R_1$ is ($C_1$-$C_{15}$)alkyl, ($C_2$-$C_{15}$)alkenyl, ($C_2$-$C_{15}$)alkynyl, ($C_1$-$C_{15}$)alkoxy, ($C_1$-$C_{15}$)alkanoyl, ($C_2$-$C_{15}$)alkenylcarbonyl, ($C_2$-$C_{15}$)alkynylcarbonyl, ($C_1$-$C_{15}$)alkoxycarbonyl, or N($R_a$)($R_b$); $R_2$, $R_3$, and $R_4$ are each independently hydrogen, halo, cyano, hydroxy, nitro, trifluoromethyl, trifluoromethoxy, ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, sulfino ($SO_2H$), or sulfo ($SO_3H$); $R_5$ is hydrogen or ($C_1$-$C_6$)alkyl; X is a direct bond or methylene (—$CH_2$—); each $R_a$ and $R_b$ is independently hydrogen, ($C_1$-$C_{15}$)alkyl, ($C_2$-$C_{15}$) alkenyl, ($C_2$-$C_{15}$)alkynyl, ($C_1$-$C_{15}$)alkanoyl, ($C_1$-$C_{15}$) alkoxycarbonyl, ($C_2$-$C_{15}$)alkenylcarbonyl, ($C_2$-$C_{15}$)alkynylcarbonyl; wherein any $(C_1-C_{15})$alkyl, $(C_2-C_{15})$alkenyl, $(C_2-C_{15})$alkynyl, or $(C_1-C_{15})$alkoxy of $R_1$ is optionally substituted with one or more substituents (e.g. 1, 2, 3, or 4) selected from the group consisting of halo, cyano, nitro, carboxy, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, hydroxy, oxo, and $N(R_a)(R_b)$; or a pharmaceutically acceptable salt thereof.

For a compound of formula (XI) $R_1$ can specifically be $(C_6-C_{15})$alkenyl, $(C_6-C_{15})$alkenylcarbonyl, or $N(R_a)(R_b)$, wherein $R_a$ is hydrogen and $R_b$ is $(C_6-C_{15})$alkenyl, or $(C_6-C_{15})$alkenylcarbonyl; or $R_1$ can specifically be 10-undecenoylamino or 9-decenoyl; $R_2$ can specifically be hydrogen; $R_3$ can specifically be sulfo; $R_4$ can specifically be hydrogen; and $R_5$ can specifically be hydrogen.

An analog of WAQ useful in the methods of the invention is a compound of formula (XII):

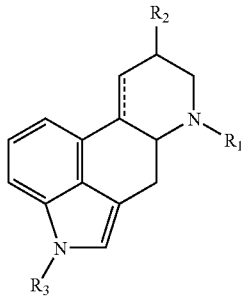

wherein: $R_1$ is hydrogen or $(C_1-C_6)$alkyl; $R_2$ is hydrogen, $(C_1-C_6)$alkyl, $(C_1-C_6)$alkanoyl, an amino acid, (amino acid) $(C_1-C_6)$alkyl, (amino acid) $(C_1-C_6)$alkanoyl, or $N(R_a)(R_b)$, wherein each $R_a$ and $R_b$ is independently hydrogen, $(C_1-C_6)$ alkanoyl, an amino acid, phenyl, benzyl or phenethyl; $R_3$ is hydrogen, $(C_1-C_6)$alkyl, $(C_1-C_6)$alkanoyl, phenyl, benzyl, or phenethyl; and the bond represented by—is absent or present; wherein the benz ring of formula (XII) may optionally be substituted with 1, 2, or 3 substituents independently selected from the group consisting of halo, cyano, hydroxy, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, sulfino ($SO_2H$), sulfo ($SO_3H$), and methylenedioxy; or a pharmaceutically acceptable salt thereof.

A specific compound of formula (XII) is a compound of the following formula:

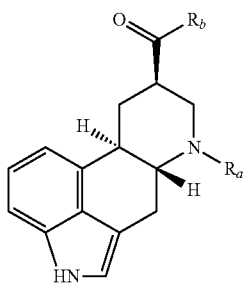

wherein: $R_a$ is hydrogen or $(C_1-C_6)$alkyl; and $R_b$ is hydrogen or an amino acid; or a pharmaceutically acceptable salt thereof.

For a compound of formula (XII) $R_1$ can specifically be methyl or ethyl; and $R_2$ can specifically be glutamine linked through the amine nitrogen to form an amide.

Specific compounds of formula (XII) are compounds wherein the carbon bearing $R_2$ has the R absolute configuration, however, the invention also provides the corresponding compounds of the S absolute configuration.

Specific compounds of formula (XII) are compounds wherein $R_2$ is —C(=O)—(N-glutamine), or $N(R_a)(R_b)$, wherein $R_a$ is hydrogen and $R_b$ is glutamine linked to N through the carboxy terminus to form an amide.

Specific compounds of formula (XII) are compounds wherein $R_3$ is hydrogen.

Other compounds of the invention include compounds of formula (VIII):

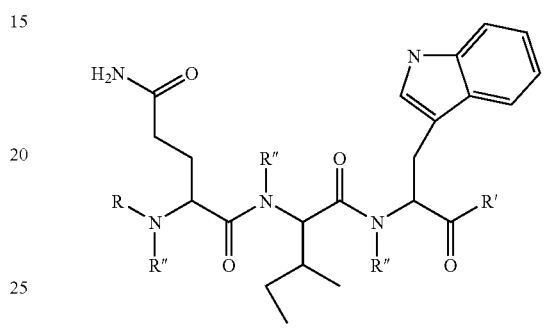

wherein
R is $(C_1-C_6)$alkyl, $(C_1-C_6)$alkanoyl, aryl, heteroaryl, $(C_1-C_6)$alkoxycarbonyl, or benzyloxycarbonyl, wherein aryl, heteroaryl, and the phenyl ring of the benzyloxycarbonyl can optionally be substituted with one or more (e.g. 1, 2, 3, or 4), halo, hydroxy, cyano nitro, trifluoromethyl, trifluoromethoxy, $(C_1-C_6)$alkyl, $(C_1-C_6)$alkoxy, $(C_1-C_6)$alkanoyl, $(C_2-C_6)$alkanoyloxy or $(C_1-C_6)$alkoxycarbonyl;

R' is $(C_1-C_6)$alkoxy, aryloxy, or $NR_aR_b$, wherein $R_a$ and $R_b$ are each independently hydrogen, $(C_1-C_6)$alkyl, aryl, benzyl, or phenethyl; or $R_a$, and $R_b$ together with the nitrogen to which they are attached are a 5-6 membered heterocyclic ring (e.g. pyrrolidino, piperidino, or morpholino); and each R" is independently hydrogen, $(C_1-C_6)$alkyl, phenyl, benzyl, or phenethyl;

or a pharmaceutically acceptable salt thereof. Preferably, R is benzyloxycarbonyl and R' is dimethyl amino or diethylamine, or R is benzyloxycarbonyl; and R' is benzyloxy.

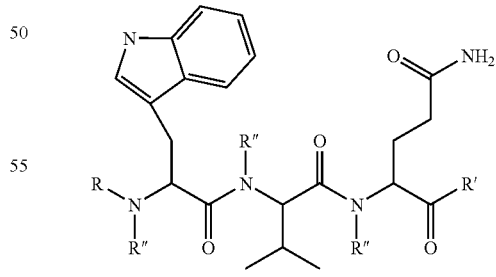

Other compounds of the invention include compounds of formula (IX): wherein
R is $(C_1-C_6)$alkyl, $(C_1-C_6)$alkanoyl, aryl, heteroaryl, $(C_1-C_6)$alkoxycarbonyl, or benzyloxycarbonyl, wherein aryl, heteroaryl, and the phenyl ring of the benzyloxycarbonyl can optionally be substituted with one or more (e.g. 1, 2, 3, or 4), halo, hydroxy, cyano nitro, trifluoromethyl, trifluoromethoxy, $(C_1-C_6)$alkyl, $(C_1-C_6)$alkoxy, $(C_1-C_6)$alkanoyl, $(C_2-C_6)$alkanoyloxy or $(C_1-C_6)$alkoxycarbonyl;

R' is $(C_1-C_6)$alkoxy, aryloxy, or $NR_aR_b$, wherein $R_a$ and $R_b$ are each independently hydrogen, $(C_1-C_6)$alkyl, aryl, benzyl, or phenethyl; or $R_a$, and $R_b$ together with the nitrogen to which they are attached are a 5-6 membered heterocyclic ring (e.g. pyrrolidino, piperidino, or morpholino); and each R" is independently hydrogen, $(C_1-C_6)$alkyl, phenyl, benzyl, or phenethyl;

or a pharmaceutically acceptable salt thereof. Preferably, R is benzyloxycarbonyl and R' is dimethyl amino or diethylamine, or R is benzyloxycarbonyl; and R' is benzyloxy.

Another preferred analog of chemokine peptide 3 is an analog of KXK. Thus, the invention includes a compound of formula (V):

wherein
$R^4$ is $NR_kR_l$; $R^5$ is $NR_mR_n$; $R^6$ is $NR_oR_p$; $R^7$ is the side chain of a natural or unnatural amino acid or is $-(CH_2)_2C(=O)NR_qR_r$; $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues; $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl; $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues; $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; wherein $R_s$ are $R_t$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl or the C-terminal residue of an amino acid or a peptide of 2 to about 25 amino acid residues; and $R_q$ are $R_r$ are each independently hydrogen, $(C_1-C_{10})$alkyl, or $(C_3-C_6)$cycloalkyl.

Preferably, $R^7$ is $-(CH_2)_2C(=O)NR_qR_r$.

Preferably, $R^7$ is methyl, 3-guanidinopropyl, aminocarbonylmethyl, carboxymethyl, mercaptomethyl, (2-carboxyl-2-aminoethyl)dithiomethyl, 2-carboxyethyl, 2-(aminocarbonyl)ethyl, hydrogen, 5-imadazoylmethyl, 4-amino-3-hydroxy propyl, 2-butyl, 2-methylprop-1-yl, 4-amino butyl, 2-(methylthio)ethyl, benzyl, hydroxy methyl, 1-hydroxyethyl, 3-indolylmethyl, 4-hydroxybenzyl, or isopropyl.

More preferably, $R^7$ is hydrogen, benzyl, 4-hydroxybenzyl, methyl, 2-hydroxy methyl, or mercaptomethyl.

A preferred compound of formula (V) includes an analog of KGK, KFK, KYK, KAK, KSK, KCK or KQK. For example, an analog of KQK includes a compound of formula (V):
wherein $R^4$ is $NR_kR_l$; $R^5$ is $NR_mR_n$; $R^6$ is $NR_oR_p$; $R^7$ is $NR_qR_r$; $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues; $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl; $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues; $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; $R_s$ are $R_t$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl or the C-terminal residue of an amino acid or a peptide of 2 to about 25 amino acid residues; and $R_q$ are $R_r$ are each independently hydrogen, $(C_1-C_{10})$alkyl, or $(C_3-C_6)$cycloalkyl.

Another preferred analog of chemokine peptide 3 is an analog of WVQ.

Thus, the invention provides a compound of formula (VI):
wherein
$R^{10}$ is $NR^iR^j$; $R^{11}$ is aryl, heteroaryl, aryl$(C_1-C_3)$alkyl, heteroaryl$(C_1-C_3)$alkyl, coumaryl, coumaryl$(C_1-C_3)$alkyl, chromanyl or chromanyl$(C_1-C_3)$alkyl; wherein any aryl or heteroaryl group, or the benz-ring of any coumaryl or chromanyl group may optionally be substituted with one, two or three substituents selected from the group consisting of halo, nitro, cyano, hydroxy, $(C_1-C_6)$alkyl, $(C_1-C_6)$alkoxy, $(C_1-C_6)$alkanoyl, $(C_2-C_6)$alkanoyloxy, $-C(=O)(C_1-C_6)$alkoxy, $C(=O)NR^gR^h$, $NR^eR^f$; $R^{12}$ is $(C_1-C_6)$alkyl; $R^{13}$ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, hydroxy, or $N(R^a)(R^b)$; $R^{14}$ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^c)(R^d)$; Y is oxo or thioxo;

wherein $R^a$-$R^j$ are each independently hydrogen, $(C_1$-$C_{10})$ alkyl, $(C_1$-$C_{10})$alkanoyl, phenyl, benzyl, or phenethyl; or $R^a$ and $R^b$, $R^c$ and $R^d$, $R^e$ and $R^f$, $R^g$ and $R^h$ or $R^i$ and $R^j$ together with the nitrogen to which they are attached form a ring selected from pyrrolidino, piperidino, or morpholino; or a pharmaceutically acceptable salt thereof. Preferably, $R^{10}$ is amino; $R^{11}$ is 2-benzimidazolyl; $R^{12}$ is $(C_1$-$C_6)$alkyl; $R^{13}$ is hydroxy; and $R^{14}$ is amino.

Also provided is a compound of formula (VI):

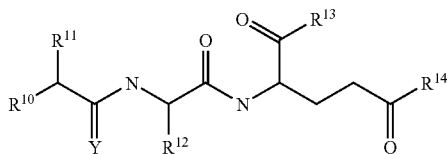

wherein
$R^{10}$ is $NR^iR^j$;
$R^{11}$ is aryl, heteroaryl, aryl($C_1$-$C_3$)alkyl, heteroaryl($C_1$-$C_3$) alkyl, coumaryl, coumaryl($C_1$-$C_3$)alkyl, chromanyl or chromanyl($C_1$-$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, $(C_1$-$C_6)$alkyl, $(C_1$-$C_6)$alkoxy, $(C_1$-$C_6)$alkanoyl, $(C_2$-$C_6)$alkanoyloxy, —C(=O)($C_1$-$C_6)$alkoxy, C(=O)$NR^gR^h$, $NR^eR^f$;
$R^{12}$ is $(C_1$-$C_6)$alkyl;
$R^{13}$ is $(C_1$-$C_{10})$alkyl, $(C_3$-$C_6)$cycloalkyl, $(C_3$-$C_6)$cycloalkyl($C_1$-$C_6)$alkyl, $(C_1$-$C_{10})$alkoxy, $(C_3$-$C_6)$cycloalkyl $(C_1$-$C_6)$alkoxy, hydroxy, or $N(R^a)(R^b)$;
$R^{14}$ is $(C_1$-$C_{10})$alkyl, $(C_3$-$C_6)$cycloalkyl, $(C_3$-$C_6)$cycloalkyl($C_1$-$C_6)$alkyl, $(C_1$-$C_{10})$alkoxy, $(C_3$-$C_6)$cycloalkyl $(C_1$-$C_6)$alkoxy or $N(R^c)(R^d)$;
Y is oxo or thioxo;
wherein $R^a$-$R^j$ are each independently hydrogen, $(C_1$-$C_{10})$ alkyl, $(C_1$-$C_{10})$alkanoyl, phenyl, benzyl, or phenethyl; or $R^a$ and $R^b$, $R^c$ and $R^d$, $R^e$ and $R^f$, $R^g$ and $R^h$ or $R^i$ and $R^j$ together with the nitrogen to which they are attached form a ring selected from pyrrolidino, piperidino, or morpholino; or a pharmaceutically acceptable salt thereof.

Yet another analog of chemokine peptide 3 is an analog of WGQ. Thus, the invention provides a compound of formula (XV):

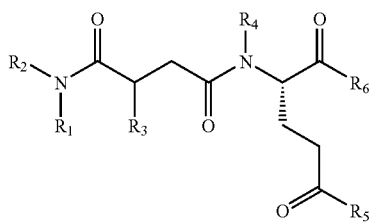

wherein $R_1$ is aryl, heteroaryl, aryl($C_1$-$C_{10}$)alkyl, aryl($C_1$-$C_{10}$)alkanoyl, heteroaryl($C_1$-$C_{10}$)alkyl, or heteroaryl($C_1$-$C_{10}$)alkanoyl; $R_2$ is hydrogen, $(C_1$-$C_{15})$alkyl, $(C_3$-$C_8)$cycloalkyl, $(C_3$-$C_8)$cycloalkyl($C_1$-$C_{10})$alkyl, aryl, or aryl($C_1$-$C_{10})$alkyl; $R_3$ is hydrogen, or $(C_1$-$C_{10})$alkyl, $R_4$ is hydrogen, or $(C_1$-$C_{10})$alkyl; $R_5$ is $N(R^a)(R^b)$; $R_6$ is $N(R^a)(R^b)$; and each $R^a$ and $R^b$ is independently hydrogen, $(C_1$-$C_{10})$alkyl, $(C_1$-$C_{10})$alkanoyl, or aryl($C_1$-$C_{10})$alkyl; or $R^a$ and $R^b$ together with the nitrogen to which they are attached form a pyrrolidino, piperidino or morpholino ring; wherein any aryl or heteroaryl is optionally substituted with 1, 2, 3, or 4 substituents independently selected from the group consisting of halo, cyano, hydroxy, nitro, trifluoromethyl, trifluoromethoxy, $(C_1$-$C_6)$alkyl, $(C_1$-$C_6)$alkoxy, $(C_1$-$C_6)$alkanoyl, $(C_1$-$C_6)$alkanoyloxy, $(C_1$-$C_6)$alkoxycarbonyl, and methylenedioxy; or a pharmaceutically acceptable salt thereof.

For a compound of formula (XV), $R_1$ can specifically be 3-indolylmethyl; $R_2$ can specifically be isopropyl, tert-butyl, or phenyl; $R_3$ can specifically be methyl; $R_4$ can specifically be hydrogen; $R_5$ can specifically be amino; and $R_6$ can specifically be dimethylamino, benzylamino, or hydroxybenzylamino.

Yet another analog of WGQ useful in the methods of the invention is a compound of formula (XIX):

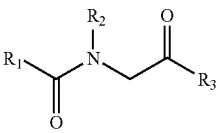

wherein: $R_1$ is $(C_7$-$C_{15})$alkyl, $(C_7$-$C_{15})$alkenyl, $(C_7$-$C_{15})$alkynyl, $(C_7$-$C_{15})$alkoxy, aryl($C_5$-$C_{10})$alkyl, or heteroaryl($C_5$-$C_{10})$alkyl; $R_2$ is hydrogen or $(C_1$-$C_{15})$alkyl; and $R_3$ is hydroxy, $(C_1$-$C_6)$alkoxy, or $N(R_a)(R_b)$, wherein each $R_a$ and $R_b$ is independently hydrogen, $(C_1$-$C_6)$alkyl, $(C_1$-$C_6)$alkanoyl, $(C_1$-$C_6)$alkoxycarbonyl, aryl, aryl($C_1$-$C_6)$alkyl, aryl $(C_1$-$C_6)$alkoxy, aryl($C_1$-$C_6)$alkanoyl, aryl($C_1$-$C_6)$alkoxycarbonyl, heteroaryl, heteroaryl($C_1$-$C_6)$alkyl, heteroaryl($C_1$-$C_6)$ alkoxy, heteroaryl($C_1$-$C_6)$alkanoyl, or heteroaryl($C_1$-$C_6)$ alkoxycarbonyl; wherein any $(C_7$-$C_{15})$alkyl, $(C_7$-$C_{15})$ alkenyl, $(C_7$-$C_{15})$alkynyl, or $(C_7$-$C_{15})$alkoxy of $R_1$ is optionally substituted with one or more substituents selected from the group consisting of halo, cyano, nitro, carboxy, trifluoromethyl, trifluoromethoxy, $(C_1$-$C_6)$alkyl, $(C_1$-$C_6)$ alkoxy, $(C_1$-$C_6)$alkanoyl, $(C_1$-$C_6)$alkanoyloxy, $(C_1$-$C_6)$ alkoxycarbonyl, hydroxy, oxo, and $N(R_a)(R_b)$; and wherein any aryl or heteroaryl of $R_1$, $R_a$, and $R_b$, is optionally substituted with 1, 2, 3, or 4 substituents independently selected from the group consisting of halo, cyano, hydroxy, nitro, trifluoromethyl, trifluoromethoxy, $(C_1$-$C_6)$alkyl, $(C_1$-$C_6)$ alkoxy, $(C_1$-$C_6)$alkanoyl, $(C_1$-$C_6)$alkanoyloxy, $(C_1$-$C_6)$ alkoxycarbonyl, sulfino ($SO_2H$), sulfo ($SO_3H$), and methylenedioxy; or a pharmaceutically acceptable salt thereof.

A preferred group of compounds of formula (XIX) are compounds wherein $R_1$ is 9-decenyl, $R_2$ is hydrogen, and $R_3$ is hydroxy, amino, or methoxy. A more preferred compound of formula (XIX) is a compound wherein $R_1$ is 9-decenyl, $R_2$ is hydrogen, and $R_3$ is amino; or a pharmaceutically acceptable salt thereof.

It is envisioned that the therapeutic agents of the invention include compounds having a chiral center that can be isolated in optically active and racemic forms.

Also provided are pharmaceutical compositions, delivery systems, and kits comprising the therapeutic agents of the invention.

The invention further provides methods to treat chemokine-associated indications. For example, the invention provides a method of preventing or inhibiting an indication associated with chemokine-induced activity. The method comprises administering to a mammal afflicted with, or at risk of, the indication an amount of a chemokine peptide 3, a fragment thereof, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof, effective to prevent or inhibit said activity. Preferably, the peptide is not an IL-8 peptide, a NAP-2 peptide, or a PF4 peptide. Preferably, the administration is effective to inhibit the activity of more than one chemokine (i.e., the peptide is a pan-selective inhibitor). Preferred pan-chemokine inhibitors are analogs of WVQ, e.g., YII (see page 54), analogs of WIQ, analogs of WGQ, e.g., All (see page 56), $Leu_4Ile_{11}$peptide 3(3-12)[MCP-1], $Leu_4Ile_{11}$peptide 3(1-12)[MCP-1] and CRD-$Cys_{13}Leu_4Ile_{11}$peptide 3(3-12). These agents are useful to treat indications such as multiple sclerosis, asthma, psoriasis, allergy, rheumatoid arthritis, organ transplant rejection, and autoimmune disorders. Preferred chemokine peptides useful to treat or inhibit these indications include peptide 2 and/or peptide 3 from MCP-1, MCP-2, MCP-3, MCP-4, RANTES, MIP1α, ENA78, MIG, GROα, GROβ, GROγ, GCP-1, HCC-1, I-309, SCM-1, eotaxin, IP10, MIPβ and SDF-1.

Moreover, as peptide 3, its variants and derivatives may decrease Th2 responses and increase Th1 responses, these compounds may be particularly useful to treat or prevent specific diseases in which a decrease in Th2 response and an increase in Th1 response is indicated.

The invention also provides a method of preventing or inhibiting an indication associated with histamine release from basophils or mast cells. The method comprises administering to a mammal at risk of, or afflicted with, the indication an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof.

Also provided is a method of preventing or inhibiting an indication associated with monocyte, macrophage, neutrophil, B cell, T cell or eosinophil recruitment, or B cell or T cell activation or proliferation. The method comprises administering an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. For example, a chemokine peptide 3, a variant thereof, or a derivative thereof may be useful to prevent or treat autoimmune or granulomatous indications.

Further provided is a therapeutic method to prevent or treat vascular indications, comprising: administering to a mammal in need of such therapy an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof, wherein the indication is coronary artery disease, myocardial infarction, unstable angina pectoris, atherosclerosis or vasculitis, e.g., Behçet's syndrome, giant cell arteritis, polymyalgia rheumatica, Wegener's granulomatosis, Churg-Strauss syndrome vasculitis, Henoch-Schönlein purpura and Kawasaki disease. Preferred chemokine peptides for this embodiment of the invention include chemokine peptides of MCP-1, RANTES, GROα, GROβ, GROγ, GCP-1, HCC-1, I-309, SCM-1, MIP1α, IP10, MCP-4, and MIP1β.

The invention also provides a method to prevent or treat an autoimmune disorder. The method comprises administering to a mammal in need of said therapy an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. A preferred variant of peptide 3 useful to prevent or treat autoimmune disorders is $Leu_4Ile_{11}$peptide 3(1-12)[MCP-1] (SEQ ID NO:14) or peptide 3 having WVQ. A preferred chemokine peptide 3 for use in preventing or treating multiple sclerosis includes SEE and peptide 3(1-14)[MIP1α] (SEQ ID NO:42). Other preferred peptides are chemokine peptides of RANTES.

Further provided is a method to modulate the chemokine-induced activity of macrophage, B cells, T cells or other hematopoietic cells, e.g., neutrophils, eosinophils or mast cells, at a preselected physiological site. The method comprises administering a dosage form comprising an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof, wherein the dosage form is linked, either covalently or noncovalently, to a targeting moiety. The targeting moiety binds to a cellular component at the preselected physiological site, e.g., to an antigen that is specific for tumor cells.

Moreover, it is also envisioned that an agent of the invention may be a targeting moiety, as some of the agents are selective chemokine inhibitors, rather than pan-chemokine inhibitors. For example, an agent of the invention, e.g., peptide 3, may be useful in the targeted delivery of an isotope or other cytotoxic molecule to certain cells. Similarly, an agent of the invention that specifically targets a particular cell type may be useful in diagnostics. Thus, these agents can be radiolabeled (Chianelli et al., *Nucl. Med. Comm.*, 18, 437 (1997)), or labeled with any other detectable signal, such as those useful in diagnostic imaging (e.g., MRI and CAT) to image sites of inflammation in disorders like rheumatoid arthritis and diabetes mellitus (type I).

The invention also provides a therapeutic method to prevent or inhibit asthma. The method comprises administering to a mammal in need of such therapy an effective amount of an agent that inhibits airway reactivity and a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. As described hereinbelow in Example 12, a peptide of the invention inhibited cellular inflammation and IgE responses in the lung of mice exposed to ovalbumin.

Preferably, in this embodiment of the invention, a therapeutic agent is administered to the upper and/or lower respiratory tract. Preferred peptides useful in this embodiment of the invention are chemokine peptides of RANTES, MCP-1 and MIP1α.

Further provided is a therapeutic method to prevent or inhibit viral, e.g., poxvirus, herpesvirus (e.g., *Herpesvirus samiri*), cytomegalovirus (CMV) or lentivirus, infection or replication. The method comprises administering to a mammal in need of such therapy an effective amount of a chemokine peptide 3, a variant thereof, a derivative thereof, a compound of formula (IV), or a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. Preferably, the therapeutic agents are employed to prevent or treat HIV. More preferably, the agent is administered before, during or after the administration of an anti-viral agent, e.g., for HIV AZT, a non-nucleoside reverse transcriptase inhibitor, a protease inhibitor or a combination thereof. It is also envisioned that a combination of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), or a compound of formula (XIX) may be useful in the anti-viral methods and compositions of the invention. Preferred chemokine peptides useful to prevent or inhibit viral infection are those from IP10, MIP1α, MIP1β, SDF-1, IL-8, GROα, GROβ, GROγ, GCP-1, HCC-1, I-309, SCM-1, RANTES, and MCP-1.

A therapeutic method to prevent or treat low bone mineral density is also provided. The method comprises administering to a mammal in need of such therapy an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. A preferred derivative of a variant of peptide 3 to prevent or treat low mineral bone density is CRD-$Cys_{13}Leu_4Ile_{11}$peptide 3(3-12)[MCP-1]. A preferred fragment of SEQ ID NO:1 useful in preventing or treating low mineral bone density is KQK.

Also provided is a method of suppressing tumor growth in a vertebrate animal comprising administering to said vertebrate a therapeutically effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. Preferably, the method increases or enhances maerophage, B cell-, T cell- or other immune cell-associated activity at a tumor site. A preferred peptide for use in this embodiment of the invention is a MCP-1 peptide.

Further provided is a method for preventing or treating rheumatoid arthritis in a mammal, comprising: administering to the mammal an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. For this embodiment of the invention, a preferred peptide is a MCP-1, MIP1α, MIP1β, GROα, and ENA78 peptide.

Also provided is a method to prevent or treat organ transplant rejection, and/or delayed organ or graft function, e.g., in renal transplant patients. The method comprises administering an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof.

Further provided is a method for preventing or treating psoriasis in a mammal, comprising: administering to the mammal an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. Preferred peptides to prevent or treat psoriasis are peptides of MCP-1, RANTES, MIP1α, MIG, IP10, GROβ, GROα, GROγ, GCP-1, HCC-1, I-309, SCM-1, or MCP-3. A preferred derivative to prevent or treat psoriasis is a CRD-derivative of peptide 3.

Also provided is a method to enhance wound healing. The method comprises administering to a mammal an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof.

The invention also provides a method to modulate a chemokine-induced activity, e.g., to treat malaria, tuberculosis or other disorders caused by intracellular parasites. The method comprises administering to a mammal an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof.

Further provided is a method for preventing or treating an allergy in a mammal, comprising: administering to the mammal an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), a compound of formula (XIV), a compound of formula (XV), a compound of formula (XIX), or a combination thereof. Preferred peptides to prevent or treat allergies include peptides of RANTES, MIP1α, MCP-1, MCP-2, MCP-3, MCP-4, eotaxin or MIP1β.

Yet another embodiment of the invention is a method to prevent or inhibit an indication associated with elevated TNF-α. The method comprises administering an effective amount of a chemokine peptide 3, a variant thereof, a derivative thereof, a compound of formula (IV), a compound of formula (V), a compound of formula (VI), a compound of formula (VII), a compound of formula (VIII), a compound of formula (IX) a compound of formula (X), a compound of formula (XI), a compound of formula (XII), a compound of formula (XIV), a compound of formula (XV), a compound of formula (XIX), or a combination thereof.

The invention also provides methods in which the nucleic acid molecules of the invention are administered to a mammal afflicted with, or at risk of, an indication associated with a chemokine-induced activity.

The invention also provides a method to identify a region of a chemokine receptor which binds to a chemokine peptide, a variant, derivative or analog thereof. The method comprises contacting a chemokine receptor with an amount of the chemokine peptide, a variant, derivative or analog thereof so as to result in a complex between the receptor and the chemokine peptide, a variant, derivative or analog thereof. Then it is determined which region of the receptor is bound to the chemokine peptide, variant, derivative or analog thereof.

The invention further provides a method to identify a molecule which binds to a region of a chemokine receptor that is bound by a specific chemokine peptide, a variant, derivative or analog thereof. The method contacting the region with a population of molecules, and detecting or determining whether at least one molecule of the population of molecules specifically binds to the region.

Yet another embodiment of the invention is a method to identify a molecule that binds to a chemokine receptor but which molecule does not form a heterodimer with at least one chemokine that binds to the receptor. The method comprises contacting the chemokine receptor with the molecule so as to form a complex between the receptor and the molecule. The complex is contacted with at least one chemokine. Then it is determined whether the molecule in the complex forms a heterodimer with the chemokine.

A further embodiment of the invention also is a method to identify a molecule that binds to a chemokine receptor but which molecule does not form a heterodimer with a chemokine that binds to the receptor. The method comprises contacting the chemokine receptor with the molecule and at least one chemokine, and detecting or determining whether the molecule forms a heterodimer with the chemokine.

The invention also provides a method to identify an agent that inhibits antigen-induced recall response. The method comprises administering to a mammal which is sensitized to an antigen an agent selected from 1) a compound of formula (XIV), (X), (XI), or (XII); or 2) a saccharide conjugate of a chemokine peptide 3, a variant thereof, a derivative thereof, a compound of formula (IV), a compound of formula (V), a compound of formula (VI), a compound of formula (X), a compound of formula (XI), a compound of formula (XII), a compound of formula (XIV), or a compound of formula (XIX); or a pharmaceutically acceptable salt thereof; or a combination thereof. It is then determined whether the agent inhibits the recall response.

The invention further provides a method of preventing or inhibiting a recall response to an antigen, comprising: administering to a mammal which is sensitized to the antigen an amount of an agent effective to inhibit or decrease IL-4 levels in the mammal or to inhibit or decrease immunoglobulin levels in the mammal; wherein the agent is selected from: 1) a compound of formula (XIV), (X), (XI), (XIX), or (XII); and 2) a saccharide conjugate of a chemokine peptide 3, a variant thereof, a derivative thereof, a compound of formula (IV), a compound of formula (V), a compound of formula (VI), a compound of formula (X), a compound of formula (XI), a compound of formula (XII), a compound of formula (XIV), or a compound of formula (XIX); or a pharmaceutically acceptable salt thereof; or a combination thereof.

Yet a further embodiment of the invention is a method of suppressing the immune response of a mammal subjected to a therapy which employs an immunogenic therapeutic molecule, comprising: administering to the mammal an amount of an agent effective to inhibit antigen-induced recall response to the immunogenic therapeutic molecule; wherein the agent is selected from: 1) a compound of formula (XIV), (X), (XI), (XIX), and (XII); and 2) a saccharide conjugate of a chemokine peptide 3, a variant thereof, a derivative thereof, a compound of formula (IV), a compound of formula (V), a compound of formula (VI), a compound of formula (X), a compound of formula (XI), a compound of formula (XII), a compound of formula (XIV), or a compound of formula (XIX); or a pharmaceutically acceptable salt thereof; or a combination thereof.

The invention also provides a method to identify an agent which inhibits chemokine activity but does not compete with native chemokine for its receptor. The method comprises contacting cells with the agent, wherein the cells comprise receptors that bind native chemokine; and detecting or determining whether the agent specifically binds to a receptor which is not the receptor which binds native chemokine and inhibits chemokine activity.

The invention also provides a method to prevent or inhibit stroke, comprising: administering to a mammal an effective amount of: 1) a compound of formula (XIV), (X), (XI), (XIX), or (XII); or 2) a saccharide conjugate of a chemokine peptide 3, a variant thereof, a derivative thereof, a compound of formula (IV), a compound of formula (V), a compound of formula (VI), a compound of formula (X), a compound of formula (XI), a compound of formula (XII), a compound of formula (XIV), or a compound of formula (XIX); or a pharmaceutically acceptable salt thereof; or a combination thereof.

The invention further provides a method to increased in vivo half-life of compound selected from chemokine peptide 3, a variant thereof, a derivative thereof, a compound of formula (IV), a compound of formula (V), a compound of formula (VI), a compound of formula (XIV), a compound of formula (X), a compound of formula (XI), a compound of formula (XIX), and a compound of formula (XII), comprising linking a saccharide to the compound. The invention also provides a saccharide linked compound prepared by the above method.

BRIEF DESCRIPTION OF THE FIGURES

FIG. 8 depicts codons for various amino acids.

FIG. 9 depicts exemplary amino acid substitutions.

FIG. 10 shows exemplary therapeutic agents of the invention (SEQ ID NOs:1, 7, 8, 9, 10, 11, 12, 13, 14, 121, 122, 123).

FIG. 11 summarizes binding and ED$_{50}$ data for selected peptides of the invention (SEQ ID NOs: 1, 2, 3, 4, 5, 7, 8, 9, 10, 11, 13, 14, 124, 125, 126, 127, 128, 129).

FIG. 12 shows an exemplary protocol to test agents in a rat dermal inflammation model (CRD-Cys$_{13}$Leu$_4$Ile$_{11}$ peptide 3(3-12)[MCP-1]=NR58-3.14.3).

FIG. 14 shows the inhibition of monocyte infiltration induced by MCP-1 in rat skin by CRD-Cys$_{13}$Leu$_4$Ile$_{11}$peptide 3(3-12)[MCP-1] in contrast to the D-ala derivative thereof ("inactive").

FIG. 18 depicts exemplary agents of the invention.

FIG. 19 shows the ED$_{50}$ for the inhibition of THP-1 migration in a transwell assay induced by either 50 ng/ml MCP-1, 100 ng/ml IL-8 or 100 nM fMLP by agents of the invention (SEQ ID NOs:1, 2, 3, 7, 8, 9, 10, 11, 13, 14). Peptides 1 and 2 had no significant effect on THP-1 migration induced by either CC or CXC chemokines even at 100 μM. The ED$_{50}$ for peptide 3 and its variants shown are the mean±SEM of three separate experiments. All the variants inhibited migration in response to both CC and CXC chemokines by more than 90% at 100 μM demonstrating that peptide 3 and its derivatives are pan-chemokine inhibitors. None of the peptides showed statistically significant inhibition of migration in response to non-chemokine chemoattractants; fMet-Leu-Phe (fMLP) or TGF-β1 at 100 μM (the highest concentration tested). Furthermore, the peptides exhibit similar properties to other CC and CXC chemokines (MIP-1α and SDF-1α).

FIG. 26A shows a bar graph of the binding of biotinylated peptide 3 to THP-1 cells using $^{125}$I-streptavidin.

FIG. 26B shows a dose-response curve for binding of biotinylated peptide 3 to THP-1 cells using $^{35}$S-streptavidin.

FIGS. 40 D-E depicts the IL-4 levels in spleen recall responses, serum IgE levels, and levels of thromboxane, LTB4 and PGE$_2$ in BAL from ovalbumin-treated mice.

FIG. 44 depicts the effect of WGQ analogs at 100 µM on THP-1 migration induced by MCP-1. Values are represented as % inhibition of THP-1 migration (as a % of control) ±SEM and are the mean of two separate experiments. The shaded boxes indicate compounds that inhibited THP-1 migration greater than 50%.

FIG. 45 shows ED$_{50}$ of WGQ analogs on THP-1 migration induced by MCP-1.

FIG. 55 illustrates three alkaphore skeleton molecules of formula (XVI), (XVII), and (XVIII).

DETAILED DESCRIPTION OF THE INVENTION

Definitions

Figure 1:
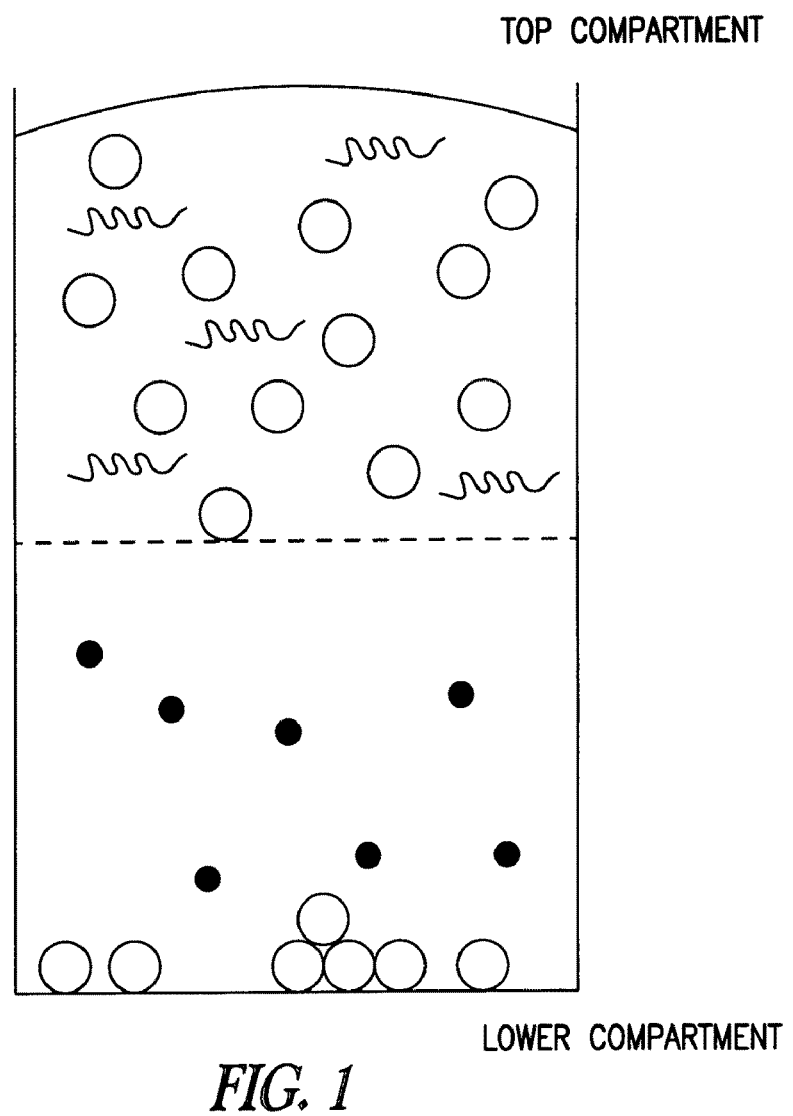
FIG. 1 is a schematic of the trans-well migration assay. In most experiments, the peptide (wavy line) is added to the upper well with about 50,000 cells (O). The upper and lower wells are separated by a 5 μm or 8 μm pore size PVP-free membrane (----). Chemokine (•) is added to the lower well. After 4 hours, the number of cells that have migrated through the membrane are measured (O in lower well).

"Chemokines" refers to a family of proinflammatory signaling molecules which act on macrophage, B cells, T cells, neutrophils, eosinophils, basophils, mast cells, smooth muscle cells, e.g., vascular smooth muscle cells, and the like (e.g., by affecting their migration, proliferation, or degranulation, or the immunomodulation of T cell development to Th1 and Th2 subtypes). Preferred chemokines are primate in origin, e.g., human, although the invention includes other mammalian chemokines, such as those of bovine, ovine, equine, canine, feline or rodent origin, as well as virally encoded chemokines. Chemokines include, but are not limited to, MCP-1 (SEQ ID NO:16), MCP-2 (SEQ ID NO:17), MCP-3 (SEQ ID NO:18), MIG, MIP1α (SEQ ID NO:19), MIP1β (SEQ ID NO:20), RANTES (SEQ ID NO:21), PF4, I-309, HCC-1, eotaxin (SEQ ID NO:25), C10, CCR-2, ENA-78, GROα, GROβ, IL-8 (SEQ ID NO:23), IP, e.g., IP-10, SDF1α (SEQ ID NO:22), SDF1β (SEQ ID NO:56), GROα, MIP3α, TCA-3, CTAPIII, NAP, MARC/FYK, β-thromboglobulin, GCP, e.g., GCP-2, PBP, HC14, MDC, Zsig-35, β-6, TECK, PARC, 6Ckine, fractakine, DC-CK1, LIX, LKN, TARC, LARC, SCM-1, STCP1, LKN, SLC, LMC, IBICK, ILINCK, MCIF, MPIF, MIG, Zchemo-8 (see WO98/54326), Ckβ, e.g., Ckβ8, Ckβ4, and Ckβ13, CCF18/MRP-2, C10, CCIII, CKα2, ENA, H1305, HCC, Dvic-1, MGSA, DGWCC, TCA4, dendrokine (see WO 97/29192), CC2/HCC1, CC3, and MIP1τ, as well as virally encoded chemokines such as ELC, vMIP-I, vMIP-II and vMIP-III (see Kledal et al., *Science*, 277, 1656 (1997)). "CXC" or "α" chemokines include, but are not limited to, IL-8, PF4, IP10, NAP-2, GROα, GROβ, GROγ, SDF1, MIP2, MGSA, γIP, CTAPIII, β-thromboglobulin, MIG, PBP, NAP-2 and ENA78. "CC" or "β" chemokines include, but are not limited to, MCP-1, MCP-2, MCP-3, MCP-4, MCP-5, RANTES, eotaxin, LARC, TARC, C10, MIP1α, MIP1β, I309, HCC-1, CKβ8, CCF18/MRP-2, MIP1τ. A third type of chemokines are "C" chemokines, e.g., lymphotactin. A fourth type of chemokines are "CX$_3$C" chemokines such as fractakine or neurotactin (Rollins et al., *Blood*, 90, 404 (1997)). A fifth type of chemokines, CX$_2$C chemokines, include CCIII.

"Peptide 3" refers to a peptide derived from a chemokine, which is generally located in (derived from) the carboxy-terminal half of the chemokine, and which inhibits the activity of at least the corresponding native chemokine, as determined by methods well known to the art. Peptide 3 comprises no more than 30, preferably about 3 to about 25, more preferably about 3 to about 15, and even more preferably about 3 to about 11, peptidyl residues which have 100% contiguous amino acid sequence homology or identity to the amino acid sequence of the corresponding native chemokine, preferably a mammalian chemokine, e.g., a primate chemokine such as a human chemokine, or a virally-encoded chemokine. For example, a preferred peptide 3 of MCP-1 that inhibits at least the activity of MCP-1 is peptide 3(1-12)[MCP-1], e.g., a peptide which has an amino acid sequence corresponding to SEQ ID NO:1, or a fragment or derivative thereof. Another preferred embodiment of the invention is peptide 3(3-12)[MCP-1], e.g., a peptide having an amino acid sequence corresponding to SEQ ID NO:7, or a fragment or derivative thereof. Preferably, a chemokine peptide 3 of the invention does not include a peptide of IL-8, PF-4 or NAP-2.

An alignment of chemokine amino acid sequences, such as the alignment depicted in Table 1, provides a general method to identify the location of peptide 3 sequences in chemokines. Generally, peptide 3 in non-MCP-1 chemokines corresponds to about residue 46 to about residue 67 of mature human MCP-1. Moreover, it is envisioned that peptide 3 may comprise moieties other than the amino acid sequence which inhibits chemokine activity, e.g., amino acid residues not present in the native chemokine (i.e., a fusion protein), nucleic acid molecules or targeting moieties such as antibodies or fragments thereof or biotin, so long as these moieties do not substantially reduce the biological activity of peptide 3. A substantial reduction in activity means a reduction in activity of greater than about 99%.

Also preferably, a peptide, variant, analog or derivative of the invention, has increased affinity for at least one chemokine receptor, e.g., about 1 μM to about 1 nM, more preferably about 1 nM to about 1 pM, and also preferably has decreased Duffy binding, relative to a corresponding peptide having the native ("wild-type") sequence or relative to the corresponding native chemokine. However, certain populations have individuals who are Duffy⁻, e.g., a certain percentage of African Americans are Duffy⁻. Thus, agents useful to treat these populations may have Duffy binding affinity that is equal to or greater than that of the corresponding native chemokine.

As used herein, the terms "isolated and/or purified" refer to in vitro preparation, isolation and/or purification of a therapeutic agent of the invention, so that it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoranidate, and the like. An oligonucleotide can include a label for detection, if desired.

The term "isolated polypeptide" means a polypeptide encoded by cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of sequence from a chemokine that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of human MCP-1.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, the terms "label" or "labeled" refer to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide, phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

An isolated "chemokine peptide variant" of peptide 3 or peptide 2 is a peptide comprising no more than 30, preferably about 3 to about 25, and more preferably about 3 to about 18, and even more preferably about 3 to about 11, peptidyl residues which have at least 50%, preferably at least about 80%, and more preferably at least about 90% but less than 100%, contiguous amino acid sequence homology or identity to the amino acid sequence of the corresponding native chemokine, e.g., Ser$_7$ peptide 3(1-12)[MCP1] (SEQ ID NO:11) has less than 100% homology to the corresponding amino acid sequence of MCP-1, i.e., peptide 3(1-12)[MCP-1] (SEQ ID NO:1). A variant of the invention may include amino acid residues not present in the corresponding native chemokine, and internal deletions relative to the corresponding native chemokine. Chemokine peptide variants include peptides having at least one D-amino acid.

Chemokine peptides or peptide variants which are subjected to chemical modifications, such as esterification, amidation, reduction, protection and the like, are referred to as chemokine "derivatives." For example, a modification known to improve the stability and bioavailability of peptides in vivo is the cyclization of the peptide, for example through one or more disulfide bonds. A preferred modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like. A preferred derivative of the invention is CRD-Cys$_0$Cys$_{13}$Leu$_4$Ile$_{11}$peptide 3[MCP-1] or CRD-Cys$_{13}$Leu$_4$Ile$_{11}$peptide 3(3-12)[MCP-1].

Also included within the scope of the term "derivative" is linear reverse D (LRD) and cyclized forward L (CFL) derivatives. LRD derivatives have the reverse (i.e., C-terminal to N-terminal) sequence of the peptide with all D-form amino acids, but are not cyclized. CFL derivatives have the forward (i.e., N-terminal to C-terminal) sequence of the peptide with all L-form amino acids, but with additional N and C terminal cys residues (if the peptide sequence does not already have cys residues at either the N or the C terminal position), followed by oxidative cyclization, or cyclization by an alternative method. Other "derivatives" of the invention include branched peptides, circular, branched and branched circular peptides.

A "chemokine analog" means a moiety that mimics or inhibits a chemokine-induced activity, or binds to or near a chemokine receptor but does not mimic or inhibit chemokine activity (neutral), wherein the portion of the moiety that mimics or inhibits the chemokine-induced activity, or binds to or near the receptor but is neutral, is not a peptide, and wherein the active portion of the analog is not a nucleic acid molecule. As used herein, the term "mimics" means that the moiety induces an activity that is induced by a native chemokine, but that the induction by the analog is not necessarily of the same magnitude as the induction of activity by the native chemokine.

It is also envisioned that the chemokine peptides, variants, analogs and derivatives thereof, of the invention may comprise moieties other than the portion which inhibits or mimics chemokine activity, or binds to or near a chemokine receptor without eliciting or inhibiting signaling, e.g., peptide or polypeptide molecules, such as antibodies or fragments thereof or fusion proteins, nucleic acid molecules, sugars, lipids, fats, a detectable signal molecule such as a radioisotope, e.g., gamma emitters, paramagnetic molecules or sound wave emitters, small chemicals, metals, salts, synthetic polymers, e.g., polylactide and polyglycolide, surfactants and glycosaminoglycans, which preferably are covalently attached or linked to the portion of the peptide, variant, analog or derivative that mimics or inhibits the chemokine-induced activity, so long as the other moieties do not alter the biological activity of the peptide, variant, analog or derivative. Also envisioned is a chemokine peptide, variant, analog or derivative that is non-covalently associated with the moieties described above.

As used herein the term "saccharide" includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and WO97/03995. A saccharide can conveniently be linked to the remainder of a compound of formula I through an ether bond.

As used herein, halo is fluoro, chloro, bromo, or iodo. The terms alkyl and alkoxy denote both straight and branched groups, but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(R$^4$) wherein R$^4$ is absent or is hydrogen, (C$_1$-C$_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetra methylene diradical thereto.

A preferred chemokine analog of the invention is a compound of formula (IV):

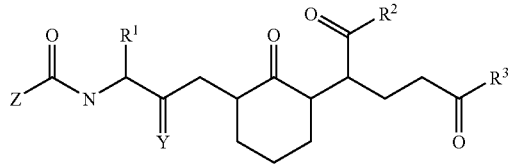

wherein $R^1$ is aryl, heteroaryl, aryl($C_1$-$C_3$)alkyl, heteroaryl ($C_1$-$C_3$)alkyl, coumaryl, coumaryl($C_1$-$C_3$)alkyl, chromanyl or chromanyl($C_1$-$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$-$C_6$)alkyl, ($C_1$-$C_6$)alkoxy, ($C_1$-$C_6$)alkanoyl, ($C_2$-$C_6$)alkanoyloxy, —C(=O)($C_1$-$C_6$)alkoxy, C(=O)NR$^g$R$^h$, NR$^i$R$^j$;

wherein $R^2$ is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy or N(R$^a$)(R$^b$);

wherein $R^3$ is ($C_1$-$C_{10}$)alkyl, ($C_3$-$C_6$)cycloalkyl, ($C_3$-$C_6$) cycloalkyl($C_1$-$C_6$)alkyl, ($C_1$-$C_{10}$)alkoxy, ($C_3$-$C_6$)cycloalkyl ($C_1$-$C_6$)alkoxy or N(R$^c$)(R$^d$);

wherein Y is oxo or thioxo;

wherein Z is ($C_1$-$C_{15}$)alkyl, ($C_3$-$C_6$)cycloalkyl, ($C_3$-$C_6$) cycloalkyl($C_1$-$C_6$)alkyl, ($C_1$-$C_{15}$)alkoxy, ($C_3$-$C_6$)cycloalkyl ($C_1$-$C_6$)alkoxy or N(R$^e$)(R$^f$); and wherein R$^a$-R$^j$ are each independently hydrogen, ($C_1$-$C_{10}$) alkyl, ($C_1$-$C_{10}$)alkanoyl, phenyl, benzyl, or phenethyl; or R$^a$ and R$^b$, R$^c$ and R$^d$, R$^e$ and R$^f$, R$^g$ and R$^h$, or R$^i$ and R$^j$ together with the nitrogen to which they are attached form a ring selected from pyrrolidino, piperidino, or morpholino; or a pharmaceutically acceptable salt thereof.

A preferred embodiment of a compound of formula (IV) includes a compound of formula (IV) wherein $R^1$ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein $R^2$ is N(R$^a$)(R$^b$); and $R^3$ is N(R$^c$)(R$^d$). Yet another preferred embodiment of a compound of formula (IV) includes a compound of a formula (IV) wherein Z is ($C_1$-$C_{15}$)alkyl.

A further preferred compound is a compound of formula (IV) wherein $R^1$ is indolyl; $R^2$ is N(R$^a$)(R$^b$); $R^3$ is N(R$^c$)(R$^d$); Y is S; Z is hydrogen; and R$^a$, R$^b$, R$^c$, and R$^d$ are each methyl.

Yet another preferred compound of formula (IV) includes a compound wherein $R^1$ is 2-benzimidazolyl; for $R^2$ is N(R$^a$) (R$^b$); $R^3$ is N(R$^c$)(R$^d$); Y is oxo; and Z is N(R$^e$)(R$^f$) or a pharmaceutically acceptable salt thereof. Another preferred compound of formula (IV) is a compound wherein $R^1$ is 2-benzimidazolyl; $R^2$ is N(Me)$_2$; $R^3$ is N(Me)$_2$; Y is oxo; and Z is N(Me)$_2$; or a pharmaceutically acceptable salt thereof.

Another preferred chemokine analog of the invention is a compound of formula (V):

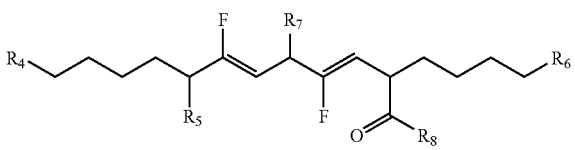

wherein $R^4$ is NR$_k$R$_l$; wherein $R^5$ is NR$_m$R$_n$; wherein $R^6$ is NR$_o$R$_p$; wherein $R^7$ is Nr$_q$R$_r$; wherein $R^8$ is hydrogen, hydroxy, ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy, NR$_s$R$_t$, the amino terminus of an amino acid or the N-terminal residue of a peptide of 2 to about 25 amino acid residues; wherein R$_k$, R$_l$, R$_o$, and R$_p$ are each independently hydrogen, ($C_1$-$C_{10}$)alkyl, ($C_3$-$C_6$)cycloalkyl, ($C_3$-$C_6$) cycloalkyl($C_1$-$C_6$)alkyl, ($C_1$-$C_{10}$)alkanoyl, phenyl, benzyl or phenethyl; wherein R$_m$ are R$_n$ are each independently hydrogen, ($C_1$-$C_{10}$)alkyl, ($C_3$-$C_6$)cycloalkyl, ($C_3$-$C_6$)cycloalkyl ($C_1$-$C_6$)alkyl, ($C_1$-$C_{10}$)alkoxy, ($C_1$-$C_{10}$)alkanoyl, ($C_1$-$C_{10}$) alkoxycarbonyl, 9-fluorenylmethoxycarbonyl, phenyl, benzyl, phenethyl, the C-terminal residue of an amino acid or a peptide of 2 to about 25 amino acid residues; wherein R$_q$ are R$_r$ are each independently hydrogen, ($C_1$-$C_{10}$)alkyl, ($C_3$-$C_6$) cycloalkyl, ($C_3$-$C_6$)cycloalkyl($C_1$-$C_6$)alkyl, phenyl, benzyl or phenethyl; wherein R$_s$ are R$_t$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, phenyl, benzyl or phenethyl; or a pharmaceutically acceptable salt thereof.

Preferably R$_k$, R$_l$, R$_o$, and R$_p$ are each hydrogen; R$_m$ are R$_n$ are each independently hydrogen, acetyl, ($C_1$-$C_{10}$)alkyl, ($C_3$-$C_6$)cycloalkyl, propoxy, butoxy, tert-butoxycarbonyl, 9-fluorenylmethoxycarbonyl, the C-terminal residue of an amino acid or a peptide of 2 to about 25 amino acid residues; and R$_q$ are R$_r$ are each

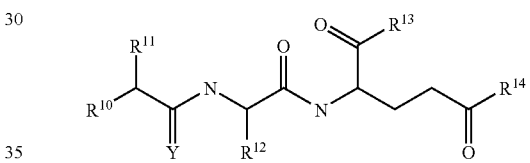

independently hydrogen, ($C_1$-$C_{10}$)alkyl, or ($C_3$-$C_6$)cycloalkyl.

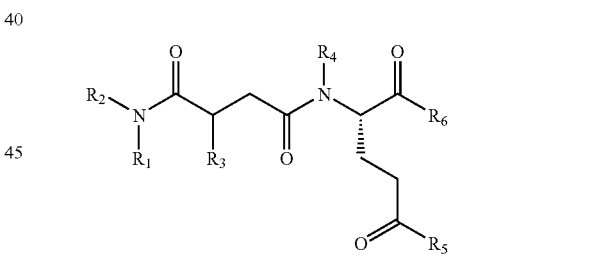

Another preferred analog of a chemokine is a compound of formula (XIII): wherein $R_1$ is aryl, heteroaryl, aryl($C_1$-$C_{10}$) alkyl, aryl($C_1$-$C_{10}$)alkanoyl, heteroaryl($C_1$-$C_{10}$)alkyl, or heteroaryl($C_1$-$C_{10}$)alkanoyl; $R_2$ is hydrogen, ($C_1$-$C_{15}$)alkyl, ($C_3$-$C_8$)cycloalkyl, ($C_3$-$C_8$)cycloalkyl($C_1$-$C_{10}$)alkyl, aryl, or aryl ($C_1$-$C_{10}$)alkyl; $R_3$ is hydrogen, or ($C_1$-$C_{10}$)alkyl, $R_4$ is hydrogen, or ($C_1$-$C_{10}$)alkyl; $R_5$ is N(R$^a$)(R$^b$); $R_6$ is N(R$^a$) (R$^b$); and each R$^a$ and R$^b$ is independently hydrogen, ($C_1$-$C_{10}$) alkyl, ($C_1$-$C_{10}$)alkanoyl, or aryl($C_1$-$C_{10}$)alkyl; or R$^a$ and R$^b$ together with the nitrogen to which they are attached form a pyrrolidino, piperidino or morpholino ring; wherein any aryl or heteroaryl is optionally substituted with 1, 2, 3, or 4 substituents independently selected from the group consisting of halo, cyano, hydroxy, nitro, trifluoromethyl, trifluoromethoxy, ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, and methylenedioxy; or a pharmaceutically acceptable salt thereof.

For a compound of formula (XIII), $R_1$ can specifically be 3-indolylmethyl; $R_2$ can specifically be isopropyl, tert-butyl, or phenyl; $R_3$ can specifically be methyl; $R_4$ can specifically be hydrogen; $R_5$ can specifically be amino; and $R_6$ can specifically be dimethylamino, benzylamino, or hydroxybenzylamino.

Another preferred analog of the invention is a compound of formula (XI):

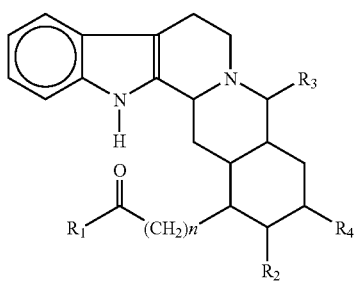

wherein $R_1$ is O(Ra) wherein Ra is H, $(C_1-C_6)$alkyl, $(C_1-C_6)$alkanoyl, $(C_1-C_6)$alkanoyloxy, $(C_6-C_{10})$aryl or $(C_6-C_{10})$heteroaryl; or N(Rb)(Rc) wherein each Rb and Rc is independently H or $(C_1-C_6)$alkyl; $R_2$ is O(Ra) wherein Ra is H, $(C_1-C_6)$alkyl, $(C_1-C_6)$alkanoyl, $(C_1-C_6)$alkanoyloxy, $(C_6-C_{10})$aryl or $(C_6-C_{10})$heteroaryl; or N(Rb)(Rc) wherein each Rb and Rc is independently H or $(C_1-C_6)$alkyl; $R_3$ is H, C(=O) or C(=S); $R_4$ is H; C(=O); C(=S); O(Ra) wherein Ra is H, $(C_1-C_6)$alkyl, $(C_1-C_6)$alkanoyloxy, $(C_1-C_6)$alkanoyl, $(C_6-C_{10})$aryl or $(C_6-C_{10})$heteroaryl; or N(Rb)(Rc) wherein each Rb and Rc is independently H or $(C_1-C_6)$alkyl; and n is an integer between 0 and 6, inclusive; wherein any $(C_6-C_{10})$ aryl, $(C_1-C_6)$alkyl, $(C_1-C_6)$alkanoyloxy, $(C_6-C_{10})$heteroaryl or $(C_1-C_6)$alkanoyl is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$ alkoxycarbonyl, methoxydioxy, hydroxy, C(=O), and N(Rb)(Rc) wherein each Rb and Rc is independently H or $(C_1-C_6)$ alkyl; or a pharmaceutically acceptable salt thereof.

Specific compounds of formula XIV are shown in the following table.

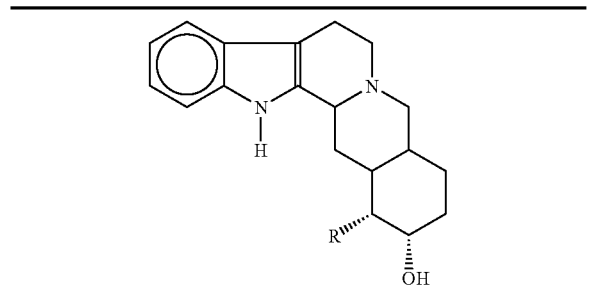

| Compound | R |
| --- | --- |
| Y-I | R = methoxycarbonyl |
| Y-II | R = aminocarbonyl |
| Y-III | R = methylaminocarbonyl |
| Y-IV | R = dimethylaminocarbonyl |
| Y-V | R = N-(methyl)glutamino |
| Y-VI | R = aminocarbonylmethyl |

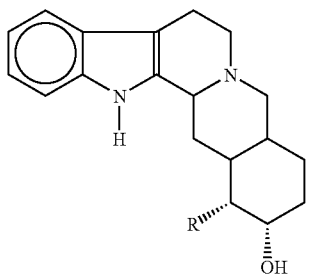

| Compound | R |
| --- | --- |

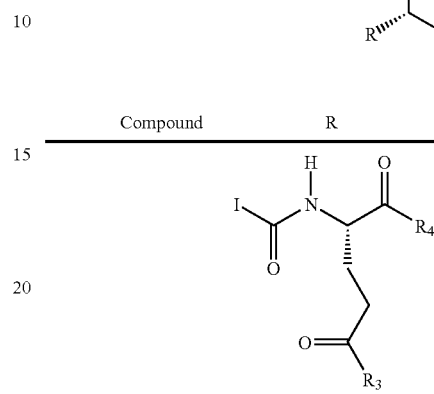

Specific compounds of formula (X) are shown in the following table.

| Compound | $R_1$ | $R_3$ | $R_4$ |
| --- | --- | --- | --- |
| NR58.1 | 9-decenyl | amino | hydroxy |
| NR58.2 | 9-decenyl | amino | amino |
| NR58.3 | 9-decenyl | amino | 4-hydroxybenzyl-amino |
| NR58.5 | tert-butyl | amino | hydroxy |
| NR58.6 | tert-butyl | amino | amino |
| NR58.7 | tert-butyl | amino | 4-hydroxybenzyl-amino |
| NR58.9 | phenyl | amino | hydroxy |
| NR58.10 | phenyl | amino | amino |
| NR58.11 | 4-hydroxyphenyl | amino | 4-hydroxybenzyl-amino |
| NR58.13 | tert-butyl | amino | hydroxy |
| NR58.14 | benzoylaminomethyl | amino | hydroxy |
| NR58.15 | 4-hydroxybenzyloxy-carbonylaminomethyl | amino | hydroxy |

Other specific compounds of formula (X) include [3S]-3-(undec-10-enoylamino)piperidine-2,6-dione (compound 58,4) and N-benzoyl-L-pyroglutamate (compound 58,12).

Other specific compounds of formula (X) are shown in the following table.

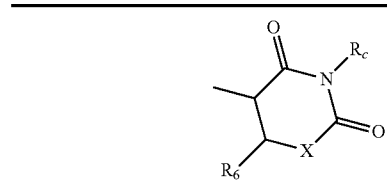

| Compound | X | $R_6$ | $R_c$ | R |
| --- | --- | --- | --- | --- |
| A-I (NR58,4) | $CH_2$ | H | H | 10-undecenoylamino |
| A-II | $CH_2$ | H | H | 10-undecanoylamino |
| A-III | $CH_2$ | H | H | 8-nonenoylamino |
| A-IV | $CH_2$ | H | H | 6-heptenoylamino |
| A-V | $CH_2$ | H | H | 4-pentenoylamino |
| A-VI | $CH_2$ | H | H | 2-propenoylamino |
| A-VIII | $CH_2$ | H | H | N-methyl-10-undecenoylamino |

-continued

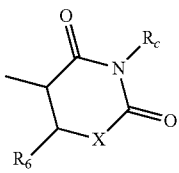

| Compound | X | $R_6$ | $R_c$ | R |
|---|---|---|---|---|
| A-IX | $CH_2$ | H | Me | 10-undecenoylamino |
| A-X | $CH_2$ | H | Me | N-methyl-10-undecenoylamino |
| A-XI | direct bond | H | H | 10-undecenoylamino |
| A-XII | NH | oxo | H | 10-undecenoylamino |
| A-XIII | NH | oxo | H | N-methyl-10-undecenoylamino |

Specific compounds of formula (XI) are shown in the following table.

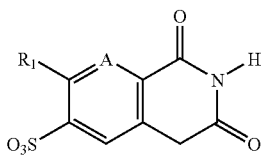

| Compound | $R_1$ | A |
|---|---|---|
| B-I | 10-undecenoylamino | CH |
| B-II | 9-decenyl | N |
| B-III | 9-decenyl | CH |

Specific compounds of formula (XII) are shown in the following table.

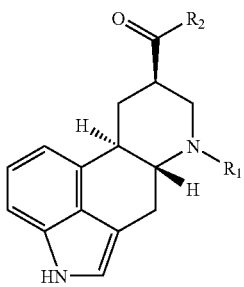

| Compound | $R_1$ | $R_2$ |
|---|---|---|
| L-I | Me | OH |
| L-II | Me | L-glutamino |

It will be appreciated by those skilled in the art that compounds of formula (IV), (V), (VI), (XIII), (XIV), (X), (XI), (XIX), and (XII), and compounds of the invention which are peptides having chiral centers, may exist in and be isolated in optically active and racemic forms. For example, compounds of the invention comprise α-amino acid residues in D or L form, or mixtures thereof. Some compounds may exhibit polymorphism. It is to be understood that the present invention encompasses any racemic, optically-active, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis, from optically-active starting materials, by chiral synthesis, or by chromatographic separation using a chiral stationary phase). It is also well known to the art how to determine a compounds ability to inhibit or enhance chemokine-induced activity using the standard tests described herein, or using other tests which are well known in the art.

Specific and preferred values listed herein for radicals, substituents, and ranges, are for illustration only and they do not exclude other defined values or other values within defined ranges for the radicals and substituents. Specifically, $(C_1-C_{15})$alkyl can be methyl, ethyl, propyl, isopropyl, butyl, iso-butyl, sec-butyl, pentyl, 3-pentyl, hexyl, heptyl, octyl, nonyl, decyl, undecyl, 9-methylundecyl, dodecyl; $(C_1-C_6)$alkyl can be methyl, ethyl, propyl, isopropyl, butyl, iso-butyl, sec-butyl, pentyl, 3-pentyl, or hexyl; $(C_1-C_3)$alkyl can be methyl, ethyl, or propyl; $(C_3-C_6)$cycloalkyl can be cyclopropyl, cyclobutyl, cyclopentyl, or cyclohexyl; $(C_1-C_{10})$alkoxy can be methoxy, ethoxyl, propoxy, isopropoxy, butoxy, iso-butoxy, sec-butoxy, pentoxy, 3-pentoxy, hexyloxy, heptyloxy, octyloxy, nonyloxy, or decyloxy; $(C_1-C_6)$alkoxy can be methoxy, ethoxyl, propoxy, isopropoxy, butoxy, iso-butoxy, sec-butoxy, pentoxy, 3-pentoxy, or hexoxy; $(C_1-C_{10})$alkanoyl can be formyl, acetyl, propanoyl, butanoyl, pentanoyl, hexanoyl, heptanoyl, octanoyl, nonanoyl, or decanoyl; $(C_1-C_6)$alkanoyl can be formyl, acetyl, propanoyl, butanoyl, pentanoyl, or hexanoyl; $(C_2-C_6)$alkanoyloxy can be acetoxy, propanoyloxy, butanoyloxy, pentanoyloxy, or hexanoyloxy; aryl can be phenyl, indenyl, or naphthyl; and heteroaryl can be furyl, imidazolyl, tetrazolyl, pyridyl, (or its N-oxide), thienyl, benzimidazolyl (or its N-oxide), pyrimidinyl (or its N-oxide), indolyl, or quinolyl (or its N-oxide).

In addition, it is understood that the agents of the invention (e.g. peptide 3, varients or derivatives thereof, a compound of formula (IV), a compound of formula (V), a compound of formula (VI), a compound of formula (XIII), a compound of formula (XIV), a compound of formula (X), a compound of formula (XI), a compound of formula (XIX), or a compound of formula (XII)), may be modified to include O-linked sugars and sugar chains (e.g. a saccharide), e.g., at hydroxyl, amide and/or ester groups, so as to yield a "saccharide conjugate". A preferred saccharide conjugate is the peptide derivative CRD-$Leu_4Ile_{11}CyS_{13}$ peptide 3(3-12)[MCP-1] linked to a one or more saccharides. For example the peptide derivative may be linked to the saccharide by an aminoglycosidic bond to either or both the amino terminus and one or both lysine ε-amino groups (for example as prepared in example 18).

Preferably, the therapeutic agents of the invention are biologically active. The biological activity of a chemokine peptide, peptide variant, analog or derivative thereof, can be measured by methods known to the art, some of which are described hereinbelow. For example, biologically active peptide 3[MCP-1] variants falling within the scope of the invention have at least about 1%, preferably at least about 10%, more preferably at least about 50%, and even more preferably at least about 90%, the activity of the corresponding native peptide sequence, e.g., peptide 3(1-12)[MCP-1] (SEQ ID NO:1), or the native chemokine, e.g., MCP-1 (SEQ ID NO:16). Thus, a peptide 3 variant, e.g., $Leu_4Ile_{11}$peptide 3(1-12)[MCP-1], falling within the scope of the invention has an $ED_{50}$ for inhibition that is at least about 1%, preferably at least about 10%, more preferably at least about 50%, and even more preferably at least about 90%, the maximal activity of peptide 3(1-12)[MCP-1] (SEQ ID NO:1) at 100 μM.

As used herein, "a chemokine-induced activity" includes, but is not limited to, an activity that is elicited through the binding of a chemokine, a therapeutic agent of the invention or other moiety, e.g., viral protein, to a chemokine receptor, or the binding of a therapeutic agent or other moiety in close physical proximity to the receptor so that the activity is altered. Chemokine receptors include, but are not limited to, CCR1 (CC-CKRI), CCR2a, CCR2b, CCR3, CCR4, CCR5, CCR6, CCR7, CCR8, HGBER32 (WO98/09171), CXCR1 (IL8RI), CXCR2, CXCR3, $CX_3CR1$, CXCR4 and CXCR5. Chemotide receptors play a role in cell migration, cell activation, viral or parasite entry, release of proinflammatory compounds, and the like.

As used herein, "indications associated with chemokine-induced activity" includes, but is not limited to, atherosclerosis and other forms of local or systemic vasculitis, e.g., Behçet's syndrome, giant cell arteritis, polymyalgia rheumatica, Wegener's granulomatosis, Churg-Strauss syndrome vasculitis, Henoch-Schönlein purpura, Kawasaki disease, microscopic polyanglitis, Takayasu's arteritis, essential cryoglobulinemic vasculitis, cutaneous leukocytoclastic anglitis, polyarteritis nodosa, primary granulomatous central nervous system vasculitis, drug-induced antineutrophil cytoplasmic autoantibodies (ANCA)-associated vasculitis, cryoglobulinemic vasculitis, lupus vasculitis, rheumatoid vasculitis, Sjögren's syndrome vasculitis, hypocomplemtemic urticarial vasculitis, Goodpasture's syndrome, serum-sickness vasculitis, drug-induced immune complex vasculitis, paraneoplastic small vessel vasculitis (e.g., lymphoproliferative neoplasm-induced vasculitis, myeloproliferative neoplasm-induced vasculitis, and carcinoma-induced vasculitis), and inflammatory bowel disease vasculitis, diseases such as myocardial infarction, stroke, acute ischemia which is secondary to atherosclerosis; hypertension; reperfusion injury (Kumar et al., Circulation, 95, 693 (1997)); aortic aneurysms; vein graft hyperplasia (Stark et al., Athero., Thrombosis, and Vascular Biology, 17, 1614 (1997)); angiogenesis; hypercholesterolemia; congestive heart failure; Kawasaki's disease; stenosis or restenosis, particularly in patients undergoing angioplasty; pathologically low bone mineral density, such as osteoporosis (Posner et al., Bone, 21, 321 (1997)); ulcerative colitis; chronic obstructive pulmonary disease; stroke; infection with human immunodeficiency virus (HIV), other lentiviruses or retroviruses with similar mechanisms of cell entry via chemokine receptor(s), or infection with other viruses, e.g., cytomegalovirus (Sozzani et al., J. Leukoc. Biol., 62, 30 (1997)), or viral infection resulting in viral meningitis; organ transplantation, such as acute transplant rejection or delayed graft function, allograft rejection and graft versus host disease; transplant vasculopathy; malaria and other consequences of infection by parasites related to plasmodium; asthma; allergic diseases, such as atopy (IgE-mediated components), allergic rhinitis, atopic dermatitis, anaphylaxis, allergic bronchopulmonary aspergillosis (IgE-mediated), and hypersensitivity pneumonitis (high IgG and reactive T cells) (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; urticaria; eczema; pulmonary fibrosis such as idiopathic pulmonary fibrosis; cystic fibrosis; hemolytic uremic syndrome (Van Setten et al., Pediatr. Res., 43, 759 (1998)); autoimmune disorders, including, but not limited to, type I diabetes, Crohn's disease, multiple sclerosis, arthritis, rheumatoid arthritis (Ogata et al., J. Pathol., 182, 106 (1997); Gong et al., J. Exp. Med., 186, 131 (1997)), systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; eye diseases such as uveitis or blinding Herpes stromal keratitis; liver disease; erhlichiosis or Lyme disease including Lyme arthritis; aberrant hematopoiesis; otitis extema, e.g., formulated as a topical ear cleaner for domestic animals such as dogs and cats; intraperitoneal adhesions, e.g., adhesions which develop post-surgery, particularly after gynecologic or intestinal surgeries (Zeyneloglu et al., Am. J. Obstet. Gynecol., 179, 438 (1998)); scarring after surgery; radiation-induced fibrosis; renal disorders; post-trauma inflammation, e.g., post-surgical inflammation such as that following orthopedic surgeries, e.g., prosthetic implants, as well as atherectomy, circulatory surgeries, and tissue replacements; nephritis due to, for example, autosomal dominant polycystic kidney disease, diabetic nephropathy, IgA nephropathy, interstitial fibrosis, or lupus; as well as other disease states resulting from inappropriate inflammation, either local or systemic, for example, irritable or inflammatory bowel syndrome (Mazzucchelli et al., J. Pathol., 178, 201 (1996)), skin diseases such as psoriasis (Gillitzer et al., Arch. Dermatol. Res., 284, 26 (1992); Yu et al., Lab Investig., 71, 226 (1994)) and lichen planus, delayed type hypersensitivity, Alzheimer's disease (Johnstone et al., J. Neuroimmunol., 93, 182 (1999)), chronic pulmonary inflammation, e.g., pulmonary alveolitis and pulmonary granuloma, gingival inflammation or other periodontal disease, and osseous inflammation associated with lesions of endodontic origin (Volejnikova et al., Am. J. Pathol., 150, 1711 (1997)), hypersensitivity lung diseases such as hypersensitivity pneumonitis (Sugiyama et al., Eur. Respir. J., 8, 1084 (1995)), and inflammation related to histamine release from basophils (Dvorak et al., J. Allergy Clin. Immunol., 98, 355 (1996)), such as hay fever, histamine release from mast cells (Galli et al., Ciba Foundation Symposium, 147, 53 (1989)), or mast cell tumors, types of type 1 hypersensitivity reactions (anaphylaxis, skin allergy, hives, allergic rhinitis, and allergic gastroenteritis); glomerulonephritis (Gesualdo et al., Kidney International, 51, 155 (1997)); inflammation associated with peritoneal dialysis (Sach et al., Nephrol, Dial. Transplant, 12, 315 (1997)); emphysema; and pancreatitis.

Other indications falling within the scope of the invention include, but are not limited to, neoplasia, e.g., histocytoma, glioma, sarcoma, osteosarcoma, osteoma (Zheng et al., J. Cell Biochem., 70, 121 (1998)), melanoma, Kaposi's sarcoma, small cell lung cancer, and ovarian carcinoma as well as myelosuppression and mucositis associated with chemotherapy; inflammatory pseudotumor of the lung; brain or spinal cord trauma, such as after disc surgery (Ghirnikar et al., J. Neurosci. Res., 46, 727 (1996); Berman et al., J. Immunol., 156, 3017 (1996)); gout; lung disease, e.g., due to respiratory syncicial virus infection of humans, cattle, pigs and the like, or lung injury (Lukacs et al., Adv. Immunol., 62, 257 (1996)); adult respiratory distress syndrome (see Robbins, Pathologic Basis of Disease, Cotran et al. (Eds.), 5th ed.); strokes; Loeffler's syndrome; chronic eosinophilic pneumonia; pulmonary fibrosis; wound healing; bacterial infection, e.g., bacterial peritonitis, meningitis or gram negative sepsis; toxic shock syndrome; granulomatous diseases such as Mycobacteriosis, Pneumocystosis, Histoplasmosis, Blastomycosis, Coccidiomycosis, Cryptococcosis, Aspergillosis, granulomatous enteritis, Candidiasis, foreign body granulomas and peritonitis, pulmonary granulomatosis, Wegener's granulomatosis (Del Papa et al., *Arthritis Rheum.*, 39, 758 (1996)), leprosy, syphilis, cat-scratch disease, schistosomiasis (Jacobs et al., *Am. J. Pathol.*, 150, 2033 (1997)), silicosis, sarcoidosis (Iida et al., *Thorax*, 52, 431 (1997); Car et al., *Am. J. Respir. Crit. Care Med.*, 149, 655 (1994)) and berylliosis; lethal endotoxemia (Zisman et al., *J. Clin. Invest.*, 99, 2832 (1997)); and indications associated with a weak inflammatory response, e.g., which occur in parasitic infection, e.g., Leishmaniasis (Moll, *Biol. Abs.*, 104, 21765 (1997)), trypanosome, *Mycobacterium leprae* or *Mycobacterium tuberculosis* infection, helminth infections, such as nematodes (round worms); (Trichuriasis, Enterobiasis, Ascariasis, Hookworm, Strongyloidiasis, Trichinosis, filariasis); trematodes (fluxes) (Schistosomiasis, Clonorchiasis), cestode (tape worms) (Echinococcosis, Taeniasis saginata, Cysticercosis); visceral works, visceral larva migrans (e.g., *Toxocara*), eosinophilic gastroenteritis (e.g., *Anisaki* spp., *Phocanema* ssp.), cutaneous larva migrans (*Ancylostoma braziliense, Ancylostoma caninum*), or fungal infection.

The peptides of the invention may also be useful as contraceptives or to induce abortion, in acute respiratory distress syndrome, and diseases where steroids are routinely used (e.g., relapsing Beheers colitis and asthma).

Also included within the scope of the invention are indications associated with tumor necrosis factor α (TNFα), e.g., rheumatoid arthritis or endotoxemia, or indications associated with elevated levels of TNFα. These indications include, but are not limited to, endotoxic shock; Crohn's disease; fever, and flu-like symptoms; acute interstitial pneumonitis; septic and nonseptic shock; acute respiratory distress syndrome; thromboembolic conditions; bone resorption; arthritis; acute graft versus host disease; leprosy; malaria; cerebral malaria; cachexia of tuberculosis or cancer; and idiopathic fibrosis.

I. Identification of Therapeutic Agents Falling within the Scope of the Invention Agents useful in the practice of the invention include agents that inhibit or reduce (e.g., chemokine receptor antagonists), or increase, augment or enhance (e.g., chemokine receptor agonists), chemokine-induced activity, e.g., monocyte or macrophage recruitment. These agents can be identified by in vitro and in vivo assays, such as the assays described hereinbelow. It is recognized that not all agents falling within the scope of the invention can inhibit or enhance chemokine-induced activity in vitro and in vivo. The therapeutic agents of the invention may be direct receptor binding agonists and/or antagonists, or may act by a different mechanism, e.g., duplex formation of antisense nucleic acid with chemokine mRNA, or by more than one mechanism, so as to result in the alteration of chemokine-induced activity.

A. Peptides, Variants, Derivatives and Analogs

1. In Vitro Chemotaxis

To determine whether an agent inhibits a chemokine-induced activity, such as macrophage recruitment, varying amounts of the agent are mixed with cells in the presence of a known chemoattractant. For example, a range of known concentrations of an agent, e.g., a chemokine peptide, is incubated with a defined number (e.g., $10^4$-$10^6$) of human THP-1 monocyte cells in individual wells of the top compartment of a trans-well plate. Chemokine (such as MCP-1, MIP1α, IL8 or SDF-1α), at a concentration known to cause significant migration of THP-1 cells in the trans-well migration assay, is placed in the lower compartment (FIG. 1). Cells are then incubated at 37° C. for a period sufficient to allow migration, e.g., 4 hours. After incubation, the cells are gently removed from the top of the filter with a pipette, 20 μl of 20 mM EDTA in simple PBS is added into each top well, and incubated for 20 minutes at 4° C. The filter is carefully flushed with media using a gentle flow, and removed. A standard curve consisting of a two-fold dilution series of THP-1 cells (in 29 μl) is prepared to accurately quantify the number of cells that have migrated. Migrated cells are stained with 3 μl of MTT stock dye solution which is added directly into each well (5 mg/ml in RPMI-1640 without phenol red, Sigma Chemical Co.) and incubated at 37° C. for 4 hours. The media is carefully aspirated from each well, and the converted dye is solubilized by 20 μl of DMSO. Absorbance of converted dye is measured at a wavelength of 595 nm using an ELISA plate reader. The number of migrated cells in each well is then determined by interpolation of the standard curve (see also Imai et al., *J. Biol. Chem.*, 272, 15036 (1997)).

Any method suitable for counting cells can be used, for example, counting with a hemocytometer, incubation of the cells with MTT (see above), or FACS analysis. A negative control assay is also performed, using TGF-β or another non-chemokine chemoattractant (e.g., IL1β or TNFα). To assess whether the agent is cytotoxic, the same concentrations of agent are incubated with THP-1 cells. Agents which 1) are not cytotoxic at levels which inhibit migration, 2) are ineffective at inhibiting the negative control-induced migration, and 3) reduce or inhibit chemokine-induced THP-1 migration, are agents which fall within the scope of the invention.

Agents may also be screened in a chemotactic assay which employs human neutrophils, eosinophils, mast cells, basophils, platelets, lymphocytes or monocytes. For monocytes, 9 mls of fresh blood are transferred to a tube containing 1 ml of 3.8% sodium citrate, and left at room temperature for 15 minutes. Five mls of this anti-coagulated blood are carefully layered over 3.5 ml Polymorphprep® (Nycomed Pharma, Oslo), and centrifuged at 500 g for 35 minutes per the manufacturer's instructions. The top band at the sample/medium interface contains monocytes. The monocytes are carefully removed with a glass pipette, and reconstituted to the original volume (5 ml). The cells are washed with PBS plus 10% fetal calf serum, and centrifuged at 400 g for 10 minutes. The washing step is repeated three times before the cells are counted. Cells are resuspended at $1\times10^7$ cells/ml in RPMI-1640+10% fetal calf serum (FCS). The monocytes are cultured for two days at 37° C. in a humidified atmosphere of 5% $CO_2$.

On day 2, the cells are counted, spun down, and reconstituted to $1\times10^7$ cells/ml in Gey's balanced salt solution+1 mg/ml bovine serum albumin (BSA). Chemotaxis is induced in a 48 or 96-well disposable chemotaxis chamber fitted with a 5-8 μm polycarbonate filter for monocytes, neutrophils or eosinophils, or a 3 μm filter for lymphocytes (Uguccioni et al, *Eur. J. Immunol.*, 25, 64 (1995); Loetscher et al., *J. Exp. Med.*, 184, 569 (1996); Weber et al., *J. Immunol.*, 4166 (1995)) (PVP free, ChemoTX, Neuroprobe Inc., Cabin John, Md.). Twenty-nine μl of chemoattractant or control are added to the lower compartment of each well. The framed filter is aligned with the holes in the corner of the filter frame and placed over the wells. Two and one-half×$10^5$ monocytes in 25 μl of Gey's balanced salt solution+1 mg/ml BSA are added to the upper compartment. The agent is dissolved in MilliQ water and then serially diluted in the Gey's balanced salt solution. In most cases, the serially diluted agent is added to the upper compartment of the chemotaxis chamber. The chamber is incubated at 37° C. in a humidified atmosphere of 5% $CO_2$ for 1.5 hours.

2. Enzyme Release

The release of N-acetyl-β-D-glucosaminidase from monocytes may be employed to determine whether a therapeutic agent inhibits a cytokine-associated activity. Samples of $1.2 \times 10^6$ monocytes in 0.3 ml of prewarmed medium (136 mM NaCl, 4.8 mM KCl, 1.2 mM $KH_2PO_4$, 1 mM $CaCl_2$, 20 mM Hepes, pH 7.4, 5 mM D-glucose, and 1 mg/ml fatty acid-free BSA) are pretreated for 2 minutes with cytochalasin B (2.7 mg/ml) and then stimulated with a chemokine in the presence or absence of the therapeutic agent. The reaction is stopped after 3 minutes by cooling on ice and centrifugation, and the enzyme activity is determined in the supernatant (Uguccioni et al., *Eur. J. Immunol.*, 25, 64 (1995)).

The release of elastase from neutrophils may also be employed to determine whether a therapeutic agent inhibits a cytokine-associated activity (Pereri et al., *J. Exp. Med.*, 1547 (1988); Clark-Lewis et al., *J. Biol. Chem.*, 269, 16075 (1994)).

3. Cytosolic Free $Ca^{2+}$ Concentration ($[Ca^{2+}]_i$) Changes

Monocytes, eosinophils, neutrophils and lymphocytes loaded with Fura-2 (0.1 nmol/$10^5$ cells) are stimulated with a chemokine in the presence or absence of the therapeutic agent, and $[Ca^{2+}]_i$-related fluorescence changes are recorded (Von Tschanner et al., *Nature,* 324, 369 (1986)). For example, to determine cytosolic $Ca^{2+}$ concentrations in monocytes, monocytes are incubated with 0.5 μM Fura-2/AM for 30 minutes at 37° C. in HEPES-buffered saline (145 mM NaCl, 5 mM KCl, 1 mM $MgCl_2$, 10 mM HEPES, and 10 mM glucose), pH 7.4, at 37° C., supplemented with 1% albumin (w/v) and 1 mM $CaCl_2$. After loading with Fura-2, the cells are centrifuged for 5 minutes at 300×g and then resuspended in buffer containing no added albumin, to a cell density of $1.5 \times 10^6$ cells/ml, and kept at room temperature until use. This protocol results in a cytosolic Fura-2 concentration of about 100 μM. Serial dilutions of chemokines in PBS plus 0.1% albumin (w/v) (sterile filtered) are added to aliquots (0.7 ml) of cell suspension. The Fura-2 fluorescence of the monocyte suspension is measured at 37° C. in a single excitation, single emission (500 nm) wavelength Perkin-Elmer LS5 fluorometer. $[Ca^{2+}]_i$ is calculated from changes in fluorescence measured at a single excitation wavelength of 340 nm.

$[Ca^{2+}]_i$ measurements in cells that are stably transformed with a molecularly cloned chemokine receptor which is not expressed in the corresponding non-transformed cells are performed essentially as described above. After loading with Fura-2/AM, cells ($1 \times 10^6$/ml) are kept in ice-cold medium (118 mM NaCl, 4.6 mM KCl, 25 mM $NaHCO_3$, 1 mM $KH_2PO_4$, 11 mM glucose, 50 mM HEPES, 1 mM $MgCl_2$, 1 mM $CaCl_2$, 0.1% gelatin (pH 7.4). Aliquots (2 ml) of cell suspension are prewarmed at 37° C. for 5 minutes in 3-ml plastic cuvettes, and fluorescence is measured in a fluorometer (Johnson Foundation Biomedical Group) with magnetic stirring and temperature controlled at 37° C. Excitation is set at 340 nm, and emission is set at 510 nm. $[Ca^{2+}]_i$ is calculated as described above.

For studies in monocytes on cross-desensitization of calcium responses, chemokines are added sequentially with a 2-minute interval, and $[Ca^{2+}]_i$ transients are recorded. The concentrations used in these types of studies vary for each chemokine and are set at levels known to induce the maximal response for $[Ca^{2+}]_i$ mobilization (see Forssmann et al., *FEBS Lett.*, 408, 211 (1997); Sozzani et al., *J. Leukoc. Biol.*, 57, 788 (1995); Berkhout et al., *J. Biol. Chem.*, 272, 16404 (1997)).

4. Chemokine Binding and Binding Displacement

In general, specific binding is calculated as the amount of labeled agent bound in the absence of cold competitor minus the amount of labeled agent bound in the presence of cold competitor. The amount of specific binding in the presence of varied amounts of cold competitor can be used to determine the association constant for the agent, as well as the number of binding sites on the cell for the agent, using, for example, Scatchard Analysis. The agent may be labeled by radiolabeling (e.g., iodination) or with a suitable biochemical tag (e.g., biotin) or by addition of a photoactivatable crosslinking group. Agents with an association constant lower than 100 μM (i.e., which bind more strongly than an agent with an association constant of 100 μM) and which have at least about 2,500, preferably at least about 10,000, and more preferably greater than 25,000, binding sites per cell for at least one cell type which expresses a chemokine receptor, fall under the scope of this invention. THP-1 cells have at least about 5,000 MCP-1 receptors/cell.

For example, monocytes are suspended in RPMI 1640 medium without bicarbonate containing 0.2% bovine serum albumin and 0.1% azide. Radiolabeled chemokine peptide is incubated with $1$–$2 \times 10^6$ cells, e.g., THP-1 cells, in the presence or absence of increasing concentrations of unlabeled chemokine (MCP-1, MCP-3, MCP-4, RANTES or MIP-1α) for 15 minutes at 37° C. in a 96-well plate in a final volume of 0.2 ml (e.g., PBS+0.5% FCS). After the incubation, 0.5 ml of ice-cold wash buffer (20 mM Tris, 0.5 M NaCl, pH 7.4) is added, and cells are collected onto a polyethyleneimine-treated Whatman GF/C filter using a Brandall cell harvester. Filters are washed with 4 ml of cold wash buffer, and the radioactivity bound to the filters is counted in a γ-counter.

For competition studies, the $IC_{50}$ is calculated with a curve fitting program (GraFit, Erithacus Software, London), using a four-parameter logistic, $cpm_{bound} = cpm_{max}/(1+([L]/IC_{50})^s) + cpm_{ns}$, where $cpm_{max}$ represents the binding without competitor, [L] is the competitor concentration, $cpm_{ns}$ is the non-specific binding, and s is the slope factor. The $cmp_{bound}$ is corrected for "no cell" controls. To obtain the $K_d$ and capacity of binding specific binding, data from homologous displacement experiments are fitted into a single-site ligand binding equation using the GraFit best fit program.

Chemokine binding to cells stably transformed with a molecularly cloned chemokine receptor is performed essentially as described above except that radiolabeled agent is diluted with unlabeled chemokine. Cells are incubated with radiolabeled agent plus or minus unlabeled chemokines for 30 minutes at 37° C. (see also, Imai et al., supra; Sozzani et al. (1995), supra; Berkhout et al., supra; WO 97/22698).

5. Binding to the Duffy Antigen Receptor for Chemokines (DARC)

The affinity of the therapeutic agent to DARC may be determined by any method known in the art, e.g., the ability of the agent to inhibit the binding of radio-iodinated MCP-1 to red blood cells. Agents which bind to DARC with a lower association constant (i.e., stronger binding) than they bind to chemokine receptors (i.e., a DARC selectivity ratio of <1), and which bind to DARC with an association constant lower than 100 μM, preferably lower than 10 μM and more preferably lower than 1 μM, are useful in particular embodiments of the methods of the invention. In contrast, agents which do not bind DARC, or do not bind to DARC with an affinity that is greater than their affinity for chemokine receptors (i.e., a selectivity ratio >1), are useful in the practice of other embodiments of the methods of the invention.

6. Inhibition of the Co-Mitogenic Activity of Chemokines

Many chemokines are co-mitogenic with low concentrations of FCS, e.g., 50 ng/ml MCP-1+0.5% FCS is a mitogen for smooth muscle cells. Assays well known to the art for determination of DNA synthesis induced by any known chemokine plus a low concentration (<5%) of FCS on suitable cells (e.g., smooth muscle cells) in the presence and absence of the agent may be employed to screen agents for such inhibitory activity. See Porreca et al., *J. Vasc. Res.*, 34, 58 (1997), the disclosure of which is incorporated by reference herein.

7. Agonists

To determine whether an agent of the invention is a chemokine receptor agonist, varying amounts of a labeled form of the agent, e.g., biotinylated, are mixed with cells that express the receptor, e.g., THP-1 cells express receptors for MCP-1, MIP1α, SDF-1α and IL-8, while Jurkat cells express functional receptors for SDF-1. The affinity of the labeled agent for the cells is then determined. Agents that bind to receptors with a reasonable affinity and interact with the receptor by inducing signaling, are within the scope of the invention. While not encompassed by the term "agonist" or "antagonist", agents that bind to or near the receptor but elicit no response are also within the scope of the invention, and are termed "neutral" agents.

Agents with agonist activity may also be identified using the transwell migration assay, where the cells are placed in the upper compartment (see FIG. 1) in the absence of agent, and the agent, e.g. peptide 2[MCP-1], is placed at varying concentrations in the lower compartment in place of the chemokine. If the agent(s) have agonist activity, more cells are found in the lower compartment at the end of the assay in wells containing the agent(s) than in wells containing inactive control, i.e., agent or medium alone. Preferably, agents having agonist activity also stimulate migration of primary human cells, e.g., monocytes, in a transwell migration assay.

Moreover, weak agonists or neutral agonists (agents which bind to the receptor but do not inhibit binding of native chemokine and its subsequent signaling, nor do they induce signaling themselves) can be identified by screening the agents for ability to displace the binding of HIV gp120, specifically the V3 loop of gp120, to the surface of THP-1 cells or Jurkat cells. Cells are incubated with labeled (for example, radioiodinated) recombinant gp120 protein in an amount effective to bind to the virus receptor, in the presence and absence of various concentrations of the agent(s). Agents which reduce or abolish gp120 binding are agonists or neutral agonists within the scope of the invention.

8. In Vivo

A rapid method to determine whether an agent of the invention inhibits or augments an inflammatory response is to inject a selected chemokine into the skin of an animal in the presence or absence of an agent of the invention. At some later point in time, animals are sacrificed and the number of inflammatory cells at the chemokine injection site in animals exposed to both chemokine and the test agent is compared to the number of inflammatory cells at the chemokine injection site in animals exposed to chemokine alone, e.g., by quantitative immunofluorescence, relative to control animals.

B. Nucleic Acid Molecules of the Invention

1. Sources of the Nucleic Acid Molecules of the Invention

Sources of nucleotide sequences from which the present nucleic acid molecules encoding a chemokine peptide, a variant thereof or the nucleic acid complement thereof, include total or polyA$^+$ RNA from any eukaryotic, preferably mammalian, cellular source from which cDNAs can be derived by methods known in the art. Other sources of the DNA molecules of the invention include genomic libraries derived from any eukaryotic cellular source. Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular chemokine.

2. Isolation of a Gene Encoding a Chemokine

A nucleic acid molecule encoding a chemokine can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone chemokine cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic chemokines. One primer is prepared which is predicted to anneal to the antisense strand, and another primer prepared which is predicted to anneal to the sense strand, of a DNA molecule which encodes a chemokine.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode a chemokine is to screen a cDNA library. Screening for DNA fragments that encode all or a portion of a cDNA encoding a chemokine can be accomplished by probing the library with a probe which has sequences that are highly conserved between genes believed to be related to the chemokine, e.g., the homolog of a particular chemokine from a different species, or by screening of plaques for binding to antibodies that specifically recognize the chemokine. DNA fragments that bind to a probe having sequences which are related to the chemokine, or which are immunoreactive with antibodies to the chemokine, can be subcloned into a suitable vector and sequenced and/or used as probes to identify other cDNAs encoding all or a portion of the chemokine.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated, and/or expressed. For example, "isolated chemokine nucleic acid" is RNA or DNA containing greater than 9, preferably 36, and more preferably 45 or more, sequential nucleotide bases that encode at least a portion of a chemokine, or a variant thereof, or a RNA or DNA complementary thereto, that is complementary or hybridizes, respectively, to RNA or DNA encoding the chemokine and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated chemokine nucleic acid is RNA or DNA that encodes human MCP-1 and shares at least about 80%, preferably at least about 90%, and more preferably at least about 95%, sequence identity with the MCP-1 polypeptide having SEQ ID NO:16.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.,* 9, 6103 (1981), and Goeddel et al., *Nucleic Acids Res.,* 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of a chemokine peptide are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the chemokine peptide.

Oligonucleotide-mediated mutagenesis is a preferred method for preparing amino acid substitution variants of a chemokine peptide. This technique is well known in the art as described by Adelman et al., *DNA,* 2, 183 (1983). Briefly, chemokine DNA is altered by hybridizing an oligonucleotide encoding the desired mutation to a DNA template, where the template is the single-stranded form of a plasmid or bacteriophage containing the unaltered or native DNA sequence of the chemokine. After hybridization, a DNA polymerase is used to synthesize an entire second complementary strand of the template that will thus incorporate the oligonucleotide primer, and will code for the selected alteration in the chemokine DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.,* 75, 5765 (1978).

The DNA template can be generated by those vectors that are either derived from bacteriophage M13 vectors (the commercially available M13mp18 and M13 mp 19 vectors are suitable), or those vectors that contain a single-stranded phage origin of replication as described by Viera et al., *Meth. Enzymol.,* 153, 3 (1987). Thus, the DNA that is to be mutated may be inserted into one of these vectors to generate single-stranded template. Production of the single-stranded template is described in Sections 4.21-4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the chemokine, and the other strand (the original template) encodes the native, unaltered sequence of the chemokine. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

For example, a preferred embodiment of the invention is an isolated and purified DNA molecule comprising a preselected DNA segment encoding peptide 3 (1-12)[MCP-1] having SEQ ID NO: 1, wherein the DNA segment or variants thereof have nucleotide substitutions which are "silent" (see FIG. 8). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant at the tenth codon in the mature polypeptide (GTC) includes the substitution of GTT, GTA or GTG for GTC. Other "silent" nucleotide substitutions which can encode peptide 3 (1-12)[MCP-1] having SEQ ID NO:1 can be ascertained by reference to FIG. 8 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other mammalian, preferably human, chemokines may be modified in a similar manner. Thus, nucleic acid molecules encoding at least a portion of, for example, MCP-2, MCP-3, MCP 4, MIP1α, MIP1β, RANTES, SDF1α, IL8, GROα, eotaxin, MIG, PF-4, I309, HCC-1, C10, CCR-2, ENA-78, GROβ, IP10, SDF1β, GROα, MIP3α, TCA-3, CTAPIII, MARC/FYK, β-thromboglobulin, GCP-2, PBP, HC14, MDC, TECK, PARC, 6Ckine, fracktakine, DC-CK1, LIX, TARC, LARC, MIG, Ckβ8, CCF18/MRP-2, CCIII, CKα2, H1305, Dvic-1, DGWCC, TCA4, dendrokine, CC2/HCC1, CC3, and MIP1τ, as well as virally encoded chemokines such as vMIP-I, vMIP-II and vMIP-III or the complement thereto, may be modified so as to yield nucleic acid molecules of the invention having silent nucleotide substitutions, or to yield nucleic acid molecules having nucleotide substitutions that result in amino acid substitutions (see peptide variants hereinbelow).

C. In Vivo Studies

To further determine whether a particular agent is useful in the practice of the methods of the invention, an animal model is identified for a human disease. Transgenic animal models for human disease may also be employed to identify agents useful in the methods of the invention. For example, models of chemokine-induced macrophage recruitment associated with human atherosclerosis include, but are not limited to, mice with a homozygous deletion of the apolipoprotein E (apoE) gene, mice overexpressing human apoB and Watanabe heritable hyperlipidemic rabbits. Models for autoimmune disease include the collagen-induced arthritis in DBA/1 mice and myelin basic protein-induced experimental autoimmune encephalomyelitis. Models for osteoporosis include ovariectomized female rats, mice, monkeys, rats treated with heparin or with glucocorticoids as well as suspension-induced osteoporosis in rats. Models for HIV infection include infection of monkeys with SIV, SIV isolates, HIV or HIV isolates, SCID-Hu mice with HIV or HIV isolates, or rabbits with HIV or HIV isolates. Other animal models for lentiviral infection include cats infected with FIV, horses with EIAV, and goats infected with CAEV (which is also an animal model for arthritis).

The efficacy of an agent of the invention for anti-inflammatory therapy may be assessed by measuring the extent of inflammation, or the extent of macrophage infiltration of affected tissues. Macrophage infiltration can be detected by staining tissue sections with antibodies which specifically detect macrophages (e.g., mac-1 antiserum). Inflammation or other symptoms of disease may be detected by measuring appropriate clinical parameters, using techniques which are well known to those skilled in the art. For example, apoE knockout mice are treated with an agent, such as CRD-leu$_4$ile$_{11}$peptide 3, e.g., by intraperitoneal injection, for a period of twelve weeks, while control litter mates receive a suitable control peptide with no known biological activity. At the end of twelve weeks, the animals are sacrificed and the effect of the agent is assessed by measuring the reduction in macrophage recruitment into the vessel wall by quantitative immunohistochemistry using mac-1 antiserum, and by measuring the reduction in the extent of vascular lipid lesion formation by histochemistry using oil red O staining in accordance with Paigen, *Arteriosclerosis*, 10, 316 (1990).

Apo(a) transgenic mice develop lesions when fed a lipid-rich diet. These lesions do not contain any macrophages. In contrast, C57B16 inbred mice develop lipid lesions of similar size and severity to those in apo(a) transgenic mice, but these lesions are rich in infiltrating macrophage. Lesions of apo(a) mice, C57B16 mice, and 6 other strains of mice which develop lipid lesions rich with macrophage, were screened by quantitative immunofluorescence for levels of pro-inflammatory mediators, e.g., TNF-α, MCP-1, MIP-1α, IL1β, ICAM-1, VCAM-1, and P-selectin. TNF-α, MIP-1α, IL1β, ICAM-1, VCAM-1 and P-selectin were all expressed at identical levels in the apo(a) mouse lesions and the C57B16 lesions. Thus, while these pro-inflammatory mediators may be necessary to infiltration, they are not sufficient alone. In marked contrast, MCP-1 was completely absent from the lesions of apo(a) mice, but expressed at high levels in lesions from all other mouse lines which had macrophage-rich lesions.

Confocal microscopic analysis of sections of blood vessel wall with lesions triple stained with antibodies specific for SM-α-actin (smooth muscle cells; IA4 antibody), macrophages (Mac-1 antibodies) and MCP-1, showed that MCP-1 is not exclusively expressed by macrophage. That is, both smooth muscle cells and macrophages expressed MCP-1. Thus, MCP-1 may be the missing "inflammatory mediator" in the apo(a) mouse model of atherosclerosis. These results suggest that the lack of MCP-1 in apo(a) mice lesions may not be a consequence of the absence of macrophages, but instead contribute to the cause of lack of monocyte infiltration. Moreover, these results provide evidence that the chemokine MCP-1 plays a role in atherosclerotic vascular inflammation. Thus, MCP-1 can provide the basis for analogs which block the recruitment activity of this chemokine.

Chemokines other than MCP-1 may also be involved in macrophage recruitment, inflammation and pathogenesis of atherosclerosis, and in other diseases associated with inappropriate proliferation. For example, MIP1α has been implicated in the inappropriate inflammation in multiple sclerosis.

Thus, sequences analogous to peptide 2 and 3 from MIP1α may be particularly useful to treat or prevent multiple sclerosis. Therefore, when a particular chemokine is implicated in a particular disease, sequences from that particular chemokine may be especially useful to treat or prevent that disease. Preferred agents falling within the scope of the invention are inhibitors of signaling of more than one chemokine, and preferably of all chemokines. Thus, it may be preferable to prepare chemokine peptide analogs having sequences from a chemokine other than the one(s) associated with a particular disease process. Selection of a particular agent to treat a particular disease may be based on bioavailability, toxicity, DARC binding or other similar criteria.

Other models include, but are not limited to those reported by Lukacs (*Adv. Immunol.*, pp. 257-304, Academic Press (1996)), for lung injury; Lloyd et al. (*J. Leuko. Biol.*, 185, 1371 (1997)) and Tam et al. (*Kid. Int.*, 49, 715 (1996)), for nephritis; Volejnikova (*Am. J. Pathol.*, 150, 1711 (1997), for bone; Ghinikar et al. (*J. Neurosci. Res.*, 46, 727 (1996)) and Ransoholf et al. (*J. Leuko. Biol.*, 62, 645 (1997)), for brain; Kaul et al. (*Am. J. Trop. Med. Hyg.*, 58, 240 (1995)), for malaria; Ajeubar et al. (*J. Leuko. Biol.*, 63, 108 (1998)), for peritonitis; Furukawa et al. (*Lupus*, 6, 193 (1997)), for systemic lupus; Suzuki et al. (*J. Heart & Lung Transpl.*, 16, 1141 (1967)), Abbott et al. (*Arch. Surg.*, 89, 645 (1964)), Corry et al. (*Transpl.*, 16, 343 (1973)), Dworkin et al. (*J. Heart Lung Transpl.*, 10, 591 (1991)), Laden et al. (*Arch. Path.*, 93, 240 (1972)) and Mitchell et al. (*Transpl.*, 49, 835 (1990)), for transplants; U.S. Pat. No. 5,661,132 for wound healing; Burhardt et al. (*Rheum. Int.*, 17, 91 (1997)) for autoimmunity; Elson et al. (*Gastroenter.*, 109, 1344 (1998)) for inflammatory bowel disease; Hayes et al. (*Arterio. Thromb. Vasc. Biol.*, 18, 397 (1998)) and Wang et al. (*Arterio. Thromb.*, 11, 1166 (1991)), for cardiovascular disease; Wegner et al. (*Science*, 247, 456 (1990) for eosinophilic infiltration into the lung; Brahn (*Ciinorth and Rel. Res.*, 265, 42 (1991)), Wooley (*Curr. Op. Rheum.*, 3, 407 (1991)) and Gay et al. (*Curr. Op. Rheum.*, 7, 199 (1995), SCID-human synovial implant model)) for rheumatoid arthritis); Beamer et al. (*Blood*, 86, 3220 (1998)), Nakaguma (*Int. J. Exp. Path.*, 76, 65 (1998)), Nanney et al. (*J. Invest. Dermat.*, 106, 1169 (1996)), Nickoff et al. (*AJP*, 146, 580 (1995)), Sundberg et al. (*Pathobiol.*, 65, 271 (1997)), and Wolf et al. (*Int. J. Dermat.*, 30, 448 (1998)) for psoriasis; and Conti et al. (*Blood*, 89, 4120 (1997)), Gonzalo et al. (*JCI*, 98, 2332 (1996)), Teiyeira et al. (*JCI*, 100, 1657 (1997)), Ceri et al. (*Allergy*, 52, 739 (1997)), Freed (*Eur. Res. J.*, 8, 1770 (1998)), Griffiths-Johnson et al. (*Meth. Enzy.*, 288, 241 (1991)), Herz et al. (*New Horizons in Allergy Immunoth.*, 25-32 Plenum Press, 1996) and Kane (*Eur. Resp. J.*, 7 555 (1991)) for allergy.

II. Preparation of Agents Falling within the Scope of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding a chemokine is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a chemokine, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a pre-sequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding a chemokine or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, over expressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the Transfected DNA is a chromosomally integrated recombinant DNA sequence, which comprises a gene encoding the chemokine or its complement, which host cell may or may not express significant levels of autologous or "native" chemokine.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular chemokine, e.g., by immunological means (ELISAs and Western blots) or by assays described hereinabove to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides, Peptide Variants, and Derivatives Thereof

The present isolated, purified chemokine peptides, peptide variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., *Meth. Enzmmol.*, 287, 233 (1997). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given chemokine peptide can be readily prepared. For example, amides of the chemokine peptide or chemokine peptide variants of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the chemokine peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., *Science*, 276, 276 (1997)).

In addition, the amino acid sequence of a chemokine peptide can be modified so as to result in a chemokine peptide variant. The modification includes the substitution of at least one amino acid residue in the peptide for another amino acid residue, including substitutions which utilize the D rather than L form, as well as other well known amino acid analogs, e.g., unnatural amino acids such as α,α-disubstituted amino acids, N-alkylamino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N, N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

One or more of the residues of the peptide can be altered, so long as the peptide variant is biologically active. For example, for peptide 3[MCP-1] variants, e.g., $Ser_7$peptide 3(1-12)[MCP-1], it is preferred that the variant has at least about 10% of the biological activity of the corresponding non-variant peptide, e.g., a peptide having SEQ ID NO:1. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide.

Whether an amino acid change results in a functional peptide can readily be determined by assaying the specific activity of the peptide variant. Assays are described in detail herein.

Conservative substitutions are shown in FIG. 9 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions peptide variants with non-conservative substitutions. Non-conservative substitutions entail exchanging a member of one of the classes described above for another.

Acid addition salts of the peptide or variant peptide or of amino residues of the peptide or variant peptide may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Moreover, it is also envisioned that the agents of the invention, e.g., chemokine peptides, are modified in a manner that increases their stability in vivo, e.g., their half-life or bioavailability. These modified agents are termed "derivatives." Methods to prepare such derivatives are well known to the art. One method to stabilize peptides is to prepare derivatives which are cyclized peptides (see EPA 471,453 (amide bonds), such as that between lysine and aspartic acid side chains; EPA 467,701 (disulfide bonds); EPA 467,699 (thioether bonds). Other modifications which may increase in vivo stability are disclosed in Jameson et al. (*Nature*, 368 744 (1994)); U.S. Pat. No. 4,992,463; U.S. Pat. No. 5,596,078 and U.S. Pat. No. 5,091,396. A preferred embodiment of the invention is a chemokine peptide or variant that has been cyclized by addition of one or more cysteine residues to the N and/or C terminus of the peptide, as well as peptides which are constructed of the reverse sequence (i.e., reading C-terminal to N-terminal) of D-form amino acids. A more preferred embodiment of this invention is a peptide which is both cyclized and constructed with the reverse sequence of D-form amino acids, i.e., a CRD derivative.

It is also envisioned that the invention includes antibodies specific for the therapeutic agents of the invention. For example, rabbits were immunized with CRD-$Leu_4Ile_{11}Cys_{13}$ peptide 3(3-12)[MCP-1]. The resulting antisera had a high titer but did not cross react with MCP-1. The antibodies may be useful in an immunoassay to detect CRD-$Leu_4Ile_{11}Cys_{13}$ peptide 3(3-12)[MCP-1].

C. Chemokine Analogs

Chemokine analogs have properties analogous to those of the corresponding peptide. These analogs can be referred to as "peptide mimetics" or "peptidomimetics" (Fauchere, J. (1986) *Adv. Dru Res.*, 15:29; Veber and Freidinger (1985) TINS p. 392; and Evans et al. (1987) *J. Med. Chem.*, 30:1229, which are incorporated herein by reference) and can be developed with the aid of computerized molecular modeling. These analogs include structures having one or more peptide linkages optionally replaced by a linkage selected from the group consisting of: —CH$_2$NH—, —CH$_2$S—, —CH$_2$—CH$_2$—, —CH=CH-(cis and trans), —CH=CF-(trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds. Marcel Dekker, New York, P. 267 (1983); Spatola, A. F., Vega Data (March 1983), Vol. 1, Issue 3, "Peptide Backbone Modifications" (general review); Morley, J. S., *Trends Pharm. Sci.* (1980) pp. 463-468 (general review); Hudson, D. et al., *Int. J. Pept. Prot. Res.* (1979) 14:177-185 (—CH$_2$NH—, CH$_2$CH$_2$—); Spatola, A. F. et al., *Life Sci.* (1986) 38:1243-1249 (—CH$_2$—S); Hann, M. M., *J. Chem. Soc. Perkin Trans* I (1982) 307-314 (—CH—CH—, cis and trans); Almquist, R. G. et al., *J. Med. Chem.* (1980) 23:1392-1398 (—COCH$_2$—); Jennings-White, C. et al., *Tetrahedron Lett.* (1982) 23:2533 (—COCH$_2$—); Szelke, M. et al. European Appln. EP 45665 (1982) CA; 97:39405 (1982) (—CH(OH)CH$_2$—); Holladay, M. W. et al., *Tetrahedron Lett.* (1983) 24:4401-4404 (—C(OH)CH$_2$—); and Hruby, V. J., *Life Sci.* (1982) 31:189-199 (—CH$_2$S—); each of which is incorporated herein by reference. A particularly preferred non-peptide linkage is —CH$_2$NH—. Such analogs may have greater chemical stability, enhanced pharmacological properties (half-life, absorption, potency, efficacy, etc.), altered specificity (e.g., a broad-spectrum of biological activities), reduced antigenicity, and be economically prepared. Labeling of analogs usually involves covalent attachment of one or more labels, directly or through a spacer (e.g., an amide group), to non-interfering positions(s) on the analog that are predicted by quantitative structure-activity data and/or molecular modeling. Such non-interfering positions generally are positions that do not form direct contacts with the macromolecule(s) to which the analog binds to produce the therapeutic effect. Systematic substitution of one or more amino acids of a consensus sequence with a D-amino acid of the same type (e.g., D-lysine in place of L-lysine) may also be used to generate more stable peptides.

1. Isosteres of Chemokine Tripeptides (a Compound of Formula (IV))

A compound of formula (IV), wherein Z=CH$_3$; R$^1$=indolyl; Y=O; and X=CH$_3$, can be prepared from N-tBOC-NinBOC-L-tryptophan-OH and cyclohexenone. For example, 2-cyclohexen-1-one (Aldrich C10,281-4) can be reacted with lithium dimethylcuprate in the presence of trimethylsilyl chloride prior to use in the reaction, by methods well known to those skilled in the art (e.g., House et al., *J. Org. Chem.*, 40, 1460 (1975)). The addition of α-β unsaturated ketones by organocuprates is described, for example, in House et al., *J. Org. Chem.*, 31, 3128 (1966). Similarly, capture of the enolate by trimethyl silyl chloride is described in House et al., *J. Org. Chem.*, 36, 2361 (1971). The trapped enolate is then resolved to the α-iododerivative, for example, by addition of molecular iodine in the presence of acetoxy-silver and tetrabutylammonium fluoride, according to the method of Rubottom (*J. Org. Chem.*, 44, 1731 (1979)) to give the trans-disubstituted cyclohexanone of formula 100.

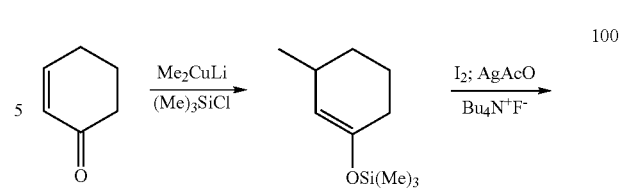

Conversion of the iodide of formula 100, to a secondary alcohol, and formation of an ester, for example, with acetic anhydride yields a compound of

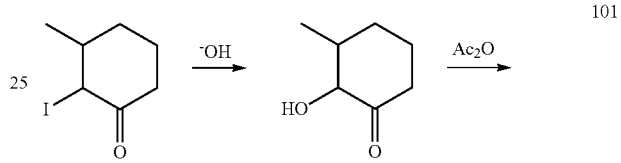

formula 101.

A compound of formula 101 can alternatively be prepared by conversion of the above trimethylsilyl ether enolate to the α-hydroxy ketone followed by formation of the ester, using procedures which are well known in the art.

A compound of formula 101 can be alkylated, for example, with vinyl magnesium bromide under standard conditions, and dehydrated (for example, in the presence of molecular iodine and heat) to yield a diene of formula 102:

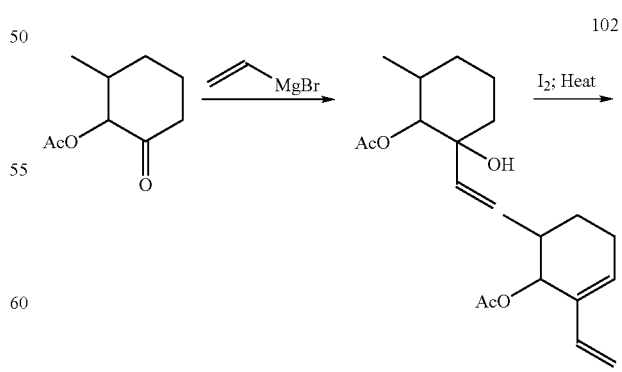

Diels-Alder reaction between the diene of formula 102 and ethyl acrylate (Aldrich E970-6) gives a stereospecific and regiospecific product of formula 103.

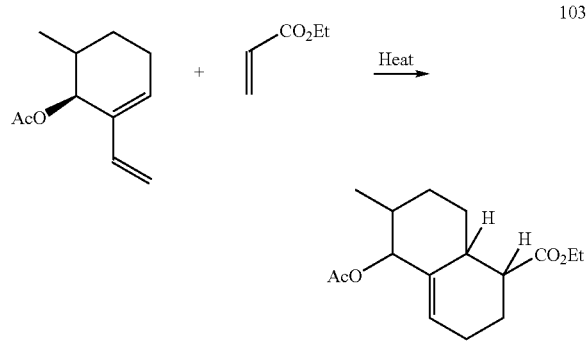

For example, the cyclization reaction can be performed by mixing the compound of formula 102 and ethyl acrylate in a sealed tube and heating, essentially as described by Green et al. (*Adv. Pest Control Res.*, 3, 129 (1960)).

Oxidative cleavage of the double bond in a compound of formula 103 gives a diacid of formula 104.

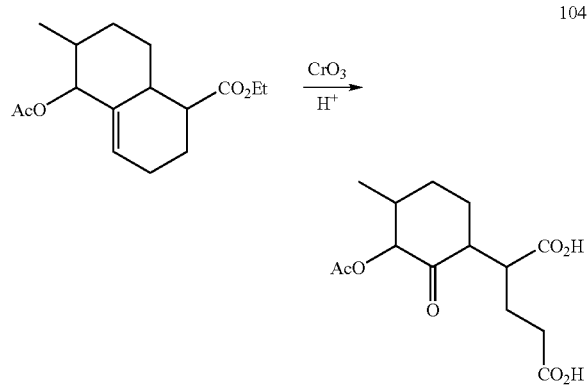

Such an oxidative cleavage may conveniently be carried out by ozonolysis or by oxidation with an acid chromate. For example, using $CrO_3$ in acid, the compound of formula 104 may be prepared, essentially as described by Eschenmoser & Winter, *Science*, 196, 1410 (1977).

Activation of the diacid with $POCl_5$ and subsequent reaction with dimethylamine gives a di-amide of formula 105.

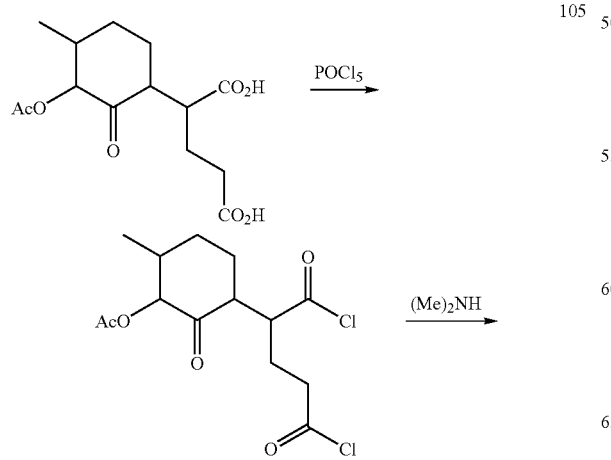

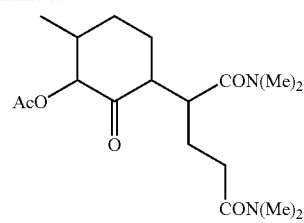

Hydrolysis of the acetoxy group of a compound of formula 105 followed by formation of the mesylate (or other suitable leaving group) and addition of sodium iodide in THF gives a compound of formula 106.

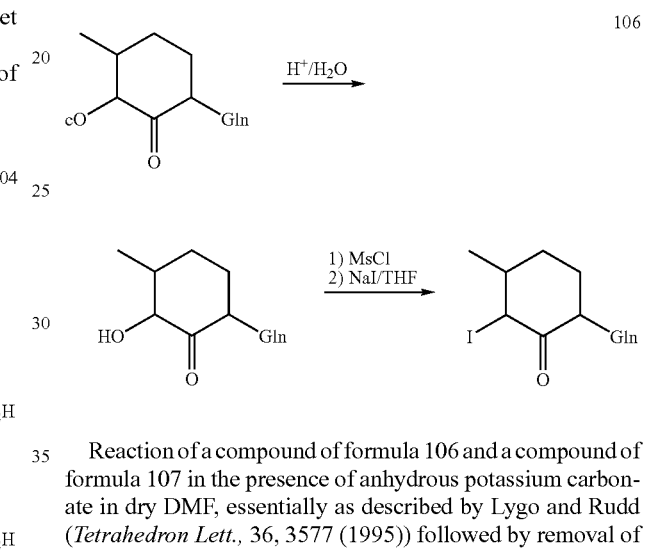

Reaction of a compound of formula 106 and a compound of formula 107 in the presence of anhydrous potassium carbonate in dry DMF, essentially as described by Lygo and Rudd (*Tetrahedron Lett.*, 36, 3577 (1995)) followed by removal of the sulfone, for example, using $SmI_2$, gives a compound of formula 108 which can be deprotected and acylated to give a compound of formula (IV) wherein $R^2$ and $R^3$ are $NMe_2$.

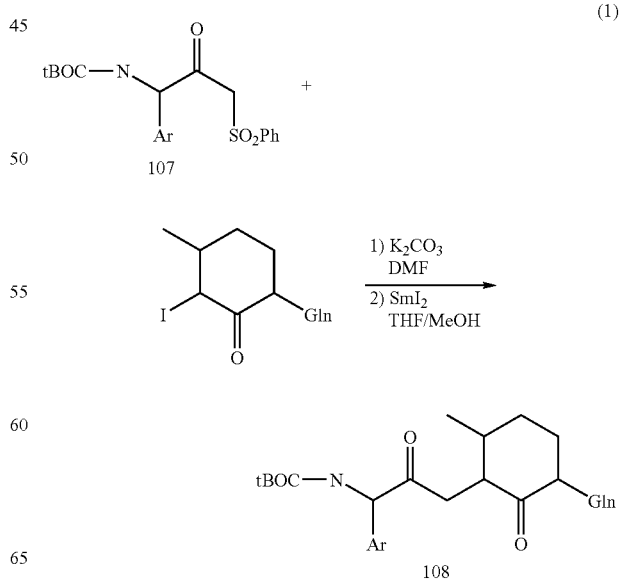

-continued
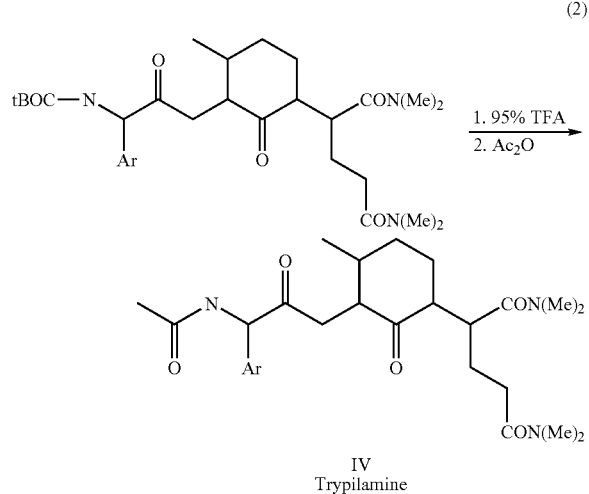
IV
Trypilamine
An intermediate of formula 107 may conveniently be prepared from a protected tryptophan (for example, N-α-tBOC—N$_{in}$tBOC-L-tryptophan-OH; Novabiochem 04-12-0201) by reaction with the dianion derived of
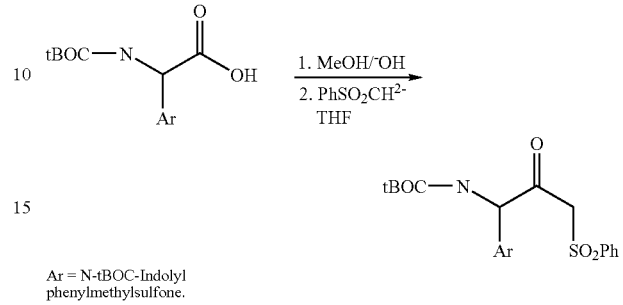
Ar = N-tBOC-Indolyl phenylmethylsulfone.
A preferred synthesis for a compound of formula (IV) illustrated in the
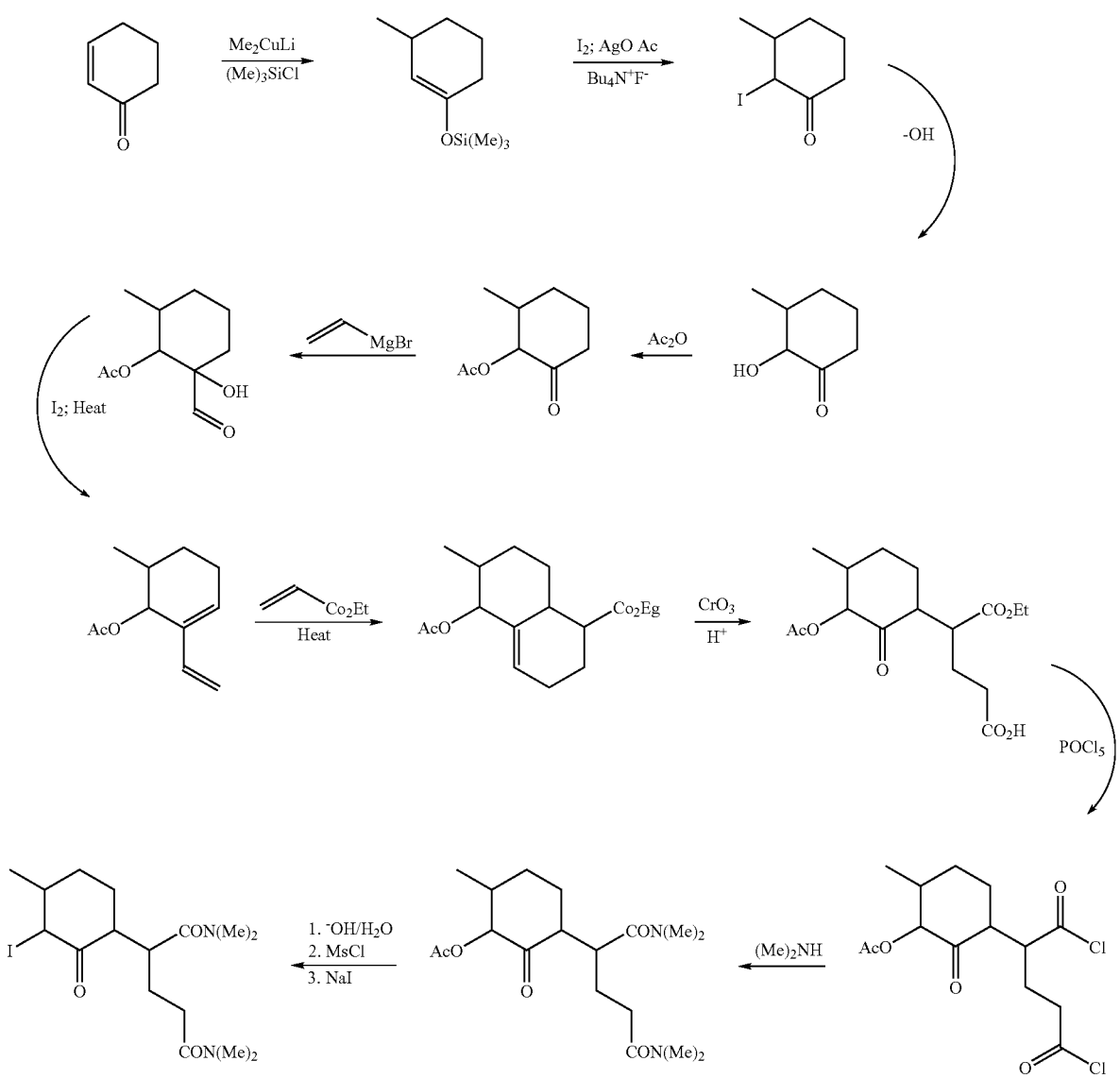

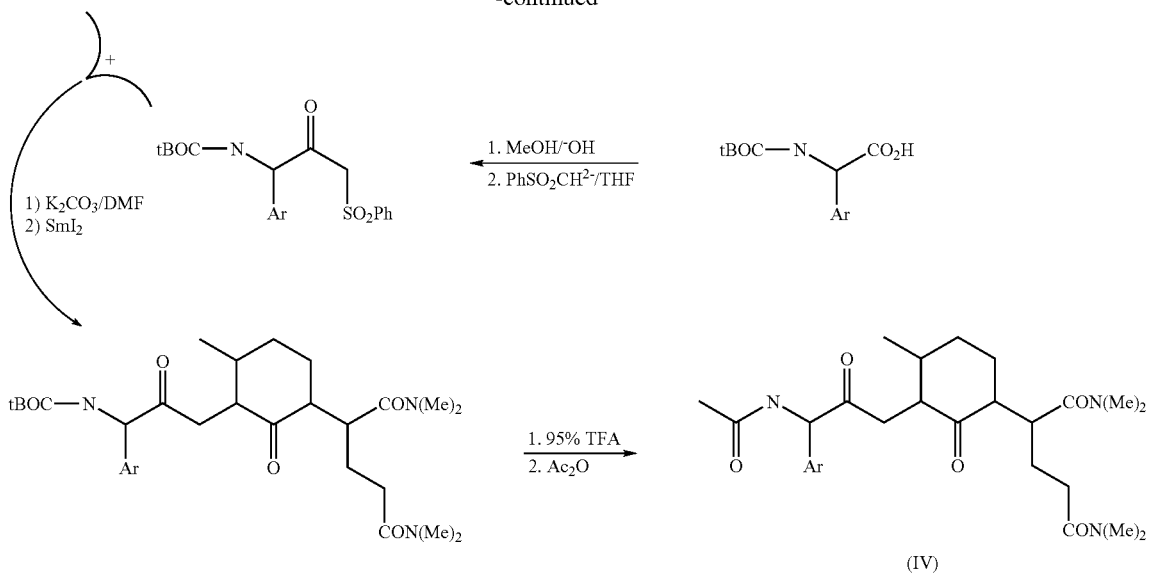

following diagram.

Thioketone derivatives (Y=S) may be synthesized by insertion of an additional reaction, in which the β-ketosulfone derivative of protected tryptophan 107 is converted to the thioketone derivative. For example, reaction with a dithiol, such as 1,2-ethanedithiol, forms a thioacetal which can be hydrolyzed in the presence of $H_2S$ under anhydrous conditions, to yield the thioketone.

As illustrated below, a compound of formula (V) can conveniently be prepared from an ester of formula 13. Deprotonation with lithium diisopropylamide followed by alkylation with bromide 14 gives a compound of formula 15. Selective reduction of the ester, for example with diisobutylaluminum hydride, gives an aldehyde of formula 16, which can be converted to the difluoroalkene 17 by a Wittig

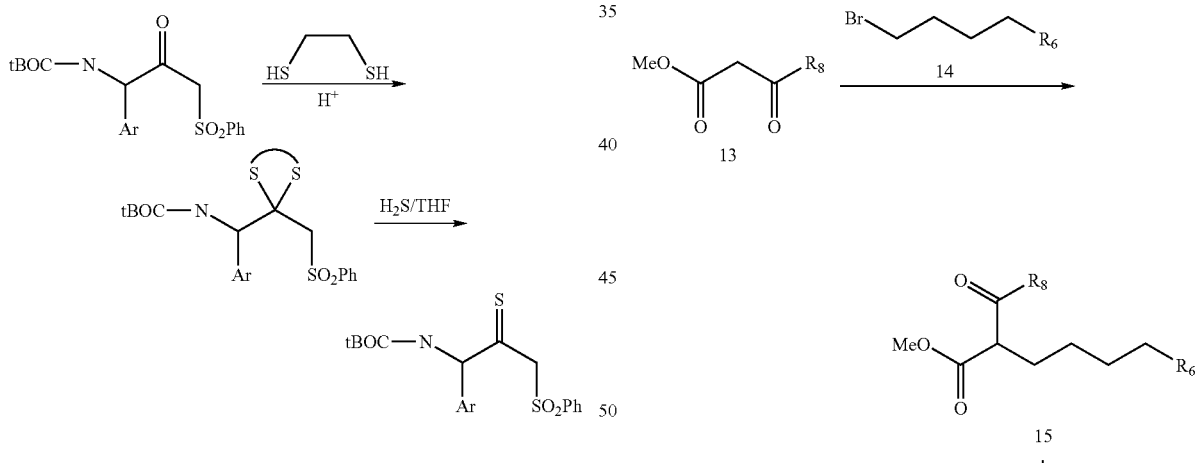

The conversion may also be carried out using [2,4-bis(4-methoxy-phenyl)-1,3-dithia-2,4-diphos-phetane-2,4 disulfide] (Lawesson's Reagent). Reaction of the thioketone derivative with the compound of formula 106 gives a compound of formula (IV) wherein Y=S.

Aryl substituents other than indolyl require preparation of suitably protected β-ketosulfone derivatives of the appropriate amino acid. Where the amino acid is readily available, the reaction can be performed using the appropriate tBOC or Fmoc protected amino acid (phenylalanine and tyrosine, respectively), for example, from Novabiochem. When the amino acid is not readily available (e.g., R=coumaryl), the suitably protected amino acid must first be prepared by methods well established in the art for synthesis of non-standard amino acids (for example, see Yuan and Hruby, *Tetrahedron Lett.*, 38, 3853 (1997)).

reaction with $PPh_3=CF_2$ (Hayashi et al., *Chemistry Letters*, 1980, pages 935-938).

Aldehyde 18 can be converted to bromide 19 using a procedure similar to that described in Visweswariah et al., *Synthesis*, 1982, pages 309-310, by treatment with phenyltrimethylammonium tribromide, followed by formation of the acetal under standard conditions. Conversion of the bromide to the corresponding alkyllithium by treatment with n-butyllithium, followed by reaction with difluoride 17, yields a compound of formula 20 (*Chemistry Letters*, 1980, pages 935-940). Deprotection under acidic conditions gives aldehyde 21, which can be reacted with $PPh_3=CF_2$ to give trifluoride 22. Subsequent treatment of 22, with the alkyllithium derived from bromide 23 yields a compound of formula (V). It will be understood by one skilled in the art that a variety of other known protecting groups can be utilized in the above procedures and that certain protecting groups may be preferred over others depending on the structure of the groups $R_4$-$R_8$.

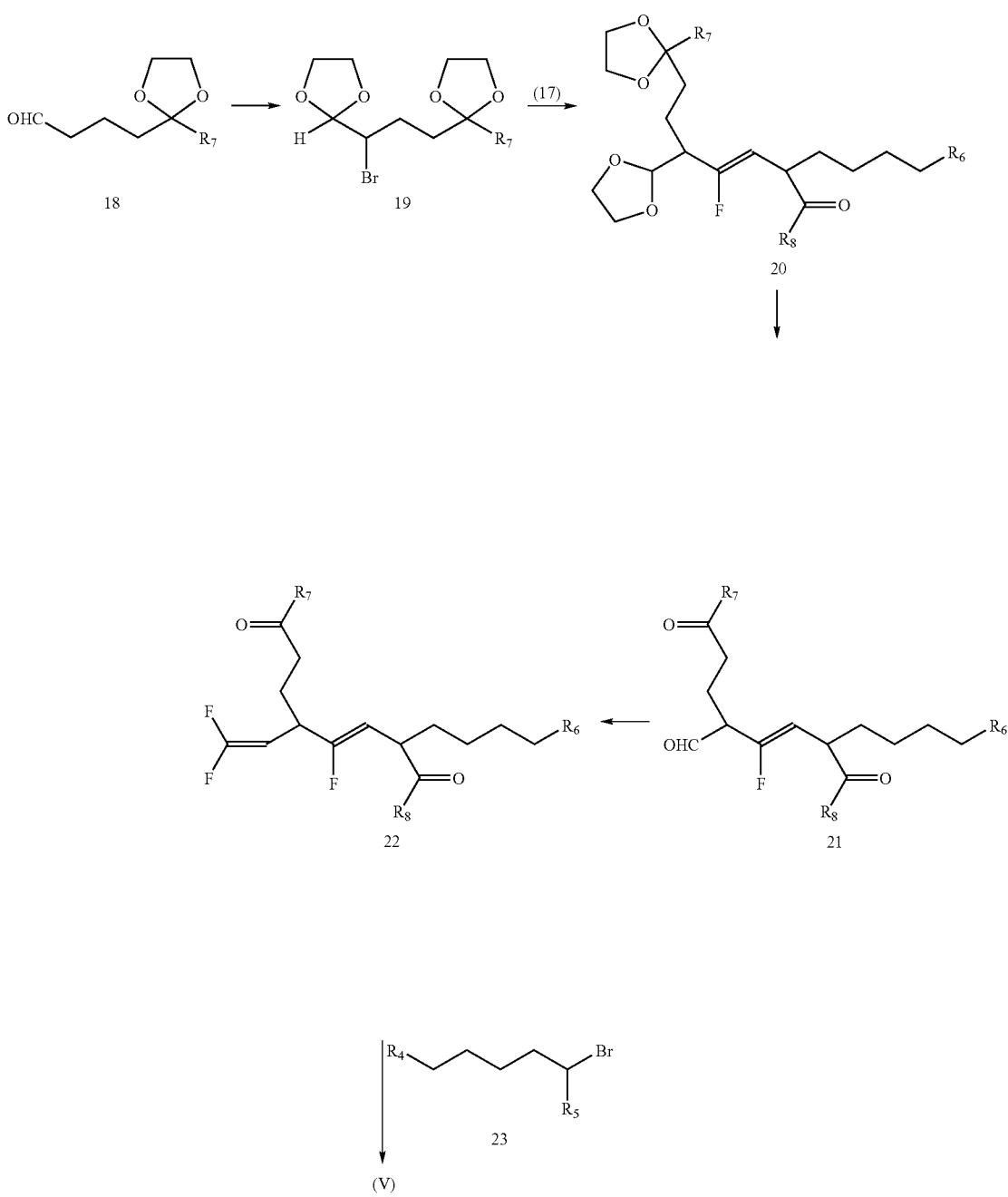

A compound of formula (XIII) can be prepared as shown in the following scheme.

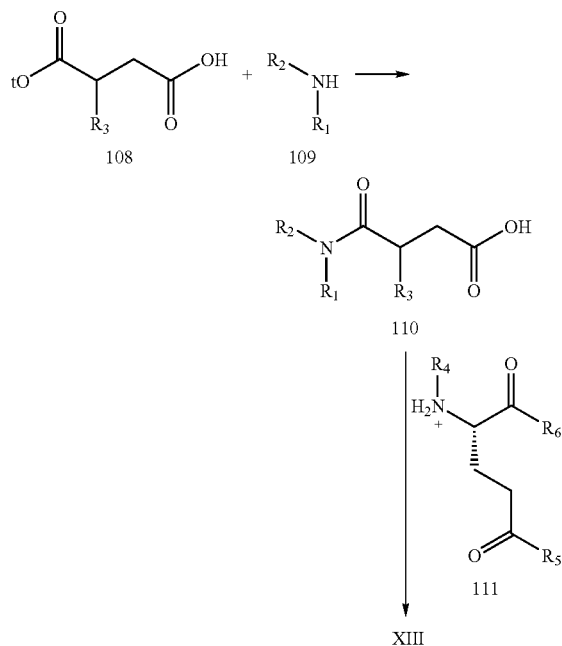

Reaction of ester 108 with an amine of formula 109 yields an acid of formula 110. Activation of the carboxylic acid using techniques known in the art (e.g. with N-bromosuccinimide) and coupling with an amine of formula III yields a compound of formula (XIII).

A compound of formula (XIV) can be prepared from Yohimbine using procedures similar to those known in the art. As illustrated in Example 23, treatment of yohimbine with sodamide provides the corresponding amide of formula (XIV) wherein $R_1$ is amino. Further alkylation or acylation of this amide using standard conditions provides other compounds of formula (XIV).

A compound of formula (X) wherein $R_3$ and $R_4$ form a ring can be prepared

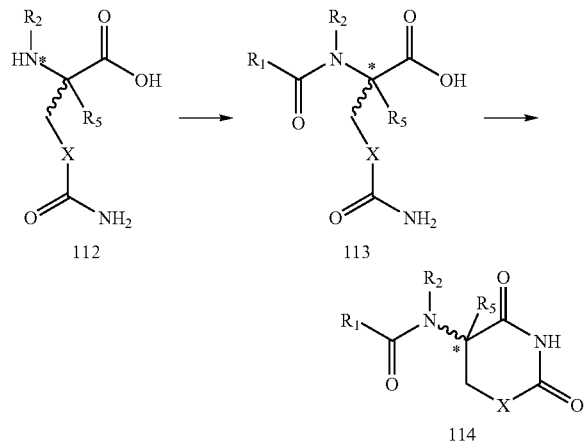

using the following general scheme.

Acylation of the amine 112 under standard conditions followed by ring closure provides a compound of formula 114, which is a compound of formula (X). A compound of formula 114 can be used as a starting material for preparing other compounds of formula (X).

A compound of formula (X) wherein $R_3$ and $R_4$ form a ring can also be prepared using the following general scheme.

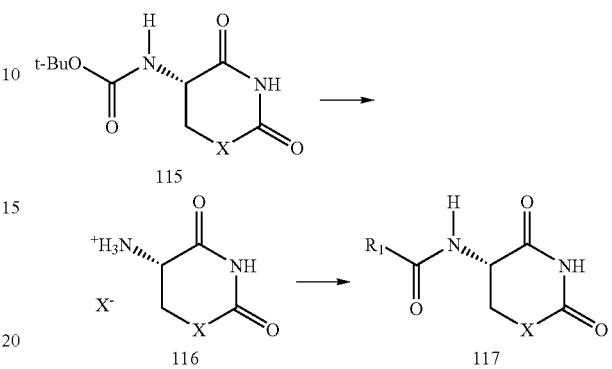

Hydrolysis of the carbamate 115 under standard conditions, for example using trifluoroacetic acid, yields a salt of formula 116 wherein X is a suitable counterion (e.g. triflate). Treatment of the amine salt 116 with the requisite activated acid ($R_1COOH$) gives a compound of formula 117, which is a compound of formula (X). The amine salt of formula 116 is a particularly useful intermediate for preparing compounds of formula (X).

Compounds of formula (XII) can conveniently be prepared from lysergic acid using procedures similar to those known in the art. For example, compounds of formula (XII) can be prepared as described in Example 24.

Other useful chemokine analogs may be identified by the methods described hereinabove. In particular, chemokine analogs that are orally bioavailable, and stable and potent inhibitors of chemokine activity are preferred.

D. Targeting of the Therapeutic Agent

Chemokine peptides, variants, analogs or derivatives thereof may be targeted to a specific therapeutic site by linking the therapeutic agent to a moiety that specifically binds to a cellular component, e.g., antibodies or fragments thereof, lectins, transferrin (for liver targeting) and small molecule drugs, so as to form a therapeutic conjugate. Targeting of the therapeutic agents of the invention can result in increased concentration of the therapeutic agent at a specific anatomic location. Moreover, the linking of a therapeutic agent of the invention to a binding moiety may increase the stability of the therapeutic agent in vivo. For example, an anti-CD4 mimetic that binds to the CD4 receptor may be linked to a therapeutic agent of the invention so as to result in a therapeutic conjugate, a portion of which binds to the HIV co-receptor. This may enhance the ability to target the therapeutic agent to a particular cell type and thus block HIV infection of that cell type.

For neoplasia, anti-tumor antibodies such as NR-LU-10 (anti-carcinoma), NR-ML-5 (anti-melanoma), or anti-CD45 (anti-lymphoma), may be useful to localize the therapeutic agent to a particular type of tumor. For infectious disease, antibodies which recognize a pathogen-specific epitope, such as mAb 17.41 (*Cryptosporidium parvum*), may be employed. To target to joints for treating rheumatoid arthritis, anti-synovium or chondroitin sulfate (e.g., Catalog No. C8035, Sigma Chemical Co., St. Louis, Mo.) antibodies can be linked to a therapeutic agent of the invention). To treat or prevent asthma or pneumonia, antibodies to the bronchial epithelium may be useful to prepare immunoconjugates for use in the methods of the invention.

Other antibodies useful in targeting a therapeutic agent of the invention to a specific site or cell type include antibodies specific for blood vessels or lymphatics (e.g., Ulex europaeus-I lectin, Catalog No. U4754, Sigma Chemical Co., St. Louis, Mo.), blood clots or platelets (e.g., Catalog Nos. F9902, F4639, F2506, F8512, Sigma Chemical Co., St. Louis, Mo.), T cells (e.g., Catalog Nos. C7048 (CD3); C1805 (CD4); C7173 (CD5); and C7298 (CD7), Sigma Chemical Co., St. Louis, Mo.), brain (e.g., Catalog Nos. S2644 and S2407, Sigma Chemical Co., St. Louis, Mo.), tumors (e.g., Catalog No. C2331, Sigma Chemical Co., St. Louis, Mo.), epithelial cells (e.g., Catalog Nos. E6011 and C1041, Sigma Chemical Co., St. Louis, Mo.), fibroblasts (e.g., Catalog Nos. F4771 and V4630, Sigma Chemical Co., St. Louis, Mo.), macrophage (e.g., Catalog No. M1919, Sigma Chemical Co., St. Louis, Mo.), stomach lumen (e.g., Catalog No. M5293, Sigma Chemical Co., St. Louis, Mo.), neutrophils (e.g., Catalog Nos. N1890 and N1765, Sigma Chemical Co., St. Louis, Mo.), tendons (e.g., Catalog No. E4013, Sigma Chemical Co., St. Louis, Mo.), skin (e.g., Catalog No. K4252, Sigma Chemical Co., St. Louis, Mo.) mammary tissue or epithelium (e.g., Catalog No. C6930, Sigma Chemical Co., St. Louis, Mo.) and skeletal muscle (e.g., Catalog Nos. D8281 and D1033, Sigma Chemical Co., St. Louis, Mo.).

To prepare immunoconjugates useful for targeting a malignant or virus-infected cell, an antibody or fragment thereof having a specificity for a surface antigen on a malignant cell or virus-infected is attached to a therapeutic agent of the invention. Preferably, a chemokine peptide or variant thereof is attached via peptide bonds to the carboxyl termini regions, e.g., CH3, of antibody heavy chains. The immunoconjugates can be prepared by genetic engineering techniques, i.e, by forming a nucleic acid construct encoding the chimeric immunoconjugate. Preferably, the gene construct encoding the immunoconjugate includes, in 5' to 3' orientation, a DNA segment which encodes a heavy chain variable region, a DNA segment encoding the heavy chain constant region, and a DNA segment coding for the chemokine peptide, peptide variant, or repeats thereof. The fused gene is inserted into an expression vector for transfection of the appropriate recipient cells where it is expressed. The hybrid chain can be combined with a light (or heavy) chain counterpart to form monovalent and divalent immunoconjugates.

The heavy chain constant region for the conjugates can be selected from any of the five isotypes: alpha, delta, epsilon, gamma or mu. Heavy chains or various subclasses (such as the IgG subclasses 1-4) can be used. The light chains can have either a kappa or lambda constant chain. DNA sequences for these immunoglobulin regions are well known in the art (see, e.g., Gillies et al., *J. Immunol. Meth.,* 125, 191 (1989)).

In preferred embodiments, the variable region is derived from an antibody specific for the target antigen (an antigen associated with a diseased cell such as a cancer cell or virus-infected cell), and the constant region includes the CH1, CH2 and CH3 domains. The gene encoding the chemokine peptide or variant is joined, e.g., by appropriate linkers, e.g., by DNA encoding $(Gly_4\text{-}Ser)_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the chemokine peptide or variant, can be designed to provide for proteolytic release of the chemokine peptide or variant at the target site. For example, it is well known that plasmin and trypsin cleave after lysine and arginine residues at sites that are accessible to the proteases. Many other site-specific endoproteases and the amino acid sequences they attack are well known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

Genes encoding appropriate variable regions can be obtained generally from Ig-producing lymphoid cells. For example, hybridoma cell lines producing Ig specific for tumor associated antigens or viral antigens can be produced by standard somatic cell hybridization techniques. These Ig-producing cell lines provide the source of variable region genes in functionally rearranged form. The variable region genes are typically of murine origin because the murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate polypeptide. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion (see Gillies et al., *Biotechnol.,* 7, 798-804 (1989)). Alternative methods include electroporation or calcium phosphate precipitation.

Other useful methods of producing the immunoconjugates include the preparation of an RNA sequence encoding the construct and its translation in an appropriate in vivo or in vitro system.

Methods for purifying recombinant immunoglobulins are well known. For example, a well known method of purifying antibodies involves protein A purification because of the propensity of protein A to bind the Fc region of antibodies. The antigen binding activity of the purified immunoconjugates can then be measured by methods well known to the art, such as described in Gillies et al. (*J. Immunol. Method.,* 125, 191 (1989)). For example, immunoconjugate activity can be determined using antigen-coated plates in either a direct binding or competition assay format.

In particular, it is preferred that humanized antibodies are prepared and then assayed for their ability to bind antigen. Methods to determine the ability of the humanized antibodies to bind antigen may be accomplished by any of numerous known methods for assaying antigen-antibody affinity. For example, the murine antibody NR-LU-13 binds an approximately 40 kilodalton glycoprotein expressed on numerous carcinomas. This antigen has been characterized in Varki et al., *Cancer Res.,* 44, 681 (1984); Okabe et al., *Cancer Res.,* 44, 5273 (1989). Thus, it is routine to test the ability of humanized antibodies to bind the NR-LU-13 antigen. Moreover, methods for evaluating the ability of antibodies to bind to epitopes of this antigen are known.

Humanized antibodies (or fragments thereof) are useful tools in methods for therapeutic purposes. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies can be found, for example, in U.S. Pat. Nos. 4,877,868, 5,175,343, 5,213,787, 5,120,526, and 5,202,169.

To target vascular smooth muscle cells (VSMC), VSMC binding proteins, e.g., polypeptides or carbohydrates, proteoglycans and the like, that are associated with the cell membranes of vascular smooth muscle cells can be employed to prepare therapeutic conjugates. In a preferred embodiment, the binding moiety is exemplified by chondroitin sulfate proteoglycans (CSPGs) synthesized by vascular smooth muscle cells and pericytes, and a discrete portion (termed an epitope herein) of the CSPG molecule having an apparent molecular weight of about 250 kD is especially preferred. The 250 kD target is an N-linked glycoprotein that is a component of a larger 400 kD proteoglycan complex. In one presently preferred embodiment of the invention, a vascular smooth muscle binding protein is provided by NR-AN-01 monoclonal antibody (a subculture of NR-ML-05) that binds to an epitope in a vascular smooth muscle CSPG target molecule. The monoclonal antibody designated NR-ML-05 reportedly binds a 250 kD CSPG synthesized by melanoma cells (Morgan et al., U.S. Pat. No. 4,897,255). Smooth muscle cells and pericytes also reportedly synthesize a 250 kD CSPG as well as other CSPGs. NR-ML-05 binding to smooth muscle cells has been disclosed (Fritzberg et al., U.S. Pat. No. 4,879,225). Subculture NR-ML-05 No. 85-41-41-A2, freeze # A2106, has been deposited with the American Type Culture Collection, Rockville, Md. and granted Accession No. HB-9350. NR-ML-05 is the parent of, and structurally and functionally equivalent to, subclone NR-AN-01, disclosed herein. It will be recognized that NR-AN-01 is just one example of a vascular smooth muscle binding protein that specifically associates with the 400 kD CSPG target, and that other binding proteins associating with this target and other epitopes in this target are also useful in the therapeutic conjugates and methods of the invention.

It will be recognized that the inventors also contemplate the utility of human monoclonal antibodies or "humanized" murine antibody as a vascular smooth muscle binding protein in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 0,411,893 A2. Humanized vascular smooth muscle binding partners will be recognized to have the advantage of decreasing the immunoreactivity of the antibody or polypeptide in the host recipient, which may thereby be useful for increasing the in vivo half-life and reducing the possibility of adverse immune reactions. See also, N. Lonberg et al. (U.S. Pat. Nos. 5,625,126; 5,545,806; and 5,569,825); and Surani et al. (U.S. Pat. No. 5,545,807).

Useful binding peptides for cancer treatment embodiments of the present invention include those associated with cell membrane and cytoplasmic epitopes of cancer cells and the like. These binding peptides localize to the surface membrane of intact cells and internal epitopes of disrupted cells, respectively, and deliver the therapeutic agent for assimilation into the target cells. Minimal peptides, mimetic organic compounds and human or humanized antibodies that localize to the requisite tumor cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$ M.

Methods useful to prepare antibody-peptide conjugates are well known to the art. See, for example U.S. Pat. No. 5,650,150, the disclosure of which is incorporated by reference herein. Representative "coupling" methods for linking the therapeutic agent through covalent or non-covalent bonds to the targeting moiety include chemical cross-linkers and heterobifunctional cross-linking compounds (i.e., "linkers") that react to form a bond between reactive groups (such as hydroxyl, amino, amido, or sulfhydryl groups) in a therapeutic agent and other reactive groups (of a similar nature) in the targeting moiety. This bond may be, for example, a peptide bond, disulfide bond, thioester bond, amide bond, thioether bond, and the like. In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr, *J. of Immunol.* 133:i-vii, 1984). In another illustrative example where the conjugate contains a radionuclide cytostatic agent, U.S. Pat. No. 4,897,255, Fritzberg et al., incorporated herein by reference, is instructive of coupling methods that may be useful. In one embodiment, the therapeutic conjugate contains a vascular smooth muscle binding protein coupled covalently to a chemokine peptide or variant. In this case, the covalent bond of the linkage may be formed between one or more amino, sulfhydryl, or carboxyl groups of the vascular smooth muscle binding protein and the chemokine peptide or variant.

In a preferred embodiment of the invention, an antibody conjugate is used in pretargeting methods. Essentially, such pretargeting methods are characterized by an improved targeting ratio or increased absolute dose to the target cell sites in comparison to conventional cancer diagnosis or therapy. A general description of pretargeting methods may be found in U.S. Pat. Nos. 4,863,713, 5,578,287, and 5,630,996. Typical pretargeting approaches are summarized below.

Pretargeting methods are of two general types: three-step pretargeting methods and two-step pretargeting methods. A three-step pretargeting protocol includes the administration of a targeting moiety-ligand conjugate, which is allowed to localize at a target site and to dilute in the circulation. This is followed by administration of an anti-ligand which binds to the targeting moiety-ligand conjugate and clears unbound targeting moiety-ligand conjugate from the blood, as well as binds to targeting moiety-ligand conjugate at the target site. Thus, the anti-ligand fulfills a dual function by clearing targeting moiety-ligand conjugate not bound to the target site as well as attaches to the target site to form a targeting moiety-ligand: anti-ligand complex. Finally, a therapeutic agent-ligand conjugate that exhibits rapid whole body clearance is administered.

When the therapeutic agent-ligand conjugate in circulation comes into close proximity to the targeting moiety-ligand:anti-ligand complex bound to the target site, the anti-ligand portion of the complex binds to the ligand portion of the circulating therapeutic agent-ligand conjugate, thus producing a targeting moiety-ligand:anti-ligand:ligand-therapeutic agent "sandwich" at the target site. Furthermore, because the unbound therapeutic agent is attached to a rapidly clearing ligand (rather than a slowly clearing targeting moiety, such as antibody or antibody fragment), this technique provides decreased non-target exposure to the active agent.

Alternatively, two-step pretargeting methods eliminate the step of administering the above identified anti-ligand. These "two-step" procedures feature targeting moiety-ligand or targeting moiety-anti-ligand administration, followed by the administration of a therapeutic agent which is conjugated to the opposite member of the ligand/anti-ligand pair.

As an optional step in the two-step pretargeting method, ligand or anti-ligand, designed specifically to provide a clearance function, is administered to facilitate the clearance of circulating targeting moiety-ligand or targeting moiety-anti-ligand. Thus, in the two-step pretargeting approach, the clearing agent does not become bound to the target cell population, either directly or through the previously administered target cell bound targeting moiety-anti-ligand or targeting moiety-ligand conjugate.

A targeting moiety in a pretargeting method binds to a defined target cell population, such as tumor cells. Preferred targeting moieties useful in this regard are antibodies (polyclonal or monoclonal), such as human monoclonal antibodies, or "humanized" murine or chimeric antibodies. Some examples of humanized antibodies include those that are CHO produced, produced in hosts such as plant (for example corn, soybean, tobacco, and the like), insect, mammalian, yeast, and bacterial. The humanized antibodies may be those that bind to the antigen bound by antibody NR-LU-13. Preferably, the humanized antibody may not possess N-linked glycosylation or its N-linked glycosylation has been modified post expression to reduce immunogenicity or toxicity.

Ligand/anti-ligand pairs suitable for use in targeting protocols include biotin/avidin or streptavidin, haptens and epitopes/antibody, fragments or analogs thereof, including mimetics, lectins/carbohydrates, zinc finger proteins/dsDNA fragments, enzyme inhibitors/enzymes; and analogs and derivatives thereof. Preferred ligands and anti-ligands bind to each other with an affinity of at least about $K_A \geqq 10^9 M^{-1}$ or $K_D \leqq 10^{-9} M$. Biotin/avidin or streptavidin is a preferred ligand/anti-ligand pair.

In general, such pretargeting methods preferably include the administration of an anti-ligand that provides a clearance function. The clearance is probably attributable to cross-linking and/or aggregation of conjugates that are circulating in the blood, which leads to complex/aggregate clearance by the recipient's RES (reticuloendothelial system). The anti-ligand clearance of this type is preferably accomplished with a multivalent molecule. However, a univalent molecule of sufficient size to be cleared by the RES on its own could also be employed.

Alternatively, receptor-based clearance mechanisms, e.g., Ashwell receptor or other receptors, may be exploited by addition of hexose residues, such as galactose or mannose residues, to provide for clearance of the anti-ligand, anti-ligand conjugate or humanized antibody via the liver. Such clearance mechanisms are less dependent upon the valency of the clearing agent than the RES complex/aggregate clearance mechanisms described above.

For example, if the targeting moiety-ligand or targeting moiety-anti-ligand has been derivatized to provide for clearance (i.e., addition of a hexose residue) a clearing agent should not be necessary. Preferred clearing agents are disclosed in U.S. Pat. Nos. 5,624,896 and 5,616,690; as well as PCT Application Publication Number WO 95/15978.

One skilled in the art, based on the teachings herein and the applications referenced herein, can readily determine an effective therapeutic effective dosage and treatment protocol. This will depend upon factors such as the particular selected therapeutic agent, route of delivery, the type of target site(s), affinity of the targeting moiety for target site of interest, any cross-reactivity of the targeting moiety with normal tissue, condition of the patient, whether the treatment is effected alone or in combination with other treatments, among other factors.

For example, in the case of humanized antibody—avidin or streptavidin conjugates in pretargeting strategies, a suitable dosage ranges from about 10 to about 2500 mg, more preferably from about 50 to 1500 mg, and most preferably from about 100 to 800 mg. The dosage of the ligand-therapeutic agent conjugate, generally ranges from about 0.001 to about 10 mg and more preferably from about 0.1 to 2 mg.

In general, such pretargeting methods include the administration of a clearing agent. The dosage of the clearing agent is an amount which is sufficient to substantially clear the previously administered conjugate from the circulation, i.e., at least about 50%, more preferably at least about 90%, and most preferably approaching or at 100%. In general, the clearing agent is administered several days after administration of the humanized antibody—streptavidin conjugate, preferably about 1 to 5 days after, more preferably at least about 1 to 2 days after. Generally, the determination of when to administer the clearing agent depends on the target uptake and endogenous clearance of targeting moiety conjugate. Particularly preferred clearing agents are those which provide for Ashwell receptor mediated clearance, such as galactosylated proteins, e.g., galactosylated biotinylated human serum albumin (HSA) and small molecule clearing agents containing galactose and biotin. In the case of HSA based clearing agents, a typical dosage of the clearing agent will range from about 100 to 1000 mg, and more preferably about 200-500 mg. If a clearing agent is administered, the ligand-therapeutic agent conjugate is preferably administered about 2 to 12 hours after.

The conjugates may be administered by known methods of administration. Known methods of administration include, by way of example, intraperitoneal injection, intravenous injection, intramuscular injection, intranasal administration, among others. Intravenous administration is generally preferred.

III. Indications Amenable to Treatment by the Agents of the Invention

The agents of the invention are useful to treat a mammal afflicted with, to inhibit in a mammal at risk of, or to augment in a mammal at risk of, an indication associated with chemokine-induced activity, such as aberrant or pathological inflammatory processes. The chemokines participate in a broad range of inflammatory processes, both physiological and pathological. Thus, broad specificity chemokine inhibitors may be useful to treat or prevent a wide range of inflammatory diseases. Moreover, the use of rationally designed chemokine inhibitors, i.e., inhibitors with relative specificity for various chemokines, may reduce or inhibit side-effects associated with chronic therapies of broad spectrum chemokine inhibitors. Thus, these inhibitors may be designed to treat particular diseases, thereby minimizing side effects resulting from disrupting unrelated physiological processes.

Atherosclerosis. Development of atherosclerosis is a complex process involving smooth muscle cells, endothelial cells and inflammatory cells, and, in particular, monocyte-derived tissue macrophages, B or T cells. Once endothelial cells are activated, they express adhesion molecules important for the extravasation of inflammatory cells. For example, in the TGFβ1 knockout (−/−) mouse, the absence of this cytokine resulted in endothelial cell activation. The activated endothelial cells express, among other adhesion molecules, E-selectin, P-selectin, and ICAM-1, which in turn participate in the extravasation of leukocytes. Potent pro-inflammatory cytokines were also expressed at the sites of incipient vascular lesions. TNF-α, IL-1, as well as several chemokines including IL-8 and MCP-1, have been detected at elevated levels in atherosclerotic lesions. Results described hereinabove show that the chemokine MCP-1 in particular plays a role in atherosclerotic vascular inflammation.

It is now well accepted that the acute stability of vascular lesions is a more important determinant of short-term, e.g., less than several years, risk of myocardial infarction than is total plaque burden. The degree of macrophage infiltration is probably the major determinant of relative plaque stability. At least two factors contribute to plaque stability: macrophages secrete an excess of matrix-degrading enzymes (such as the matrix metalloproteinases) over their inhibitors, resulting in the loss of extracellular matrix (ECM) in the macrophage-rich shoulder and fibrous cap regions, a common feature of unstable or ruptured plaques; and macrophage-derived foam cells become necrotic, possibly in response to toxic oxidative metabolites of lipids, resulting in a lipid-filled extracellular pool which further destabilizes the local vessel wall architecture.

Inhibitors of chemokine action, and in particular inhibitors of MCP-1, may improve plaque stability and thus rapidly reduce the risk of myocardial infarction, without necessarily reducing the total atherosclerotic plaque burden. In particular, the agents of the invention may decrease lipid lesion formation and/or lipid lesion progression as well as increasing plaque stability (Boring et al., Nature, 394, 894 (1998)). Thus, agents of the invention, e.g., peptide 3(1-12)[MCP-1] (SEQ ID NO:1), KQK, peptide 3[7-12] (SEQ ID NO:9), as well as variants, e.g., $Leu_4Ile_{11}$peptide 3(1-12)[MCP-1] (SEQ ID NO:14), or derivatives thereof (e.g. NR58,4, Y-II, and L-II), may be useful to treat and/or prevent unstable angina pectoris, atherosclerosis, as well as other diseases characterized by local or systemic vasculitis, as well as the symptoms and diseases which occur secondarily to the vessel wall inflammation such as myocardial infarction.

Moreover, the agents of the invention are also useful in combination with lipid lowering agents, such as the statins, or TGF-beta elevating agents (see, for example, WO 96/40098, the disclosure of which is incorporated by reference herein).

Osteoporosis. Low bone mineral density, often categorized as osteoporosis, results from an imbalance between bone matrix deposition by osteoblasts and its subsequent resorption by osteoclasts. The balance between these two dynamic processes determines bone density. One strategy to increase bone density has been the use of analogs of tamoxifen, such as raloxifene, which mimic the effects of estrogen on bone and thus, promote osteoblast differentiation (increasing bone matrix deposition) and inhibit osteoclast recruitment (decreasing resorption). An alternative strategy is to decrease matrix resorption by directly inhibiting the mechanism by which osteoclasts are recruited to the bone. Measurement of bone matrix degradation products (such as the N-terminal and C-terminal telopeptides of collagen as well as pyridinium cross-links) in plasma and urine confirm that bone resorption is increased in osteoporosis, and hence inhibition of osteoclast activity is likely to prove an effective therapeutic strategy.

Unlike osteoblasts, which are locally derived, osteoclasts are continuously recruited to bone as precursor cells which circulate in the monocyte fraction, and which may be identical to monocytes. Once recruited, the precursors differentiate into osteoclasts which then resorb matrix until they die by apoptosis. Thus, the number of osteoclasts in bone tissue (and hence the osteoclast activity) can be rapidly regulated by modulating the osteoclast recruitment process.

A number of lines of evidence now suggest that the monocyte recruitment into bone is a molecular parallel of the pathological monocyte recruitment into the blood vessel wall that occurs during atherogenesis. In particular, the chemokine MCP-1 is implicated in both processes. Thus, MCP-1 inhibitors may act to reduce monocyte recruitment and thus decrease osteoclast recruitment and/or decrease the number of cells differentiating into osteoclasts, which would result in a rapid increase in bone density, for example, over a period of weeks rather than years. The ability of the present therapeutic agents to increase bone density contrasts with existing drugs which prevent a further decrease in bone density but do not increase bone density. Therefore, peptide 3, e.g., peptide 3(7-12)[MCP-1], and variants (e.g., $Leu_4Ile_{11}$peptide 3(1-12)[MCP-1]) and derivatives (e.g., $CRD-Cys_{13}Leu_4Ile_{11}$peptide 3(3-12)[MCP-1]) thereof, may be useful to inhibit or prevent low bone density. In particular, derivatives with specificity for CC chemokines, such as KQK analogs and the WAQ analogs are preferred agents for the treatment of osteoporosis.

HIV Infection and AIDS. In addition to the CD4 receptor, additional cell surface molecules (termed co-receptors) are required for the productive infection of a cell by HIV isolates. HIV isolates can be divided into two subtypes, which depend on whether they can infect monocyte/macrophages (M-tropic strains) or helper T lymphocytes (T-tropic strains). Experiments with chemokine ligands suggest that the chemokine receptors function as the HIV co-receptors: MIP1α and RANTES inhibited the infection of monocytes with M-tropic strains (but not infection of T-cells by T-tropic strains), while SDF-1 inhibited T cell infection (but not monocyte infection). Further molecular analyses confirmed that the MIP1α/

RANTES receptor CCR-5 is the HIV co-receptor on monocytes while the SDF-1 receptor CXCR-4 (also termed LESTR and fusin) is the co-receptor on T-cells. Early in infection, M-tropic virus predominates, a virus which is non-syncytium forming, less virulent and does not deplete T-cells. At a later time, selection favors conversion to the more virulent, syncytium forming T-tropic strain, a strain which depletes helper T cells and leads to acquired immunodeficiency (AIDS). Some isolates of HIV have been reported which can efficiently use other chemokine receptors (such as CCR2a or CCR3), while other isolates which predominantly use CCR5 can use CCR2a at lower efficiency (Doranz et al., *Cell*, 85, 1149 (1996); Ross et al., *Proc. Natl. Acad. Sci. USA*, 95, 7682 (1998)). These findings suggest that a blockade of any one chemokine receptor may be ineffective, at least once an infection has been established and the viral load is relatively high (Cairns et al., *Nat. Med.*, 4, 563 (1998)). This limits the likely impact of the small number of chemokine receptor antagonists described to date (reviewed in Cairns et al., *Nat. Med.*, 4, 563 (1998)), all of which are specific for one, or a small subset, of chemokine receptors. Thus, to provide an effective agent to inhibit HIV, the agent preferably inhibits virus binding to more than one receptor, i.e., an agent would have to have broad specificity for chemokine receptors.

Genetic studies have identified a mutation in CCR5 which renders individuals essentially immune to HIV infection. This mutation, termed CCR5Δ32, results in a truncated mRNA for CCR-5. The expression of the truncated CCR-5 does not produce any detectable CCR-5 protein on the cell surface. Individuals homozygous for this deficiency have been reported to be entirely resistant to HIV infection, even under exposure to extremely high viral challenge, although there is now a single report of a homozygous mutant individual seropositive for HIV infection. Thus, these observations demonstrate that effective blockade of the CCR-5 receptor may effectively prevent infection. Moreover, CCR-5 mediated chemokine signaling does not have a crucial role in normal physiology, since CCR-5Δ32 homozygotes have no detectable phenotype other than HIV resistance.

Therefore, inhibitors of chemokine receptors, such as peptide 3, its variants, analogs or derivatives, may inhibit HIV infection as these agents have broad specificity. As described hereinbelow (Example 5), peptide 3[MCP-1] inhibited HIV binding and infection of Jurkat cells and macrophage. A preferred agent to prevent or inhibit HIV infection and/or replication is CRD-Cys$_{13}$Leu$_4$Ile$_{11}$peptide 3(3-12)[MCP-1]. In particular, peptide 3, its variants, analogs or derivatives, e.g., CRD-Cys$_{13}$Leu$_4$Ile$_{11}$peptide 3(3-12)[MCP-1], may be especially useful to inhibit infection of M-tropic strains of HIV.

Peptide 2, its variants, analogs or derivatives, are also useful to prevent or inhibit HIV infection and/or replication, as peptide 2 inhibited HIV replication in T cells and macrophage. Preferred therapeutic agents have decreased Duffy binding and increased co-receptor affinity (in at least about the nM range) (see Example 5) relative to the corresponding chemokine or peptide having the native or wild-type sequence. Preferably, Peptide 2, its variants, analogs or derivatives, e.g., LRD derivatives, are useful to inhibit T-tropic strains of HIV.

Thus, a combination of peptide 3, its variants, analogs or derivatives, and peptide 2, its variants, analogs or derivatives, may be particularly useful to prevent or treat HIV infection.

Thus, these agents are useful for the treatment, as well as the prevention, of both HIV seropositives and of progression of seropositive patients to AIDS, when used, either alone, in combination, or in combination with other anti-viral therapies. When used in combination, it is preferred that an infected individual is pre-treated with viral inhibitors (such as a cocktail of reverse transcriptase and viral protease inhibitors) and then given doses of a general chemokine inhibitor, preferably peptide 3, peptide 2, their variants or derivatives, more preferably peptide 2[MIP1α], its analogs or derivatives. Moreover, since resistance to other therapies (such as protease inhibitors or reverse transcriptase inhibitors) arise because of viral replication, agents which reduce virus infectivity may drastically increase the success of these existing therapies. Specifically, unlike all currently exploited therapeutic targets such as reverse transcriptase or the viral protease, chemokine agonists and/or antagonists target the susceptible cell rather than the virus itself. Although the virus can rapidly mutate to generate strains resistant to the virus-targeted agents, cells mutate less readily and are under less or no selective pressure to mutate. The extent to which the mutations in the HIV virus must occur to circumvent the use of a chemokine co-receptor is likely to be much greater than the mutations necessary to render a reverse transcriptase resistant to a reverse transcriptase inhibitor. Thus, the administration of chemokine analogs is likely to prove effective either alone or in combination with the virus-targeted therapies. Furthermore, chemokine inhibitors may have limited side effects in vivo, i.e., limited physiological impact, and therefore have a good therapeutic index when used in vivo.

Stroke. Inflammatory processes have been implicated in the pathophysiology of stroke or cerebral ischemia. The effects of the inflammatory response following stroke are detrimental, thus, there is a benefit afforded by preventing or inhibiting the inflammatory response. Activated neutrophils promote cerebral ischaemic injury by vascular plugging and by production of cytotoxic substances. For example, the early post ischemic recruitment and influx of vascular leukocytes, mainly neutrophils, into the brain represents a therapeutic target for the agents of the invention. Selective chemokine expression by central nervous system cells is important for post-ischaemic vascular leukocyte targeting, e.g., MCP-1 as well as other chemokines are upregulated in the central nervous system of stroke patients.

Psoriasis. Psoriasis is an inflammatory disorder that is associated with MCP-1 and monocyte recruitment. Topical application of a therapeutic agent of the invention, e.g., peptide 3, is preferred to prevent or treat psoriasis as this delivery method reduces bioavailability problems. Derivatives of the therapeutic agents of the invention, e.g., CRD peptides, which are administered topically may exhibit enhanced bioavailability relative to non-derivatized counterparts. Alternatively, psoriasis may be treated by systemic administration of an agent of the invention such as for example, CRD-Leu4Ile11Cys13-peptide 3(3-13)[MCP-1], NR58,4, Y-II, and L-II).

Autoimmune Diseases. Autoimmune diseases, such as multiple sclerosis, Crohn's disease, rheumatoid arthritis and systemic lupus erythematosus, are characterized by inappropriate activation of the immune system, orchestrated by autoreactive leukocytes. Although it remains unclear what factors lead to the initial inappropriate recognition of self-antigens, a number of pro-inflammatory cytokines have been implicated in the continuing inflammation which underlies the tissue destruction that, in turn, leads to the morbidity and mortality associated with these diseases. Of these inflammatory cytokines, TNF-α and the chemokines (in particular MIP-1α) have been implicated.

For example, elevated MIP-1α expression is detected in experimental autoimmune encephalomyelitis, a model of T-cell mediated autoimmune disease with some common characteristics to human multiple sclerosis. Elevated MIP1α activity is also detected in the cerebrospinal fluid of patients with multiple sclerosis. Antibody therapy to reduce chemokine levels has been shown to be effective in animal models of autoimmune diseases, but this method exhibits tachyphalaxis and only lowers chemokine levels for a short period, and is unlikely to be useful in human therapy. In contrast, a general antagonist of chemokine signaling is likely to suppress the inappropriate inflammation indefinitely. Thus, peptide 3, its derivatives and variants, may be useful to prevent and/or treat autoimmune disorders including, but not limited to, type I diabetes, multiple sclerosis, rheumatoid arthritis and systemic lupus erythematosus.

Moreover, different chemokine expression patterns may be associated with different autoimmune disorders, and hence each autoimmune disease may require a different derivative or variant of peptide 3. For example, MIP1α may play a central role in multiple sclerosis. MIP1α is a CC chemokine. Thus, the administration of a CC-selective agent of the invention can be used to treat multiple sclerosis (e.g., KQK compounds, compounds of formula (V), or $Ser_7Glu_8Glu_9$peptide 3(1-12)[MCP-1]).

Following wounding, there is a complex process of wound healing involving recruitment and proliferation of different cell types, elaboration of matrix, and increased immune surveillance. In the fetus (where increased immune surveillance is not required) this wound healing process leads to complete restoration of the normal tissue architecture (e.g., normal dermal architecture is restored after incisional wounding). In marked contrast, in the adult, incisional wounding results in a wound healing process that does not restore normal dermal architecture. Matrix is elaborated in excess amounts and in inappropriate spatial organization. The result is a scar. In some cases, such as in children following severe wounding such as from burns, the scars are hypertrophic having huge excess of matrix deposition and are particularly disfiguring.

In adults, the risk of infection following wounding is high. Leukocytes, particularly neutrophils, are recruited rapidly to the wound site, while monocyte/macrophages appear several days after wounding, resulting in a rapid formation of granulomatous tissue. Studies with antibodies have suggested that CXC chemokines such as IL-8 play an important role in neutrophil attraction to the wound site, and that inhibition of IL-8 production reduces both neutrophil accumulation and subsequent scarring. Experiments blocking CC chemokines have similarly shown that they have a role in the attraction of macrophages to the wound site, and these cells may also promote rapid healing at the expense of wound quality. Hence inhibition of either CXC or CC chemokines, or both, may result in a decrease in the wound-induced inflammatory reaction, and in turn promote a balance between fast healing and good restoration of dermal architecture.

To prevent or reduce scarring and/or enhance wound healing, a preferred embodiment of the invention is the topical application of a therapeutic agent of the invention that inhibits chemokine action at the site of the wound. Thus, a broad spectrum chemokine inhibitor, such as peptide 3(1-12)[MCP-1], $Leu_4Ile_{11}$peptide 3(1-12)[MCP-1], $CRD-Leu_4-Ile_{11}$peptide 3[MCP-1], NR58,4, Y-II, L-II, or WVQ, or combinations thereof may be administered. Alternatively, a selective inhibitor of IL-8, such as KEN, or a selective inhibitor of MCP-1, such as KQK, as well as combinations thereof may be administered. In addition, a combination of a broad spectrum inhibitor and a selective inhibitor may be administered. In this way, the various components of the wound-induced inflammatory process may be controlled as desired and the wound may be allowed to heal more slowly (under conditions where it is protected from infection, e.g., by simultaneous use of antibiotics) but with enhanced recovery of dermal architecture. See U.S. Pat. No. 5,202,118 for methods to determine the efficacy of an agent to treat or enhance wound healing.

Hypertension. Hypertension is a risk factor for atherosclerosis. To determine whether an agent of the invention is useful to inhibit or treat hypertension, a rabbit model is employed. New Zealand white rabbits are fed an atherogenic diet for three weeks to induce plaque formation. One half of each group of rabbits is administered an agent of the invention. Aortic coarctation is created in one group of the rabbits by wrapping a Dacron band around the midportion of the descending thoracic aorta (stenosis group). Another group of rabbits undergo the banding technique without aortic constriction. Yet another group of rabbits serve as nonoperated controls. Monocyte binding to the aortic endothelial surface is determined with epifluorescent microscopy on standard aortic segments proximal and distal to the band. Immunohistochemistry is performed using the following antibodies: VCAM-1, RAM11, CD11b, and factor VIII. In rabbits that did not receive the agent, hypertensive regions of the aorta proximal to the stenosis, monocyte adhesion and endothelial VCAM-1 expression are increased, with intimal thickening and accumulation of macrophage. In agent-treated rabbits, monocyte adhesion and endothelial VCAM-1 expression, intimal thickening and accumulation of macrophage are decreased relative to non-agent-treated rabbits. Thus, agents of the invention (e.g., $CRD-Leu_4Ile_{11}Cys_{13}$-peptide 3(3-13)[MCP-1], NR58,4, Y-II, and L-II) may be useful to ameliorate the vascular remodeling which accompanies, and may cause, human hypertension. It is preferred, however, that agents of the invention that are used to treat hypertension have little or no adrenoreceptor binding. Thus, preferred agents for treating hypertension may exclude compounds of formula (XIV).

Basophil-mediated diseases. Asthma is a disease characterized by hyper-reactive airways and chronic inflammation resulting from an influx of many cell types and inflammatory mediators. The interaction and causal effects of all the inflammatory mediators in asthma is not entirely understood. MCP-1 can play a role in asthma through several different effector functions such as: monocyte recruitment, basophil recruitment, lymphocyte recruitment, monocyte activation or by triggering the release of histamine from basophils or resident mast cells (Bischoff et al., *J. Exp. Med.*, 175(5), 1271 (1992)). Inhibition of these processes are likely to reduce the severity of the disease. Allergic diseases, like asthma, are manifested through a complex interaction of inflammatory mediators including monocytes/macrophages, lymphocytes and histamine release from mast cells and basophils.

A preferred mode for administration of a therapeutic agent of the invention to treat or inhibit the symptoms associated with asthma is by inhalation. As red blood cells are not normally present in the respiratory tract, the DARC specificity of the therapeutic agent is less important for administration to the respiratory tract than for other modes of administration.

Endotoxemia. Endotoxemia is an acute systemic illness often mediated by LPS, a major component in the cell wall of gram-negative bacteria. LPS stimulates the release of proinflammatory cytokines. MCP-1 and MCP-2 are expressed in endotoxemia and exert their effect by recruiting leukocytes to target organs. The intraperitoneal administration of recombinant murine MCP-1 to LPS-challenged mice protected them from endotoxic lethality (Zisman et al., *J. Clin. Invest.*, 99, 2832 (1997)). Thus, preferred peptides for use in this embodiment of the invention are MCP-1 and MCP-2 peptides.

Myocardial Infarction/Acute Ischemia. Myocardial infarction is the result of acute closure of a coronary vessel usually due to thrombosis secondary to rupture of an atherosclerotic plaque. The damage to the adjacent myocardium and resultant heart failure is secondary to the period of ischemia and the damage caused during the reperfusion period. Reperfusion injuries are associated with increased oxygen free radicals and inflammatory mediators. MCP-1 is up-regulated during the reperfusion period and is a key inflammatory mediator (Kumar et al., Circulation, 90, 1427 (1994); Kumar et al., Circulation, 95, 693 (1997)). Inhibition of MCP-1 and the resultant inflammatory input may decease damage to the myocardium during recovery and reduce the incidence of heart failure.

Rheumatoid Arthritis. Rheumatoid arthritis is a multi-systemic inflammatory disease involving primarily the joints but also the skin, blood vessels, heart, lung and muscle. The characteristic pathology of rheumatoid arthritis involves the accumulation of non-suppurative inflammatory cell infiltrate consisting of macrophages and lymphocytes within the joint. MCP-1 is produced by both synovial cells and infiltrating monocyte/macrophages in rheumatoid arthritis and is thought to contribute to the accumulation of inflammatory cells within the joint. Native MCP-1 and an antagonist of MCP-1 (residues 9-76 of native MCP-1) have been assessed in the MRL-1pr model of chronic arthritis. Treatment with the antagonist MCP-1 (9-76) but not native MCP-1 resulted in a reduction of the symptoms and histopathology of chronic arthritis in this model (Gong et al., J. Exp. Med., 186, 131 (1997); Plater-Zyberk et al., Immunol. Lett., 57, 117 (1997); Wilder, Clin. Rheumat., 10, 259 (1996)). Thus, peptide 3, its variants, analogs and derivatives may be especially useful to treat or prevent rheumatoid arthritis.

Contraception. Knockout mice for the CXCR4 chemokine receptor exhibit embryonic lethality. Agents of the invention have been identified which block the CXCR4 receptor (see Example 5) and other chemokine receptors. Thus, the agents of the invention may be useful in inducing abortion or providing contraception. Blockade of the CXCR4 receptor could provide an alternative to traditional contraceptives and could be used post-coitus.

IV. Dosages, Formulations and Routes of Administration of the Agents of the Invention The therapeutic agents of the invention, including a compound of formula (I)-(XV) and (XIX), including their salts, are preferably administered so as to achieve serum levels of about 0.01 pM to about 100 nM, more preferably at doses of about 0.01 pM to about 5 nM, and even more preferably at doses of about 0.1 pM to about 2 nM, of the therapeutic agent. To achieve these levels, the agent may be administered at dosages of at least about 0.01 to about 100 mg/kg, more preferably about 0.1 to about 50 mg/kg, and even more preferably about 0.1 to about 30 mg/kg, of body weight, although other dosages may provide beneficial results. The amount administered will vary depending on various factors including, but not limited to, the agent chosen, the disease, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., Immunity, 3, 165 (1995); Stevenson et al., Immunol. Rev., 145, 211 (1995); Molling, J. Mol. Med., 75, 242 (1997); Donnelly et al., Ann. N.Y. Acad. Sci., 772, 40 (1995); Yang et al., Mol. Med. Today, 2, 476 (1996); Abdallah et al., Biol. Cell, 85, 1 (1995)). Pharmaceutical formulations, dosages and routes of administration for nucleic acids are generally disclosed, for example, in Felgner et al., supra.

The amount of therapeutic agent administered is selected to treat a particular indication. The therapeutic agents of the invention are also amenable to chronic use for prophylactic purposes, preferably by systemic administration.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the therapeutic agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For longterm applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, poly-esters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include poly-methacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other therapeutic agents, for example, oral contraceptives, bronchodilators, anti-viral agents e.g., ddI, ddC, AZT, protease inhibitors, or any combination thereof, steroids, leukotriene inhibitors, cyclosporin A, methotrexate, azathioprene, anti-IgE, Enbrel, Xenapax and the like.

Sustained Released Dosage Forms

Sustained release dosage forms of the invention may comprise microparticles and/or nanoparticles having a therapeutic agent dispersed therein. The therapeutic dosage forms of this aspect of the present invention may be of any configuration suitable for sustained release. Preferred sustained release therapeutic dosage forms exhibit one or more of the following characteristics:

microparticles (e.g., from about 0.5 micrometers to about 100 micrometers in diameter, with about 0.5 to about 2 micrometers more preferred; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, with about 50 to about 250 nanometers being more preferred; or from about 0.01 nanometer to about 1000 nanometers in diameter, preferably from about 50 to about 200 nanometers), free flowing powder structure;

biodegradable structure designed to biodegrade over a period of time preferably between from about 0.5 to about 180 days, preferably from about 1-3 to about 150 days, or from about 3 to about 180 days, with from about 10 to about 21 days more preferred; or non-biodegradable structure to allow therapeutic agent diffusion to occur over a time period of between from about 0.5 to about 180 days, more preferably from about 30 to about 120 days; or from about 3 to about 180 days, with from about 10 to about 21 days preferred;

biocompatible with target tissue and the local physiological environment into which the dosage form to be administered, including yielding biocompatible biodegradation products;

facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to therapeutic agents.

Preferred sustained release dosage forms of the present invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

Polymers derived from the condensation of alpha hydroxycarboxylic acids and related lactones are preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown below, with the values of x and y being manipulable by a practitioner in the art to achieve desirable microparticle or nanoparticle properties.

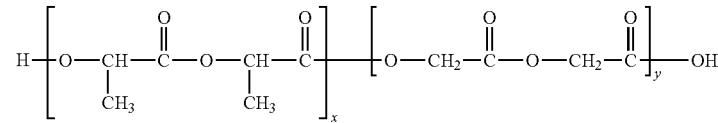

Other agents suitable for forming particulate dosage forms of the present invention include polyorthoesters and polyacetals (*Polymer Letters,* 18:293 (1980) and polyorthocarbonates (U.S. Pat. No. 4,093,709) and the like.

Preferred lactic acid/glycolic acid polymer containing matrix particles of the present invention are prepared by emulsion-based processes, that constitute modified solvent extraction processes, see, for example, processes described by Cowsar et al., "Poly(Lactide-Co-Glycolide) Microcapsules for Controlled Release of Steroids," *Methods Enzymology,* 112:101-116, 1985 (steroid entrapment in microparticles); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity,* 59:2978-2986, 1991 (toxoid entrapment); Cohen et al., "Controlled Delivery Systems for Proteins Based on Poly(Lactic/Glycolic Acid) Microspheres," *Pharmaceutical Research,* 8(6):713-720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science,* 73(9):1294-1297, 1984 (peptide entrapment).

In general, the procedure for forming particle dosage forms of the present invention involves dissolving the polymer in a halogenated hydrocarbon solvent, dispersing a therapeutic agent solution (preferably aqueous) therein, and adding an additional agent that acts as a solvent for the halogenated hydrocarbon solvent but not for the polymer. The polymer precipitates out from the polymer-halogenated hydrocarbon solution onto droplets of the therapeutic agent containing solution and entraps the therapeutic agent. Preferably the therapeutic agent is substantially uniformly dispersed within the sustained release dosage form of the present invention. Following particle formation, they are washed and hardened with an organic solvent. Water washing and aqueous nonionic surfactant washing steps follow, prior to drying at room temperature under vacuum.

For biocompatibility purposes, particulate dosage forms, characterized by a therapeutic agent dispersed in the matrix of the particles, are sterilized prior to packaging, storage or administration. Sterilization may be conducted in any convenient manner therefor. For example, the particles can be irradiated with gamma radiation, provided that exposure to such radiation does not adversely impact the structure or function of the therapeutic agent dispersed in the therapeutic agent-polymer matrix or the binding protein/peptide attached thereto. If the therapeutic agent or binding protein/peptide is so adversely impacted, the particle dosage forms can be produced under sterile conditions.

Release of the therapeutic agent from the particle dosage forms of the present invention can occur as a result of both diffusion and particle matrix erosion. The biodegradation rate directly effects the kinetics of therapeutic agent release. The biodegradation rate is regulable by alteration of the composition or structure of the sustained release dosage form. For example, alteration of the lactide/glycolide ratio in preferred dosage forms of the present invention can be conducted, as described by Tice et al., "Biodegradable Controlled-Release Parenteral Systems," *Pharmaceutical Technology*, pp. 26-35, 1984; by inclusion of agents that alter the rate of polymer hydrolysis, such as citric acid and sodium carbonate, as described by Kent et al., "Microencapsulation of Water Soluble Active Polypeptides," U.S. Pat. No. 4,675,189; by altering the loading of therapeutic agent in the lactide/glycolide polymer, the degradation rate being inversely proportional to the amount of therapeutic agent contained therein, by judicious selection of an appropriate analog of a common family of therapeutic agents that exhibit different potencies so as to alter said core loadings; and by variation of particle size, as described by Beck et al., "Poly(DL-Lactide-Co-Glycolide)/Norethisterone Microcapsules: An Injectable Biodegradable Contraceptive," *Biol. Reprod.*, 28:186-195, 1983, or the like. All of the aforementioned methods of regulating biodegradation rate influence the intrinsic viscosity of the polymer containing matrix, thereby altering the hydration rate thereof.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding of the protein/peptide to the particle dosage form are optionally included in or on the particle matrix and are attached to the non-degradable or biodegradable polymeric units. Functional groups that are useful for this purpose include those that are reactive with peptides, e.g., carboxyl groups, amine groups, sulfhydryl groups and the like. Preferred binding enhancement moieties include the terminal carboxyl groups of the preferred (lactide-glycolide) polymer containing matrix or the like.

V. Detection of the Agents of the Invention in Physiological Fluid

Analysis of peptide 3 in blood and urine was performed on a semi-permeable surface (SPS)HPLC column (restricted access media). Serum or other protein-containing samples can be injected directly onto an SPS column (e.g., SPS-C18 with a column size of 4.6 mm×250 mm; using a mobile phase: A: 0.1% TFA in water, B: 0.1% TFA in acetonitrile: 0-5 min—5% B, 5-30 min—60% B, 30-40 min—5% B detector; 215 nm). The outer phase of the column forms a semipermeable surface that prevents large molecules from reaching the inner phase. Small molecules penetrate the semipermeable surface and interact with the inner reversed phase.

Standards of peptide 3 (range of 1.5 µg/ml to 1000 µg/ml) in PBS were injected and a standard curve was created. 20 µl of serum and urine were injected and the areas under the peptide 3 peaks were obtained. The concentration was then calculated from the standard curve. This method can detect at least about 20 µg/ml of a peptide in physiological fluid samples.

The peptides of the invention may also be detected and/or quantitated in physiological fluid, e.g., urine or serum, using LC-MS. Using electrospray ionization (ESI), an LCQ ion trap mass spectrometer (Thermoquest Finnigan, San Jose, Calif.) is operated in the positive ion mode with the heated capillary set to 200° C., and 4.25 kV applied to the electrospray needle. The sheath gas flow rate is set to 55 units, while the auxiliary gas is turned off. The data are acquired with a maximum ion time of 500 ms and 1 total microscan. The analysis is performed using a full scan MS with m/z [335-1400] and/or a full scan MS/MS with m/z [280-1500] generated by fragmentation of the doubly charged ion with m/z 680.1 set to an isolation width of 2.0 amu and a collisional energy of 28%.

HPLC grade solvents ('Baker Analyzed' from J. T. Baker, Phillipsburg, N.J.), and formic acid (99%, ACS, Sigma, St. Louis, Mo.) were used. A Zorbax Eclipse XDB-C18 3.0×150 mm, 3.5 micron ('Zorbax', Hewlett-Packard, Palo Alto, Calif.) equipped with a 'SafeGuard' guard column containing a C18 cartridge (Phenomenex, Torrence, Calif.) is operated at a column temperature of 35° C. and a maximum pressure of 400 bar. The flow rate is set to 0.500 mL/min. An HP1100 binary system (Hewlett-Packard, Palo Alto, Calif.) generates a 20 minute gradient starting with 0% B (acetonitrile) and 100% A (water/0.1% formic acid) at 0.0 to 3.0 minutes, then ramps up to 15% B at 3.5 minutes and runs isocratically until 12.0 minutes. This elution step is followed by a high organic wash step ramping up to 95% B from 12.0 to 14.0 minutes while increasing the flow rate to 0.800 mL/min at 14.1 minutes. At 16.0 to 16.5 minutes the system is resetting to 0% B and re-equilibrates for 3.5 minutes at 0.800 mL/min. Alternatively, a 15 minute gradient is generated starting with 98% A (water/0.1% formic acid (acetonitrile)) at 0-2.5 minutes, then ramps to 17% B at 2.5 minutes up to 11 minutes, then ramps to 95% B at 11 minutes. The flow rate is increased to 0.800 mL/minute at 11.1 minutes. At 13.2 minutes, the system resets to 1% B until 15 minutes. The LCQ divert valve is set to direct the flow to the detector between 8 and 11 minutes. 10 µl of each sample is injected using an HP1100 autosampler (Hewlett-Packard, Palo Alto, Calif.). Under the first set of conditions, CRD-Leu$_4$Ile$_{11}$Cys$_{13}$ peptide 3(3-12)[MCP-1] elutes at a retention time of 9.69 minutes.

Under the second set, CRD-Leu$_4$Ile$_{11}$Cys$_{13}$ peptide 3(3-12)[MCP-1] (triacetate salt) eluted at a retention time of 8.3 minutes while CRD-L-Leu$_4$Ile$_{11}$Cys$_{13}$ peptide 3(3-12)[MCP-1] (triacetate salt) eluted at 8.9 minutes. The standard analytes are prepared by adding different levels of CRD-Leu$_4$Ile$_{11}$Cys$_{13}$ peptide 3(3-12)[MCP-1] and a fixed amount of CRD-L-Leu$_4$Ile$_{11}$Cys$_{13}$ peptide 3(3-12)[MCP-1] triacetate salt to rat urine filtrated through a 'Sterile Acrodisc 13 0.2 µm' filter (Gelman Sciences, Prod. #4454) or serum. The following levels of free base CRD-Leu$_4$Ile$_{11}$Cys$_{13}$ peptide 3(3-12)[MCP-1] in rat urine were each injected three times and processed using LCQuan to generate a standard curve: 0.05 µg/mL, 0.1 µg/mL, 0.5 µg/mL, 1.0 µg/mL, 2.0 µg/mL, 3.0 µg/mL, 5.0 µg/mL, 10 µg/mL, 20 µg/mL, 30 µg/mL, and 50 µg/mL. Rat urine samples are analyzed after filtration as described above.

Rat serum samples are analyzed as described above, for fast screens without prior purification, otherwise after liquid/liquid extraction with ice-cold acetonitrile followed by solvent removal in a speed vac over night and reconstitution in water/formic acid (0.1%) or HPLC grade water. For example, 400 µl of ice cold acetonitrile is mixed with serum (about 100 µl) and centrifuged for 10 minutes at 10,000 rpm. 400 µl of supernatants were transferred into fresh tubes, dried under vacuum and reconstituted in 80 µl of HPLC grade water. Samples were spun for 10 minutes at 10,000 rpm and 70 µl transferred into 100 µl glass inserts in 2 mL HPLC vials for LC-MS analysis. An internal standard such as deuterated CRD-Leu$_4$Ile$_{11}$Cys$_{13}$ peptide 3(3-12)[MCP-1] can be added to account for losses during sample preparation. The standard curves are prepared accordingly.

The invention will be further described by, but is not limited to, the following examples.

Example 1

Identification and Characterization of Pan-Chemokine Peptide Inhibitors

Both human and mouse MCP-1 bind to and positively signal through the human chemokine receptor. Thus, regions of homology between human and murine MCP-1 may represent regions that are involved in binding and/or signaling. Based on an alignment of human and murine MCP-1 sequences, three regions in MCP-1 were identified which were conserved between all the species examined. Three peptides (12-15mers) were prepared which had the greatest sequence homology between the human and mouse MCP-1 sequences (Table 1), and were purified to >95% purity. These peptides were screened for their ability to inhibit hMCP-1 induced THP-1 migration. A similar analysis was done for a non-chemokine, i.e., TGF-beta. The sequences of *Xenopus laevis* TGF-beta1 and TGF-beta3 and human TGF-beta1 and TGF-beta3 were compared, and 3 regions (each 10mer) of perfect homology were identified.

For this assay, THP-1 cells were maintained at a density of $4\times10^5$ cells per ml in RPMI-1640 supplemented with 10% fetal calf serum+20 µM 2-mercaptoethanol. Chemotaxis was induced in a 96-well disposable chemotaxis chamber fitted with a 5 µM polycarbonate filter (PVP free, ChemoTX, Neuroprobe Inc., Cabin John). Twenty-nine µl of chemoattractant (recombinant human chemokine; 50 ng/ml, i.e., 5.9 nM) or control (100 ng/ml TGFβ) was added to the lower compartment of each well. The framed filter was aligned with the holes in the corner of the filter frame and placed over the wells. Five×$10^4$ THP-1 cells in 25 µl of RPMI-1640 were added to the upper compartment. Peptides were dissolved in Milli Q water and then serially diluted in culture medium. In most cases, the serially diluted peptides were added to the upper compartment of the chemotaxis chamber. The chamber was incubated at 37° C. in a humidified atmosphere of 5% $CO_2$ for 4 hours.

After incubation, the cells were gently removed from the top of the filter with a pipette, 20 µl of 20 mM EDTA in PBS was added into each top well, and the mixture was incubated for 20 minutes at 4° C. The filter was then carefully flushed with media using a gentle flow, and removed. A standard curve was prepared to accurately quantify the number of THP-1 cells that had migrated. The curve was based on a two-fold dilution series of THP-1 cells (top standard 100,000 cells in 29 µl). Cells which had migrated, and in separate wells, the cells in the standards, were stained with 3 µl of MTT stock solution which was added directly into each well (5 mg/ml in RPMI 1640 without phenol red, Sigma Chemical Co.) and incubated at 37° C. for 4 hours. The media was carefully aspirated from each well, and the converted dye was solubilized by 20 µl of DMSO. Absorbance of converted dye was measured at a wavelength of 595 nM using an ELISA plate reader. The number of cells that had migrated in each well was determined by interpolation of the standard curve.

Peptide 1[MCP-1] (see Table 1; SEQ ID NO:2), i.e., the N-terminal peptide of human MCP-1, was only weakly active in the migration inhibition assay ($ED_{50}$>100 µM; 10% inhibition at 100 µM, p=0.27). Peptide 2[MCP-1] (Table 1; SEQ ID NO:3) was also a weak inhibitor of chemokine-induced migration ($ED_{50}$>100 µM; 19% inhibition at 100 µM, p=0.09). Thus, in the presence of a strong agonist, i.e., MCP-1, peptide 2[MCP-1] having SEQ ID NO:3, a weak agonist, displaces MCP-1 from its receptor. However, in the absence of a strong agonist, i.e., MCP-1, peptide 2[MCP-1] exhibited weak agonist properties, i.e., peptide 2[MCP-1] stimulated chemotaxis. Surprisingly, peptide 2(1-15)[SDF1α] had potent pan-chemokine antagonist properties.

Figure 2:
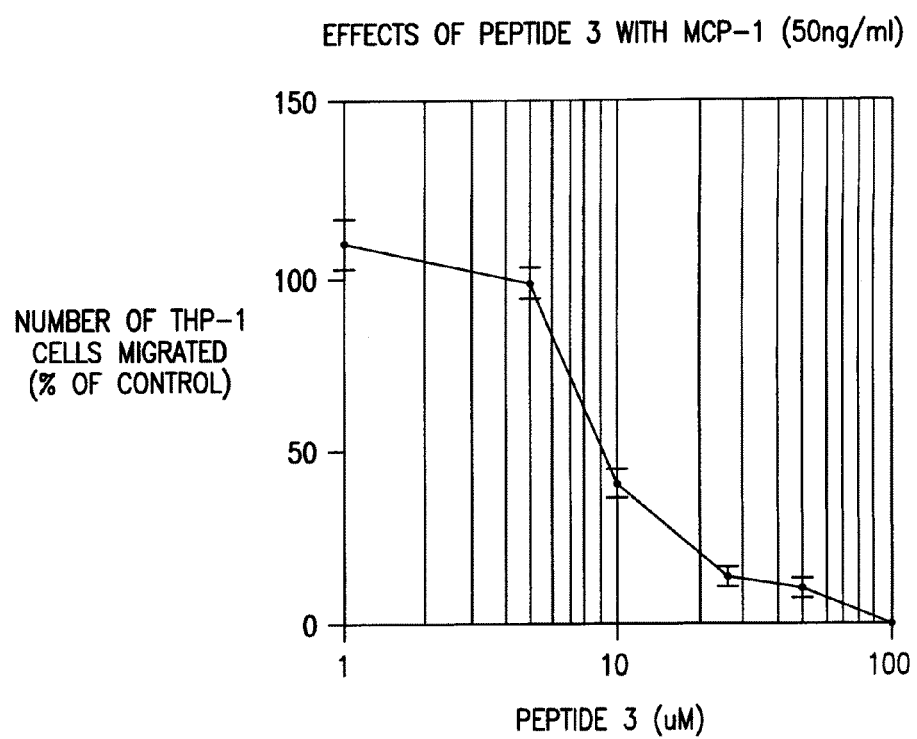
FIG. 2 shows a dose-response curve for the peptide 3 (SEQ ID NO:1) inhibition of MCP-1-induced THP-1 cell migration.

In contrast, peptide 3(1-12)[MCP-1] (Table 1; SEQ ID NO:1) was a highly effective inhibitor of MCP-1 induced THP-1 migration with a dose giving 50% inhibition ($ED_{50}$) of 8±1 µM (n=4). A typical dose response curve is shown in FIG. 2. At concentrations above 50 µM, peptide 3(1-12)[MCP-1] having SEQ ID NO:1 abolished all of the MCP-1 induced THP-1 migration.

TABLE 1

Alignment of Chemokine Sequences

```
AQPDAINAPV TCCYNFTNRK ISVQRLASYR RITSSKCPKE AVIFKTIVAK EICADPKQKW VQDSMDHLDK QTQTPKT hMCP1      (SEQ ID
*****.***. **** **   . *    ** **. *****.**** ** * *  . . *.***** * **     **.                NO: 16)
AQPDAVNAPL TCCYSPTSKM IPMSRLESYK RITSSRCPKE AVVFVTKLKR EVCADPKKEW VQTYIKNLDR NQMR.....mMCP1    (SEQ ID
                                                                                                NO: 26)

Peptide 1              Peptide 2              Peptide 3

GICADPKQKWVQ rabbit MCP1
                                              (SEQ ID NO: 115)
                                              EICADPNKEWVQ rat MCP1
                                              (SEQ ID NO: 116)
                                              EICADPNKEWVQ dog MCP1
                                              (SEQ ID NO: 116)
                                              ELCADPKQKWVQ bovine MCP1
                                              (SEQ ID NO: 117)
                                              EVCADPTQKWVQ guinea pig MCP1
```

TABLE 1-continued

Alignment of Chemokine Sequences

```
                                                                           (SEQ ID NO: 118)
                                                                           EICAEPKQKWVQ  pig MCP1
                                                                           (SEQ ID NO: 119)

AQPDSVSIPI TCCPNVINRK IPIQRLESYR RITNIQCPKE AVIFKTKRGK EVCADPKERW VRDSNKHLDQ IFQNLKP    hMCP2     (SEQ ID
                                                                                                  NO: 17)
AQPVGINTST TCCYRFINKK IPKQRLESYR RTTSSHCPRE AVIFKTKLDK EICADPTQKW VQDFMKHLDK KTQTPKL    hMCP3     (SEQ ID
                                                                                                  NO: 18)
SASLAADTPT ACCESYTSRQ IPQNFIADYF E-TSSQCSKP GVIFLTKRSR QVCADPSEEW VQKYVSDLEL SA         hMIP1a    (SEQ ID
                                                                                                  NO: 19)
SAPMGSDPPT ACCFSYTARK LPRNFVVDYY E-TSSLCSQP AVVFQTKRSK QVCADPSESW VQEYVYDLEL N          hMIP1b    (SEQ ID
                                                                                                  NO: 20)
SAPMGSDPPT ACCFSYTARK LPRNFVVDYY E-TSSLCSQP AVVFQTKRSK QVCADPSESW VQEYVYDLEL N          RANTES    (SEQ ID
                                                                                                  NO: 21)
    HPGIPS ACCYNFTNKK ISFQRLKSYK IITSSKCPQT AIVFEIKPDK MICADPKxxW VQDAKKYLDQ ISQxTKP    Eotaxin   (SEQ ID
                                                                                                  NO: 25)
LPRSAKELRC QCIKTYSKPF HPKFIKELRV IESGPHCANT EIIVRLSDGR ELCLDPKENW VQRVEKFLKR AENS       hIL-8     (SEQ ID
                                                                                                  NO: 23)
   GKPVSLSY RCPCRFFESH IARANVKHLK ILNTPNCALQ IVARLKNNNR QVCIDPKLKW IQEYEKALNK           hSDF1b    (SEQ ID
                                                                                                  NO: 22)
                                                                   CALDTVGW VQ         I-309     (SEQ ID
                                                                                                  NO: 131)
.......... .C...F.... I.......... ..T...C... AVI......K .VCADP...W VQ.....L.. .....CONSENSUS
```

To determine whether the peptides were MCP-1 receptor antagonists, the peptides were introduced with the chemokine in the lower compartment (as opposed to with the cells in the upper compartment in the experiments described above; in the trans-well THP-1 migration assay. Under these conditions, peptide 1[MCP-1] having SEQ ID NO:2 was a more efficient inhibitor of MCP-1 induced chemokine migration that it had been when it was incubated with the cells, inhibiting 48% of the MCP-1 induced migration at 100 μM compared to 10% inhibition when peptide 1[MCP-1] (SEQ ID NO:2) was incubated with the cells. This result is consistent with published reports which show that peptide 1[MCP-1] (SEQ ID NO:2) and its derivatives act by disrupting the MCP-1 dimer, forming inactive monomers. Peptide 1[MCP-1] (SEQ ID NO:2) is not, therefore, a classical receptor-level antagonist of MCP-1 function. In marked contrast, peptide 3(1-12)[MCP-1] having SEQ ID NO:1 was much less effective when incubated with the chemokine than with the cells (17% inhibition at 100 μM compared with >99% inhibition), suggesting that a peptide having SEQ ID NO:1 inhibits MCP-1 induced migration by directly interacting with the cells, rather than by binding to the chemokine ligand. To confirm this observation, the binding affinity of an N-terminally biotinylated derivative of peptide 3(1-12)[MCP-1] (SEQ ID NO:1) was determined. This derivative bound to the surface of THP-1 cells with a ka of about 10 μM.

Peptide 3(1-12)[MCP-1] (SEQ ID NO:1) also inhibited other functions of MCP-1, which may be mediated by different combinations of receptors. MCP-1 has been reported to be a weak co-mitogen with 0.5% fetal calf serum for cultured smooth muscle cells. It was found that 100 μM peptide 3(1-12)[MCP-1] (SEQ ID NO:1) completely abolished the co-mitogenic effect of MCP-1 for cultured smooth muscle cells, also consistent with the hypothesis that peptide 3(1-12)[MCP-1] (SEQ ID NO:1) is an MCP-1 receptor antagonist. The observation that peptide 3(1-12)[MCP-1] (SEQ ID NO:1) completely inhibits different responses to MCP-1 in different cell types suggests that peptide 3 may be a general antagonist of all chemokine receptors capable of binding and signaling in response to MCP-1.

To investigate the receptor specificity of peptide 3 inhibition, the $ED_{50}$ was determined for peptide 3(1-12)[MCP-1] (SEQ ID NO:1) inhibition of THP-1 migration induced by chemokines which signal through different receptors than MCP-1 receptors. Representative chemokines included a beta-chemokine ("CC"), MIP-1α and RANTES, and two alpha-chemokines ("CXC"), IL-8 and SDF-1α. Additionally, to determine the specificity of peptide 3(1-12)[MCP-1] (SEQ ID NO:1) for chemokine receptors, TGF-beta was selected as a migration-inducing agent unrelated to the chemokine family, and as an agent which elicits a biological activity by signaling through identified, unrelated receptors.

Peptide 3(1-12)[MCP-1] (SEQ ID NO:1) inhibited the THP-1 migration induced response to all four of the selected chemokines, with the order of potency: MIP-1α≧MCP-1>SDF1α≧IL-8 (see Table 2). In contrast, peptide 1[MCP-1] (SEQ ID NO:2) or peptide 2(1-15)[MCP-1] (SEQ ID NO:3) did not inhibit migration in response to any of these chemokines by more than 20%, even at 100 μM (Table 2). Peptide 3 binds to THP-1 cells with an association constant of about 10 μM.

TABLE 2

(a) $ED_{50}$ for inhibition of THP-1 migration

| PEPTIDE | $ED_{50}$ (μM) versus | | | | |
|---|---|---|---|---|---|
| | MCP-1 | MIP1α | IL8 | SDF-1α | TGFβ1 |
| Peptide 1 (SEQ ID NO: 2) | n.s.[b] | n.s.[b] | n.s. | n.s. | n.s. |
| Peptide 2 (SEQ ID NO: 3) | n.s. | n.s. | n.s. | n.s. | n.s. |
| Peptide 3[a] (SEQ ID NO: 1) | 8 ± 1 | 8 ± 1 | 14 ± 1 | 10 ± 0 | n.s. |

TABLE 2-continued (b) Extent of inhibition of THP-1 migration at 100 µM

| PEPTIDE | % inhibition at 100 µM versus | | | | |
|---|---|---|---|---|---|
| | MCP-1 | MIP1α | IL8 | SDF-1α | TGFβ1 |
| Peptide 1 (SEQ ID NO: 2) | n.s.[b] | n.s.[b] | n.s. | n.s. | n.s. |
| Peptide 2 (SEQ ID NO: 3) | n.s. | n.s. | n.s. | n.s. | n.s. |
| Peptide 3 (SEQ ID NO: 1) | 112 | 99 | 103 | 107 | n.s. |

(c) Extent of inhibition of human monocyte migration at 100 µM

| PEPTIDE | % inhibition at 100 µM versus | | | | |
|---|---|---|---|---|---|
| | MCP-1 | MIP1α | IL8 | SDF-1α | TGFβ1 |
| Peptide 1 (SEQ ID NO: 2) | n.s. | n.s. | n.s. | n.s. | n.s. |
| Peptide 2 (SEQ ID NO: 3) | 23 | n.s. | n.s. | n.s. | n.s. |
| Peptide 3 (SEQ ID NO: 1) | 108 | 120 | 106 | 108 | n.s. |

[a] mean ± SEM of at least three determinations
[b] Peptide 1 caused significant inhibition only when added to the lower compartment
n.s. = no statistically significant inhibition (p > 0.05)

Furthermore, peptide 3(1-12)[MCP-1] having SEQ ID NO:1 (as well as peptide 1[MCP-1] (SEQ ID NO:2) and peptide 2(1-15)[MCP-1] (SEQ ID NO:3)) did not significantly inhibit THP-1 migration induced by TGF-beta even at 100 µM. Taken together, these results demonstrated that peptide 3(1-12)[MCP-1] (SEQ ID NO:1) is a general (i.e., inhibits all chemokines tested) and specific (i.e., only inhibits chemokines) inhibitor of chemokine signaling. Although peptide 3(1-12)[MCP-1] (SEQ ID NO:1) shows weak selectivity for CC chemokines over CXC chemokines, nevertheless, at 100 µM, peptide 3(1-12)[MCP-1] (SEQ ID NO:1) inhibits >99% of the migration induced by any of the chemokines of either chemokine family tested (Table 2). Thus, although MCP-1 signals through multiple related receptors, peptide 3(1-12)[MCP-1] (SEQ ID NO:1) blocks all of the receptors which participate in the chemotactic and mitogenic signaling pathways elicited by MCP-1.

To exclude the possibility that peptide 3(1-12)[MCP-1] (SEQ ID NO:1) was more effective on THP-1 cells than primary human monocytes, the effect of peptide 3(1-12)[MCP-1] (SEQ ID NO:1) on the chemokine-induced migration of freshly prepared peripheral blood monocytes from 3 donors was tested. Similar to the results for THP-1 cells, 100 µM of peptide 3(1-12)[MCP-1] (SEQ ID NO:1), but not peptide 1[MCP-1] (SEQ ID NO:2) or peptide 2(1-15)[MCP-1] (SEQ ID NO:3), inhibited all or almost all (>95%) of the migration induced with each of the four chemokines, but did not affect TGF-beta induced migration. Thus, peptide 3(1-12)[MCP-1] (SEQ ID NO:1) is an inhibitor of a broad range of pro-inflammatory chemokines which act on a wide range of target cells (smooth muscle cells, THP-1, Jurkat T-cell line and primary human monocytes). Note that in contrast to THP-1 cells, peptide 2(1-15)[MCP-1] (SEQ ID NO:3) inhibition of MCP-1 induced migration of primary human monocytes (20%) was statistically significant (Table 2).

Example 2

Characterization of Fragments and Variants of Peptide 3(1-12)[MCP-1] and Peptide 2 [MCP-1]

To determine whether a fragment of peptide 3 has biological activity and selectivity, two 6mer "half-peptides" were analyzed (Table 3): EICADP (SEQ ID NO:8), corresponding to peptide 3(1-6)[MCP-1], and KQKWVQ (SEQ ID NO:9), corresponding to peptide 3(7-12)[MCP-1]. Peptide 3(7-12)[MCP-1] (SEQ ID NO:9) was as potent an inhibitor of CC chemokine signaling as peptide 3(1-12)[MCP-1] (SEQ ID NO:1), but was noticeably more potent as an inhibitor of CXC chemokines (Table 4). In contrast, peptide 3(1-6)[MCP-1] (SEQ ID NO:8) was much less potent as an inhibitor than peptide 3(1-12)[MCP-1] (SEQ ID NO:1).

TABLE 3

| NAME | SEQUENCE | SOURCE |
|---|---|---|
| Peptide 1 family | | |
| Pep 1 | AQPDAINAPVTCC (SEQ ID NO: 2) | Residues 1-13 of mature hMCP-1 |
| Peptide 2 family | | |
| Pep2(1-15)[MCP1] | SYRRITSSKCPKEAV (SEQ ID NO: 3) | Residues 28-42 of mature hMCP-1 |
| Pep2(1-15)[SDF1] | HLKILNTPNCALQIV (SEQ ID NO: 4) | Residues 26-40 of mature hSDF-1β |
| Pep2(1-14)[MIP1α] | DYFETSSQCSKPGV (SEQ ID NO: 5) | Residues 28-41 of mature hMIP1α |
| Pep2(1-16)[IL8] | ELRVIESGPHCANTEI (SEQ ID NO: 6) | Residues 27-42 of mature hIL-8 |
| Peptide 3 family | | |
| Pep3(1-12)[MCP-1] | EICADPKQKWVQ (SEQ ID NO: 1) | Residues 50-61 of mature hMCP-1 |
| Pep3(3-12)[MCP-1] | CADPKQKWVQ (SEQ ID NO: 7) | Residues 52-61 of mature hMCP-1 |
| Pep3(1-6)[MCP-1] | EICADP (SEQ ID NO: 8) | Residues 50-55 of mature hMCP-1 |
| Pep3(7-12)[MCP-1] | KQKWVQ (SEQ ID NO: 9) | Residues 56-61 of mature hMCP-1 |
| Leu$_4$Pep3 (1-12)[MCP-1] | EICLDPKQKWVQ (SEQ ID NO: 10) | Mutant of peptide 3 |
| Ser$_7$Pep3 (1-12)[MCP-1] | EICADPSQKWVQ (SEQ ID NO: 11) | Mutant of peptide 3 |
| Ser$_7$Glu$_8$Glu$_9$Pep3 (1-12)[MCP-1] | EICADPSEEWVQ (SEQ ID NO: 12) | Residues 50-61 of mature hMIP1α |
| Ile$_{11}$Pep3 (1-12)[MCP-1] | EICADPKQKWIQ (SEQ ID NO: 13) | Mutant of peptide 3 |
| Leu$_4$Ile$_{11}$Pep3 (1-12)[MCP-1] | EICLDPKQKWIQ (SEQ ID NO: 14) | Mutant of peptide 3 |
| Unrelated control peptide | | |
| Peptide C | CPSLEDSFIQVA (SEQ ID NO: 15) | C-terminus of h Apo(a)RG-C protein |

TABLE 4

Effect of Mutant Sequence Peptide 3 Derivatives on THP-1 Migration

| PEPTIDE | ED$_{50}$ (µM) versus | | | | |
|---|---|---|---|---|---|
| | MCP1 | MIP1α | IL8 | SDF1α | TGFβ1 |
| Peptide 3 (SEQ ID NO: 1) | 8 | 8 | 14 | 10 | n.s. |
| Peptide 3[3-12] (SEQ ID NO: 7) | 8 | 7 | 9 | 9 | n.s. |
| Peptide 3[1-6] (SEQ ID NO: 8) | 33 | 25 | 17 | 19 | n.s. |
| Peptide 3[7-12] (SEQ ID NO: 9) | 7 | 5 | 6 | 6 | n.s. |
| Leu$_4$peptide 3 (SEQ ID NO: 10) | 8 | 7 | 3 | 3 | n.s. |
| Ser$_7$peptide 3 | 7 | 6 | 3 | 4 | n.s. |

TABLE 4-continued

Effect of Mutant Sequence Peptide 3 Derivatives on THP-1 Migration

| PEPTIDE | ED$_{50}$ (µM) versus | | | | |
|---|---|---|---|---|---|
| | MCP1 | MIP1α | IL8 | SDF1α | TGFβ1 |
| (SEQ ID NO: 11) Ile$_{11}$peptide 3 (SEQ ID NO: 13) | 6 | 4 | 2 | 7 | n.s. |
| Leu$_4$Ile$_{11}$peptide 3 (SEQ ID NO: 14) | 2 | 1 | 3 | 3 | n.s. |
| Ser$_7$Glu$_8$Glu$_9$pep3 (SEQ ID NO: 12) | 7 | 2 | 9 | 5 | n.s. |
| WVQ | 8 | <1 | <1 | <1 | n.s. |
| KQK | 7 | n.s. | n.s. | n.s. | n.s. |
| SEE | n.s. | 6 | n.s. | n.s. | n.s. |

Peptide 3(7-12)[MCP-1] (SEQ ID NO:9) showed essentially no selectivity, inhibiting migration by all chemokines tested with an ED$_{50}$ in the range of 7-9 µM, i.e., it was a pan-chemokine inhibitor. Peptide 3(1-6)[MCP-1] (SEQ ID NO:8) was much less efficient at inhibiting the CC chemokines (ED$_{50}$ of about 30 µM) but only slightly less efficient at inhibiting CXC chemokines (18 µM) compared with peptide 3(1-12)[MCP-1] (SEQ ID NO:1). The selectivity ratio is defined as the average ED$_{50}$ for MCP-1 and MIP1α divided by the average ED$_{50}$ for IL-8 and SDF1α. Selectivity ratios of greater than 1 indicate greater inhibition of CC chemokines relative to CXC chemokines; selectivity ratios of less than 1 indicate greater inhibition of CXC chemokines relative to CC chemokines; and a selectivity ratio of 1 indicates that both families of cytokines are inhibited to the same extent. Hence, although it is overall a markedly weaker inhibitor of chemokine signaling, peptide 3(1-6)[MCP-1] (SEQ ID NO:8) showed a 2-fold selectivity for CXC chemokines. Thus, peptide 3(1-6)[MCP-1] (SEQ ID NO:8) is a preferred inhibitor of the CXC chemokines, with a selectivity ratio of 0.7, while peptide 3(7-12)[MCP-1] (SEQ ID NO:9) is a preferred inhibitor of both classes of chemokines, with a selectivity ratio of 1.1. The selectivity ratio for peptide 3(1-12)[MCP-1] (SEQ ID NO:1) is 1.5.

Peptide 3(3-12)[MCP-1] (SEQ ID NO:7) had very similar properties to peptide 3(1-12)[MCP-1] (SEQ ID NO:1). This result suggested that the glutamate (E) and isoleucine (I) residues at positions 1 and 2 of the peptide 3(1-12)[MCP-1] (SEQ ID NO:1) sequence, which are not conserved in chemokine sequences other than MCP-1, are unimportant for receptor binding. Alignment of all human chemokine sequences in the peptide 3 region indicate a common conserved motif present in almost all chemokines whether of the alpha or beta subfamily (Table 3). This motif is: Cx$_1$DPx$_2$x$_3$x$_4$Wx$_5$Q (SEQ ID NO:151).

Furthermore, there is a pattern of amino acids in the variable positions x$_1$ through x$_5$ which suggests that the nature of the amino acid at these positions may play a role in determining the selectivity of receptor binding. For example, in the CC chemokine family, position x$_1$ is usually occupied by alanine (A), whereas this position is commonly leucine (L) in the CXC chemokines except in SDF1 (Isoleucine (I) in SDF-1). To test this hypothesis, the selectivity of Leu$_4$peptide 3(1-12)[MCP-1] (SEQ ID NO:10) was compared to peptide 3(1-12)[MCP-1] (SEQ ID NO:1). While Leu$_4$peptide 3(1-12)[MCP-1] (SEQ ID NO:10) showed an approximately 4-fold increase in potency as an inhibitor of CXC chemokines compared with ala-containing peptide 3(1-12)[MCP-1] (SEQ ID NO:1), there was no decrease in the potency of CC chemokine inhibition (Table 4). Thus, Leu$_4$peptide 3(1-12)[MCP-1] (SEQ ID NO:10) showed some CXC selectivity (a selectivity ratio of 0.37) and was the most CXC selective of all the derivatives tested other than the tripeptides (see below).

As noted for position x$_1$ above, only three different amino acids appear at position x$_5$ (Table 1). Most chemokines have valine (V) at position x$_5$ as do the CXC chemokines IL-8 and MIP. In contrast, SDF-1 and IP10 have isoleucine (I) at this position, while ENA78 is the only chemokine with leucine (L) at this position. The results showed that Ile$_{11}$peptide 3(1-12)[MCP-1] (SEQ ID NO:13) showed some CXC selectivity, though not as marked as Leu$_4$peptide 3(1-12)[MCP-1] (SEQ ID NO:10) (a selectivity ratio of 0.9), but surprisingly showed the greatest selectivity for IL-8 (which has valine at this position) not SDF-1. This analog was the most selective inhibitor of IL-8 signaling other than the tripeptides, i.e., the analog had a selectivity of IL-8 over other chemokines by about 3 fold.

An analog having both the Leu$_4$ and Ile$_{11}$ substitutions did not show any greater specificity as an inhibitor of CXC chemokines than either single mutant Leu$_4$peptide 3(1-12)[MCP-1] (SEQ ID NO:10) or Ile$_{11}$peptide 3(1-12)[MCP-1] (SEQ ID NO:13) (Table 6). However, Leu$_4$Ile$_{11}$peptide 3(1-12)[MCP-1] (SEQ ID NO:14) was approximately 5-fold more potent as an inhibitor of CC chemokines than peptide 3(1-12)[MCP-1] (SEQ ID NO:1), or the single mutants Leu$_4$peptide 3(1-12)[MCP-1] (SEQ ID NO:10) or Ile$_{11}$peptide 3(1-12)[MCP-1] (SEQ ID NO:13). Thus, Leu$_4$Ile$_{11}$peptide 3(1-12)[MCP-1] (SEQ ID NO:14) was a more potent general chemokine inhibitor, with an average ED$_{50}$ of 2.3 µM compared with 10 µM for peptide 3(1-12)[MCP-1] (SEQ ID NO:1). Furthermore, the Leu$_4$Ile$_{11}$peptide 3(1-12)[MCP-1] (SEQ ID NO:14) unexpectedly preserved the modest CC selectivity of peptide 3(1-12)[MCP-1] (SEQ ID NO:1) with a selectivity ratio of 2.0. Surprisingly, therefore, the Leu$_4$Ile$_{11}$peptide 3(1-12)[MCP-1] (SEQ ID NO:1) was approximately 5-fold more potent as an inhibitor of MCP-1 signaling than peptide 3(1-12)[MCP-1] (SEQ ID NO:1), despite the fact that peptide 3(1-12)[MCP-1] (SEQ ID NO:1) contains the cognate sequence from human MCP-1. Moreover, it was found that the Leu$_4$Ile$_{11}$peptide 3(3-12)[MCP-1] (SEQ ID NO:1), like Leu$_4$Ile$_{11}$peptide 3(1-12)[MCP-1] (SEQ ID NO:14), was a higher affinity peptide analog of peptide 3(1-12)[MCP-1] (SEQ ID NO:1).

For positions x$_2$ through x$_4$, all chemokines described to date have at least one charged amino acid in this tripeptide region (Table 1). Many chemokines have two basic residues occupying x$_2$ and x$_4$ (e.g., KQK in MCP-1, KER in MCP-2 and KLK in SDF-1) while others have two acidic residues (e.g., SEE in MIP1α, SES in MIP1β, and SES in RANTES). A recent report (Nature Med., 3, 367 (1997)) suggested that the charge in the extracellular loops of the chemokine receptors may be an important determinant of ligand specificity, e.g., CXCR4 which binds SDF-1 is negatively charged, while CCR5, which binds MIP1α, MIP1β and RANTES is positively charged. Thus, residues X$_2$-X$_4$ may play an important role in receptor specificity.

To test this hypothesis, several variants were prepared: Ser$_7$peptide 3(1-12)[MCP-1] (SEQ ID NO:11) substitutes the positively charged K residue present in MCP-1, MCP-2, Eotaxin, IL-8 and SDF-1 with the hydroxylated S residue present in MIP-1α, MIP1β and RANTES. However, this alteration did not markedly alter the selectivity. In particular, this alteration did not decrease the potency of inhibition of MCP-1 signaling, nor increase the potency of inhibition of MIP1α signaling (Table 4). The only detectable change was a modest shift from the moderate CC selectivity of peptide 3(1-12)[MCP-1] (SEQ ID NO:1) to a moderate CXC selectivity of the Ser$_7$peptide 3(1-12)[MCP-1] (SEQ ID NO:11) variant (a selectivity ratio of 0.5). Another variant, Ser$_7$Glu$_8$Glu$_9$peptide 3(1-12)[MCP-1] (SEQ ID NO:12) which converts the peptide from being the cognate of the MCP-1 sequence to the cognate of the MIP1α sequence, resulted in a more selective MIP1α inhibitor, although the selectivity ratio for MIP1α versus all other chemokines was only about 3 fold.

None of the peptide 3(1-12)[MCP-1] variants had any detectable activity as an inhibitor of TGF-beta induced migration of THP-1 cells, even at 100 µM (Table 4). Thus, all these variants were highly selective inhibitors of chemokine-induced signaling. There were no substitutions which altered an amino acid residue in peptide 3(1-12)[MCP-1] to any other amino acid regions found in the chemokine sequences described above which markedly reduced the potency of the general chemokine inhibition observed. However, certain alterations resulted in a shift in selectivity. For example, the CC selectivity of peptide 3(1-12)[MCP-1] (SEQ ID NO:1) can be converted to CXC selectivity by mutating A to L at position 4 ($x_1$) or by mutating V to I at position 11 ($x_5$). In particular, two variants had greater than 3-fold selectivity for one chemokine over the average ED$_{50}$ for all the others, i.e., Ile$_{11}$peptide 3(1-12)[MCP-1] (SEQ ID NO:13) had weak overall selectivity for IL8 inhibition and Ser$_7$Glu$_8$Glu$_9$peptide 3(1-12)[MCP-1] (SEQ ID NO:12) had weak overall selectivity for MIP1α.

In summary, although peptide 3(1-12)[MCP-1] variants varied to a small extent in their ED$_{50}$s and their specificity for either the α family or β family of chemokines, nevertheless, they were all similar to peptide 3(1-12)[MCP-1] (SEQ ID NO:1). The results in Table 6 showed that peptide 3(1-12)[MCP-1] (SEQ ID NO:1) and peptide 3(1-12)[MCP-1] variants inhibited migration induced by MCP-1, MIP1α, IL8 and SDF1α chemokines to a similar extent. While some peptides or peptide variants showed slight preference for CC chemokines, others showed slight preference for CXC chemokines but in no case did the CC-specificity exceed two-fold. Peptide 3(1-12)[MCP-1] (SEQ ID NO:1), peptide 3(1-6)[MCP-1] (SEQ ID NO:8) and peptide 3(7-12)[MCP-1] (SEQ ID NO:9) also showed no significant CC or CXC selectivity.

Example 3

Identification, Preparation and Characterization of Therapeutic Agents of the Invention for In Vivo Use A. Derivatives Peptides are generally susceptible to chemical or enzymatic hydrolysis. In particular, peptides are not normally bioavailable by the oral route since they are not stable in the acid and proteolytic environment of the stomach. Thus, chemical or enzymatic hydrolysis leads to a very short in vivo half-life for peptides. To extend the half-life of agents susceptible to hydrolysis, in vitro active agents are modified in a manner that results in a derivative which may be orally bioavailable, have improved pharmacokinetics, and the administration of which may achieve concentrations in blood that inhibit chemokine activity. For example, cyclic-reverse-D (CRD) peptides may be prepared. CRD peptides are prepared by synthesizing the reverse sequence of the peptide (C-terminal to N-terminal) using the opposite stereoisomer (D-amino acids in place of L amino acids). The resulting peptide is then cyclized via N- and C-terminal cysteine residues. These derivatives retain a very similar steric arrangement of atoms to non-CRD peptide, but are not subject to enzymatic hydrolysis. Other derivatives which may exhibit an extended half-life in vivo include thienyl or pyridyl derivatives (e.g., U.S. Pat. No. 4,992,463; U.S. Pat. No. 5,091,396).

Figure 3:
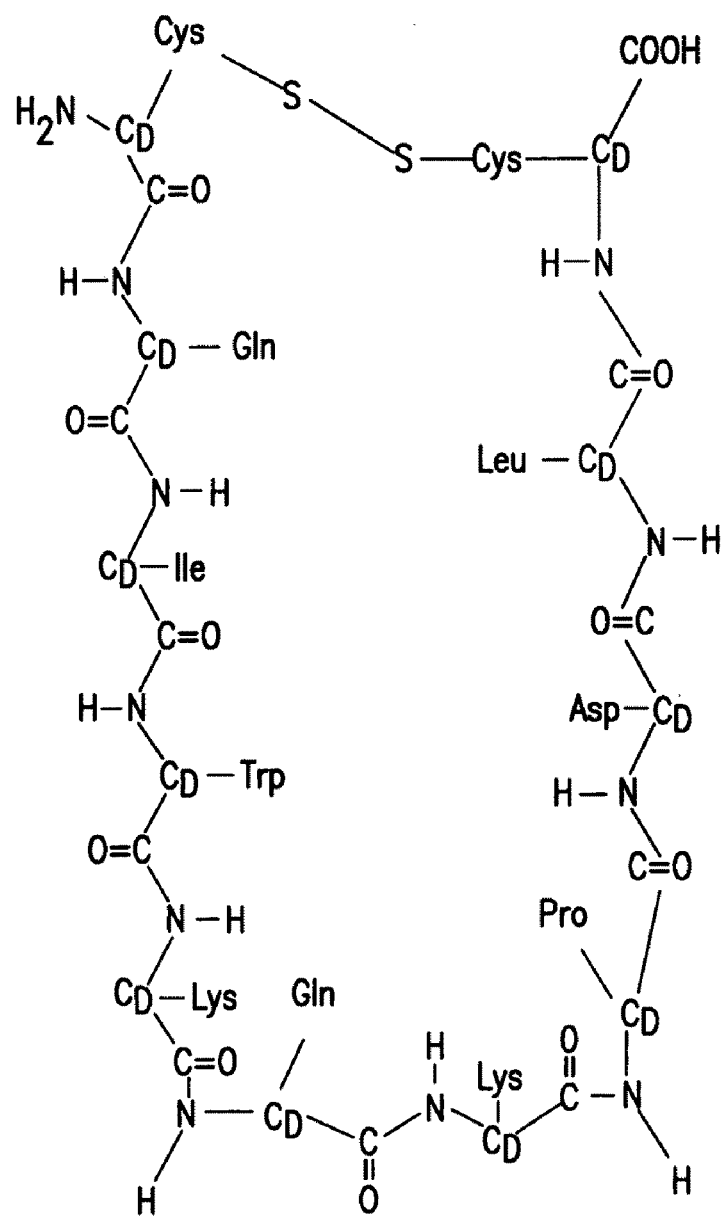
FIG. 3 shows the structure of CRD-Cys$_{13}$Leu$_4$Ile$_{11}$peptide 3(3-12)[MCP-1], which is cyclized via disulphide bonds. The main chain a carbons are indicated by $C_D$ which indicates that the D form of the amino acid is present.
Figure 4:
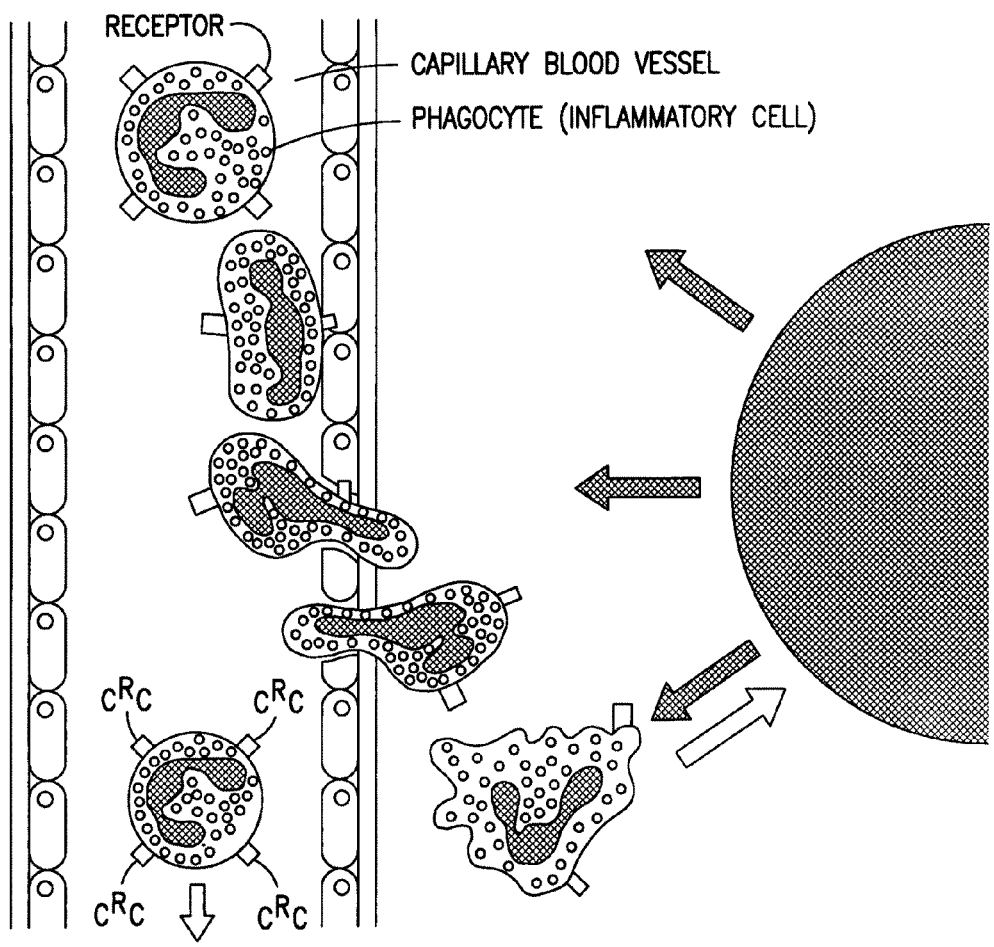
FIG. 4 depicts a schematic of inhibition of cell migration by a therapeutic agent of the invention, e.g., by inhibiting the functional activity induced by the binding of native chemokine to its chemokine receptor. $C^RC$=a therapeutic agent of the invention. Chemokine receptors are shown as blackened rectangles.
Figure 5A:
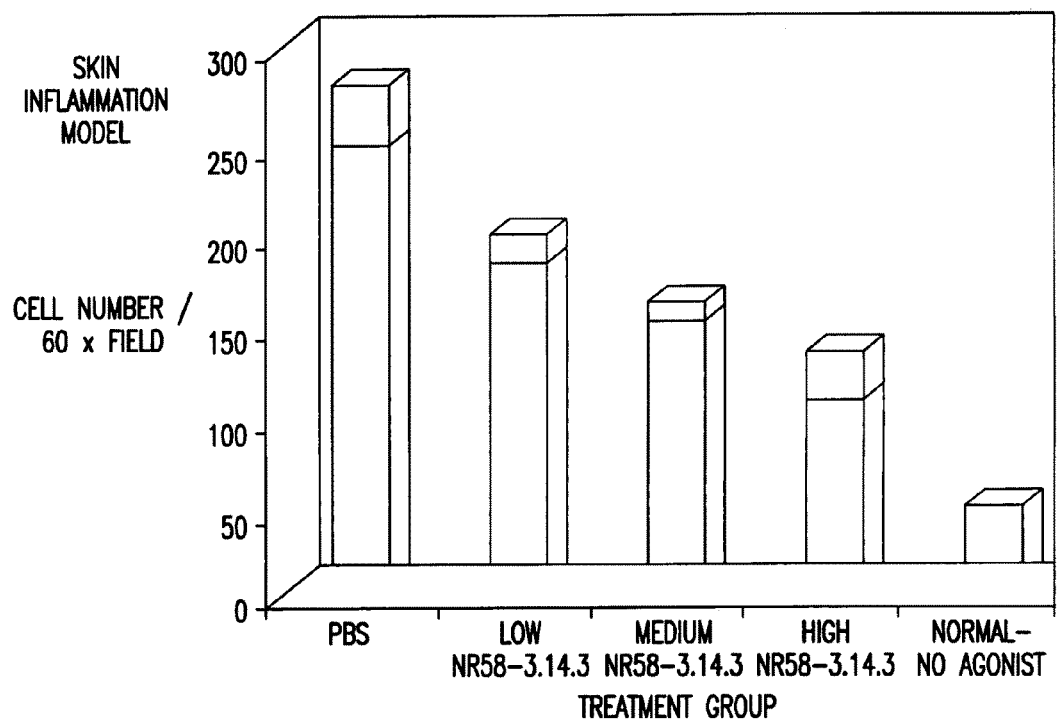
FIG. 5 shows the dose-dependent inhibition of inflammation (A) and endotoxemia (B) in animal models by peptide 3 (CRD-Cys$_{13}$Leu$_4$Ile$_{11}$ peptide 3(3-12)[MCP-1]=NR58-3.14.3).
Figure 5B:
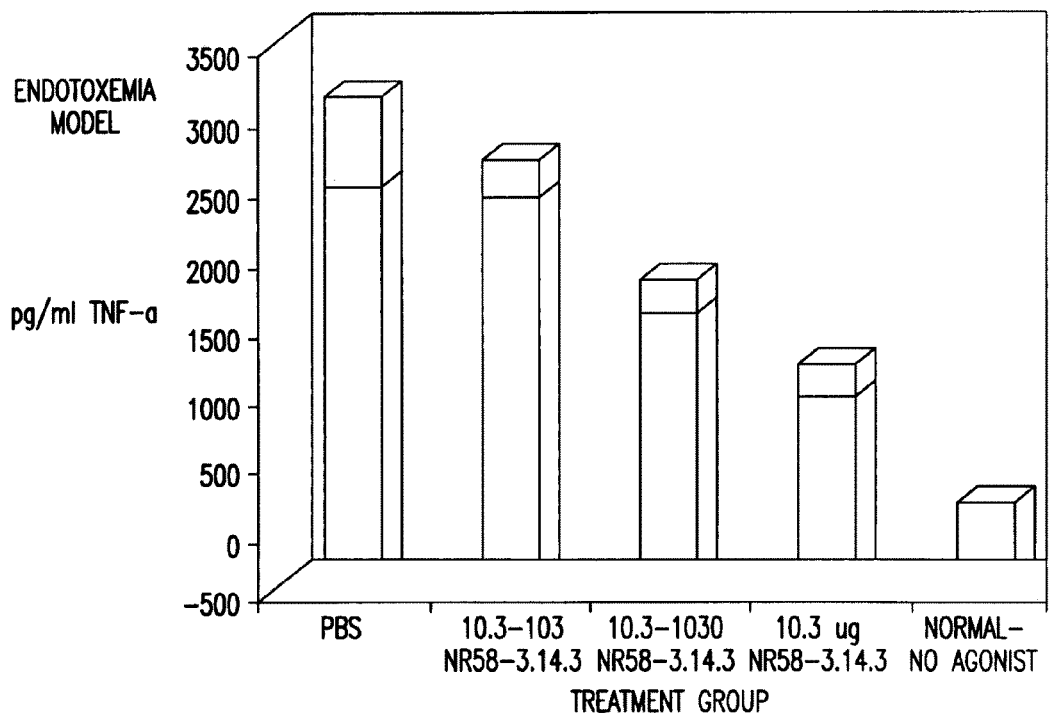
Figure 6:
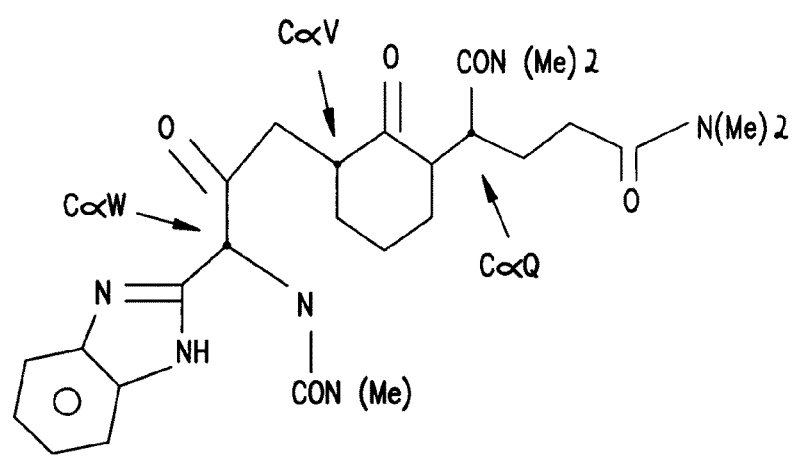
FIG. 6 shows an analog of peptide WVQ.

For example, to prepare a peptide 3 derivative, peptide 3(3-12)[MCP-1] was modified according to Jameson et al. (Nature, 368, 744 (1994)), which yielded CRD-Cys$_{13}$Leu$_4$Ile$_{11}$peptide 3(3-12)[MCP-1] (FIG. 3). CRD-Cys$_{13}$Leu$_4$Ile$_{11}$peptide 3(3-12)[MCP-1], which had very similar properties to peptide 3(1-12)[MCP-1] (SEQ ID NO:1) in the in vitro assays described hereinabove, was found to be stable against both acid hydrolysis (<10% degradation at pH 2.0 for 2 hrs at 37° C.) and enzymatic destruction (5 units trypsin for 2 hrs at 37° C.). CRD-Cys$_{13}$Leu$_4$Ile$_{11}$peptide 3(3-12)[MCP-1] was also resistant to hydrolysis in vivo and allowed therapeutically useful plasma concentrations to be achieved (>10 µM 24 hours after a single intraperitoneal dose of 1 mg of CRD-Cys$_{13}$Leu$_4$Ile$_{11}$peptide 3(3-12)[MCP-1] in 250 µL saline).

Cyclic-reverse D (CRD), linear reverse-D (LRD), cyclic forward L (CFL), and linear forward L (LFL) (i.e., the standard form of peptides) derivatives of Leu$_4$Ile$_{11}$peptide 3 were prepared and their MCP-1 inhibitory activity in the THP-1 transwell assay determined. The results were

| | |
|---|---|
| LFL-Leu$_4$Ile$_{11}$peptide 3 | 1-5 µM |
| LRD-Leu$_4$Ile$_{11}$peptide 3 | 200-400 nM |
| CFL-Cys$_{13}$Leu$_4$Ile$_{11}$peptide 3 | 500-700 nM |
| CRD-Cys$_{13}$Leu$_4$Ile$_{11}$peptide 3 | 5-100 nM |

These results show, somewhat surprisingly, that both cyclization and reverse-D derivatization independently improve activity. This improvement is then additive in the CRD derivative. Thus, cyclization improved activity, possibly by constraining the conformations of the peptide. However, it was not expected that the reverse-D derivatization would be so beneficial, possibly by increasing stability of the molecule.

CRD-Cys$_{13}$Leu$_4$Ile$_{11}$peptide 3(3-12)[MCP-1] was found to be a very potent inhibitor of MCP-1 induced THP-1 migration (ED$_{50}$ of about 1-10 nM). This increased potency compared to the parent Leu$_4$Ile$_{11}$peptide 3(1-12)[MCP-1] (SEQ ID NO:14) may reflect increased stability, even in vitro, or it may reflect the increased conformational stability of the peptide. Moreover, this compound binds to the signaling receptor with the same affinity as native full-length MCP-1 but does not signal.

To determine if CRD-Leu$_4$Ile$_{11}$Cys$_{13}$peptide 3(3-12)[MCP-1] inhibited or enhanced the proliferation of T or B cells to conconavalin A or tetanus toxoid in culture, proliferation of CD4 T cells and B cells was assessed by CFSE-FITC cell labeling. 50 ng of CRD-Leu$_4$Ile$_{11}$Cys$_{13}$peptide 3(3-12)[MCP-1] inhibited ConA proliferation of CD4 T cells by 50% and 5 ng of CRD-Leu$_4$Ile$_{11}$Cys$_{13}$peptide 3(3-12)[MCP-1] reduced ConA proliferation of CD4 T cells by <3%. CRD-Leu$_4$Ile$_{11}$Cys$_{13}$peptide 3(3-12)[MCP-1] had no effect on proliferation of B cells to tetanus toxoid.

Computer modeling was employed to determine whether specific amino acid replacements affected the conformation of the peptide derivative CRD-Leu$_4$Ile$_{11}$Cys$_{13}$peptide 3(3-12)[MCP-1]. The peptide sequence was entered into Hyper-Chem 5.0 (HyperCube). A minimum energy conformation was sought using the Amber Force Field parameters and the Polak-Ribiere algorithm. The initial model was manipulated both by molecular dynamics simulations (300° K, 2 nsec) and manual sidechain rotations, followed by geometry optimization, until an apparent global minimum energy conformation was reached. Convergence criterion was <0.01 Kcal/mol A. A conformation was obtained using this procedure with an energy of about 213.4 kcal/mol.

To test the sensitivity of the model peptide to perturbations, each of the residues except the terminal cysteines forming the disulfide bond was mutated individually from D to L, and the geometry re-optimized, starting with the minimum conformation of the all D peptide. For these perturbations each mutant was first run through the geometry optimization routine, then a molecular dynamics simulation, then another geometry optimization. The resulting mutant peptides were compared to the all-D form by overlaying the disulfide bond and one adjacent atom, and visually assessing the difference between the peptide backbones. The overall conformation was insensitive to change of chirality at positions 2, 3, 4, 8, 9, and 10, but was sensitive to change of chirality at positions 5, 6, and 7. Generally, changes in sidechain position were minor except when the backbone conformation changed significantly. Energies for the mutants varied from −187.9 to −226.1 Kcal/mol, but the energy change (from −213.4 for the starting conformation) did not correlate with conformational change.

Figure 13:
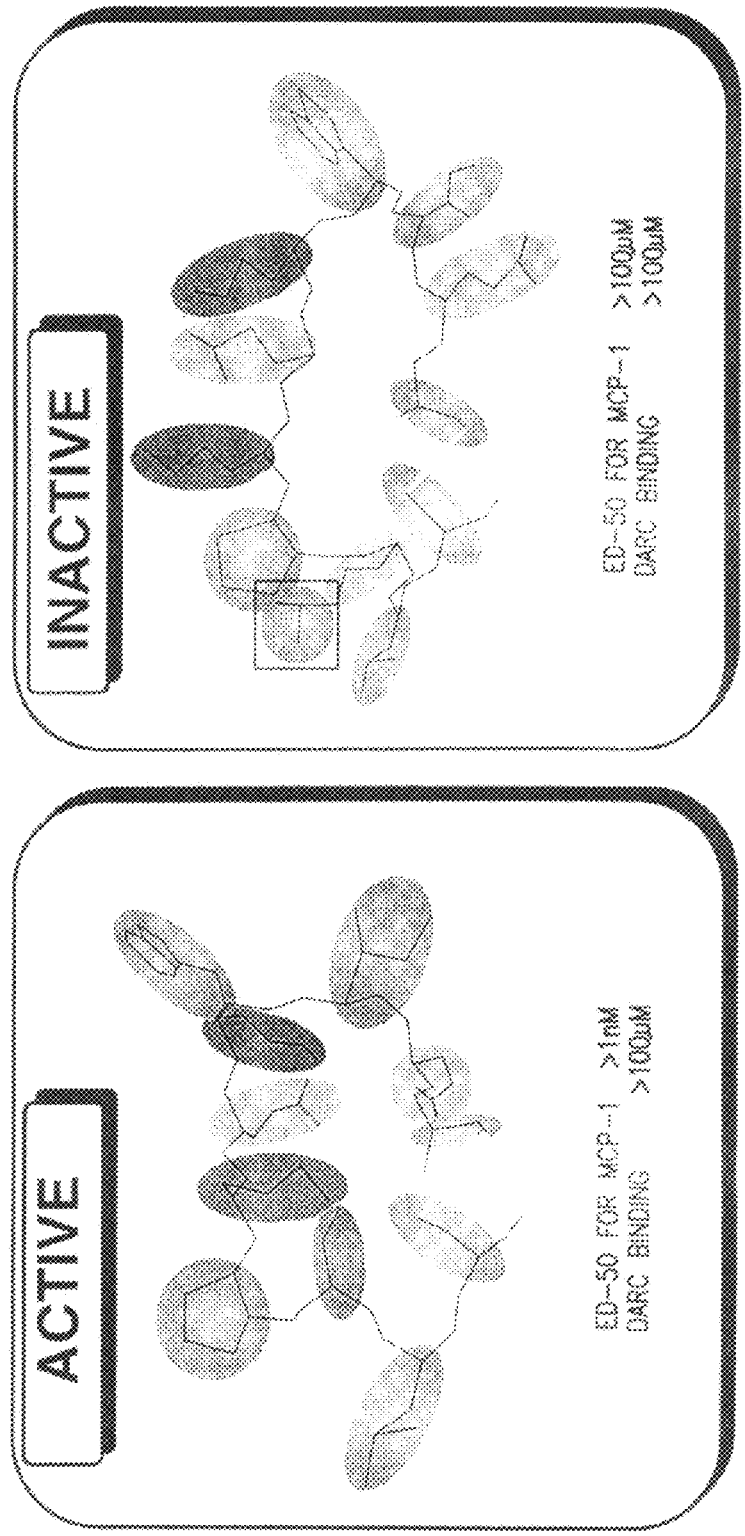
FIG. 13 depicts the structure and ED$_{50}$ of CRD derivatives of peptide 3, CRD-Cys$_{13}$Leu$_4$Ile$_{11}$peptide 3(3-12)[MCP-1] and the D-ala derivative thereof ("inactive").

In addition, the effect of modifying the aspartate residue at position 9 was examined by converting it sidechain carboxyl group to the D-alanyl amide. A minimum energy conformation of the modified peptide was sought using the same routine as for the chiral mutants, starting from the same minimum energy conformation. Condensation of D-alanine to the residue 9 sidechain carboxyl caused a major change in the conformation of the peptide. This is consistent with the in vitro monocyte migration data which demonstrated a significant loss in biological activity of the D-ala peptide relative to CRD-Leu$_4$Ile$_{11}$Cys$_{13}$peptide 3(3-12)[MCP-1]. That is, CRD-Cys$_{13}$Leu$_4$Ile$_{11}$peptide 3(3-12) was synthesized (left panel of FIG. 13) and was found to be 1000-fold more potent as an inhibitor of THP-1 migration induced by MCP-1 than the D-ala derivative thereof (right panel of FIG. 13). The D-alanine prevents the salt bridge formation between an aspartic acid and lysine residue, and so renders this derivative inactive even at a concentration of 100 μM.

Molecular modeling indicated that L-Leu-CRD-Leu$_4$Ile$_{11}$Cys$_{13}$peptide 3(3-12)[MCP-1], which is CRD-Leu$_4$Ile$_{11}$Cys$_{13}$peptide 3(3-12)[MCP-1] with the D-Leu replaced with an L-Leu, should result in very little change to the conformation of the peptide backbone. In vitro migration studies with the L-Leu-derivative showed that it retained functional activity as well. Thus, to select for particular amino acid substitutions which retain the conformation of a biologically active molecule of the invention, molecular modeling may be employed.

The following D-amino acid to L-amino acid changes had no significant impact on the structure of the peptide backbone as assessed by modeling.

| Amino Acid | Position | kcal/mole |
|---|---|---|
| GLN | 2 | −205.5 |
| ILE | 3 | −202.4 |
| TRP | 4 | −222.0 |
| PRO | 8 | −226.1 |
| LEU | 10 | −211.9 |

The following D-amino acid to L-amino acid changes had a significant impact on the structure of the peptide backbone as assessed by this technique.

| Amino Acid | Position | kcal/mole |
|---|---|---|
| LYS | 5 | −200.1 |
| GLN | 6 | −211.6 |
| LYS | 7 | −187.9 |
| ASP | 9 | −214.9 |

B. DARC Binding

A further consideration for bioavailability is non-specific binding of the therapeutic agent. Red blood cells have a signaling-deficient chemokine receptor or binding protein, termed the Duffy Antigen Receptor for Chemokines (DARC). Although it does not signal, this receptor has a high affinity for chemokines (10 nM) and may play a role in clearing them from the circulation. Unfortunately, any chemokine receptor antagonist which has a high affinity for DARC may be sequestered by the huge pool of binding sites on red blood cells, and hence be unavailable to inhibit productive chemokine signaling in other tissues. Similarly, agonists which bind DARC with high affinity are unavailable to productively signal through specific chemokine receptors. For in vivo use, an agent of the invention preferably has some affinity for DARC, since peptides which do not bind to DARC are rapidly cleared at first pass by glomerular filtration. Thus, preferred agents have DARC binding (affinity constant) in the range 100 nM to 1 mM, more preferably in the range 1 μM to 100 μM and even more preferably in the range of 10 to 100 μM.

Although the interaction of chemokines with DARC is high affinity (5-10 nM association constant), kinetically the interaction is characterized by extremely rapid on and off rates. Consequently, incubation with labeled chemokine leads to saturation of the DARC binding sites, but most of the bound label is lost within minutes of removing the unbound label (>90% loss within 3 minutes). As a result, it is difficult to directly determine the binding of peptides to DARC by assaying direct binding of biotinylated peptide, since the rapid off rates make determination of the amount of bound label impossible or inaccurate.

To overcome this difficulty, the ka for association of DARC with peptide 3(1-12)[MCP-1] (SEQ ID NO:1) and peptide 2(1-15)[MCP-1] (SEQ ID NO:3) was estimated by incubating red blood cells expressing DARC with $^{125}$I-labeled MCP-1 in the presence of varying concentrations of peptide. Nine mls of freshly drawn blood is transferred to a tube containing 1 ml 3.8% sodium citrate, and left at room temperature for 15 minutes. Five mls of anti-coagulated blood is layered over 3.5 ml Polymorphprep (Nycomed Pharma, Oslo), and centrifuged at 500×g for 35 minutes. The erythrocytes are removed and reconstituted to the original volume with binding medium (PBS+1 mg/ml fatty acid free BSA, pH 7.4), and centrifuged at 900×g for 10 minutes. This is repeated four times prior to counting the cell and adjusting the volume to 1×10$^8$ erythrocytes per well in a "v" bottomed microtiter plate. The cells are sedimented for 5 minutes at 670×g and resuspended in binding medium containing 0.5 nM $^{125}$-I MCP-1 (specific activity 2000 Ci/mmol; Amersham) in the presence of non-labeled MCP-1 or test agent.

After binding reached equilibrium (30 minutes at 37° C.), the cells are separated from the unbound label by centrifugation for 5 minutes through a sucrose gradient. Counts associated with the cells are then determined by gamma-counting scintigraphy. In the absence of all peptides, the association constant for $^{125}$I-labeled MCP-1 on human red blood cells was 5.45 nM, a value which is in accord with a previous report. Furthermore, Scatchard analysis confirmed the presence of a single high affinity binding site with 500-1000 copies per cell, consistent with the known properties of DARC. Thus, determination of $^{125}$I-MCP-1 binding to red blood cells in this assay in the presence of various concentrations of the peptide(s) allows the association constant of the peptide for DARC to be accurately estimated.

The DARC specificity ratio is also determined. The DARC specificity ratio is defined as the estimated ka for association with DARC divided by the $ED_{50}$ for biological activity. A DARC specificity ratio greater than 1 indicates that a peptide associates poorly with DARC and is bioavailable for modulating chemokine signaling, either as an antagonist or agonist. A DARC specificity ratio of about 1 indicates that the peptide binds DARC and the THP-1 signaling receptors with similar affinity. Thus, it may be difficult to achieve biologically active (as a chemokine inhibitor) concentrations of such peptides in vivo without further modifications of the peptide. A DARC specificity ratio less than 1 indicates much higher affinity for DARC than for chemokine signaling receptors.

Peptide 1[MCP-1] (SEQ ID NO:2) (which does not bind to chemokine receptors but functions in a dominant negative fashion) showed no binding to DARC (estimated ka >100 µM). In marked contrast, the weak agonist peptide 2(1-15) [MCP-1] (SEQ ID NO:3) showed high affinity binding to DARC. The association constant for peptide 2(1-15)[MCP1] (SEQ ID NO:3) for chemokine receptors on THP-1 cells was estimated at 2 µM using competition binding analysis. However, this peptide had an affinity for DARC of less than 500 nM, also assessed by competition binding analysis, using red blood cells. Thus, peptide 2(1-15)[MCP1] (SEQ ID NO:3) binds to THP-1 cell chemokine receptors, although it does not inhibit signaling through the receptors, and it binds DARC even more strongly (DARC selectivity ratio=0.1-0.2). Thus, peptide 2 is a preferred therapeutic agent for the treatment or prevention of malaria (an action requiring DARC inhibition, but not modulation of chemokine signaling).

Peptides, such as peptide 2(1-15)[MCP-1] (SEQ ID NO:3) which have very high affinity for the DARC receptor, may have strong biological agonist activity in vivo (although they are only weak agonists or neutral agonists in vitro). Moreover, peptide 2, variants and derivatives thereof may be strongly pro-inflammatory in vivo, or strongly exacerbate existing inflammation by preventing DARC from performing the function of binding chemokines. If DARC functions as a sink to remove chemokines from the circulation, then the concentration of chemokines may be markedly increased by the presence of peptide 2. Under conditions where chemokines are being made a released into the circulation (e.g., during inflammation), peptide 2 may exacerbate that inflammation, allow the inflammation to persist longer than in the absence of the peptide or otherwise change the qualitative nature of the inflammatory reaction. For these reasons, peptides with a low DARC specificity ratio are useful for the treatment of conditions which require improved immune function, or conditions which are characterized by a pathologically inadequate inflammatory response.

MIP1-α has previously been shown to be the only chemokine which does not bind with significant affinity to DARC. Peptide 2(1-9)[MCP-1] had a Duffy affinity of about 50 µM while peptide 2(1-15)[MIP1-α] (SEQ ID NO:5) was a potent receptor binding agent for the MIP1-α receptor and had excellent specificity over DARC. That is, peptide 2(1-15) [MIP1α] (SEQ ID NO:5) did not bind to DARC (association constant >50 µM) but bound strongly to chemokine receptors on THP-1 cells (association constant=100-900 nM; number of binding sites is about 150,000 per cell). Moreover, this agent did not inhibit THP-1 cell migration induced by MCP-1, MIP1α, IL-8, or SDF1α. Thus, this latter agent may be particularly useful as a neutral chemokine receptor binding agent in vivo, highly selective over DARC.

Peptide 3(1-12)[MCP-1] (SEQ ID NO:1) also binds to DARC, although it binds to DARC with only a similar affinity to which it binds to the chemokine receptors (low µM concentration range). Leu$_4$Ile$_{11}$peptide 3(1-12)[MCP-1] (SEQ ID NO:14) had essentially no DARC binding capacity (and at least 20-fold selectivity for receptors on THP-1 cells), while inhibiting MCP1 induced migration at concentrations around 1 µM. Thus, peptide 3 derivatives, such as leu$_4$ile$_{11}$peptide 3(1-12)[MCP-1] (SEQ ID NO:14) may achieve antagonist properties in vivo.

The shorter fragments of peptide 3[MCP-1] (e.g., peptide 3(7-12)[MCP-1] (SEQ ID NO:9)) showed progressively higher DARC specificity ratios (about 3.0 for peptide 3(7-12) [MCP-1] (SEQ ID NO:9) versus 1.0 for peptide 3(1-12) [MCP-1] (SEQ ID NO:1)), indicating that where chemokine signaling receptor specificity is desired, shorter peptide fragments which retain full chemokine antagonist or agonist activity are in general to be preferred over the full length peptides.

Peptide 3(1-12)[MCP-1] (SEQ ID NO:1) (DARC specificity ratio=1.00) is unlikely to be useful as a pan-chemokine inhibitor in vivo, whereas the Leu$_4$Ile$_{11}$peptide 3[MCP-1] (SEQ ID NO:14) (DARC specificity ratio=37.83), or its derivatives such as CRD-Cys$_{13}$Leu$_4$Ile$_{11}$peptide 3(3-12) [MCP-1], which bound only weakly to DARC (association constant=90 µM) but bound very strongly to chemokine receptors on THP-1 cells (association constant=100-500 nM; number of binding sites is about 150,000 per cell), are a preferred embodiment for the treatment or prevention of atherosclerosis, osteoporosis, and autoimmune diseases, and HIV infection (chemokine signaling receptor binding functions). Moreover, CRD-Cys$_{13}$Leu$_4$Ile$_{11}$peptide 3(3-12) [MCP-1] inhibited THP-1 cell migration induced by MCP-1, MIP1α, IL-8, and SDF1, with very similar $ED_{50}$s.

CRD-peptide 2(1-15)[MCP-1] has more functional potency, less Duffy binding activity compared with the LFL derivative. LRD peptide 2(1-15)[MCP-1] had approximately a 100-fold decrease in Duffy binding (25 µM versus 100 µM for LFL).

An alternative approach to preparing agents that are bioavailable is the preparation of non-peptide analogs of chemokines (see Examples 17-22 below). An exemplary non-peptide analog of the invention includes an isostere of WIQ, e.g., a compound of formula (IV), wherein Z=CH$_3$; Y=O; X=CH$_3$; and Ar=indolyl. This compound did not bind to DARC (association constant=>30 µM) but bound very strongly to chemokine receptors to THP-1 cells (association constant=100 nM-1 µM; number of binding sites is about 150,000 per cell). This agent inhibited THP-1 cell migration induced by MCP-1, MIP1α, IL-8 and SDF1α with very similar $ED_{50}$s.

Other preferred analogs include an analog of WxQ. For example, using a series wherein x=Gly (H), Ala (Me), EtGly (ethyl), Val (isopropyl), Ile (isobutyl) and alloIle (alloisobutyl), it was found that the most active compounds are those with the smallest alkyl side chains (Gly and Ala) with a trend to Ile being the least active, i.e., WGQ>WAQ>>WEtG=WVQ=WAlloIQ>WIQ.

TABLE 5

| PEPTIDE | SEQUENCE | CC SPECIFICITY$_a$ | DUFFY SELECTIVITY$_b$ | AVERAGE ED$_{50}$ (μM)$^c$ |
|---|---|---|---|---|
| Pep2[MCP1] | SYRRITSSKCPKEAV (SEQ ID NO: 3) | — | 0.18$^d$ | 2$^e$ |
| Pep2[SDF1] | HLKILNTPNCALQIV (SEQ ID NO: 4) | — | <1$^d$ | 1-10$^e$ |
| Pep2[MIP1$_a$] | DYFETSSQCSKPGV (SEQ ID NO: 5) | — | >100$^d$ | 1-10$^e$ |
| Pep2[IL8] | ELRVIESGPHCANTEI (SEQ ID NO: 6) | — | <1$^d$ | 1-10$^e$ |
| Pep3 | EICADPKQKWVQ (SEQ ID NO: 1) | 1.5 | 1.00 | 10 |
| Pep3[3-12] | CADPKQKWVQ (SEQ ID NO: 7) | 1.2 | 1.21 | 8 |
| Pep3[1-6] | EICADP (SEQ ID NO: 8) | 0.7 | 5.32 | 24 |
| Pep3[7-12] | KQKWVQ (SEQ ID NO: 9) | 1.0 | 2.94 | 6 |
| Leu$_4$pep3 | EICLDPKQKWVQ (SEQ ID NO: 10) | 0.4 | n.d. | 5 |
| Ser$_7$pep3 | EICADPSQKWVQ (SEQ ID NO: 11) | 0.5 | 2.00 | 5 |
| Ile$_{11}$pep3 | EICADPKQKWIQ (SEQ ID NO: 13) | 0.9 | n.d. | 5 |
| Leu$_4$Ile$_{11}$pep3 | EICLDPKQKWIQ (SEQ ID NO: 14) | 2.0 | 37.83 | 2 |
| Ser$_7$Glu$_8$Glu$_9$ | EICADPSEEWVQ (SEQ ID NO: 12) | 1.6 | 0.59 | 6 |
| — | KQK | >100 | 22.34 | 6$^f$ |
| Pep3[10-12] | WVQ | 1.1 | 24.81 | 2 |
| — | WIQ | 1.0 | n.d. | 2 |
| — | SEE | >100 | n.d. | 0.8$^f$ |
| — | KLK | <0.1 | n.d. | 0.1-10$^f$ |
| — | KEN | <0.1 | n.d. | 0.1-10$^f$ |
| CRD-Cys$_{13}$pep3 [3-12] | -CQVWKQKPDAC-- | n.d. | 8.82 | 0.8 |
| LRD-Cys$_{13}$Leu$_4$ Ile$_{11}$pep3 [3-12] | CQVWKQKPDAC | n.d. | 4.59 | 1 |

TABLE 5-continued

| PEPTIDE | SEQUENCE | CC SPECIFICITY[a] | DUFFY SELECTIVITY[b] | AVERAGE $ED_{50}$ (μM)[c] |
|---|---|---|---|---|
| CRD-Cys$_{13}$Leu$_4$Ile$_{11}$pep3 [3-12] | -C*QIWKQKPDL*C-- | n.d. | >100 | 0.1 |

Footnotes
[a] 'CC-specificity' is the average inhibitory $ED_{50}$ versus SDF1 and IL8 divided by average inhibitory $ED_{50}$ versus MCP-1 and MIP1α.
[b] 'Duffy selectivity' is the estimated ka for binding to red blood cells divided by average inhibitory $ED_{50}$ versus each of the chemokines (except for peptide 2; see footnote d below).
[c] 'Average $ED_{50}$' is the average inhibitory $ED_{50}$ for inhibition of THP-1 migration induced by each of the chemokines (except for peptide 2; see footnote e below).
[d] For the peptide 2 family, the 'average $ED_{50}$' is the estimated ka for binding to THP-1 cells.
[e] For the peptide 2 family, the 'Duffy selectivity' is calculated as the ka for binding to red blood cells divided by the ka for binding THP1-1 cells.
[f] For tripeptide derivatives so marked, the peptide is highly specific for one of the four exemplary chemokines. In these cases, the $ED_{50}$ shown is for inhibition of that chemokine.
n.d. = not determined.
Abbreviations
CRD = Cyclic reverse-D derivative
LRD = Linear reverse-D derivative
CFL = Cyclic derivative of standard L-form peptide
LFL = Standard, linear L-form peptide [NB; all peptides are LFL unless stated otherwise]
Amino acids in italics are D-form amino acids, all others are L-form
-- = Cyclization linking two cysteines so marked

Example 4

Preparation and Characterization of Tripeptide Therapeutic Agents of the Invention To determine whether fragments of peptide 3(1-12)[MCP-1] possessed biological activity, fragments of peptide 3 were prepared. Peptide 3(10-12)[MCP-1], i.e., WVQ was found to be a potent inhibitor of all chemokines tested (Table 6). The amino acid residues at positions 10-12 (WVQ) are conserved in many other chemokines, e.g., MCP-3, MIP1α, MIP1β, RANTES, EOTAXIN, and IL8, although SDF1 has the sequence WIQ. WVQ inhibited all four of the exemplary chemokines tested, although, unlike peptide 3(1-12)[MCP-1] (SEQ ID NO:1), it was a more potent inhibitor of all the chemokines other than MCP-1, with $ED_{50}$s around 1 μM. Thus, these tripeptides, WVQ and WIQ, as well as non-peptide analogs based on these tripeptides, are pan-specific chemokine inhibitors. Moreover, it was found that WVQ had good DARC selectivity (i.e., selectivity of 10).

Peptide 3(7-9)[MCP-1], i.e, KQK, did not bind to DARC (association constant=>50 μM) but bound strongly to chemokine receptors on THP-1 cells (association constant=500 nM-1 μM; number of binding sites is about 15,000 per cell). This agent inhibited THP-1 cell migration induced by MCP-1, but did not inhibit migration induced by MIP1α, IL-8 or SDF1α. Thus, KQK with an $ED_{50}$=2-5 μM was found to be a specific inhibitor of MCP-1, i.e., it had no effect on MIP1α, SDF1α or IL8 induced activity even at 100 μM. Four tripeptides and a dipeptide of random sequence (RGD, GGR, TTT, APG, and VE) were also tested. None of these significantly inhibited migration induced by any of the chemokines. Thus, the tripeptide KQK was specific for inhibiting MCP-1 activity, showing more than 100-fold specificity for MCP-1 over all the other chemokines tested.

Tripeptide equivalents of KQK from MIP1α, SDF1α and IL8, based on an alignment of conserved cysteine residues in chemokine sequences, were then tested for their inhibition of chemokine-induced THP-1 migration. In each case, the tripeptide was highly specific for its cognate chemokine (>100-fold specific in each case). For example, SEE, the cognate peptide from MIP-α, showed greater than 100-fold selectivity for MIP1-α over the other chemokines. Moreover, KLK was a specific and potent inhibitor of SDF1, and KEN was a specific and potent inhibitor of IL8. It is envisioned that tripeptides in which a conservative substitution is made may have the same specificity as the native tripeptide. Moreover, the corresponding tripeptides in other chemokines may be specific for their cognate chemokines.

TABLE 6

| Tripeptide | Chemoattractant | | | | |
|---|---|---|---|---|---|
|  | MCP-1 | MIP1α | RANTES | IL-8 | SDF1α |
| KQK[a] | 95 ± 8[b] | — | — | — | 29 ± 1 |
| SEE | — | 65 ± 3 | — | — | — |
| SES | — | — | 87 ± 4 | — | — |
| KEN | 21 ± 2 | — | — | 70 ± 4 | — |
| KLK | — | — | — | — | 87 ± 6 |
| WVQ[c] | 8 μM | 7.5 μM | 1.5 μM | 1 μM | 2 μM |

For each peptide shown (except WVQ), a number indicates the percentage inhibition of migration induced by that chemoattractant by that tripeptide at 100 μM concentration (mean ± range: two experiments). A dash indicates no statistically significant reduction in migration (all combinations of chemoattractant and tripeptide have been tested. The tripeptide WVQ inhibited migration in response to all chemoattractants tested and for this tripeptide the numbers shown are the $ED_{50}$ for the inhibition (mean of at least two determinations). Note that none of the tripeptides shown inhibited TGF-β1 induced migration at 100 μM. The bolded values indicate the inhibition by each peptide of migration, induced by the chemoattractant from which it was derived, i.e., KQK was derived from MCP-1, etc.
[a] The affinity constant for KQK binding to DARC is 15 μM.
[b] The $ED_{50}$ for KQK inhibiting MCP-1 induced migration is 7 μM.
[c] The affinity constant for WVQ binding to DARC is 2 μM.

Example 5

In Vivo Pharmacokinetics and Toxicity

When $^3$H-D-ala peptide 3(1-12)[MCP-1] ($^3$H-D-ala was attached to Asp) was given as an intravenous (IV) or subcutaneous (SQ) bolus to mice, peak serum concentrations were reached within 1 hour. This radiolabeled peptide was rapidly excreted (approximately 4 hours), primarily via the kidney. Biodistribution data indicated that the primary target organ was the kidney with much smaller amounts detected in blood, liver and intestine. Direct comparison of $^3$H-D-ala peptide 3(1-12)[MCP-1] (no DARC binding and rapidly cleared) and CRD-L-Leu$_4$Ile$_{11}$Cys$_{13}$peptide 3(3-12)[MCP-1] (weak Duffy binding and good serum half-life) indicates that agents of the invention may be particularly useful to increase the half-life of other pharmaceutical agents.

A modified LD$_{50}$ technique was used to determine the mouse intravenous LD$_{50}$ value for CRD-Leu$_4$Ile$_{11}$Cys$_{13}$peptide 3(3-12)[MCP-1]. The LD$_{50}$=11.4 mg/mouse IV, which is 569 mg/kg. This is ten times more than the efficacious dose seen in either the asthma model or the endotoxemia model (see Examples below). Intraperitoneal administration of 11 mg did not result in lethality. Histologically, toxicity was confined to the kidneys and lymphoid tissues.

At the lethal dose, apoptosis of lymphocytes was seen in the spleen and gut-associated lymphoid tissue. The rate limiting toxicity was to the kidney. There was a dose dependent increase in acute renal tubular nephrosis. This is most likely due to the huge intravenous bolus (569 mg/kg) of a small molecular weight peptide which is excreted very rapidly (first pass) by the kidney. Acute tubular nephrosis is also seen in patients with massive release of myoglobin or hemoglobin after crush injuries or massive hemolysis.

Using an in-life phase of an acute rat toxicity study of CRD-Leu$_4$Ile$_{11}$Cys$_{13}$ peptide 3(3-12)[MCP-1] at 1 or 10 mg (5-50 mg/kg) i.v., no clinically detectable changes associated with test agent administration of doses up to 10 mg were found. That is, all animals remained clinically normal throughout. No dose dependent or clinically significant changes were seen in serum chemistry, CBC, urinalysis, gross necropsy, or histology. In a 7-day repeat dose toxicity study in rats which employed subcutaneous implantation of an osmotic mini-pump that delivered about 43 µg/hr of CRD-Leu$_4$Ile$_{11}$Cys$_{13}$ peptide 3(3-12)[MCP-1] continuously for 7 days (7.2 mg), no dose dependent or clinically significant changes were seen in serum chemistry, CBC, urinalysis, gross necropsy, or histology in treated animals.

Thus, toxicity studies indicate that CRD-Leu$_4$Ile$_{11}$Cys$_{13}$ peptide 3(3-12)[MCP-1] is safe in rodents at levels greater than 10 times those which demonstrated efficacy (see below). Thus, the systemic administration of an effective pan-chemokine inhibitor is not associated with acute or chronic (up to seven days) side effects. Pan-inhibition of chemokines is therefore a viable strategy for novel anti-inflammatory therapies.

Example 6

Use of a CRD-Peptide of the Invention in a Rat Dermal Inflammation Model

To assess the efficacy of an agent of the invention in the prevention of lipopolysaccharide (LPS)- and MCP-1-induced dermal inflammation in the rat, three different doses of CRD-Leu$_4$Ile$_{11}$Cys$_{13}$peptide 3(3-12)[MCP-1] were administered. An inflammatory response was elicited by intradermal injection (ventral abdomen) of either 500 ng MCP-1 or 100 ng MCP-1 along with endotoxin-free phosphate-buffered saline vehicle (as a negative control) and bacterial lipopolysaccharide (LPS; as a positive control). Each substance was injected at a different site. The results obtained from animals were compared to CRD-Leu$_4$Ile$_{11}$Cys$_{13}$ peptide 3(3-12)[MCP-1] treated, and PBS (diluent control) treated, animals. Thirty minutes prior to intradermal agonist administration, the animals received an intravenous loading dose (3, 30 or 300 mg) and a subcutaneous depot dose (0.1, 1 or 10 mg) (on dorsum) of the pan-chemokine inhibitor CRD-Leu$_4$Ile$_{11}$Cys$_{13}$peptide 3(3-12) [MCP-1] (see, for example, FIG. 12). Animals were sacrificed at 20-24 hours post injection. Serum and urine were collected. The intradermal sites of agonist injection were collected, bisected and the extent of the inflammatory response was assessed by histopathology and quantitative immunofluorescence (fixed and frozen) (for example, following MCP-1 injection, the number of monocyte/macrophages in the skin was determined using the anti-CD14 (MCA342 from Serotec; clone ED2) at 3 µg/ml overnight at 4° C. The second antibody was rat anti-mouse FITC (415-096-100 from Jackson ImmunoResearch) at 28 µg/ml for 6 hours at room temperature). In addition, toxicity of CRD-Leu$_4$Ile$_{11}$Cys$_{13}$peptide 3(3-12)[MCP-1] was assessed by collection of the following tissue samples in 10% neutral buffered formalin for histologic analysis: lung, liver, kidney, spleen, thymus, heart, and antagonist (test agent) injection site.

Figure 7A:
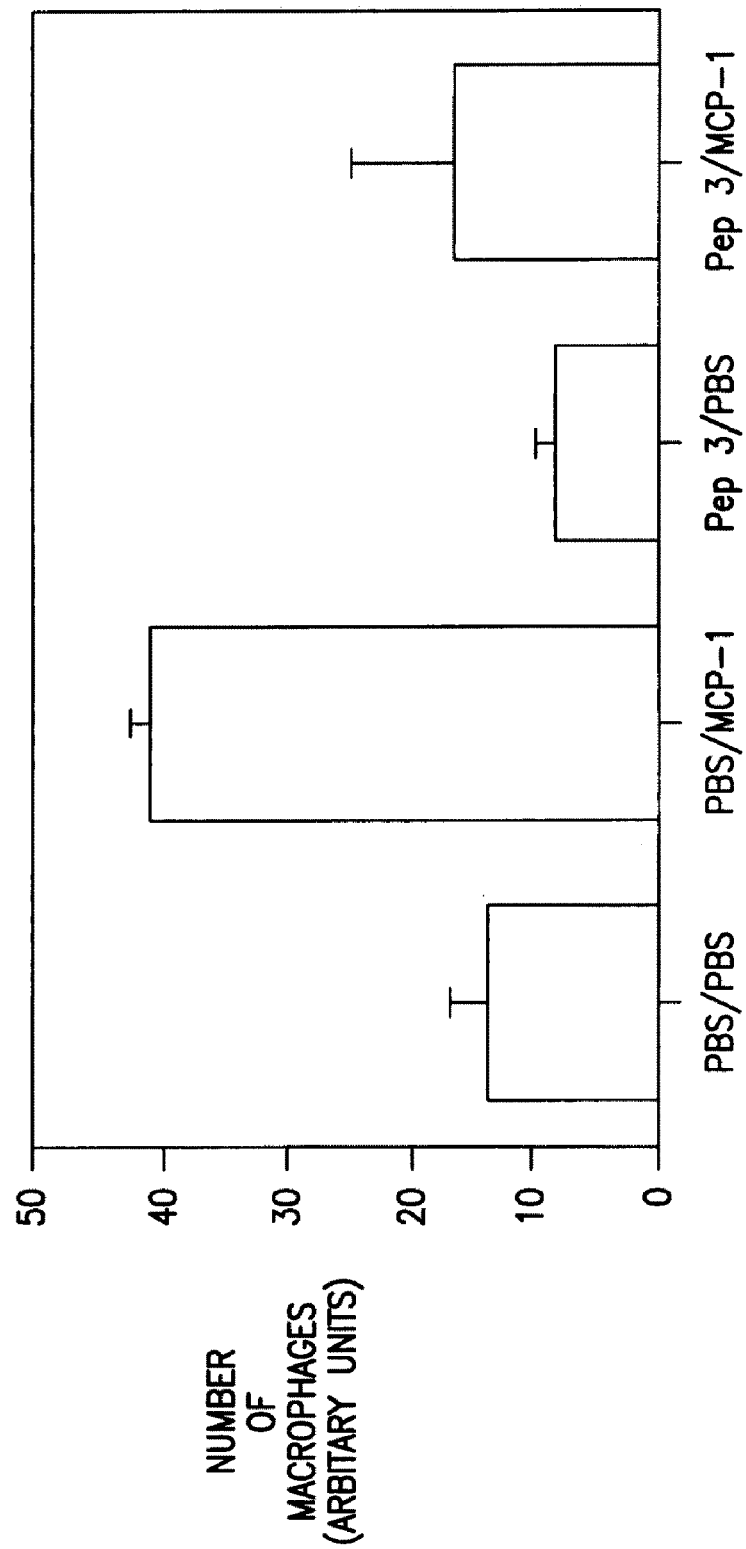
FIG. 7A shows a graph of the percent fractional area staining for macrophage at the site of MCP-1 administration in a rat in the presence or absence of a peptide of the invention.
Figure 7B:
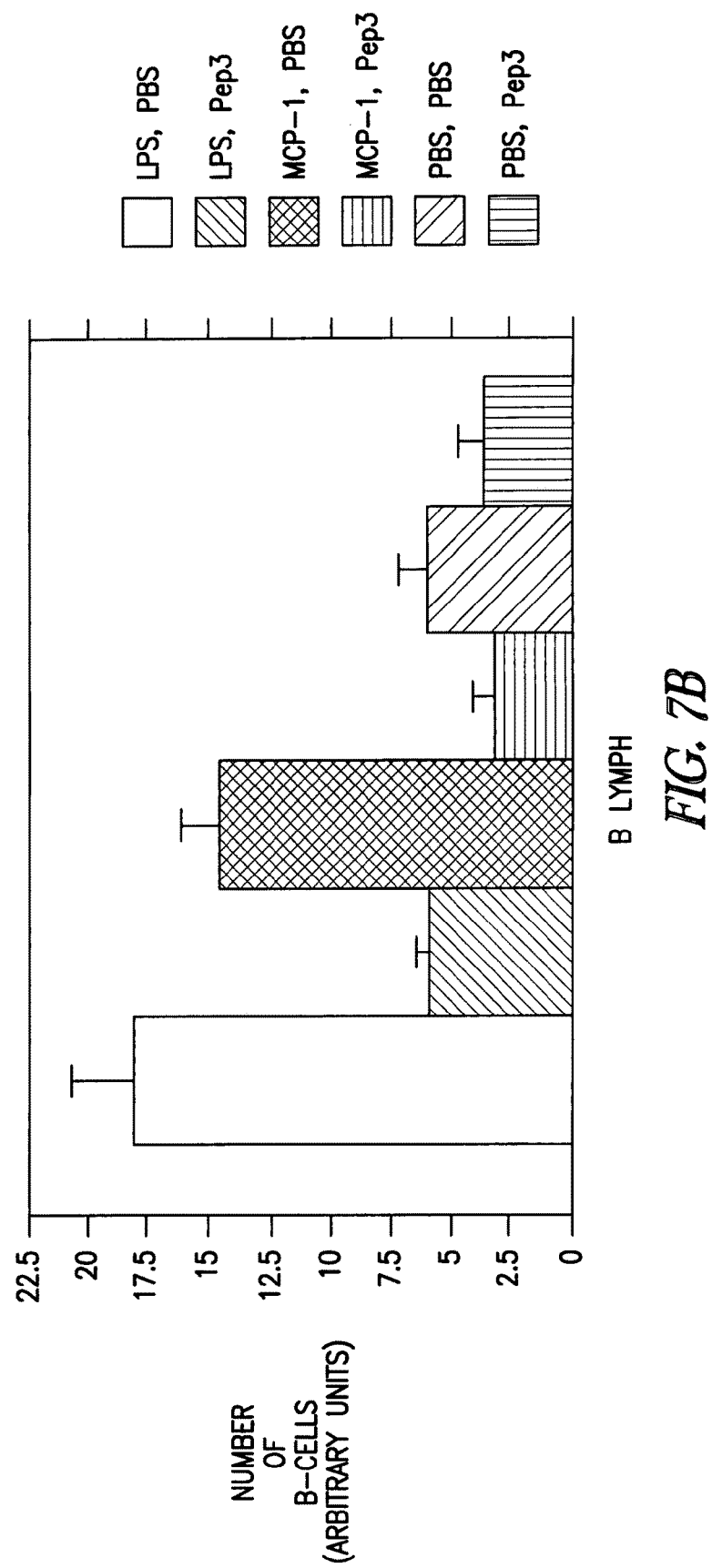
FIG. 7B shows a graph of the percent fractional area staining for B cells at the site of LPS and MCP-1 administration in a rat in the presence or absence of a peptide of the invention.

The results of a typical experiment are shown in FIGS. 7A and 7B. Systemic treatment with CRD-Leu$_4$Ile$_{11}$Cys$_{13}$ peptide 3(3-12)[MCP-1] completely abolished MCP-1 induced recruitment of monocyte/macrophages. This is consistent with potent inhibition of MCP-1-induced migration seen in vitro with this agent. Furthermore, CRD-Leu$_4$Ile$_{11}$Cys$_{13}$ peptide 3(3-12)[MCP-1] reduced the number of resident tissue monocyte/macrophages in the site that received PBS alone, and also in untreated skin. This is consistent with a systemic downregulation of monocyte/macrophage recruitment in the 24 hours following a single treatment with CRD-Leu$_4$Ile$_{11}$Cys$_{13}$ peptide 3(3-12)[MCP-1]. In contrast, in the study described below, the D-ala derivative (FIG. 13) had no effect in vivo (p=0.754), in accord with its lack of in vitro activity in the migration assay.

A substantial reduction (>80%) in the number of monocyte/macrophages recruited in response to injected bacterial LPS was also noted. LPS was a stronger inducer of macrophage recruitment than MCP-1 even at 500 ng dose. Previous studies suggested that LPS-mediated macrophage accumulation was heavily dependent on TNF-α (a non-chemokine chemoattractant) since neutralizing antibodies to TNF-α markedly reduced LPS-induced inflammation. However, in endotoxemia models (Example 10) CRD-Leu$_4$Ile$_{11}$Cys$_{13}$ peptide 3(3-12)[MCP-1] markedly reduced LPS-induced increases in plasma TNF-α suggesting that chemokines may play a role in the induction of TNF-α, and that both chemokine signaling and TNF-α signaling may be necessary for maximal LPS-induced inflammation.

Although MCP-1 is fairly specific as a monocyte/macrophage chemoattractant, dermal injection of LPS induces recruitment of a broader range of leukocytes, including T- and B-cells and neutrophils. Specific antibodies to rat B-cells (MCA 1432 from Serotec) were used at 10 µg/ml overnight at 4° C. to determine whether CRD-Leu$_4$Ile$_{11}$Cys$_{13}$ peptide 3(3-12) [MCP-1] affected the recruitment of this leukocyte subpopulation. Secondary antibody was anti-mouse FITC (415-096-100 from Jackson ImmunoResearch, as above). As for monocyte/macrophages, CRD-Leu$_4$Ile$_{11}$Cys$_{13}$ peptide 3(3-12)[MCP-1] substantially inhibited the recruitment of B-cells to the site of the LPS injection (FIG. 7B).

In another study, three groups (n=5) of rats were injected subcutaneously with either PBS, "inactive" peptide 3 (the D-ala derivative shown in FIG. 13) or CRD-Leu$_4$Ile$_{11}$Cys$_{13}$peptide 3(3-12)[MCP-1] (10 mg in 200 µl subcutaneous). Thirty minutes later, PBS, 50 ng LPS and 500 ng MCP-1 were injected into three separate sites on the ventral abdomen of each rat. Animals were sacrificed 24 hours later and the intradermal site was excised, and frozen in OCT embedding media. Five μm sections were collected from each rat intradermal site and stored at −20° C. The number of monocytes (anti-rat CD 14, Serotec), T cells, neutrophils (anti-rat granulocytes, Harlan Seralab), B-lymphocytes (anti-rat B cells, Serotec), and MCP-1, IL-8, and TNF-α (anti-mouse TNF-α, R and D Systems) were measured. Eight test sections and two control sections were stained at each site for each animal through a distance of 2.5 mm. The median percentage area was determined for each animal and for each group using NIH image, as the largest variability of staining was between sections rather than in any one section.

Panel A of FIG. 14 shows the normal level of monocytes patrolling the rat skin surface. When 500 ng of MCP-1 was injected in the rat abdomen, there is a significant increase in monocyte staining (FIG. 14, panel B). These levels remain unaltered if treated with PBS or control peptide. However, when treating the rats with 10 mg of the CRD-Leu$_4$Ile$_{11}$Cys$_{13}$peptide 3(3-12) the inflammatory response is abolished (panels C and D of FIG. 14).

Figure 15A:
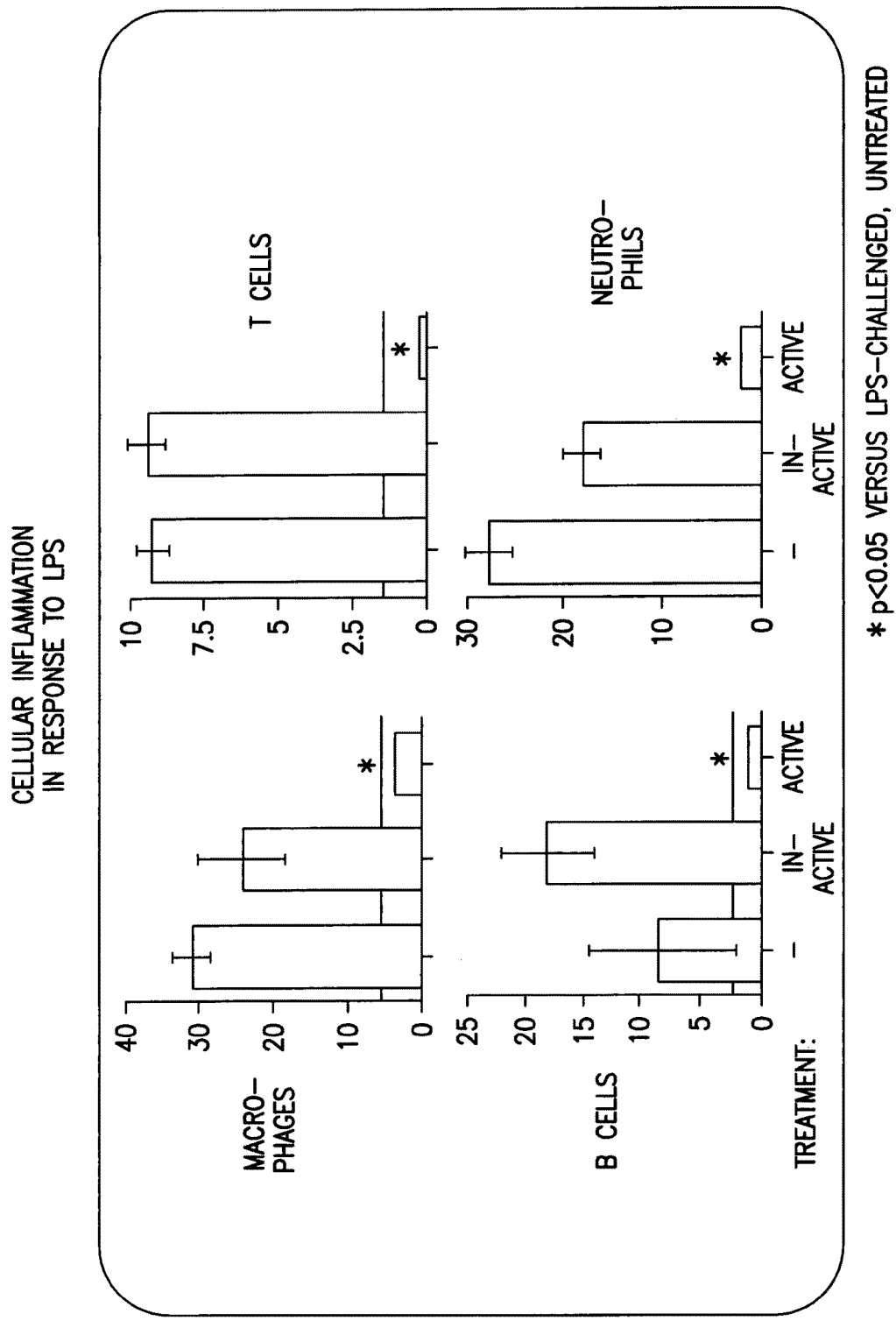
FIG. 15 depicts the inhibition of neutrophils, monocytes and lymphocytes, and the reduction in TNF-α levels, in the skin of rats exposed to LPS in the presence of CRD-Cys$_{13}$Leu$_4$Ile$_{11}$peptide 3(3-12)[MCP-1]. Inactive=the D-ala derivative of CRD-Cys$_{13}$Leu$_4$Ile$_{11}$peptide 3(3-12)[MCP-1].
Figure 15B:
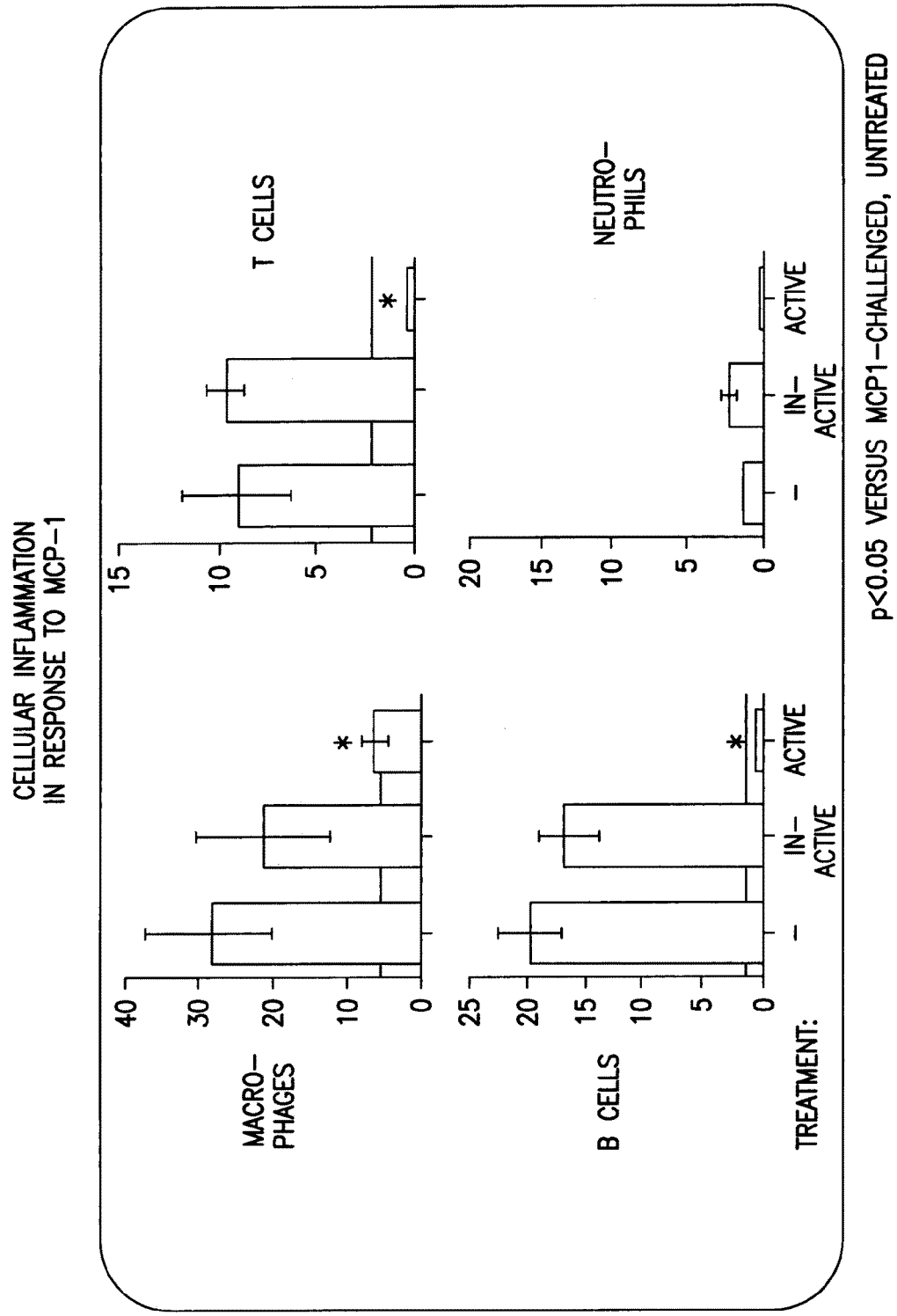
Figure 15C:
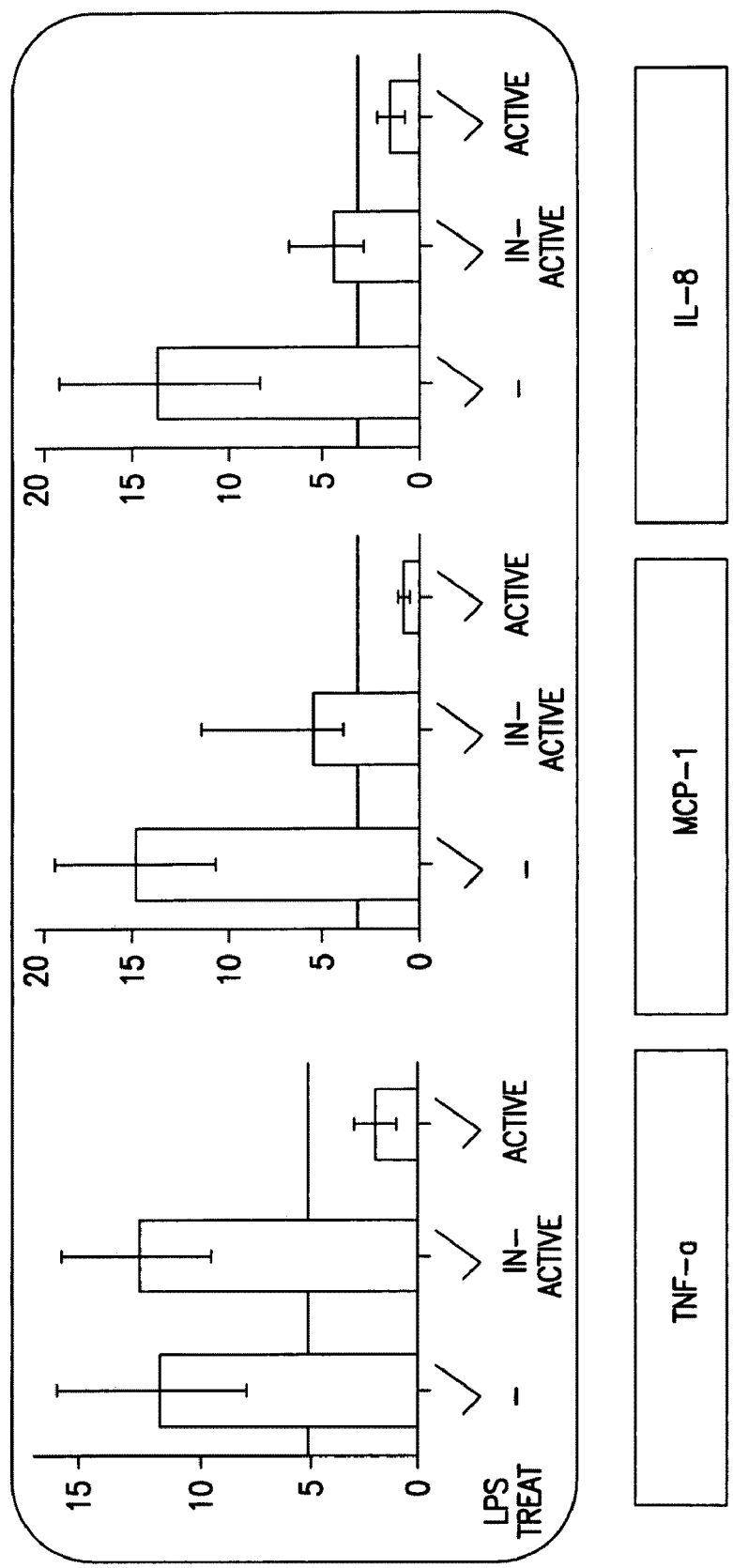

Sections from the LPS intradermal site (three rats in total) were stained for pro-inflammatory cytokines and cellular infiltrates using quantitative immunofluorescence. Using specific antibodies for neutrophils, monocytes, CD4+ T lymphocytes, and B-lymphocytes, the data showed that the median percentage area stained for each cell type was abolished in each case compared to the PBS and inactive peptide controls (FIG. 15). In addition, when TNF-α, IL-8 and MCP-1 were measured in the same sections, TNF-α, IL-8 and MCP-1 were also substantially reduced when rats were treated with the active peptide, a pan-chemokine inhibitor. Furthermore, several groups have shown that using neutralizing antibodies against a variety of individual chemokines did not alter the LPS inflammatory response in a mouse endotoxemia model. Thus, multiple chemokines lie upstream of TNF-α in the inflammatory response pathway, and while inhibition of any of them singly does not inhibit TNF-α upregulation, inhibition of more than one at the same time (such as in response to the pan-chemokine inhibitors of this invention) reduces or abolishes TNF-alpha upregulation.

Thus, the anti-inflammatory effects of CRD-Leu$_4$Ile$_{11}$Cys$_{13}$ peptide 3(3-12)[MCP-1] and other peptide 3 derivatives, analogs and variants are not limited to reducing or inhibiting macrophage (monocyte) accumulation but also inhibit recruitment of other leukocyte subsets, e.g., B cells, neutrophils, and CD4+ T lymphocytes, and inhibited the intra-lesional levels of TNF-α, IL-8 and MCP-1.

Example 7

Use of a CRD-Peptide of the Invention in a Murine Endotoxemia Model

A mouse endotoxemia model is used to screen agents of the invention for in vivo functional anti-inflammatory activity in a rapid manner. Female CD-1 mice are injected i.p. (ventral abdomen) with 583 μg LPS. mRNA and protein levels of TNF-α, IFN-γ, IL-4 and MCP-1 and other markers of the inflammatory response are then determined. Thirty minutes prior to LPS administration, the animals were administered one of three different doses of CRD-Leu$_4$Ile$_{11}$Cys$_{13}$peptide 3(3-12)[MCP-1] as an intravenous loading dose and a subcutaneous bolus dose (on dorsum). PBS treated animals with and without LPS administration were positive and negative controls. Two hours later, animals were euthanized and serum collected. Serum was separated from the cell pellet and frozen until ELISA analysis of cytokine levels. Lung and liver samples were collected for mRNA analyses and histopathology. CRD-Leu$_4$Ile$_{11}$Cys$_{13}$peptide 3(3-12)[MCP-1] demonstrated a dose-dependent decrease in serum TNF-α. Serum levels and mRNA levels of IL-4, IFN-γ and MCP-1 are also determined.

Levels of serum MCP-1 and liver MCP-1 RNA were elevated in LPS treated animals with no modulation by CRD-Leu$_4$Ile$_{11}$Cys$_{13}$peptide 3(3-12)[MCP-1]. Levels of serum IL-4 and IFN-γ and liver IL-4 RNA were low or undetectable in all animals. Liver IFN-γ RNA was increased in all LPS treated animals. There was a dose dependent decrease in serum TNF-α in CRD-Leu$_4$Ile$_{11}$Cys$_{13}$peptide 3(3-12)[MCP-1] treated animals with statistical significance reached in the high dose group. Liver TNF-α RNA was high in all LPS treated animals.

Thus, CRD-Leu$_4$Ile$_{11}$Cys$_{13}$peptide 3(3-12)[MCP-1] treated mice may modulate the immune response via alterations in TNF-α levels.

Example 8

Use of a CRD-Peptide of the Invention in Normal Monkeys and Mice, and in a Murine Asthma Model To determine whether increasing doses of CRD-Leu$_4$Ile$_{11}$Cys$_{13}$ peptide 3(3-12)[MCP-1] alters the cell number and type of cell within the lungs of normal mice, mice were injected intravenously, intravenously and intratracheally, or intratracheally alone with CRD-Leu$_4$Ile$_{11}$Cys$_{13}$ peptide 3(3-12)[MCP-1]. Mice were sacrificed at 20-24 hours post injection. Lungs were collected for isolation of cells, which were subsequently counted and characterized by surface staining for CD3, CD4, CD8, B220, and Mac-1.

The total number of cells isolated from the lungs was higher in all groups receiving a low dose of CRD-Leu$_4$Ile$_{11}$Cys$_{13}$ peptide 3(3-12)[MCP-1] (0.3 μg IV and/or 10 μg IT) compared to PBS-treated mice. There were no significant differences in the total number of cells isolated from lungs of mice treated with the high dose CRD-Leu$_4$Ile$_{11}$Cys$_{13}$ peptide 3(3-12)[MCP-1] compared to PBS controls.

By FACS analysis, high dose CRD-Leu$_4$Ile$_{11}$Cys$_{13}$ peptide 3(3-12)[MCP-1] significantly reduced the percentages of CD3, CD4, and B220 cells by all routes of administration compared to PBS controls. In contrast, there were not significant differences in the percentages of CD3, CD4, or B220 cells in the groups treated with low dose CRD-Leu$_4$Ile$_{11}$Cys$_{13}$ peptide 3(3-12)[MCP-1] by all routes of administration.

Three further studies assessed the ability of two increasing doses of CRD-Leu$_4$Ile$_{11}$Cys$_{13}$ peptide 3(3-12)[MCP-1] to reduce the pulmonary inflammatory infiltrate, inhibit IgE antibody increases, and alter the percentages of specific inflammatory cells in the lung and blood in mice challenged intratracheally with ovalbumin. See Gonzalo et al., *J. Clin. Invest.*, 98, 2332 (1996); Gonzalo et al., *J. Exp. Med.*, 188, 157 (1998).

In the first study, the chemokine inhibitor was applied both before sensitization and prior to subsequent challenge. Mice were sensitized with 0.1 mg of ovalbumin (OVA) in 100 μl PBS (diluent control) intraperitoneally. Eight days following sensitization, mice received an intravenous loading dose (0.3 or 30 μg) and a subcutaneous depo dose (10 μg or 1 mg) of the pan-chemokine inhibitor CRD-Leu$_4$Ile$_{11}$Cys$_{13}$peptide 3(3-12)[MCP-1]. Thirty minutes following CRD-Leu$_4$Ile$_{11}$Cys$_{13}$ peptide 3(3-12)[MCP-1] administration, mice were challenged with 1% ovalbumin or PBS (diluent control) intratracheally. Twenty-one days following sensitization, mice received a second intravenous loading dose (0.3 or 30 µg) and a subcutaneous dose (10 µg or 1 mg) of the pan-chemokine inhibitor CRD-Leu$_4$Ile$_{11}$Cys$_{13}$peptide 3(3-12)[MCP-1]. Thirty minutes following CRD-Leu$_4$Ile$_{11}$Cys$_{13}$peptide 3(3-12)[MCP-1] administration, mice were challenged with 2% ovalbumin or PBS (diluent control) intratracheally. Mice were sacrificed 3 hours post-ovalbumin challenge on day 21. Lungs were collected for histopathology and for isolation of cells for total cell counts and FACS analysis. PBLs were collected for FACS analysis.

By FACS analysis, there were significantly lower numbers of CD3, CD4, B220, and Mac-1 cells in the lungs of mice treated with both doses of CRD-Leu$_4$Ile$_{11}$Cys$_3$ peptide 3(3-12)[MCP-1] (0.3 IV/10 µg subcutaneously or 30 µg IV/1 mg subcutaneously) compared to mice which received PBS prior to challenge with OVA. The percentage of CD8 cells was similar in all groups. In addition, the total number of cells isolated from lungs of CRD-Leu$_4$Ile$_{11}$Cys$_{13}$ peptide 3(3-12) [MCP-1] mice was similar to PBS-treated mice but significantly lower than mice treated with OVA and PBS, suggesting that the agent altered trafficking of inflammatory cells into the lung. In the blood, there were significantly higher percentages of CD3 and CD4 cells and lower percentages of B220 in mice treated with both doses of CRD-Leu$_4$Ile$_{11}$Cys$_{13}$ peptide 3(3-12)[MCP-1] compared to OVA-treated mice (positive control) and to PBS-treated mice (diluent control). Mice treated with the high dose had fewer Mac-1 cells in the PBL compartment compared to all other groups.

Histologically, all mice treated with the high dose CRD-Leu$_4$Ile$_{11}$Cys$_{13}$ peptide 3(3-12)[MCP-1] had minimal to no inflammatory infiltrates in the lung, similar to mice treated with PBS alone. Mice that received low dose CRD-Leu$_4$Ile$_{11}$Cys$_{13}$peptide 3(3-12)[MCP-1] also had minimal inflammation compared to mice treated with PBS and OVA. Rare eosinophils were seen only in the PBS OVA group (positive control), which is an expected response to OVA sensitization.

IgE levels were significantly higher in mice treated with PBS and OVA compared to all other groups. IgE was not detectable above background in all groups of mice treated with CRD-Leu$_4$Ile$_{11}$Cys$_{13}$ peptide 3(3-12)[MCP-1]. Thus, treatment with the pan-chemokine inhibitor CRD-Leu$_4$Ile$_{11}$Cys$_{13}$ peptide 3(3-12)[MCP-1] before sensitization and before challenge prevented any inflammatory response being set up in response to OVA.

A second study in the ovalbumin-induced hypersensitivity model was then performed to determine whether CRD-Leu$_4$Ile$_{11}$Cys$_{13}$ peptide 3(3-12)[MCP-1] could reduce the inflammatory response to OVA in mice which had been sensitized in the absence of test agent. Mice were sensitized with 0.1 mg of ovalbumin or PBS (diluent control) intraperitoneally. Eight days following sensitization, mice received a subcutaneous dose (10.3 µg, 103 µg, or 1.03 mg) of the pan-chemokine inhibitor CRD-Leu$_4$Ile$_{11}$Cys$_{13}$ peptide 3(3-12)[MCP-1]. Thirty minutes following CRD-Leu$_4$Ile$_{11}$Cys$_{13}$ peptide 3(3-12)[MCP-1] administration, mice were challenged with 1% ovalbumin or PBS (diluent control) intratracheally. Fifteen, eighteen, and twenty-one days following sensitization, mice received subcutaneous doses (10.3 µg, or 103 µg, or 1.03 mg) of the pan-chemokine inhibitor CRD-Leu$_4$Ile$_{11}$Cys$_{13}$ peptide 3(3-12)[MCP-1]. Thirty minutes following CRD-Leu$_4$Ile$_{11}$Cys$_{13}$ peptide 3(3-12)[MCP-1] administration, mice were challenged with 2% ovalbumin or PBS intratracheally, on day 21. Mice were sacrificed 3 hours post-challenge. Lungs were collected for histopathology and for isolation of cells for total cell counts and FACS analysis. Serum was collected for IgE and IL-4 levels.

Figure 16A:
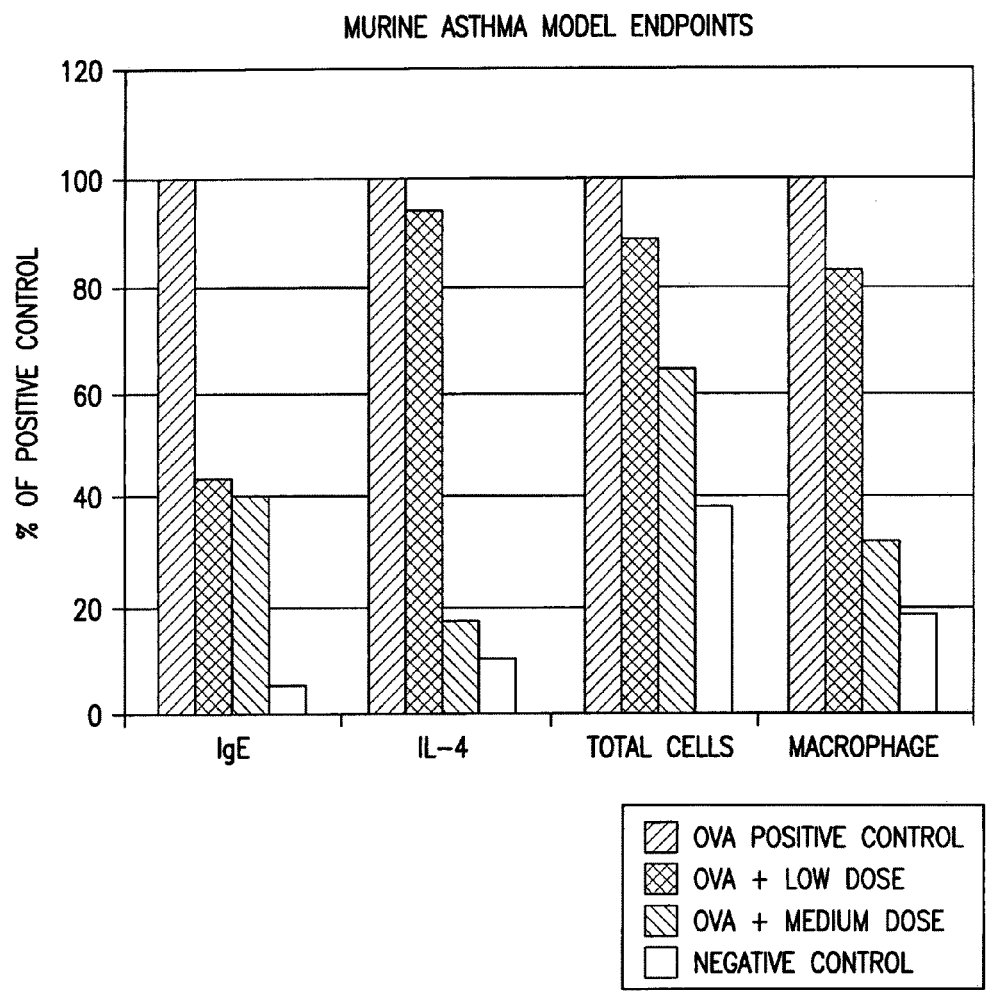
FIG. 16 shows the results from ovalbumin-sensitized mice treated with an agent of the invention. (A) IgE, IL-4, total cells, and macrophages in ovalbumin-sensitized mice treated with two different amounts of CRD-Leu$_4$Ile$_{11}$Cys$_{13}$peptide 3(3-12)[MCP-1]. (B) Results from FACS analysis of ovalbumin-sensitized mice treated with CRD-Leu$_4$Ile$_{11}$Cys$_{13}$peptide 3(3-12)[MCP-1]. There were significantly lower numbers of macrophages in the lungs of mice treated with CRD-Leu$_4$Ile$_{11}$Cys$_{13}$peptide 3(3-12)[MCP-1] as compared to mice that received only PBS prior to ovalbumin challenge. (C) Serum IgE and (D) IL-4 levels from ovalbumin-sensitized mice treated with CRD-Leu$_4$Ile$_{11}$Cys$_{13}$peptide 3(3-12)[MCP-1]. Serum IgE and IL-4 levels were significantly lower in mice treated with CRD-Leu$_4$Ile$_{11}$ Cys$_{13}$peptide 3(3-12)[MCP-1] than in mice that received only PBS prior to ovalbumin challenge.

Dose-dependent reductions in IgE (60%), IL-4 (85%), total cells in the lung (approximately 50%) and macrophages (74%) were observed (FIG. 16A).

Figure 16B:
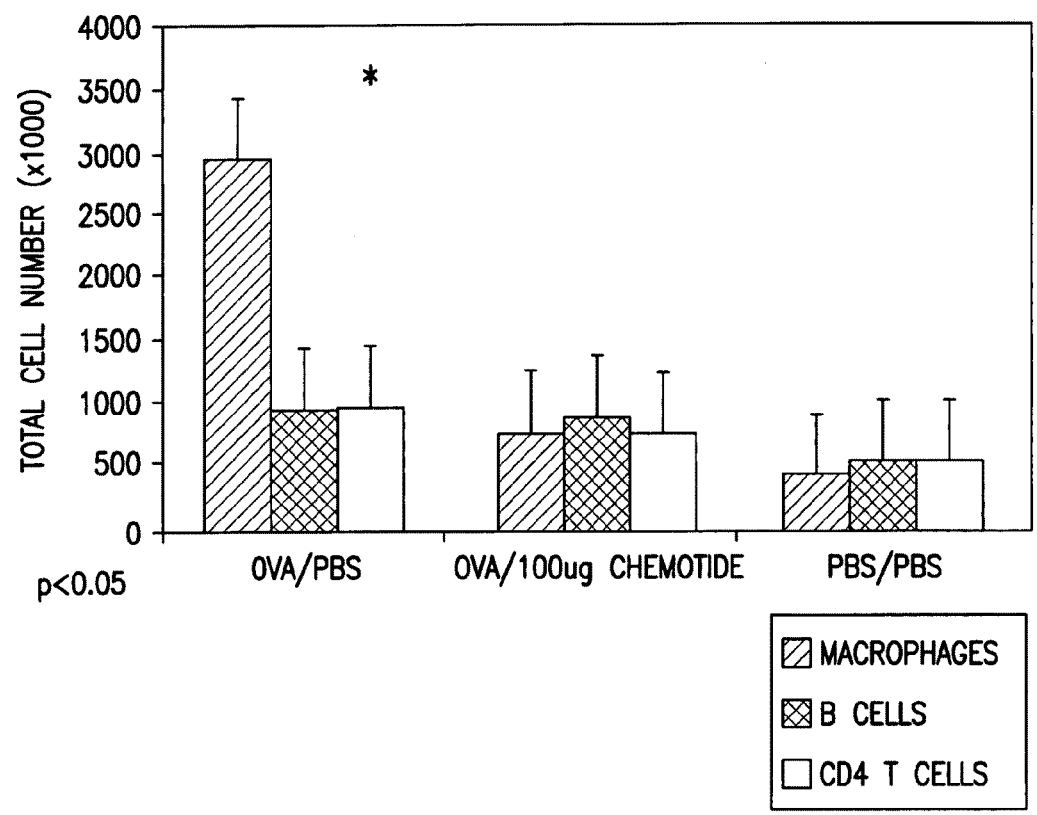
Figure 16C:
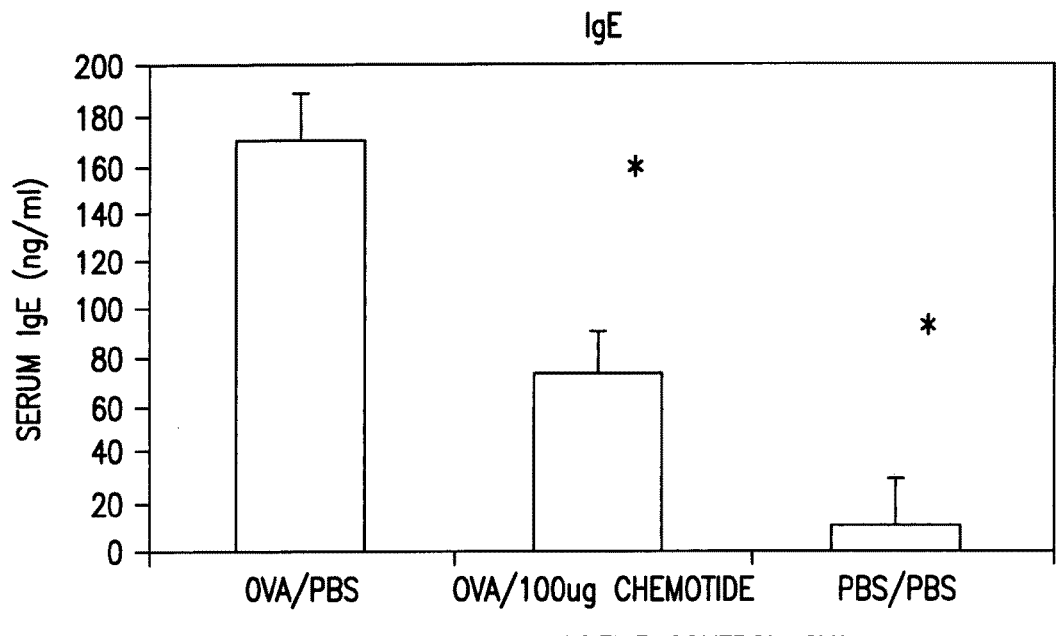
Figure 16D:
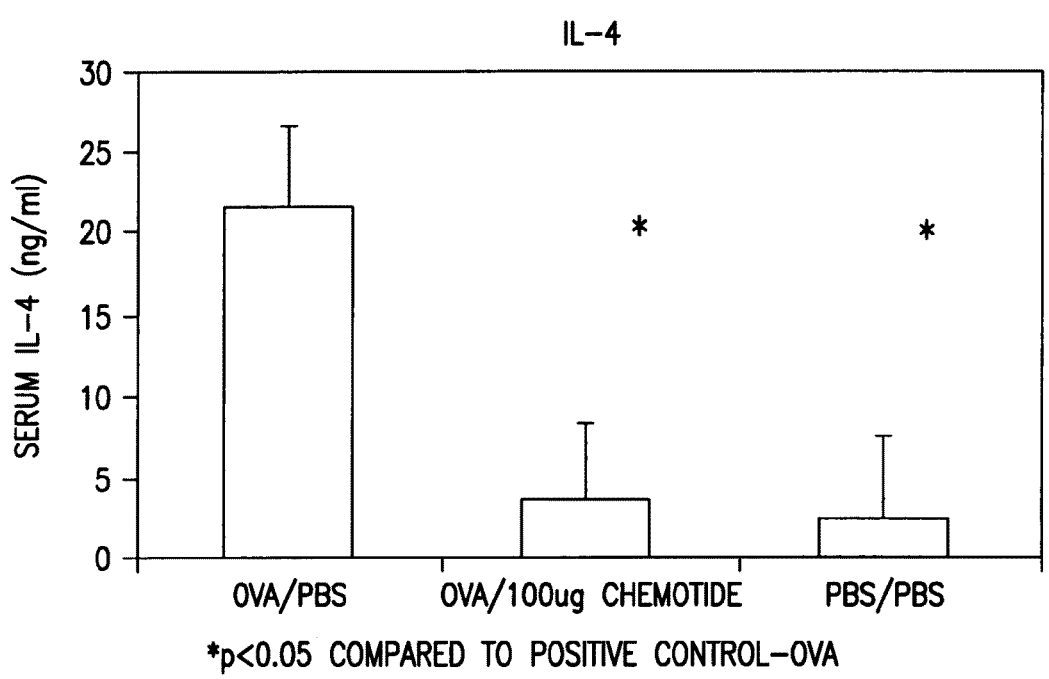
Figure 17:
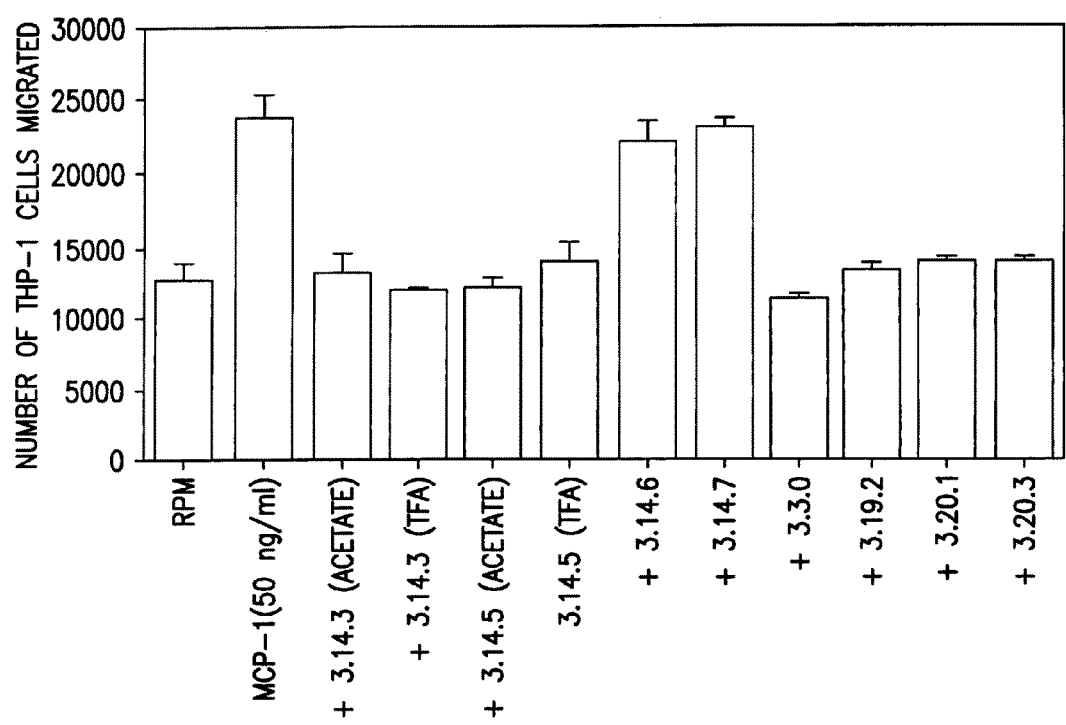
FIG. 17 is a graph of results obtained in the THP-1 migration assay with 100 μM peptide. 3.14.3 is CRD-Cys$_{13}$Leu$_4$Ile$_{11}$peptide 3(3-12)[MCP-1], 3.14.5 is L-Leu$_4$CRD-Cys$_{13}$Ile$_{11}$peptide 3(3-12)[MCP-1], 3.14.6 is CRD-Tyr$_3$Leu$_4$Ile$_{11}$β-Ala$_1$βAla$_2$peptide 3(3-12)[MCP-1] (N-terminal extension), 3.14.7 is CRD-Leu$_4$Asn$_5$Ile$_{11}$β-Ala$_3$βAla$_4$ Tyr$_{15}$peptide 3(3-12)[MCP-1] (C-terminal extension), 3.3.0 is peptide 3(7-12)[MCP-1], 3.19.2 is LRD-peptide 3(7-12)[MCP-1], 3.20.1 is CFL-peptide 3(7-12)[MCP-1], and 3.20.3 is CRD-peptide 3(7-12)[MCP-1].

By FACS analysis, there were significantly lower percentages of macrophages in the lungs of mice treated with 100 µg of CRD-Leu$_4$Ile$_{11}$Cys$_{13}$ peptide 3(3-12)[MCP-1] compared to mice which received PBS only prior to challenge with OVA (FIG. 16B). Thus, CRD-Leu$_4$Ile$_{11}$Cys$_{13}$ peptide 3(3-12) [MCP-1] alters trafficking of these cells. Histologically, all mice treated with the high or medium dose CRD-Leu$_4$Ile$_{11}$Cys$_{13}$ peptide 3(3-12)[MCP-1] had fewer inflammatory infiltrates in the lung compared to mice that were not treated with the peptide but challenged with OVA (positive control). Mice treated with PBS alone had minimal to no inflammation in the lung. All mice challenged with OVA had eosinophils in the lung. Similar to mice treated with PBS only (negative control), IgE levels were significantly lower in mice treated with CRD-Leu$_4$Ile$_{11}$Cys$_{13}$ peptide 3(3-12)[MCP-1] compared to mice treated with PBS and OVA (positive control) (FIG. 16B). Likewise, serum IL-4 levels were significantly reduced in mice (FIG. 16C). Thus, treatment with CRD-Leu$_4$Ile$_{11}$Cys$_{13}$ peptide 3(3-12)[MCP-1] just prior to OVA challenge significantly reduces the inflammatory response to OVA in sensitized mice.

A third study assessed the efficacy of daily dosing with CRD-Leu$_4$Ile$_{11}$Cys$_{13}$ peptide 3(3-12)[MCP-1] to reduce OVA-induced pulmonary inflammation. Mice were sensitized with 0.1 mg of ovalbumin or PBS (diluent control) intraperitoneally in the absence of the test agent. Eight days following initial sensitization, mice were treated with either 10.3 µg or 1.03 mg CRD-Leu$_4$Ile$_{11}$Cys$_{13}$ peptide 3(3-12) [MCP-1], or 1.03 mg of the inactive D-ala peptide, by the subcutaneous route. These treatments were given daily from day 8 through day 21. On day 8, thirty minutes following treatment, mice were challenged intratracheally with 1% ovalbumin or PBS. On days 15, 18, and 21, thirty minutes following treatment, mice were challenged intratracheally with 2% ovalbumin or PBS. Mice were sacrificed 3 hours post-ovalbumin challenge, on day 21. Lungs were collected for histopathology, and for isolation of cells for total cell counts and FACS analysis. Bronchalveolar lavage (BAL) was collected for eicosinoid levels. Serum was collected for IgE and IL-4 levels. Spleens were collected for cytokine recall responses.

Figure 40A:
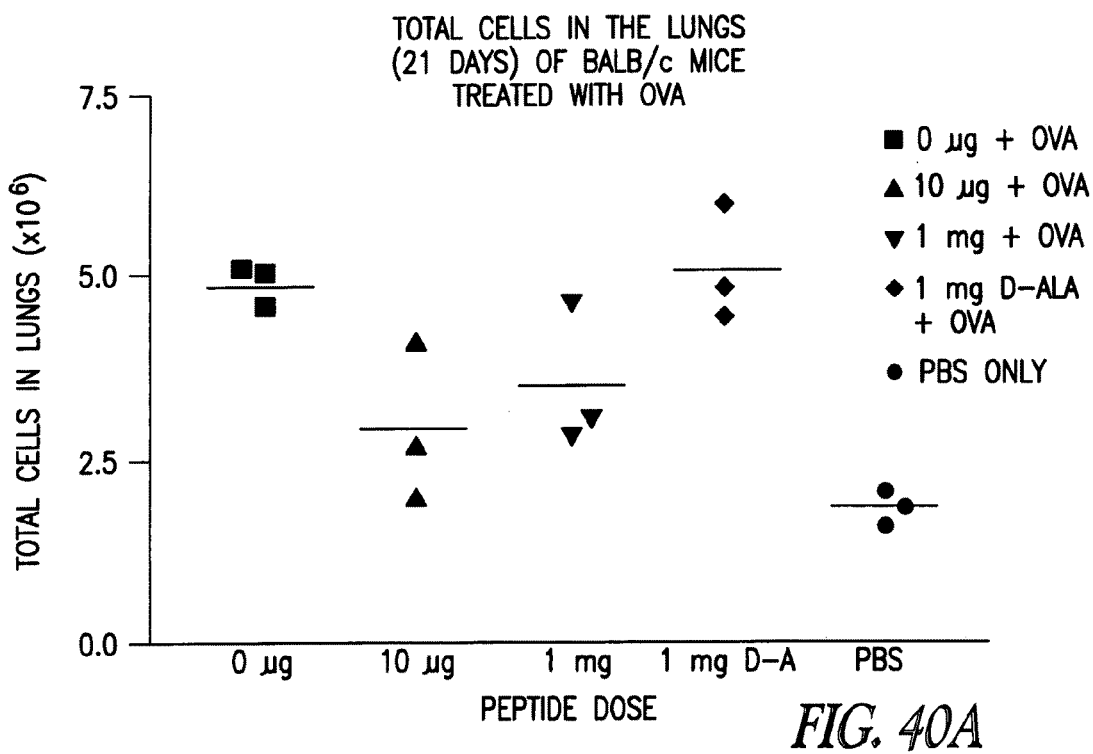
FIGS. 40A-C show the total cells, macrophages and B cells in the lungs of ovalbumin-treated mice.
Figure 40B:
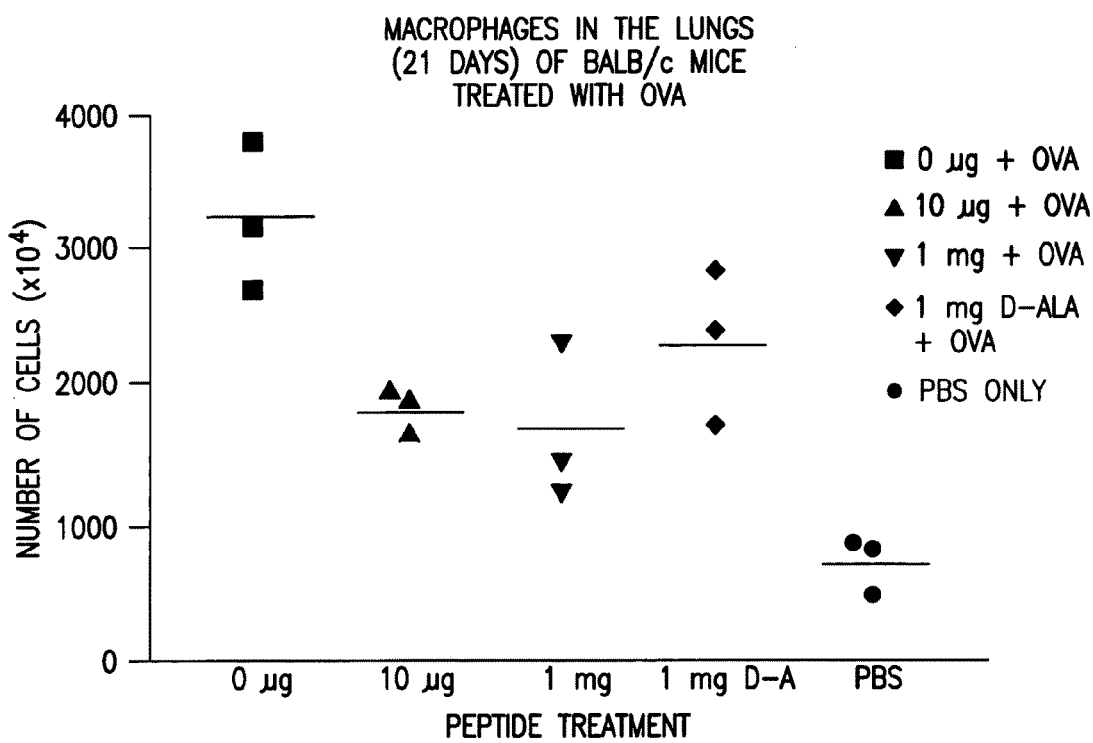
Figure 40C:
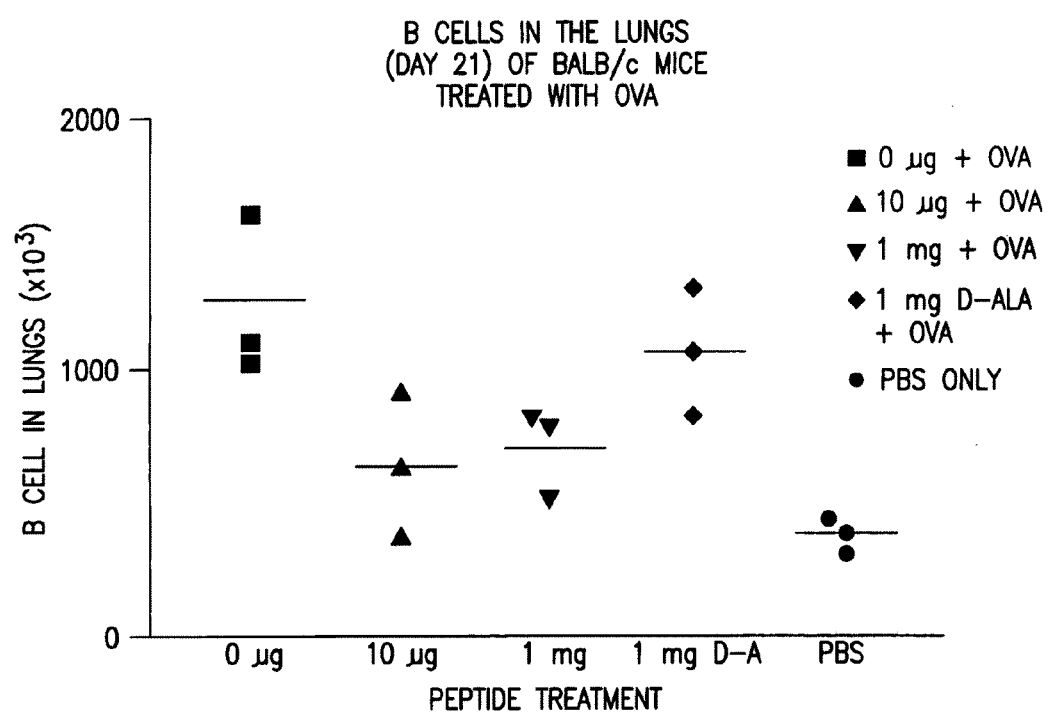
Figure 41:
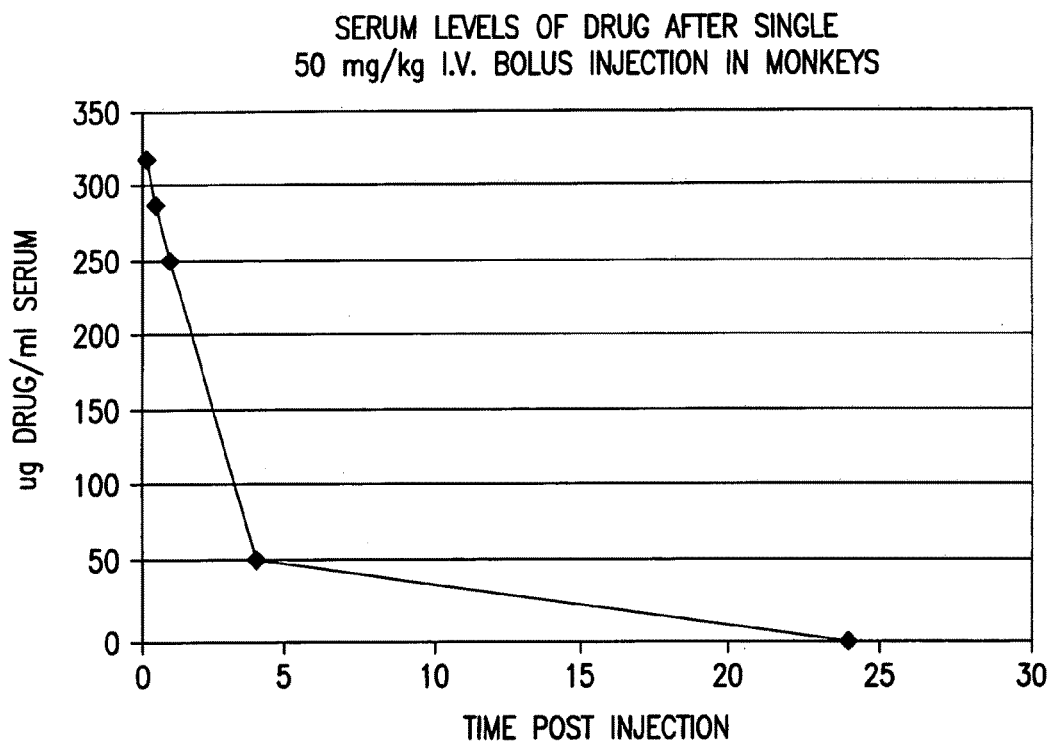
FIG. 41 shows serum levels of CRD-Leu$_4$Ile$_{11}$Cys$_{13}$ peptide 3(3-12)[MCP-1] over time in monkeys administered the agent.

There were significantly (p<0.05) fewer total cells in the lungs of mice treated with the low dose (10.3 µg) CRD-Leu$_4$Ile$_{11}$Cys$_{13}$ peptide 3(3-12)[MCP-1], as compared to positive controls or mice treated with the inactive peptide (FIG. 41). By FACS analysis, there were significantly lower numbers of macrophages, and B cells in the lungs of mice treated with the low dose (10.3 µg) of CRD-Leu$_4$Ile$_{11}$Cys$_{13}$ peptide 3(3-12)[MCP-1] as compared to positive controls or mice treated with the inactive peptide (FIG. 40). In addition, B cells were significantly (p<0.05) reduced in mice treated with high dose (1.03 mg) of CRD-Leu$_4$Ile$_{11}$Cys$_{113}$ peptide 3(3-12)[MCP-1] as compared to controls (FIG. 40). There was no significant differences in T cell number. Histologically, all mice treated with the high or medium dose CRD-Leu$_4$Ile$_{11}$Cys$_{13}$ peptide 3(3-12)[MCP-1] had fewer inflammatory infiltrates in the lung compared to mice that were not treated with the peptide but challenged with OVA (positive control) or treated with the inactive peptide, although the inflammation is reduced, not eliminated. Mice treated with PBS alone had minimal to no inflammation in the lung. All mice challenged with OVA had eosinophils in the lung, including those mice treated with CRD-Leu$_4$Ile$_{11}$Cys$_{13}$ peptide 3(3-12)[MCP-1].

In a series of in vitro experiments, the recall responses of culture splenocytes from the sensitized animals to OVA were performed. Splenocytes from mice treated with CRD-Leu$_4$Ile$_{11}$Cys$_{13}$peptide 3(3-12)[MCP-1] produced significantly less IL-4 in response to OVA (as did splenocytes from unsensitized mice) than splenocytes from untreated mice (OVA positive control) or from mice treated with inactive peptide (FIG. 40). IgE levels were significantly reduced (p<0.05) in mice treated with all doses of CRD-Leu$_4$Ile$_{11}$Cys$_{13}$ peptide 3(3-12)[MCP-1] compared to controls (FIG. 41). The inactive peptide significantly reduced (p<0.05) thromboxane B2 in the BAL (FIG. 40). There were no significant differences in eicosinoid levels (thromboxane B2, leukotriene B4, or prostaglandin E2), although different volumes may introduce artifactual differences and large variations within groups.

These results established that CRD-Leu$_4$Ile$_{11}$Cys$_{13}$ peptide 3(3-12)[MCP-1], when delivered daily between days 8 and 21, by subcutaneous injection just prior to OVA challenge, reduced the trafficking of macrophages and B cells into the lung following exposure to the antigen OVA. More significantly, CRD-Leu$_4$Ile$_{11}$Cys$_{13}$ peptide 3(3-12)[MCP-1] reduced IgE antibody levels in the serum, and IL-4 levels in supernatants from spleen recall cultures, which are strongly associated with asthma. IgE responses are dependent on a Th2 cell response, which produces IL-4 and IL-5. Therefore, the observation that CRD-Leu$_4$Ile$_{11}$Cys$_{13}$ peptide 3(3-12)[MCP-1] has an effect on reducing IgE upon challenge with OVA strongly indicates that CRD-Leu$_4$Ile$_{11}$Cys$_{13}$ peptide 3(3-12)[MCP-1] reduces IL-4 and IL-5.

In another study, BALB/c mice were sensitized with 0.1 mg of ovalbumin (OVA) or PBS (diluent control) intraperitoneally. Eight days following initial sensitization mice were challenged intratracheally with 1% ovalbumin or PBS (diluent control). On days fifteen, eighteen, twenty one, and thirty four, mice were challenged intratracheally with 2% ovalbumin of PBS. To determine if a single dose of CRD-Leu$_4$Ile$_{11}$Cys$_{13}$ peptide 3(3-12)[MCP-1] had an effect on reducing pulmonary inflammation, IL-4 or IgE in mice with an established asthma phenotype, mice were treated with a 100 μg i.v. bolus of CRD-Leu$_4$Ile$_{11}$Cys$_{13}$ peptide 3(3-12)[MCP-1] or PBS. Thirty minutes following treatment, mice were challenged intratracheally with 2% OVA and sacrificed 3 hours after OVA challenge. To determine if daily treatment with 100 μg of CRD-Leu$_4$Ile$_{11}$Cys$_{13}$ peptide 3(3-12)[MCP-1] caused regression of pulmonary inflammation and reduced IL-4 and IgE levels, mice were injected subcutaneously from day 21 to day 34 with CRD-Leu$_4$Ile$_{11}$Cys$_{13}$ peptide 3(3-12)[MCP-1] or PBS. On day 34 mice were re-challenged intratracheally with either 2% OVA or PBS. Mice were sacrificed 3 hours after challenge. Following sacrifice on day 21 or 34, lungs were collected for histopathology and for isolation of cells for total cell counts and identification by FACS analysis. Serum was collected for IgE and IL-4 levels. Spleens were collected for cytokine and antibody recall responses.

Figure 27A:
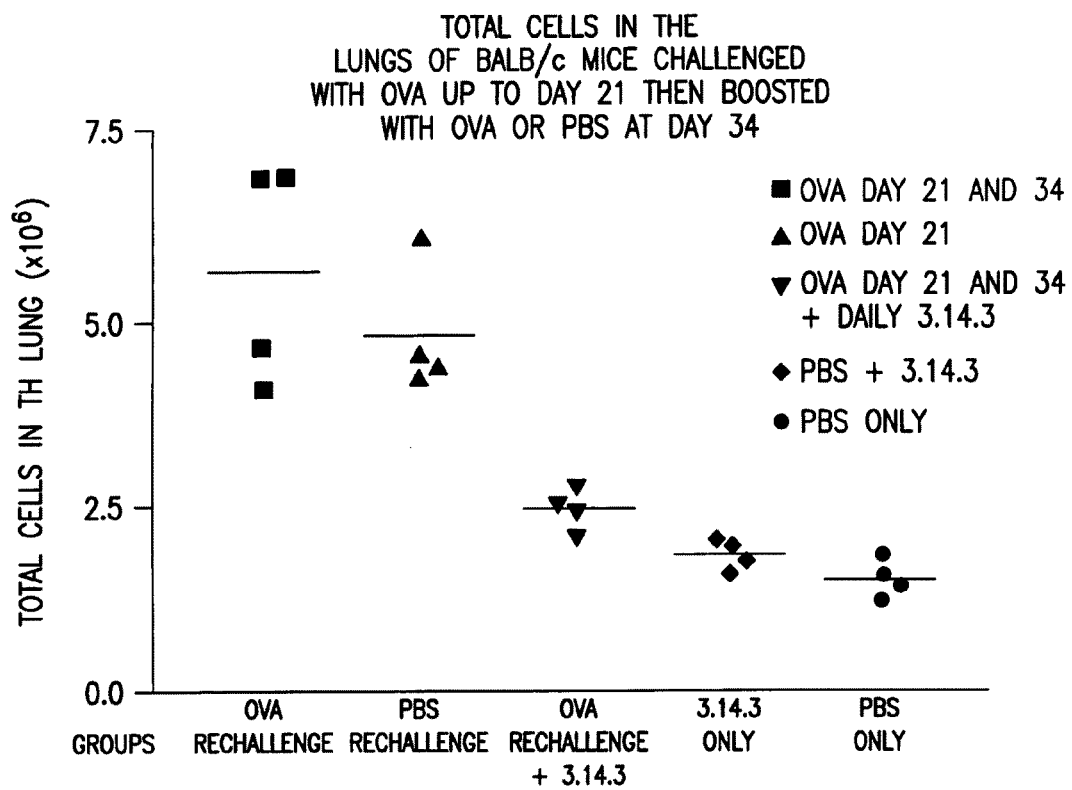
FIG. 27 shows total cell number and cell types in the lung of unchallenged and ovalbumin-challenged mice administered CRD-Leu$_4$Ile$_{11}$Cys$_{13}$ peptide 3(3-12)[MCP-1]. A) total cells, B) macrophage, C) B cells, and D) CD4 T cells.
Figure 27B:
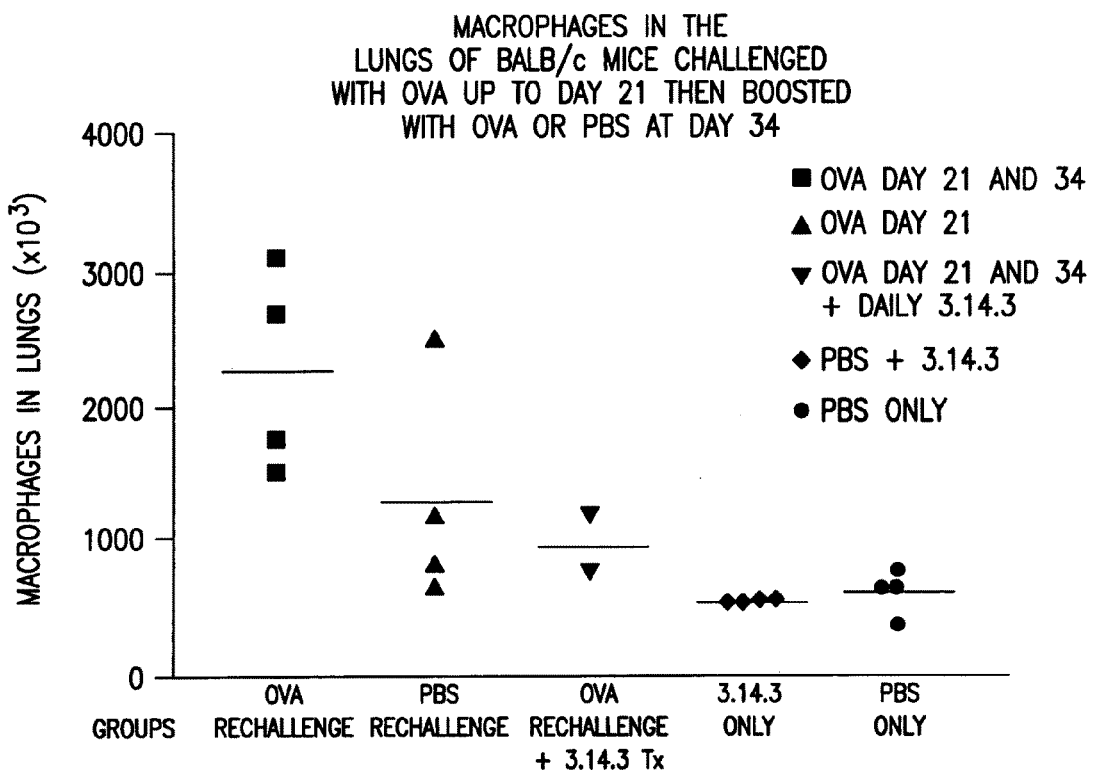
Figure 27C:
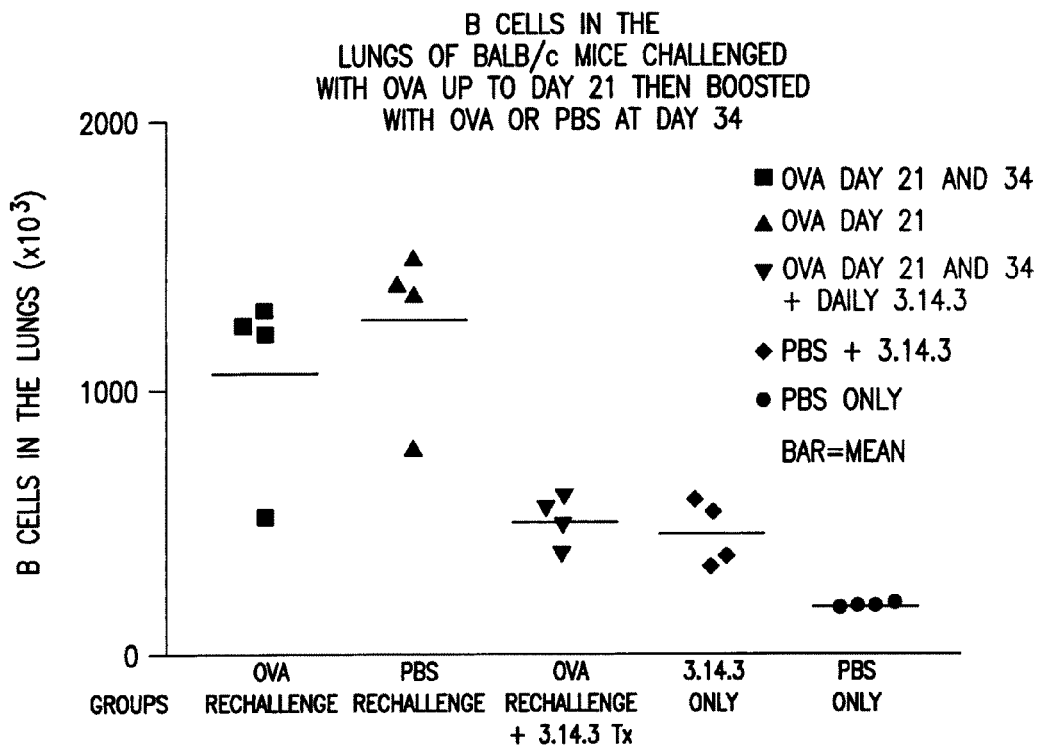
Figure 27D:
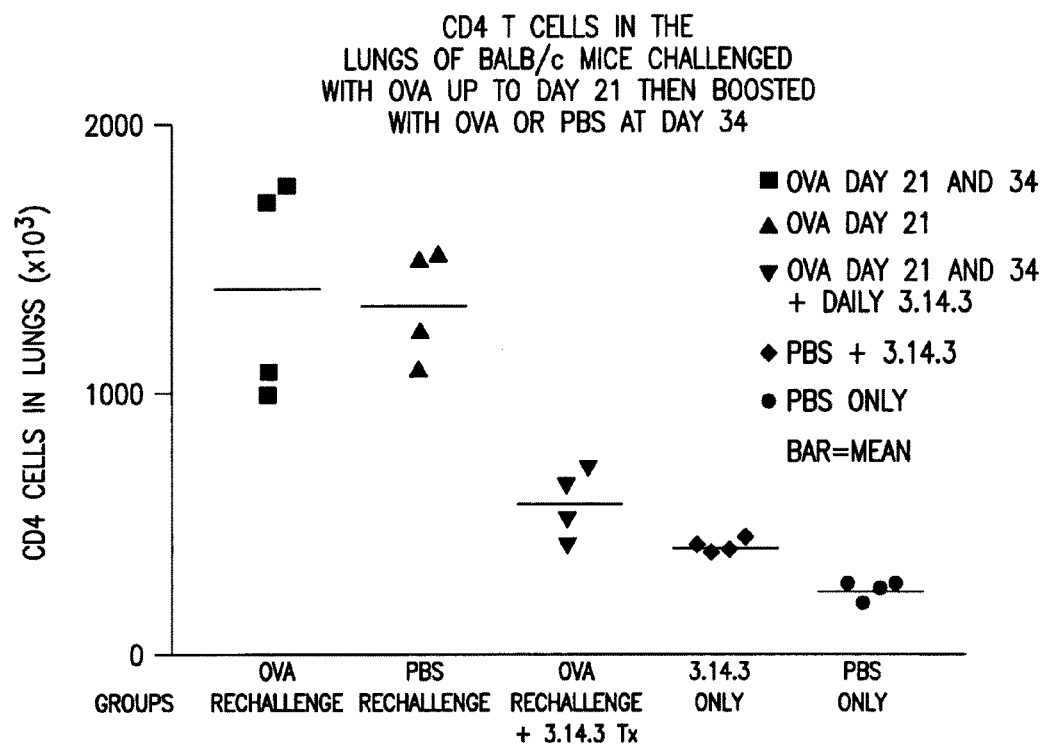
Figure 28:
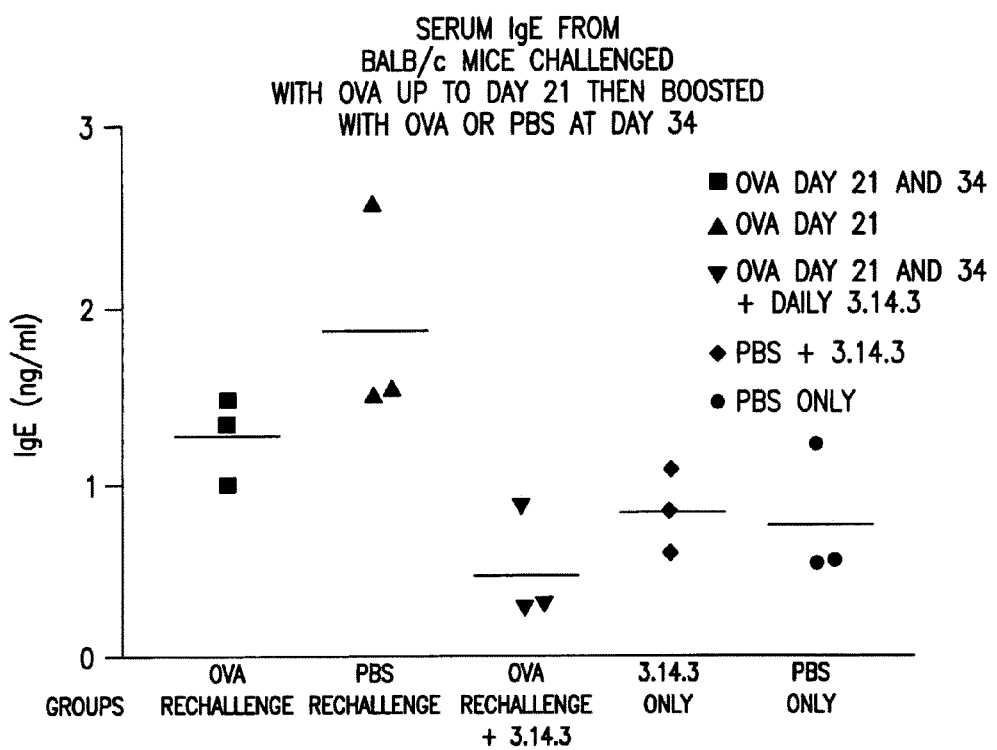
FIG. 28 shows IgE levels in unchallenged and ovalbumin-challenged mice administered CRD-Leu$_4$Ile$_{11}$Cys$_{13}$ peptide 3(3-12)[MCP-1].

Mice treated daily with CRD-Leu$_4$Ile$_{11}$Cys$_{13}$ peptide 3(3-12)[MCP-1] for 2 weeks, then re-challenged with OVA, had significantly (p<0.01) fewer total cells in the lungs compared to mice treated with PBS and re-challenged with OVA or PBS (positive controls) (FIG. 27A). By FACS analysis, there were also significantly lower numbers of macrophages, B cells, and CD4+ T cells in the lungs of mice treated with CRD-Leu$_4$Ile$_{11}$Cys$_{13}$ peptide 3(3-12)[MCP-1] compared to positive controls (FIGS. 27 B, C and D). In addition, mice treated with CRD-Leu$_4$Ile$_{11}$Cys$_{13}$ peptide 3(3-12)[MCP-1] had significantly (p<0.05) reduced levels of serum IgE compared to positive controls (FIG. 28 and Table 10). Following stimulation of splenocytes with OVA (no CRD-Leu$_4$Ile$_{11}$Cys$_{13}$ peptide 3(3-12)[MCP-1] added), there were significantly (p<0.05) reduced levels of IL-4, IgE, and total IgG and IgM in culture supernatants from mice treated in vivo with CRD-Leu$_4$Ile$_{11}$Cys$_{13}$ peptide 3(3-12)[MCP-1] compared to positive controls (FIGS. 30 A, B and C; Table 9). Complete suppression of antibody production persisted up to 1 week in recall cultures (FIGS. 30 A and B; Tables 8 and 11).

Figure 30A:
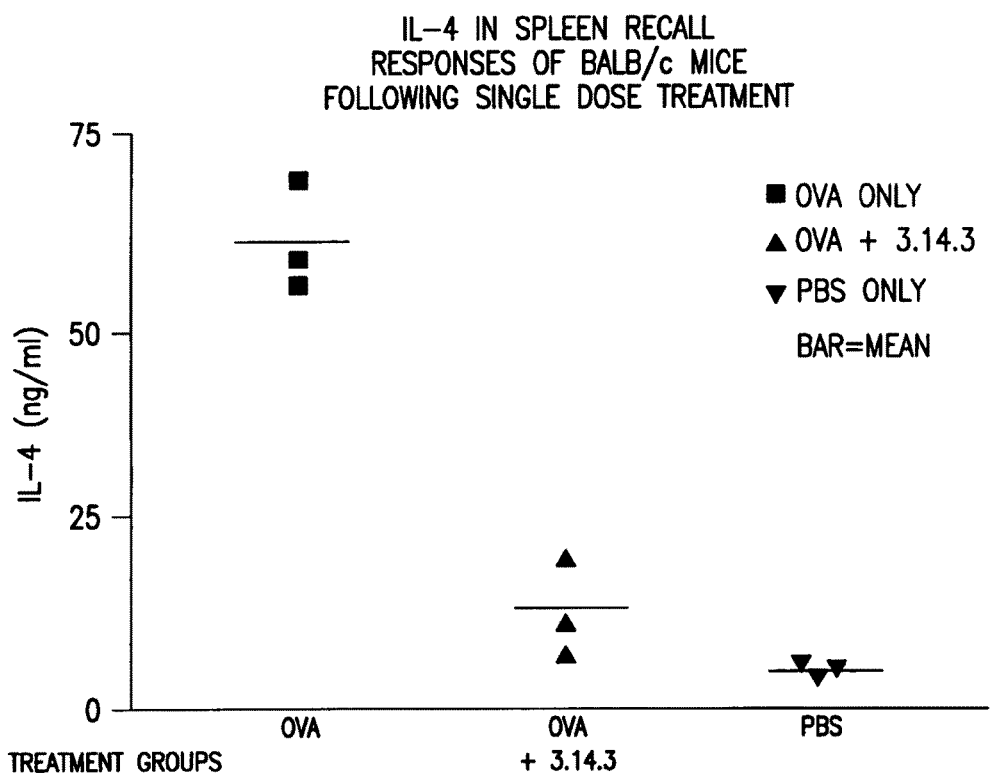
FIG. 30 depicts IL-4 levels in spleen recall responses from unchallenged and ovalbumin-challenged mice administered CRD-Leu$_4$Ile$_{11}$Cys$_{13}$ peptide 3(3-12)[MCP-1]. A) IL-4 levels after single dose. B) IL-4 levels after OVA challenge and boost.
Figure 30B:
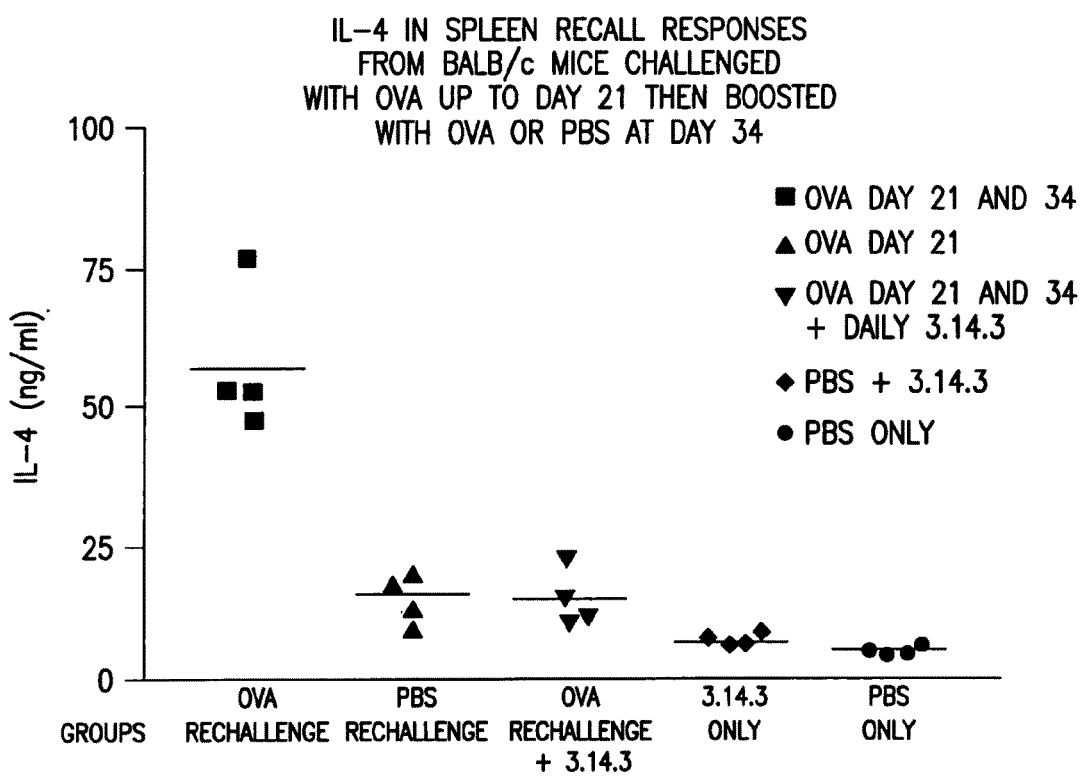
Figure 31:
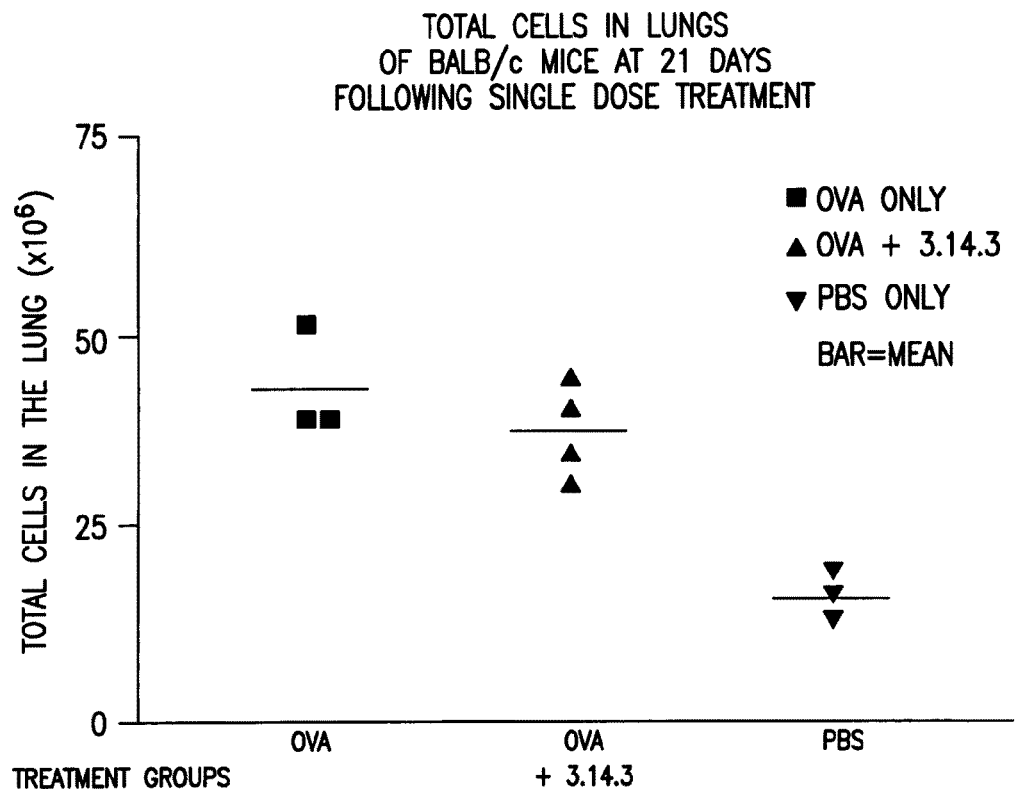
FIG. 31 shows total cells in the lung of unchallenged and ovalbumin-challenged mice.
Figure 32:
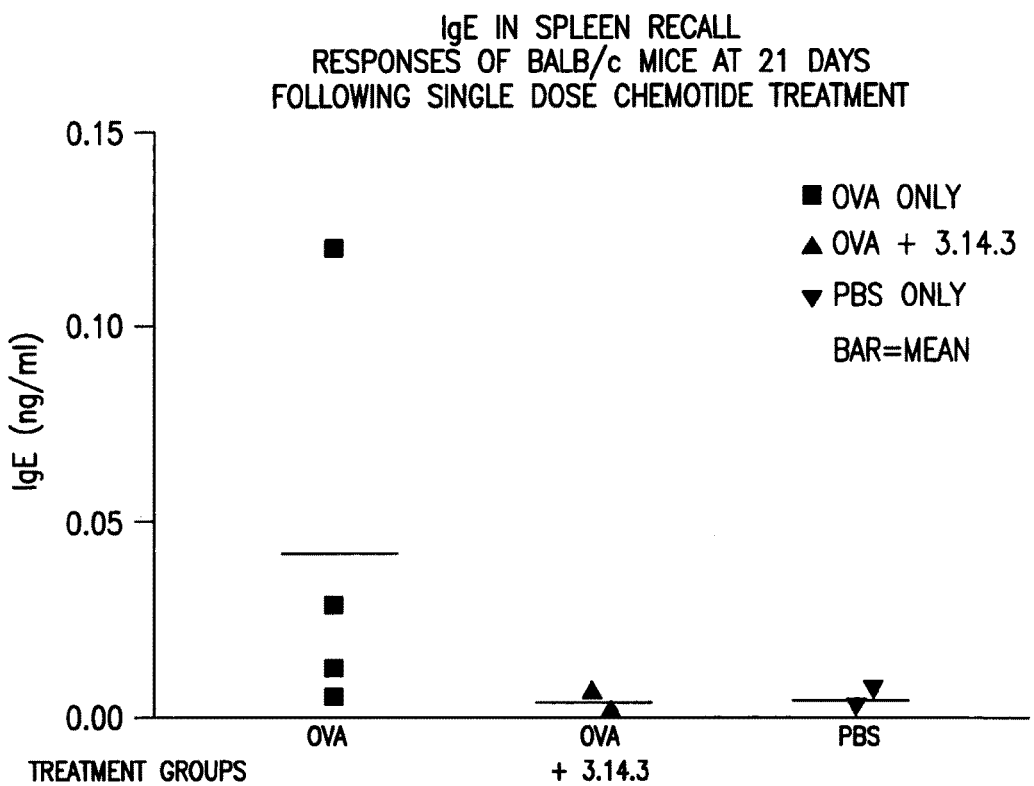
FIG. 32 depicts IgE in spleen recall responses of unchallenged and ovalbumin-challenged mice.
Figure 33A:
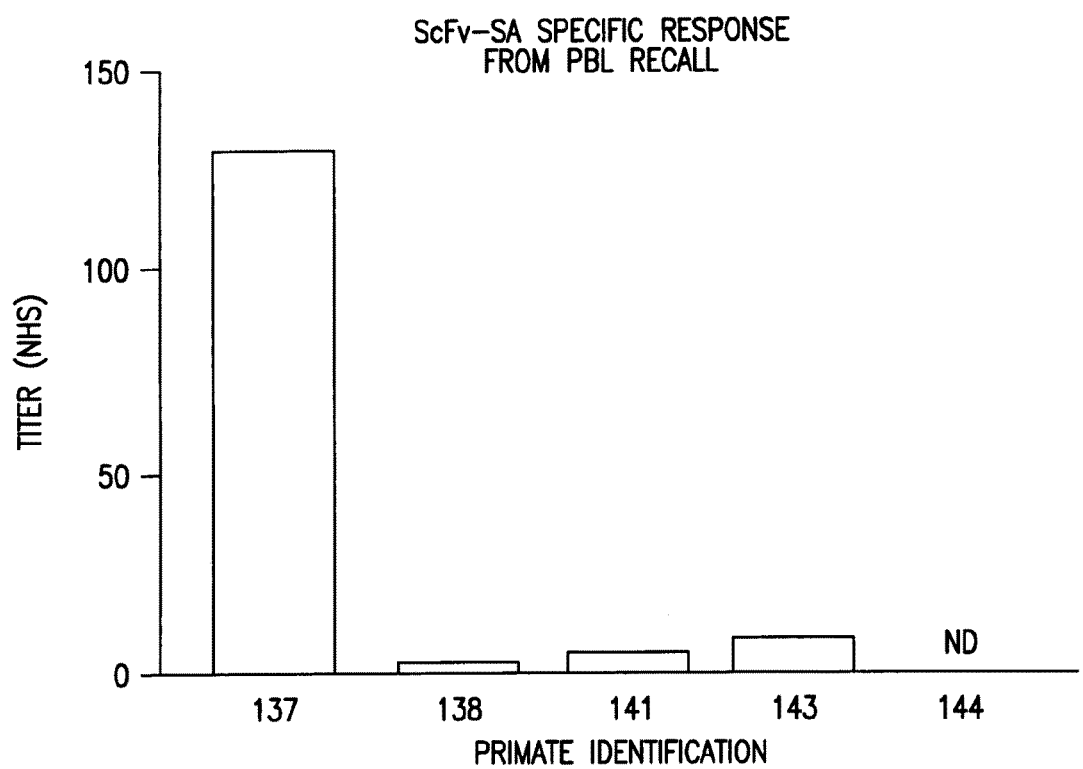
FIG. 33 depicts antibody-specific recall responses in monkeys treated with CRD-Leu$_4$Ile$_{11}$Cys$_{13}$ peptide 3(3-12) [MCP-1]. Animals #137 and #144 were diluent (PBS) controls. Animals #138, #141 and #143 were treated with CRD-Leu$_4$Ile$_{11}$Cys$_{13}$ peptide 3(3-12)[MCP-1].
Figure 33B:
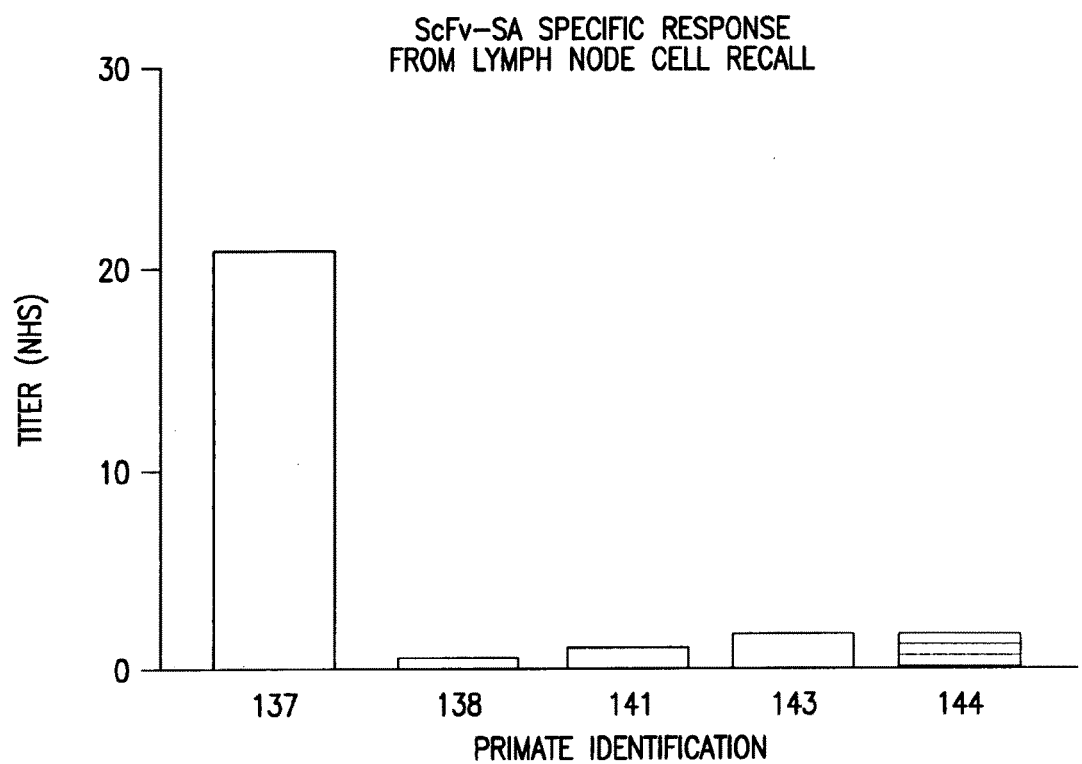
Figure 33C:
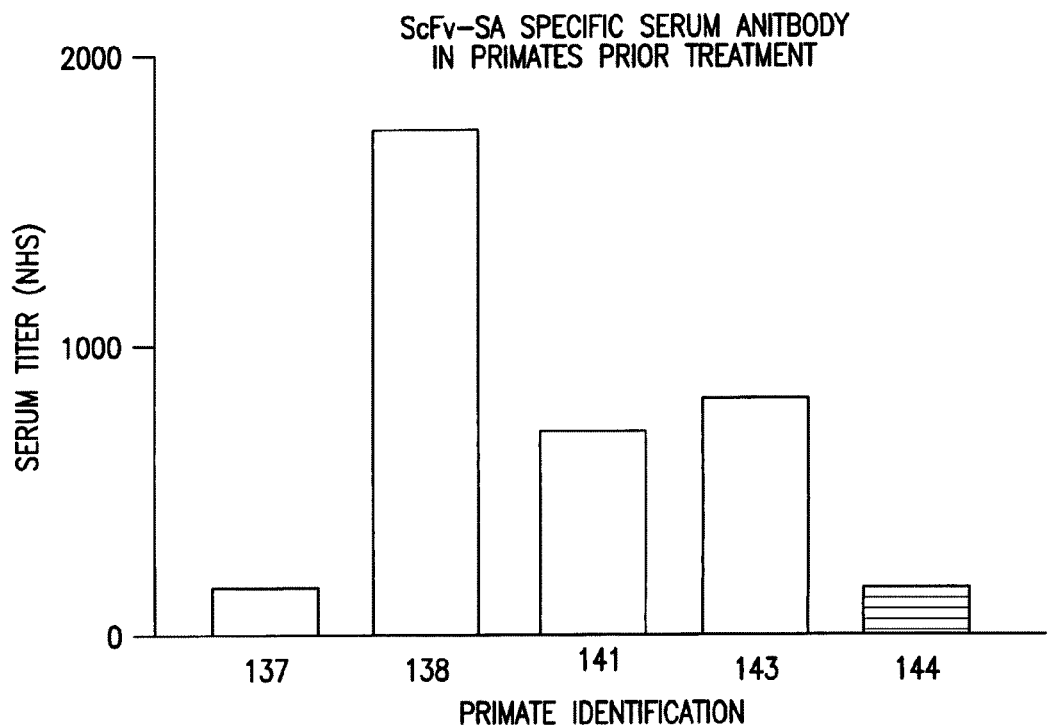
Figure 33D:
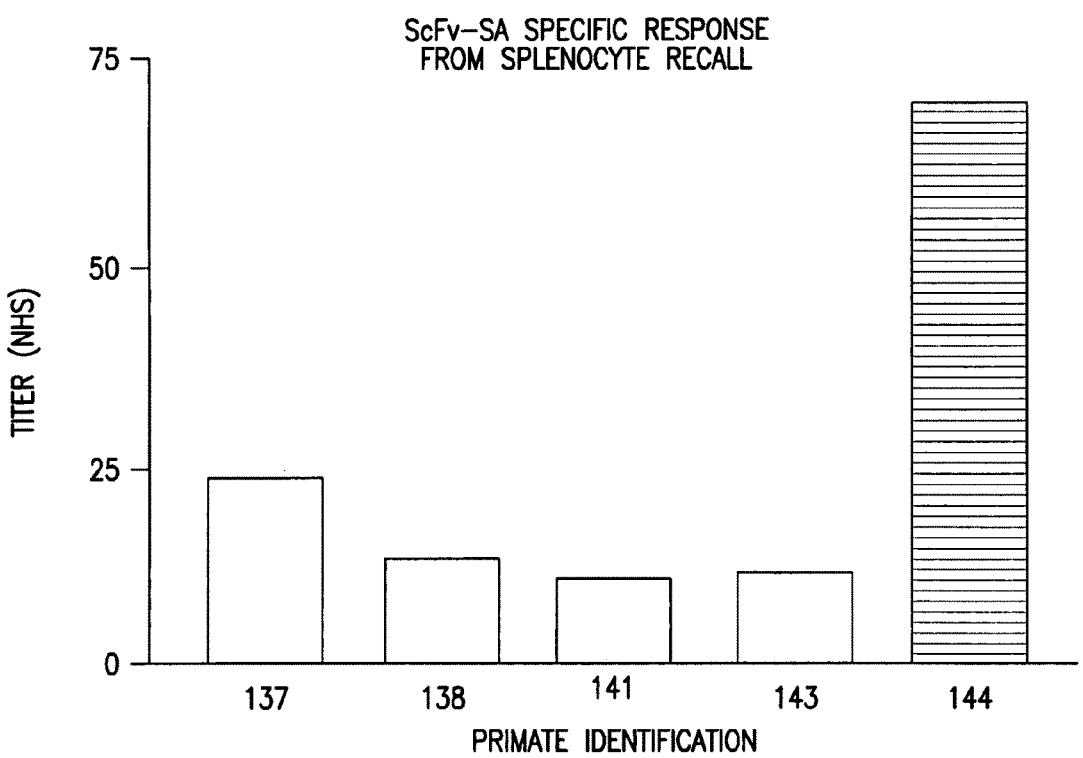
Figure 34A:
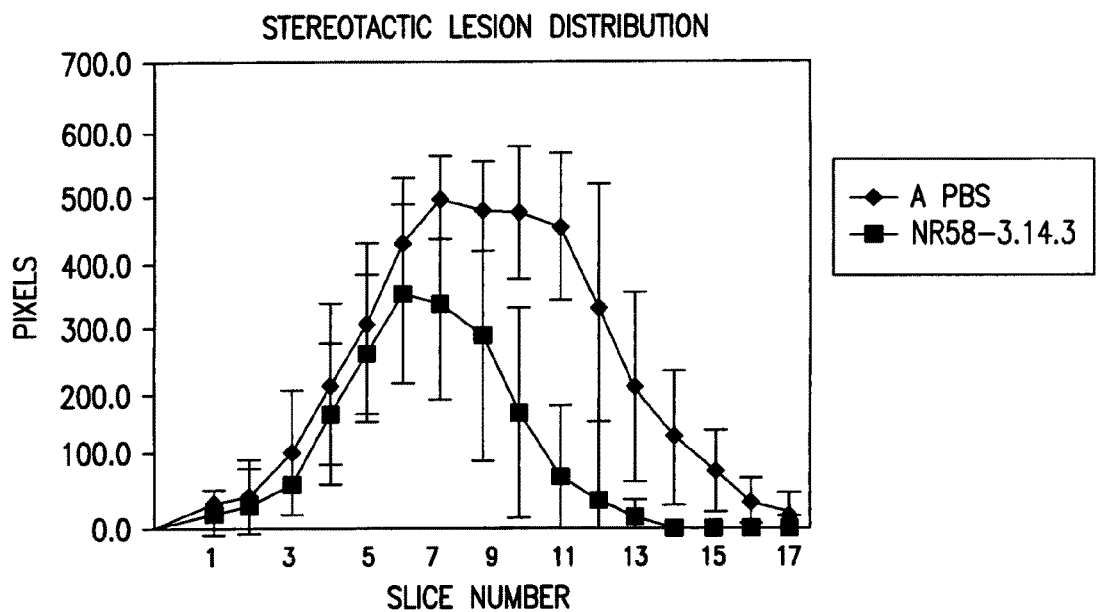
FIG. 34 depicts lesion volume by slice (rostral to caudal) in an ischemic reperfusion injury model in rats 24 hours post ictus. N=7. Results are mean±SD.
Figure 34B:
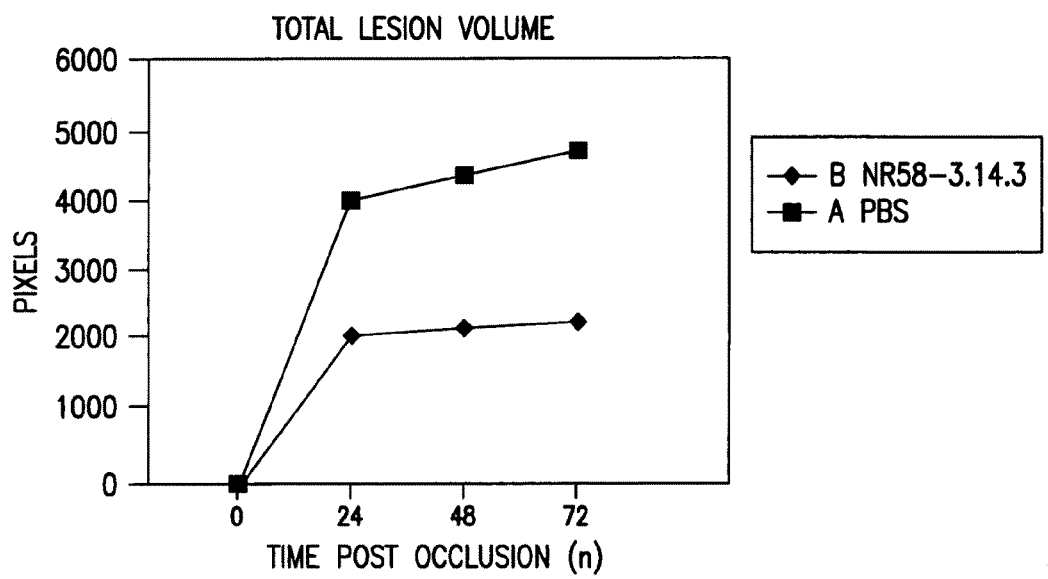
Figure 34C:
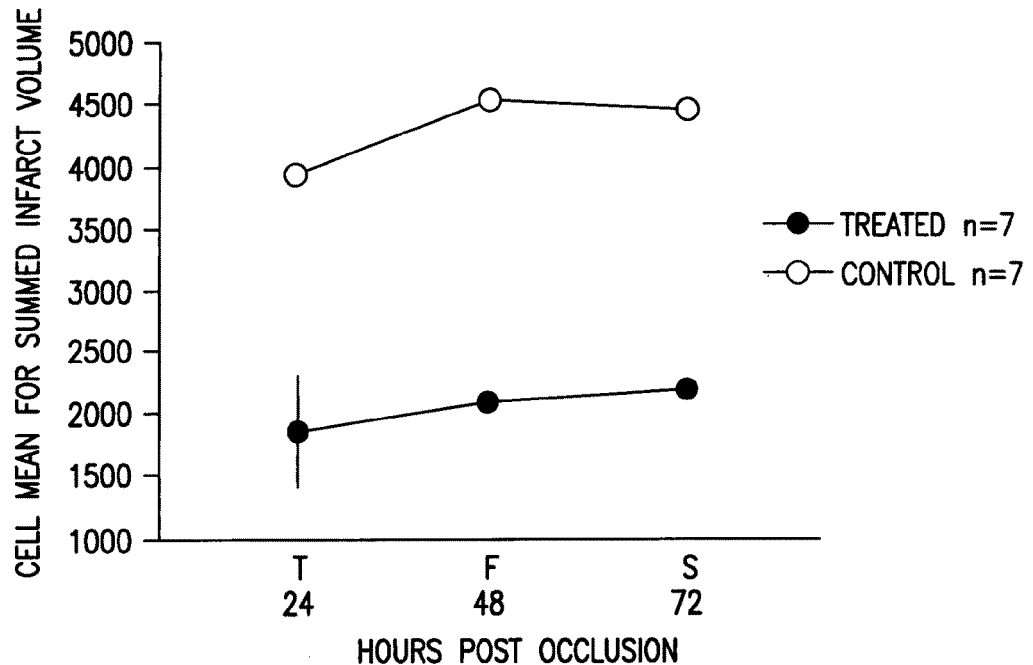
Figure 34D:
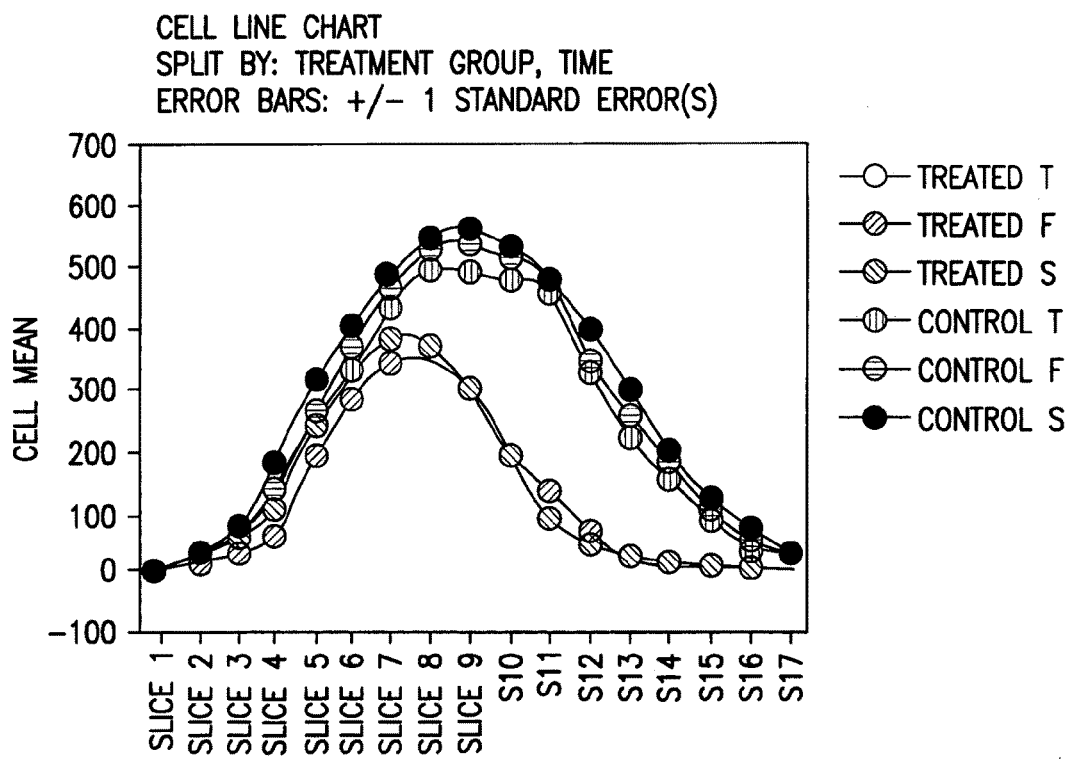
Figure 35:
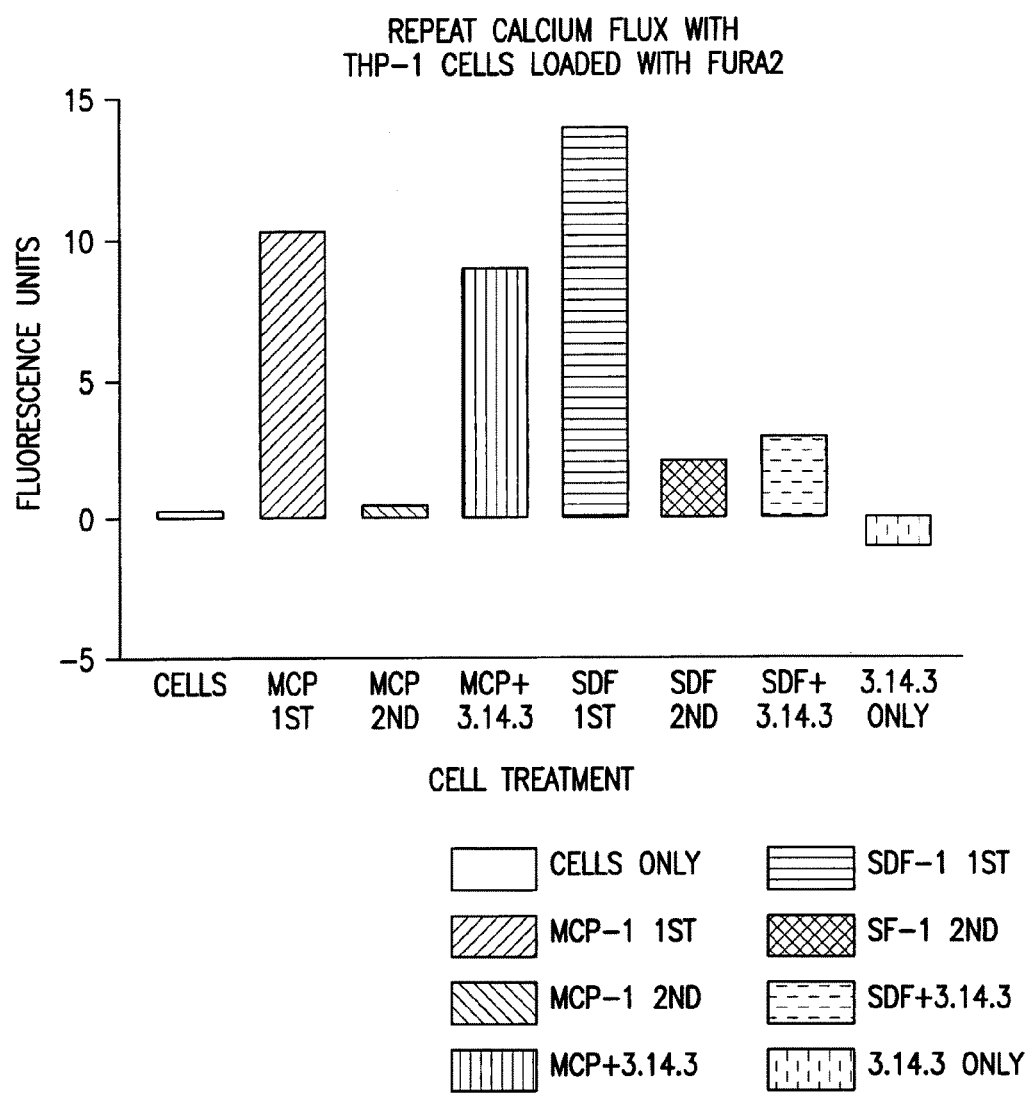
FIG. 35 shows intracellular calcium influx in THP-1 cells loaded with Fura2. CRD-Leu$_4$Ile$_{11}$Cys$_{13}$ peptide 3(3-12) [MCP-1] at 6.7 µg/ml was incubated with THP-1 cells (2×10$^6$ cells/ml) for 25 minutes prior to exposure to agonist (10 ng/ml) and measurement of flux. The second exposure to agonist is 2 minutes later. Fluorescence is measured at 510 nm.

However, following 2 weeks in culture, antibody levels in supernatants from CRD-Leu$_4$Ile$_{11}$Cys$_{13}$ peptide 3(3-12) [MCP-1] treated mice were higher than negative controls, equivalent to mice that were re-challenged with PBS, and significantly (p<0.05) lower than mice re-challenged with OVA (FIGS. 30 A and B). Histologically, lungs from mice treated daily with CRD-Leu$_4$Ile$_{11}$Cys$_{13}$ peptide 3(3-12) [MCP-1] resembled normal mice and had markedly fewer inflammatory infiltrates in the lung compared to mice that were treated with PBS and re-challenged with OVA (positive control). Mice treated with PBS alone and never challenged with OVA had minimal to no inflammation in the lung. All mice challenged with OVA had eosinophils in the lung. However, those mice treated with CRD-Leu$_4$Ile$_{11}$Cys$_{13}$ peptide 3(3-12)[MCP-1] had fewer of any inflammatory cells including eosinophils.

Figure 29A:
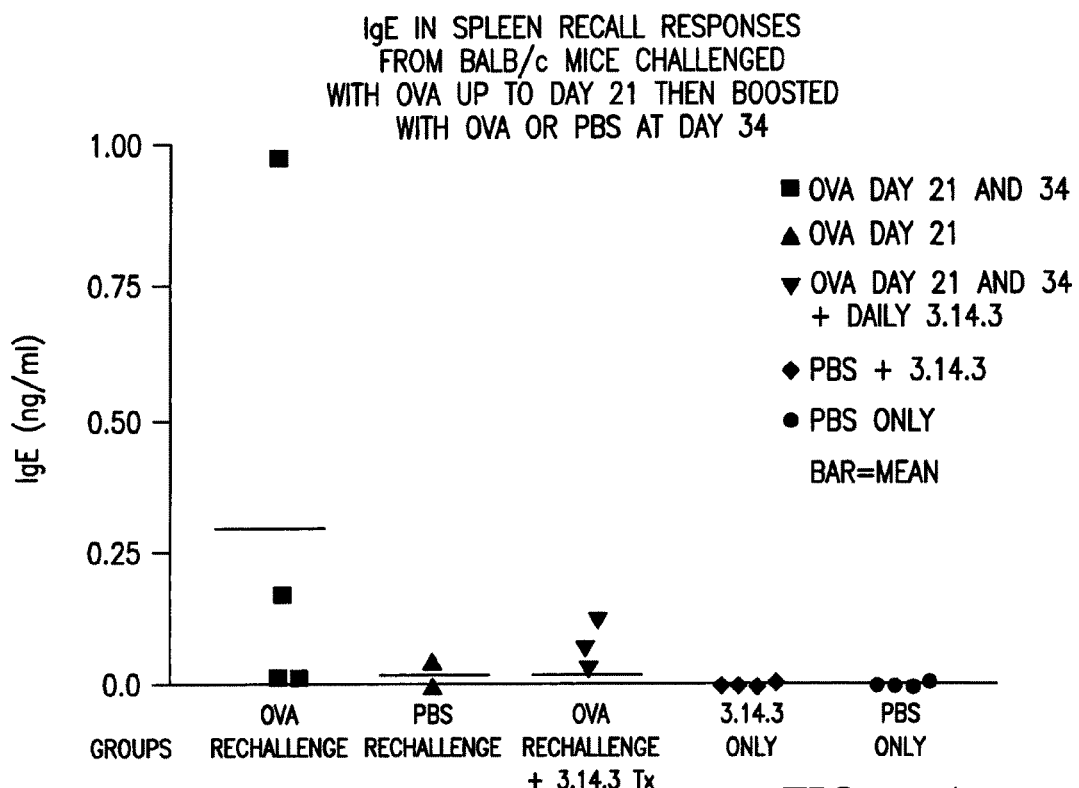
FIG. 29 shows IgE and total IgM and IgG in spleen recall responses in unchallenged and ovalbumin-challenged mice administered CRD-Leu$_4$Ile$_{11}$Cys$_{13}$ peptide 3(3-12)[MCP-1]. A) IgE, and B) total IgG and IgM.
Figure 29B:
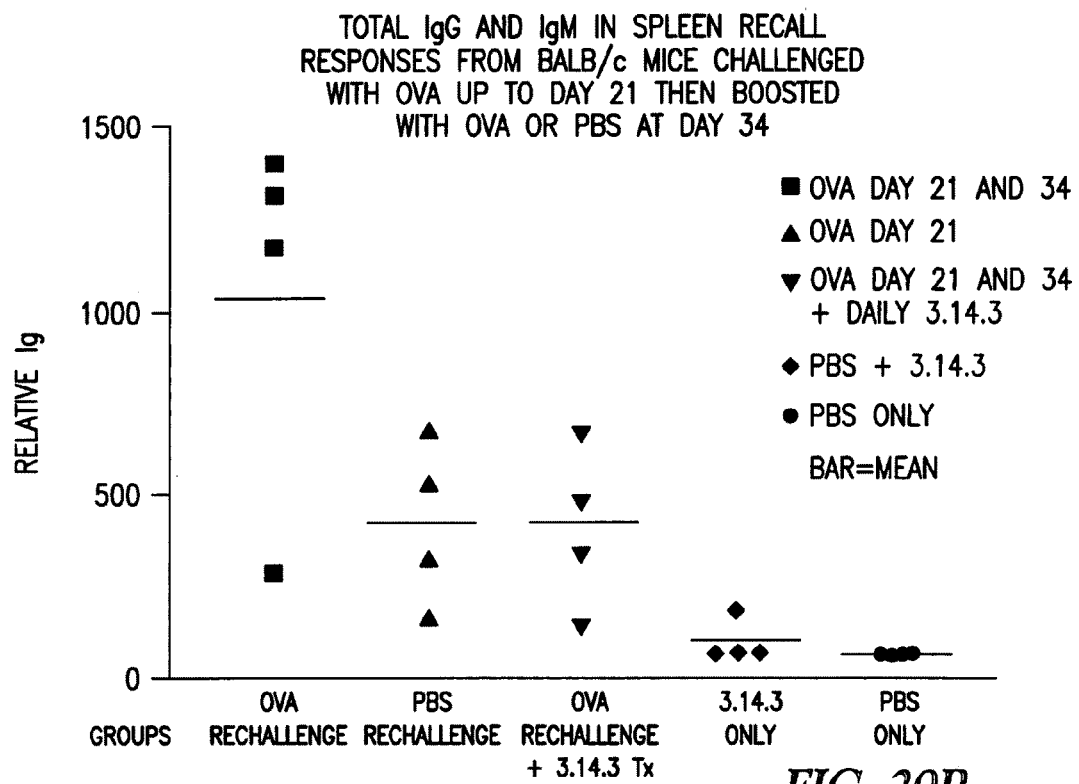
Figure 38:
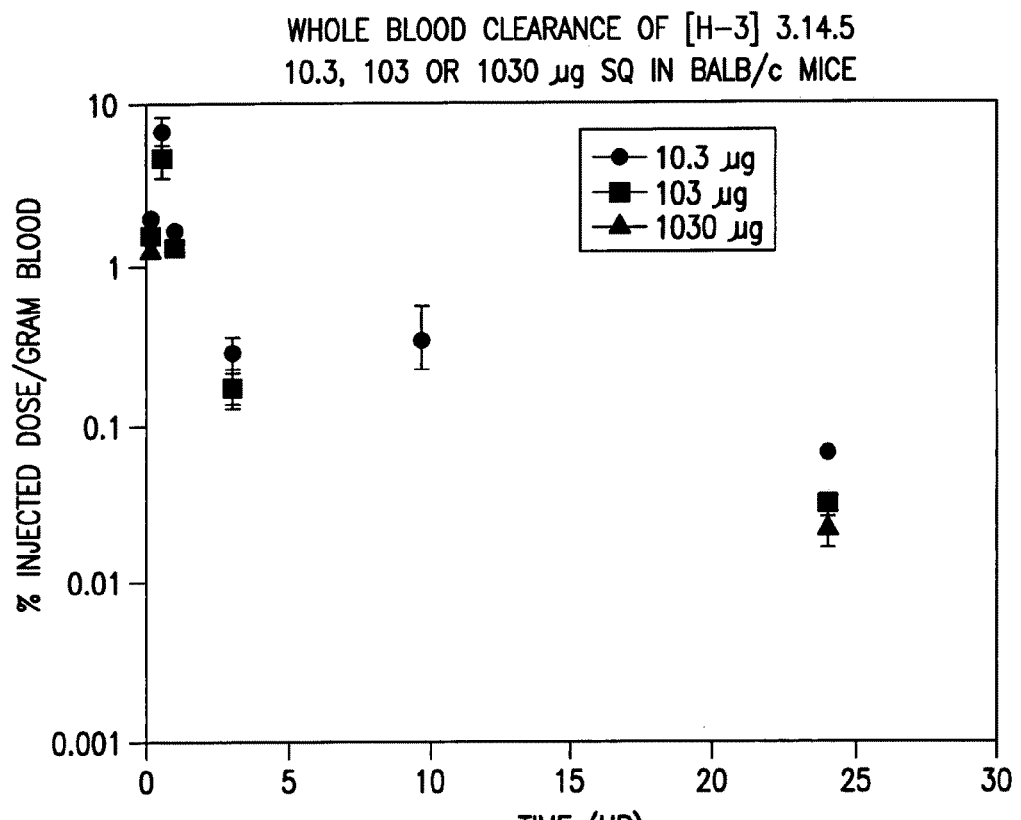
FIG. 38 shows whole blood clearance over time after a single subcutaneous bolus dose of either 10.3, 103 or 1030 µg $^3$H-CRD-L-Leu$_4$Ile$_{11}$Cys$_{13}$ peptide 3(3-12)[MCP-1]. Values are represented as % of the injected dose per gram of blood.

In those mice treated with only a single dose of CRD-Leu$_4$Ile$_{11}$Cys$_{13}$ peptide 3(3-12)[MCP-1] prior to challenge with OVA on day 21, and sacrificed on day 21, there was no significant reduction of total cells in the lungs (FIG. 29 D). However, following stimulation of splenocytes with OVA, there was significantly (p<0.05) reduced IL-4 and IgE levels compare to PBS treated mice (FIGS. 29E and 38).

This established that CRD-Leu$_4$Ile$_{11}$Cys$_{13}$ peptide 3(3-12) [MCP-1], when delivered daily for 2 weeks to mice with an established asthma phenotype, caused regression of the pulmonary inflammation. In addition, upon re-challenge with OVA the CRD-Leu$_4$Ile$_{11}$Cys$_{13}$ peptide 3(3-12)[MCP-1] treated mice had reduced trafficking of macrophages, B cells, and CD4+ T cells into the lungs, suggesting that treatment blocked recurrence of inflammation to the site of antigen exposure. More significantly, CRD-Leu$_4$Ile$_{11}$Cys$_{13}$ peptide 3(3-12)[MCP-1] reduced serum IgE antibody levels, and IL-4 levels in supernatants from spleen recall cultures. There was also a striking reduction of total IgG and IgM antibody produced in splenocyte cultures.

TABLE 7

Total IgM + IgG (1 week splenocyte cultures)

| Group | | μg/ml Ova | m1 | m2 | m3 | m4 | Avg. | STDEV |
|---|---|---|---|---|---|---|---|---|
| 1 | Ova on days 8, 15, 18, 21 | 0 | 26.92 | 758.47 | 49.74 | 538.73 | 343.46 | 363.70 |
| 1 | PBS treat 1 × day 21 | 5 | 357.56 | 21.08 | ND | ND | 150.46 | 237/93 |
| 1 | sacrifice day 21 | 50 | 71.72 | 55.4 | 142.98 | 46.54 | 79.16 | 43.80 |
| 2 | Ova on days 8, 15, 18, 21 | 0 | 108.00 | 24.97 | 40.65 | 56.17 | 57.45 | 36.03 |
| 2 | CRD-Leu$_4$Ile$_{11}$Cys$_{13}$ peptide | 5 | 254.36 | 46.56 | ND | ND | 150.46 | 146.94 |

TABLE 7-continued

| | Total IgM + IgG (1 week splenocyte cultures) | | | | | | | |
|---|---|---|---|---|---|---|---|---|
| 2 | 3(3-12)[MCP-1] treat 1 × day 21 sacrifice day 21 | 50 | 137.57 | 176.41 | 331.79 | 321.23 | 241.75 | 99.24 |
| 3 A + B | Ova on days 8, 15, 18, 21 & 35 | 0 | 20.19 | 66.09 | 12.48 | 18.97 | 29.43 | 24.67 |
| 3 A + B | PBS treat BID 14 days | 5 | 1145.29 | 1099.18 | 278.52 | 425.36 | 737.09 | 449.15 |
| 3 A + B | sacrifice day 35 (recent Ova challenge) | 50 | 1424.09 | 1341.16 | 289.83 | 1191.84 | 1061.73 | 523.50 |

| Group | | µg/ml Ova | m9 | m10 | m11 | m12 | Avg. | STDEV |
|---|---|---|---|---|---|---|---|---|
| 3 C + D | Ova on days 8, 15, 18, 21 | 0 | 20.26 | 24.73 | 13.32 | 24.89 | 20.80 | 5.43 |
| 3 C + D | PBS treat BID 14 days | 5 | 158.69 | 182.09 | 206.16 | 145.68 | 173.15 | 26.67 |
| 3 C + D | sacrifice day 34 (No recent Ova challenge) | 50 | 333.07 | 688.18 | 521.93 | 177.71 | 430.22 | 222.22 |

| Group | | µg/ml Ova | m1 | m2 | m3 | m4 | Avg. | STDEV |
|---|---|---|---|---|---|---|---|---|
| 4 | Ova on days 8, 15, 18, 21 & 35 | 0 | 15.32 | 25.86 | 14.87 | 12.60 | 17.16 | 5.92 |
| 4 | CRD-Leu$_4$Ile$_{11}$Cys$_{13}$ peptide 3(3-12)[MCP] treat BID 14 days | 5 | 189.07 | 249.75 | 148.16 | 68.83 | 163.95 | 75.92 |
| 4 | sacrifice day 35 (recent Ova challenge) | 50 | 338.50 | 679.86 | 487.87 | 161.20 | 416.86 | 220.39 |
| 5 | PBS on days 8, 15, 18, 21 | 0 | 26.54 | 15.44 | 21.35 | 16.89 | 20.05 | 5.00 |
| 5 | CRD-Leu$_4$Ile$_{11}$Cys$_{13}$ peptide 3(3-12)[MCP-1] treat BID 14 days | 5 | 64.20 | 31.21 | 67.94 | 49.53 | 53.22 | 16.69 |
| 5 | sacrifice day 34 (No recent Ova challenge) | 50 | 86.16 | 80.04 | 189.70 | 89.74 | 111.41 | 52.35 |
| 6 | No Ova stim. | 0 | 10.74 | 14.80 | | | 12.77 | 2.87 |
| 6 | PBS treat BID 14 days | 5 | ND | ND | | | | |
| 6 | sacrifice day 35 | 50 | 75.09 | 77.64 | | | 76.36 | 1.80 |

TABLE 8

| | IL-4 Assays | | | | | | |
|---|---|---|---|---|---|---|---|
| | | | | µg/ml IL-4 | | | |
| Group | | pg/ml Ova | m1 | mn2 | m3 | m4 | Avg. of Group |
| 1 | Ova on days 8, 15, 18, 21 | 0 | 4.90 | 1.30 | 3.40 | 12.60 | 6.08 |
| 1 | PBS treat 1× day 21 | 5 | 16.30 | 23.30 | ND | ND | 19.80 |
| 1 | sacrifice day 21 | 50 | 56.70 | 21.30 | 59.70 | 70.10 | 58.20 |

| Group | | µg/ml Ova | m1 | m2 | m3 | m4 | Avg. of Group |
|---|---|---|---|---|---|---|---|
| 2 | Ova on days 8, 15, 18, 21 | 0 | 2.81 | 5.60 | 0.25 | 0.45 | 2.89 |
| 2 | CRD-Leu$_4$Ile$_{11}$Cys$_{13}$ peptide 3(3-12)[MCP-1] treat 1× day 21 | 5 | 3.18 | 8.55 | ND | ND | 5.86 |
| 2 | sacrifice day 21 | 50 | 7.10 | 11.46 | 19.15 | 75.36 | 12.57 |

| Group | | µg/ml Ova | m1 | m2 | m3 | m4 | Avg. of Group |
|---|---|---|---|---|---|---|---|
| 3 A+B | Ova on days 8, 15, 18, 21 & 35 | 0 | 2.87 | 4.71 | 2.01 | 3.18 | 3.19 |
| 3 A+B | PBS treat BID 14 days | 5 | 31.33 | 49.16 | 15.69 | 22.03 | 29.55 |
| 3 A+B | sacrifice day 35 (recent Ova challenge) | 50 | 51.96 | 76.72 | 52.41 | 46.58 | 50.84 |

| Group | | µg/ml Ova | m9 | m10 | m11 | m12 | Avg. of Group |
|---|---|---|---|---|---|---|---|
| 3 C+D | Ova on days 8, 15, 18, 21 | 0 | 5.90 | 5.15 | 0.87 | 3.52 | 3.86 |
| 3 C+D | PBS treat BID 14 days | 5 | 16.10 | 7.55 | 7.80 | 6.04 | 9.37 |
| 3 C+D | sacrifice day 34 (No recent Ova challenge) | 50 | 18.46 | 17.23 | 11.17 | 14.80 | 15.42 |

| Group | | µg/ml Ova | m1 | m2 | m3 | m4 | Avg. of Group |
|---|---|---|---|---|---|---|---|
| 4 | Ova on days 8, 15, 18, 21 & 35 | 0 | 2.61 | 1.11 | 5.08 | 2.88 | 2.92 |
| 4 | CRD-Leu$_4$Ile$_{11}$Cys$_{13}$ peptide 3(3-12)[MCP-1] treat BID 14 days | 5 | 10.40 | 12.77 | 4.59 | 4.45 | 8.05 |
| 4 | sacrifice day 35 (recent Ova challenge) | 50 | 14.38 | 22.08 | 10.25 | 11.09 | 14.45 |

TABLE 8-continued

IL-4 Assays

μg/ml IL-4

| Group | | μg/ml Ova | m1 | m2 | m3 | m4 | Avg. of Group |
|---|---|---|---|---|---|---|---|
| 5 | Ova on days 8, 15, 18, 21 | 0 | 9.09 | 3.80 | 12.89 | 6.42 | 8.05 |
| 5 | CRD-Leu$_4$Ile$_{11}$Cys$_{13}$ peptide 3(3-12)[MCP-1] treat BID 14 days | 5 | 5.70 | 4.43 | 10.09 | 5.10 | 6.33 |
| 5 | sacrifice day 34 (No recent Ova challenge) | 50 | 7.02 | 6.10 | 4.74 | 4.59 | 5.61 |

| Group | | μg/ml Ova | m1 | m2 | m3 | m4 | Avg. of Group |
|---|---|---|---|---|---|---|---|
| 6 | No Ova stim. | 0 | 1.57 | 1.88 | 1.48 | 2.34 | 1.81 |
| 6 | PBS treat BID 14 days | 5 | 4.91 | 3.61 | 5.22 | 3.26 | 4.25 |
| 6 | sacrifice day 35 | 50 | 3.83 | 4.88 | 3.32 | 4.39 | 4.10 |

TABLE 9

Total IgE (Serum)

| | m1 | m2 | m3 | m4 | Avg. | ng/ml IgE (4 × avg.) |
|---|---|---|---|---|---|---|
| Group 1 | 1.317 | 1.812 | 1.425 | 2.419 | 1.743 | 6.973 |
| Group 2 | 1.952 | 1.132 | 2.073 | 0.863 | 1.505 | 6.020 |
| Group 3 A, B | 1.419 | 0.881 | 1.477 | 1.295 | 1.268 | 5.072 |
| Group 3 C, D | 1.487 | 2.614 | 1.519 | 1.460 | 1.770 | 7.080 |
| Group 4 | 0.310 | 0.298 | 0.984 | 0.890 | 0.621 | 2.482 |
| Group 5 | 0.625 | 1.870 | 0.838 | 1.073 | 1.102 | 4.406 |
| Group 6 | 1.228 | 0.552 | 0.564 | 0.654 | 0.750 | 2.998 |

TABLE 10

Total IgE (1 week splenocyte cultures)

| Group | | μg/ml Ova | m1 | m2 | m3 | m4 | Avg. | ng/ml (=4) |
|---|---|---|---|---|---|---|---|---|
| 1 | Ova on day | 0 | 0.191 | 0.007 | 0.000 | 0.000 | 0.050 | 0.198 |
| 1 | PBS treat | 5 | 0.161 | 0.000 | ND | ND | 0.081 | 0.322 |
| 1 | sacrifice day | 50 | 0.122 | 0.005 | 0.012 | 0.029 | 0.042 | 0.168 |

| Group | | μg/ml Ova | m1 | m2 | m3 | m4 | Avg. | ng/ml |
|---|---|---|---|---|---|---|---|---|
| 2 | Ova on day | 0 | 0.000 | 0.051 | 0.007 | 0.009 | 0.017 | 0.067 |
| 2 | CRD-Leu$_4$Ile$_{11}$Cys$_{13}$ peptide 3(3-12)[MCP-1] | 5 | 0.041 | 0.023 | ND | ND | 0.032 | 0.128 |
| 2 | sacrifice day | 50 | 0.011 | 0.002 | 0.004 | 0.007 | 0.006 | 0.024 |
| 3 A + B | Ova on day | 0 | 0.022 | 0.034 | 0.009 | 0.007 | 0.018 | 0.072 |
| 3 A + B | PBS treat | 5 | 0.074 | 0.165 | 0.041 | 0.013 | 0.073 | 0.293 |
| 3 A + B | sacrifice day (recent Ova challenge) | 50 | 0.098 | 0.175 | 0.010 | 0.011 | 0.074 | 0.294 |

| Group | | μg/ml Ova | m9 | m10 | m11 | m12 | Avg. | ng/ml |
|---|---|---|---|---|---|---|---|---|
| 3 C + D | Ova on day | 0 | 0.009 | 0.000 | 0.000 | 0.030 | 0.010 | 0.039 |
| 3 C + D | PBS treat | 5 | 0.000 | 0.000 | 0.000 | 0.031 | 0.008 | 0.031 |
| 3 C + D | sacrifice day (No recent Ova challenge) | 50 | 0.008 | 0.000 | 0.054 | 0.009 | 0.018 | 0.071 |

| Group | | μg/ml Ova | m1 | m2 | m3 | m4 | Avg. | ng/ml |
|---|---|---|---|---|---|---|---|---|
| 4 | Ova on day | 0 | 0.008 | 0.001 | 0.015 | 0.002 | 0.007 | 0.026 |
| 4 | CRD-Leu$_4$Ile$_{11}$Cys$_{13}$ peptide 3(3-12)[MCP-1] | 5 | 0.009 | 0.047 | 0.009 | 0.031 | 0.024 | 0.096 |
| 4 | sacrifice day (recent Ova challenge) | 50 | 0.013 | 0.043 | 0.008 | 0.018 | 0.021 | 0.082 |
| 5 | Ova on day | 0 | 0.008 | 0.033 | 0.000 | 0.024 | 0.016 | 0.065 |
| 5 | CRD-Leu$_4$Ile$_{11}$Cys$_{13}$ peptide 3(3-12)[MCP-1] | 5 | 0.003 | 0.065 | 0.000 | 0.014 | 0.021 | 0.082 |
| 5 | sacrifice day (No recent Ova challenge) | 50 | 0.000 | 0.020 | 0.000 | 0.001 | 0.005 | 0.021 |
| 6 | No Ova stim. | 0 | 0.000 | 0.014 | 0.004 | lost | 0.006 | 0.024 |
| 6 | PBS treat | 5 | 0.000 | 0.001 | lost | lost | 0.001 | 0.002 |
| 6 | sacrifice day | 50 | 0.004 | 0.007 | lost | lost | 0.006 | 0.022 |

Cynomolgus monkeys were immunized with antigen that is a single chain Fv (scFv) protein. Each animal previously received 3 i.v. injections of the antigen and all developed high serum titers. Five animals were randomly divided into 2 groups. Two animals served as PBS treated controls and 3 were treated i.v. with 50 mg/kg CRD-Leu$_4$Ile$_{11}$Cys$_{13}$ peptide 3(3-12)[MCP-1]. Thirty minutes following CRD-Leu$_4$Ile$_{11}$Cys$_{13}$ peptide 3(3-12)[MCP-1] treatment all animals were challenged i.v. with 3.5 mg/kg antigen. In addition, animals were challenged intradermal with each of the following in a volume of 50 μl:PBS; 50 μg antigen; 5 μg antigen; 0.5 μg antigen; 500 ng MCP-1; or 50 ng LPS. Serum was collected at 10 minutes, 30 minutes, 60 minutes, 4 hours, and 24 hours. Animals were sacrificed 24 hours after CRD-$Leu_4Ile_{11}Cys_{13}$ peptide 3(3-12)[MCP-1] injection and complete necropsy performed and tissues fixed for histopathology. Fixed and frozen skin samples were harvested for histopathology and immunohistochemistry. Blood, spleen, and lymph node were harvested for assessment of cell function in migration assay, proliferation assay, and antigen specific antibody and cytokine recall. Blood was also analyzed pre- and post-CRD-$Leu_4Ile_{11}Cys_{13}$ peptide 3(3-12)[MCP-1] injection for hematology parameters and serum chemistry. Serum levels were evaluated by an LC-MS method (limit of quantitation=1 μg/ml) pre-treatment and then at 10 minutes, 30 minutes, 60 minutes, 4 hours and 20-24 hours after injection. Urinalysis was performed pre- and post-CRD-$Leu_4Ile_{11}Cys_{13}$ peptide 3(3-12)[MCP-1] injection.

Compared to PBS treated controls (animal numbers 137 and 144), all three monkeys treated with a single dose of CRD-$Leu_4Ile_{11}Cys_{13}$ peptide 3(3-12)[MCP-1] (animal numbers 138, 141, and 143) had the lowest detectable levels of antigen specific antibody in recall responses of splenocytes, lymph node cells, and peripheral blood lymphocytes (PBL's from one of the positive control animals was not evaluated due to insufficient cell numbers for culturing) (FIG. 33). IL-4 was detected in a single animal (#144) which was one of the PBS treated controls. In the migration assay and the proliferation assay, there was no consistent responder vs non-responder animals. Intradermal injection sites were evaluated histologically, however, there was no inflammatory response to the 2 positive controls (MCP-1 or LPS) so no further analysis was performed on these samples. No clinically significant changes were noted in the hematology results in any animal. No clinically significant changes were noted in the serum chemistry profiles following treatment with CRD-$Leu_4Ile_{11}Cys_{13}$ peptide 3(3-12)[MCP-1]. The levels of CRD-$Leu_4Ile_{11}Cys_{13}$ peptide 3(3-12)[MCP-1] in the serum were measured using LC-MS. No CRD-$Leu_4Ile_{11}Cys_{13}$ peptide 3(3-12)[MCP-1] was detected in monkeys administered PBS, while CRD-$Leu_4Ile_{11}Cys_{13}$ peptide 3(3-12)[MCP-1] was detected in monkeys administered 50 mg/kg CRD-$Leu_4Ile_{11}Cys_{13}$ peptide 3(3-12)[MCP-1]. Urine PH was decreased, and specific gravity increased in some animals in both groups following treatment. There was a small amount of protein in the urine of all three animals treated with CRD-$Leu_4Ile_{11}Cys_{13}$ peptide 3(3-12)[MCP-1]. Some animals in both groups had ketones in the urine. All three treated animals had detectable drug levels for the first 4 hours after treatment (FIG. 41). By 20-24 hours, drug levels had fallen below the level of quantitation (<1 μg/ml).

This study established that CRD-$Leu_4Ile_{11}Cys_{13}$ peptide 3(3-12)[MCP-1], when delivered in a single dose, resulted in reduced antigen specific antibody response in splenocyte, lymph node, and peripheral blood lymphocyte recall responses. There was no consistent response of lack of response in the other assays performed. Small sample size prevents statistical analysis. It is unknown why an intradermal inflammatory response was not invoked at the site of agonist challenge. Thus, a single dose of CRD-$Leu_4Ile_{11}Cys_{13}$ peptide 3(3-12)[MCP-1] prevents antigen specific antibody responses when measured in a recall response in 2 different species.

The data also indicated that CRD-$Leu_4Ile_{11}Cys_{13}$ peptide 3(3-12)[MCP-1] causes regression of established inflammatory responses, thus indicating that chemokine inhibition also results in the reduction of T and B lymphocyte recall responses. T lymphocyte recall responses were measured by the assessment of IL-4 production by cells stimulated with ovalbumin. B lymphocyte recall responses were measured by the assessment of immunoglobulin production by cells stimulated with ovalbumin. In both cases, a single dose of CRD-$Leu_4Ile_{11}Cys_{13}$ peptide 3(3-12)[MCP-1] in vivo resulted in a statistically significant reduction in the ability of the cells to produce IL-4, IgG+IgM or IgE in response to antigen challenge.

This is the first time a chemokine inhibitor has been shown to inhibit recall responses in B and T cells to a known allergen. This is very important in the treatment of allergic disease and is also very important in autoimmune diseases in which aberrant increases in IL-4 or Ig contribute to the pathophysiology, e.g., asthma, contact hypersensitivity, allergic rhinitis, rheumatoid arthritis, inflammatory bowel disease, as well as diseases that are mediated by aberrant immunoglobulin production or hypergammaglobulinemia, for example, immune-mediated glomerulonephritis, multiple myeloma (particularly patients with Bence Jones proteins (i.e., immunoglobulin in urine), autoimmune hemolytic anemia, myasthenia gravis, Goodpastures syndrome (anti-glomerular basement membrane induced nephritis), autoimmune uveitis, autoimmune thyroiditis, and autoimmune pancreatic islet cell destruction. Further, the agents of the invention may be useful in indications in which an antibody response to an antigen is to be suppressed (e.g., in conjunction with some immunotherapeutic products which have dose-limiting immunogenicity, such as antibody-based products).

Thus, CRD-$Leu_4Ile_{11}Cys_{13}$ peptide 3(3-12)[MCP-1], when delivered IV and subcutaneously, or subcutaneously alone, altered the trafficking of lymphocytes into the lung following exposure to an antigen. More significantly, CRD-$Leu_4Ile_{11}Cys_{13}$ peptide 3(3-12)[MCP-1] reduced the cellular inflammation in the lung, IgE responses and IL-4 concentration in the serum, which are strongly associated with asthma. IgE responses are dependent on a Th2 T cell response, which produces IL-4 and IL-5. Therefore, the observation that CRD-$Leu_4Ile_{11}Cys_{13}$ peptide 3(3-12)[MCP-1] has an effect on reducing IgE upon challenge with OVA strongly indicates that CRD-$Leu_4Ile_{11}Cys_{13}$ peptide 3(3-12)[MCP-1] may reduce IL-4 and IL-5 also.

Example 9

Preferred Tripeptides and Analogs Thereof

Preferred tripeptides of the invention include KXK peptides, where X is one of the twenty naturally occurring amino acids, e.g., KQK and KLK, as well as peptides having KXK. As described below, KXK peptides are anti-inflammatory by two distinct mechanisms. Some KXK peptides are TGF-beta activators and others are chemokine antagonists, and a subset are both (see Table 11).

TABLE 11

| Peptide | TGF-beta Activator | Chemokine antagonist |
| --- | --- | --- |
| KAK | n.d. | + |
| KCK | n.d. | n.d. |
| KDK | − | + |
| KEK | − | + |
| KFK | ++++ | − |
| KGK | − | − |
| KHK | n.d. | n.d. |
| KIK | ++ | ++ |
| KKK | − | ++++ |
| KLK | +++ | ++++ |
| KMK | n.d. | n.d. |
| KNK | n.d. | +++ |
| KPK | n.d. | n.d. |
| KQK | − | +++++ |
| KRK | n.d. | n.d. |
| KSK | − | − |
| KTK | − | − |
| KVK | n.d. | n.d. |
| KWK | − | − |
| KYK | +++++ | − |

To test whether a KXK tripeptide activates TGF-beta, a direct ELISA-type assay can be used. Recombinant human latent TGF-β1 produced in CHO cells (R&D Systems) was incubated with the test activator. For example, 200 ng of latent TGF-β1 (at 20 μg/ml) was incubated with test peptide at 100 nM final concentration at 37° C. for 90 minutes. Following incubation, the TGF-β is incubated with the recombinant extracellular domain of the Type II TGF-β receptor (R2X) which binds only the active and not the latent forms of TGF-β1 (*Clin. Chim. Acta*, 235, 11 (1995)). For example, 1 μg of purified R2X is coated onto a Maxisorp ELISA plate well in 50 μl of 100 mM sodium carbonate for 2 hours at 4° C., and non-specific protein binding then blocked incubation with 5% sucrose 5% Tween-20 in Tris-buffered saline for 1 hour at room temperature.

The TGF-β sample is then incubated with the coated and blocked wells for 2 hours at room temperature with shaking. Wells are washed 3 times quickly with Tris-buffered saline containing 0.05% Tween-20 between each incubation. If any of the latent TGF-β1 has been activated by the incubation with test peptide, it is captured by the R2X, while remaining latent TGF-β1 is washed away. Captured active TGF-β1 is then detected by incubation with a suitable detection agent, such as a peroxidase conjugated polyclonal anti-TGF-beta antibody. For example, the wells are incubated with 200 μl of BDA19 chicken anti-TGF-β1 antibody coupled to horseradish peroxidase for 90 minutes at room temperature with shaking. Any bound peroxidase is then detected using a suitable chromogenic substrate (e.g., K-BLUE TMB substrate solution). The amount of active TGF-β generated is estimated by interpolation of a standard curve constructed using known amounts of active TGF-β1 (R&D Systems).

Chemokine antagonist activity may be determined using the THP-1 transwell migration assay described above in which the peptide is incubated in the top compartment with the cells while a chemokine is used as a chemoattractant in the lower compartment. Four chemokines were tested: IL-8; SDF-1α; MCP-1 and MIP1α: pluses in Table 11 indicate that the peptide was active as an inhibitor of migration induced by at least one of these four chemoattractant chemokines. The number of pluses is a qualitative indicating of the activity of each peptide in each assay. A minus indicates no detectable activity in the assay, and n.d. indicates that no attempt to estimate the activity of the given peptide in this assay has been made to date.

KFK was as active as RFK (Schultz-Chemy et al., *J. Biol. Chem.*, 270, 7304 (1995)). However, in marked contrast to previous reports, other members of the KXK series were also active as TGF-β activators. For example, the KYK was more active than KFK. Thus, the substitution of arginine for lysine increases the range of amino acids at position 2 which activate TGF-β.

KLK and KIK are of particular interest, since these agents are dual-action anti-inflammatory molecules. These tripeptides are specific antagonists of the SDF-1α receptor CXCR4, and also activate TGF-β. Thus, KLK, KIK and their analogs and derivatives are therefore likely to be particular useful pharmaceutical agents for the prevention or treatment of a wide range of anti-inflammatory disorders.

For graft eosinophilia, such as that associated with acute transplant rejection, a pan-chemokine inhibitor, or a selective inhibitor of eosinophil recruitment (such as KKK or an analog thereof), may be particularly beneficial. Such agents may be used alone or in conjunction with lower than normal doses of steroids, such as prednisolone, which are used currently to control acute rejection episodes. Severe side-effects are associated with the use of the highest dose of prednisolone (or other steroids) used during acute rejection, and use of agents which reduce or abolish the need to give steroids would be particularly useful.

Analogs of the KXK peptides, e.g., analogs of KQK, are also envisioned. The central chain (in a compound of formula V with R7 as a substituent) is replaced by a general substituent R, where R is the side chain from any of the amino acids. These analogs (for example, the general class of fluoroalkenes of a compound of formula (VI),) are useful for the treatment of a wide variety of diseases where activation of TGF-β and/or inhibition of chemokine signaling are desired. By selecting an appropriate member of this class of molecules, it is possible to engineer the desired properties of the molecule. Thus, selection of KYK analogs provides powerful activation of TGF-β in the absence of chemokine inhibition, while analogs of KLK have both properties. Analogs of KQK have inhibitory action on one or more chemokine receptors but do not activate TGF-β.

Thus, KYK, its analogs, and derivatives may be selected for use in diseases where TGF-β upregulation is particularly beneficial, for example, in atherosclerosis or osteoporosis. In contrast, analogs of KQK may be selected where chemokine inhibition is desired but TGF-β upregulation may not be beneficial, for example, in treatment of HIV infection.

The KXK peptides, and isosteres thereof, may be useful to treat low bone mineral density, where TGF-beta elevation and selective inhibition of MCP-1 are likely to be especially synergistic.

Derivatives or analogs of the KXK class may be used alone or in combination with other therapies for the treatment of inflammatory disorders, or other diseases or indications such as those described herein. For example, derivatives, or analogs of KYK may be used in conjunction with steroids for the treatment of inflammatory conditions, allowing lower than normal doses of steroids to be used reducing the side effects associated with chronic steroid use.

It is also envisioned that conservative substitutions of the amino acids at positions 1 and 3 do not affect the activities of the molecules. Thus, one or both of the lysine side chains (either in a peptide or in an analog such as (VI)) may be substituted with an arginyl side chain or an omithinyl side chain.

Example 10

Binding Affinity of the Agents of the Invention

It is also envisioned that moieties other than those exemplified, including analogs of chemokine peptide 2 or 3, variants or derivatives thereof, which bind to DARC and/or chemokine receptors with a specific affinity, e.g., they bind to functional chemokine receptors with high affinity but bind with lower affinity to DARC or bind to DARC with a high affinity but bind to chemokine receptors with lower affinity, may be identified using methods such as those described above. Moreover, the agents of the invention may be useful in functional mapping of chemokine receptors. For example, both chemokine peptide 2 and peptide 3 block binding of the natural chemokine ligands in a competitive manner. However, they do not block binding of one another suggesting that they bind to distinct regions of the receptor and that both of these regions are important for binding of the natural ligand. In addition, peptide 2 is further distinguished from peptide 3 in their differential functional activity. Peptide 3 not only binds to the receptor but also blocks the functional activity of receptor signaling as indicated by inhibition of chemotaxis. Peptide 2 does not inhibit chemotaxis. Thus, these peptides together are particularly useful in identifying regions of chemokine receptors that are important in different functional activities. Once these regions are identified, they can be used to screen combinatorial libraries or compound banks for specific inhibitors to distinct chemokine functions that may be structurally unrelated to the starting compounds, but are functionally related.

In addition, it may be important for chemokines to form dimers to activate the receptor of interest. The peptides of the invention lack the amino terminal domains that are thought to be important for chemokine dimer formation. If dimer formation is required for cell signaling, then the agents of the invention may inhibit activation as they can bind to the receptor but are unable to form dimers, e.g., with native chemokine ligand.

Example 11

Peptide 3 Binding Studies

Although a biotinylated peptide 3 derivative was shown to interact with a cell surface molecule on THP-1 cells, peptide 3 did not compete for binding to chemokine receptors in radioligand competition experiments on cell lines expressing cloned chemokine receptors. To determine whether or not peptide 3 binds to chemokine receptors, the THP-1 migration assay was used to assess the inhibitory activity of the biotinylated derivative, and to compare it with the non-labeled version of the same peptide. In addition, a competition ELISA is employed to show whether the labeled peptide contains functional biotin, i.e., whether the biotin is capable of binding streptavidin.

Materials

Iodinated-RANTES and iodinated-MCP-1 (Amersham) were reconstituted in MilliQ water to a concentration of 50 nM (0.1 µCi/µl) with a specific activity of 2000 Ci/mmole. Iodinated-streptavidin was obtained (Amersham) at a stock concentration of 47 nM (0.1 µCi/µl) and a specific activity of 38 µCi/µg (55,000 Da). Cold RANTES and MCP-1 were purchased from R&D Systems (Minneapolis, Minn.), reconstituted in sterile PBS+1 mg/ml fatty acid free BSA (FAF-BSA) (Sigma A-6003) at 10 µg/ml (1.25 mM). Cold streptavidin (Calbiochem) was reconstituted in sterile MilliQ to a concentration of 4 mg/ml (90 µM).

FAF-BSA was used throughout. All experiments were performed in binding medium (50 mM HEPES, 1 mM $CaCl_2$, 1 mM $MgCl_2$, 0.5% FAF-BSA pH 7.5) as described by Ruffing et al. (*Cell. Immunol.*, 189, 160 (1998)) unless stated otherwise. Reactions were all performed at 4° C. and all buffers were pre-cooled to 4° C. unless stated otherwise.

The biotinylated peptide was synthesized as an N-terminal biotin conjugate of the sequence n'-CLDPKQKWIQC-c' (SEQ ID NO:152; Affiniti Research) and confirmed as >90% pure by HPLC. Every molecule has a biotin associated with it. The peptide was reconstituted to 10 mM stock concentration in MilliQ water and stored frozen in small aliquots until required. As a positive control, an N-terminal biotin-labeled derivative of peptide 2(1-15)[MCP-1] was used.

HOS parental cells and CCR1-5 and CXCR4 transformants were obtained from the AIDS Reagent Program and were maintained as described on the supplier data sheet. Selection for the chemokine receptor-expressing plasmid was maintained throughout culture. CHO parental cells and CXCR1 and CXCR2 transformants were obtained form Dr. J. Navarro (Southwestern University, TX, USA) and maintained as described by the supplier under constant selection for expression of the chemokine receptor. All cells were split at about a 1:10 dilution approximately every 4 days, releasing the cells with EDTA solution and reseeding at known density. For experiments, cells were released from the flask with EDTA solution and reseeded into 24 or 12 well plates as described at about $2 \times 10^5$ cells/well ($4.4 \times 10^4$ cells/cm²) 18-24 hours prior to the experiment. At the time of the experiment, all wells were at a nominal density of $3 \times 10^5$ cells/well.

Results

Properties of the Biotinylated Peptide.

Figure 20:
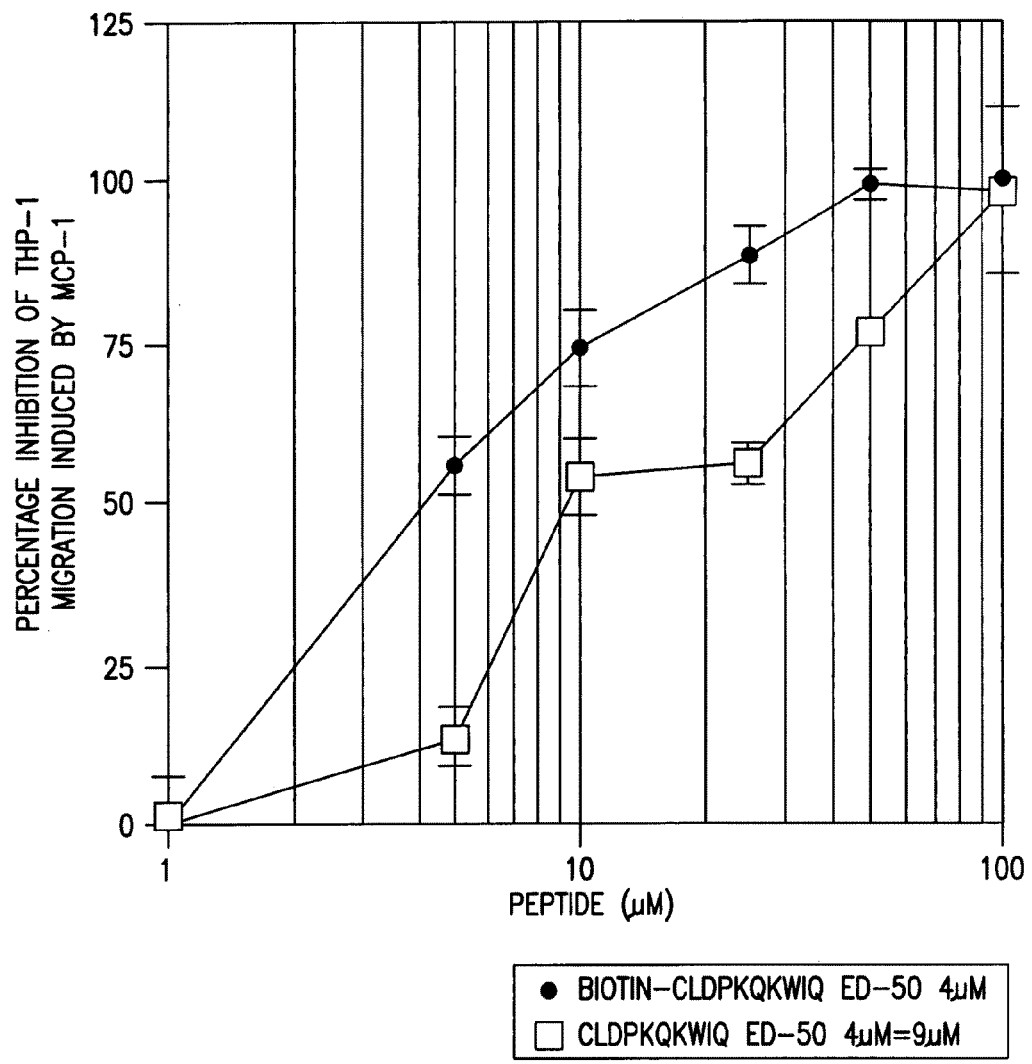
FIG. 20 shows the inhibition of MCP-1 induced migration by peptide 3 and biotinylated peptide 3.

Using that standard THP-1 migration bioassay, the biotinylated peptide was compared to the corresponding unlabeled peptide. The chemokine chemoattractant used was MCP-1 at 100 ng/ml in RPMI 1640+10% FCS. Migration was allowed to occur for 4 hours through a 5 µm filter at 37° C. MCP-1 as the chemoattractant increased the number of cells migrated by almost three fold, and this was inhibited by the presence of the unlabeled peptide in a dose-dependent fashion. The $ED_{50}$ for inhibition was about 9 µM, consistent with previously reported data for this peptide (2-3 µM). The labeled peptide also inhibited MCP-1 induced migration, with a similar $ED_{50}$ (about 4 µM) (FIG. 20). This experiment was repeated twice, and there was no statistically significant difference between the labeled and unlabeled peptides. Thus, the addition of the label did not infer with the function of the molecule.

Figure 21A:
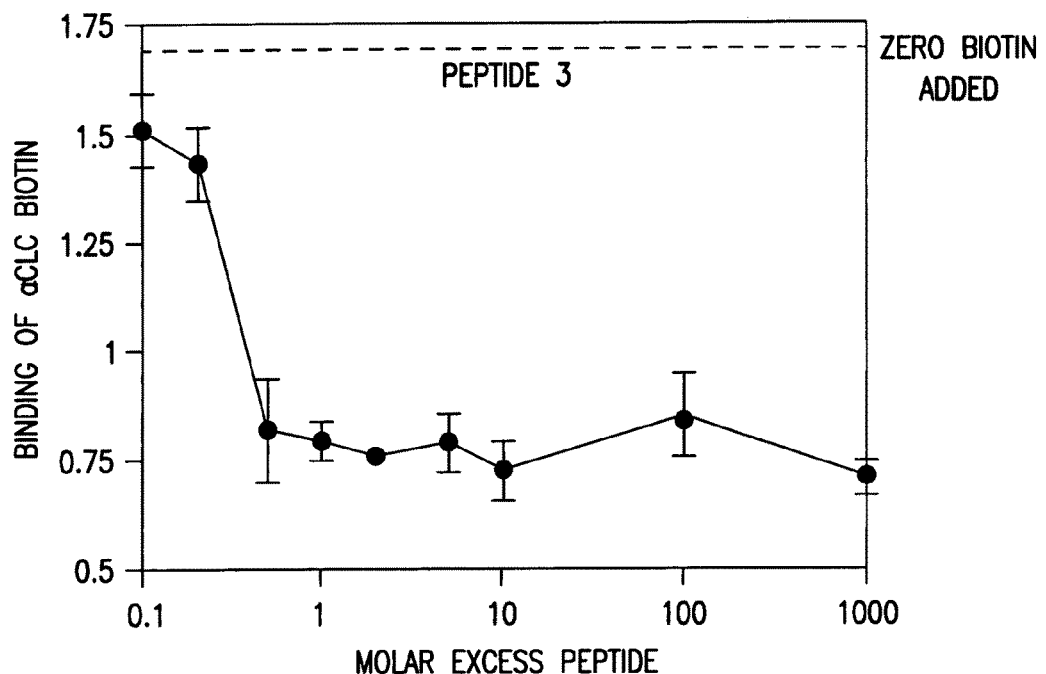
FIG. 21 shows a graph of the inhibition of binding of biotinylated mouse IgG by increasing amounts of labeled peptide 2 and 3.
Figure 21B:
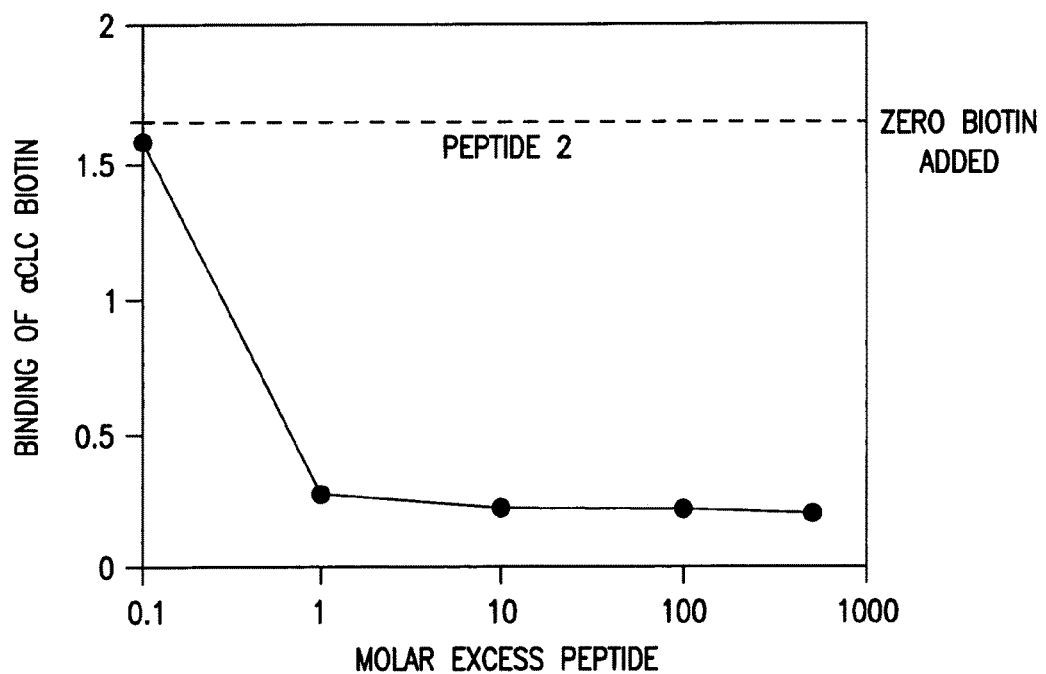

The presence of a biotin moiety in the labeled peptide which was capable of binding streptavidin was confirmed by competition ELISA. Briefly, streptavidin was coated onto ELISA plate wells (Nunc Maxisorp plates) at 10 pmoles per well for 45 minutes in 50 mM sodium carbonate pH 8.5 at 4° C. After blocking (5% sucrose/5% Tween 20 in TBS), the plate was incubated with various concentrations of labeled peptide 3 (between 0.1 and 1,000-fold molar excess over the coated streptavidin) for 1 hour at room temperature. After washing, any residual free streptavidin was detected by adding a biotinylated mouse IgG (which would only bind if any streptavidin had not been blocked by the labeled peptide). Antimouse peroxidase was used to detect the bound mouse IgG. Under the conditions of the reaction, the binding of labeled peptide 3 to the immobilized streptavidin was functionally irreversible. Thus, the concentration of labeled peptide 3 needed to prevent subsequent binding of biotinylated mouse IgG is a measure of the percentage of the peptide 3 molecules with a functional biotin (i.e., one capable of binding to streptavidin) (FIG. 21). The percentage labeling efficiency was estimated to be 100%, consistent with the fact that the biotin had been added co-synthetically.

Characterization of Chemokine-Receptor Over-Expressing Lines

Figure 22A:
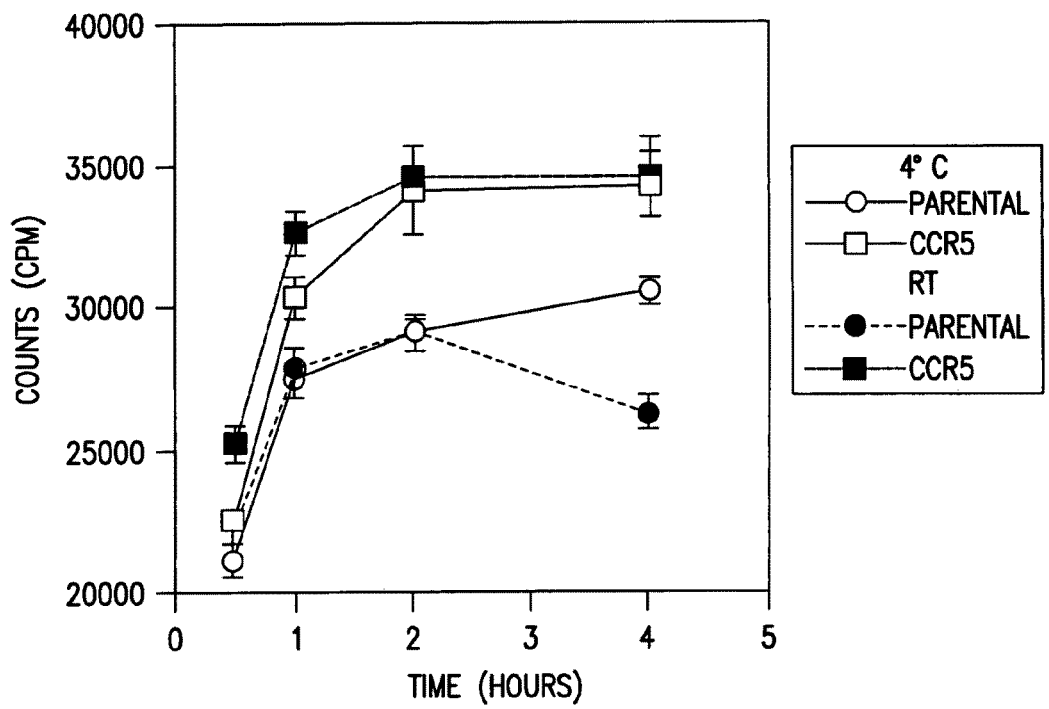
FIG. 22A depicts the equilibrium binding of RANTES to various cells.
Figure 22B:
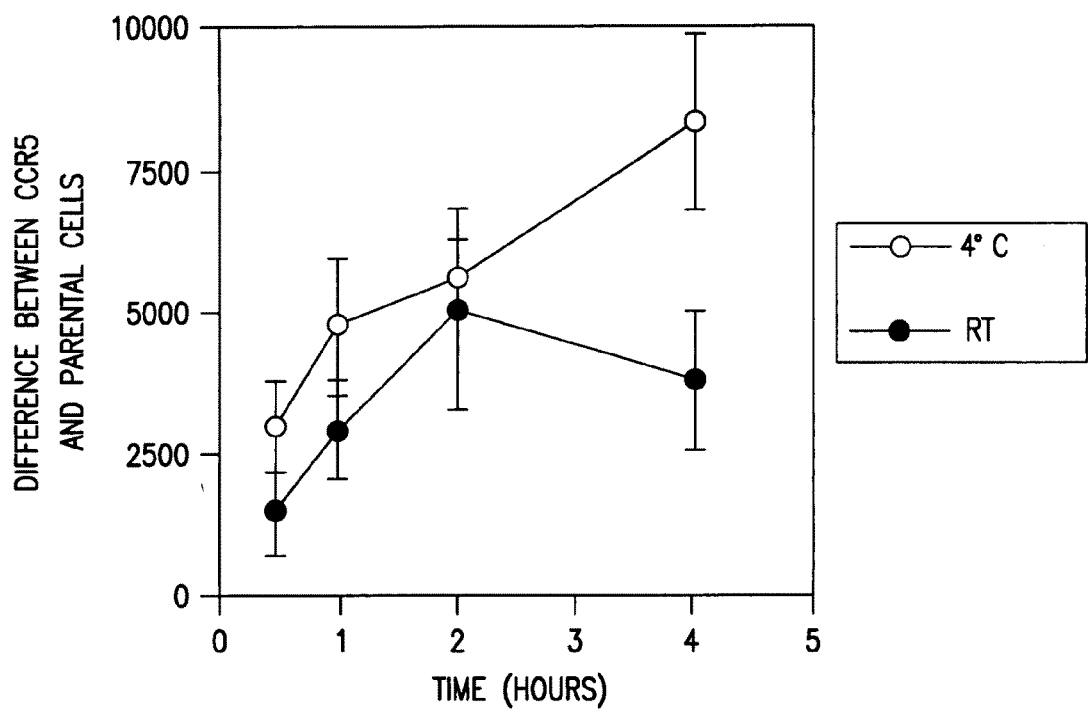
FIG. 22B shows a comparison between the binding of labeled RANTES to various cells in the presence or absence of unlabeled RANTES.
Figure 22C:
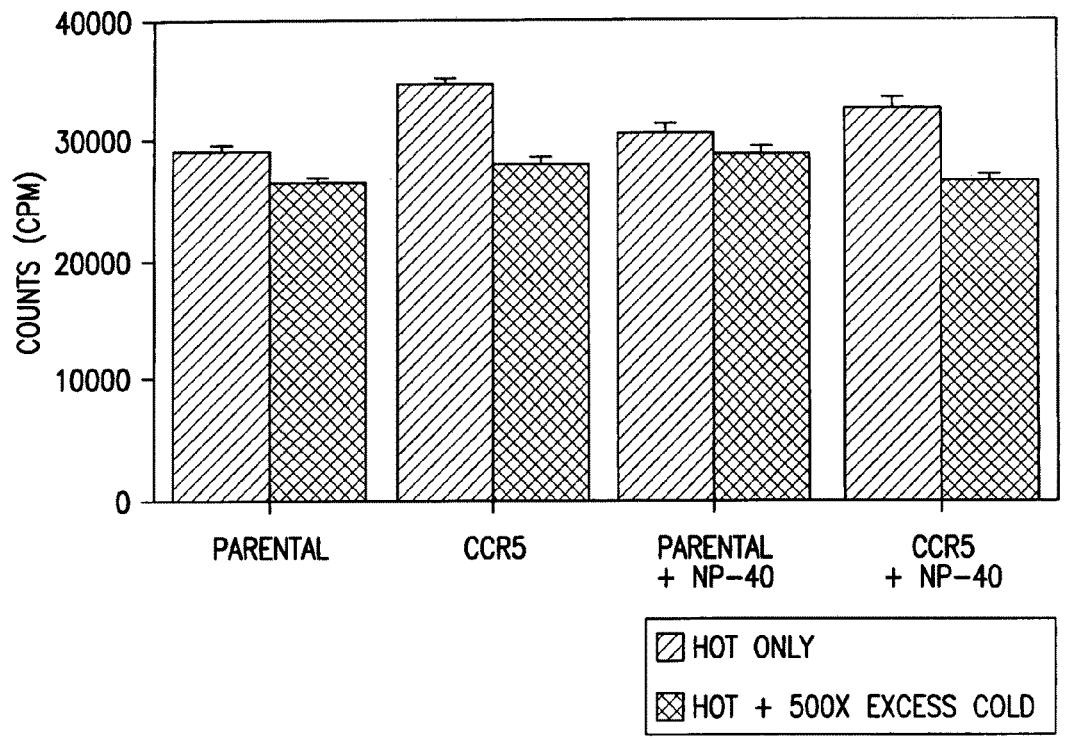

To establish the kinetics of labeled RANTES binding to CCR5, CCR5 cells and their parental line were exposed to labeled RANTES at 0.05 nM in the absence or presence of a 500-fold excess of unlabeled RANTES. Binding was performed at either 4° C. or room temperature for various periods between 30 minutes and 4 hours. All data was collected in triplicate. Equilibrium was achieved slightly quicker at room temperature than 4° C., and that in both cases binding was complete by 2 hours (FIG. 22A). Furthermore, there were significantly more cold-competable the CCR5 cells than the parental line (although the parental line also showed statistically significant high affinity RANTES binding, suggesting a background level of CCR5 receptors on these cells) (FIG. 22B). Based on this experiment, all binding experiments were done at 4° C. for 2 hours.

A Scatchard analysis was performed under the conditions determined to represent equilibrium binding. The purpose of this experiment was to estimate the number of high affinity binding sites (CCR5 receptors) on the cell surface, since the full Scatchard analysis is performed under conditions where the binding was limited by availability of binding sites, not by number of molecules RANTES added. The result indicated about 80,000 binding sites per cell on the parental line and about 200,000-400,000 binding sites per cell on the high expressing CCR5 line. Using this information, the conditions necessary to perform a full 12-point Scatchard analysis at equilibrium, limited by binding site number, were calculated. The conditions chosen were 0.03 nM labeled RANTES in 1.25 ml added to $3 \times 10^5$ cells at 4° C. for 2 hours, in the absence or presence of cold RANTES at concentrations between 0.06 and 25 nM (2-fold to 800-fold excess). The Scatchard analysis was performed on the binding data, using the 800-fold excess as a measure of non-specific binding. It was found that the sites had an affinity of about 1 nM (consistent with the expected properties of the CCR5 receptor; kd=0.4 nM), with 100,000 sites per cell on the parental line and 200,000 sites per cell on the CCR5 over-expressing line. This confirms that the plasmid is causing over-expression of the CCR5 receptor in this cell line.

Figure 23:
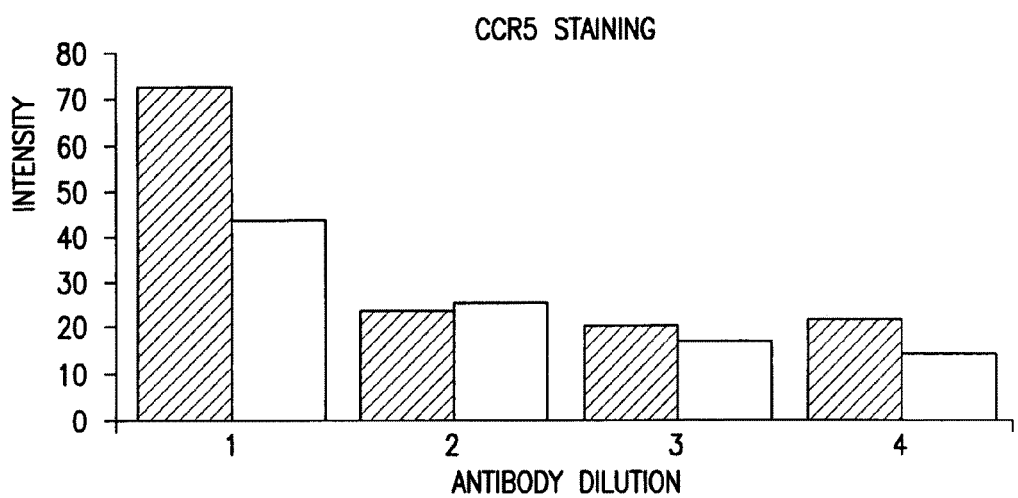
FIG. 23 depicts FITC-anti-CCR5 antibody staining of CCR5 expressing cells.

The presence of CCR5 receptors on the CCR5 over-expressing line was confirmed by immunostaining with a directly labeled (FITC-conjugated) anti-CCR5 antibody (Pharmingen; Clone 2D7). At 10 µg/ml, this antibody gave significantly higher staining that an FITC-labeled IgG control antibody (FIG. 23) confirming the presence of CCR5 protein on the cell surface. At lower dilutions, no significant staining was seen, but in common with many directly labeled antibodies (where there is no amplification step due to multivalent detection antibody binding) this antibody is recommended for use at concentrations around 25 µg/ml. Based on both the functional data and the immunofluorescence data, it is very likely that the CCR5 line is expressing functional CCR5 receptors.

Figure 24A:
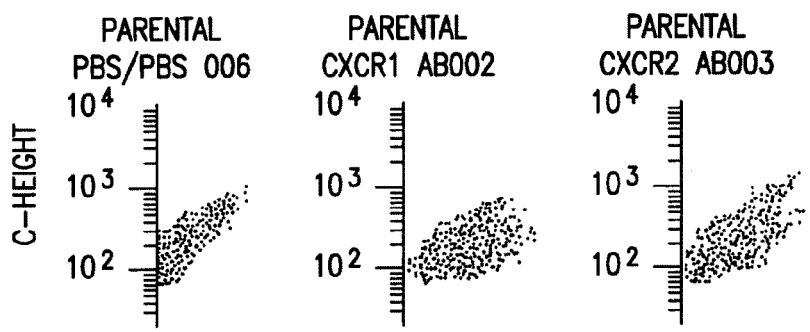
FIG. 24 depicts FITC-anti-CXCR1 antibody and FITC-anti-CXCR2 antibody staining of CXCR1 and CXCR2 expressing cells, respectively.
Figure 24B:
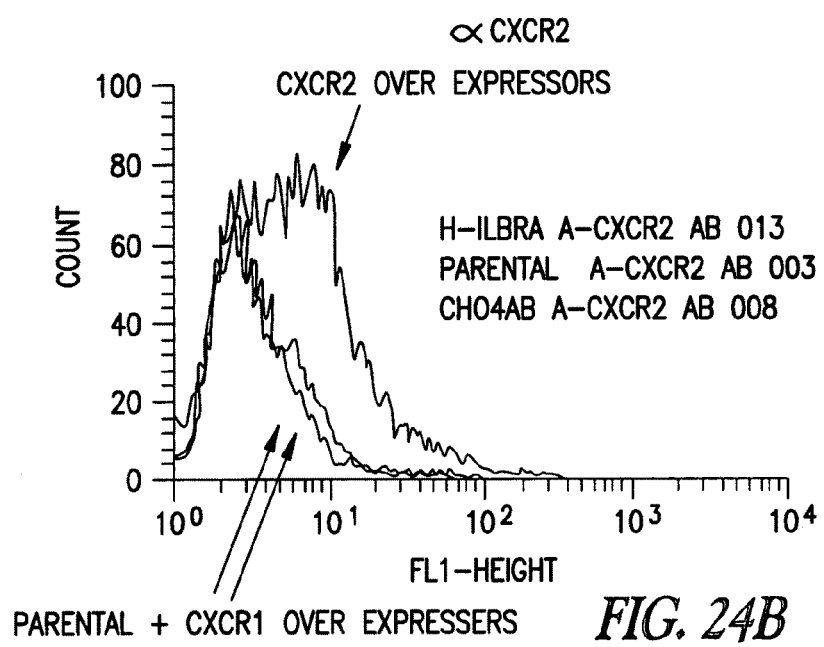
Figure 24C:
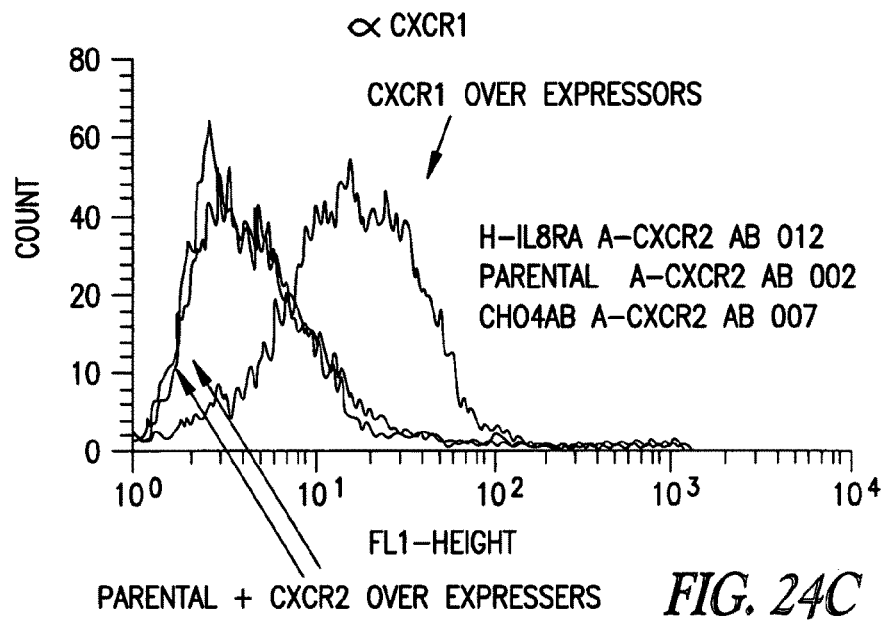

Using CXCR1 and CXCR2 specific antibodies, flow cytometry data indicated that the CXCR1 line expressed CXCR1 but not CXCR2, while the CXCR2 line expressed CXCR2 but not 1 (FIG. 24). As a functional assay for CCR2, an abbreviated Scatchard analysis was performed using radio-iodinated MCP-1 under identical conditions to the full Scatchard analysis using RANTES. No high affinity binding sites were detected on the parental cell line (Ka of highest affinity binding sites >250 nM), or on the CCR-2 over-expressing line. It is likely that the CCR-2 over-expressing line has not maintained the plasmid intact, under as functional MCP-1 binding sites were not detectable.

Binding of Labeled Peptides of the Invention

Figure 25:
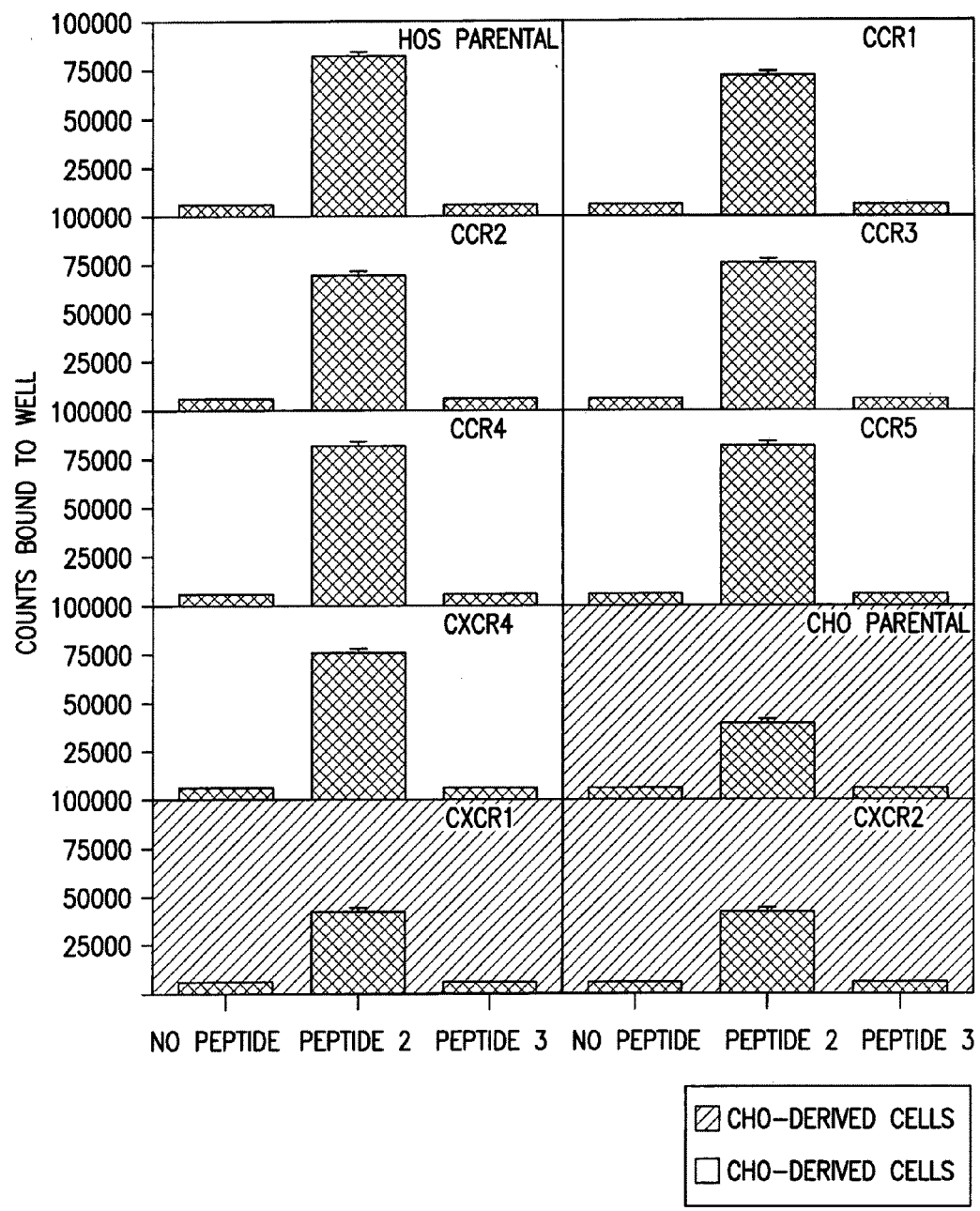
FIG. 25 shows peptide 2 and 3 binding to parent and recombinant chemokine receptor expressing cell lines.

The binding of labeled peptide 2 and labeled peptide 3 to the parental HOS, parental CHO and 8 chemokine receptor expressing lines was compared. In each case, $^{125}$I radioiodinated streptavidin was used to detect bound biotin-labeled peptide. The amount of streptavidin molecules added was calculated in each case to be approximately 50-fold in excess over the number of chemokine receptor sites. In addition, the number of molecules of labeled peptide added (at 10 µM) was $10^5$-fold in excess over the estimated number of binding sites. Thus, all these experiments were performed under conditions where the number of binding sites as limiting. No detectable binding of labeled peptide 3 to any of the cell lines tested was observed (the number of counts bound was not significantly greater than when no peptide was added). However, peptide 2 apparently bound to all the cell lines, including the parental lines to an approximately equal extent (FIG. 25).

To determine whether this apparent binding of peptide 2 was cell dependent, or whether it was binding to the plastic (or the some component of the fetal calf serum used during the cell culture), the following experiment was conducted. Three plates were evaluated: One had HOS parental cells, another had CCR5 over-expressors and the third had no cells but was incubated with the FCS-containing culture medium. Peptide 2, and to a much lesser extent peptide 3, bound to the wells with no cells. Mathematical analysis indicated that all the binding which was observed when cells were present could be accounted for the ability of the peptide to bind to the wells with no cells in them. Furthermore, for peptide 2, this indicated that more than 95% of the peptide 2 was binding to the well, while for peptide 3, about 5-10% of the peptide is binding to the well.

The propensity of these peptide substances to bind to hydrophobic surfaces (such as the plastic of the wells) may also account for much of the variability seen when the experimental protocols are transferred from one site to another (e.g., when different plastic tubes are used to handle the peptide substance).

For peptide 3, there was no evidence for any binding whatsoever to recombinant human chemokine receptors. Any binding which did occur would have a very low affinity (>>10 µM) precluding the possibility that this interaction was responsible for the chemokine inhibitory activity attributed to the peptide 3 class.

Conclusions

Thus, it appears that peptide 3 does not bind to human chemokine receptors at any appreciable affinity in vitro under the binding conditions normally used for chemokine receptor interaction studies, as well as under several other binding conditions. One possibility is that peptide 3 interacts with the chemokine receptors by collisional coupling, or by a mechanism with very short residence times. The most likely interpretation of the data is that peptide 3 is a functional chemokine inhibitor by a mechanism other than direct receptor antagonism, e.g., by preventing functional receptor ligand interactions, or by binding to a third component (other than receptor or ligand) which is necessary for ligand function. Thus, peptide 3 may bind to a cell surface site/receptor distinct from the known chemokine receptors, bind to extracellular matrix or cell membrane associated components (including, but not limited to, glycosaminoglycans (GAG), e.g., a GAG component of the plasma membrane, glycochalyx, proteoglycans, fibrinogen, chondroitin sulfate, heparin sulfate, keratin sulfate, hyaluronic acid, collagen and sulfated surface moieties), or interfere with signal transduction mechanisms in either a direct or indirect manner.

With respect to the binding of peptide 3 to a distinct receptor or to extracellular matrix or cell membrane associated components, once bound, peptide 3 interferes with chemokine activity, but does not dislodge or hinder ligand binding to the cells. The number of binding sites (receptors) for peptide 3 on THP-1 cells was estimated to be 1000 receptors/cell (FIGS. 28 and 29). To purify this receptor, a synthetic photoactivatable derivative may be employed for crosslinker aided purification of the receptor, or a ligand blotting approach may be employed. For ligand blotting, cell membrane proteins from THP-1 cells (which have the receptor) and from HOS (a human osteosarcoma cell line) cells (which do not have functional receptor) were separated by gel electrophoresis, then incubated with biotin-labeled peptide 3, preferably after renaturation of the proteins (e.g., using a graded decrease in SDS over a period of time) and then detected with streptavidin peroxidase.

Alternatively, or in addition, a cross linkable affinity probe is synthesized, e.g., biotin-SLDPKQKWIQC-X (SEQ ID NO:153; L-amino acid forward linear sequence). The purpose of the $Ser_0$ is to leave only one cys residue in the molecule. After synthesis, a photoactivatable crosslinking group is attached through the sulphahydryl group on the remaining $Cys_{13}$ residue, e.g., APDP (N-[4-(p-azidosalicylamido)butyl]-3N-(2N-pyridyldithio)propionamide). This derivative is then incubated with THP-1 cells to allow it to bind the receptor on the THP-1 cells and then the reaction is flashed with UV light which induces covalent crosslinking of the APDP group to the receptor. The cells are then disrupted and membrane proteins extracted and denatured. The protein mix is passed onto a streptavidin column. The peptide and the receptor are then released from the streptavidin column either by full denaturation (e.g., with 10 M urea) or by the use of 2-mercaptoethanol, which will uncouple the APDP from the peptide, freeing the receptor. The purified receptor is then identified by N-terminal sequencing methods, or by tandem nanoelectrospray mass spectroscopy.

After peptide 3 binds to its receptor, it may block proteins required to effect the response (e.g., block specific integrins needed for chemokine-induced migration but not fNLP or TGFb induced migration), down regulate a chemokine receptor, or interfere with signal transduction mechanisms. Interference with signal transduction mechanisms can be detected in either a direct or indirect manner (for example, using assays for measuring intracellular calcium flux, cAMP, pI3, kinase activity, and DAG). In particular, with respect to calcium flux, CRD-$Leu_4Ile_{11}Cys_{13}$ peptide 3(3-12)[MCP-1] did not block MCP-1 induced calcium flux, but did block SDF-1 induced calcium flux (FIG. 38).

Example 12

Model of Ischaemia Reperfusion Injury

The intraluminal thread (ILT) model is representative of clinical ischaemia reperfusion injury, it gives a focal ischemic lesion and is widely used in the pharmaceutical industry to test candidate compounds for neuroprotective efficacy. Fed, male Sprague Dawley rats (Charles Rivers, approximately 330 g) were anaesthetized with 2% halothane in 70/30% $N_2O/O_2$ and the left middle cerebral artery occluded (MCAo) for 90 minutes using the ILT approach. The MCAo is achieved by the placement of a 3/0 nylon suture into the internal carotid artery and advancing it approximately 18 mm from the carotid bifurcation such that its tip is positioned approximately 1 mm beyond the origin of the MCA. After the required ischemic period, the nylon suture is withdrawn into the external carotid artery and the lesion is reperfused from the normal antegrade direction.

Throughout the surgical period, rectal temperature was monitored and maintained at 37° C. with a heated blanket and feedback rectal temperature probe and arterial blood gases were measured prior to and immediately post MCAo. During the ischemic period the rats were recovered to allowing neurological deficit assessment prior to reperfusion. The neurological deficit score can be used to indirectly assess the 'quality' of the occlusion, a spontaneous right side-circling gait represents a good occlusion while animals which showed a low neurological deficit were removed from further study.

After 90 minutes of ischaemia, the rats were reanesthetized and the ILT withdrawn. The collector of the data was blinded to the identity of the test compound. Either solution A or B (PBS or 0.5 mg/ml of CRD-$Leu_4Ile_{11}Cys_{13}$ peptide 3(3-12) [MCP-1] in PBS, respectively) was administered by jugular venepuncture at a dose of 2 mg/kg. A femoral vein cannula was inserted, tunneled under the skin and exteriorized at the back of the neck. This was used to administer compound A or B by constant intravenous infusion (0.5 mg/kg/hr) over the following 72 hours. The 3 day time frame of the experiment encompasses the maximal inflammatory response typically seen in rats using this model.

The ischemic damage was assessed by conventional magnetic resonance imaging (T2, diffusion and proton density sequences) on day 1, 2 and 3 post MCAo. For all MR procedures anaesthesia was induced and maintained at 1% halothane v/v in oxygen. Rectal temperature was maintained at 37° C. MRI was performed at 4.7T using a SIS-200 imaging spectrometer (Spectroscopy Imaging Systems, Fremont, Calif., USA) and a home-built 75 mm diameter 8-legged birdcage radio frequency coil. 25 contiguous coronal slices starting at the level of the eyes, running rostral to caudal through the brain, were acquired using a 128*128 acquisition matrix covering a field of view of 4*4 cm. Each slice was 0.9 mm thick.

After the final MR analysis at 72 hour post ictus the rats were decapitated, the brains removed, stored fresh in cryoprotecting medium at −70° C. prior to quantitative immunohistochemical analysis of infiltrating leukocytes (FIG. 34). Animals treated with CRD-$Leu_4Ile_1Cys_{13}$ peptide 3(3-12) [MCP-1] had a 50% reduction ($p<0.0001$) in the mean infarct volume at all time points.

Brains were sectioned every 100 μm, stained for neutrophils, and images from four regions of the brain on each of the lesion and contralateral sides were collected. There was a complete suppression of neutrophil accumulation (measured by quantitative immunofluorescence) in the penumbra of the lesion (FIG. 47). Regions 2 and 3 overlap the core of the infarct and more neutrophils were observed in sections in the penumbra regions. This is likely to be because the penumbra region remains fully perfused but the infarcted region is largely necrotic with little or no blood supply. Region 1 is the most penumbral and had the highest neutrophil number. The inhibition by the test agent is statistically significant in the penumbra ($p<0.01$ in region 4 and $p=0.02$ in region 1). There was no significant neutrophil accumulation or effect of the agent on the contralateral side of the brain.

Example 13

Pharmacokinetics of $^3$H-CRD-L-Leu$_4$Ile$_{11}$Cys$_{13}$ Peptide 3(3-12)[MCP-1] and Unlabeled CRD Peptides in SD Rats and Mice Labeled Peptide Male (n=5, ave. body weight: 305 grams) and female (n=5, ave. body weight: 251 grams) SD rats were obtained from Hilltop Laboratories with surgically cannulated jugular veins. Animals were housed in Nalgene metabolic cages for the duration of the study, and given food and water ad libitum.

Radiolabeled CRD-L-Leu$_4$Ile$_{11}$Cys$_{13}$ peptide 3(3-12) [MCP-1] peptide (molecular weight about 1360, 2.0 Ci mmol$^{-1}$, 302.3 µCi mL$^{-1}$ in sterile water for injection (SWI)), and non-labeled peptide were prepared. Doses of 100 µg total peptide and 20 µCi of $^3$H-CRD-L-Leu$_4$Ile$_{11}$Cys$_{13}$ peptide 3(3-12)[MCP-1] in 200 µl of PBS were prepared, taking into account the impact of tritiated peptide mass on the total dose. Each rat was injected i.v. in the lateral tail vein with a weighed syringe containing approximately 200-300 µl of the peptide solution. The syringe was re-weighed, and the injection amount calculated for each individual dose. Radiolabeled counting standards were prepared from the same solution.

Serial blood samples (about 300-400 µL/timepoint) were removed via the jugular catheter at 0.17, 0.5, 1, 2, 4, 6, 20, 28, and 48 hours post-injection, and immediately placed into MICROTAINER® serum separator tubes (Becton Dickinson). The catheter was flushed with a small amount (20 µL) of heparin solution to prevent clotting, and blood volume was replaced with 400 µL of saline at each sampling. The serum tubes were centrifuged, and the resulting serum (100 µL) and cell pellet (weighed) were placed onto sample cones for processing by a Model 307 Packard sample oxidizer. The remaining serum was aliquoted and frozen for later analysis. Urine was sampled in time intervals of 0-4, 4-6, 6-10, 10-20, 20-28, 28-48, and 48-72 hours. 100 µL of each individual urine collection was placed onto sample cones for oxidation, and the remainder frozen for later analysis by HPLC and LC-MS. At 72 hours, the rats were anesthetized, exsanguinated by cardiac punctured, euthanized by cervical dislocation, and dissected to estimate the biodistribution of $^3$H-CRD-L-Leu$_4$Ile$_{11}$Cys$_{13}$ peptide 3(3-12)[MCP-1]. Processed samples were counted in the Packard.

Serum Pharmacokinetics

Figure 37A:
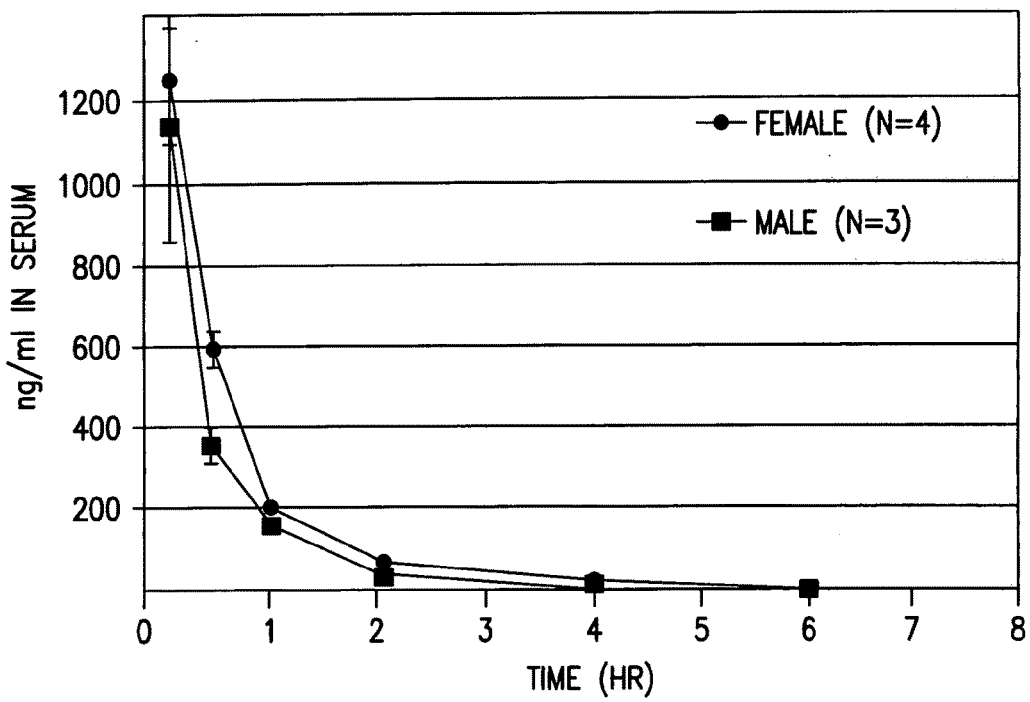
FIG. 37 depicts results from male and female, i.v. cannulated, Sprague Dawley rats which were given a single intravenous dose (100 µg) of tritiated $^3$H-CRD-L-Leu$_4$Ile$_{11}$Cys$_{13}$peptide 3(3-12)[MCP-1] via the lateral tail vein at time=0. Blood and urine were collected over time to establish pharmacokinetic parameters. $^3$H-CRD-L-Leu$_4$Ile$_{11}$Cys$_{13}$peptide 3(3-12)[MCP-1] levels were measured in whole blood, serum, cell pellets and urine. A: ng/ml $^3$H-CRD-L-Leu$_4$Ile$_{11}$Cys$_{13}$ peptide 3(3-12)[MCP-1] in serum during the first 8 hours. B & C: ng $^3$H-CRD-L-Leu$_4$Ile$_{11}$Cys$_{13}$ peptide 3(3-12)[MCP-1]/gram of sample in serum, cell pellets, and serum+cells pellets for 48 hours after dosing males=B, females=C). D) representative urinary excretion of $^3$H-CRD-L-Leu$_4$Ile$_{11}$Cys$_{13}$ peptide 3(3-12) [MCP-1] in rats after a single i.v bolus.
Figure 37B:
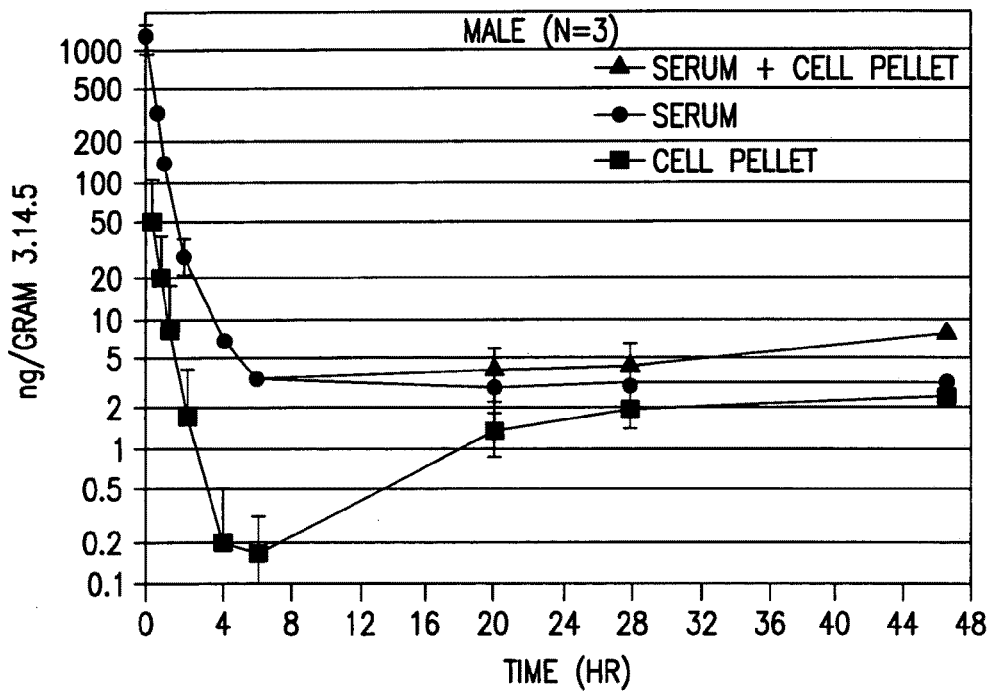
Figure 37C:
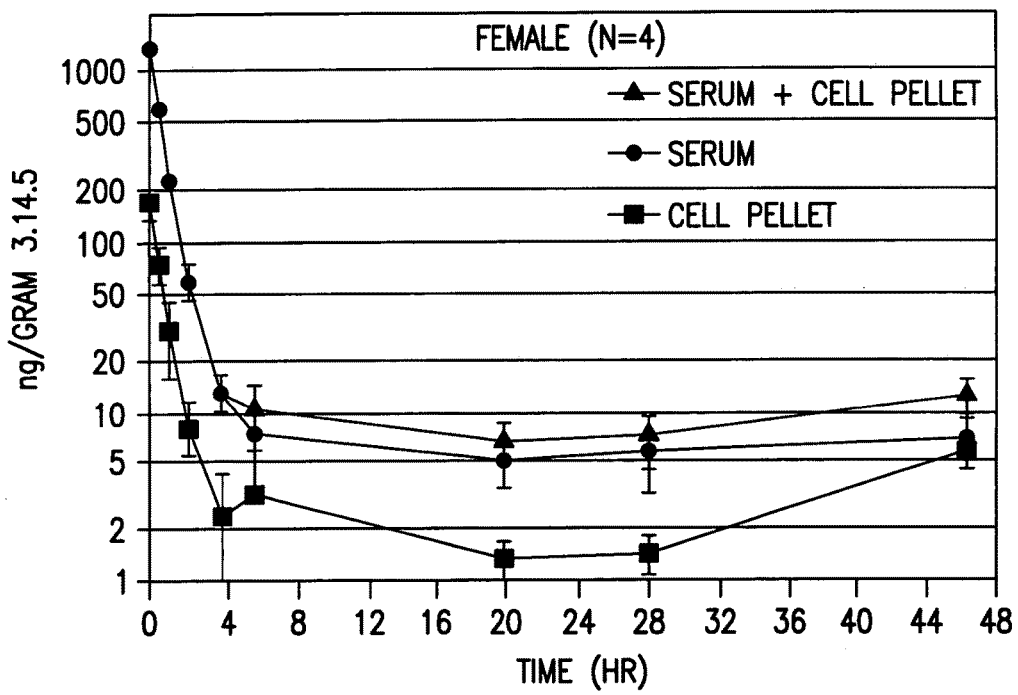

The radiolabel disappeared from serum quite rapidly in both males and females. Linear plots of concentration versus time for both genders are shown in FIG. 37A. The concentration at 10 minutes post injection was 1238±138 ng mL$^{-1}$ for females (corresponding to 12.45±1.39% of the injected dose (i.d.)) and 1141±283 ng mL$^{-1}$ for males (corresponding to 14.38±3.46% i.d.). While the absolute concentration values appear less for the males, the fact that the dose was not adjusted to body mass easily accounts for this differential, as the percent injected dose values indicate. By four hours post injection, only about 0.1% of the injected dose is present in blood. While data is reported at 6 hours and beyond, the amount of radioactivity present in these samples was less than twice background levels. This low level of activity cannot be characterized with regard to structure, nor is it robust enough for consideration as part of the kinetic modeling.

The vast majority of the radioactivity present in blood resides in the serum fraction (<12% of the total counts were present in the unwashed cell pellet at 10 minutes), although this ratio changes over time (FIGS. 38B and 38C). Cell pellet data is of low reliability (due to low counts) between 4 and 28 hours. The 48 hour data is suggestive of a "rebound" in cell-associated radioactivity, but represents an extremely low amount of material. It is unknown whether this radioactivity reflects the presence of intact peptide.

The data indicate a biphasic clearance in both sets of animals. Curve-fitting pharmacokinetic analyses were done using a basic two-compartment biexponential model to the serum data. The actual time and concentration data is entered into a fitting program (PK Analyst, MicroMath Scientific Software. Salt Lake City, Utah), and is fitted according to model selection (e.g., i.v. bolus, two-compartment distribution). Calculated concentration values are generated, and a curve is fit to the data.

From the fit generated above, the following pharmacokinetic parameters were generated:

| | | | |
|---|---|---|---|
| Elimination half-life: | 0.19 hr | alpha-phase T$_{1/2}$: | 0.07 hr |
| α: 9.59 | | beta-phase T$_{1/2}$: | 0.29 hr |
| β: 2.42 | | | |
| Maximal concentration | 1,710 ng mL$^{-1}$ | | |
| A: 48.88 µg/mL | | | |
| B: 63.64 µg/mL | | | |
| AUC | 31.43 (µg-hr)/mL | | |
| Maximal concentration/dose | 0.000017 | | |
| Vd | 0.36 L/kg | | |

Urinary Excretion

Figure 37D:
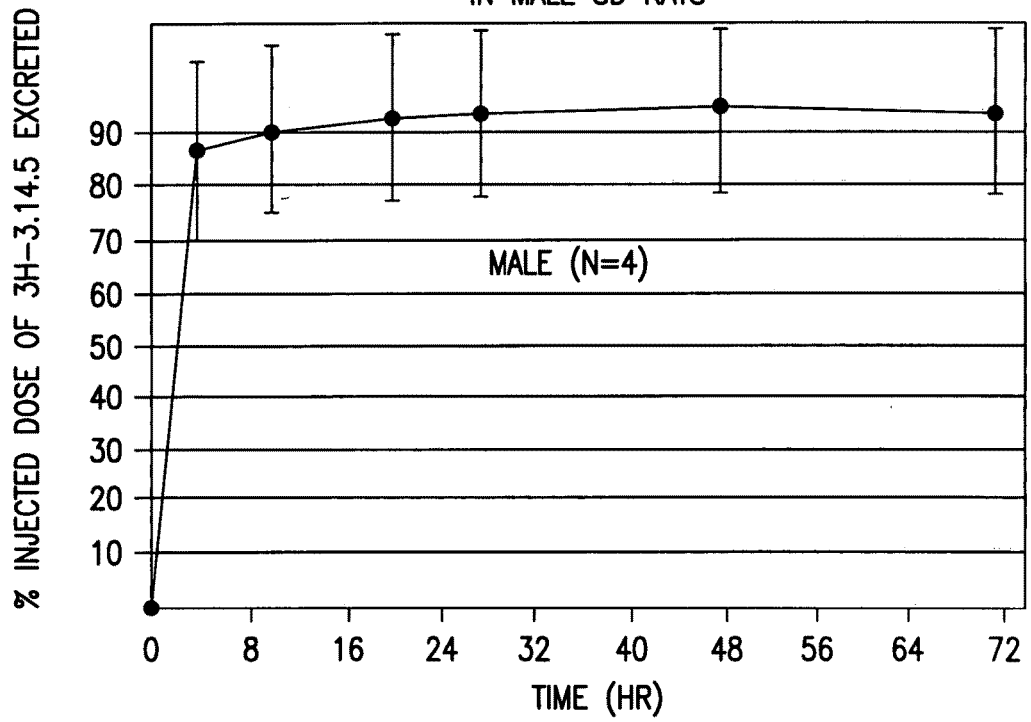

Sampling of the female rats' urine was subject to an experimental handling error. Only rat number 5 showed a pattern consistent with excretion in the male rats, eliminating >75% of the injected dose in the first 4 hours. The urine of male rats, in which the handling error was corrected for all but rat #14, yield the most consistent data (FIG. 37D). The majority of the administered dose was eliminated in the urine over the first 4 hours (86.6+/−16.5% i.d.). A subsequent experiment has confirmed that female rats administered either 1.0 or 10.0 mg of $^3$H-CRD-L-Leu$_4$Ile$_{11}$Cys$_3$ peptide 3(3-12)[MCP-1] also excrete >80% i.d., in this case measured over the first 2 hours after injection. This high rate of urinary excretion is consistent with the rapid elimination of $^3$H-CRD-L-Leu$_4$Ile$_{11}$Cys$_{13}$ peptide 3(3-12)[MCP-1] from blood, and the low organ retention values measured in subsequent dissected rats.

Urine from male rats was filtered through a 0.2µ filter (without decreasing the amount of radioactivity per unit volume), and analyzed by gradient reverse-phase HPLC with online radiodetection. The co-elution of the injected preparation (as a standard) with the 0-4 hour urine from rats 12 and 16 was observed. A single peak of radioactivity was seen in both urine samples, consistent with excretion of the $^3$H-CRD-L-Leu$_4$Ile$_{11}$Cys$_{13}$ peptide 3(3-12)[MCP-1] as an intact moiety. For definitive structural characterization of the excreted molecule, all urine samples from the male rats were analyzed by LC-MS-MS.

Using electrospray ionization (ESI), an LCQ ion trap mass spectrometer (Thermoquest Finnigan, San Jose, Calif.) is operated in the positive ion mode with the heated capillary set to 200° C., and 4.25 kV applied to the electrospray needle. The sheath gas flow rate is set to 50 units, while the auxiliary gas is turned off. The data are acquired with a maximum ion time of 500 ms and 1 total microscan. The analysis is performed using two scan events, a full scan MS with m/z [280-1500] and a data dependent full scan MS/MS with m/z [125-1300] generated by fragmentation of the doubly charged ion with m/z 680.1 set to an isolation width of 2.0 amu and a collisional energy of 28%.

HPLC grade solvents ('Baker Analyzed') are purchased from J. T. Baker, Phillipsburg, N.J., and formic acid, 99%, ACS, is purchased from Sigma, St. Louis, Mo. A Zorbax Eclipse XDB-C18 3.0×150 mm, 3.5 micron ('Zorbax', Hewlett-Packard, Palo Alto, Calif.) equipped with a 'Safe-Guard' guard column containing a C18 cartridge (Phenomenex, Torrence, Calif.) is operated at a column temperature of 35° C. and a maximum pressure of 400 bar. An HP1100 binary system (Hewlett-Packard, Palo Alto, Calif.) generates a gradient at a flow rate of 0.500 ml/min from 2% B (acetonitrile) in water/0.1% formic acid (A) from 0.0 to 0.8 min, then ramping up to 20% B for 5 min. The organic content is further increased at 6 min to 95% B at 6.5 min, combined with an increase in flow rate to 0.800 ml/min at 6.55 min to elute lipophilic contaminants or metabolites. After 1.45 min, the column is re-equilibrated at a flow rate of 0.800 ml/min at 2% B for 2 min. 10 of each sample is injected using an HP1100 autosampler (Hewlett-Packard, Palo Alto, Calif.). With these conditions CRD-Leu$_4$Ile$_{11}$Cys$_{13}$ peptide 3(3-12)[MCP-1] elutes at a retention time of 5.17 min.

The standard analytes are prepared by adding different levels of $^3$H-CRD-L-Leu$_4$Ile$_{11}$Cys$_{13}$ peptide 3(3-12)[MCP-1] to rat urine filtrated through a 'Sterile Acrodisc 13 0.2 μm' filter (Gelman Sciences, Prod. #4454). The following levels of $^3$H-CRD-L-Leu$_4$Ile$_{11}$Cys$_{13}$ peptide 3(3-12)[MCP-1] standards were each injected three times and analyzed to generate a standard curve: 0 μg/ml (no standard added), 0.5 μg/ml, 1.0 μg/ml, 2.0 μg/ml, 3 μg/ml, 5 μg/ml, and 10 μg/ml. Rat urine samples were collected at different time points after i.v. injection of a single dose of 100 μg $^3$H-CRD-L-Leu$_4$Ile$_{11}$Cys$_{13}$ peptide 3(3-12)[MCP-1] containing 86.4% of unlabeled and 13.6% of tritium-labeled compound. Samples were analyzed after filtration as described above. As the detection method only allows for the analysis of the unlabeled fraction of the sample, the overall concentration was calculated by multiplication of the measured concentration by 100/86.4.

Only samples from the first 2-3 collection periods (out to 20 hours post administration) were evaluable within the detection limits of the mass spectrometer. While there were some experimental inconsistencies (variability in the assayed amounts with the counting data, probably due to method errors and the low sample concentrations) the data show that >80% of the injected radioactivity in the urine possesses a mass consistent with the intact, cyclized structure. In these analyses, the linear peptide was assayed as a control. The linear form was found to be rapidly cyclized in room temperature urine. Similar incubations in rat serum gave the same result, confirming that the preferred conformation of the peptide in these biological fluids appears to be the cyclized compound. Given the propensity to cyclize in the serum, it is unlikely that $^3$H-CRD-L-Leu$_4$Ile$_{11}$Cys$_{13}$ peptide 3(3-12)[MCP-1] underwent significant in vivo reduction to the linear form and was oxidized back to the cyclized form in the urine, but this possibility cannot be ruled out until serial serum analysis confirms the presence of the intact $^3$H-CRD-L-Leu$_4$Ile$_{11}$Cys$_{13}$ peptide 3(3-12)[MCP-1] at all early (0-6 hour) timepoints. LC-MS-MS analysis of the serum at 10 minutes post-injection confirmed the presence of intact $^3$H-CRD-L-Leu$_4$Ile$_{11}$Cys$_{13}$ peptide 3(3-12)[MCP-1].

Summary for Labeled Peptide

The pharmacokinetic profile of a relatively small, highly polar molecule is consistent with the above parameter values and the structure of $^3$H-CRD-L-Leu$_4$Ile$_{11}$Cys$_{13}$ peptide 3(3-12)[MCP-1]. For comparative purposes, the antibiotic amikacin (a relatively small (MW about 580), polycationic aminoglycoside) exhibits a similar pharmacokinetic profile ($T_{1/2}$ about 2 hours, 98% urinary excretion, $V_d$=0.27 L/kg). Molecules within this range of distribution volumes may be distributing rapidly through the extracellular fluid. $^3$H-CRD-L-Leu$_4$Ile$_{11}$Cys$_{13}$ peptide 3(3-12)[MCP-1] appears to be rapidly and nearly quantitatively cleared via renal excretion. Serum concentrations after i.v. bolus dosing decline quickly, with less than 1% i.d. remaining in the blood by 2 hours. Given the balance between the decline in serum/whole blood and the increase in cumulative urinary excretion over the same interval, it is difficult to imagine that a significant fraction of $^3$H-CRD-L-Leu$_4$Ile$_{11}$Cys$_{13}$ peptide 3(3-12)[MCP-1] is sequestered in any tissue. Biodistribution data from another study seems to bear out this supposition. At 3 hours post injection, only about 11% i.d. could be accounted for in the 25 tissues and organs assayed.

Figure 39A:
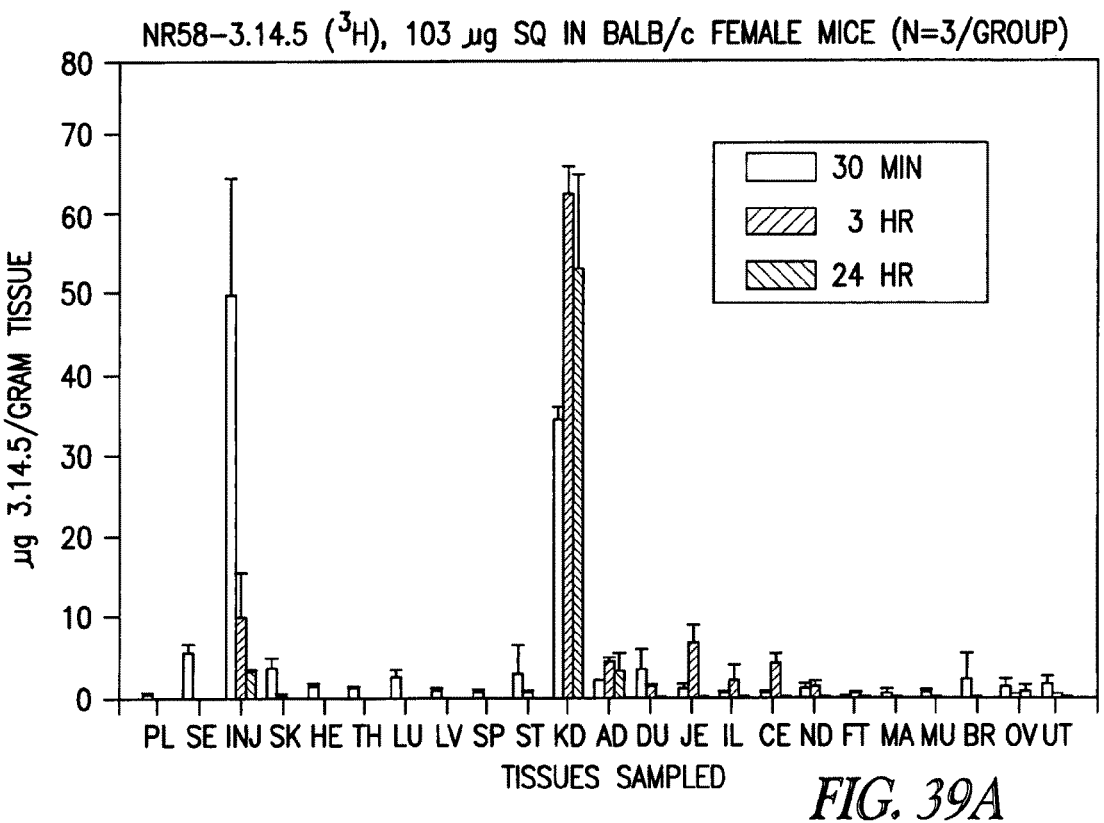
FIG. 39 shows the biodistribution of $^3$H-CRD-L-Leu$_4$Ile$_{11}$Cys$_{13}$ peptide 3(3-12)[MCP-1] in mice after a single 100.3 µg subcutaneous bolus dose. Values are represented as µg 3H-CRD-L-Leu$_4$Ile$_{11}$Cys$_{13}$ peptide 3(3-12) [MCP-1] per gram of tissue. A) Tissues from left to right are: PL=blood pellet, SE=serum, Inj=injection site, SK=skin, HE=heart, TH=thymus, LU=lung, LV=liver, SP=spleen, ST=stomach, KD=kidney, AD=adrenal gland, DU=duodenum, JE=jejunum, IL=ileum, CE=cecum+colon, ND=mesenteric lymph nodes, FT=abdominal fat, MA=bone marrow, MU=skeletal muscle, BR=brain, OV=ovaries, UT=uterus. B) Data for biodistribution of 10.3 µg, 103 µg, and 1030 µg of agent at 30 minutes, 3 hours and 24 hours in percent injected dose/g. C) Data for biodistribution of 10.3 µg, 103 µg, and 1030 µg of agent at 30 minutes, 3 hours and 24 hours in nmol/g.

A mouse study was conducted wherein female BALB/c mice received a subcutaneous dose of 10 μg $^3$H-CRD-L-Leu$_4$Ile$_{11}$Cys$_{13}$ peptide 3(3-12)[MCP-1] (see FIGS. 39-40). At 30 minutes post injection, the average serum concentrations were 503 ng/g, which compare favorably with the 591 ng/g recorded at the same timepoint in female rats. The biodistribution data at 30 minutes for these mice are similar to those values for the rat study in process. Both species exhibit similar blood clearance and distribution profiles.

Unlabeled Peptide
Materials and Methods
Chemicals and Reagents

HPLC grade water and acetonitrile ("Baker Analyzed") were purchased from J. T. Baker (Phillipsburg, N.J.). Formic acid (99%, ACS), trifluoroacetic acid (99+%, spectrophotometric grade), and 1,2-ethanedithiol (90+%) were purchased from Sigma (St. Louis, Mo.). Phosphate-Buffered Saline (Dulbecco's Phosphate-Buffered Saline, 1×) was purchased from GibcoBRL (Grand Island, N.Y.). Nitrogen used as a sheath gas for mass spectrometric analysis, was drawn from a liquid nitrogen cylinder (99.998% purity) purchased from Byrne Specialty Gases (Seattle, Wash.). Heparin sodium for injection, USP, 1000 units per ml, was purchased from Provet (Seattle, Wash.). Serum for preparation of calibration standards was prepared freshly from blood of female Sprague-Dawley rats (average body weight: 265 g) obtained from Hilltop Lab Animals (Scottdale, Pa.).

Peptides

CRD-Leu$_4$Ile$_{11}$Cys$_{13}$ peptide 3(3-12)[MCP-I] has a molecular mass of 1357.7 Da (monoisotopic), is amidated at the C-terminus, and was manufactured as triacetate salt with a purity >97% (Multiple Peptide Systems, San Diego, Calif.).

CRD-L-Leu$_4$Ile$_{11}$Cys$_{13}$ peptide 3(3-12)[MCP-1] has a molecular mass of 1357.7 Da (monoisotopic) and is a diastereomer of CRD-Leu$_4$Ile$_{11}$Cys$_{13}$ peptide 3(3-12)[MCP-1]. The diastereomer was synthesized by solid phase peptide synthesis inserting L-leucine instead of D-leucine as follows: Peptide synthesis was performed on an ABI Applied Biosystems Peptide Synthesizer 430A (Foster City, Calif.) using Fmoc chemistry with Rink amide resin (PE Applied Biosystems, Foster City, Calif.). After completion of the synthesis, the linear peptide was cleaved from the resin with trifluoracetic acid/1,2-ethanedithiol/water (95/2.5/2.5). The peptide was purified by preparative RP-HPLC using a Dynamax HPLC system with photo diode array detection (Rainin Instrument Company, Inc., Woburn, Mass.) applying a water/acetonitrile gradient containing 0.1% trifluoracetic acid. The correct molecular mass of the isolated linear peptide (1359.7 Da, monoisotopic) was verified by ESI/MS analysis of the infused compound on a Finnigan LCQ ion trap (San Jose, Calif.). The linear peptide was cyclized oxidatively by stirring a highly diluted aqueous solution of peptide (0.05-0.1 mg/ml) at pH 8.5 at room temperature in an open flask for two days to form head to tail disulfide bonds. The intramolecularly linked peptide was purified by preparative RP-HPLC as described above. The resulting trifluoroacetate salt was dissolved in water and filtered through a column packed with a 36 fold molar excess of pre-washed AG 1-X2 strong anion exchange resin, analytical grade, 200-400 mesh, acetate form (Bio-Rad Laboratories, Richmond, Calif.). The eluting peptide triacetate salt was collected and lyophilized. The correct molecular mass of the diastereomer was verified by ESI/MS analysis of the infused compound on a Finnegan LCQ ion trap (San Jose, Calif.). The purity was assessed by RP-HPLC coupled with phot diode array detection, and ESI/MS analysis of the infused compound as described above.

LC-MS Analysis

Chromatographic separation was carried out on an HP series 1100 system comprising a degasser, binary pump, auto sampler, and column compartment (Hewlett-Packard, Palo Alto, Calif.). The chromatograph was fitted with a Zorbax Eclipse XDB-C18 3.0×150 mm, 3.5 micron column (Hewlett-Packard, Palo Alto, Calif.) and a Phenomenex "SafeGuard" guard column with a C18 cartridge (Torrance, Calif.), and operated at a maximum pressure of 400 bar with a column temperature of 35° C. A flow rate of 500 μl/min was employed. The mobile phase utilized for separation of CRD-$Leu_4Ile_{11}Cys_{13}$ peptide 3(3-12)[MCP-I] and CRD-L-$Leu_4Ile_{11}Cys_{13}$ peptide 3(3-12)[MCP-1] was composed of water containing 1% formic acid (buffer A) and acetonitrile (buffer B). The gradient applied was 2% B for 2 min rising to 17% B within 0.5 min, then running isocratically for 7.5 min. A wash step was appended with 95% B for 3 min at an increased flow rate of 800 μl/min, followed by a re-equilibration step at 2% B for 3 minutes. Per sample, 10 μl was injected. CRD-$Leu_4Ile_{11}Cys_{13}$ peptide 3(3-12)[MCP-I] eluted at a retention time of 8.3 minutes, and CRD-L-$Leu_4Ile_{11}Cys_{13}$ peptide 3(3-12)[MCP-1] eluted at 8.9 minutes. The analytical column was interfaced with a Thermoquest/Finnigan LCQ ion trap (San Jose, Calif.) using ESI. The mass spectrometer was operated in the positive ion mode with the heated capillary set to 200° C., and 4.25 kV applied to the electrospray needle. The sheath gas flow rate was set to 55 units, while the auxiliary gas flow was turned off. The data were acquired in a full scan MS mode (m/z [335-1400 Da/z]) using automated gain with 1 microscan and a maximum ion time of 500 ms. The HPLC effluent was directed to waste for the first 6 minutes of the analysis, and then introduced into the electrospray source for 4 minutes.

Preparation of Calibration Standards and Samples

Two primary stock solutions of CRD-$Leu_4Ile_{11}Cys_{13}$ peptide 3(3-12)[MCP-I] triacetate salt and CRD-L-$Leu_4Ile_{11}Cys_{13}$ peptide 3(3-12)[MCP-1] triacetate salt were prepared at a concentration of 11.3 mg/ml in water. Three working solutions of CRD-$Leu_4Ile_{11}Cys_{13}$ peptide 3(3-12)[MCP-I] triacetate salt were prepared by diluting the primary stock solution ten-fold with water, followed by two hundred-fold serial dilution steps. Additionally, a 1.13 mg/ml working solution of CRD-L-$Leu_4Ile_{11}Cys_{13}$ peptide 3(3-12)[MCP-1] triacetate salt was prepared by dilution of the primary stock solution with water. Serum was prepared freshly from blood of untreated rats into Microtainer serum separator tubes (Becton Dickinson and Co., Franklin Lakes, N.J.), followed by centrifugation for 10 minutes at 16,000 g, and sampling of the upper layer.

To generate a standard curve, thirteen calibration standards were prepared by adding 2 μl of one of the CRD-$Leu_4Ile_{11}Cys_{13}$ peptide 3(3-12)[MCP-I] triacetate salt working solutions and 2 μl of the CRD-L-$Leu_4Ile_{11}Cys_{13}$ peptide 3(3-12)[MCP-1] triacetate salt working solution to 96 μl of freshly prepared serum from untreated rats. To determine levels of CRD-$Leu_4Ile_{11}Cys_{13}$ peptide 3(3-12)[MCP-I] in treated rats, serum was isolated from blood collected at a series of time points post peptide injection, and 2 μl of internal standard CRD-L-$Leu_4Ile_{11}Cys_{13}$ peptide 3(3-12)[MCP-1] triacetate salt working solution was added to 98 μl of each serum sample from CRD-$Leu_4Ile_{11}Cys_{13}$ peptide 3(3-12)[MCP-I]-treated rats. Each of the calibration standards and rat serum samples was mixed with 400 μl of ice-cold acetonitrile and centrifuged for 10 minutes at 16,000 g. 400 μl of the supernatants were transferred into Eppendorf centrifuge tubes (Fisherbrand polypropylene, Fisher Scientific, Pittsburgh, Pa.), dried overnight under vacuum in a Savant Speed Vac (Holbrook, N.Y.), and reconstituted in 100 μl of HPLC grade water. Samples were spun for 10 min at 16,000 g and 70 μl transferred into 100 μl glass inserts placed into 2 ml HPLC vials (Hewlett-Packard, Palo Alto, Calif.) for LC-MS analysis. The calibration standards' final concentrations were 0.008, 0.04, 0.08, 0.2, 0.4, 0.8, 2, 4, 8, 20, 40, 80, and 200 μg/ml of CRD-$Leu_4Ile_{11}Cys_{13}$ peptide 3(3-12)[MCP-1]. All samples contained 16 μg/ml of internal standard CRD-L-$Leu_4Ile_{11}Cys_{13}$ peptide 3(3-12)[MCP-1]. A blank sample was prepared by spiking 4 μl of water into 96 μl of serum from untreated rats followed by liquid/liquid extraction and reconstitution for LC-MS analysis as described above.

Quantitative Analysis

Using the LCQuan program (Finnigan, San Jose, Calif.), levels of CRD-$Leu_4Ile_{11}Cys_{13}$ peptide 3(3-12)[MCP-I] were determined by monitoring the summation of ion currents of the triply, doubly, and singly charged ions of CRD-$Leu_4Ile_{11}Cys_{13}$ peptide 3(3-12)[MCP-I] and CRD-L-$Leu_4Ile_{11}Cys_{13}$ peptide 3(3-12)[MCP-1] m/z 453.6 $[M+3H]^{3+}$, m/z 680.0 $[M+2H]^{2+}$, and m/z 1358.7 $[M+H]^{+}$ extracted from the full scan total ion chromatogram using an isolation width of 3 u. Thirteen calibration standards, each containing 16 μg/ml of CRD-L-$Leu_4Ile_{11}Cys_{13}$ peptide 3(3-12)[MCP-1] and prepared in serum as described above, were analyzed in triplicate. After averaging the three data points for each standard, the calibration curve was constructed by plotting the peak area ratios of analyte to CRD-$Leu_4Ile_{11}Cys_{13}$ peptide 3(3-12)[MCP-I] to internal standard CRD-L-$Leu_4Ile_{11}Cys_{13}$ peptide 3(3-12)[MCP-1] against the concentration ratios of CRD-$Leu_4Ile_{11}Cys_{13}$ peptide 3(3-12)[MCP-I] to CRD-L-$Leu_4Ile_{11}Cys_{13}$ peptide 3(3-12)[MCP-1]. A non-weighted linear regression line was fitted to the concentration ratios of CRD-$Leu_4Ile_{11}Cys_{13}$ peptide 3(3-12)[MCP-I] to CRD-L-$Leu_4Ile_{11}Cys_{13}$ peptide 3(3-12)[MCP-1] covering a concentration range of 200 ng/ml-200 μg/ml of CRD-$Leu_4Ile_{11}Cys_{13}$ peptide 3(3-12)[MCP-I]. The lower limit of quantitation (LLOQ) was determined as the level of the least concentrated calibration standard with a signal to noise ratio greater than 3:1. The accuracy of the method was calculated as % relative error (RE), and the precision as % relative standard deviation (RSD).

Pharmacokinetic Analysis

Five female Sprague-Dawley rats (average body weight: 265 g) with surgically cannulated jugular veins were obtained from Hilltop Lab Animals (Scottdale, Pa.) and housed in a facility approved by the Association for the Assessment and Accreditation of Laboratory Animal Care. All experiments involving the use of animals were approved by the Institutional Animal Care and Use Committee. During the study, animals were housed in Nalgene metabolic cages (Nalgene Company, Rochester, N.Y.) and supplied with food and water ad libitum.

Sixty mg of CRD-$Leu_4Ile_{11}Cys_{13}$ peptide 3(3-12)[MCP-I] triacetate salt was dissolved in 1.8 ml of phosphate-buffered saline and 300 µl was injected into the lateral tail vein of each rat (8.8 mg). The exact amounts of CRD-Leu$_4$Ile$_{11}$Cys$_{13}$ peptide 3(3-12)[MCP-I] injected into each animal were calculated based on the syringe weights pre- and post-injection.

From each of the five rats, serial blood samples of approximately 300 µl were removed via the jugular catheter before treatment (pre-bleed), and at 0.08, 0.25, 0.5, 1, 2, 4, 6, 24, 48, and 72 hours post injection. The removed blood was replaced with an equal volume of phosphate-buffered saline, followed by injection of approximately 30 µl of heparin as anti-coagulant. Blood samples were immediately placed into serum separator tubes, and processed and analyzed as described above. Urine was sampled at intervals of 0-4, 4-6, 6-10, 10-28, 28-48, and 48-72 hours and filtered through Acrodisc filters (Sterile Acrodisc 13, 0.2 µm, Gelman Sciences).

Concentrations of CRD-Leu$_4$Ile$_{11}$Cys$_{13}$ peptide 3(3-12)[MCP-I] were determined by LC-MS analysis as described above (data for urine samples not shown). Curve-fitting pharmacokinetic analysis was performed with a simulation program (PKAnalyst, MicroMath Scientific Software, Salt Lake City, Utah) employing a basic biexponential two-compartment model with bolus input and first order output (Model #7) following the equation: $Conc_{(Time)} = A \cdot e^{-\alpha \cdot Time} + B \cdot e^{-\beta \cdot Time}$.

Results

LC-MS Analysis

The mass spectrometric parameters were optimized for the detection of CRD-Leu$_4$Ile$_{11}$Cys$_{13}$ peptide 3(3-12)[MCP-I] and CRD-L-Leu$_4$Ile$_{11}$Cys$_{13}$ peptide 3(3-12)[MCP-1] at a flow rate of 500 µl/min, and the ESI positive mass spectra generated showed the triply, doubly, and singly charged molecular ions with m/z 453.6 ([M+3H]$^{3+}$), m/z 680.0 ([M+2H]$^{2+}$), and m/z 1358.7 ([M+H]). The most abundant ions observed throughout the analyzed concentration range were either the [M+3H]$^{3+}$ or the [M+2H]$^{2+}$ ions. Base-line separation of CRD-Leu$_4$Ile$_{11}$Cys$_{13}$ peptide 3(3-12)[MCP-I] and CRD-L-Leu$_4$Ile$_{11}$Cys$_{13}$ peptide 3(3-12)[MCP-1] in rat serum was achieved by reversed-phase HPLC (RP-HPLC) with CRD-Leu$_4$Ile$_{11}$Cys$_{13}$ peptide 3(3-12)[MCP-I] eluting first at 8.33 (±0.04, n=108) minutes and CRD-L-Leu$_4$Ile$_{11}$Cys$_{13}$ peptide 3(3-12)[MCP-1] eluting at 8.94 (±0.05, n=108) minutes. All samples prepared in serum as well as samples isolated from serum of peptide-treated animals exhibited two minor species which pre-eluted CRD-Leu$_4$Ile$_{11}$Cys$_{13}$ peptide 3(3-12)[MCP-I] and CRD-L-Leu$_4$Ile$_{11}$Cys$_{13}$ peptide 3(3-12)[MCP-1]. One of the minor species was formed from CRD-Leu$_4$Ile$_{11}$Cys$_{13}$ peptide 3(3-12)[MCP-I] while the other was formed from CRD-L-Leu$_4$Ile$_{11}$Cys$_{13}$ peptide 3(3-12)[MCP-1]. To account for this reaction, CRD-Leu$_4$Ile$_{11}$Cys$_{13}$ peptide 3(3-12)[MCP-I] was integrated as peaks of the corresponding minor species and CRD-Leu$_4$Ile$_{11}$Cys$_{13}$ peptide 3(3-12)[MCP-I] while CRD-L-Leu$_4$Ile$_{11}$Cys$_{13}$ peptide 3(3-12)[MCP-1] was integrated as the peaks of the corresponding minor species of CRD-L-Leu$_4$Ile$_{11}$Cys$_{13}$ peptide 3(3-12)[MCP-1] and CRD-L-Leu$_4$Ile$_{11}$Cys$_{13}$ peptide 3(3-12)[MCP-1]. No interfering peaks were detected in the blank serum samples.

Quantitative Analysis

Initial attempts to quantify known amounts of CRD-Leu$_4$Ile$_{11}$Cys$_{13}$ peptide 3(3-12)[MCP-I] spiked into deproteinated rat serum samples by single ion monitoring of the doubly or triply charged species, or by selected ion monitoring detecting the product ions generated from the doubly or triply charged species, yielded highly variable results with a RSD >20%. When applying SIM to integrate the summed ion currents of the singly, doubly, and triply charged species of the same samples, the reproducibility was significantly improved to a RSD <15% (data not shown). Hence, levels of CRD-Leu$_4$Ile$_{11}$Cys$_{13}$ peptide 3(3-12)[MCP-I] in rat serum were quantified by LC-MS in the SIM mode. In absence of a stable isotope, the diastereomer CRD-L-Leu$_4$Ile$_{11}$Cys$_{13}$ peptide 3(3-12)[MCP-1] was included as internal standard. The levels of the three least concentrated calibration standards analyzed containing 0.008, 0.04, and 0.08 µg/ml of CRD-Leu$_4$Ile$_{11}$Cys$_{13}$ peptide 3(3-12)[MCP-I] in serum, respectively, were not sufficiently detectable and the LLOQ was determined as <0.2 µg/ml (2 ng per injection). There was a RSD of less than 12% over the calibration range and a RE within ±11% for intra-day precision and accuracy. The response for the concentration ratios of CRD-Leu$_4$Ile$_{11}$Cys$_{13}$ peptide 3(3-12)[MCP-I] to CRD-L-Leu$_4$Ile$_{11}$Cys$_{13}$ peptide 3(3-12)[MCP-1] in deproteinated rat serum plotted against the concentration ratios of CRD-Leu$_4$Ile$_{11}$Cys$_{13}$ peptide 3(3-12)[MCP-I] to CRD-L-Leu$_4$Ile$_{11}$Cys$_{13}$ peptide 3(3-12)[MCP-1] was linear over a range of 200 ng/ml to 200 µg/ml of CRD-Leu$_4$Ile$_{11}$Cys$_{13}$ peptide 3(3-12)[MCP-I] ($r^2$=0.9996, slope 0.8488±0.005843. The curve's Y-intercept of 0.02653±0.02416 indicated an insignificant amount of interfering impurities.

As the diastereomers present the same protonation sites, the ionization efficiencies were expected to be similar. However, the serum calibration curves' slope was calculated as 0.8488 (±0.005843) suggesting a difference in sensitivities, which may be the result of a difference in the competition for charge between CRD-Leu$_4$Ile$_{11}$Cys$_{13}$ peptide 3(3-12)[MCP-I] and CRD-L-Leu$_4$Ile$_{11}$Cys$_{13}$ peptide 3(3-12)[MCP-1].

Pharmacokinetic Analysis

The method was applied to determine the serum profiles of five rats treated with a single i.v. bolus dose of 8.8 mg of CRD-Leu$_4$Ile$_{11}$Cys$_{13}$ peptide 3(3-12)[MCP-I]. With exception of one sample collected from rat #5 at 15 minutes post-injection, which exhibited a RSD of 17.7%, the analysis of all rat samples showed good precision with a RSD lower than 10%. The resulting five animals' serum concentration curves paralleled each other closely with increasing % STDEV at the later sampling time points approaching completion of elimination. With serum concentrations declining below LLOQ within four hours, CRD-Leu$_4$Ile$_{11}$Cys$_{13}$ peptide 3(3-12)[MCP-I] exhibited very rapid elimination kinetics suggesting an average serum half-life time of approximately 10 minutes. The means of all serum data sets were processed through a curve-fitting pharmacokinetic simulation program (PKAnalyst) to assess serum pharmacokinetics. When employing a basic biexponential two-compartment model with bolus i.v. input and first order output, generated and predicted data were in good agreement ($r^2$=0.9999). Using the quantitative method described above, urine levels of CRD-Leu$_4$Ile$_{11}$Cys$_{13}$ peptide 3(3-12)[MCP-I] were measured in samples collected at several time points post-injection to generate a cumulative urinary excretion profile. A total of about 70% of the administered dose was recovered over 24 hours, and greater than 55% was excreted over the first two hours. This high rate of urinary excretion is consistent with the rapid elimination of CRD-Leu$_4$Ile$_{11}$Cys$_{13}$ peptide 3(3-12)[MCP-I] from the vascular compartment and in agreement with the pharmacokinetic profiles of small, ionic, and highly polar molecules.

Discussion

ESI positive mass spectra of biomolecules, such as peptides and proteins, usually show a characteristic pattern of multiply charged species due to the presence of a number of basic sites accessible to protonation. The intensity ratio of the ions in a series of different charge states can fluctuate considerably, which renders the quantitation of multiply charged compounds by LC-MS using single ion or selective reaction monitoring difficult. When using SIM to generate a total area under the curve from the summed ion currents of all detected charge states, the reproducibility of the quantitative data can be notably improved. Carrascal et al., *J. Pharm. Bio. Ana.*, 17, 1129 (1998); Clarke et al., *FEBS Lett.*, 430, 419 (1998).

Along with a rugged analytical method, quantitative measurements of high accuracy further require the inclusion of a suitable internal standard. For mass spectrometric analysis, an ideal internal standard is analytically distinguishable from the analyte, yet, exhibits nearly identical physical and chemical properties to correct for analyte loss during sample preparation, for matrix effects, and for drifting ion currents of the mass spectrometer. One class of compounds that meets these criteria very well is stable isotope analogs. However, stable isotope analogs are often difficult to synthesize, expensive, and frequently contain isotopic impurities that interfere with the analysis. Structurally related molecules that differ in molecular weight as well as physical and chemical properties are often used as internal standards when stable isotopes are not readily available. For quantitative peptide analysis by LC-ESI/MS for instance, peptide isoforms have been used as internal standards (Carrascal et al., 1998). However, in this case the inclusion of two internal standards was necessary to compensate for variable recoveries after sample processing as well as instrumental inconsistencies.

Like stable isotope analogs, some steroisomers, including atropisomers and diastereomers, can be analytically distinguished despite similar physical and chemical properties (March, *Advanced Organic Chemistry, Reactions, Mechanisms, and Structure*, pp. 94-116, John Wiley & Sons, Inc., NY (1992)) and, therefore, may qualify well as internal standards. To further improve the reproducibility of the quantitative ESI/MS data, SIM can be applied to generate a total area under the curve from the summed ion currents of all detected charge states.

The peptide diastereomers CRD-Leu$_4$Ile$_{11}$Cys$_{13}$ peptide 3(3-12)[MCP-I] and CRD-L-Leu$_4$Ile$_{11}$Cys$_{13}$ peptide 3(3-12) [MCP-1] have the same amino acid composition, sequence, and hydrophobicity, thus, were expected to partition and react similarly during sample preparation. While RP-HPLC afforded base-line separation throughout a concentration range spanning three log scales, the diastereomers could be analyzed using the same mass spectrometric method as they show identical ESI mass spectra. In result, the calibration curve generated showed good precision and accuracy throughout a broad dynamic range. Application of this method to the quantitative analysis of CRD-Leu$_4$Ile$_{11}$Cys$_{13}$ peptide 3(3-12)[MCP-I] in serum samples collected from treated rats showed good reproducibility, and predicted serum pharmacokinetics were in agreement with the pharmacokinetic profiles of small, ionic, and highly polar molecules.

In conclusion, the diasteromer CRD-L-Leu$_4$Ile$_{11}$Cys$_{13}$ peptide 3(3-12)[MCP-1], which was readily synthesized, proved a suitable substitute for a stable isotope analog as internal standard. Moreover, interference due to partial overlap of co-eluting compounds or isotopic impurities introduced with stable isotope analogs did not present a problem. Hence, a facile and reliable quantitation of a multiply charged peptide in biological fluids was achieved using LC-MS in the SIM mode combined with the inclusion of a diasteromer as internal standard.

Example 14

Inhibition of a T Cell-Dependent Antibody Response

Figure 36A:
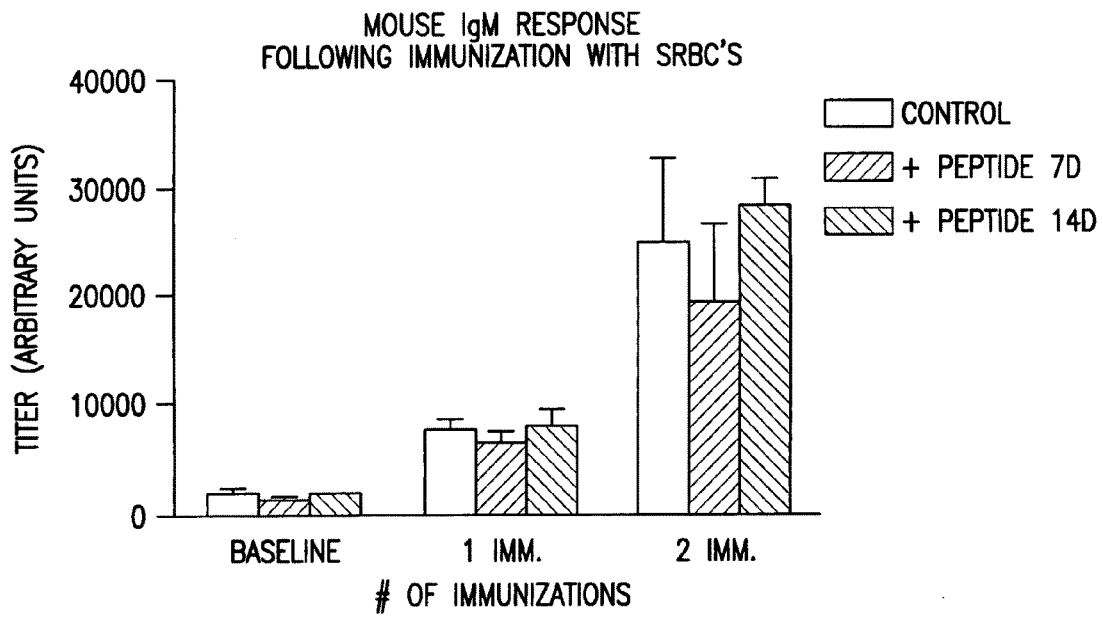
FIG. 36 depicts the inhibition of T cell-dependent antibody response in mice by CRD-Leu$_4$Ile$_{11}$Cys$_{13}$peptide 3(3-12) [MCP-1].
Figure 36B:
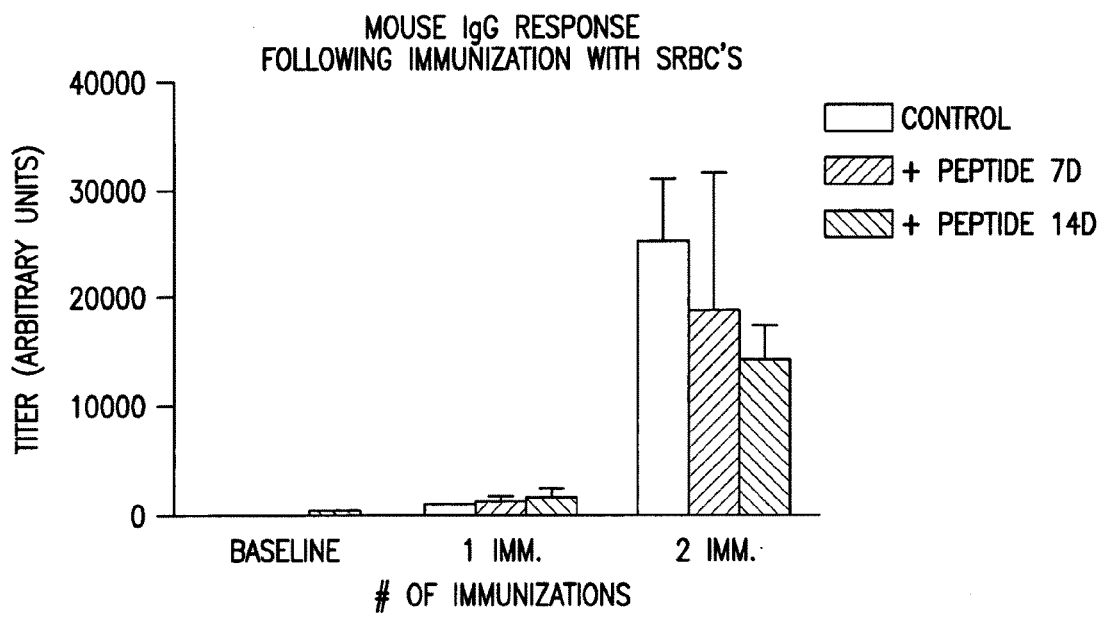

Treatment with CRD-Leu$_4$Ile$_{11}$Cys$_{13}$ peptide 3(3-12) [MCP-1] prevented a T cell-dependent antibody response but not a T cell-independent antibody response in mice immunized with sheep red blood cells (FIG. 36).

Example 15

Exemplary Peptide 3 Sequences

Preferred peptide 3 agents of the invention include reverse sequences made with D-amino acids, e.g., aqiwkqkpdlc, cqiwkqkpdlc, dqiwkqkpdlc, eqiwkqkpdlc, fqiwkqkpdlc, gqiwkqkpdlc, hqiwkqkpdlc, iqiwkqkpdlc, kqiwkqkpdlc, lqiwkqkpdlc, mqiwkqkpdlc, nqiwkqkpdlc, pqiwkqkpdlc, qqiwkqkpdlc, rqiwkqkpdlc, sqiwkqkpdlc, tqiwkqkpdlc, vqiwkqkpdlc, wqiwkqkpdlc, yqiwkqkpdlc, as well as agents having a L-amino acid in each of the bolded positions, e.g., Cqiwkqkpdlc. It is also preferred that the reverse sequences are cyclized. Other preferred peptide 3 agents of the invention include, but are not limited to, those which have one of the 19 D-amino acids in the second position of peptide3(3-12) [MCP-1], e.g., caiwkqkpdlc, cciwkqkpdlc, cdiwkqkpdlc, and cyiwkqkpdlc, as well as agents having a L-amino acid in the second position of peptide3(3-12)[MCP-1], e.g., cQiwkqkpdlc. Other preferred peptide 3 agents of the invention have one of the 19 D-amino acids in the each of the positions of peptide3(3-12)[MCP-1], as well as agents having a L-amino acid in those positions, e.g., cqawkqkpdlc, cqywkqkpdlc, cqlwkqkpdlc, cqiwkqkpdla, cqiwkqkpdlc, cqiwkqkpdld, cqiwkqkpoly, and andcqiwkqkpdlC. The entire series of peptide 3 variants are tested for their chemokine inhibitory activity and those which are positive are tested for their potency (ED$_{50}$).

Example 16

Inhibition of MCP-1 Binding to Heparin-Coated Agarose Beads

Figure 42:
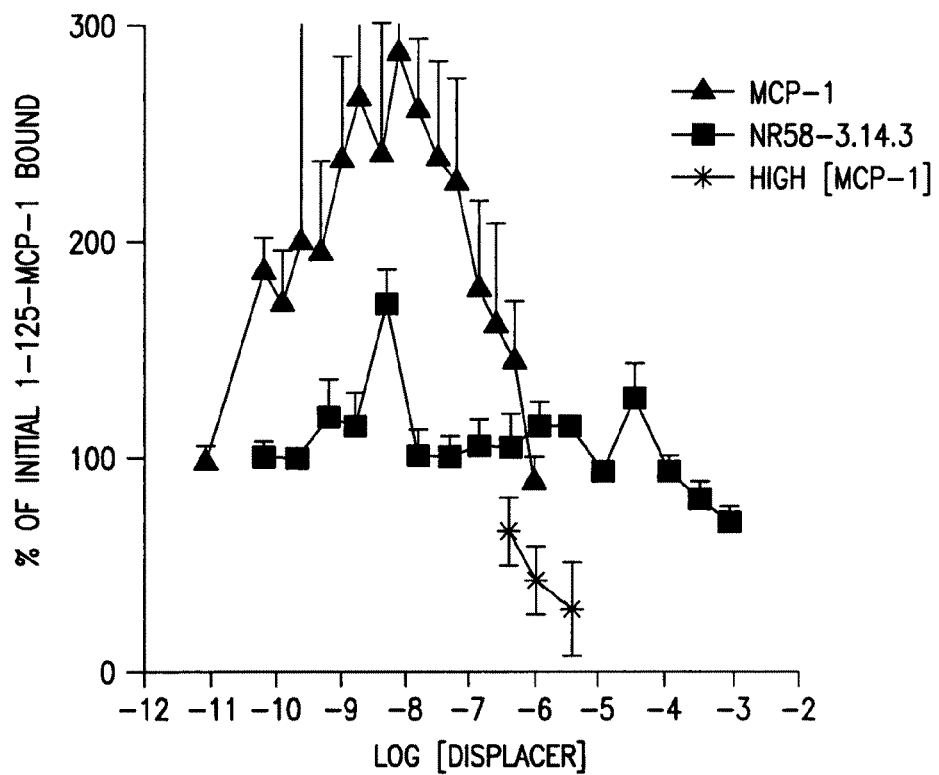
FIG. 42 depicts a competitive assay using $^{125}$I-MCP-1 in the presence of MCP-1 or CRD-Leu$_4$Ile$_{11}$Cys$_{13}$ peptide 3(3-12)[MCP-1].

Chemokines bind to glycosaminoglycans on the cell surface, which may facilitate chemokine receptor binding and subsequent signaling. To determine if CRD-Leu$_4$Ile$_{11}$Cys$_{13}$ peptide 3(3-12)[MCP-1], a pan-chemokine inhibitor, would competitively inhibit $^{125}$I-MCP-1 from binding to heparin-coated agarose beads, a protocol described by Hoogerwerf et al. (*Biochemistry*, 36, 13570 (1997)) was employed. Competition with increasing concentrations of approximately 110-1 to 10$^{-7}$ M MCP-1 resulted in an increase in bound $^{125}$I-MCP-1, consistent with MCP-1 multimer formation. This was followed by a monophasic displacement curve at concentrations of approximately 10$^{-7}$ to 10$^{-5}$ M MCP-1. In contrast, CRD-Leu$_4$Ile$_{11}$Cys$_{13}$ peptide 3(3-12)[MCP-1] at concentrations from 10$^{-11}$ to 10$^{-4}$ M did not result in displacement of MCP-1 from heparin-coated agarose beads, and concentrations of CRD-Leu$_4$Ile$_{11}$Cys$_3$ peptide 3(3-12)[MCP-1] as high as 10$^{-3}$ M failed to inhibit MCP-1 binding to heparin to the same degree as MCP-1. This suggests that CRD-Leu$_4$Ile$_{11}$Cys$_{13}$ peptide 3(3-12)[MCP-1] does not function as a chemokine inhibitor through competitive inhibition of heparin binding sites at physiologically relevant concentrations (FIG. 42).

Example 17

Synthesis of 3-(undec-10-enoylamino)-dihydropyridine-2,6(1H,2H)-dione (a Compound of Formula XV wherein R$_1$ is 9-decenyl; R$_2$ is Hydrogen, R$_3$ and R$_4$ Together with the Atoms to which they are Attached are a Six Membered Heterocyclic Ring Comprising Five Carbon Atoms and N(H); R$_5$ is Hydrogen; and the Center Marked by * has the (S) Configuration)

L-Glutamine (14.62 g, 0.1 mol) and KOH (11.2 g, 0.2 mol) were dissolved in water (200 mL) at 20° C. A solution of 10-undecenoyl chloride (20.3 g, 0.1 mol) in THF (200 mL) was then added over 10 minutes. The reaction was stirred for 16 hours at 20° C. and was then reduced in vacuo to a volume of approximately 250 mL. Concentrated HCl (circa 12M) was added dropwise until the solution was pH 1. The white solid precipitate was collected by filtration. This solid was washed with water (100 mL) and diethyl ether (100 mL). The solid was then dissolved in refluxing toluene (500 mL) and the excess water present was removed by distillation at ambient pressure using a Dean-Stark trap. The solution was then allowed to cool to 20° C. After 16 hours, the white solid precipitate was collected via filtration and recrystallized from EtOAc (500 mL). This solid was dried in vacuo to give N-α-undec-10-enoyl-glutamic acid (9.36 g, 30%) as a white powder.

N-α-Undec-10-enoyl-glutamic acid (8.00 g, 25.6 mmol) was dissolved in a mixture of THF (200 mL) and DMF (20 mL) and the solution was cooled to 0° C. N-Hydroxysuccinimide (2.94 g, 25.6 mmol) was added, followed by DCC (5.26 g, 25.6 mmol). The reaction was stirred at 0° C. for 1 hour, and was then allowed to warm to 25° C. and was stirred at this temperature for 24 hours. The reaction was filtered, and the filtrate was partitioned between EtOAc (400 mL) and 0.5 M $HCl_{(aq)}$ (300 mL). The organic layer was washed twice more with 0.5 M $HCl_{(aq)}$ (300 mL), dried over $Na_2SO_4$ and reduced in vacuo to give a white solid which was chromatographed ($SiO_2$/EtOAc) to give a white powder. This material was recrystallized from EtOAc to give the title compound as a white crystalline solid (3.14 g, 42%).

Example 18

Alternate Synthesis of 3-(undec-10-enoylamino)-dihydropyridine-2,6(1H,2H)-dione (S)-3-(tert-Butoxycarbonylamino)glutarimide (a compound of formula XV wherein $R_1$ is tert-butoxy; $R_2$ is hydrogen, $R_3$ and $R_4$ together with the atoms to which they are attached are a six membered heterocyclic ring comprising five carbon atoms and N(H); $R_5$ is hydrogen; and the center marked by * has the (S) configuration; 228 mg, 1 mmol) was dissolved in $CH_2Cl_2$ (2 mL) and the solution was cooled to 0° C. Trifluoroacetic acid (1 mL) was added dropwise, and the reaction was stirred for 1 hour. The reaction was then reduced in vacuo to give crude (S)-glutarimidyl-3-ammonium trifluoroacetate as a thick oil. This material was dissolved in DMF (1.5 mL) and (i-Pr)$_2$NEt (1.5 mL), and the resulting solution was added to a solution of 10-undecenoic acid (1 mmol) and BOP (442 mg, 1 mmol) in DMF at 25° C. This reaction was stirred for 24 hours, and was then partitioned between EtOAc (30 mL) and 0.5 M $HCl_{(aq)}$ (20 mL). The organic layer was then washed twice more with 0.5 M $HCl_{(aq)}$ (20 mL), dried over $Na_2SO_4$ and reduced in vacuo to give a white solid which was chromatographed ($SiO_2$/EtOAc) to give the title compound.

Example 19

Synthesis of Yohimbamide (Y-II; a Compound of Formula (XIV) wherein $R_1$ is Amino; $R_2$ is Hydroxy; $R_3$ is Hydrogen; $R_4$ is Hydrogen; and n is 0)

Yohimbine (2 g) was added to freshly prepared sodamide (prepared by adding 3.6 g of sodium metal to approximately 100 ml liquid ammonia under reflux). The mixture was stirred for 5-6 hours, then the condenser was removed and the liquid ammonia allowed to vaporize. The residual material was dissolved in a mixture of warm water and ethyl acetate (~1:1). After shaking, the solvents were separated and the ethyl acetate was removed using a rotary evaporator. The resulting orange powder was dried in vacuo to give the title Yohimban-17-amide (Y-II; 1.8 g; 90%), the structure of which was confirmed by NMR.

Example 20

Synthesis of lysergyl-glutamine (L-II, a Compound of Formula XVII wherein $R_1$ is Methyl; and $R_2$ is Glutamine Linked Through the Amine Nitrogen to Form an Amide)

Lysergic acid (2 g) was dissolved in dry DMF and activated by addition of 1.8 g PyBOP. The reaction was stirred at room temperature for 1 hour, and 1.4 g of Fmoc-L-glutamine was added. After 16 hours, the reaction mixture was filtered and the filtrate partitioned between ethyl acetate (400 ml) and 0.5 M sodium hydroxide (200 ml). The organic layer was washed twice more with alkali, dried over sodium sulphate, and reduced in vacuo to give a white solid, which was recrystallized from ethyl acetate to give Lysergyl-glutamine (L-II; 1.1 g; 55%) as a white crystalline solid. Compound L-II was found to possess solubility properties similar to those of valium. Accordingly, L-II can conveniently be formulated for administration in combination with carriers that are known to be useful for formulating valium. For example, L-II can be administered in a pharmaceutical composition comprising a suitable polyhydroxy carrier (e.g. polypropylene glycol). The compound L-II can also be administered in a pharmaceutical composition comprising a polyhydroxy carrier and a suitable alcohol (e.g. a composition comprising about 10%-50% polypropylene glycol and about 5%-15% ethanol; preferably about 40% polypropylene glycol and 10% ethanol).

Example 21

In Vitro and In Vivo Evaluation of Peptide Analogs

Figure 43:
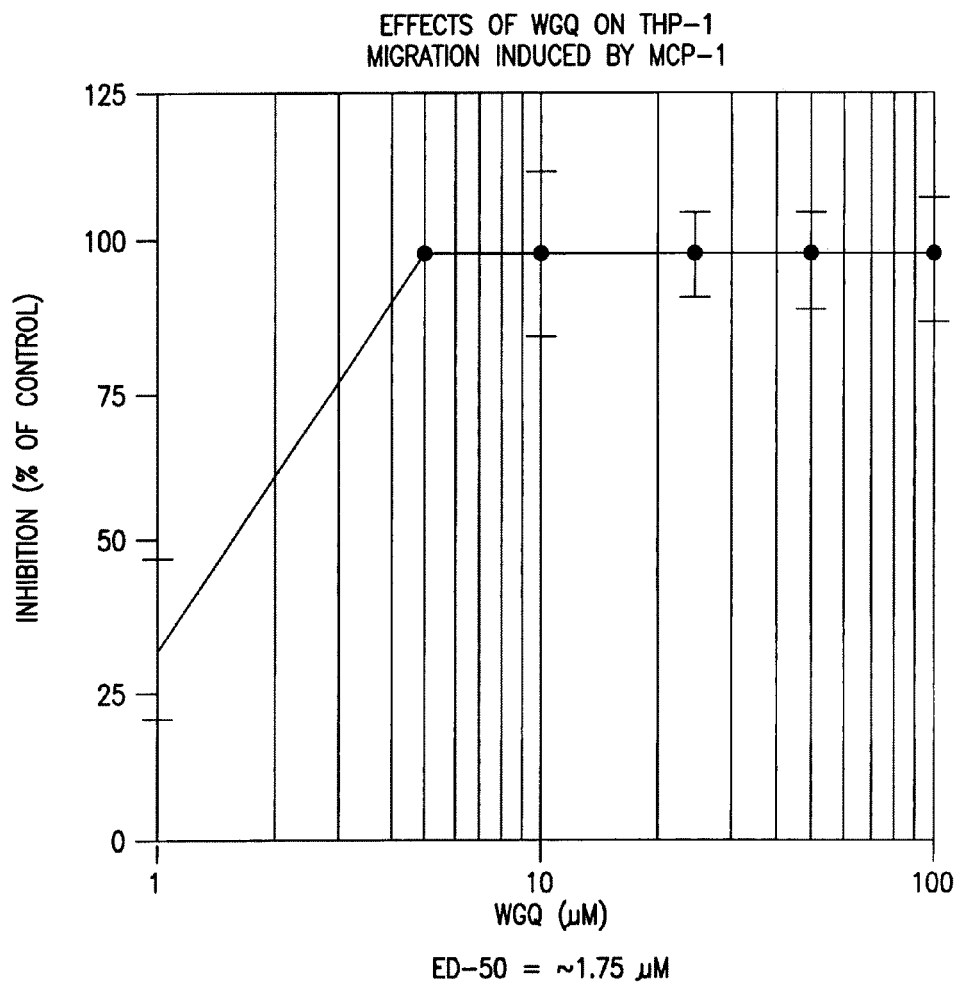
FIG. 43 shows the effect of WGQ on THP-1 migration.

WGQ inhibits THP-1 migration induced by MCP-1 with an $ED_{50}$ of about 1.75 μM (FIG. 43). Fourteen analogs of WGQ were synthesized and evaluated in a transwell THP-1 migration assay (FIG. 43). A structurally related compound, thalidomide, was also evaluated. All compounds were reconstituted in DMSO.

FIG. 43 shows the effect of these compounds at 100 μM and the percentage inhibition of THP-1 migration induced by MCP-1. For example, the N-undec-10-enoyl series inhibited THP-1 migration induced by MCP-1 back to control levels, while the benzoyl series was inactive at 100 μM (less than 40% inhibition). Interestingly, thalidomide at 100 μM also inhibited THP-1 migration induced by MCP-1.

For compounds which inhibited THP-1 migration by greater than 50%, an $ED_{50}$ was determined (FIG. 45). One compound N-undec-10-enoyl aminotetrahydropyridinedione (NR58,4 or A-I hereinafter) inhibited THP-1 migration with a more than ten-fold greater potency (1-100 nM) than WGQ. The majority of the other compounds which inhibited THP-1 migration by greater than 50%, have an $ED_{50}$ of about 10 to 20 μM, with the exception of the benzyl-glutamide analogs which have an $ED_{50}$ of about 40 μM (FIG. 45). Thalidomide had an $ED_{50}$ of approximately 50 μM.

To determine whether NR58,4 and thalidomide reduced inflammation in the murine sub-lethal endotoxemia model, 36 female CD-1 adult mice were divided into groups of 6 (Table 12). Each animal received a pretreatment (200 μl) by sub-cutaneous injection into the scruff at the back of the neck. All pre-treatment agents were administered at 1 mg per animal (approximately 40-50 mg/kg). After 30-45 minutes, animals in groups 2 through 6 received 750 µg bacterial lipopolysaccharide (LPS) in 300 µl PBS by intraperitoneal injection. Animals in group 1 received PBS vehicle alone.

After 3 hours (2 hours post-LPS), all animals were sacrificed by terminal anaesthesia followed by cardiac puncture. Approximately 1 ml of blood was withdrawn and serum was prepared. Blood was allowed to clot at room temperature for approximately 2 hours, then the clot was spun out and the serum aliquoted and stored at −20° C. until tested. Serum from each animal was assayed in duplicate for TNF-α using the Quantikine M kit (R&D Systems) calibrated by interpolation of the standard curve.

Figure 46:
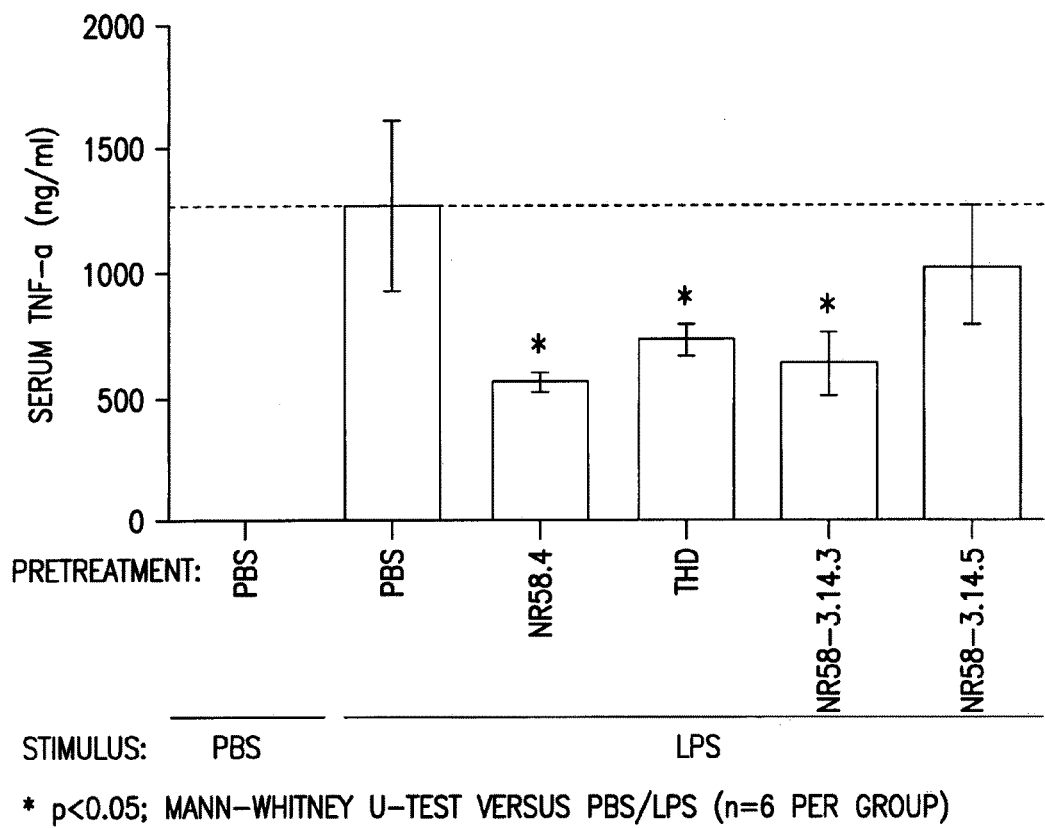
FIG. 46 shows serum TNF-α levels in mice treated with various agents or PBS and then exposed to LPS. All agents were administered subcutaneously 45 minutes prior to LPS (1 mg/mouse) administration. THD=thalidomide. Data is pooled from three replicate experiments. NR58,4 was administered as the potassium salt.
Figure 47A:
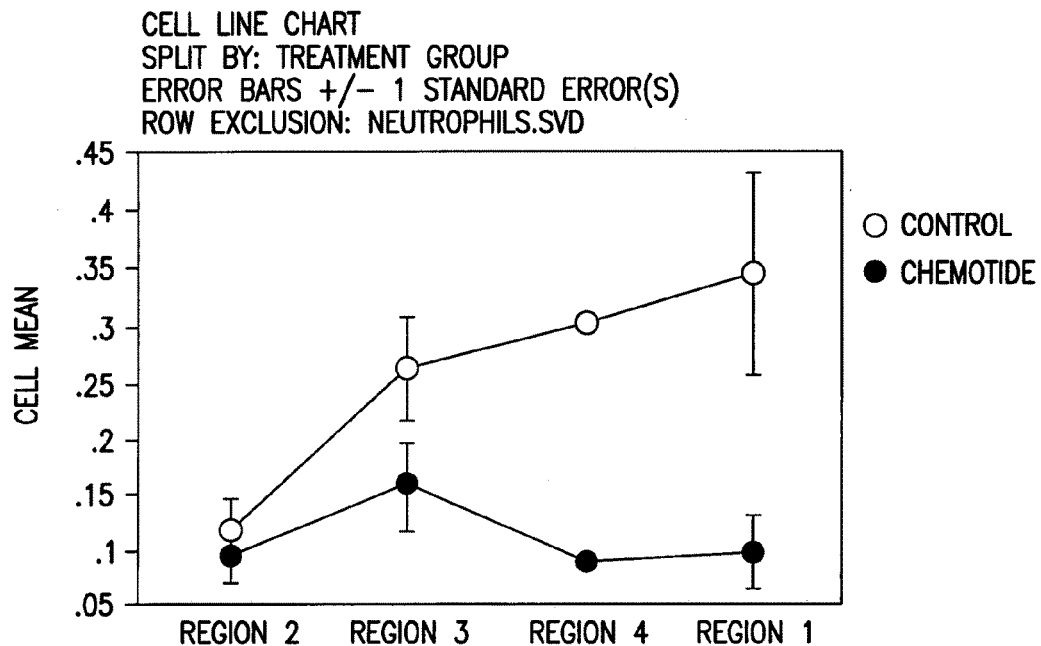
FIG. 47 shows neutrophil data from a rat model for stroke (see FIG. 34).
Figure 47B:
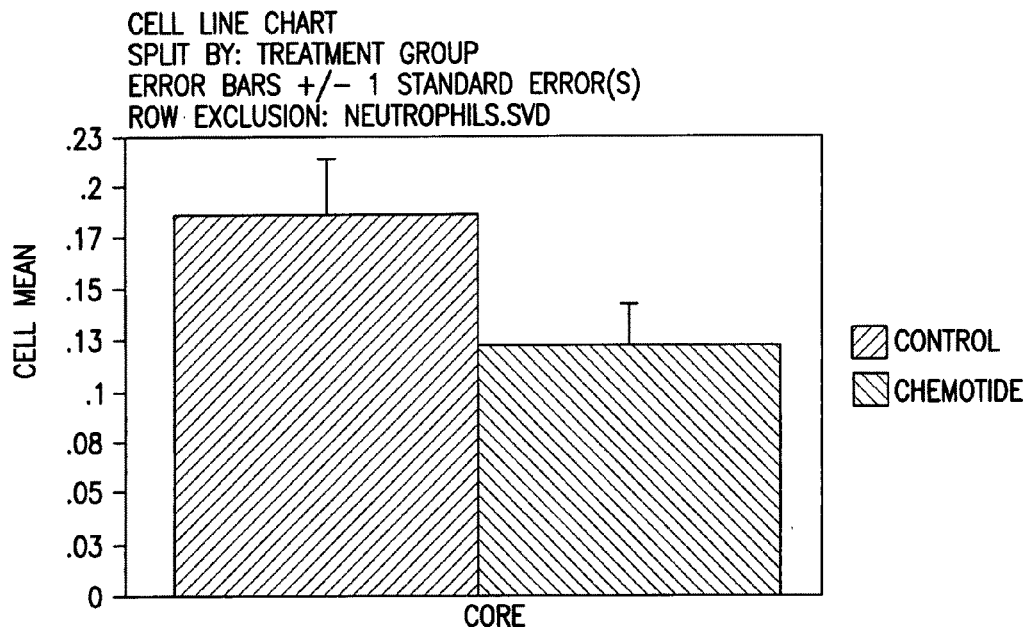
Figure 47C:
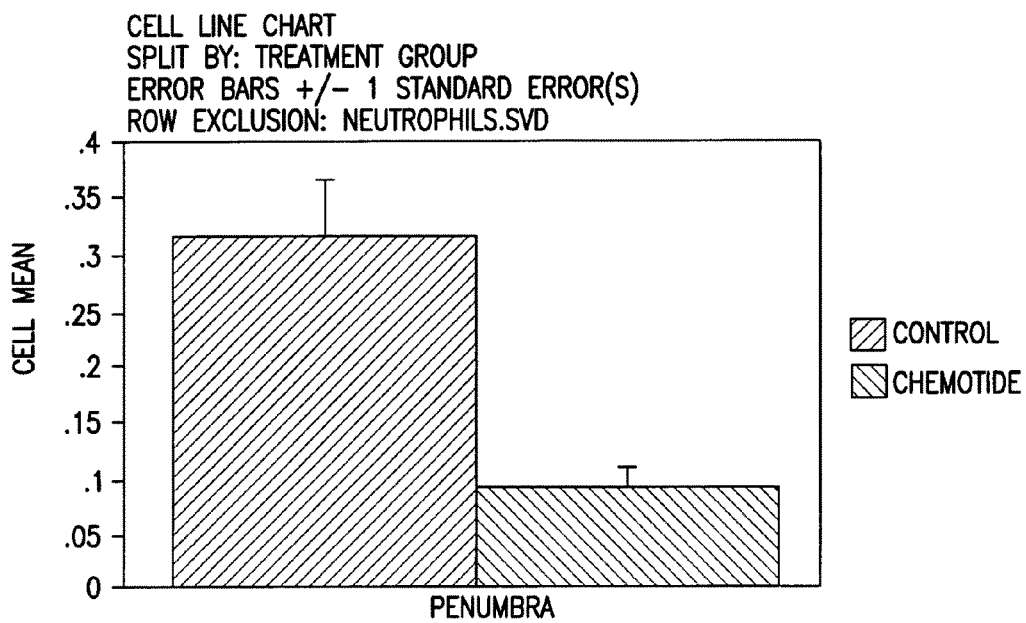
Figure 47D:
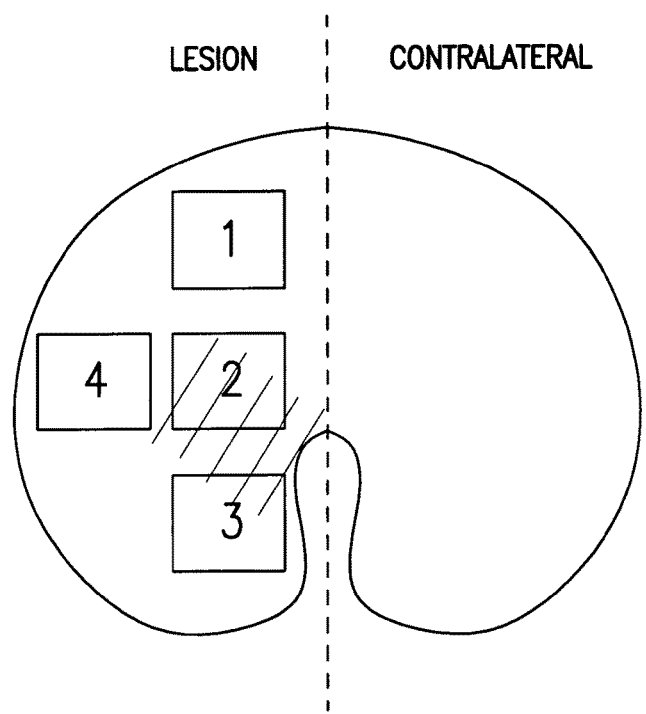
Figure 48:
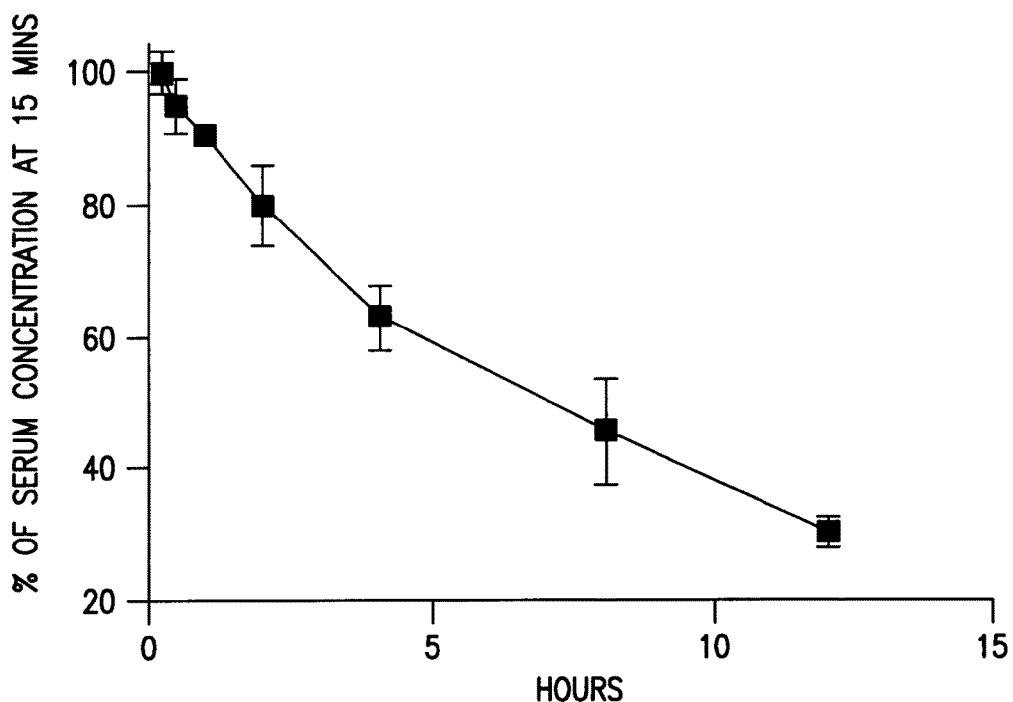
FIG. 48 depicts levels of CRD-Leu$_4$Ile$_{11}$Cys$_{13}$ peptide 3(3-12)[MCP-1]-glucoside in serum.

There was very little TNF-α in the unchallenged animals (<10 pg/ml), but massive stimulation in response to LPS (about 1500 pg/ml) (FIG. 46 and Table 12). A dose-dependent inhibition of this LPS stimulation was observed with CRD-Leu$_4$Ile$_{11}$Cys$_{13}$ peptide 3(3-12)[MCP-1]. As expected, the negative control compound (inactive D-ala derivative) had no effect. The dose response for CRD-Leu$_4$Ile$_{11}$Cys$_{13}$ peptide 3(3-12)[MCP-1] gives a half-maximal dose of approximately 100 µg per animal. The potassium salt of NR58,4 at 1 mg per animal reduced TNF-α by just over 60%. However, NR58,4 suppressed TNF-α release generation to an equal or greater extent than CRD-Leu$_4$Ile$_{11}$Cys$_{13}$ peptide 3(3-12)[MCP-1], suggesting that NR58,4 which has similar potency as a chemokine inhibitor in vitro may also have similar anti-inflammatory properties in vivo.

The mice showed no obvious acute toxicity during treatment with the drug, although irritation was noted at the site of injection of the NR58,4, which may be due to the relatively high pH of the injected solution (the potassium salt was used).

Thus, NR58,4 is at least as effective an anti-inflammatory agent as CRD-Leu$_4$Ile$_{11}$Cys$_3$ peptide 3(3-12)[MCP-1] (it is active at <100 nM and likely ≦10 nM). Moreover, NR58,4, as a lipophilic molecule, may have a substantially longer residence time in vivo. Interestingly, thalidomide was also effective at lowering TNF-α levels in vivo, although it is questionable as to whether this effect is mediated through chemokine inhibition, since thalidomide is more than 4 orders of magnitude less potent as a chemokine inhibitor in vitro compared with NR58,4.

TABLE 12

| | Pretreatment/Treatment | TNF-α (pg/ml) |
|---|---|---|
| GROUP 1 | PBS/PBS | 4 ± 1 |
| GROUP 2 | PBS/LPS | 1348 ± 125 |
| GROUP 3a | 3.14.3 (100 µg)/LPS | 1270 ± 270 |
| GROUP 3b | 3.14.3 (1 mg)/LPS | 845 ± 110* |
| GROUP 4 | 3.14.4 (1 mg)/LPS | 1167 ± 305 |
| GROUP 5 | NR58.4/LPS | 552 ± 25* |
| GROUP 6 | Thalidomide/LPS | 793 ± 40* |

*= p < 0.05 (Student's t-test on log-transformed data)

The ED$_{50}$ (the concentration required to inhibit by 50% the migration induced by MCP-1 in the chemotaxis assay) for a number of agents is summarized in Table 13.

TABLE 13

| Compound | ED$_{50}$ v MCP-1 |
|---|---|
| Thalidomide | 50 µM |
| Yohimbine | 30 nM |

TABLE 13-continued

| Compound | ED$_{50}$ v MCP-1 |
|---|---|
| α-Yohimbine | 500 nM |
| Glutethimide | 50 µM |
| Phenytoin | 10 µM |
| Oxymetazoline | 75 µM |
| Yohimbamide (Y-II) | 0.5 nM |
| NR58.4 (A-I) | 2 nM |
| Lysergyl-glutamine (L-II) | 5 nM |

Figure 51A:
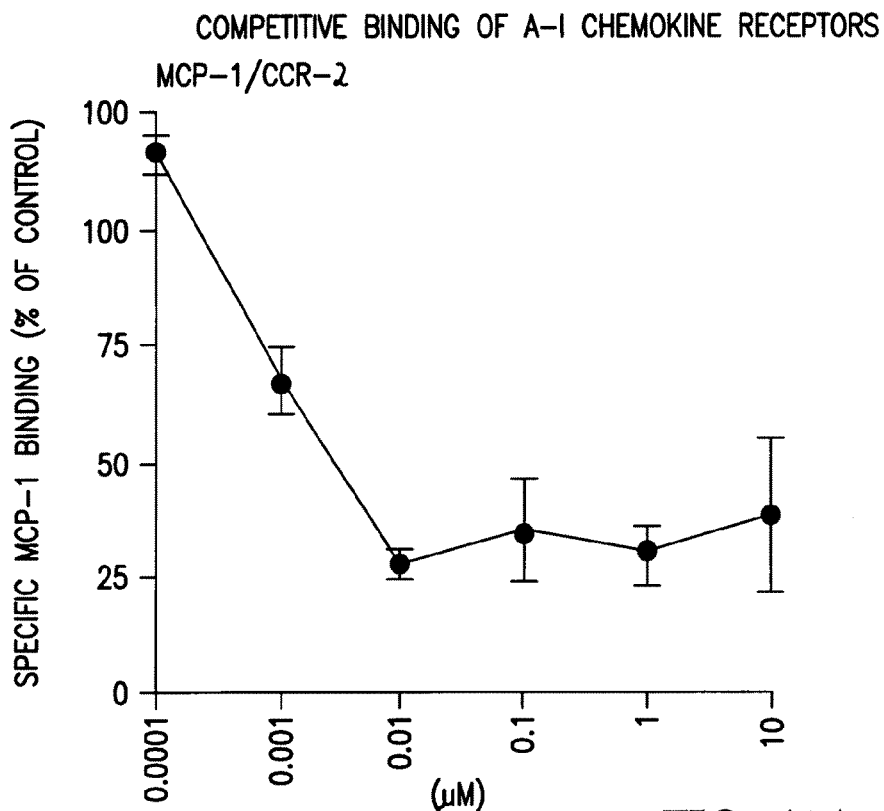
FIG. 51 depicts the competitive binding of A-I to chemokine receptors in the presence of chemokine A) MCP-1 and CCR-2, and B) IL-8 and CXCR-2.
Figure 51B:
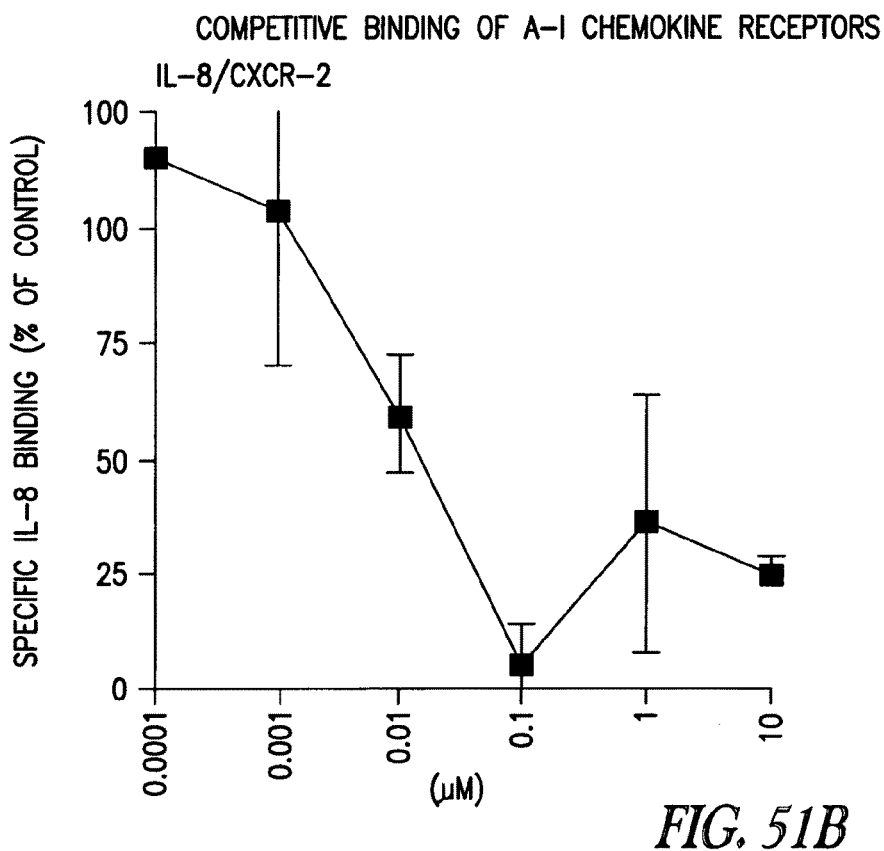

For each agent tested, a single "wide-range" assay was performed testing concentrations of the agent between 100 pM and 100 µM (FIG. 51) and MCP-1, RANTES or MIP-1α. Similar data has been generated for SDF-1α and IL-8 (see Table 14). Once an estimate of the working range has been obtained in these "wide-range" assays, "narrow-range" assays are performed 2 logs either side of the estimated ED$_{50}$ (FIG. 51). This is repeated three times to obtain an accurate estimate of the functional ED$_{50}$.

Example 22

Characterization of the Binding Specificity of the Agents of the Invention

Materials and Methods

For α2-adrenoreceptor binding, membranes (A-213, RBI/Sigma)) are diluted into binding buffer (75 mM Tris pH 7.4, 12.5 mM MgCl$_2$ and 2 mM EDTA). For example, 10 µl of membranes are diluted in 500 µl of binding buffer (i.e., 1:50 dilution), which is aliquoted into tubes. Cold competitor or test competitor is added, for example, 5 µl of 1 mM oxymetazoline (O-110, RBI/Sigma, 1 mM stock in MilliQ water). Radioligand is then added (3H-RS-79948-197, TRK 1036, Amersham, 50 µCi in 250 µl, 2.1 µmM at 95 Ci/mmol). For competition studies, 1 nM is used. A 100× stock (i.e., 100 nM) is made by diluting the commercial stock 1:20 in binding buffer, and 5 µl is added to every tube. Control tubes have radioligand but no membranes. The mixtures are vortexed, then spun very briefly. The mixtures are then incubated for 1 hour at 27° C. in a water bath. The mixture is filtered through GF/C filters over a vacuum. Each filter is pre-soaked in polyethyleneimine (0.3% in water; add 1 ml of 10% stock (P-261; RBI/Sigma) to 33 ml of MilliQ water). The tubes are washed with 2-3 ml of wash buffer (50 mM Tris pH 7.4) and the wash filtered. The filters are then rinsed with 3×5 ml of wash buffer, air dried, placed in a scintillation vial and 4.5 ml of scintillant added. The activity on the filter is then determined.

For 5HT1a serotonin receptors, membranes (S-160, RBI/Sigma) are diluted into binding buffer (50 mM Tris pH 7.4 10 mM MgCl$_2$ and 0.5 mM EDTA, with ascorbate at 1 mg/ml added immediately before use), e.g., 10 µl of membranes in 500 µl assay volume (i.e., 1:50 dilution). Cold competitor or test competitor is then added, e.g., 5 µl of 100× stock solution such as 5 µl of 1 mM oxymetazoline. Radioligand (3H-8-OH-DPAT, TRK850, Amersham, 250 µCi in 250 µl; 4.5 µM at 222 Ci/mmol) is then added. For competition studies, ligand is employed (e.g., a 100× stock (i.e., 150 nM) is prepared by diluting the commercial stock 1:30 in binding buffer). Control tubes are prepared which have radioligand but no membranes. The tubes are vortexed then spun briefly. The mixtures are incubated for 1 hour at 4° C. The mixtures are filtered through GF/C filters pre-soaked in polyethyleneimine (0.3% in MilliQ water). The tubes are washed with 2-3 ml of wash buffer and filtered. The filter is washed with 3×5 ml of wash buffer, and air dried. 4.5 ml of scintillant is added to the dried filter in a scintillation vial and the filter counted on a tritium channel.

For dopamine receptor binding, membranes (D-179, RBI/Sigma) are diluted into binding buffer (75 mM Tris pH 7.4, 12.5 mM $MgCl_2$ and 2 mM EDTA). For example, 10 μl of membranes are diluted in 500 μl of binding buffer (i.e., 1:50 dilution), which is aliquoted into labelled tubes. Cold competitor or test competitor is added, (e.g., 5 μl of 100× stock solution; 5 μl of 1 mM haloperidol solution (H-100, RBI/Sigma in DMSO). Radioligand is then added (3H-Spiperone, TRK 818, Amersham, 250 μCi in 250 μl, 10.5 μM at 95 Ci/mmol). For competition studies, 0.5 nM is used. A 100× stock (i.e., 50 nM) is made by diluting the commercial stock 1:210 in binding buffer, and 5 μl is added to every tube. Control tubes have radioligand but no membranes. The mixtures are vortexed, then spun very briefly. The mixtures are then incubated for 1 hour at 27° C. in a water bath. The mixture is filtered through GF/C filters over a vacuum. Each filter is pre-soaked in polyethyleneimine (0.3% in water; add 1 ml of 10% stock (P-261; RBI/Sigma) to 33 ml of MilliQ water). The tubes are washed with 2-3 ml of wash buffer (50 mM Tris pH 7.4) and the wash filtered. The filters are then rinsed with 3×5 ml of wash buffer, air dried, placed in a scintillation vial and 4.5 ml of scintillant added. The activity on the filter is then determined.

For opioid receptor binding, membranes (0-116, RBI/Sigma) are diluted into binding buffer (75 mM Tris pH 7.4, 12.5 mM $MgCl_2$ and 2 mM EDTA). For example, 10 μl of membranes are diluted in 500 μl of binding buffer (i.e., 1:50 dilution), which is aliquoted into labelled tubes. Cold competitor or test competitor is added (e.g. 5 μl of 100× stock solution; 5 μl of 100 μM naltrindole solution (N-115, RBI/Sigma in DMSO). Radioligand is then added ($^3$H-Diprenorphine, TRK 1060, Amersham, 250 μCi in 250 μl, 10.5 μM at 95 Ci/mmol). For competition studies, 0.5 nM is used. A 100× stock (i.e., 50 mM) is made by diluting the commercial stock 1:210 in binding buffer, and 5 μl is added to every tube. Control tubes have radioligand but no membranes. The mixtures are vortexed, then spun very briefly. The mixtures are then incubated for 1 hour at 27° C. in a water bath. The mixture is filtered through GF/C filters over a vacuum. Each filter is pre-soaked in polyethyleneimine (0.3% in water; add 1 ml of 10% stock (P-261; RBI/Sigma) to 33 ml of MilliQ water). The tubes are washed with 2-3 ml of wash buffer (50 mM Tris pH 7.4) and the wash filtered. The filters are then rinsed with 3×5 ml of wash buffer, air dried, placed in a scintillation vial and 4.5 ml of scintillant added. The activity on the filter is then determined.

Results

A competitive binding assay was used to determine the binding of A-I to chemokine receptors. These experiments were performed under 'Horuk' conditions (Hesselgesser et al., *J. Biol. Chem.*, 273, 15687 (1998)), except that CHO cells expressing CCR-2 or CXCR-2 (AIDS Reagent Program, MRC London) were used. In each case, the specific binding of 0.25 nM labeled ligand to the cells was determined as the counts bound which were competable by 100 nM cold ligand. In each experiment, A-I was added from a stock solution in DMSO (with <0.1% DMSO final concentration in the assay).

Figure 53:
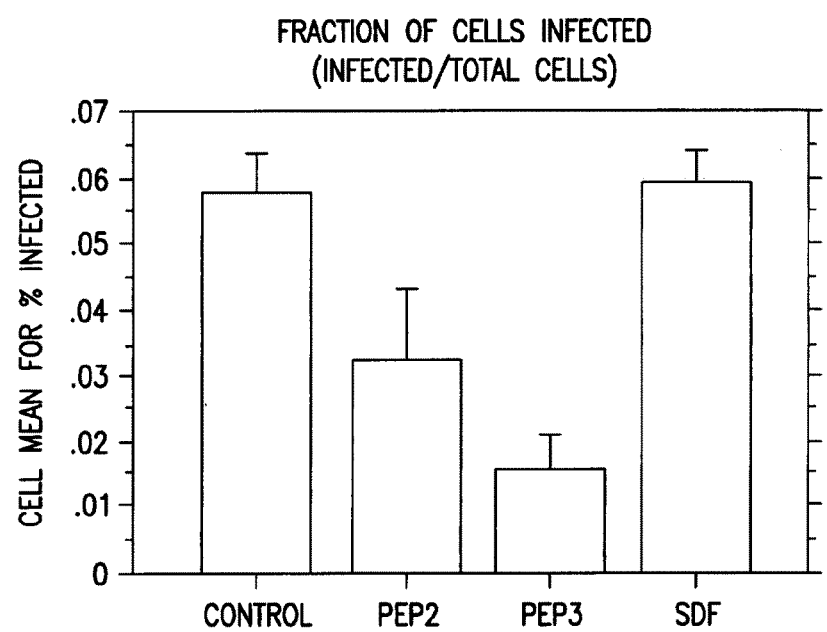
FIG. 53 shows a graph of the fraction of HIV infected THP-1 cells in the presence of peptide 2 or peptide 3 using a quantitative immunofluorescent (QIF) assay.

Two typical experiments are shown in FIG. 53, in which A-I inhibits MCP-1 binding to CCR-2 and IL-8 binding to CXCR-2 with $k_i$ concentrations similar to the functional $ED_{50}$s reported in Table 14. Similar data was obtained using PBS as the incubation buffer.

TABLE 14

Summary of Properties of A-I (NR58.4)

| Assay | $ED_{50}$ | Notes |
|---|---|---|
| In vitro | | |
| MCP-1 chemotaxis assay | 2 nM | |
| MIP1α chemotaxis assay | 0.2 nM | |
| RANTES chemotaxis assay | 0.3 nM | |
| SDF1α chemotaxis assay | 8 nM | |
| IL-8 chemotaxis assay | <10 nM | |
| fMLP chemotaxis assay | >100 μM | fMLP is not a chemokine |
| Binding to CCR-2 | 5 nM | |
| Binding to α2-adrenoceptors | >100 μM | No binding detected |
| Binding to HT-1a serotonin receptors | 80 μM | |
| Binding to D2s dopamine receptors | >100 μM | No binding detected |
| Binding to ∂-opioid receptors | — | Not yet determined |
| Physical | | |
| Molecular weight | 293 | Free acid |
| PKa (approximate) | 11 | Very weak acid |
| Solubility in water | negligible | |
| Solubility in water (potassium salt) | 5 mg/ml | Solution at pH 11 |
| Solubility in DMSO | >200 mg/ml | |
| In vivo | | |
| Effect on LPS-induced TNFα in vivo (1 mg s.c. injection) | 65% inhibition | |

The specificity of some of the agents against related G-protein coupled 7TM receptors, e.g., α2-adrenoreceptors, 5-HT-1α serotonin receptors, D2s dopamine receptors, and δ-opioid receptors, is shown in Table 15. In all cases 100 μM was the highest concentration tested. Where '>100 μM' is shown, no significant effect was observed at any concentration (including 100 μM).

Thus, CRD-Leu$_4$Ile$_{11}$Cys$_{13}$ peptide 3(3-12)[MCP-1], A-I, yohimbamide (Y-II), L-II and WVQ are highly specific for chemokines over the other receptor types tested. In contrast, although yohimbine and thalidomide are chemokine inhibitors, they have greater activity against one (or more) other G-protein coupled receptors tested. For example, yohimbine is selective for adrenoreceptors over chemokines and thalidomide for dopamine receptors over chemokines. A-I was the most selective (approximately 40,000 fold selective for MCP-1 inhibition over serotonin receptor binding). The most potent agent against MCP-1 (Y-II) was less selective, showing only 1,500 fold selectivity for chemokine inhibition of alpha-adrenoreceptor binding.

TABLE 15

Chemokine specificity of various inhibitors

| Compound | MCP-1[a] | α2-A[b] | 5-HT1a[c] | D2s[d] | ∂-opioid[e] |
|---|---|---|---|---|---|
| NR58-3.14.3 | 10 nM | >100 μM | >100 μM | >100 μM | >100 μM |
| NR58,4 (A-I) | 2 nM | >100 μM | 80 μM | >100 μM | n.d.[f] |
| Yohimbamide (Y-II) | 0.5 nM | 770 nM | 5 μM | 70 μM | n.d. |
| Lysergyl-glutamine (L-II) | 5 nM | n.d. | 1 μM | n.d. | n.d. |
| WVQ | 1 μM | >100 μM | >100 μM | n.d. | n.d. |
| Yohimbine | 30 nM | 4 nM | 2 μM | n.d. | n.d. |

TABLE 15-continued

Chemokine specificity of various inhibitors

| Compound | MCP-1[a] | α2-A[b] | 5-HT1a[c] | D2s[d] | ∂-opioid[e] |
|---|---|---|---|---|---|
| Thalidomide | 50 μM | >100 μM | n.d. | >100 μM | n.d. |
| LII | 5 nM | n.d | 1 μM | n.d. | n.d. |

[a]MCP-1 = $ED_{50}$ versus MCP-1 induced chemotaxis
[b]α2-A = $ED_{50}$ for competition of RS79943 binding to α2-adrenoceptors
[c]5-HT1a = $ED_{50}$ for competition of 8-OH-DPAT binding to 5-HT1a receptors
[d]D2s = $ED_{50}$ for competition of spiperone binding to short splice variant D2 dopamine receptor
[e]∂-opioid = $ED_{50}$ for competition of diprenorphine binding to ∂-opioid receptors.
[f]n.d. = not yet determined.

Example 23

Plasma Half-Life of a Glucose Conjugate

To determine whether sugar conjugates of an agent of the invention had increased plasma half-lives, a glucose conjugate of CRD-Leu$_4$Ile$_{11}$Cys$_{13}$ peptide 3(3-12)[MCP-1] was prepared and administered to rats. The conjugate was synthesized by mixing D-glucose (50 mM) and CRD-Leu$_4$Ile$_{11}$Cys$_{13}$ peptide 3(3-12)[MCP-1] (1 mM) in phosphate buffered saline and incubating at room temperature for 16 hours. The reaction mixture was then subject to analytical HPLC which indicated a yield of about 30%. The material was then treated with cyanoborohydride to effect reduction of the schiffs base linkage and stabilize the glucosides for purification. The stabilized glucosides were then subjected to preparative HPLC and the mono- and di-substituted glucosides prepared separately. The monoglucoside was obtained at >90% purity in approximately 10% yield, and it is likely that the material is a mixture of Lys5-glucoside and Lys-7 glucoside.

The CRD-Leu$_4$Ile$_{11}$Cys$_{13}$ peptide 3(3-12)[MCP-1] monoglucoside was injected into 3 rats (5 mg per rat via s.c. route in sterile PBS). Blood samples were withdrawn through an i.v. cannula at various time points, and CRD-Leu$_4$Ile$_{11}$Cys$_{13}$ peptide 3(3-12)[MCP-1] glucoside was quantitated in the serum. Using a one-compartment fit to the data suggested, the T½α for the CRD-Leu$_4$Ile$_{11}$Cys$_{13}$ peptide 3(3-12)[MCP-1] monoglucoside was determined to be approximately 7 hours, which represents an increase of more than 25-fold compared to the unmodified cyclic peptide (T½α=15 minutes).

Example 24

Agonist Activity

To evaluate the agonist activity of CRD-Leu$_4$Ile$_{11}$Cys$_{13}$ peptide 3(3-12)[MCP-1], CRD-Leu$_4$Ile$_{11}$Cys$_{13}$ peptide 3(3-12)[MCP-1] was placed in the lower compartment of the migration chamber at various concentrations and 50,000 THP-1 cells were placed in the upper compartment. The number of cells in the lower compartment after 4 hours was then determined using the vital dye MTT. No agonist activity was detected in the concentration range where inhibitory effects on chemokine-induced migration are seen (<1 μM). At higher concentrations (1 μM and 10 μM), there may be a small stimulation of migration in this experiment, although the magnitude of this migratory response was less than that seen with 3.25 ng/ml recombinant MCP-1. CRD-Leu$_4$Ile$_{11}$Cys$_{13}$ peptide 3(3-12)[MCP-1] is unlikely to have any agonist activity that is significant at concentrations attainable in vivo.

Figure 49:
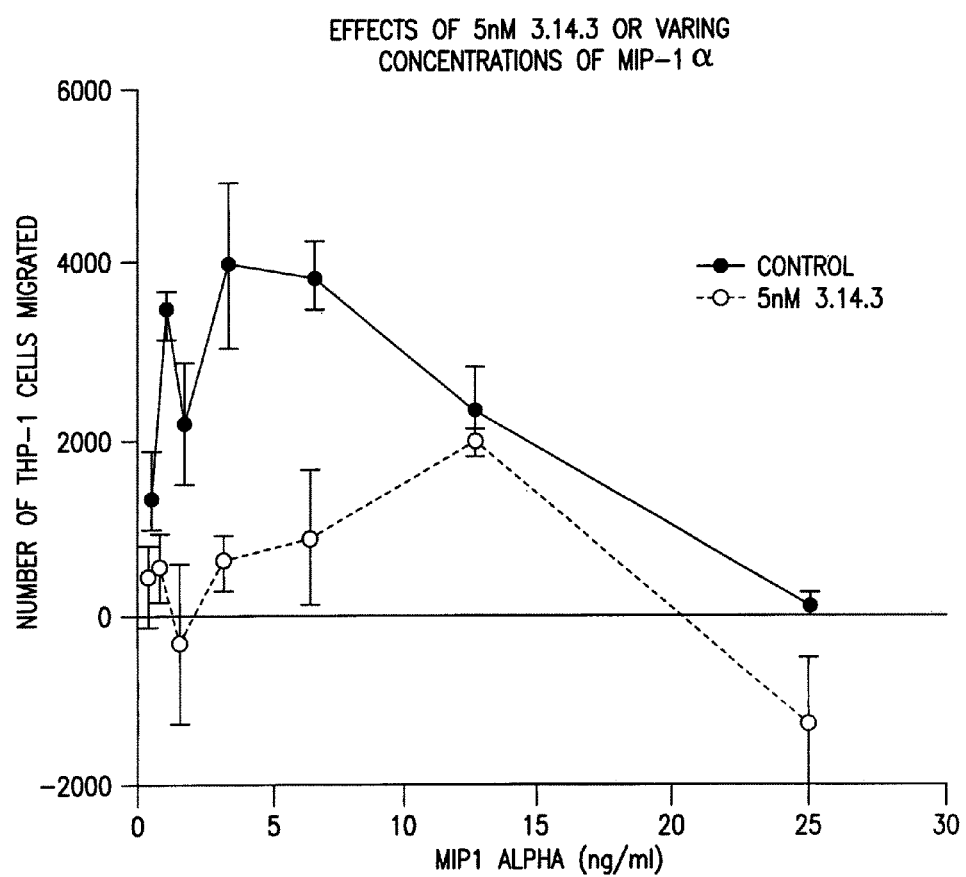
FIG. 49 depicts effect of CRD-Leu$_4$Ile$_{11}$Cys$_{13}$ peptide 3(3-12)[MCP-1] on MIP-1α-induced chemotaxis.
Figure 50A:
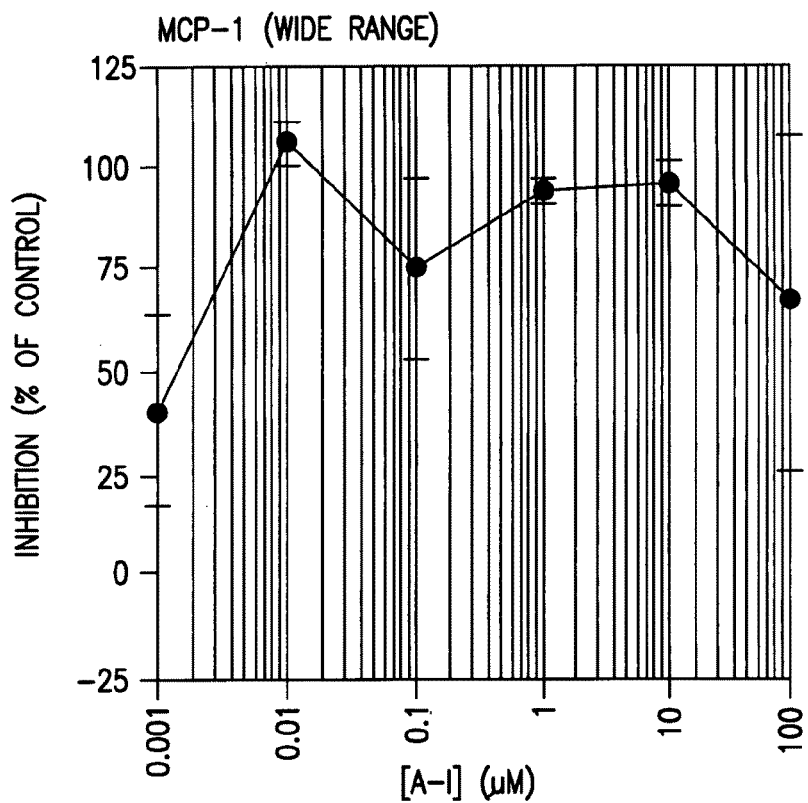
FIG. 50 shows the inhibitory effect of A-I in the presence of A) MCP-1, B) MCP-1, C) RANTES, and D) MIP-1α.
Figure 50B:
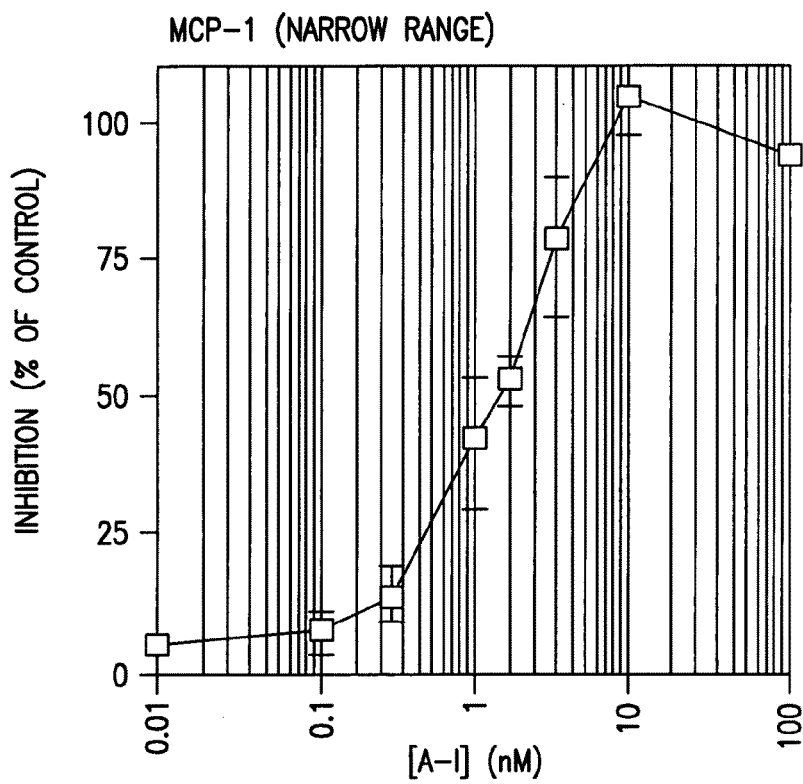
Figure 50C:
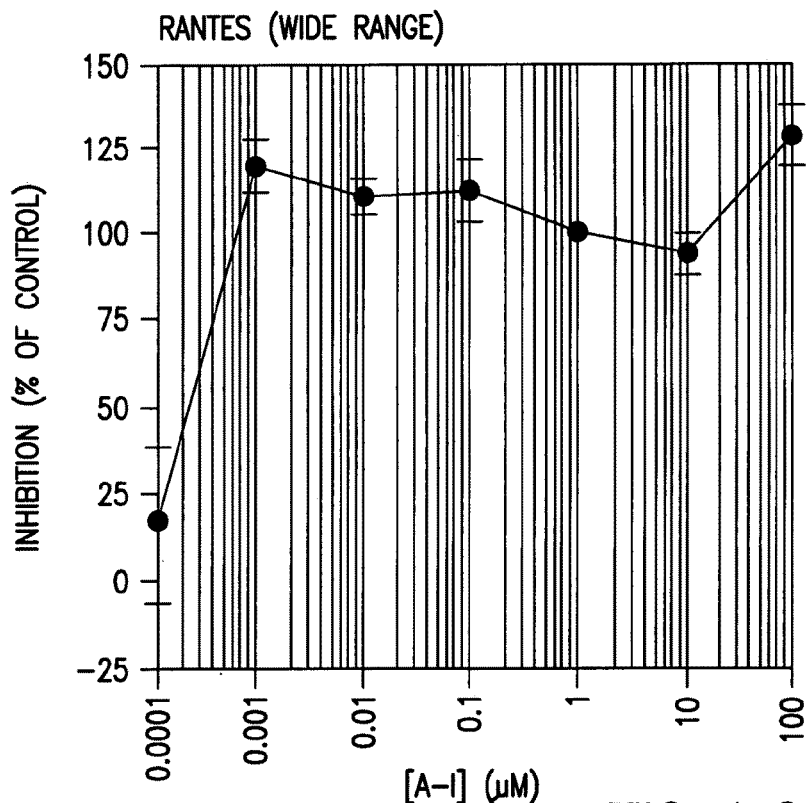
Figure 50D:
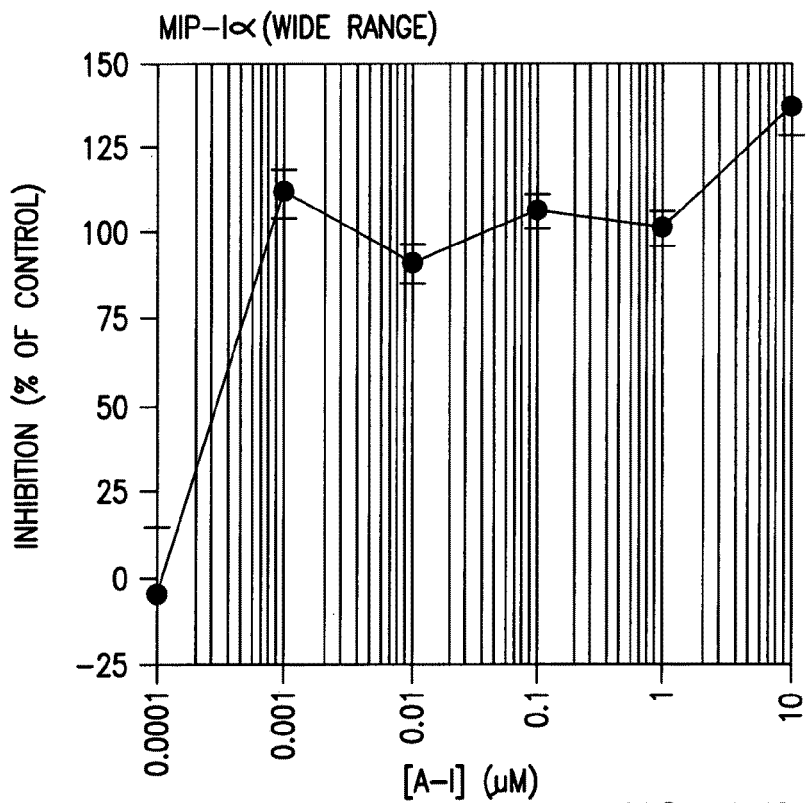

The concentration of MIP-1α in the bottom of the chemotaxis chamber was varied in the presence or absence of a half-maximally active dose of the inhibitor in the upper chamber of the plate (with the cells). Consistent with previous observations, increasing the concentration of MIP-1a in the absence of inhibitor first stimulates migration (at concentrations up to approximately 5 ng/ml) and thereafter further increases in MIP-1α decrease migration. At 100 ng/ml MIP-1α, there is no stimulation of migration (FIG. 49). This biphasic (or bell-shaped curve) is seen with any pro-migratory agent which is purely chemotactic (rather than chemokinetic), similar to the chemokines. At higher concentrations in the bottom of the well, diffusion rapidly destroys the gradient across the membrane, such that the receptors all around the target cells are fully occupied by the chemokine. In the absence of a gradient, chemotactic agents do not stimulate movement. When the dose-response to MIP1α is performed side by side in the presence of a sub-maximal dose of the inhibitor, a similar biphasic (or bell-shaped curve) is seen. However, the dose response curve is shifted markedly to higher concentrations (this assay is not sufficiently accurate to allow the extent of the shift to be estimated, but it lies in the range of 5-100 fold). This experiment therefore provides some evidence for a competitive mode of action for the inhibitor acting against MIP1α-induced chemotaxis. The experiment shown is typical of three replicate experiments, and was also performed using MCP-1.

Example 25

Binding Affinity of the Agents of the Invention

It is also envisioned that moieties other than those exemplified, including analogs of chemokine peptide 2 or 3, variants or derivatives thereof, which bind to DARC and/or chemokine receptors with a specific affinity, e.g., they bind to functional chemokine receptors with high affinity but bind with lower affinity to DARC or bind to DARC with a high affinity but bind to chemokine receptors with lower affinity, may be identified using methods such as those described above. Moreover, the agents of the invention may be useful in functional mapping of chemokine receptors. For example, both chemokine peptide 2 and peptide 3 block binding of the natural chemokine ligands in a competitive manner. However, they do not block binding of one another suggesting that they bind to distinct regions of the receptor and that both of these regions are important for binding of the natural ligand. In addition, peptide 2 is further distinguished from peptide 3 in their differential functional activity. Peptide 3 not only binds to the receptor but also blocks the functional activity of receptor signaling as indicated by inhibition of chemotaxis. Peptide 2 does not inhibit chemotaxis. Thus, these peptides together are particularly useful in identifying regions of chemokine receptors that are important in different functional activities. Once these regions are identified, they can be used to screen combinatorial libraries or compound banks for specific inhibitors to distinct chemokine functions that may be structurally unrelated to the starting compounds, but are functionally related.

In addition, it may be important for chemokines to form dimers to activate the receptor of interest. The peptides of the invention lack the amino terminal domains that are thought to be important for chemokine dimer formation. If dimer formation is required for cell signaling, then the agents of the invention may inhibit activation as they can bind to the receptor but are unable to form dimers, e.g., with native chemokine ligand.

Example 26

Anti-HIV Activity of the Agents of the Invention

To demonstrate that the agents of the invention inhibit HIV binding and infection of cells, human T-cell derived Jurkat cells were incubated with an infectious T-tropic HIV isolate in the presence of (i) no inhibitor, (ii) peptide C (Table 17) as an inactive control peptide, (iii) 100 μM peptide 3(1-12)[MCP-1] (SEQ ID NO:1), or (iv) 100 ng/ml SDF-1, which should bind to and block all CXCR-4 receptors. After 3 weeks in culture, viral replication was assessed by a reverse transcriptase assay of the culture medium. Peptide 3(1-12)[MCP-1] (SEQ ID NO:1) was found to be an effective inhibitor of Jurkat cell infection by HIV.

Since peptide 2(1-15)[MCP1] (SEQ ID NO:3) binds to chemokine receptors on the surface of Jurkat cells (Ka=250 nM; B=55,000 sites/cell) and THP-1 cells (Ka=300 nM; B=130,000 sites/cell), but does not inhibit productive signaling by chemokines, it is possible that peptide 2(1-15)[MCP-1] (SEQ ID NO:3) binds and inhibits an epitope used by HIV for cell entry but not by MCP-1 for signaling. To test this hypothesis, the same HIV infection assay described above was employed to test whether peptide 2(1-15)[MCP-1] (SEQ ID NO:3) inhibits HIV infection of Jurkat cells. At 100 μM, peptide 2(1-15)[MCP-1] (SEQ ID NO:3) was more effective than peptide 3(1-12)[MCP-1] (SEQ ID NO:1), and as effective as SDF1α, in preventing virus entry.

Figure 52:
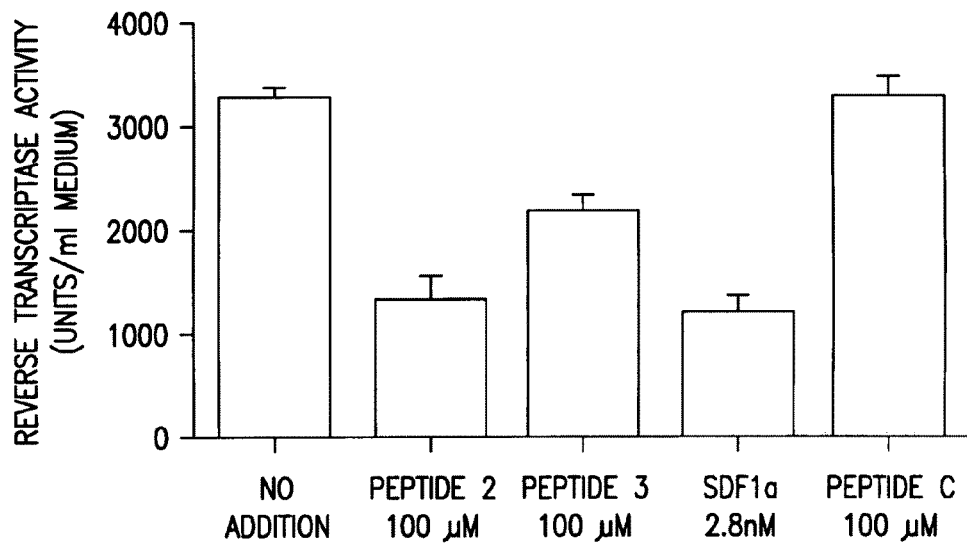
FIG. 52 shows the reverse transcriptase activity present in the culture medium at day 21 after infection of Jurkat cells with a T-tropic HIV. Peptides were added on day 0, one hour prior to infection of the cells with HIV isolate. The full length chemokine SDF-1α was used as a positive control.

Peptide 2 derivatives (FIG. 52) are better inhibitors of Jurkat T cell infection by HIV (a CXCR4 mediated event) than peptide 3 derivatives, while surprisingly peptide 3 is a better inhibitor of THP-1 cell infection (a CCR-5 mediated event). Thus, combinations of peptide 2 and peptide 3 may be particularly useful for anti-HIV therapy, e.g., to inhibit productive infections by both M-tropic and T-tropic isolates.

Moreover, as LRD peptide 2(1-15)[MCP-1] had a 100 nM affinity constant or lower for CCR5/CXCR4 and a 100 fold decrease in Duffy binding relative to LFL peptide 2[MCP-1], LRD derivatives may be more efficacious than their LFL counterparts (25 μM versus 100 μM for LFL).

Current therapies for inhibition of HIV focus on the virus, for example reverse transcriptase inhibitors or viral protease inhibitors. These therapies are only effective for a limited period. In each case, the efficacy is reduced because the virus is undergoing rapid replication, and there is selection in favor of mutants which are resistant to the inhibitors. Although combination therapies are more effective, they are unlikely to result in clearance of the virus from an infected individual. Eventually, mutant virus will arise which circumvents the drug cocktail and progression will again occur in the now drug-resistant individual. Thus, strategies which are based on co-receptor inhibition (i.e., viral entry) target a host protein, rather than a virus protein, may have increased efficacy as more extensive mutations in the virus may be necessary to circumvent an inhibited co-receptor. Indeed, the resistance to infection of CCR-5Δ32 homozygotes suggests that the virus cannot readily adapt to use of an alternative co-receptor, at least while the virus population is small. Thus, the agents of the invention may be used in conjunction with other anti-viral therapies, e.g., protease inhibitors, reverse transcriptase inhibitors, or a combination thereof.

Preferably, a Ser10 variant of peptide 2(1-15)[MCP-1] (SYRRITSSKSPKEAV) (SEQ ID NO:120), or its LRD $Cys_0Ser_{10}Cys_{16}$ derivative (cvaekpsksstirrysc) or CRD derivative, is employed. DARC binding of SYRRITSSKSP-KEAV (SEQ ID NO:120) is in the range 20 μM to 100 μM and activity in the range 1-100 nM as an anti-HIV agent.

Example 27

Rapid Screening Method for Infectivity

Current assays for HIV infection in vitro are time consuming and lack reproducibility. For example, infection is often monitored by the production of viral reverse transcriptase (RT) activity using a radiolabelled RT substrate. Unfortunately, RT production is low, even when a laboratory adapted HIV strain is used to infect a high permissive line such as the Jurkat human T cell line. As a result, it is necessary for the infected cells to be cultured for two or more weeks to allow sufficient infection to occur for RT production be measurable. In addition to being time consuming, this assay has a number of other disadvantages: most importantly, it relies on multiple rounds of secondary infection to increase the viral titer sufficiently for RT activity to become detectable. As a result, small differences in primary infection are magnified, and since primary infection frequency is low, stochastic differences between identically treated wells become significant. The assay therefore requires many replicate wells for each analysis, with as many as 24 replicates being routinely used. For example, in a typical assay groups of 24 wells of Jurkat cells in 96-well plates are infected with replicate aliquots of HIV virus stock, with one group receiving treatment with peptide 2 as a chemokine co-receptor inhibitor, another group receiving SDF-1α (the CXCR-4 natural ligand) and a third group is untreated. After three weeks, the cells were harvested and RT activity measured. The co-efficient of variation in the untreated wells was 37%. As a result, although peptide 2 inhibited RT activity by 75%, this was significant only with p=0.02 because of the high well to well variability. This necessitates the use of many replicate making the assay cumbersome for screening purposes.

An alternative method is to use direct visualization of the HIV proteins, for example, by immunofluorescence microscopy. Unfortunately, even the most highly expressed HIV proteins (such as p24gag) are present at fairly low levels in cells. Thus, direct detection the earliest stages after infection has been difficult and error prone. Therefore, the following method was employed to enhance the sensitivity of immunofluorescence, allowing the number of HIV infected cells to be accurately determined between 24 hours and 72 hours after infection. Furthermore, the signal to noise ratio of this technique allows automated counting of the infected cells using image analysis software.

For THP-1 cells, the cells are adhered to glass multiwell slides (for example, 16-well chamber slides; Nunc) using PMA and hydrocortisone. The cells are then exposed to virus in the chamber slide in the presence of various test agents. For non-adherent cells such as Jurkat cells, infections are carried out in, for example, 96-well culture plates as for RT assays, but prior to analysis the cells are attached to glass slides using a cytospin apparatus in accordance with the manufacturer's instructions. The infected cells on the glass slides are fixed between 24 hours and 72 hours after infection, for example, by immersing the slides in ice cold acetone for 90 seconds. Other methods of fixation compatible with quantitative immunofluorescence may also be used (see J. Histochem. Cytochem., 44, 1043 (1997) for a discussion of quantitative immunofluorescence procedures). Following fixation, non-specific binding of proteins to the cells is blocked, e.g., by incubation in 3% w/v fatty acid free bovine serum albumin in phosphate buffered saline (3% FAF-BSA in PBS) for 30 minutes at room temperature. Alternatively, other blocking solutions (e.g., 5% sucrose, 5% Tween-20 in PBS) may be used. The blocked sections are then stained for HIV protein, for example, using a specific antiserum to p24gag. Slides are incubated with the antiserum at a suitable concentration (usually in the range 1-100 µg/ml of specific IgG) in 3% FAF-BSA in PBS. Antibodies to other HIV antigens may be used, although relatively highly expressed antigens such as p24gag are preferred.

This incubation should be left on for at least 16 hours. Traditional immunofluorescence procedures use primary antibody incubation periods typically 1-2 hours in length, but longer incubation increases signal without increasing background (*J. Histochem. Cytochem.*, 44, 1043 (1997)). The incubation may be left on for up to 36 hours without deleterious effects on the signal to noise ratio. Unbound antibody is then washed off. Typically, this involves 3×3 minute washes in PBS, although other washing regimens may be used (see *J. Histochem. Cytochem.*, 44, 1043 (1997)) for a comparison of washing methods). Normally, second antibody labelled with an appropriate fluorophore is then used to detect the unbound primary antibody. However, to prevent primary antibody from falling off the antigen, primary antibody is post-fixed to the section. This may be achieved, for example, by incubating the slide in freshly prepared 4% paraformaldehyde in PBS for 10 minutes at room temperature. After three further washes, e.g., 3×3 minutes in PBS, the slides are exposed to a secondary antibody specific for the species of the primary antibody coupled to an appropriate fluorophore (for example, antirabbit-IgG FITC conjugate at 1-100 µg/ml). A non-specific nuclear stain should be included in this incubation. For example, Hoescht 33342 at 1-100 ng/ml could be used, or propidium iodide at 1-100 ng/ml. This incubation is for a minimum of about 4 hours, preferably at least 8 hours and may be left up to 24 hours without detrimental effect on the signal to noise ratio. Slides are then washed, for example, 3×3 minutes in PBS, to remove unbound second antibody and mounted with a suitable mounting medium such as Citifluor AF1. Slides are left at least about 18 hours after mounting but less than about 72 hours in a dark box following mounting prior to analysis.

Analysis may be performed manually using any suitable microscope with epifluorescence visualization capability and appropriate filter sets to allow examination of the fluorescence of the secondary antibody fluorophore selected (e.g., FITC) and the non-specific nuclear staining selected (e.g., Hoescht 33342) separately. The number of cells in each field of view is determined by counting nuclei using filters to visualize the non-specific nuclear stain. The number of cells infected with HIV in the same field of view is then determined by switching the filter set to visualize the fluorophore coupled to the secondary antibody. In each case, the number of cells may be determined by manual counting. Alternatively, image analysis software (for example, OpenLab software: Improvision, U.K.) may be used to apply a consistent threshold to each image and count the number of separate objects above that threshold. Deagglomeration algorithms, standard in the field of image analysis, may be applied if required according to the density of the cells on the slides. Provided that constant set of illumination conditions are used during image acquisition and that a constant threshold is applied, the fraction of HIV stained cells may be rapidly and accurately determined without reference to subjective considerations.

Example 28

Use of the Agents of the Invention to Block gp120 Binding

A number of studies, for example using chimeric receptors, have begun to localize the binding site for the HIV envelope protein gp120 and the chemokine ligands on the CCR5 receptor. These reports suggest that the N-terminal region is important for both gp120 and chemokine binding (Wells et al., *Methods*, 10, 126 (1996); Ross et al., *J. Virol.*, 72, 1918 (1998); Alkhatib et al., *J. Biol. Chem.*, 272, 19771 (1997); Dragic et al., *J. Virol.*, 72, 279 (1998); Monteclaro et al., *J. Biol. Chem.*, 272, 23186 (1997)) but that the two bind to overlapping but non-identical sites involving not only the N-terminal region but also the extracellular loops of the receptor (Ross et al., *J. Virol.*, 72, 1918 (1998); Farzan et al., *J. Biol. Chem.*, 272, 6854 (1997)).

Methods

Peptides. The peptides were prepared by Affinity (Exeter, U.K.) by standard solid phase chemistry, followed by reverse phase HPLC purification to greater than 95% purity. Peptide 2 (derived from amino acids 28-42 of mature human MCP-1) has the sequence SYRRITSSKCPKEAV (SEQ ID NO:3). Peptide 3 (derived from amino acids 51-62 of mature human MCP-1) has the sequence EICADPKQKWVQ (SEQ ID NO:1). Labeled peptides were synthesized with an N-terminal biotin moiety. Peptides were also synthesized corresponding to the sequence of the full-length V3 loop (including terminal cysteine residues) of gp120 from HIV-1 IIIb and HIV-1 BaL. All peptides were prepared as TFA salts and dissolved in sterile MilliQ to give 10 mM stock solutions which were stored at −20° C. until used.

Binding assays. Cells (either Jurkat T-cells or THP-1 cells) were grown in RPMI 1640 medium supplemented with 10% fetal calf serum, 2 mM glutamine, 20 µM β-mercaptoethanol, 100 U/ml penicillin and 100 µg/ml streptomycin and maintained between $2 \times 10^5$ and $1 \times 10^6$ cells/ml. Prior to performing a binding assay, cells were spun out (100×g; 4 minutes) and washed 3 times in ice-cold PBS. A volume of cell suspension in PBS containing $10^6$ cells (for Jurkat cells) or $4 \times 10^5$ cells (for THP-1 cells) was pipetted into each well of a V-bottom 96-well plate (Gibco BRL) and spun out (100×g; 4 minutes). Triplicate wells were then resuspended in 100 µl binding medium (PBS pH 7.2 containing 0.1% fatty acid-free bovine serum albumin (BSA)) containing labeled peptide in the presence or absence of various concentrations of unlabeled peptide. The plate was then incubated on ice for 90 minutes. Cells were washed 3 times with 380 µl of ice-cold PBS, spinning out the cells each time (100×g; 4 minutes), and resuspended in 100 µl binding medium containing streptavidin-peroxidase (Amersham International) at 1:1000 dilution. Cells were incubated for a further 15 minutes on ice to allow labeling of any bound biotinylated peptide, then washed 4 times as above. Cells were then incubated with 200 µl TMB substrate (K-Blue, Bionostics) for 20 minutes at room temperature, and the reaction stopped by addition of 50 µl 2 M HCl. The plate was spun (3,000×g; 3 minutes) and 200 µl of the colored product was transferred to an empty 96-well ELISA plate and the absorbance at 450 nm determined. For each assay, the absorbance of a blank reaction (no peptide added) was subtracted from all readings before further analysis.

For Scatchard analysis, the absorbance readings at 450 nm were calibrated, by reference to a standard curve in which known amounts of labeled peptide were coupled to derivatized sepharose beads (activated thiol-sepharose 4B; Sigma T8512) via the cysteine residue in each peptide. Briefly, known amounts (1 fmol to 1 pmol) of biotin-labeled peptide were incubated with 1 mg of activated thiol-sepharose beads in 100 μl of PBS at 37° C. for 1 hour. Free activated thiols were then blocked by addition of cysteine to a final concentration of 10 mM. The peptide-conjugated beads were then washed 5 times in PBS and treated exactly as for the cells described above. The absorbance at 450 nm obtained when a known amount of peptide was coupled to the beads was used to construct a standard curve which was used to convert the absorbance readings obtained with cells into number of molecules of labeled peptide which had bound. This method has a sensitivity <1 fmol of labeled peptide bound, allowing Scatchard analysis of binding even where the affinity is moderate or the number of binding sites relatively small.

Binding experiments with labeled peptide 2 were performed with 10 nM labeled peptide in each reaction. Labeled peptide 3 was used at 250 nM and labeled peptides from the V3 loop of gp120 from HIV-1 were used at 100 μM, unless stated otherwise.

Immunofluorescence Detection of p24$^{gag}$

Figure 54A:
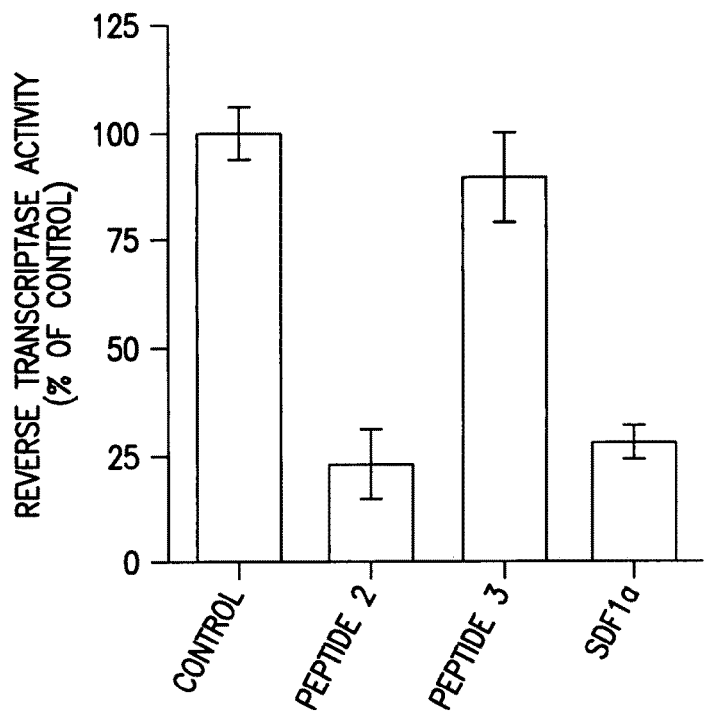
FIG. 54 shows chemokine peptide inhibition of HIV infectivity in vitro. (a) HIV (IIIb) replication in cultures of Jurkat T-cells was estimated by measuring the supernatant reverse transcriptase activity two weeks after infection. Peptide 2 and peptide 3 were at 100 µM final concentration and SDF-1α was added at 100 ng/ml final concentration 1 hour prior to exposure to virus. Values are mean±SEM from 12 wells, expressed as the percentage of the reverse transcriptase activity in the supernatant from the control wells. The experiment shown is typical of six separate experiments. (b) HIV (IIIb) infectivity of Jurkat T-cells was estimated by staining cells treated identically to those in (a) for p24$^{gag}$ expression. Values are mean±S.D. percentage of cells stained for p24gag averaged from 12 fields of view from each of two separate wells. (c) HIV (MN) infectivity of THP-1 cells measured as in (b). MIP-1α was used at 100 ng/ml final concentration. (d) Immunofluorescence micrographs of THP-1 cells 48 hours after exposure to HIV (MN) in the absence (top panel) or presence (lower panel) of 100 µM peptide 3, stained for p24$^{gag}$. Several cells in the upper panel, but not the lower panel, show strong, punctuate staining for p24$^{gag}$ antigen. Both fields of view contain 40-50 cells (assessed by Hoeschst 33345 staining viewed under UV illumination conditions).
Figure 54B:
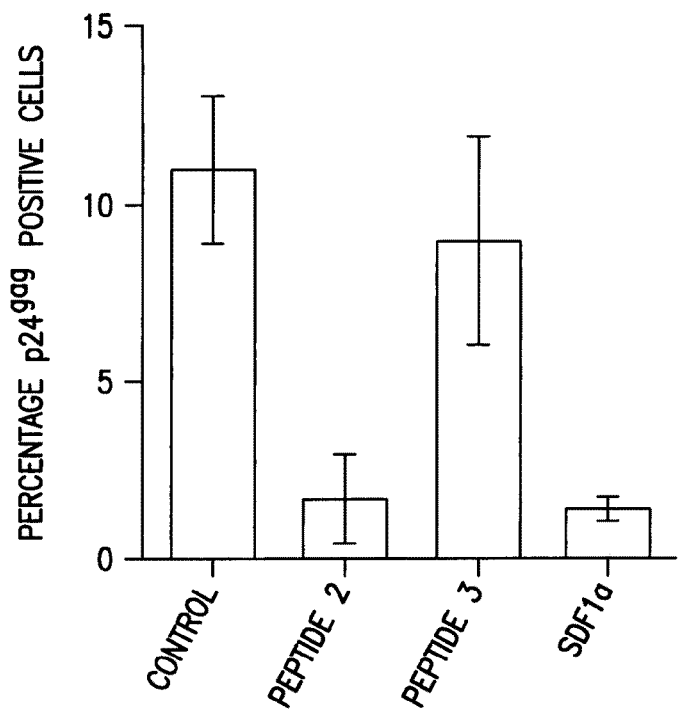

Jurkat cells following HIV infection were attached to 8-well chamber slides (Becton-Dickinson) by spinning the slides using a plate rotor in a Labofuge centrifuge (Haeraeus) at 3,000×g for 5 minutes. Attached Jurkat cells or THP-1 cells were then fixed by dipping the slides into ice-cold 70% ethanol for 90 seconds. Non-specific binding was blocked by incubation with 3% fatty acid-free BSA in TBS for 1 hour at room temperature. Cells were incubated with the mouse monoclonal anti-HIV-1 p24$^{gag}$ antibody EH12E1 (Ferns et al., *J. Gen. Virol.*, 68, 1543 (1987); AIDS Reagent Program, NIBSC) at 10 μg/ml in 3% BSA in TBS at room temperature overnight. Unbound antibody was removed with 3×3 minute washes in PBS, and bound antibody was then fixed to the slide by incubation with 3.8% phosphate-buffered formalin pH 7.2 for 10 minutes at room temperature, followed by 3 further 3 minute washes in PBS. Bound antibody was visualized using donkey anti-mouse IgG FITC conjugate (715-095-150; Jackson Immunoresearch) at 30 μg/ml in 3% BSA/TBS+1 ng/ml Hoescht 33342 for 6 hours at room temperature. Twelve fields of view (100× magnification) were captured from each well of the chamber slide using an Olympus Provis AX electronic microscope connected to a Power Macintosh 8500, running OpenLab image analysis software (Improvision), under both FITC illumination conditions (NIBA filter block; λex=470-490 nm, dichroic mirror=505 nm, λem=515-550 nm) and UV illumination conditions (Chroma 31000; λex=340-380 nm, dichroic mirror=400 nm, λem=435-485 nm). Images were acquired with a Hamamatsu C4742-05 monochrome digital camera with 10 bit depth in a 1280-1024 pixel field connected to a DIG Snapper frame grabber. The exposure time, amplifier gain and offset values were controlled by the OpenLab software and were held constant throughout the experiment. A background (an image captured without a slide under the objective) was digitally subtracted from every image. A threshold was then applied to each image which was the lowest threshold that detected <1% of the pixels of an image of uninfected cells stained under identical conditions. The number of objects exceeding this threshold in each field of view were counted. This process, for example, detected 9 objects in the field of view shown in the upper panel of FIG. 54D and 1 object in the field of view shown in the lower panel. A similar procedure was used to determine the total number of nuclei in the same field of view, using the image captured under UV illumination conditions. The ratio of positively stained objects to nuclei in each field of view was reported as the percentage of cells stained for p24$^{gag}$.

Results

Binding of Peptides to THP-1 and Jurkat Cells

To test whether peptide 2 and peptide 3 were likely to bind to the same or to different sites on the chemokine receptors, the effect of unlabeled peptide 2 on the binding of biotinylated peptide 3 and vice versa was analyzed. The affinity constant for peptide 3 binding to THP-1 cells was similar in the presence (8 μM) and absence (7 μM) of 100 μM peptide 2. Similarly, the affinity constant for peptide 2 binding was unaffected by the presence of 100 μM peptide 3 (250 nM in each case). These data suggest that peptide 2 and peptide 3 bind to distinct sites on the chemokine receptors. Similar data was obtained using Jurkat T-cells.

Effect of Peptides on gp120 Binding

The binding of gp120 to chemokine receptors is likely to involve sequences in the V3 loop of gp120 (Ross et al., *Proc. Nat'l Acad. Sci. U.S.A.*, 95, 7682 (1998); Cocchi et al., *Nat. Med.*, 2, 1244 (1996); Jiang et al., *Nat. Med.*, 3, 367 (1997)). Therefore peptide sequences were synthesized from the V3 loop of the M-tropic BaL strain and the T-tropic IIIB strain and analyzed the binding of these biotinylated peptides to the THP-1 and Jurkat cells. Specific binding of gp120:V3(BaL) to THP-1 cells was detected at 100 μM (Table 17), although the combination of low number of binding sites per cell and moderate affinity of the interaction precluded accurate Scatchard analysis of the binding. In contrast, specific binding of gp120:V3(BaL) to Jurkat cells was not detected even at concentrations up to 500 μM (Table 17). These observations are consistent with the hypothesis that gp120:V3(BaL) binds specifically to CCR5, which is expressed on the surface of the THP-1 monocytic cells but not the Jurkat T-cells.

TABLE 17

| ΔA450 nm | alone | +100-fold excess unlabeled peptide | Specific binding |
|---|---|---|---|
| Jurkat T-cells | | | |
| gp120:V3(IIIb) | 0.878 ± 0.013 | 0.189 ± 0.010 | 0.689 |
| gp120:V3(BaL) | 0.167 ± 0.019 | 0.168 ± 0.020 | <0 |
| THP-1 cells | | | |
| gp120:V3(IIIb) | 0.268 ± 0.024 | 0.131 ± 0.011 | 0.137 |
| gp120:V3(BaL) | 0.642 ± 0.009 | 0.107 ± 0.015 | 0.535 |

N-terminally biotinylated peptides corresponding to the V3 loop sequence (including the terminal cysteines, residues 303-339 in gp120(IIIb)) from HIV IIIb of BaL were incubated at 100 μM with Jurkat cells ($10^6$ cells per reaction) or THP-1 cells ($4×10^5$ cells per reaction) at 4° C. in binding medium. Bound peptide was then labeled with streptavidin-peroxidase and visualized using the chromogenic substrate TMB. Each reaction was performed in triplicate both in the absence or presence of 100-fold excess of the same peptide lacking the biotin label, to estimate the contribution of non-specific binding.

Specific binding of gp120:V3(IIIb) at 100 μM to both Jurkat T-cells and THP-1 cells was detected, but again the low number of binding sites per cell and moderate affinity of the interaction precluded accurate Scatchard analysis of the binding. There was approximately 5-fold greater specific binding to the Jurkat cells than the THP-1 cells (Table 17). These observations are consistent with the hypothesis that gp120:V3(IIIb) binds specifically to CXCR4, which is expressed on both THP-1 and Jurkat cells, but at higher levels on the T-cell line.

Effect of Peptides on HIV Infection In Vitro

HIV infection of Jurkat T-cells using the laboratory-adapted T-tropic isolate IIIb was monitored using two different assays. Firstly, Jurkat T-cells in 96-well plates were pretreated with either peptide 2, peptide 3, vehicle (as a negative control) or SDF1α (as a positive control) for 1 hour, then exposed to HIV virus ($10^6$ $TCID_{50}$) and pulsed at 2-3 day intervals with peptide, SDF1α or medium alone as appropriate. After two weeks in culture, the extent of viral infection was assayed by measuring the reverse transcriptase activity in the supernatant, as a measure of viral replication in the culture. Peptide 2 (100 μM) but not peptide 3 (100 μM) markedly inhibited virus replication following HIV exposure (FIG. 54A), suggesting this peptide had inhibited HIV infectivity in vitro. No effect was seen on cell viability. Reverse transcriptase activity was inhibited by an average of 75% in six similar experiments, and in each case the inhibition achieved with peptide 2 was similar to that with SDF-1α.

HIV infection of Jurkat T-cells was also monitored by high sensitivity quantitative immunofluorescence detection of viral $p24^{gag}$ expression. Jurkat cells were infected with HIV in the presence or absence of peptide 2 (100 μM), peptide 3 (100 μM) or SDF1α (100 ng/ml) as described above. Approximately 48 hours after infection, the cells were attached to glass slides using a cytospin and then fixed by emersion in ice-cold 70% ethanol for 90 seconds. Expression of $p24^{gag}$ was determined using quantitative immunofluorescence as previously described (Mosedale et al., *J. Histochem. Cytochem.*, 44, 1043 (1996)), except that the primary antibody was post-fixed to the section using paraformaldehyde to increase the sensitivity of the technique. Viral infectivity was expressed as the number of cells stained for $p24^{gag}$ expressed as a proportion of the total number of cells (detected using Hoechst 33342 nuclear dye). Consistent with the reverse transcriptase assay results, peptide 2 and SDF1α inhibited viral infectivity by more than 80% (FIG. 54B), while peptide 3 was ineffective.

Figure 54C:
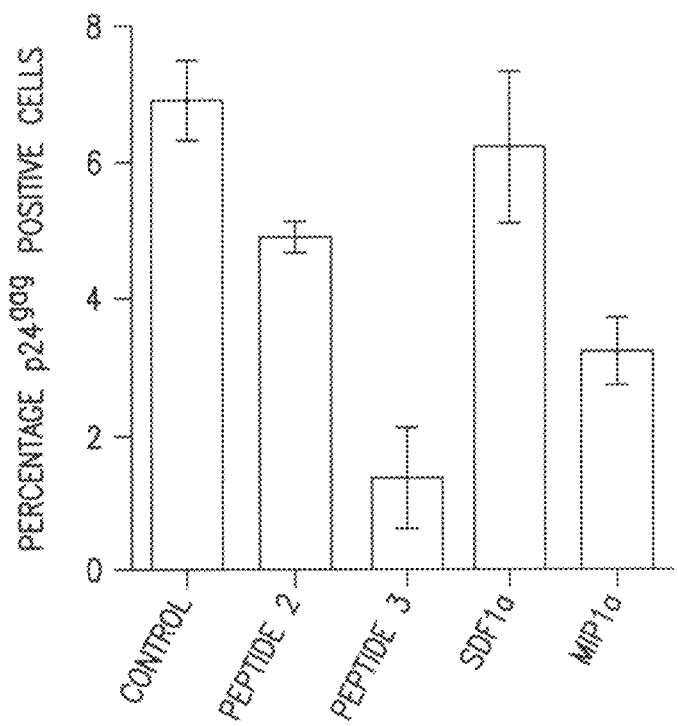
Figure 54D:
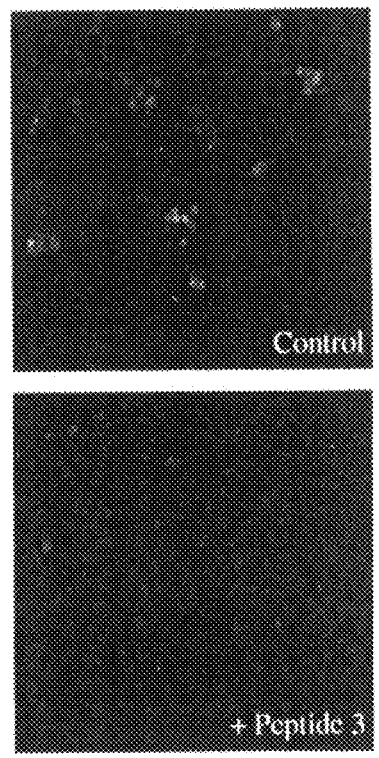

Infection of THP-1 cells with M-tropic isolates does not generate high levels of virus particles and hence the reverse transcriptase assay is not sufficiently sensitive to monitor the progress of the infection. However, it was possible to assess HIV infectivity of THP-1 cells using high sensitivity immunofluorescent detection of $p24^{gag}$. THP-1 cells were differentiated with hydrocortisone and PMA, then treated with TNFα, resulting in adherent monolayers on glass chamber slides. The THP-1 cells were then treated with either peptide 2 (100 μM), peptide 3 (100 μM), MIP1α (100 ng/ml) or SDF1α (100 ng/ml) as for the Jurkat cells. THP-1 cells were infected with HIV strain MN at a concentration previously validated to produce easily detectable infection and growth for 72 hours prior to fixation and staining for $p24^{gag}$. Peptide 2 inhibited HIV infectivity of THP-1 cells by 28±5% (p<0.05; Mann-Whiney U test), while peptide 3 inhibited infection of THP-1 cells by more than 80% (FIGS. 54C, D).

Table 18 summarizes the DARC binding, ED50s for chemokine and gp120, as well as the percent of virus inhibition by various peptide 2 sequences.

Discussion

Two different oligopeptide sequences from human MCP-1 are able to inhibit cellular infection by HIV-1 isolates in vitro. One of these sequences, peptide 2, inhibited both M-tropic and T-tropic infection, suggesting that, unlike agents which specifically target individual chemokine receptors (Cairns et al., *Nat. Med.*, 4, 563 (1998); Simmons et al., *Science*, 276, 276 (1997)), it may be possible to simultaneously inhibit usage of a wide range of related co-receptors using a single molecule. Moreover, this peptide substantially reduces CXCR4-dependent HIV infection of Jurkat T-cells (assayed either by reverse transcriptase production (75±10% inhibition) or immunofluorescence staining for $p24^{gag}$ (80±3% inhibition). Peptide 2 also reduces CCR5-dependent HIV infection of THP-1 cells (28%±5% inhibition, assayed by immunofluorescence staining). However, peptide 2 did not inhibit chemokine signaling through the receptors, since both SDF1α and MIP1α were fully chemotactic for THP-1 cells in the presence of peptide 2. A second peptide, spanning amino acids 51 to 62 of human MCP-1, did not inhibit CXCR4-dependent HIV infection of Jurkat T-cells (despite inhibiting SDF1α-mediated chemotaxis) but strongly inhibited CCR5-mediated HIV infection of THP-1 cells (83±7% inhibition assayed by immunofluorescence staining).

TABLE 18

| Peptide 2 Sequences | DARC binding (=M) | MCP-1 ED-50 (=M) | MIP1a ED-50 (=M) | SDF1a ED-50 (=M) | gp120 ED-50 (=M) | % virus inhibition |
| --- | --- | --- | --- | --- | --- | --- |
| SYRRITSSKCPKEAV (SEQ ID NO: 3) | 0.1 | ns | ns | ns | 0.4 | 85 |
| Vaekpcksstirrys | 18 | ns | ns | ns | 3 | 72 |
| HLKILNTPNCALQIV (SEQ ID NO: 4) | 19 | 10 | 40 | 7 | 35 | 42 |
| DYFETSSQCSKPGV (SEQ ID NO: 5) | ns | ns | ns | ns | >100 | n.d. |
| vgpkscqsstefyd | ns | ns | ns | ns | ns | ns |
| SYRRITSSKC (SEQ ID NO: 124) | 22 | ns | ns | ns | 60 | ns |
| CPKEAV (SEQ ID NO: 125) | >100 | ns | ns | ns | ns | ns |
| SYRRI (SEQ ID NO: 126) | ns | ns | ns | ns | ns | ns |
| TSSKC (SEQ ID NO: 127) | ns | ns | ns | ns | ns | ns |

TABLE 18-continued

| Peptide 2 Sequences | DARC binding (=M) | MCP-1 ED-50 (=M) | MIPIa ED-50 (=M) | SDF1a ED-50 (=M) | gp120 ED-50 (=M) | % virus inhibition |
|---|---|---|---|---|---|---|
| DYFETSSQC (SEQ ID NO: 128) | ns | ns | ns | ns | ns | ns |
| CSKPGV (SEQ ID NO: 129) | ns | ns | ns | ns | ns | ns |
| CSYRRITSSKSPKEAVC (SEQ ID NO: 130) | ns | ns | ns | ns | >100 | ns |
| cvaekpsksstirrysc | >100 | ns | ns | ns | ns | ns |
| =cvaekpsksstirrysc= | ns | ns | ns | ns | ns | ns |

Notes:
ns = not significant (assay performed, but peptide was not significantly different from control)
n.d. = not determined
>100 = ED50 not determined Consistent with extensive previous studies using chemokine receptors with selected amino acid substitutions (for example, see Ross et al., *J. Virol.*, supra; Alkhatib et al., supra; Dragic et al., supra and the references therein), the results described herein suggest that HIV gp120 binds to both CXCR4 and CCR5 at a site overlapping with, but not identical to, the chemokine ligand binding site. Both Ross et al. (1995) and Dragic et al. (1998) highlight the importance of residues in the amino terminal region of CCR5 for gp120 binding, although both studies recognize that residues in the other extracellular loops of the receptor are likely to play a role in productive binding of gp120. Since peptide 2 blocks gp120:V3 loop peptides from binding to cells, this tentatively suggests that peptide 2 may be binding to a site in the N-terminal region of the receptor (see FIG. 16). This is consistent with the studies of Wells and colleagues who showed that the residues in the peptide 2 region of CC-chemokines interacted with the N-terminus of the chemokine receptors (Monteclaro et al., supra; Lusti-Narasimhan et al., *J. Biol. Chem.*, 271, 3148 (1996); Lusti-Narasimhan et al., *J. Biol. Chem.*, 270, 2716 (1995)). Interestingly, however, they showed that the tyrosine residue at position 2 in the peptide 2 sequence is important for determining receptor specificity: chemokines with leucine at this position bound to CXCR receptors, while chemokines with tyrosine bound to CCR receptors. The results described herein suggest that as an isolated 15mer peptide (as opposed to in the context of the whole chemokine), the tyrosine-containing sequence from MCP-1 is able to interact with both CXCR and CCR receptors. Indeed, the tyrosine-containing peptide 2 was a more effective inhibitor of CXCR4-dependent T-tropic HIV infection than of CCR5-dependent M-tropic infection. It will be interesting to determine the effect, if any, of introducing a Tyr->Leu substitution into the peptide 2 sequence.

Although the studies by Wells and colleagues implicate the N-terminal region of CCR5 in chemokine ligand binding (Monteclaro et al., supra; Lusti-Narasimhan et al., *J. Biol. Chem.*, 271, 3148 (1996); Lusti-Narasimahn et al., *J. Biol. Chem.*, 270, 2716 (1995)), peptide 2 inhibits gp120:V3 loop binding without affecting chemokine binding and signaling. This is consistent with the work of Ross et al. (1998) who found that some amino acid substitutions in the N-terminal region inhibited gp120 binding but not binding and signaling by the natural chemokine ligand. In marked contrast, peptide 3 binds to region on CCR5 which is required for both gp120:V3 loop binding and for chemokine binding and signaling. Experiments with peptide 3, therefore, indicate a difference in the properties of CXCR4 and CCR5: peptide 3 inhibits SDF1α signaling, but does not affect gp120:V3 loop binding or CXCR4-dependent HIV infection. Taken together, these observations suggest that the gp120 binding site and chemokine ligand binding site are more distinct on the CXCR4 receptor (FIG. 16), although binding of the full-length chemokine is still able to prevent gp120 binding (Cocchi et al., *Science*, 270, 1811 (1995); Zaguny et al., *Proc. Nat'l Acad. Sci. U.S.A.*, 95, 3857 (1998); Wells et al., *Methods*, 10, 126 (1996)).

In addition, the observations reported herein are consistent with both peptide 2 and peptide 3 binding directly to the chemokine receptors and inhibiting gp120:V3 loop binding and HIV-1 infection. Moreover, the peptides inhibit gp120:V3 loop binding. However, the affinity of the interaction between the isolated V3 loop peptide and cells was of only moderate affinity and may not be a relevant model for the intact virus particle docking with the chemokine receptors. This is consistent with data suggesting that other regions of gp120, such as the V1/V2 loops, are also important in co-receptor binding (Ross et al., *Proc. Nat'l Acad. Sci. U.S.A.*, 95, 7682 (1998)). The inhibition of infectivity could result from a number of different mechanisms: the peptides may act as simple competitive inhibitors for virus particle binding to the coreceptor. Alternatively, the peptides may induce internalization and inhibit recycling of chemokine receptors as previously described for AOP-RANTES (Mack et al., *J. Exp. Med.*, 187, 1215 (1998)), although this mechanism could not account for the inhibition of gp120:V3 loop binding, since these binding experiments were performed at 4° C.

In summary, oligopeptide sequences derived from the chemokine MCP-1 are able to inhibit HIV infection in vitro to a similar extent to full-length chemokines. Furthermore, one of the sequences (peptide 2), uniquely among chemokine antagonists described to date, inhibits both M-tropic and T-tropic HIV infection raising the possibility that single agents may simultaneously block the ability of HIV to utilize a variety of chemokine co-receptors and hence provide a more complete block on HIV infectivity.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the detailed herein may be varied considerably without departing from the basic principles of the invention.

What is claimed is:

1. A method of inhibiting a respiratory disease associated with a chemokine-induced activity, comprising: administering to a human afflicted with, the respiratory disease, or a human in need thereof, an amount of:
a compound of formula (XIV);
or a pharmaceutically acceptable salt thereof;
effective to inhibit said respiratory disease, wherein the respiratory disease is asthma and wherein formula (XIV) is:

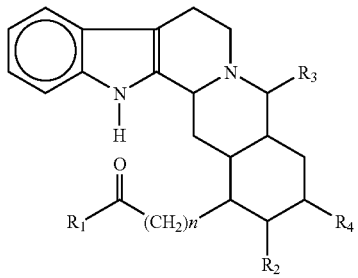

wherein $R_1$ is N(Rb)(Rc) wherein each Rb and Rc is independently H or $(C_1-C_6)$alkyl; $R_2$ is OH; $R_3$ is H; $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, methoxydioxy, hydroxy, C(=O), $SO_2H$, $SO_3H$, and N(Rb)(Rc).

2. A method of treating a human afflicted with, a respiratory disease, or human in need thereof associated with chemokine-induced activity, comprising: administering to a human afflicted with, the respiratory disease, or a human in need thereof, an amount of:
a compound of formula (XIV);
or a pharmaceutically acceptable salt thereof;
effective to treat said respiratory disease, wherein the respiratory disease is asthma and wherein formula (XIV) is:

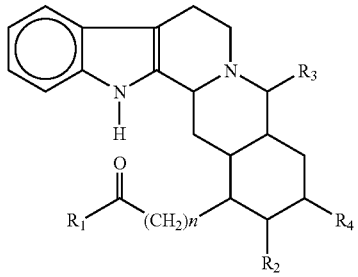

wherein $R_1$ is N(Rb)(Rc) wherein each Rb and Rc is independently H or $(C_1-C_6)$alkyl; $R_2$ is OH; $R_3$ is H; $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, methoxydioxy, hydroxy, C(=O), $SO_2H$, $SO_3H$, and N(Rb)(Rc).

3. A method of inhibiting a respiratory disease associated with a chemokine-induced activity, comprising: administering to a human afflicted with, the respiratory disease, or a human in need thereof, an amount of a compound of formula (XIV);
or a pharmaceutically acceptable salt thereof;
effective to inhibit said respiratory disease, wherein the respiratory disease is chronic obstructive pulmonary disease (COPD) and wherein formula (XIV) is:

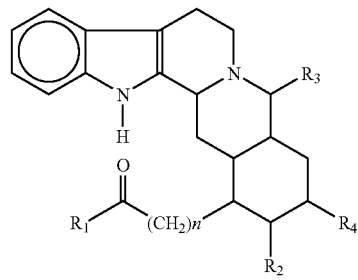

wherein $R_1$ is N(Rb)(Rc) wherein each Rb and Rc is independently H or $(C_1-C_6)$alkyl; $R_7$ is OH; $R_3$ is H; $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, methoxydioxy, hydroxy, C(=O), $SO_2H$, $SO_3H$, and N(Rb)(Rc).

4. A method of inhibiting a respiratory disease associated with a chemokine-induced activity, comprising: administering to a human afflicted with, the respiratory disease, or a human in need thereof, an amount of a compound of formula (XIV);
or a pharmaceutically acceptable salt thereof;
effective to inhibit said respiratory disease, wherein the respiratory disease is allergic rhinitis and wherein formula (XIV) is:

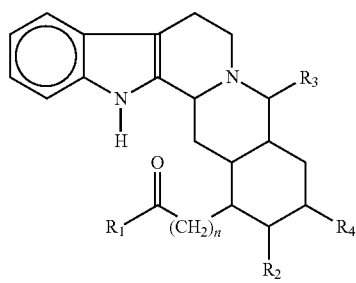

wherein $R_1$ is N(Rb)(Rc) wherein each Rb and Rc is independently H or $(C_1-C_6)$alkyl; $R_9$ is OH; $R_3$ is H, $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, methoxydioxy, hydroxy, C(=O), $SO_2H$, $SO_3H$, and N(Rb)(Rc).

5. A method of treating a human afflicted with, a respiratory disease, or human in need thereof associated with chemokine-induced activity, comprising: administering to a human afflicted with, the respiratory disease, or a human in need thereof, an amount of:

a compound of formula (XIV);
or a pharmaceutically acceptable salt thereof;
effective to treat said respiratory disease, wherein the respiratory disease is chronic obstructive pulmonary disease (COPD) and wherein formula (XIV) is:

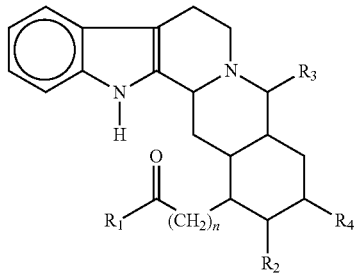

wherein $R_1$ is $N(Rb)(Rc)$ wherein each Rb and Rc is independently H or $(C_1-C_6)$alkyl; $R_2$ is OH; $R_3$ is H; $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, methoxydioxy, hydroxy, $C(=O)$, $SO_2H$, $SO_3H$, and $N(Rb)(Rc)$.

6. A method of treating a human afflicted with, a respiratory disease, or human in need thereof associated with chemokine-induced activity, comprising: administering to a human afflicted with, the respiratory disease, or a human in need thereof, an amount of:
a compound of formula (XIV);
or a pharmaceutically acceptable salt thereof; effective to treat said respiratory disease, wherein the respiratory disease is allergic rhinitis and wherein formula (XIV) is:

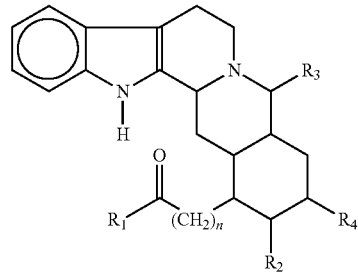

wherein $R_1$ is $N(Rb)(Rc)$ wherein each Rb and Rc is independently H or $(C_1-C_6)$alkyl; $R_2$ is OH; $R_3$ is H; $R_4$ is H; and n is 0 or 1; wherein any $(C_1-C_6)$alkyl or the benzo ring in formula (XIV) is optionally substituted with at least one substituent selected from the group consisting of halo, cyano, nitro, trifluoromethyl, trifluoromethoxy, $(C_1-C_6)$alkyl, $(C_1-C_o)$alkoxy, $(C_1-C_6)$alkanoyl, $(C_1-C_6)$alkanoyloxy, $(C_1-C_6)$alkoxycarbonyl, methoxydioxy, hydroxy, $C(=O)$, $SO_2H$, $SO_3H$, and $N(Rb)(Rc)$.

* * * * *

SEQUENCE LISTING

<160> NUMBER OF SEQ ID NOS: 156

<210> SEQ ID NO 1
<211> LENGTH: 12
<212> TYPE: PRT
<213> ORGANISM: Homo sapiens

<400> SEQUENCE: 1

Glu Ile Cys Ala Asp Pro Lys Gln Lys Trp Val Gln
1               5                   10

<210> SEQ ID NO 2
<211> LENGTH: 13
<212> TYPE: PRT
<213> ORGANISM: Homo sapiens

<400> SEQUENCE: 2

Ala Gln Pro Asp Ala Ile Asn Ala Pro Val Thr Cys Cys
1               5                   10

<210> SEQ ID NO 3
<211> LENGTH: 15
<212> TYPE: PRT
<213> ORGANISM: Homo sapiens

<400> SEQUENCE: 3

Ser Tyr Arg Arg Ile Thr Ser Ser Lys Cys Pro Lys Glu Ala Val
1               5                   10                  15

<210> SEQ ID NO 4
<211> LENGTH: 15
<212> TYPE: PRT
<213> ORGANISM: Homo sapiens

<400> SEQUENCE: 4

His Leu Lys Ile Leu Asn Thr Pro Asn Cys Ala Leu Gln Ile Val
1               5                   10                  15

<210> SEQ ID NO 5
<211> LENGTH: 14
<212> TYPE: PRT
<213> ORGANISM: Homo sapiens

<400> SEQUENCE: 5

Asp Tyr Phe Glu Thr Ser Ser Gln Cys Ser Lys Pro Gly Val
1               5                   10

<210> SEQ ID NO 6
<211> LENGTH: 16
<212> TYPE: PRT
<213> ORGANISM: Homo sapiens

<400> SEQUENCE: 6

Glu Leu Arg Val Ile Glu Ser Gly Pro His Cys Ala Asn Thr Glu Ile
1               5                   10                  15

<210> SEQ ID NO 7
<211> LENGTH: 10
<212> TYPE: PRT
<213> ORGANISM: Homo sapiens

<400> SEQUENCE: 7

Cys Ala Asp Pro Lys Gln Lys Trp Val Gln
1               5                   10

```
<210> SEQ ID NO 8
<211> LENGTH: 6
<212> TYPE: PRT
<213> ORGANISM: Homo sapiens

<400> SEQUENCE: 8

Glu Ile Cys Ala Asp Pro
1               5

<210> SEQ ID NO 9
<211> LENGTH: 6
<212> TYPE: PRT
<213> ORGANISM: Homo sapiens

<400> SEQUENCE: 9

Lys Gln Lys Trp Val Gln
1               5

<210> SEQ ID NO 10
<211> LENGTH: 12
<212> TYPE: PRT
<213> ORGANISM: Artificial Sequence
<220> FEATURE:
<223> OTHER INFORMATION: A synthetic peptide

<400> SEQUENCE: 10

Glu Ile Cys Leu Asp Pro Lys Gln Lys Trp Val Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: A synthetic peptide

<400> SEQUENCE: 11

Glu Ile Cys Ala Asp Pro Ser Gln Lys Trp Val Gln
1               5                   10

<210> SEQ ID NO 12
<211> LENGTH: 12
<212> TYPE: PRT
<213> ORGANISM: Homo sapiens

<400> SEQUENCE: 12

Glu Ile Cys Ala Asp Pro Ser Glu Glu Trp Val Gln
1               5                   10

<210> SEQ ID NO 13
<211> LENGTH: 12
<212> TYPE: PRT
<213> ORGANISM: Artificial Sequence
<220> FEATURE:
<223> OTHER INFORMATION: A synthetic peptide

<400> SEQUENCE: 13

Glu Ile Cys Ala Asp Pro Lys Gln Lys Trp Ile Gln
1               5                   10

<210> SEQ ID NO 14
<211> LENGTH: 12
<212> TYPE: PRT
<213> ORGANISM: Artificial Sequence
<220> FEATURE:
<223> OTHER INFORMATION: A synthetic peptide
```

<400> SEQUENCE: 14

Glu Ile Cys Leu Asp Pro Lys Gln Lys Trp Ile Gln
1               5                   10

<210> SEQ ID NO 15
<211> LENGTH: 12
<212> TYPE: PRT
<213> ORGANISM: Homo sapiens

<400> SEQUENCE: 15

Cys Pro Ser Leu Glu Asp Ser Phe Ile Gln Val Ala
1               5                   10

<210> SEQ ID NO 16
<211> LENGTH: 77
<212> TYPE: PRT
<213> ORGANISM: Homo sapiens

<400> SEQUENCE: 16

Ala Gln Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Met Asp His Leu Asp Lys Gln Thr Gln Thr Pro Lys Thr
65                  70                  75

<210> SEQ ID NO 17
<211> LENGTH: 77
<212> TYPE: PRT
<213> ORGANISM: Homo sapiens

<400> SEQUENCE: 17

Ala Gln Pro Asp Ser Val Ser Ile Pro Ile Thr Cys Cys Pro Asn Val
1               5                   10                  15

Ile Asn Arg Lys Ile Pro Ile Gln Arg Leu Glu Ser Tyr Arg Arg Ile
            20                  25                  30

Thr Asn Ile Gln Cys Pro Lys Glu Ala Val Ile Phe Lys Thr Lys Arg
        35                  40                  45

Gly Lys Glu Val Cys Ala Asp Pro Lys Glu Arg Trp Val Arg Asp Ser
    50                  55                  60

Asn Lys His Leu Asp Gln Ile Phe Gln Asn Leu Lys Pro
65                  70                  75

<210> SEQ ID NO 18
<211> LENGTH: 77
<212> TYPE: PRT
<213> ORGANISM: Homo sapiens

<400> SEQUENCE: 18

Ala Gln Pro Val Gly Ile Asn Thr Ser Thr Thr Cys Cys Tyr Arg Phe
1               5                   10                  15

Ile Asn Lys Lys Ile Pro Lys Gln Arg Leu Glu Ser Tyr Arg Arg Thr
            20                  25                  30

Thr Ser Ser His Cys Pro Arg Glu Ala Val Ile Phe Lys Thr Lys Leu
        35                  40                  45

```
Asp Lys Glu Ile Cys Ala Asp Pro Thr Gln Lys Trp Val Gln Asp Phe
 50                  55                  60

Met Lys His Leu Asp Lys Lys Thr Gln Thr Pro Lys Leu
 65                  70                  75
```

```
<210> SEQ ID NO 19
<211> LENGTH: 71
<212> TYPE: PRT
<213> ORGANISM: Homo sapiens

<400> SEQUENCE: 19

Ser Ala Ser Leu Ala Ala Asp Thr Pro Thr Ala Cys Cys Phe Ser Tyr
 1               5                  10                  15

Thr Ser Arg Gln Ile Pro Gln Asn Phe Ile Ala Asp Tyr Phe Glu Thr
             20                  25                  30

Ser Ser Gln Cys Ser Lys Pro Gly Val Ile Phe Leu Thr Lys Arg Ser
         35                  40                  45

Arg Gln Val Cys Ala Asp Pro Ser Glu Glu Trp Val Gln Lys Tyr Val
 50                  55                  60

Ser Asp Leu Glu Leu Ser Ala
 65                  70
```

```
<210> SEQ ID NO 20
<211> LENGTH: 70
<212> TYPE: PRT
<213> ORGANISM: Homo sapiens

<400> SEQUENCE: 20

Ser Ala Pro Met Gly Ser Asp Pro Pro Thr Ala Cys Cys Phe Ser Tyr
 1               5                  10                  15

Thr Ala Arg Lys Leu Pro Arg Asn Phe Val Val Asp Tyr Tyr Glu Thr
             20                  25                  30

Ser Ser Leu Cys Ser Gln Pro Ala Val Val Phe Gln Thr Lys Arg Ser
         35                  40                  45

Lys Gln Val Cys Ala Asp Pro Ser Glu Ser Trp Val Gln Glu Tyr Val
 50                  55                  60

Tyr Asp Leu Glu Leu Asn
 65                  70
```

```
<210> SEQ ID NO 21
<211> LENGTH: 70
<212> TYPE: PRT
<213> ORGANISM: Homo sapiens

<400> SEQUENCE: 21

Ser Ala Pro Met Gly Ser Asp Pro Pro Thr Ala Cys Cys Phe Ser Tyr
 1               5                  10                  15

Thr Ala Arg Lys Leu Pro Arg Asn Phe Val Val Asp Tyr Tyr Glu Thr
             20                  25                  30

Ser Ser Leu Cys Ser Gln Pro Ala Val Val Phe Gln Thr Lys Arg Ser
         35                  40                  45

Lys Gln Val Cys Ala Asp Pro Ser Glu Ser Trp Val Gln Glu Tyr Val
 50                  55                  60

Tyr Asp Leu Glu Leu Asn
 65                  70
```

```
<210> SEQ ID NO 22
<211> LENGTH: 68
<212> TYPE: PRT
<213> ORGANISM: Homo sapiens
```

<400> SEQUENCE: 22

Gly Lys Pro Val Ser Leu Ser Tyr Arg Cys Pro Cys Arg Phe Phe Glu
1               5                   10                  15

Ser His Ile Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Glu Lys
    50                  55                  60

Ala Leu Asn Lys
65

<210> SEQ ID NO 23
<211> LENGTH: 74
<212> TYPE: PRT
<213> ORGANISM: Homo sapiens

<400> SEQUENCE: 23

Leu Pro Arg Ser Ala Lys Glu Leu Arg Cys Gln Cys Ile Lys Thr Tyr
1               5                   10                  15

Ser Lys Pro Phe His Pro Lys Phe Ile Lys Glu Leu Arg Val Ile Glu
            20                  25                  30

Ser Gly Pro His Cys Ala Asn Thr Glu Ile Ile Val Arg Leu Ser Asp
        35                  40                  45

Gly Arg Glu Leu Cys Leu Asp Pro Lys Glu Asn Trp Val Gln Arg Val
    50                  55                  60

Glu Lys Phe Leu Lys Arg Ala Glu Asn Ser
65                  70

<210> SEQ ID NO 24

<400> SEQUENCE: 24

000

<210> SEQ ID NO 25
<211> LENGTH: 73
<212> TYPE: PRT
<213> ORGANISM: Homo sapiens
<220> FEATURE:
<221> NAME/KEY: SITE
<222> LOCATION: 54, 55, 70
<223> OTHER INFORMATION: Xaa = any amino acid

<400> SEQUENCE: 25

His Pro Gly Ile Pro Ser Ala Cys Cys Tyr Asn Phe Thr Asn Lys Lys
1               5                   10                  15

Ile Ser Phe Gln Arg Leu Lys Ser Tyr Lys Ile Ile Thr Ser Ser Lys
            20                  25                  30

Cys Pro Gln Thr Ala Ile Val Phe Glu Ile Lys Pro Asp Lys Met Ile
        35                  40                  45

Cys Ala Asp Pro Lys Xaa Xaa Trp Val Gln Asp Ala Lys Lys Tyr Leu
    50                  55                  60

Asp Gln Ile Ser Gln Xaa Thr Lys Pro
65                  70

<210> SEQ ID NO 26
<211> LENGTH: 74
<212> TYPE: PRT
<213> ORGANISM: Mus musculus

<400> SEQUENCE: 26

Ala Gln Pro Asp Ala Val Asn Ala Pro Leu Thr Cys Cys Tyr Ser Pro
1               5                   10                  15

Thr Ser Lys Met Ile Pro Met Ser Arg Leu Glu Ser Tyr Lys Arg Ile
            20                  25                  30

Thr Ser Ser Arg Cys Pro Lys Glu Ala Val Val Phe Val Thr Lys Leu
        35                  40                  45

Lys Arg Glu Val Cys Ala Asp Pro Lys Lys Glu Trp Val Gln Thr Tyr
    50                  55                  60

Ile Lys Asn Leu Asp Arg Asn Gln Met Arg
65                  70

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

```
<210> SEQ ID NO 36

<400> SEQUENCE: 36

000

<210> SEQ ID NO 37

<400> SEQUENCE: 37

000

<210> SEQ ID NO 38
<211> LENGTH: 12
<212> TYPE: PRT
<213> ORGANISM: Homo sapiens

<400> SEQUENCE: 38

Gln Val Cys Ile Asp Pro Lys Leu Lys Trp Ile Gln
 1               5                  10

<210> SEQ ID NO 39

<400> SEQUENCE: 39

000

<210> SEQ ID NO 40
<211> LENGTH: 12
<212> TYPE: PRT
<213> ORGANISM: Homo sapiens

<400> SEQUENCE: 40

Glu Leu Cys Leu Asp Pro Lys Glu Asn Trp Val Gln
 1               5                  10

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000
```

```
<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
```

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80

```
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000
```

-continued

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 13
<212> TYPE: PRT
<213> ORGANISM: Homo sapiens

<400> SEQUENCE: 111

Leu Tyr Ile Asp Phe Arg Gln Asp Leu Gly Trp Lys Trp
 1               5                  10

<210> SEQ ID NO 112
<211> LENGTH: 11
<212> TYPE: PRT
<213> ORGANISM: Homo sapiens

<400> SEQUENCE: 112

His Glu Pro Lys Gly Tyr His Ala Asn Phe Cys
 1               5                  10

<210> SEQ ID NO 113
<211> LENGTH: 7
<212> TYPE: PRT

<213> ORGANISM: Homo sapiens

<400> SEQUENCE: 113

Val Tyr Tyr Val Gly Arg Lys
1               5

<210> SEQ ID NO 114
<211> LENGTH: 13
<212> TYPE: PRT
<213> ORGANISM: Homo sapiens

<400> SEQUENCE: 114

Lys Val Glu Gln Leu Ser Asn Met Val Val Lys Ser Cys
1               5                   10

<210> SEQ ID NO 115
<211> LENGTH: 12
<212> TYPE: PRT
<213> ORGANISM: Oryctolagus cuniculus

<400> SEQUENCE: 115

Gly Ile Cys Ala Asp Pro Lys Gln Lys Trp Val Gln
1               5                   10

<210> SEQ ID NO 116
<211> LENGTH: 12
<212> TYPE: PRT
<213> ORGANISM: Rattus norvegicus

<400> SEQUENCE: 116

Glu Ile Cys Ala Asp Pro Asn Lys Glu Trp Val Gln
1               5                   10

<210> SEQ ID NO 117
<211> LENGTH: 12
<212> TYPE: PRT
<213> ORGANISM: Bos taurus

<400> SEQUENCE: 117

Glu Leu Cys Ala Asp Pro Lys Gln Lys Trp Val Gln
1               5                   10

<210> SEQ ID NO 118
<211> LENGTH: 12
<212> TYPE: PRT
<213> ORGANISM: Cavia porcellus

<400> SEQUENCE: 118

Glu Val Cys Ala Asp Pro Thr Gln Lys Trp Val Gln
1               5                   10

<210> SEQ ID NO 119
<211> LENGTH: 12
<212> TYPE: PRT
<213> ORGANISM: Sus scrofa

<400> SEQUENCE: 119

Glu Ile Cys Ala Glu Pro Lys Gln Lys Trp Val Gln
1               5                   10

<210> SEQ ID NO 120
<211> LENGTH: 15
<212> TYPE: PRT
<213> ORGANISM: Artificial Sequence
<220> FEATURE:
<223> OTHER INFORMATION: A synthetic peptide

```
<400> SEQUENCE: 120

Ser Tyr Arg Arg Ile Thr Ser Ser Lys Ser Pro Lys Glu Ala Val
1               5                   10                  15

<210> SEQ ID NO 121
<211> LENGTH: 10
<212> TYPE: PRT
<213> ORGANISM: Artificial Sequence
<220> FEATURE:
<223> OTHER INFORMATION: A synthetic peptide

<400> SEQUENCE: 121

Leu Asp Pro Lys Gln Lys Trp Ile Gln Cys
1               5                   10

<210> SEQ ID NO 122
<211> LENGTH: 4
<212> TYPE: PRT
<213> ORGANISM: Artificial Sequence
<220> FEATURE:
<223> OTHER INFORMATION: A synthetic peptide

<400> SEQUENCE: 122

Trp Val Gln Cys
1

<210> SEQ ID NO 123
<211> LENGTH: 4
<212> TYPE: PRT
<213> ORGANISM: Artificial Sequence
<220> FEATURE:
<223> OTHER INFORMATION: A synthetic peptide

<400> SEQUENCE: 123

Trp Ile Gln Cys
1

<210> SEQ ID NO 124
<211> LENGTH: 10
<212> TYPE: PRT
<213> ORGANISM: Homo sapiens

<400> SEQUENCE: 124

Ser Tyr Arg Arg Ile Thr Ser Ser Lys Cys
1               5                   10

<210> SEQ ID NO 125
<211> LENGTH: 6
<212> TYPE: PRT
<213> ORGANISM: Homo sapiens

<400> SEQUENCE: 125

Cys Pro Lys Glu Ala Val
1               5

<210> SEQ ID NO 126
<211> LENGTH: 5
<212> TYPE: PRT
<213> ORGANISM: Homo sapiens

<400> SEQUENCE: 126

Ser Tyr Arg Arg Ile
1               5

<210> SEQ ID NO 127
```

```
<211> LENGTH: 5
<212> TYPE: PRT
<213> ORGANISM: Homo sapiens

<400> SEQUENCE: 127

Thr Ser Ser Lys Cys
1               5

<210> SEQ ID NO 128
<211> LENGTH: 9
<212> TYPE: PRT
<213> ORGANISM: Homo sapiens

<400> SEQUENCE: 128

Asp Tyr Phe Glu Thr Ser Ser Gln Cys
1               5

<210> SEQ ID NO 129
<211> LENGTH: 6
<212> TYPE: PRT
<213> ORGANISM: Homo sapiens

<400> SEQUENCE: 129

Cys Ser Lys Pro Gly Val
1               5

<210> SEQ ID NO 130
<211> LENGTH: 17
<212> TYPE: PRT
<213> ORGANISM: Artificial Sequence
<220> FEATURE:
<223> OTHER INFORMATION: A synthetic peptide

<400> SEQUENCE: 130

Cys Ser Tyr Arg Arg Ile Thr Ser Ser Lys Ser Pro Lys Glu Ala Val
1               5                   10                  15
Cys

<210> SEQ ID NO 131
<211> LENGTH: 10
<212> TYPE: PRT
<213> ORGANISM: Homo sapiens

<400> SEQUENCE: 131

Cys Ala Leu Asp Thr Val Gly Trp Val Gln
1               5                   10

<210> SEQ ID NO 132
<211> LENGTH: 9
<212> TYPE: PRT
<213> ORGANISM: Homo sapiens

<400> SEQUENCE: 132

Ser Tyr Arg Arg Ile Thr Ser Ser Lys
1               5

<210> SEQ ID NO 133
<211> LENGTH: 16
<212> TYPE: PRT
<213> ORGANISM: Artificial Sequence
<220> FEATURE:
<223> OTHER INFORMATION: A synthetic peptide

<400> SEQUENCE: 133

Cys Ser Tyr Arg Arg Ile Thr Ser Ser Lys Cys Pro Lys Glu Ala Val
1               5                   10                  15
```

<210> SEQ ID NO 134
<211> LENGTH: 16
<212> TYPE: PRT
<213> ORGANISM: Artificial Sequence
<220> FEATURE:
<223> OTHER INFORMATION: A synthetic peptide

<400> SEQUENCE: 134

Ser Tyr Arg Arg Ile Thr Ser Ser Lys Cys Pro Lys Glu Ala Val Cys
 1               5                  10                  15

<210> SEQ ID NO 135
<211> LENGTH: 15
<212> TYPE: PRT
<213> ORGANISM: Artificial Sequence
<220> FEATURE:
<223> OTHER INFORMATION: A synthetic peptide

<400> SEQUENCE: 135

His Leu Lys Ile Leu Asn Thr Pro Asn Ser Ala Leu Gln Ile Val
 1               5                  10                  15

<210> SEQ ID NO 136
<211> LENGTH: 10
<212> TYPE: PRT
<213> ORGANISM: Artificial Sequence
<220> FEATURE:
<223> OTHER INFORMATION: A synthetic peptide

<400> SEQUENCE: 136

Cys Leu Asp Pro Lys Gln Lys Trp Ile Gln
 1               5                  10

<210> SEQ ID NO 137
<211> LENGTH: 5
<212> TYPE: PRT
<213> ORGANISM: Artificial Sequence
<220> FEATURE:
<223> OTHER INFORMATION: A synthetic peptide

<400> SEQUENCE: 137

Glu Arg Thr Lys Arg
 1               5

<210> SEQ ID NO 138
<211> LENGTH: 11
<212> TYPE: PRT
<213> ORGANISM: Artificial Sequence
<220> FEATURE:
<223> OTHER INFORMATION: A synthetic peptide

<400> SEQUENCE: 138

Ser Gly Pro Ser Ile Val His Arg Lys Cys Phe
 1               5                  10

<210> SEQ ID NO 139
<211> LENGTH: 10
<212> TYPE: PRT
<213> ORGANISM: Artificial Sequence
<220> FEATURE:
<223> OTHER INFORMATION: A synthetic peptide

<400> SEQUENCE: 139

Met Cys Glu Glu Glu Asp Ser Thr Ala Leu
 1               5                  10

```
<210> SEQ ID NO 140
<211> LENGTH: 22
<212> TYPE: PRT
<213> ORGANISM: Artificial Sequence
<220> FEATURE:
<223> OTHER INFORMATION: A synthetic peptide

<400> SEQUENCE: 140

Ser Gly Pro Ser Ile Val His Arg Lys Cys Phe Gly Met Cys Glu Glu
1               5                   10                  15

Glu Asp Ser Thr Ala Leu
            20

<210> SEQ ID NO 141
<211> LENGTH: 35
<212> TYPE: PRT
<213> ORGANISM: Human Immunodeficiency Virus

<400> SEQUENCE: 141

Cys Thr Arg Pro Asn Tyr Asn Lys Arg Lys Arg Ile His Ile Gly Pro
1               5                   10                  15

Gly Arg Ala Phe Tyr Thr Thr Lys Asn Ile Ile Gly Thr Ile Arg Gln
            20                  25                  30

Ala His Cys
        35

<210> SEQ ID NO 142
<211> LENGTH: 24
<212> TYPE: PRT
<213> ORGANISM: Human Immunodeficiency Virus

<400> SEQUENCE: 142

Asn Asn Thr Arg Lys Ser Ile Arg Ile Gln Arg Gly Pro Gly Arg Ala
1               5                   10                  15

Phe Val Thr Ile Gly Lys Ile Gly
            20

<210> SEQ ID NO 143
<211> LENGTH: 10
<212> TYPE: PRT
<213> ORGANISM: Human Immunodeficiency Virus

<400> SEQUENCE: 143

Arg Gly Pro Gly Arg Ala Phe Val Thr Ile
1               5                   10

<210> SEQ ID NO 144
<211> LENGTH: 15
<212> TYPE: PRT
<213> ORGANISM: Human Immunodeficiency Virus

<400> SEQUENCE: 144

Arg Ile Gln Arg Gly Pro Gly Arg Ala Phe Val Thr Ile Gly Lys
1               5                   10                  15

<210> SEQ ID NO 145
<211> LENGTH: 32
<212> TYPE: PRT
<213> ORGANISM: Homo sapiens

<400> SEQUENCE: 145

Cys Val Pro Gln Ala Leu Glu Pro Leu Pro Ile Val Tyr Tyr Val Gly
1               5                   10                  15

Arg Lys Pro His Val Glu Gln Leu Ser Asn Met Ile Val Arg Ser Cys
```

```
                       20                  25                  30
```

<210> SEQ ID NO 146
<211> LENGTH: 14
<212> TYPE: PRT
<213> ORGANISM: Homo sapiens

<400> SEQUENCE: 146

```
Glu Arg Ala Gln His Leu Gln Ser Ser Arg His Arg Arg Cys
 1               5                  10
```

<210> SEQ ID NO 147
<211> LENGTH: 12
<212> TYPE: PRT
<213> ORGANISM: Homo sapiens

<400> SEQUENCE: 147

```
Ser Arg His Arg Arg Ala Leu Asp Thr Asn Tyr Cys
 1               5                  10
```

<210> SEQ ID NO 148
<211> LENGTH: 12
<212> TYPE: PRT
<213> ORGANISM: Homo sapiens

<400> SEQUENCE: 148

```
Leu Val Lys Arg Lys Arg Ile Glu Ala Ile Arg Cys
 1               5                  10
```

<210> SEQ ID NO 149
<211> LENGTH: 15
<212> TYPE: PRT
<213> ORGANISM: Homo sapiens

<400> SEQUENCE: 149

```
Arg Pro Ala Ala Gly Leu Ser Thr Cys Lys Thr Ile Asp Met Glu
 1               5                  10                  15
```

<210> SEQ ID NO 150
<211> LENGTH: 10
<212> TYPE: PRT
<213> ORGANISM: Human Immunodeficiency Virus
<220> FEATURE:
<223> OTHER INFORMATION: A synthetic peptide

<400> SEQUENCE: 150

```
Arg Gly Pro Gly Arg Ala Pro Val Thr Ile
 1               5                  10
```

<210> SEQ ID NO 151
<211> LENGTH: 10
<212> TYPE: PRT
<213> ORGANISM: Homo sapiens
<220> FEATURE:
<221> NAME/KEY: SITE
<222> LOCATION: 2
<223> OTHER INFORMATION: Xaa = Ala, Leu or Ile
<220> FEATURE:
<221> NAME/KEY: SITE
<222> LOCATION: 5
<223> OTHER INFORMATION: Xaa = Lys or Ser
<220> FEATURE:
<221> NAME/KEY: SITE
<222> LOCATION: 6
<223> OTHER INFORMATION: Xaa = Gln, Leu or Glu
<220> FEATURE:
<221> NAME/KEY: SITE
<222> LOCATION: 7
<223> OTHER INFORMATION: Xaa = Lys, Arg, Glu or Ser

```
<220> FEATURE:
<221> NAME/KEY: SITE
<222> LOCATION: 9
<223> OTHER INFORMATION: Xaa = Val, Ile or Leu

<400> SEQUENCE: 151

Cys Xaa Asp Pro Xaa Xaa Xaa Trp Xaa Gln
 1               5                  10

<210> SEQ ID NO 152
<211> LENGTH: 11
<212> TYPE: PRT
<213> ORGANISM: Artificial Sequence
<220> FEATURE:
<223> OTHER INFORMATION: A synthetic peptide

<400> SEQUENCE: 152

Cys Leu Asp Pro Lys Gln Lys Trp Ile Gln Cys
 1               5                  10

<210> SEQ ID NO 153
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 12
<223> OTHER INFORMATION: Xaa = any amino acid

<400> SEQUENCE: 153

Ser Leu Asp Pro Lys Gln Lys Trp Ile Gln Cys Xaa
 1               5                  10

<210> SEQ ID NO 154
<211> LENGTH: 4
<212> TYPE: PRT
<213> ORGANISM: Artificial Sequence
<220> FEATURE:
<223> OTHER INFORMATION: A synthetic peptide

<400> SEQUENCE: 154

Lys Lys Phe Lys
 1

<210> SEQ ID NO 155
<211> LENGTH: 4
<212> TYPE: PRT
<213> ORGANISM: Artificial Sequence
<220> FEATURE:
<223> OTHER INFORMATION: A synthetic peptide

<400> SEQUENCE: 155

Arg Lys Pro Lys
 1

<210> SEQ ID NO 156
<211> LENGTH: 4
<212> TYPE: PRT
<213> ORGANISM: Artificial Sequence
<220> FEATURE:
<223> OTHER INFORMATION: A synthetic peptide

<400> SEQUENCE: 156

Lys Arg Phe Lys
 1
```